(12) United States Patent
Durrant et al.

(10) Patent No.: US 11,834,441 B2
(45) Date of Patent: Dec. 5, 2023

(54) SUBSTITUTED TETRAHYDROFURANS AS MODULATORS OF SODIUM CHANNELS

(71) Applicant: Vertex Pharmaceuticals Incorporated, Boston, MA (US)

(72) Inventors: Steven John Durrant, Headington (GB); Nadia Ahmad, Berkshire (GB); Elizabeth Mary Beck, Abingdon (GB); Lidio Marx Carvalho Meireles, San Marcos, CA (US); Ewa Iwona Chudyk, Wantage (GB); Gorka Etxebarria Jardi, Badalona (ES); Bhairavi Galan, Abingdon (GB); Sara S. Hadida Ruah, La Jolla, CA (US); Dennis James Hurley, San Marcos, CA (US); Ronald Marcellus Knegtel, Abingdon (GB); Timothy Donald Neubert, San Diego, CA (US); Joanne Louise Pinder, Didcot (GB); Joseph Pontillo, San Diego, CA (US); Robert Pullin, Oxford (GB); Yvonne Schmidt, San Diego, CA (US); David Matthew Shaw, Oxford (GB); Sarah Skerratt, Cambridge (GB); Dean Stamos, Carlsbad, CA (US); Stephen Andrew Thomson, Durham, NC (US); Anisa Nizarali Virani, Thatcham (GB); Christopher Wray, Berkshire (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 17/112,156

(22) Filed: Dec. 4, 2020

(65) Prior Publication Data
US 2021/0198241 A1 Jul. 1, 2021

Related U.S. Application Data

(60) Provisional application No. 62/944,869, filed on Dec. 6, 2019.

(51) Int. Cl.
*C07D 405/12* (2006.01)
*C07D 307/24* (2006.01)
*C07D 405/14* (2006.01)

(52) U.S. Cl.
CPC ......... *C07D 405/12* (2013.01); *C07D 307/24* (2013.01); *C07D 405/14* (2013.01); *C07B 2200/13* (2013.01)

(58) Field of Classification Search
CPC ................ C07D 405/12; C07D 307/24; C07D 405/14
See application file for complete search history.

(56) References Cited

U.S. PATENT DOCUMENTS

| | | | |
|---|---|---|---|
| 4,844,732 A | 7/1989 | Goto et al. | |
| 5,304,121 A | 4/1994 | Sahatjian | |
| 5,356,897 A | 10/1994 | Oku et al. | |
| 5,387,709 A | 2/1995 | Lardy et al. | |
| 5,403,842 A | 4/1995 | Leonardi et al. | |
| 5,886,026 A | 3/1999 | Hunter et al. | |
| 5,942,508 A | 8/1999 | Sawa | |
| 5,968,965 A | 10/1999 | Dinsmore et al. | |
| 5,977,108 A | 11/1999 | Kikuchi et al. | |
| 6,099,562 A | 8/2000 | Ding et al. | |
| 6,179,882 B1 | 1/2001 | Vidal et al. | |
| 6,355,669 B1 | 3/2002 | Yamauchi et al. | |
| 8,389,734 B2 | 3/2013 | Chen | |
| 8,466,188 B2 | 6/2013 | Chafeev et al. | |
| 8,486,950 B2 | 7/2013 | Goodacre et al. | |
| 8,519,137 B2 | 8/2013 | Joshi | |
| 8,779,197 B2 | 7/2014 | Chen | |
| 8,841,483 B2 | 9/2014 | Joshi | |
| 8,865,771 B2 | 10/2014 | Chen | |
| 8,883,840 B2 | 11/2014 | Chafeev et al. | |
| 9,051,270 B2 | 6/2015 | Hadida-Ruah | |
| 9,108,903 B2 | 8/2015 | Hadida-Ruah | |
| 9,139,529 B2 | 9/2015 | Hadida-Ruah | |
| 9,163,042 B2 | 10/2015 | Anderson | |
| 9,393,235 B2 | 7/2016 | Hadida-Ruah | |
| 9,421,196 B2 | 8/2016 | Hadida-Ruah | |
| 9,464,102 B2 | 10/2016 | Anderson | |

(Continued)

FOREIGN PATENT DOCUMENTS

| | | | |
|---|---|---|---|
| CA | 2742435 A1 | 5/2011 | |
| CA | 2851462 A1 | 5/2014 | |

(Continued)

OTHER PUBLICATIONS

National Center for Biotechnology Information (2022); PubChem Compound Summary for CID 136583999. Created Jan. 24, 2019; Retrieved Apr. 1, 2022 from https://pubchem.ncbi.nlm.nih.gov/compound/136583999 (Year: 2019).*

Akopian, A.N., L. Sivilotti, and J.N. Wood, "A tetrodotoxin-resistant voltage-gated sodium channel expressed by sensory neurons." *Nature*, 1996. 379(6562): p. 257-62).

Black, J.A., et al., "Multiple sodium channel isoforms and mitogen-activated protein kinases are present in painful human neuromas." *Ann Neurol*, 2008. 64(6): p. 644-53.

Blair, N.T. and B.P. Bean, "Roles of tetrodotoxin (TTX)-sensitive Na+ current, TTX-resistant Na+ current, and Ca2+ current in the action potentials of nociceptive sensory neurons." *J Neurosci.*, 2002. 22(23): p. 10277-90).

(Continued)

*Primary Examiner* — Matthew P Coughlin
(74) *Attorney, Agent, or Firm* — Barnes & Thornburg LLP

(57) ABSTRACT

Compounds, and pharmaceutically acceptable salts thereof, useful as inhibitors of sodium channels are provided. Also provided are pharmaceutical compositions comprising the compounds or pharmaceutically acceptable salts and methods of using the compounds, pharmaceutically acceptable salts, and pharmaceutical compositions in the treatment of various disorders, including pain.

62 Claims, 16 Drawing Sheets

(56) References Cited

U.S. PATENT DOCUMENTS

| | | |
|---|---|---|
| 9,758,483 B2 | 9/2017 | Hadida-Ruah |
| 9,783,501 B2 | 10/2017 | Hadida-Ruah |
| 9,828,397 B2 | 11/2017 | Anderson |
| 10,087,143 B2 | 10/2018 | Hadida Ruah |
| 10,253,054 B2 | 4/2019 | Anderson |
| 10,647,661 B2 | 5/2020 | Ahmad |
| 10,738,009 B2 | 8/2020 | Hadida Ruah |
| 10,787,472 B2 | 9/2020 | Anderson |
| 11,203,571 B2 | 12/2021 | Hadida-Ruah et al. |
| 11,358,977 B2 | 6/2022 | Jiang et al. |
| 11,529,337 B2 | 12/2022 | Agarwal et al. |
| 2002/0002183 A1 | 1/2002 | Zhu et al. |
| 2003/0195231 A1 | 10/2003 | Takemoto et al. |
| 2004/0180936 A1 | 9/2004 | Auvin et al. |
| 2004/0229839 A1 | 11/2004 | Babu et al. |
| 2005/0009894 A1 | 1/2005 | Babin et al. |
| 2007/0105943 A1 | 5/2007 | Nakamoto et al. |
| 2007/0238733 A1 | 10/2007 | Joshi |
| 2008/0312235 A1 | 12/2008 | Lane et al. |
| 2009/0048306 A1 | 2/2009 | Bagal et al. |
| 2009/0074884 A1 | 3/2009 | Chesney et al. |
| 2009/0099233 A1 | 4/2009 | Joshi |
| 2009/0118333 A1 | 5/2009 | Chen |
| 2009/0118338 A1 | 5/2009 | Chen |
| 2009/0163545 A1 | 6/2009 | Goldfarb |
| 2009/0326020 A1 | 12/2009 | Miller et al. |
| 2010/0069417 A1 | 3/2010 | Bouaboula et al. |
| 2010/0075948 A1 | 3/2010 | Ding et al. |
| 2010/0093668 A1 | 4/2010 | Babin et al. |
| 2010/0099694 A1 | 4/2010 | Babin et al. |
| 2010/0152190 A1 | 6/2010 | Bartkovitz et al. |
| 2010/0186626 A1 | 7/2010 | Shin et al. |
| 2010/0256113 A1 | 10/2010 | Onda et al. |
| 2011/0257196 A1 | 10/2011 | Lu et al. |
| 2011/0301181 A1 | 12/2011 | Maue et al. |
| 2011/0306607 A1 | 12/2011 | Hadida-Ruah et al. |
| 2012/0108630 A1 | 5/2012 | Chen et al. |
| 2012/0196869 A1 | 8/2012 | Hadida Ruah et al. |
| 2012/0220605 A1 | 8/2012 | Pajouhesh et al. |
| 2012/0245136 A1 | 9/2012 | Hadida-Ruah et al. |
| 2012/0264055 A1 | 10/2012 | Ichikawa et al. |
| 2012/0264749 A1 | 10/2012 | Hadida-Ruah et al. |
| 2013/0158031 A1 | 6/2013 | Cai et al. |
| 2013/0231370 A1 | 9/2013 | Chen |
| 2013/0274243 A1 | 10/2013 | Bagal et al. |
| 2013/0303535 A1 | 11/2013 | Tsuboi et al. |
| 2014/0005181 A1 | 1/2014 | Smith et al. |
| 2014/0011763 A1 | 1/2014 | Lakshman |
| 2014/0187533 A1 | 7/2014 | Pajouhesh et al. |
| 2014/0200215 A1 | 7/2014 | Buckman et al. |
| 2014/0213616 A1 | 7/2014 | Hadida-Ruah |
| 2014/0213623 A1 | 7/2014 | Miller et al. |
| 2014/0221435 A1 | 8/2014 | Hadida-Ruah et al. |
| 2014/0228371 A1 | 8/2014 | Hadida-Ruah |
| 2014/0296313 A1 | 10/2014 | Bagal et al. |
| 2015/0005304 A1 | 1/2015 | Hadida-Ruah et al. |
| 2015/0076062 A1 | 3/2015 | Barthelemy et al. |
| 2015/0166589 A1 | 6/2015 | Anderson et al. |
| 2015/0166890 A1 | 6/2015 | Archetti et al. |
| 2015/0210640 A1 | 7/2015 | Ikuma et al. |
| 2015/0246028 A1 | 9/2015 | Hadida-Ruah |
| 2015/0305999 A1 | 10/2015 | Daubresse |
| 2015/0322027 A1 | 11/2015 | Fujiwara et al. |
| 2015/0328196 A1 | 11/2015 | Hadida-Ruah |
| 2015/0336945 A1 | 11/2015 | Hadida-Ruah |
| 2015/0361038 A1 | 12/2015 | Smith et al. |
| 2015/0376174 A1 | 12/2015 | Kawana et al. |
| 2016/0009743 A1 | 1/2016 | Anderson |
| 2016/0046863 A1 | 2/2016 | Archetti et al. |
| 2016/0115151 A1 | 4/2016 | Kai |
| 2016/0145304 A1 | 5/2016 | Baumann et al. |
| 2016/0152561 A1 | 6/2016 | Hadida-Ruah |
| 2016/0208171 A1 | 7/2016 | Kim et al. |
| 2016/0238930 A1 | 8/2016 | Hasegawa et al. |
| 2016/0333009 A1 | 11/2016 | Bartlett et al. |
| 2016/0376295 A1 | 12/2016 | Anderson |
| 2017/0037009 A1 | 2/2017 | Hadida-Ruah |
| 2017/0256727 A1 | 9/2017 | Lee et al. |
| 2018/0016235 A1 | 1/2018 | Hadida-Ruah |
| 2018/0044361 A1 | 2/2018 | Anderson et al. |
| 2018/0201600 A1 | 7/2018 | Jeschke et al. |
| 2018/0258076 A1 | 9/2018 | Sato et al. |
| 2019/0016671 A1 | 1/2019 | Ahmad et al. |
| 2019/0248745 A1 | 8/2019 | Hadida Ruah et al. |
| 2019/0276483 A1 | 9/2019 | Anderson et al. |
| 2019/0343817 A1 | 11/2019 | Agarwal et al. |
| 2020/0024270 A1 | 1/2020 | Li et al. |
| 2020/0030312 A1 | 1/2020 | Shao et al. |
| 2020/0079795 A1 | 3/2020 | Zhang et al. |
| 2020/0140411 A1 | 5/2020 | Arasappan et al. |
| 2020/0377535 A1 | 12/2020 | Anderson et al. |
| 2021/0047271 A1 | 2/2021 | Hadida Ruah et al. |
| 2021/0052610 A1 | 2/2021 | Agarwal et al. |
| 2021/0094906 A1 | 4/2021 | Ahmad et al. |
| 2021/0155643 A1 | 5/2021 | Jiang et al. |
| 2021/0198241 A1 | 7/2021 | Durrant |
| 2022/0110923 A1 | 4/2022 | Thomson |
| 2023/0009251 A1 | 1/2023 | Beck et al. |

FOREIGN PATENT DOCUMENTS

| | | |
|---|---|---|
| CN | 101855210 | 10/2010 |
| CN | 101883758 | 11/2010 |
| CN | 102264722 | 11/2011 |
| CN | 105906591 A | 8/2016 |
| CN | 105985330 A | 10/2016 |
| CN | 106518766 A | 3/2017 |
| CN | 106518767 A | 3/2017 |
| CN | 107033149 A | 8/2017 |
| CN | 108689942 A | 10/2018 |
| CN | 109320509 A | 2/2019 |
| CN | 109384712 A | 2/2019 |
| CN | 109553608 A | 4/2019 |
| CN | 112409331 A | 2/2021 |
| EP | 1336602 A1 | 8/2003 |
| EP | 1882475 A1 | 1/2008 |
| EP | 3023816 A1 | 5/2016 |
| FR | 3030242 A1 | 12/2014 |
| GB | 2300856 A | 11/1996 |
| IT | 1992RM0025 A1 | 7/1993 |
| JP | S 62198663 A | 9/1987 |
| JP | S 62198664 A | 9/1987 |
| JP | H 05107574 A | 4/1993 |
| JP | H 10213820 A | 8/1998 |
| JP | 2003/034671 A | 2/2003 |
| JP | 2005/145858 A | 6/2005 |
| JP | 2005/531501 | 10/2005 |
| JP | 2009/051827 A | 3/2009 |
| JP | 2009/051828 A | 3/2009 |
| JP | 2009/242540 A | 10/2009 |
| JP | 2010/059131 A | 3/2010 |
| JP | 2011/500599 | 1/2011 |
| JP | 2011/500600 | 1/2011 |
| JP | 2012/167027 A | 9/2012 |
| JP | 2013/195630 A | 9/2013 |
| JP | 2013/254084 A | 12/2013 |
| JP | 2014/232188 A | 12/2014 |
| JP | 2016/079098 A | 5/2016 |
| JP | WO 2017/090743 A1 | 6/2017 |
| KR | 201900076339 A | 7/2019 |
| KR | 10-2092838 B1 | 3/2020 |
| KR | 202000065978 A | 6/2020 |
| RU | 2010/118467 | 11/2011 |
| RU | 2010/118481 | 11/2011 |
| WO | WO 1991/000858 | 1/1991 |
| WO | WO 1992/001696 | 2/1992 |
| WO | WO 1993/000313 | 1/1993 |
| WO | WO 1993/017007 | 9/1993 |
| WO | WO 1994/008962 | 4/1994 |
| WO | WO 1997/014419 | 4/1997 |
| WO | WO 1997/027852 | 8/1997 |
| WO | WO 1998/016186 | 4/1998 |
| WO | WO 1998/018466 | 5/1998 |
| WO | WO 1999/026941 | 6/1999 |

(56) References Cited

FOREIGN PATENT DOCUMENTS

| | | |
|---|---|---|
| WO | WO 2000/018725 | 4/2000 |
| WO | WO 2000/025789 | 5/2000 |
| WO | WO 2000/064876 | 11/2000 |
| WO | WO 2001/012183 | 2/2001 |
| WO | WO 2001/019788 | 3/2001 |
| WO | WO 2001/019798 | 3/2001 |
| WO | WO 2001/030795 | 5/2001 |
| WO | WO 2001/064642 | 9/2001 |
| WO | WO 2001/064643 | 9/2001 |
| WO | WO 2001/066098 | 9/2001 |
| WO | WO 2002/020492 | 3/2002 |
| WO | WO 2002/036553 | 5/2002 |
| WO | WO 2002/051831 | 7/2002 |
| WO | WO 2002/055012 | 7/2002 |
| WO | WO 2002/060905 | 8/2002 |
| WO | WO 2002/070483 | 9/2002 |
| WO | WO 2002/083628 | 10/2002 |
| WO | WO 2003/000245 | 1/2003 |
| WO | WO 2003/026652 | 4/2003 |
| WO | WO 2003/037871 | 5/2003 |
| WO | WO 2003/045921 | 6/2003 |
| WO | WO 2003/048081 | 6/2003 |
| WO | WO 2003/048158 | 6/2003 |
| WO | WO 2003/062221 | 7/2003 |
| WO | WO 2003/068230 | 8/2003 |
| WO | WO 2003/070193 | 8/2003 |
| WO | WO 2003/070912 | 8/2003 |
| WO | WO 2003/072099 | 9/2003 |
| WO | WO 2003/072757 | 9/2003 |
| WO | WO 2004/041277 | 5/2004 |
| WO | WO 2004/062601 | 7/2004 |
| WO | WO 2004/063151 | 7/2004 |
| WO | WO 2004/083174 | 9/2004 |
| WO | WO 2004/090154 | 10/2004 |
| WO | WO 2004/091499 | 10/2004 |
| WO | WO 2005/000298 | 1/2005 |
| WO | WO 2005/000300 | 1/2005 |
| WO | WO 2005/000309 | 1/2005 |
| WO | WO 2005/013914 | 2/2005 |
| WO | WO 2005/019236 | 3/2005 |
| WO | WO 2005/019237 | 3/2005 |
| WO | WO 2005/021568 | 3/2005 |
| WO | WO 2005/044797 | 5/2005 |
| WO | WO 2005/049019 | 6/2005 |
| WO | WO 2005/051393 | 6/2005 |
| WO | WO 2006/011050 A2 | 2/2006 |
| WO | WO 2006/017896 | 2/2006 |
| WO | WO 2006/028904 | 3/2006 |
| WO | WO 2006/094347 | 9/2006 |
| WO | WO 2006/113615 | 10/2006 |
| WO | WO 2006/122072 | 11/2006 |
| WO | WO 2006/123257 | 11/2006 |
| WO | WO 2006/124780 | 11/2006 |
| WO | WO 2006/127329 | 11/2006 |
| WO | WO 2006/130493 | 12/2006 |
| WO | WO 2007/024021 | 3/2007 |
| WO | WO 2007/052843 | 5/2007 |
| WO | WO 2007/081597 A2 | 7/2007 |
| WO | WO 2007/081966 | 7/2007 |
| WO | WO 2007/088999 | 8/2007 |
| WO | WO 2007/095187 | 8/2007 |
| WO | WO 2007/097940 | 8/2007 |
| WO | WO 2007/106525 | 9/2007 |
| WO | WO 2007/109105 | 9/2007 |
| WO | WO 2007/120647 | 10/2007 |
| WO | WO 2007/146712 | 12/2007 |
| WO | WO 2008/001195 | 1/2008 |
| WO | WO 2008/005542 | 1/2008 |
| WO | WO 2008/014291 | 1/2008 |
| WO | WO 2008/018129 | 2/2008 |
| WO | WO 2008/019124 | 2/2008 |
| WO | WO 2008/033743 | 3/2008 |
| WO | WO 2008/033746 | 3/2008 |
| WO | WO 2008/065068 | 6/2008 |
| WO | WO 2008/073670 | 6/2008 |
| WO | WO 2008/094507 | 8/2008 |
| WO | WO 2008/115262 | 9/2008 |
| WO | WO 2008/115263 | 9/2008 |
| WO | WO 2008/133753 | 11/2008 |
| WO | WO 2008/135826 A2 | 11/2008 |
| WO | WO 2008/156783 | 12/2008 |
| WO | WO 2009/000413 | 12/2008 |
| WO | WO 2009/012482 | 1/2009 |
| WO | WO 2009/036012 | 3/2009 |
| WO | WO 2009/036051 | 3/2009 |
| WO | WO 2009/036066 | 3/2009 |
| WO | WO 2009/041521 A1 | 4/2009 |
| WO | WO 2009/047798 | 4/2009 |
| WO | WO 2009/049181 | 4/2009 |
| WO | WO 2009/049183 | 4/2009 |
| WO | WO 2009/056693 | 5/2009 |
| WO | WO 2009/069132 | 6/2009 |
| WO | WO 2009/076593 | 6/2009 |
| WO | WO 2009/091941 | 7/2009 |
| WO | WO 2009/114470 | 9/2009 |
| WO | WO 2009/126691 | 10/2009 |
| WO | WO 2010/003048 | 1/2010 |
| WO | WO 2010/027512 | 3/2010 |
| WO | WO 2010/031713 | 3/2010 |
| WO | WO 2010/037127 | 4/2010 |
| WO | WO 2010/037129 | 4/2010 |
| WO | WO 2010/048149 | 4/2010 |
| WO | WO 2010/051926 | 5/2010 |
| WO | WO 2010/060952 | 6/2010 |
| WO | WO 2010/063996 | 6/2010 |
| WO | WO 2010/066028 | 6/2010 |
| WO | WO 2010/072607 | 7/2010 |
| WO | WO 2010/075282 | 7/2010 |
| WO | WO 2010/107739 | 9/2010 |
| WO | WO 2010/115736 | 10/2010 |
| WO | WO 2010/129323 | 11/2010 |
| WO | WO 2010/129864 A2 | 11/2010 |
| WO | WO 2010/137351 | 12/2010 |
| WO | WO 2010/138575 | 12/2010 |
| WO | WO 2010/138576 | 12/2010 |
| WO | WO 2011/005860 | 1/2011 |
| WO | WO 2011/026240 A1 | 3/2011 |
| WO | WO 2011/032169 | 3/2011 |
| WO | WO 2011/037731 | 3/2011 |
| WO | WO 2011/047320 | 4/2011 |
| WO | WO 2011/098398 | 8/2011 |
| WO | WO 2011/103468 | 8/2011 |
| WO | WO 2011/109059 | 9/2011 |
| WO | WO 2011/140425 A1 | 11/2011 |
| WO | WO 2011/141909 | 11/2011 |
| WO | WO 2011/151619 | 12/2011 |
| WO | WO 2012/007409 | 1/2012 |
| WO | WO 2012/016133 | 2/2012 |
| WO | WO 2012/017020 | 2/2012 |
| WO | WO 2012/020725 | 2/2012 |
| WO | WO 2012/048222 A1 | 4/2012 |
| WO | WO 2012/049460 | 4/2012 |
| WO | WO 2012/052540 | 4/2012 |
| WO | WO 2012/056113 | 5/2012 |
| WO | WO 2012/069856 | 5/2012 |
| WO | WO 2012/073138 | 6/2012 |
| WO | WO 2012/080727 | 6/2012 |
| WO | WO 2012/080729 | 6/2012 |
| WO | WO 2012/094328 | 7/2012 |
| WO | WO 2012/097330 | 7/2012 |
| WO | WO 2012/106499 A1 | 8/2012 |
| WO | WO 2012/106534 | 8/2012 |
| WO | WO 2012/112743 A1 | 8/2012 |
| WO | WO 2012/125613 A1 | 9/2012 |
| WO | WO 2012/125797 A1 | 9/2012 |
| WO | WO 2012/129562 | 9/2012 |
| WO | WO 2012116440 A1 | 9/2012 |
| WO | WO 2012/155066 | 11/2012 |
| WO | WO 2012/166951 | 12/2012 |
| WO | WO 2012/170371 | 12/2012 |
| WO | WO 2012/178123 | 12/2012 |
| WO | WO 2013/004995 | 1/2013 |
| WO | WO 2013/005057 | 1/2013 |
| WO | WO 2013/022740 | 2/2013 |

(56) References Cited

FOREIGN PATENT DOCUMENTS

| | | |
|---|---|---|
| WO | WO 2013/040059 | 3/2013 |
| WO | WO 2013/049725 | 4/2013 |
| WO | WO 2013/061205 A2 | 5/2013 |
| WO | WO 2013/109521 A1 | 7/2013 |
| WO | WO 2013/114250 A1 | 8/2013 |
| WO | WO 2013/117707 | 8/2013 |
| WO | WO 2013/124040 | 8/2013 |
| WO | WO 2013/131018 A1 | 9/2013 |
| WO | WO 2013/132376 | 9/2013 |
| WO | WO 2013/132991 | 9/2013 |
| WO | WO 2013/151975 | 10/2013 |
| WO | WO 2013/178570 | 12/2013 |
| WO | WO 2013/188881 | 12/2013 |
| WO | WO 2014/003153 | 1/2014 |
| WO | WO 2014/005125 | 1/2014 |
| WO | WO 2014/014874 | 1/2014 |
| WO | WO 2014/015523 A1 | 1/2014 |
| WO | WO 2014/015675 A1 | 1/2014 |
| WO | WO 2014/018891 | 1/2014 |
| WO | WO 2014/020152 | 2/2014 |
| WO | WO 2014/039595 | 3/2014 |
| WO | WO 2014/045156 | 3/2014 |
| WO | WO 2014/047110 | 3/2014 |
| WO | WO 2014/075393 | 5/2014 |
| WO | WO 2014/078479 | 5/2014 |
| WO | WO 2014/088920 | 6/2014 |
| WO | WO 2014/108407 | 7/2014 |
| WO | WO 2014/118133 | 8/2014 |
| WO | WO 2014/120808 A1 | 8/2014 |
| WO | WO 2014/120815 A1 | 8/2014 |
| WO | WO 2014/120820 A1 | 8/2014 |
| WO | WO 2014/130856 | 8/2014 |
| WO | WO 2014/134127 | 9/2014 |
| WO | WO 2014/151958 | 9/2014 |
| WO | WO 2014/179785 | 11/2014 |
| WO | WO 2014/200078 A1 | 12/2014 |
| WO | WO 2014/202763 | 12/2014 |
| WO | WO 2015/003723 | 1/2015 |
| WO | WO 2015/003816 | 1/2015 |
| WO | WO 2015/003991 | 1/2015 |
| WO | WO 2015/010065 | 1/2015 |
| WO | WO 2015/011284 | 1/2015 |
| WO | WO 2015/035051 | 3/2015 |
| WO | WO 2015/038596 | 3/2015 |
| WO | WO 2015/049651 | 4/2015 |
| WO | WO 2015/051173 | 4/2015 |
| WO | WO 2015/054337 | 4/2015 |
| WO | WO 2014/120808 A9 | 5/2015 |
| WO | WO 2015/084796 | 6/2015 |
| WO | WO 2015/085238 | 6/2015 |
| WO | WO 2015/089361 A1 | 6/2015 |
| WO | WO 2015/089511 | 6/2015 |
| WO | WO 2015/103317 | 7/2015 |
| WO | WO 2015/157559 A2 | 10/2015 |
| WO | WO 2015/162244 | 10/2015 |
| WO | WO 2015/196118 | 12/2015 |
| WO | WO 2015/196128 | 12/2015 |
| WO | WO 2015/196130 | 12/2015 |
| WO | WO 2016/003929 | 1/2016 |
| WO | WO 2016/007837 | 1/2016 |
| WO | WO 2016/011209 A1 | 1/2016 |
| WO | WO 2016/012457 | 1/2016 |
| WO | WO 2016/029146 | 2/2016 |
| WO | WO 2016/040449 | 3/2016 |
| WO | WO 2016/040505 | 3/2016 |
| WO | WO 2016/073633 | 5/2016 |
| WO | WO 2016/094682 | 6/2016 |
| WO | WO 2016/100385 | 6/2016 |
| WO | WO 2016/145142 | 9/2016 |
| WO | WO 2016/170010 | 10/2016 |
| WO | WO 2016/172631 | 10/2016 |
| WO | WO 2016/196593 | 12/2016 |
| WO | WO 2016/198908 | 12/2016 |
| WO | WO 2017/001924 A1 | 1/2017 |
| WO | WO 2017/011371 | 1/2017 |
| WO | WO 2017/051319 | 3/2017 |
| WO | WO 2017/059385 A1 | 4/2017 |
| WO | WO 2017/059446 | 4/2017 |
| WO | WO 2017/062751 | 4/2017 |
| WO | WO 2017/066705 | 4/2017 |
| WO | WO 2017/066781 | 4/2017 |
| WO | WO 2017/066782 | 4/2017 |
| WO | WO 2017/066791 | 4/2017 |
| WO | WO 2017/090743 A1 | 6/2017 |
| WO | WO 2017/103615 | 6/2017 |
| WO | WO 2017/158381 | 9/2017 |
| WO | WO 2017/161028 | 9/2017 |
| WO | WO 2017/173274 | 10/2017 |
| WO | WO 2017/223260 | 12/2017 |
| WO | WO 2018/014819 | 1/2018 |
| WO | WO 2018/045106 | 3/2018 |
| WO | WO 2018/055235 | 3/2018 |
| WO | WO 2018/060110 | 4/2018 |
| WO | WO 2018/064119 | 4/2018 |
| WO | WO 2018/067636 | 4/2018 |
| WO | WO 2018/138358 | 8/2018 |
| WO | WO 2018/161033 | 9/2018 |
| WO | WO 2018/177297 | 10/2018 |
| WO | WO 2018/183782 A1 | 10/2018 |
| WO | WO 2018/183871 A1 | 10/2018 |
| WO | WO 2018/183923 | 10/2018 |
| WO | WO 2018/186365 | 10/2018 |
| WO | WO 2018/191146 | 10/2018 |
| WO | WO 2018/195439 | 10/2018 |
| WO | WO 2018/195450 | 10/2018 |
| WO | WO 2018/213426 A1 | 11/2018 |
| WO | WO 2018/237194 | 12/2018 |
| WO | WO 2019/014352 A1 | 1/2019 |
| WO | WO 2019/036562 | 2/2019 |
| WO | WO 2019/036657 | 2/2019 |
| WO | WO 2019/079596 | 4/2019 |
| WO | WO 2019/079607 | 4/2019 |
| WO | WO 2019/084271 | 5/2019 |
| WO | WO 2019/086579 | 5/2019 |
| WO | WO 2019/094732 | 5/2019 |
| WO | WO 2019/097515 A1 | 5/2019 |
| WO | WO 2019/122420 | 6/2019 |
| WO | WO 2019/137201 | 7/2019 |
| WO | WO 2019/154953 | 8/2019 |
| WO | WO 2019/154956 | 8/2019 |
| WO | WO 2019/195439 | 10/2019 |
| WO | WO 2019/206925 | 10/2019 |
| WO | WO 2019/207081 | 10/2019 |
| WO | WO 2019/222414 | 11/2019 |
| WO | WO 2019/246343 | 12/2019 |
| WO | WO 2020/014243 A1 | 1/2020 |
| WO | WO 2020/014246 A1 | 1/2020 |
| WO | WO 2020/025030 | 2/2020 |
| WO | WO 2020/033413 | 2/2020 |
| WO | WO 2020/034058 | 2/2020 |
| WO | WO 2020/034062 | 2/2020 |
| WO | WO 2020/051207 | 3/2020 |
| WO | WO 2020/069330 | 4/2020 |
| WO | WO 2020/072835 A1 | 4/2020 |
| WO | WO 2020/073949 | 4/2020 |
| WO | WO 2020/081572 | 4/2020 |
| WO | WO 2012/082187 A1 | 5/2020 |
| WO | WO 2020/092667 A1 | 5/2020 |
| WO | WO 2020/118036 | 6/2020 |
| WO | WO 2020/123675 | 6/2020 |
| WO | WO 2020/146612 A1 | 7/2020 |
| WO | WO 2020/146682 A1 | 7/2020 |
| WO | WO 2020/147739 | 7/2020 |
| WO | WO 2020/152079 | 7/2020 |
| WO | WO 2020/159576 | 8/2020 |
| WO | WO 2020/160225 | 8/2020 |
| WO | WO 2020/191227 A1 | 9/2020 |
| WO | WO 2020/191501 | 10/2020 |
| WO | WO 2020/221677 | 11/2020 |
| WO | WO 2020/228922 | 11/2020 |
| WO | WO 2020/230134 A1 | 11/2020 |
| WO | WO 2020/230136 A1 | 11/2020 |
| WO | WO 2020/251974 | 12/2020 |
| WO | WO 2020/254493 A1 | 12/2020 |

(56) References Cited

FOREIGN PATENT DOCUMENTS

| | | |
|---|---|---|
| WO | WO 2021/001739 A1 | 1/2021 |
| WO | WO 2021/074357 A1 | 4/2021 |
| WO | WO 2021/113627 A1 | 6/2021 |
| WO | WO 2021/125797 A1 | 6/2021 |
| WO | WO 2021/229571 A1 | 11/2021 |
| WO | WO 2021/239117 A1 | 12/2021 |
| WO | WO 2002/008748 A3 | 1/2022 |
| WO | WO 2022/023772 A1 | 2/2022 |
| WO | WO 2022/063902 A1 | 3/2022 |
| WO | WO 2022/070048 A1 | 4/2022 |
| WO | WO 2022/086986 A1 | 4/2022 |

OTHER PUBLICATIONS

CAS Registry Compounds, database entry dates no later than Oct. 2017.

CAS Registry Compounds, database entry dates no later than Sep. 2018.

Catterall, W. A., Goldin, A. L., and Waxman, S. G., International Union of Pharmacology. XLVII. "Nomenclature and structure-function relationships of voltage-gated sodium channels." *Pharmacol Rev* 57 (4), p. 397 (2005).

Chahine, M., Chatelier, A., Babich, O., and Krupp, J. J., "Voltage-gated sodium channels in neurological disorders." *CNS Neurol Disord Drug Targets* 7 (2), p. 144-58 (2008).

Choi, J.S. and S.G. Waxman, "Physiological interactions between NaV1.7 and NaV1.8 sodium channels: a computer simulation study." *J Neurophysiol.* 106(6): p. 3173-84.

Coward, K., et al., "Immunolocalization of SNS/PN3 and NaN/SNS2 sodium channels in human pain states." *Pain*, 2000. 85(1-2): p. 41-50.

Dieleman, J.P., et al., "Incidence rates and treatment of neuropathic pain conditions in the general population." *Pain*, 2008. 137(3): p. 681-8.

Ding, Qingjie et al., "Discovery of RG7388, a Potent and Selective p53-MDM2 Inhibitor in Clinical Development," J. Med. Chem., 56(14), pp. 5979-5983 (2013).

Dong, X.W., et al., "Small interfering RNA-mediated selective knockdown of Na(V)1.8 tetrodotoxin-resistant sodium channel reverses mechanical allodynia in neuropathic rats." *Neuroscience*, 2007. 146(2): p. 812-21.

England, S., "Voltage-gated sodium channels: the search for subtype-selective analgesics." *Expert Opin Investig Drugs* 17 (12), p. 1849-64 (2008).

Huang, H.L., et al., "Proteomic profiling of neuromas reveals alterations in protein composition and local protein synthesis in hyper-excitable nerves." *Mol Pain*, 2008. 4: p. 33.

International Search Report and Written Opinion for PCT/US2020/063290, dated Feb. 2, 2021, 13 pgs.

Jarvis, M.F., et al., "A-803467, a potent and selective Na$_v$1.8 sodium channel blocker, attenuates neuropathic and inflammatory pain in the rat." *Proc Natl Acad Sci. U S A*, May 15, 2007. 104(20): p. 8520-5.

Joshi, S.K., et al., "Involvement of the TTX-resistant sodium channel Nav1.8 in inflammatory and neuropathic, but not post-operative, pain states." Pain, 2006. 123(1-2): pp. 75-82.

Kato, Tetsuzo et al., "Antitumor activity of compounds derived from diketene and their related compounds," Pharm. Inst., 97(6), pp. 676-684 (1977).

Krafte, D. S. and Bannon, A. W.,"Sodium channels and nociception: recent concepts and therapeutic opportunities." *Curr Opin Pharmacol* 8 (1), p. 50-56 (2008).

Lai, J., et al., "Inhibition of neuropathic pain by decreased expression of the tetrodotoxin-resistant sodium channel, NaV1.8." *Pain*, 2002. 95(1-2): p. 143-52.

Liu, Jianzhong et al., "Pd(II)—Catalyzed Pyridine N-Oxides Directed Arylation of Unactivated Csp3-H Bonds," Am. Chem. Society, 80(9), pp. 4618-4626 (2015).

Qiu, F., et al.,"Increased expression of tetrodotoxin-resistant sodium channels NaV1.8 and NaV1.9 within dorsal root ganglia in a rat model of bone cancer pain." *Neurosci. Lett.* 512(2): p. 61-6).

Renganathan, M., T.R. Cummins, and S.G. Waxman, "Contribution of Na(V)1.8 sodium channels to action potential electrogenesis in DRG neurons." *J Neurophysiol.*, 2001. 86(2): p. 629-40.

Roza, C., et al., "The tetrodotoxin-resistant Na+ channel NaV1.8 is essential for the expression of spontaneous activity in damaged sensory axons of mice." *J Physiol.*, 2003. 550(Pt 3): p. 921-6).

Ruangsri, S., et al., "Relationship of axonal voltage-gated sodium channel 1.8 (NaV1.8) mRNA accumulation to sciatic nerve injury-induced painful neuropathy in rats." *J Biol Chem.* 286(46): p. 39836-47).

Rush, A.M. and T.R. Cummins, "Painful Research: Identification of a Small-Molecule Inhibitor that Selectively Targets NaV1.8 Sodium Channels." *Mol Interv*, 2007. 7(4): p. 192-5).

Rush, A.M., et al., "A single sodium channel mutation produces hyper- or hypoexcitability in different types of neurons." *Proc Natl Acad Sci USA*, 2006. 103(21): p. 8245-50).

Soderpalm, B., "Anticonvulsants: aspects of their mechanisms of action." *Eur J Pain* 6 Suppl A, p. 3-9 (2002).

Strickland, I.T., et al., "Changes in the expression of NaV1.7, NaV1.8 and NaV1.9 in a distinct population of dorsal root ganglia innervating the rat knee joint in a model of chronic inflammatory joint pain." *Eur J Pain*, 2008. 12(5): p. 564-72.

Sun, W., et al., "Reduced conduction failure of the main axon of polymodal nociceptive C-fibres contributes to painful diabetic neuropathy in rats." Brain. 135(Pt 2): p. 359-75.

Wang et al., "NHC-Catalyzed Asymmetric Synthesis of Functionalized Succinimides from Enals and α-Ketoamides," Chem. A EP Jour. 21(22), (2015), pp. 8033-8037.

Wang, G. K., Mitchell, J., and Wang, S. Y., "Block of persistent late Na+ currents by antidepressant sertraline and paroxetine." *J Membr Biol* 222 (2), p. 79-90 (2008).

Yiangou, Y., et al., "SNS/PN3 and SNS2/NaN sodium channel-like immunoreactivity in human adult and neonate injured sensory nerves." *FEBS Lett*, 2000. 467(2-3): p. 249-52.

"Instruction Manual For CHIRALPAK AS-H," Chiral Technologies, Inc., Daicel Group (Jul. 2013), 4 pages;

"Regis' Chiral Stationary Phase, Pirkle-Type, Polysaccharide-Based, and Crown Ether Phases," Regis Technologies, Inc., (Oct. 2008), 4 pages.

Berge S.M., et al. "Pharmaceutical Salts," *J. Pharmaceutical Sciences*, 66, (Jan. 1977), pp. 1-19.

Fornwald, J.A. et al., "Gene Expression in Mammalian Cells Using BacMam, a Modified Baculovirus System," *Methods in Molecular Biology*, 1350, (2016), pp. 95-116.

Gonzalez, J.E. and Tsien, R.Y. Improved indicators of cell membrane potential that use fluorescence resonance energy transfer, *Chem. Biol.* 4, (1997), pp. 269-277.

Gonzalez, J.E. and Tsien, R.Y. "Voltage Sensing by Fluorescence Resonance Energy Transfer in Single Cells," *Biophys. J.* 69, (Oct. 1995), pp. 1272-1280.

Harbeson, S.L. and R. D. Tung, "Deuterium In Drug Discovery and Development," *Ann. Rep. Med. Chem.*, 46, (2011), pp. 403-417.

Huang, C.J. et al. "Characterization of voltage-gated sodium channel blockers by electrical stimulation and fluorescence detection of membrane potential," *Nature Biotech.* 24, 4, (Apr. 2006), pp. 439-446.

Sheldrick, G.M., "A Short History of SHELX.," *Acta Crystallographica Section A*, A64, (2008), pp. 112-122. http://dx.doi.org/10.1107/S0108767307043930.

\* cited by examiner

SUBSTITUTED TETRAHYDROFURANS AS MODULATORS OF SODIUM CHANNELS

CROSS-REFERENCE TO RELATED APPLICATIONS

This application claims the benefit of U.S. Provisional Application No. 62/944,869, filed Dec. 6, 2019, which is incorporated by reference in its entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post-herpetic neuropathy, diabetic neuropathy, and drug-induced neuropathy. Discrete nerve injury indications include post-amputation pain, post-surgical nerve injury pain, and nerve entrapment injuries like neuropathic back pain.

Voltage-gated sodium channels ($Na_Vs$) are involved in pain signaling. $Na_Vs$ are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_Vs$ in pain sensation (Rush, A. M. and T. R. Cummins, *Painful Research: Identification of a Small-Molecule Inhibitor that Selectively Targets $Na_V1.8$ Sodium Channels*. Mol. Interv., 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). $Na_Vs$ mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, Mass., 2001)). Because of the role $Na_Vs$ play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anti-convulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_Vs$ form a subfamily of the voltage-gated ion channel super-family and comprises 9 isoforms, designated $Na_V1.1$-$Na_V1.9$. The tissue localizations of the nine isoforms vary. $Na_V1.4$ is the primary sodium channel of skeletal muscle, and $Na_V1.5$ is primary sodium channel of cardiac myocytes. $Na_Vs$ 1.7, 1.8 and 1.9 are primarily localized to the peripheral nervous system, while $Na_Vs$ 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V1.8$ channels were identified as likely targets for analgesia (Akopian, A. N., U. Sivilotti, and J. N. Wood, A tetrodotoxin-resistant voltage-gated sodium channel expressed by sensory neurons. *Nature*, 1996. 379 (6562): p. 257-62). Since then, $Na_V1.8$ has been shown to be a carrier of the sodium current that maintains action potential firing in small dorsal root ganglia (DRG) neurons (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J. Neurosci.*, 2002. 22(23): p. 10277-90). $Na_V1.8$ is involved in spontaneous firing in damaged neurons, like those that drive neuropathic pain (Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc. Natl. Acad. Sci. USA*, 2007. 104(20): p. 8520-5; Joshi, S. K., et al., Involvement of the TTX-resistant sodium channel $Na_V1.8$ in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na_V1.8$ tetrodotoxin-resistant sodium channel reverses mechanical allodynia in neuropathic rats. *Neuroscience*, 2007. 146(2): p. 812-21; Huang, H. L., et al., Proteomic profiling of neuromas reveals alterations in protein composition and local protein synthesis in hyper-excitable nerves. *Mol. Pain*, 2008. 4: p. 33; Black, J. A., et al., Multiple sodium channel isoforms and mitogen-activated protein kinases are present in painful human neuromas. *Ann. Neurol.*, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett.*, 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J. Biol. Chem.*

286(46): p. 39836-47). The small DRG neurons where Na$_V$1.8 is expressed include the nociceptors involved in pain signaling. Na$_V$1.8 mediates large amplitude action potentials in small neurons of the dorsal root ganglia (Blair, N. T. and B. P. Bean, Roles of tetrodotoxin (TTX)-sensitive Na$^+$ current, TTX-resistant Na$^+$ current, and Ca$^{2+}$ current in the action potentials of nociceptive sensory neurons. *J. Neurosci.*, 2002. 22(23): p. 10277-90). Na$_V$1.8 is necessary for rapid repetitive action potentials in nociceptors, and for spontaneous activity of damaged neurons. (Choi, J. S. and S. G. Waxman, Physiological interactions between Na$_V$1.7 and Na$_V$1.8 sodium channels: a computer simulation study. *J. Neurophysiol.* 106(6): p. 3173-84; Renganathan, M., T. R. Cummins, and S. G. Waxman, Contribution of Na(v)1.8 sodium channels to action potential electrogenesis in DRG neurons. *J. Neurophysiol.*, 2001. 86(2): p. 629-40; Roza, C., et al., The tetrodotoxin-resistant Na$^+$ channel Na$_V$1.8 is essential for the expression of spontaneous activity in damaged sensory axons of mice. *J. Physiol.*, 2003. 550(Pt 3): p. 921-6). In depolarized or damaged DRG neurons, Na$_V$1.8 appears to be a driver of hyper-excitablility (Rush, A. M., et al., A single sodium channel mutation produces hyper- or hypoexcitability in different types of neurons. *Proc. Natl. Acad. Sci. USA*, 2006. 103(21): p. 8245-50). In some animal pain models, Na$_V$1.8 mRNA expression levels have been shown to increase in the DRG (Sun, W., et al., Reduced conduction failure of the main axon of polymodal nociceptive C-fibers contributes to painful diabetic neuropathy in rats. *Brain*, 135(Pt 2): p. 359-75; Strickland, I. T., et al., Changes in the expression of Na$_V$1.7, Na$_V$1.8 and Na$_V$1.9 in a distinct population of dorsal root ganglia innervating the rat knee joint in a model of chronic inflammatory joint pain. *Eur. J. Pain*, 2008. 12(5): p. 564-72; Qiu, F., et al., Increased expression of tetrodotoxin-resistant sodium channels Na$_V$1.8 and Na$_V$1.9 within dorsal root ganglia in a rat model of bone cancer pain. *Neurosci. Lett.*, 512(2): p. 61-6).

The primary drawback to some known Na$_V$ inhibitors is their poor therapeutic window, and this is likely a consequence of their lack of isoform selectivity. Since Na$_V$1.8 is primarily restricted to the neurons that sense pain, selective Na$_V$1.8 blockers are unlikely to induce the adverse events common to non-selective Na$_V$ blockers. Accordingly, there remains a need to develop additional Na$_V$ channel modulators, preferably those that are highly potent and selective for Na$_V$1.8.

SUMMARY

In one aspect, the invention relates to a compound described herein, or a pharmaceutically acceptable salt thereof.

In another aspect, the invention relates to a pharmaceutical composition comprising the compound, or a pharmaceutically acceptable salt thereof, and one or more pharmaceutically acceptable carriers or vehicles.

In still another aspect, the invention relates to a method of inhibiting a voltage gated sodium channel in a subject by administering the compound, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, and cardiac arrhythmia, by administering the compound, pharmaceutically acceptable salt, or pharmaceutical composition to the subject.

DETAILED DESCRIPTION

Figure 1:
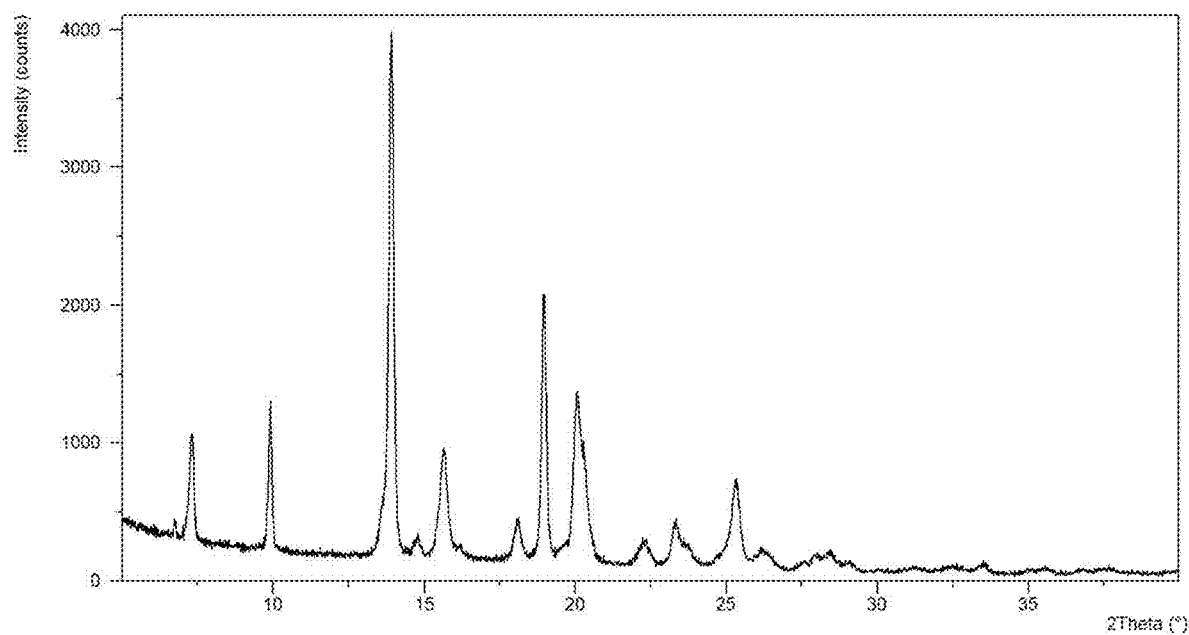
FIG. 1 depicts an XRPD pattern characteristic of Compound 7, Form A.

In one aspect, the invention relates to a compound of formula (I)

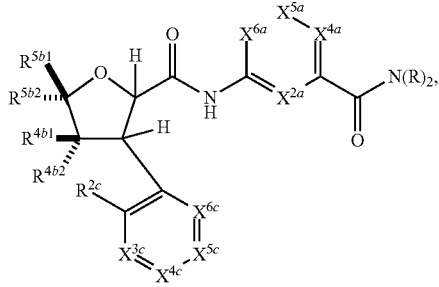

I or a pharmaceutically acceptable salt thereof, wherein:
$X^{2a}$ is N, $N^+$—$O^-$, or C—$R^{2a}$;
$X^{4a}$ is N, $N^+$—$O^-$, or C—$R^{4a}$;
$X^{5a}$ is N, $N^+$—$O^-$, or C—$R^{5a}$;
$X^{6a}$ is N, $N^+$—$O^-$, or C—$R^{6a}$;
each R is independently H or $C_1$-$C_6$ alkyl;
$R^{2a}$, $R^{4a}$, $R^{5a}$, and $R^{6a}$ are each independently H, halo, $C_1$-$C_6$ alkyl, or $C_1$-$C_6$ haloalkyl;
$R^{4b1}$ and $R^{4b2}$ are each independently H, $C_1$-$C_6$ alkyl, $C_3$-$C_6$ cycloalkyl, or $C_1$-$C_6$ haloalkyl;
$R^{5b1}$ and $R^{5b2}$ are each independently H, $C_4$-$C_6$ alkyl, $C_3$-$C_6$ cycloalkyl, or $C_1$-$C_6$ haloalkyl;
$X^{3c}$ is N or C—$R^{3c}$;
$X^{4c}$ is N or C—$R^{4c}$;
$X^{5c}$ is N or C—$R^{5c}$;
$X^{6c}$ is N or C—$R^{6c}$;
$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;
$L^1$ is a bond or O;
$L^2$ is a bond or $C_1$-$C_6$ alkylene;
$R^{3c}$ is H, halo, $C_1$-$C_6$ alkyl, or $C_1$-$C_6$ haloalkyl;
$R^{4c}$ is H, halo, $C_1$-$C_6$ alkyl, or $C_1$-$C_6$ haloalkyl;
$R^{5c}$ is H, halo, $C_1$-$C_6$ alkyl, or $C_1$-$C_6$ haloalkyl; and
$R^{6c}$ is H, halo, $C_1$-$C_6$ alkyl, or $C_1$-$C_6$ haloalkyl;
provided that no more than two of $X^{2a}$, $X^{4a}$, $X^{5a}$, and $X^{6a}$ are N or $N^+$—$O^-$; and
provided that no more than one of $X^{3c}$, $X^{4c}$, $X^{5c}$, and $X^{6c}$ are N.

In some embodiments, the invention relates to a compound of formula (I), or a pharmaceutically acceptable salt thereof, wherein $X^{2a}$ is C—$R^{2a}$; $X^{5a}$ is C—$R^{5a}$; $X^{6a}$ is C—$R^{6a}$; $R^{4b1}$ and $R^{4b2}$ are each independently H, $C_1$-$C_6$ alkyl, or $C_1$-$C_6$ haloalkyl; $R^{5b1}$ and $R^{5b2}$ are each independently H, $C_1$-$C_6$ alkyl, or $C_1$-$C_6$ haloalkyl; $X^{3c}$ is C—$R^{3c}$; $X^{4c}$ is C—$R^{4c}$; $X^{5c}$ is C—$R^{5c}$; $X^{6c}$ is C—$R^{6c}$; and $R^{2c}$ is H, OH, halo, $C_1$-$C_6$ alkyl, $C_1$-$C_6$ haloalkyl, $C_1$-$C_6$ alkoxy, or $C_1$-$C_6$ haloalkoxy.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As used herein, the term "compounds of the invention" refers to the compounds of formulas (I), (I-A), (I-A-1), (I-B), (I-B-1), (I-C), and (I-C-1), and all of the embodiments thereof, as described herein, and to the compounds identified in Table A, Table B, and Table C.

As described herein, the compounds of the invention comprise multiple variable groups (e.g., R, $X^{4a}$, $R^{5b}$, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The chemical structures depicted herein are intended to be understood as they would be understood by one of ordinary skill in the art. For example, with respect to formulas (I), (I-A), (I-B), and (I-C), one of ordinary skill in the art would understand that $X^{5a}$ and $X^{6a}$ are connected by a double bond and that $X^{4c}$ and $X^{5c}$ are connected by a single bond, even though the bonds between these groups may be obscured by the atom labels in the chemical structures. Moreover, one of ordinary skill would understand that a substituent depicted as "$CF_3$" or "$F_3C$" in a chemical structure refers to a trifluoromethyl substituent, regardless of which depiction appears in the chemical structure.

As used herein, the term "halo" means F, Cl, Br or I.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkenyl" refers to a straight or branched hydrocarbon chain radical group consisting solely of carbon and hydrogen atoms, containing one or more carbon-carbon double bonds, and having the specified number of carbon atoms, which is attached to the rest of the molecule by a single bond. For example, a "$C_2$-$C_6$ alkenyl" group is an alkenyl group having between two and six carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond. For example, a "$C_3$-$C_8$ cycloalkyl" group is a cycloalkyl group having between three and eight carbon atoms.

As used herein, the term "alkylene" refers to a divalent, straight or branched hydrocarbon chain radical group consisting solely of carbon and hydrogen atoms, containing no unsaturation, and having the specified number of carbon atoms, which is attached to the rest of the molecule by two single bonds. For example, a "$C_1$-$C_6$ alkylene" group is an alkylene group having between one and six carbon atoms.

As used herein, the term "optionally substituted" refers to a group that is either unsubstituted or substituted with the subsequently identified substituents. For example, a group that is "optionally substituted with 1-2 halo" is either unsubstituted, substituted with 1 halo group, or substituted with 2 halo groups.

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers of the compounds identified by the chemical names and chemical structures provided herein. In addition, single stereoisomers, double bond isomers, conformational isomers, and tautomers as well as mixtures of stereoisomers, double bond isomers, conformational isomers, and tautomers are within the scope of the invention.

As used herein, in any chemical structure or formula, a bold or hashed straight bond ( $\nearrow$ $\cdots$ , respectively) attached to a stereocenter of a compound, such as in

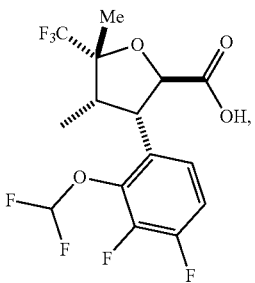

denotes the relative stereochemistry of the stereocenter, relative to other stereocenter(s) to which bold or hashed straight bonds are attached.

As used herein, in any chemical structure or formula, a bold or hashed wedge bond ( $\nearrow$ or $\cdots$ , respectively) attached to a stereocenter of a compound, such as in

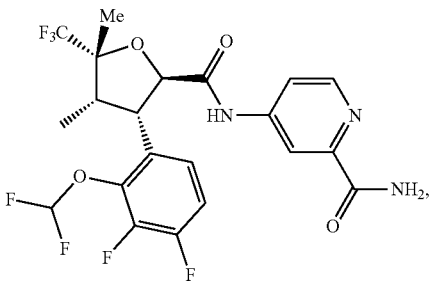

denotes the absolute stereochemistry of the stereocenter, as well as the relative stereochemistry of the stereocenter, relative to other stereocenter(s) to which bold or hashed wedge bonds are attached.

As used herein, the prefix "rac-," when used in connection with a chiral compound, refers to a racemic mixture of the compound. In a compound bearing the "rac-" prefix, the (R)- and (S)-designators in the chemical name reflect the relative stereochemistry of the compound.

As used herein, the prefix "rel-," when used in connection with a chiral compound, refers to a single enantiomer of unknown absolute configuration. In a compound bearing the "rel-" prefix, the (R)- and (S)-designators in the chemical name reflect the relative stereochemistry of the compound, but do not necessarily reflect the absolute stereochemistry of the compound.

As used herein, the term "compound," when referring to the compounds of the invention, refers to a collection of molecules having identical chemical structures, except that there may be isotopic variation among the constituent atoms of the molecules. The term "compound" includes such a collection of molecules without regard to the purity of a given sample containing the collection of molecules. Thus, the term "compound" includes such a collection of molecules in pure form, in a mixture (e.g., solution, suspension, colloid, or pharmaceutical composition, or dosage form) with one or more other substances, or in the form of a hydrate, solvate, or co-crystal.

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^1$H and D. In the Examples, where an atom is designated as "H," no effort was made to enrich that atom in a particular isotope of hydrogen, and therefore a person of ordinary skill in the art would understand that such hydrogen atom likely was present at approximately the natural abundance concentration of hydrogen.

As used herein, "$^1$H" refers to protium. Where an atom in a compound of the invention, or a pharmaceutically acceptable salt thereof, is designated as protium, protium is present at the specified position at at least the natural abundance concentration of protium.

As used herein, "D," "d," and "$^2$H" refer to deuterium.

In some embodiments, the compounds of the invention, and pharmaceutically acceptable salts thereof, include each constituent atom at approximately the natural abundance isotopic composition of the specified element.

In some embodiments, the compounds of the invention, and pharmaceutically acceptable salts thereof, include one or more atoms having an atomic mass or mass number which differs from the atomic mass or mass number of the most abundant isotope of the specified element ("isotope-labeled" compounds and salts). Examples of stable isotopes which are commercially available and suitable for the invention include without limitation isotopes of hydrogen, carbon, nitrogen, oxygen, and phosphorus, for example $^2$H, $^{13}$C, $^{15}$N, $^{18}$O, $^{17}$O, and $^{31}$P, respectively.

The isotope-labeled compounds and salts can be used in a number of beneficial ways, including as medicaments. In some embodiments, the isotope-labeled compounds and salts are deuterium ($^2$H)-labeled. Deuterium ($^2$H)-labeled compounds and salts are therapeutically useful with potential therapeutic advantages over the non-$^2$H-labelled compounds. In general, deuterium ($^2$H)-labeled compounds and salts can have higher metabolic stability as compared to those that are not isotope-labeled owing to the kinetic isotope effect described below. Higher metabolic stability translates directly into an increased in vivo half-life or lower dosages, which under most circumstances would represent a preferred embodiment of the present invention. The isotope-labeled compounds and salts can usually be prepared by carrying out the procedures disclosed in the synthesis schemes, the examples and the related description, replacing a non-isotope-labeled reactant by a readily available isotope-labeled reactant.

The deuterium ($^2$H)-labeled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For example, if deuterium is bonded to a carbon atom at a non-exchangeable position, rate differences of $k_H/k_D=2-7$ are typical. For a further discussion, see S. F. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labeled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (~45% deuterium incorporation). In some embodiments, the isotopic enrichment factor is at least 3500 (~52.5% deuterium incorporation), at least 4000 (~60% deuterium incorporation), at least 4500 (~67.5% deuterium incorporation), at least 5000 (~75% deuterium incorporation), at least 5500 (~82.5% deuterium incorporation), at least 6000 (~90% deuterium incorporation), at least 6333.3 (~95% deuterium incorporation), at least 6466.7 (~97% deuterium incorporation), at least 6600 (~99% deuterium incorporation), or at least 6633.3 (~99.5% deuterium incorporation).

In some embodiments, the invention relates to a compound of formula (I), or a pharmaceutically acceptable salt thereof, wherein each R is H. In other embodiments, each R is independently H or $CH_3$. In other embodiments, $N(R)_2$ is $NHCH_3$.

In some embodiments, the invention relates to a compound of formula (I), or a pharmaceutically acceptable salt thereof, wherein $X^{2a}$ is N. In other embodiments, $X^{2a}$ is $C-R^{2a}$. In some embodiments, $R^{2a}$ is H, D, halo, or $C_1$-$C_6$ alkyl. In other embodiments, $R^{2a}$ is H, D, F, or $CH_3$. In some embodiments, $X^{2a}$ is N, C—H, C-D, C—($C_1$-$C_6$ alkyl), or C-halo. In other embodiments, $X^{2a}$ is N, C—H, C-D, C—$CH_3$, or C—F.

In some embodiments, the invention relates to a compound of formula (I), or a pharmaceutically acceptable salt thereof, wherein $X^{2a}$ is $C-R^{2a}$; and $R^{2a}$ is H.

In some embodiments, the invention relates to a compound of formula (I), or a pharmaceutically acceptable salt thereof, wherein $X^{4a}$ is N. In other embodiments, $X^{4a}$ is $N^+$—$O^-$. In other embodiments, $X^{4a}$ is $C-R^{4a}$. In some embodiments, $R^{4a}$ is halo. In other embodiments, $R^{4a}$ is H or halo. In other embodiments, $R^{4a}$ is H or F. In other embodiments, $X^{4a}$ is C—F. In some embodiments, $X^{4a}$ is N, $N^+$—$O^-$, C—H, or C-halo. In other embodiments, $X^{4a}$ is N, $N^+$—$O^-$, C—H, or C—F.

In some embodiments, the invention relates to a compound of formula (I), or a pharmaceutically acceptable salt thereof, wherein $X^{4a}$ is $C-R^{4a}$; and $R^{4a}$ is halo.

In some embodiments, the invention relates to a compound of formula (I), or a pharmaceutically acceptable salt thereof, wherein $X^{5a}$ is N. In other embodiments, $X^{5a}$ is $C-R^{5a}$. In some embodiments, $R^{5a}$ is H, D, halo, or $C_1$-$C_6$ alkyl. In other embodiments, $R^{5a}$ is H, D, F, or $CH_3$. In some embodiments, $X^{5a}$ is N, C—H, C-D, C—($C_1$-$C_6$ alkyl), or C-halo. In other embodiments, $X^{5a}$ is N, C—H, C-D, C—$CH_3$, or C—F.

In some embodiments, the invention relates to a compound of formula (I), or a pharmaceutically acceptable salt thereof, wherein $X^{5a}$ is $C-R^{5a}$; and $R^{5a}$ is H.

In some embodiments, the invention relates to a compound of formula (I), or a pharmaceutically acceptable salt thereof, wherein $X^{6a}$ is N. In other embodiments, $X^{6a}$ is $C-R^{6a}$. In some embodiments, $R^{6a}$ is H, D, halo, or $C_1$-$C_6$ alkyl. In other embodiments, $R^{6a}$ is H, D, F, or $CH_3$. In some embodiments, $X^{6a}$ is N, C—H, C-D, C—($C_1$-$C_6$ alkyl), or C-halo. In other embodiments, $X^{6a}$ is N, C—H, C-D, C—$CH_3$, or C—F.

In some embodiments, the invention relates to a compound of formula (I), or a pharmaceutically acceptable salt thereof, wherein $X^{6a}$ is $C-R^{6a}$; and $R^{6a}$ is H.

In some embodiments, the invention relates to a compound of formula (I), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H, $C_1$-$C_6$ alkyl, or $C_3$-$C_6$ cycloalkyl. In other embodiments, $R^{4b1}$ and $R^{4b2}$ are each independently H or $CH_3$. In other embodiments, $R^{4b1}$ and $R^{4b2}$ are each independently H, $CH_3$, $CH_2CH_3$, or cyclopropyl. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $C_1$-$C_6$ alkyl, or $C_1$-$C_6$ haloalkyl. In other embodiments, $R^{5b1}$ and $R^{5b2}$ are each independently H, $CH_3$, or $CF_3$. In other embodiments, $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo. In other embodiments, $R^{2c}$ is H. In other embodiments, $R^{2c}$ is $C_1$-$C_6$ alkoxy. In other embodiments. $R^{2c}$ is $C_1$-$C_6$ haloalkoxy. In other embodiments, $R^{2c}$ is -$L^1$-$L^2$-($C_3$-$C_6$ cycloalkyl), wherein said cycloalkyl is optionally substituted with 1-2 halo. In other embodiments, $R^{2c}$ is OH, $OCH_3$, $OCD_3$, $OCH_2CH_3$, or $OCHF_2$. In other embodiments, $R^{2c}$ is H, F, $CH_3$, $CH=CH_2$, OH, $OCH_3$, $OCD_3$, $OCH_2CH_3$, $OCH(CH_3)_2$, $OCHF_2$,

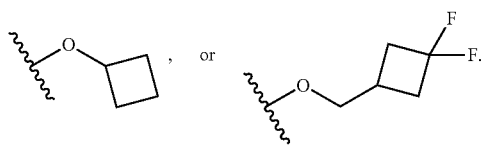 [SMILES: *OC1CCC1 ; *OCC1CC(F)(F)C1]

In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I), or a pharmaceutically acceptable salt thereof, wherein $X^{3c}$ is N. In other embodiments, $X^{3c}$ is C—$R^{3c}$. In other embodiments, $R^{3c}$ is H, halo, $C_4$-$C_6$ alkyl, or $C_1$-$C_6$ haloalkyl. In other embodiments, $R^{3c}$ is H, $CH_3$, $CH_2CH_3$, $CHF_2$, $CF_3$, F, or Cl. In some embodiments, $X^{3c}$ is N, C—H, C—$CH_3$, C—$CH_2CH_3$, C—$CHF_2$, C—$CF_3$, C—F, or C—Cl.

In some embodiments, the invention relates to a compound of formula (I), or a pharmaceutically acceptable salt thereof, wherein $X^{3c}$ is C—$R^{3c}$; and $R^{3c}$ is H, halo, or $C_1$-$C_6$ alkyl. In other embodiments, $R^{3c}$ is halo. In other embodiments. $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I), or a pharmaceutically acceptable salt thereof, wherein $X^{4c}$ is N. In other embodiments, $X^{4c}$ is C—$R^{4c}$. In other embodiments, $R^{4c}$ is H, halo, or $C_1$-$C_6$ haloalkyl. In other embodiments, $R^{4c}$ is H, $CHF_2$, $CF_3$, or F. In some embodiments, $X^{4c}$ is N, C—H, C—$CHF_2$, C—$CF_3$, or C—F.

In some embodiments, the invention relates to a compound of formula (I), or a pharmaceutically acceptable salt thereof, wherein $X^{4c}$ is C—$R^{4c}$; and $R^{4c}$ is halo. In other embodiments, $R^{4c}$ is F.

In some embodiments, the invention relates to a compound of formula (I), or a pharmaceutically acceptable salt thereof, wherein $X^{5c}$ is N. In other embodiments, $X^{5c}$ is C—$R^{5c}$. In other embodiments, $R^{5c}$ is H or halo. In other embodiments, $R^{5c}$ is H, D, or Cl. In some embodiments, $X^{5c}$ is N, C—H, C-D, or C—Cl.

In some embodiments, the invention relates to a compound of formula (I), or a pharmaceutically acceptable salt thereof, wherein $X^{5c}$ is C—$R^{5c}$; and $R^{5c}$ is H.

In some embodiments, the invention relates to a compound of formula (I), or a pharmaceutically acceptable salt thereof, wherein $X^{6c}$ is N. In other embodiments, $X^{6c}$ is C—$R^{6c}$. In other embodiments, $R^{6c}$ is H or halo. In other embodiments, $R^{6c}$ is H or F. In some embodiments, $X^{6c}$ is N, C—H, or C—F.

In some embodiments, the invention relates to a compound of formula (I), or a pharmaceutically acceptable salt thereof, wherein $R^{6c}$ is H.

In some embodiments, the invention relates to a compound of formula (I), or a pharmaceutically acceptable salt thereof, wherein $X^{2a}$ is N, C—H, C-D, C—($C_1$-$C_6$ alkyl), or C-halo; $X^{4a}$ is N, $N^+$—$O^-$, C—H, or C-halo; $X^{5a}$ is N, C—H, C-D, C—($C_1$-$C_6$ alkyl), or C-halo; $X^{6a}$ is N, C—H, C-D, C—($C_1$-$C_6$ alkyl), or C-halo; each R is H or $CH_3$; $R^{4b1}$ and $R^{4b2}$ are each independently H, $C_1$-$C_6$ alkyl, or $C_3$-$C_6$ cycloalkyl; $R^{5b1}$ and $R^{5b2}$ are each independently H, $C_1$-$C_6$ alkyl, or $C_1$-$C_6$ haloalkyl; $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo; $X^{3c}$ is C—$R^{3c}$; $R^{3c}$ is H, halo, $C_1$-$C_6$ alkyl, or $C_1$-$C_6$ haloalkyl; $X^{4c}$ is C—$R^{4c}$; $R^{4c}$ is H, halo, or $C_1$-$C_6$ haloalkyl; $X^{5c}$ is C—$R^{5c}$; $R^{5c}$ is H or halo; $X^{6c}$ is C—$R^{6c}$; and $R^{6c}$ is H or halo.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{2a}$ is N, C—H, C-D, C—$CH_3$, or C—F; $X^{4a}$ is N, $N^+$—$O^-$, C—H, or C—F; $X^{5a}$ is N, C—H, C-D, C—$CH_3$, or C—F; $X^{6a}$ is N, C—H, C-D, C—$CH_3$, or C—F; each R is H or $CH_3$; $R^{4b1}$ and $R^{4b2}$ are each independently H, $CH_3$, $CH_2CH_3$, or cyclopropyl; $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$; $R^{2c}$ is H, F, $CH_3$, $CH=CH_2$, OH, $OCH_3$, $OCD_3$, $OCH_2CH_3$, $OCH(CH_3)_2$, $OCHF_2$,

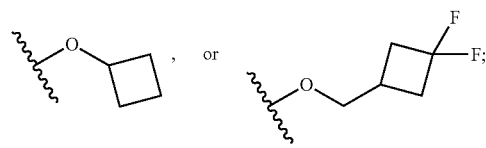 [SMILES: *OC1CCC1 ; *OCC1CC(F)(F)C1]

$X^{3c}$ is N, C—H, C—$CH_3$, C—$CH_2CH_3$, C—$CHF_2$, C—$CF_3$, C—F, or C—Cl; $X^{4c}$ is N, C—H, C—$CHF_2$, C—$CF_3$, or C—F; $X^{5c}$ is N, C—H, C-D, or C—Cl; and $X^{6c}$ is N, C—H, or C—F.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ and $R^{4b2}$ are each independently H or $CH_3$; $R^{5b1}$ and $R^{5b2}$ are each independently H, $CH_3$, or $CF_3$; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is $C_1$-$C_6$ alkyl; $R^{4b2}$ is H; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is H; $R^{4b2}$ is $C_1$-$C_6$ alkyl; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is $C_1$-$C_6$ alkyl; $R^{4b2}$ is H; $R^{5b1}$ is $C_1$-$C_6$ haloalkyl; $R^{5b2}$ is $C_1$-$C_6$ alkyl; $R^{2c}$ is OH, $C_1$-$C_6$, alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $C_1$-$C_6$ haloalkyl; $R^{5b2}$ is $C_1$-$C_6$ alkyl; $R^{4b1}$ is H; $R^{4b2}$ is $C_1$-$C_6$ alkyl; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CH_3$; $R^{5b2}$ is $CF_3$; $R^{4b1}$ is $CH_3$; $R^{4b2}$ is H; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CH_3$; $R^{5b2}$ is $CF_3$; $R^{4b1}$ is H; $R^{4b2}$ is $CH_3$; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CF_3$; $R^{5b2}$ is $CH_3$; $R^{4b1}$ is $CH_3$; $R^{4b2}$ is H; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CF_3$; $R^{5b2}$ is $CH_3$; $R^{4b1}$ is H, and $R^{4b2}$ is $CH_3$; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I) (including any of the foregoing embodiments thereof), i.e., the compound in non-salt form.

In some embodiments, the invention relates to a compound of formula (I-A)

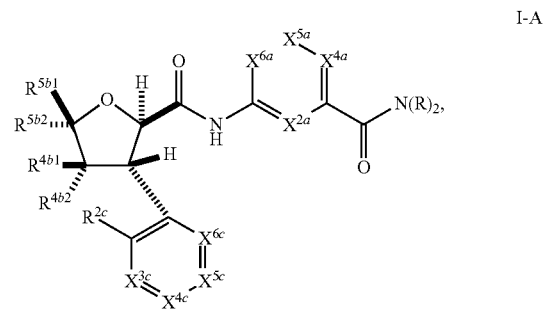

I-A or a pharmaceutically acceptable salt thereof, wherein:
$X^{2a}$ is N, $N^+$—$O^-$, or C—$R^{2a}$;
$X^{4a}$ is N, $N^+$—$O^-$, or C—$R^{4a}$;
$X^{5a}$ is N, $N^+$—$O^-$, or C—$R^{5a}$;
$X^{6a}$ is N, $N^+$—$O^-$, or C—$R^{6a}$;
each R is independently H or $C_1$-$C_6$ alkyl;
$R^{2a}$, $R^{4a}$, $R^{5a}$, and $R^{6a}$ are each independently H, halo, $C_1$-$C_6$ alkyl, or $C_1$-$C_6$ haloalkyl;
$R^{4b1}$ and $R^{4b2}$ are each independently H, $C_1$-$C_6$ alkyl, $C_3$-$C_6$ cycloalkyl, or $C_1$-$C_6$ haloalkyl;
$R^{5b1}$ and $R^{5b2}$ are each independently H, $C_1$-$C_6$ alkyl, $C_3$-$C_6$ cycloalkyl, or $C_1$-$C_6$ haloalkyl;
$X^{3c}$ is N or C—$R^{3c}$;
$X^{4c}$ is N or C—$R^{4c}$;
$X^{5c}$ is N or C—$R^{5c}$;
$X^{6c}$ is N or C—$R^{6c}$;
$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;
$L^1$ is a bond or O;
$L^2$ is a bond or $C_1$-$C_6$ alkylene;
$R^{3c}$ is H, halo, $C_1$-$C_6$ alkyl, or $C_1$-$C_6$ haloalkyl;
$R^{4c}$ is H, halo, $C_1$-$C_6$ alkyl, or $C_1$-$C_6$ haloalkyl;
$R^{5c}$ is H, halo, $C_1$-$C_6$ alkyl, or $C_1$-$C_6$ haloalkyl; and
$R^{6c}$ is H, halo, $C_1$-$C_6$ alkyl, or $C_1$-$C_6$ haloalkyl;
provided that no more than two of $X^{2a}$, $X^{4a}$, $X^{5a}$, and $X^{6a}$ are N or $N^+$—$O^-$; and
provided that no more than one of $X^{3c}$, $X^{4c}$, $X^{5c}$, and $X^{6c}$ are N.

In some embodiments, the invention relates to a compound of formula (I-A), or a pharmaceutically acceptable salt thereof, wherein $X^{2a}$ is C—$R^{2a}$; $X^{5a}$ is C—$R^{5a}$; $X^{6a}$ is C—$R^{6a}$; $R^{4b1}$ and $R^{4b2}$ are each independently H, $C_1$-$C_6$ alkyl, or $C_1$-$C_6$ haloalkyl; $R^{5b1}$ and $R^{5b2}$ are each independently H, $C_1$-$C_6$ alkyl, or $C_1$-$C_6$ haloalkyl; $X^{3c}$ is C—$R^{3c}$; $X^{4c}$ is C—$R^{4c}$; $X^{5c}$ is C—$R^{5c}$; $X^{6c}$ is C—$R^{6c}$; and $R^{2c}$ is H, OH, halo, $C_1$-$C_6$ alkyl, $C_1$-$C_6$ haloalkyl, $C_1$-$C_6$ alkoxy, or $C_1$-$C_6$ haloalkoxy.

In some embodiments, the invention relates to a compound of formula (I-A), or a pharmaceutically acceptable salt thereof, wherein each R is H. In other embodiments, each R is independently H or $CH_3$. In other embodiments, $N(R)_2$ is $NHCH_3$.

In some embodiments, the invention relates to a compound of formula (I-A), or a pharmaceutically acceptable salt thereof, wherein $X^{2a}$ is N. In other embodiments, $X^{2a}$ is C—$R^{2a}$. In some embodiments, $R^{2a}$ is H, D, halo, or $C_1$-$C_6$ alkyl. In other embodiments, $R^{2a}$ is H, D, F, or $CH_3$. In some embodiments, $X^{2a}$ is N, C—H, C-D, C—($C_1$-$C_6$ alkyl), or C-halo. In other embodiments, $X^{2a}$ is N, C—H, C-D, C—$CH_3$, or C—F.

In some embodiments, the invention relates to a compound of formula (I-A), or a pharmaceutically acceptable salt thereof, wherein $X^{2a}$ is C—$R^{2a}$; and $R^{2a}$ is H.

In some embodiments, the invention relates to a compound of formula (I-A), or a pharmaceutically acceptable salt thereof, wherein $X^{4a}$ is N. In other embodiments, $X^{4a}$ is $N^+$—$O^-$. In other embodiments, $X^{4a}$ is C—$R^{4a}$. In some embodiments, $R^{4a}$ is halo. In other embodiments, $R^{4a}$ is H or halo. In other embodiments, $R^{4a}$ is H or F. In other embodiments, $X^{4a}$ is C—F. In some embodiments, $X^{4a}$ is N, $N^+$—$O^-$, C—H, or C-halo. In other embodiments, $X^{4a}$ is N, $N^+$—$O^-$, C—H, or C—F.

In some embodiments, the invention relates to a compound of formula (I-A), or a pharmaceutically acceptable salt thereof, wherein $X^{4a}$ is C—$R^{4a}$; and $R^{4a}$ is halo.

In some embodiments, the invention relates to a compound of formula (I-A), or a pharmaceutically acceptable salt thereof, wherein $X^{5a}$ is N. In other embodiments, $X^{5a}$ is C—$R^{5a}$. In some embodiments, $R^{5a}$ is H, D, halo, or $C_1$-$C_6$ alkyl. In other embodiments, $R^{5a}$ is H, D, F, or $CH_3$. In some embodiments, $X^{5a}$ is N, C—H, C-D, C—($C_1$-$C_6$ alkyl), or C-halo. In other embodiments, $X^{5a}$ is N, C—H, C-D, C—$CH_3$, or C—F.

In some embodiments, the invention relates to a compound of formula (I-A), or a pharmaceutically acceptable salt thereof, wherein $X^{5a}$ is C—$R^{5a}$; and $R^{5a}$ is H.

In some embodiments, the invention relates to a compound of formula (I-A), or a pharmaceutically acceptable salt thereof, wherein $X^{6a}$ is N. In other embodiments, $X^{6a}$ is C—$R^{6a}$. In some embodiments, $R^{6a}$ is H, D, halo, or $C_1$-$C_6$ alkyl. In other embodiments, $R^{6a}$ is H, D, F, or $CH_3$. In some embodiments, $X^{6a}$ is N, C—H, C-D, C—($C_1$-$C_6$ alkyl), or C-halo. In other embodiments, $X^{6a}$ is N, C—H, C-D, C—$CH_3$, or C—F.

In some embodiments, the invention relates to a compound of formula (I-A), or a pharmaceutically acceptable salt thereof, wherein $X^{6a}$ is C—$R^{6a}$; and $R^{6a}$ is H.

In some embodiments, the invention relates to a compound of formula (I-A), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H, $C_1$-$C_6$ alkyl, or $C_3$-$C_6$ cycloalkyl. In other embodiments, $R^{4b1}$ and $R^{4b2}$ are each independently H or $CH_3$. In other embodiments, $R^{4b1}$ and $R^{4b2}$ are each independently H, $CH_3$, $CH_2CH_3$, or cyclopropyl. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I-A), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $C_1$-$C_6$ alkyl, or $C_1$-$C_6$ haloalkyl. In other embodiments, $R^{5b1}$ and $R^{5b2}$ are each independently H, $CH_3$, or $CF_3$. In other embodiments, $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I-A), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo. In other embodiments, $R^{2c}$ is H. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is -$L^1$-$L^2$-($C_3$-$C_6$ cycloalkyl), wherein said cycloalkyl is optionally substituted with 1-2 halo. In other embodiments, $R^{2c}$ is OH, $OCH_3$, $OCD_3$, $OCH_2CH_3$, or $OCHF_2$. In other embodiments, $R^{2c}$ is H, F, $CH_3$, CH=$CH_2$, OH, $OCH_3$, $OCD_3$, $OCH_2CH_3$, OCH$(CH_3)_2$, $OCHF_2$,

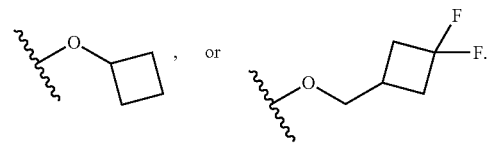 [SMILES: *OC1CCC1 ; *OCC1CC(F)(F)C1]

In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I-A), or a pharmaceutically acceptable salt thereof, wherein $X^{3c}$ is N. In other embodiments, $X^{3c}$ is C—$R^{3c}$. In other embodiments, $R^{3c}$ is H, halo, $C_1$-$C_6$ alkyl, or $C_1$-$C_6$ haloalkyl. In other embodiments, $R^{3c}$ is H, $CH_3$, $CH_2CH_3$, $CHF_2$, $CF_3$, F, or Cl. In some embodiments, $X^{3c}$ is N, C—H, C—$CH_3$, C—$CH_2CH_3$, C—$CHF_2$, C—$CF_3$, C—F, or C—Cl.

In some embodiments, the invention relates to a compound of formula (I-A), or a pharmaceutically acceptable salt thereof, wherein $X^{3c}$ is C—$R^{3c}$; and $R^{3c}$ is H, halo, or $C_1$-$C_6$ alkyl. In other embodiments, $R^{3c}$ is halo. In other embodiments, $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I-A), or a pharmaceutically acceptable salt thereof, wherein $X^{4c}$ is N. In other embodiments, $X^{4c}$ is C—$R^{4c}$. In other embodiments, $R^{4c}$ is H, halo, or $C_1$-$C_6$ haloalkyl. In other embodiments, $R^{4c}$ is H, $CHF_2$, $CF_3$, or F. In some embodiments, $X^{4c}$ is N, C—H, C—$CHF_2$, C—$CF_3$, or C—F.

In some embodiments, the invention relates to a compound of formula (I-A), or a pharmaceutically acceptable salt thereof, wherein $X^{4c}$ is C—$R^{4c}$; and $R^{4c}$ is halo. In other embodiments, $R^{4c}$ is F.

In some embodiments, the invention relates to a compound of formula (I-A), or a pharmaceutically acceptable salt thereof, wherein $X^{5c}$ is N. In other embodiments, $X^{5c}$ is C—$R^{5c}$. In other embodiments, $R^{5c}$ is H or halo. In other embodiments, $R^{5c}$ is H, D, or Cl. In some embodiments, $X^{5c}$ is N, C—H, C-D, or C—Cl.

In some embodiments, the invention relates to a compound of formula (I-A), or a pharmaceutically acceptable salt thereof, wherein $X^{5c}$ is C—$R^{5c}$; and $R^{5c}$ is H.

In some embodiments, the invention relates to a compound of formula (I-A), or a pharmaceutically acceptable salt thereof, wherein $X^{6c}$ is N. In other embodiments, $X^{6c}$ is C—$R^{6c}$. In other embodiments, $R^{6c}$ is H or halo. In other embodiments, $R^{6c}$ is H or F. In some embodiments, $X^{6c}$ is N, C—H, or C—F.

In some embodiments, the invention relates to a compound of formula (I-A), or a pharmaceutically acceptable salt thereof, wherein $R^{6c}$ is H.

In some embodiments, the invention relates to a compound of formula (I-A), or a pharmaceutically acceptable salt thereof, wherein $X^{2a}$ is N, C—H, C-D, C—($C_1$-$C_6$ alkyl), or C-halo; $X^{4a}$ is N, $N^+$—$O^-$, C—H, or C-halo; $X^{5a}$ is N, C—H, C-D, C—($C_1$-$C_6$ alkyl), or C-halo; $X^{6a}$ is N, C—H, C-D, C—($C_1$-$C_6$ alkyl), or C-halo; each R is H or $CH_3$; $R^{4b1}$ and $R^{4b2}$ are each independently H, $C_1$-$C_6$ alkyl, or $C_3$-$C_6$ cycloalkyl; $R^{5b1}$ and $R^{5b2}$ are each independently H, $C_1$-$C_6$ alkyl, or $C_1$-$C_6$ haloalkyl; $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo; $X^{3c}$ is C—$R^{3c}$; $R^{3c}$ is H, halo, $C_1$-$C_6$ alkyl, or $C_1$-$C_6$ haloalkyl; $X^{4c}$ is C—$R^{4c}$; $R^{4c}$ is H, halo, or $C_1$-$C_6$ haloalkyl; $X^{5c}$ is C—$R^{5c}$; $R^{5c}$ is H or halo; $X^{6c}$ is C—$R^{6c}$; and $R^{6c}$ is H or halo.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{2a}$ is N, C—H, C-D, C—$CH_3$, or C—F; $X^{4a}$ is N, $N^+$—$O^-$, C—H, or C—F; $X^{5a}$ is N, C—H, C-D, C—$CH_3$, or C—F; $X^{6a}$ is N, C—H, C-D, C—$CH_3$, or C—F; each R is H or $CH_3$; $R^{4b1}$ and $R^{4b2}$ are each independently H, $CH_3$, $CH_2CH_3$, or cyclopropyl; $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$; $R^{2c}$ is H, F, $CH_3$, CH=$CH_2$, OH, $OCH_3$, $OCD_3$, $OCH_2CH_3$, OCH$(CH_3)_2$, $OCHF_2$,

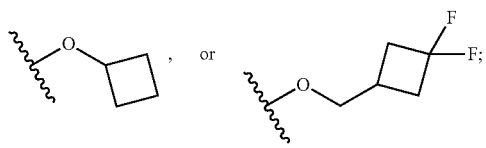 [SMILES: *OC1CCC1 ; *OCC1CC(F)(F)C1]

$X^{3c}$ is N, C—H, C—$CH_3$, C—$CH_2CH_3$, C—$CHF_2$, C—$CF_3$, C—F, or C—Cl; $X^{4c}$ is N, C—H, C—$CHF_2$, C—$CF_3$, or C—F; $X^{5c}$ is N, C—H, C-D, or C—Cl; and $X^{6c}$ is N, C—H, or C—F.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C-$R^{5a}$; $R^{5a}$ is H; $X^{6a}$ is C—$R^{6a}$; $R^{6a}$ is H; $R^{4b1}$ and $R^{4b2}$ are each independently H or $CH_3$; $R^{5b1}$ and $R^{5b2}$ are each independently H, $CH_3$, or $CF_3$; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is $C_1$-$C_6$ alkyl; $R^{4b2}$ is H; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is H; $R^{4b2}$ is $C_1$-$C_6$ alkyl; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is $C_1$-$C_6$ alkyl; $R^{4b2}$ is H; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $C_1$-$C_6$ haloalkyl; $R^{5b2}$ is $C_1$-$C_6$ alkyl; $R^{4b1}$ is H; $R^{4b2}$ is $C_1$-$C_6$ alkyl; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CH_3$; $R^{5b2}$ is $CF_3$; $R^{4b1}$ is $CH_3$; $R^{4b2}$ is H; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CH_3$; $R^{5b2}$ is $CF_3$; $R^{4b1}$ is H; $R^{4b2}$ is $CH_3$; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CF_3$; $R^{5b2}$ is $CH_3$; $R^{4b1}$ is $CH_3$; $R^{4b2}$ is H; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H;

$R^{5b1}$ is $CF_3$; $R^{5b2}$ is $CH_3$; $R^{4b1}$ is H, and $R^{4b2}$ is $CH_3$; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-A) (including any of the foregoing embodiments thereof), i.e., the compound in non-salt form.

In some embodiments, the invention relates to a compound of formula (I-A-1)

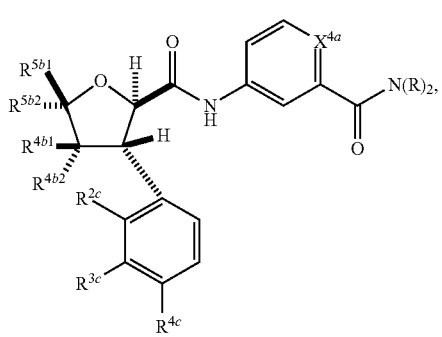

I-A-1 or a pharmaceutically acceptable salt thereof, wherein:
$X^{4a}$ is N, $N^+$—$O^-$, or C—$R^{4a}$;
each R is independently H or $C_1$-$C_6$ alkyl;
$R^{4a}$ is H, halo, $C_1$-$C_6$ alkyl, or $C_1$-$C_6$ haloalkyl;
$R^{4b1}$ and $R^{4b2}$ are each independently H, $C_1$-$C_6$ alkyl, or $C_1$-$C_6$ haloalkyl;
$R^{5b1}$ and $R^{5b2}$ are each independently H, $C_1$-$C_6$ alkyl, or $C_1$-$C_6$ haloalkyl;
$R^{2c}$ is H, OH, halo, $C_1$-$C_6$ alkyl, $C_1$-$C_6$ haloalkyl, $C_1$-$C_6$ alkoxy, or $C_1$-$C_6$ haloalkoxy;
$R^{3c}$ is H, halo, $C_1$-$C_6$ alkyl, or $C_1$-$C_6$ haloalkyl; and
$R^{4c}$ is H, halo, $C_1$-$C_6$ alkyl, or $C_1$-$C_6$ haloalkyl.

In some embodiments, the invention relates to a compound of formula (I-A-1), or a pharmaceutically acceptable salt thereof, wherein $X^{4a}$ is N. In other embodiments, $X^{4a}$ is $N^+$—$O^-$. In other embodiments, $X^{4a}$ is C—$R^{4a}$. In other embodiments, $X^{4a}$ is C—F.

In some embodiments, the invention relates to a compound of formula (I-A-1), or a pharmaceutically acceptable salt thereof, wherein each R is H. In other embodiments, each R is independently H or $CH_3$. In other embodiments, $N(R)_2$ is $NHCH_3$.

In some embodiments, the invention relates to a compound of formula (I-A-1), or a pharmaceutically acceptable salt thereof, wherein $R^{4a}$ is halo.

In some embodiments, the invention relates to a compound of formula (I-A-1), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H or $CH_3$. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I-A-1), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $CH_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I-A-1), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is OH, $OCH_3$, $OCD_3$, $OCH_2CH_3$, or $OCHF_2$. In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I-A-1), or a pharmaceutically acceptable salt thereof, wherein $R^{3c}$ is H, halo, or $C_1$-$C_6$ alkyl. In other embodiments, $R^{3c}$ is halo. In other embodiments. $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I-A-1), or a pharmaceutically acceptable salt thereof, wherein $R^{4c}$ is halo. In other embodiments, $R^{4c}$ is F.

In some embodiments, the invention relates to a compound of formula (I-A-1), or a pharmaceutically acceptable salt thereof, wherein $X^{4a}$ is N; each R is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ and $R^{4b2}$ are each independently H or $CH_3$; $R^{5b1}$ and $R^{5b2}$ are each independently H, $CH_3$, or $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is $C_1$-$C_6$ alkyl; $R^{4b2}$ is H; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is H; $R^{4b2}$ is $C_1$-$C_6$ alkyl; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is $C_1$-$C_6$ alkyl; $R^{4b2}$ is H; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is H; $R^{4b2}$ is $C_1$-$C_6$ alkyl; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is $CH_3$; $R^{4b2}$ is H; $R^{5b1}$ is $CH_3$; $R^{5b2}$ is $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is H; $R^{4b2}$ is $CH_3$; $R^{5b1}$ is $CH_3$; $R^{5b2}$ is $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is $CH_3$; $R^{4b2}$ is H; $R^{5b1}$ is $CF_3$; $R^{5b2}$ is $CH_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1), or a pharmaceutically acceptable salt thereof, wherein $X^{4a}$ is N; each R is H; $R^{4b1}$ is H, and $R^{4b2}$ is $CH_3$; $R^{5b1}$ is $CF_3$; $R^{5b2}$ is $CH_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-A-1) (including any of the foregoing embodiments thereof), i.e., the compound in non-salt form.

In some embodiments, the invention relates to a compound of formula (I-B)

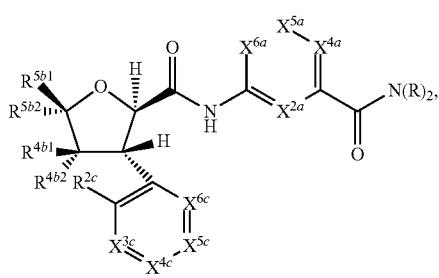

I-B or a pharmaceutically acceptable salt thereof, wherein:
$X^{2a}$ is N, $N^+$—$O^-$, or C—$R^{2a}$;
$X^{4a}$ is N, $N^+$—$O^-$, or C—$R^{4a}$;
$X^{5a}$ is N, $N^+$—$O^-$, or C—$R^{5a}$;
$X^{6a}$ is N, $N^+$—$O^-$, or C—$R^{6a}$;
each R is independently H or $C_1$-$C_6$ alkyl;
$R^{2a}$, $R^{4a}$, $R^{5a}$, and $R^{6a}$ are each independently H, halo, $C_1$-$C_6$ alkyl, or $C_1$-$C_6$ haloalkyl;
$R^{4b1}$ and $R^{4b2}$ are each independently H, $C_1$-$C_6$ alkyl, $C_3$-$C_6$ cycloalkyl, or $C_1$-$C_6$ haloalkyl;
$R^{5b1}$ and $R^{5b2}$ are each independently H, $C_1$-$C_6$ alkyl, $C_3$-$C_6$ cycloalkyl, or $C_1$-$C_6$ haloalkyl;
$X^{3c}$ is N or C—$R^{3c}$;
$X^{4c}$ is N or C—$R^{4c}$;
$X^{5c}$ is N or C—$R^{5c}$;
$X^{6c}$ is N or C—$R^{6c}$;
$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;
$L^1$ is a bond or O;
$L^2$ is a bond or $C_1$-$C_6$ alkylene;
$R^{3c}$ is H, halo, $C_1$-$C_6$ alkyl, or $C_1$-$C_6$ haloalkyl;
$R^{4c}$ is H, halo, $C_1$-$C_6$ alkyl, or $C_1$-$C_6$ haloalkyl;
$R^{5c}$ is H, halo, $C_1$-$C_6$ alkyl, or $C_1$-$C_6$ haloalkyl; and
$R^{6c}$ is H, halo, $C_1$-$C_6$ alkyl, or $C_1$-$C_6$ haloalkyl;

provided that no more than two of $X^{2a}$, $X^{4a}$, $X^{5a}$, and $X^{6a}$ are N or $N^+$—$O^-$; and provided that no more than one of $X^{3c}$, $X^{4c}$, $X^{5c}$, and $X^{6c}$ are N.

In some embodiments, the invention relates to a compound of formula (I-B), or a pharmaceutically acceptable salt thereof, wherein $X^{2a}$ is C—$R^{2a}$; $X^{5a}$ is C—$R^{5a}$; $X^{6a}$ is C—$R^{6a}$; $R^{4b1}$ and $R^{4b2}$ are each independently H, $C_1$-$C_6$ alkyl, or $C_1$-$C_6$ haloalkyl; $R^{5b1}$ and $R^{5b2}$ are each independently H, $C_1$-$C_6$ alkyl, or $C_1$-$C_6$ haloalkyl; $X^{3c}$ is C—$R^{3c}$; $X^{4c}$ is C—$R^{4c}$; $X^{5c}$ is C—$R^{5c}$; $X^{6c}$ is C—$R^{6c}$; and $R^{2c}$ is H, OH, halo, $C_1$-$C_6$ alkyl, $C_1$-$C_6$ haloalkyl, $C_1$-$C_6$ alkoxy, or $C_1$-$C_6$ haloalkoxy.

In some embodiments, the invention relates to a compound of formula (I-B), or a pharmaceutically acceptable salt thereof, wherein each R is H. In other embodiments, each R is independently H or $CH_3$. In other embodiments, $N(R)_2$ is $NHCH_3$.

In some embodiments, the invention relates to a compound of formula (I-B), or a pharmaceutically acceptable salt thereof, wherein $X^{2a}$ is N. In other embodiments, $X^{2a}$ is C—$R^{2a}$. In some embodiments, $R^{2a}$ is H, D, halo, or $C_1$-$C_6$ alkyl. In other embodiments, $R^{2a}$ is H, D, F, or $CH_3$. In some embodiments, $X^{2a}$ is N, C—H, C-D, C—($C_1$-$C_6$ alkyl), or C-halo. In other embodiments, $X^{2a}$ is N, C—H, C-D, C—$CH_3$, or C—F.

In some embodiments, the invention relates to a compound of formula (I-B), or a pharmaceutically acceptable salt thereof, wherein $X^{2a}$ is C—$R^{2a}$; and $R^{2a}$ is H.

In some embodiments, the invention relates to a compound of formula (I-B), or a pharmaceutically acceptable salt thereof, wherein $X^{4a}$ is N. In other embodiments, $X^{4a}$ is $N^+$—$O^-$. In other embodiments, $X^{4a}$ is C—$R^{4a}$. In some embodiments, $R^{4a}$ is halo. In other embodiments, $R^{4a}$ is H or halo. In other embodiments, $R^{4a}$ is H or F. In other embodiments, $X^{4a}$ is C—F. In some embodiments, $X^{4a}$ is N, $N^+$—$O^-$, C—H, or C-halo. In other embodiments, $X^{4a}$ is N, $N^+$—$O^-$, C—H, or C—F.

In some embodiments, the invention relates to a compound of formula (I-B), or a pharmaceutically acceptable salt thereof, wherein $X^{4a}$ is C—$R^{4a}$; and $R^{4a}$ is halo.

In some embodiments, the invention relates to a compound of formula (I-B), or a pharmaceutically acceptable salt thereof, wherein $X^{5a}$ is N. In other embodiments, $X^{5a}$ is C—$R^{5a}$. In some embodiments, $R^{5a}$ is H, D, halo, or $C_1$-$C_6$ alkyl. In other embodiments, $R^{5a}$ is H, D, F, or $CH_3$. In some embodiments, $X^{5a}$ is N, C—H, C-D, C—($C_1$-$C_6$ alkyl), or C-halo. In other embodiments, $X^{5a}$ is N, C—H, C-D, C—$CH_3$, or C—F.

In some embodiments, the invention relates to a compound of formula (I-B), or a pharmaceutically acceptable salt thereof, wherein $X^{5a}$ is C—$R^{5a}$; and $R^{5a}$ is H.

In some embodiments, the invention relates to a compound of formula (I-B), or a pharmaceutically acceptable salt thereof, wherein $X^{6a}$ is N. In other embodiments, $X^{6a}$ is C—$R^{6a}$. In some embodiments, $R^{6a}$ is H, D, halo, or $C_1$-$C_6$ alkyl. In other embodiments, $R^{6a}$ is H, D, F, or $CH_3$. In some embodiments, $X^{6a}$ is N, C—H, C-D, C—($C_1$-$C_6$ alkyl), or C-halo. In other embodiments, $X^{6a}$ is N, C—H, C-D, C—$CH_3$, or C—F.

In some embodiments, the invention relates to a compound of formula (I-B), or a pharmaceutically acceptable salt thereof, wherein $X^{6a}$ is C—$R^{6a}$; and $R^{6a}$ is H.

In some embodiments, the invention relates to a compound of formula (I-B), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H, $C_1$-$C_6$ alkyl, or $C_1$-$C_6$ cycloalkyl. In other embodiments, $R^{4b1}$ and $R^{4b2}$ are each independently H or $CH_3$. In other embodiments, $R^{4b1}$ and $R^{4b2}$ are each independently H, $CH_3$, $CH_2CH_3$, or cyclopropyl. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I-B), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $C_1$-$C_6$ alkyl, or $C_1$-$C_6$ haloalkyl. In other embodiments, $R^{5b1}$ and $R^{5b2}$ are each independently H, $CH_3$, or $CF_3$. In other embodiments, $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I-B), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo. In other embodiments, $R^{2c}$ is H. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is -$L^1$-$L^2$-($C_3$-$C_6$ cycloalkyl), wherein said cycloalkyl is optionally substituted with 1-2 halo. In other embodiments, $R^{2c}$ is OH, $OCH_3$, $OCD_3$, $OCH_2CH_3$, or $OCHF_2$. In other embodiments, $R^{2c}$ is H, F, $CH_3$, $CH=CH_2$, OH, $OCH_3$, $OCD_3$, $OCH_2CH_3$, $OCH(CH_3)_2$, $OCHF_2$,

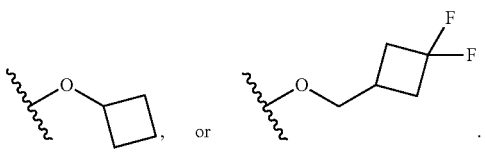 [SMILES: *OC1CCC1 ; *OCC1CC(F)(F)C1]

In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I-B), or a pharmaceutically acceptable salt thereof, wherein $X^{3c}$ is N. In other embodiments, $X^{3c}$ is C—$R^{3c}$. In other embodiments, $R^{3c}$ is H, halo, $C_1$-$C_6$ alkyl, or $C_1$-$C_6$ haloalkyl. In other embodiments, $R^{3c}$ is H, $CH_3$, $CH_2CH_3$, $CHF_2$, $CF_3$, F, or Cl. In some embodiments, $X^{3c}$ is N, C—H, C—$CH_3$, C—$CH_2CH_3$, C—$CHF_2$, C—$CF_3$, C—F, or C—Cl.

In some embodiments, the invention relates to a compound of formula (I-B), or a pharmaceutically acceptable salt thereof, wherein $X^{3c}$ is C—$R^{3c}$; and $R^{3c}$ is H, halo, or $C_1$-$C_6$ alkyl. In other embodiments, $R^{3c}$ is halo. In other embodiments, $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I-B), or a pharmaceutically acceptable salt thereof, wherein $X^{4c}$ is N. In other embodiments, $X^{4c}$ is C—$R^{4c}$. In other embodiments, $R^{4c}$ is H, halo, or $C_1$-$C_6$ haloalkyl. In other embodiments, $R^{4c}$ is H, $CHF_2$, $CF_3$, or F. In some embodiments, $X^{4c}$ is N, C—H, C—$CHF_2$, C—$CF_3$, or C—F.

In some embodiments, the invention relates to a compound of formula (I-B), or a pharmaceutically acceptable salt thereof, wherein $X^{4c}$ is C—$R^{4c}$; and $R^{4c}$ is halo. In other embodiments, $R^{4c}$ is F.

In some embodiments, the invention relates to a compound of formula (I-B), or a pharmaceutically acceptable salt thereof, wherein $X^{5c}$ is N. In other embodiments, $X^{5c}$ is C—$R^{5c}$. In other embodiments, $R^{5c}$ is H or halo. In other embodiments, $R^{5c}$ is H, D, or Cl. In some embodiments, $X^{5c}$ is N, C—H, C-D, or C—Cl.

In some embodiments, the invention relates to a compound of formula (I-B), or a pharmaceutically acceptable salt thereof, wherein $X^{5c}$ is C—$R^{5c}$; and $R^{5c}$ is H.

In some embodiments, the invention relates to a compound of formula (I-B), or a pharmaceutically acceptable salt thereof, wherein $X^{6c}$ is N. In other embodiments, $X^{6c}$ is C—$R^{6c}$. In other embodiments, $R^{6c}$ is H or halo. In other embodiments, $R^{6c}$ is H or F. In some embodiments, $X^{6c}$ is N, C—H, or C—F.

In some embodiments, the invention relates to a compound of formula (IB), or a pharmaceutically acceptable salt thereof, wherein $R^{6c}$ is H.

In some embodiments, the invention relates to a compound of formula (I-B), or a pharmaceutically acceptable salt thereof, wherein $X^{2a}$ is N, C—H, C-D, C—($C_1$-$C_6$ alkyl), or C-halo; $X^{4a}$ is N, $N^+$—$O^-$, C—H, or C-halo; $X^{5a}$ is N, C—H, C-D, C—($C_1$-$C_6$ alkyl), or C-halo; $X^{6a}$ is N, C—H, C-D, C—($C_1$-$C_6$ alkyl), or C-halo; each R is H or $CH_3$; $R^{4b1}$ and $R^{4b2}$ are each independently H, $C_1$-$C_6$ alkyl, or $C_3$-$C_6$ cycloalkyl; $R^{5b1}$ and $R^{5b2}$ are each independently H, $C_1$-$C_6$ alkyl, or $C_1$-$C_6$ haloalkyl; $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo; $X^{3c}$ is C—$R^{3c}$; $R^{3c}$ is H, halo, $C_1$-$C_6$ alkyl, or $C_1$-$C_6$ haloalkyl; $X^{4c}$ is C—$R^{4c}$; $R^{4c}$ is H, halo, or $C_1$-$C_6$ haloalkyl; $X^{5c}$ is C—$R^{5c}$; $R^{5c}$ is H or halo; $X^{6c}$ is C—$R^{6c}$; and $R^{6c}$ is H or halo.

In some embodiments, the invention relates to a compound of formula (I-B), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-B), or a pharmaceutically acceptable salt thereof, wherein $X^{2a}$ is N, C—H, C-D, C—$CH_3$, or C—F; $X^{4a}$ is N, $N^+$—$O^-$, C—H, or C—F; $X^{5a}$ is N, C—H, C-D, C—$CH_3$, or C—F; $X^{6a}$ is N, C—H, C-D, C—$CH_3$, or C—F; each R is H or $CH_3$; $R^{4b1}$ and $R^{4b2}$ are each independently H, $CH_3$, $CH_2CH_3$, or cyclopropyl; $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$; $R^{2c}$ is H, F, $CH_3$, $CH=CH_2$, OH, $OCH_3$, $OCD_3$, $OCH_2CH_3$, $OCH(CH_3)_2$, $OCHF_2$,

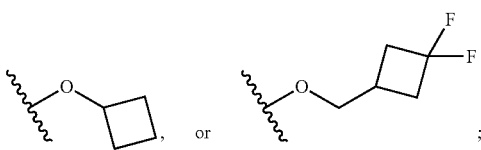 [SMILES: *OC1CCC1 ; *OCC1CC(F)(F)C1]

$X^{3c}$ is N, C—H, C—CH$_3$, C—CH$_2$CH$_3$, C—CHF$_2$, C—CF$_3$, C—F, or C—Cl; $X^{4c}$ is N, C—H, C—CHF$_2$, C—CF$_3$, or C—F; $X^{5c}$ is N, C—H, C-D, or C—Cl; and $X^{6c}$ is N, C—H, or C—F.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{4b1}$ and $R^{4b2}$ are each independently H or CH$_3$; $R^{5b1}$ and $R^{5b2}$ are each independently H, CH$_3$, or CF$_3$; $R^{2c}$ is OH, C$_1$-C$_6$ alkoxy, or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{4b1}$ is C$_1$-C$_6$ alkyl; $R^{4b2}$ is H; $R^{5b1}$ is C$_1$-C$_6$ alkyl; $R^{5b2}$ is C$_1$-C$_6$ haloalkyl; $R^{2c}$ is OH, C$_1$-C$_6$ alkoxy, or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{4b1}$ is H; $R^{4b2}$ is C$_1$-C$_6$ alkyl; $R^{5b1}$ is C$_1$-C$_6$ alkyl; $R^{5b2}$ is C$_1$-C$_6$ haloalkyl; $R^{2c}$ is OH, C$_1$-C$_6$ alkoxy, or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{4b1}$ is C$_1$-C$_6$ alkyl; $R^{4b2}$ is H; $R^{5b1}$ is C$_1$-C$_6$ haloalkyl; $R^{5b2}$ is C$_1$-C$_6$ alkyl; $R^{2c}$ is OH, C$_1$-C$_6$ alkoxy, or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{5b1}$ is C$_1$-C$_6$ haloalkyl; $R^{5b2}$ is C$_1$-C$_6$ alkyl; $R^{4b1}$ is H; $R^{4b2}$ is C$_1$-C$_6$ alkyl; $R^{2c}$ is C$_1$-C$_6$ alkoxy or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{5b1}$ is CH$_3$; $R^{5b2}$ is CF$_3$; $R^{4b1}$ is CH$_3$; $R^{4b2}$ is H; $R^{2c}$ is C$_1$-C$_6$ alkoxy or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{5b1}$ is CH$_3$; $R^{5b2}$ is CF$_3$; $R^{4b1}$ is H; $R^{4b2}$ is CH$_3$; $R^{2c}$ is C$_1$-C$_6$ alkoxy or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{5b1}$ is CF$_3$; $R^{5b2}$ is CH$_3$; $R^{4b1}$ is CH$_3$; $R^{4b2}$ is H; $R^{2c}$ is C$_1$-C$_6$ alkoxy or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B), or a pharmaceutically acceptable salt thereof, wherein $X^{4a}$ is N; each R is H; $X^{2a}$ is C—R$^{2a}$; $R^{2a}$ is H; $X^{5a}$ is C—R$^{5a}$; $R^{5a}$ is H; $X^{6a}$ is C—R$^{6a}$; $R^{6a}$ is H; $R^{5b1}$ is CF$_3$; $R^{5b2}$ is CH$_3$; $R^{4b1}$ is H, and $R^{4b2}$ is CH$_3$; $R^{2c}$ is C$_1$-C$_6$ alkoxy or C$_1$-C$_6$ haloalkoxy; $X^{3c}$ is C—R$^{3c}$; $R^{3c}$ is H, halo, or C$_1$-C$_6$ alkyl; $X^{4c}$ is C—R$^{4c}$; $R^{4c}$ is halo; $X^{5c}$ is C—R$^{5c}$; $R^{5c}$ is H; $X^{6c}$ is C—R$^{6c}$; and $R^{6c}$ is H.

In some embodiments, the invention relates to a compound of formula (I-B) (including any of the foregoing embodiments thereof), i.e., the compound in non-salt form.

In some embodiments, the invention relates to a compound of formula (I-B-1)

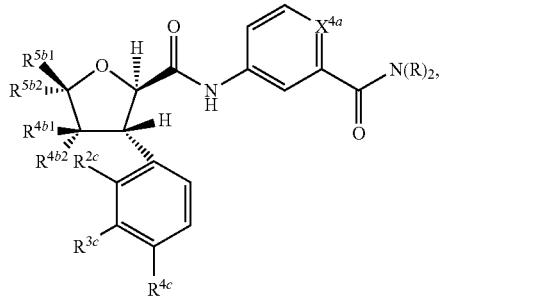

I-B-1 or a pharmaceutically acceptable salt thereof, wherein:
$X^{4a}$ is N, N$^+$—O$^-$, or C—R$^{4a}$;
each R is independently H or C$_1$-C$_6$ alkyl;
$R^{4a}$ is H, halo, C$_1$-C$_6$ alkyl, or C$_1$-C$_6$ haloalkyl;
$R^{4b1}$ and $R^{4b2}$ are each independently H, C$_1$-C$_6$ alkyl, or C$_1$-C$_6$ haloalkyl;
$R^{5b1}$ and $R^{5b2}$ are each independently H, C$_1$-C$_6$ alkyl, or C$_1$-C$_6$ haloalkyl;
$R^{2c}$ is H, OH, halo, C$_1$-C$_6$ alkyl, C$_1$-C$_6$ haloalkyl, C$_1$-C$_6$ alkoxy, or C$_1$-C$_6$ haloalkoxy;
$R^{3c}$ is H, halo, C$_1$-C$_6$ alkyl, or C$_1$-C$_6$ haloalkyl; and
$R^{4c}$ is H, halo, C$_1$-C$_6$ alkyl, or C$_1$-C$_6$ haloalkyl.

In some embodiments, the invention relates to a compound of formula (I-B-1), or a pharmaceutically acceptable salt thereof, wherein $X^{4a}$ is N. In other embodiments, $X^{4a}$ is N$^+$—O$^-$. In other embodiments, $X^{4a}$ is C—R$^{4a}$. In some embodiments, $R^{4a}$ is halo. In other embodiments, $X^{4a}$ is C—F.

In some embodiments, the invention relates to a compound of formula (I-B-1), or a pharmaceutically acceptable salt thereof, wherein each R is H. In other embodiments, each R is independently H or CH$_3$. In other embodiments, N(R)$_2$ is NHCH$_3$.

In some embodiments, the invention relates to a compound of formula (I-B-1), or a pharmaceutically acceptable salt thereof, wherein $R^{4a}$ is halo.

In some embodiments, the invention relates to a compound of formula (I-B-1), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H or $CH_3$. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I-B-1), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $CH_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I-B-1), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is OH, $OCH_3$, $OCD_3$, $OCH_2CH_3$, or $OCHF_2$. In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I-B-1), or a pharmaceutically acceptable salt thereof, wherein $R^{3c}$ is H, halo, or $C_1$-$C_6$ alkyl. In other embodiments, $R^{3c}$ is halo. In other embodiments, $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I-B-1), or a pharmaceutically acceptable salt thereof, wherein $R^{4c}$ is halo. In other embodiments, $R^{4c}$ is F.

In some embodiments, the invention relates to a compound of formula (I-B-1), or a pharmaceutically acceptable salt thereof, wherein $X^{4a}$ is N; each R is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ and $R^{4b2}$ are each independently H or $CH_3$; $R^{5b1}$ and $R^{5b2}$ are each independently H, $CH_3$, or $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is $C_1$-$C_6$ alkyl; $R^{4b2}$ is H; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is H; $R^{4b2}$ is $C_1$-$C_6$ alkyl; $R^{5b1}$ is $C_4$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is $C_1$-$C_6$ alkyl; $R^{4b2}$ is H; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is H; $R^{4b2}$ is $C_1$-$C_6$ alkyl; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is $CH_3$; $R^{4b2}$ is H; $R^{5b1}$ is $CH_3$; $R^{5b2}$ is $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is H; $R^{4b2}$ is $CH_3$; $R^{5b1}$ is $CH_3$; $R^{5b2}$ is $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is $CH_3$; $R^{4b2}$ is H; $R^{5b1}$ is $CF_3$; $R^{5b2}$ is $CH_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1), or a pharmaceutically acceptable salt thereof, wherein $X^{4a}$ is N; each R is H; $R^{4b1}$ is H, and $R^{4b2}$ is $CH_3$; $R^{5b1}$ is $CF_3$; $R^{5b2}$ is $CH_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-B-1) (including any of the foregoing embodiments thereof), i.e., the compound in non-salt form.

In some embodiments, the invention relates to a compound of formula (I-C)

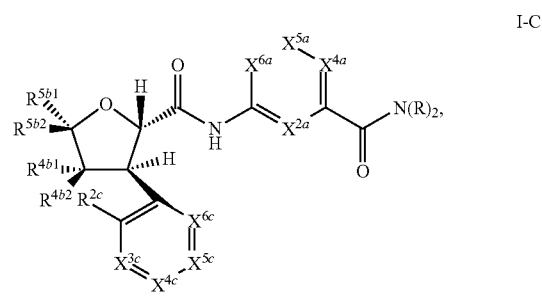

or a pharmaceutically acceptable salt thereof, wherein:
$X^{2a}$ is N, $N^+$—$O^-$, or C—$R^{2a}$;
$X^{4a}$ is N, $N^+$—$O^-$, or C—$R^{4a}$;
$X^{5a}$ is N, $N^+$—$O^-$, or C—$R^{5a}$;
$X^{6a}$ is N, $N^+$—$O^-$, or C—$R^{6a}$;
each R is independently H or $C_4$-$C_6$ alkyl;
$R^{2a}$, $R^{4a}$, $R^{5a}$, and $R^{6a}$ are each independently H, halo, $C_1$-$C_6$ alkyl, or $C_1$-$C_6$ haloalkyl;

$R^{4b1}$ and $R^{4b2}$ are each independently H, $C_1$-$C_6$ alkyl, $C_3$-$C_6$ cycloalkyl, or $C_1$-$C_6$ haloalkyl;

$R^{5b1}$ and $R^{5b2}$ are each independently H, $C_1$-$C_6$ alkyl, $C_3$-$C_6$ cycloalkyl, or $C_1$-$C_6$ haloalkyl;

$X^{3c}$ is N or C—$R^{3c}$;
$X^{4c}$ is N or C—$R^{4c}$;
$X^{5c}$ is N or C—$R^{5c}$;
$X^{6c}$ is N or C—$R^{6c}$;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;

$L^1$ is a bond or O;
$L^2$ is a bond or $C_1$-$C_6$ alkylene;
$R^{3c}$ is H, halo, $C_1$-$C_6$ alkyl, or $C_1$-$C_6$ haloalkyl;
$R^{4c}$ is H, halo, $C_1$-$C_6$ alkyl, or $C_1$-$C_6$ haloalkyl;
$R^{5c}$ is H, halo, $C_1$-$C_6$ alkyl, or $C_1$-$C_6$ haloalkyl; and
$R^{6c}$ is H, halo, $C_1$-$C_6$ alkyl, or $C_1$-$C_6$ haloalkyl;

provided that no more than two of $X^{2a}$, $X^{4a}$, $X^{5a}$, and $X^{6a}$ are N or $N^+$—$O^-$; and provided that no more than one of $X^{3c}$, $X^{4c}$, $X^{5c}$, and $X^{6c}$ are N.

In some embodiments, the invention relates to a compound of formula (I-C), or a pharmaceutically acceptable salt thereof, wherein $X^{2a}$ is C—$R^{2a}$; $X^{5a}$ is C—$R^{5a}$; $X^{6a}$ is C—$R^{6a}$; $R^{4b1}$ and $R^{4b2}$ are each independently H, $C_1$-$C_6$ alkyl, or $C_1$-$C_6$ haloalkyl; $R^{5b1}$ and $R^{5b2}$ are each independently H, $C_1$-$C_6$ alkyl, or $C_1$-$C_6$ haloalkyl; $X^{3c}$ is C—$R^{3c}$; $X^{4c}$ is C—$R^{4c}$; $X^{5c}$ is C—$R^{5c}$; $X^{6c}$ is C—$R^{6c}$; and $R^{2c}$ is H, OH, halo, $C_1$-$C_6$ alkyl, $C_1$-$C_6$ haloalkyl, $C_1$-$C_6$ alkoxy, or $C_1$-$C_6$ haloalkoxy.

In some embodiments, the invention relates to a compound of formula (I-C), or a pharmaceutically acceptable salt thereof, wherein each R is H. In other embodiments, each R is independently H or $CH_3$. In other embodiments, $N(R)_2$ is $NHCH_3$.

In some embodiments, the invention relates to a compound of formula (I-C), or a pharmaceutically acceptable salt thereof, wherein $X^{2a}$ is N. In other embodiments, $X^{2a}$ is C—$R^{2a}$. In some embodiments, $R^{2a}$ is H, D, halo, or $C_1$-$C_6$ alkyl. In other embodiments, $R^{2a}$ is H, D, F, or $CH_3$. In some embodiments, $X^{2a}$ is N, C—H, C-D, C—($C_1$-$C_6$ alkyl), or C-halo. In other embodiments, $X^{2a}$ is N, C—H, C-D, C—$CH_3$, or C—F.

In some embodiments, the invention relates to a compound of formula (I-C), or a pharmaceutically acceptable salt thereof, wherein $X^{2a}$ is C—$R^{2a}$; and $R^{2a}$ is H.

In some embodiments, the invention relates to a compound of formula (I-C), or a pharmaceutically acceptable salt thereof, wherein $X^{4a}$ is N. In other embodiments, $X^{4a}$ is $N^+$—$O^-$. In other embodiments, $X^{4a}$ is C—$R^{4a}$. In some embodiments, $R^{4a}$ is halo. In other embodiments, $R^{4a}$ is H or halo. In other embodiments, $R^{4a}$ is H or F. In other embodiments, $X^{4a}$ is C—F. In some embodiments, $X^{4a}$ is N, $N^+$—$O^-$, C—H, or C-halo. In other embodiments, $X^{4a}$ is N, $N^+$—$O^-$, C—H, or C—F.

In some embodiments, the invention relates to a compound of formula (I-C), or a pharmaceutically acceptable salt thereof, wherein $X^{4a}$ is C—$R^{4a}$; and $R^{4a}$ is halo.

In some embodiments, the invention relates to a compound of formula (I-C), or a pharmaceutically acceptable salt thereof, wherein $X^{5a}$ is N. In other embodiments, $X^{5a}$ is C—$R^{5a}$. In some embodiments, $R^{5a}$ is H, D, halo, or $C_1$-$C_6$ alkyl. In other embodiments, $R^{5a}$ is H, D, F, or $CH_3$. In some embodiments, $X^{5a}$ is N, C—H, C-D, C—($C_1$-$C_6$ alkyl), or C-halo. In other embodiments, $X^{5a}$ is N, C—H, C-D, C—$CH_3$, or C—F.

In some embodiments, the invention relates to a compound of formula (I-C), or a pharmaceutically acceptable salt thereof, wherein $X^{5a}$ is C—$R^{5a}$; and $R^{5a}$ is H.

In some embodiments, the invention relates to a compound of formula (I-C), or a pharmaceutically acceptable salt thereof, wherein $X^{6a}$ is N. In other embodiments, $X^{6a}$ is C—$R^{6a}$. In some embodiments, $R^{6a}$ is H, D, halo, or $C_1$-$C_6$ alkyl. In other embodiments, $R^{6a}$ is H, D, F, or $CH_3$. In some embodiments, $X^{6a}$ is N, C—H, C-D, C—($C_1$-$C_6$ alkyl), or C-halo. In other embodiments, $X^{6a}$ is N, C—H, C-D, C—$CH_3$, or C—F.

In some embodiments, the invention relates to a compound of formula (I-C), or a pharmaceutically acceptable salt thereof, wherein $X^{6a}$ is C—$R^{6a}$; and $R^{6a}$ is H.

In some embodiments, the invention relates to a compound of formula (I-C), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H, $C_1$-$C_6$ alkyl, or $C_3$-$C_6$ cycloalkyl. In other embodiments, $R^{4b1}$ and $R^{4b2}$ are each independently H or $CH_3$. In other embodiments, $R^{4b1}$ and $R^{4b2}$ are each independently H, $CH_3$, $CH_2CH_3$, or cyclopropyl. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I-C), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $C_1$-$C_6$ alkyl, or $C_1$-$C_6$ haloalkyl. In other embodiments, $R^{5b1}$ and $R^{5b2}$ are each independently H, $CH_3$, or $CF_3$. In other embodiments, $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I-C), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo. In other embodiments, $R^{2c}$ is H. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is -$L^1$-$L^2$-($C_3$-$C_6$ cycloalkyl), wherein said cycloalkyl is optionally substituted with 1-2 halo. In other embodiments, $R^{2c}$ is OH, $OCH_3$, $OCD_3$, $OCH_2CH_3$, or $OCHF_2$. In other embodiments, $R^{2c}$ is H, F, $CH_3$, $CH=CH_2$, OH, $OCH_3$, $OCD_3$, $OCH_2CH_3$, $OCH(CH_3)_2$, $OCHF_2$,

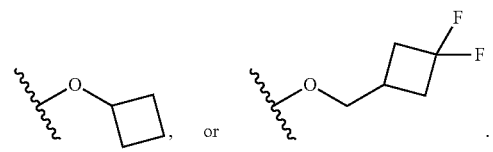 [SMILES: *OC1CCC1 ; *OCC1CC(F)(F)C1]

In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I-C), or a pharmaceutically acceptable salt thereof, wherein $X^{3c}$ is N. In other embodiments, $X^{3c}$ is C—$R^{3c}$. In other embodiments, $R^{3c}$ is H, halo, $C_1$-$C_6$ alkyl, or $C_1$-$C_6$ haloalkyl. In other embodiments, $R^{3c}$ is H, $CH_3$, $CH_2CH_3$, $CHF_2$, $CF_3$, F, or Cl. In some embodiments, $X^{3c}$ is N, C—H, C—$CH_3$, C—$CH_2CH_3$, C—$CHF_2$, C—$CF_3$, C—F, or C—Cl.

In some embodiments, the invention relates to a compound of formula (I-C), or a pharmaceutically acceptable salt thereof, wherein $X^{3c}$ is C—$R^{3c}$; and $R^{3c}$ is H, halo, or $C_1$-$C_6$ alkyl. In other embodiments, $R^{3c}$ is halo. In other embodiments, $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I-C), or a pharmaceutically acceptable salt thereof, wherein $X^{4c}$ is N. In other embodiments, $X^{4c}$ is C—$R^{4c}$. In other embodiments, $R^{4c}$ is H, halo, or $C_1$-$C_6$ haloalkyl. In other embodiments, $R^{4c}$ is H, $CHF_2$, $CF_3$, or F. In some embodiments, $X^{4c}$ is N, C—H, C—$CHF_2$, C—$CF_3$, or C—F.

In some embodiments, the invention relates to a compound of formula (I-C), or a pharmaceutically acceptable salt thereof, wherein $X^{4c}$ is C—$R^{4c}$; and $R^{4c}$ is halo. In other embodiments, $R^{4c}$ is F.

In some embodiments, the invention relates to a compound of formula (I-C), or a pharmaceutically acceptable salt thereof, wherein $X^{5c}$ is N. In other embodiments, $X^{5c}$ is C—$R^{5c}$. In other embodiments, $R^{5c}$ is H or halo. In other embodiments, $R^{5c}$ is H, D, or Cl. In some embodiments, $X^{5c}$ is N, C—H, C-D, or C—Cl.

In some embodiments, the invention relates to a compound of formula (I-C), or a pharmaceutically acceptable salt thereof, wherein $X^{5c}$ is C—$R^{5c}$; and $R^{5c}$ is H.

In some embodiments, the invention relates to a compound of formula (I-C), or a pharmaceutically acceptable salt thereof, wherein $X^{6c}$ is N. In other embodiments, $X^{6c}$ is C—$R^{6c}$. In other embodiments, $R^{6c}$ is H or halo. In other embodiments, $R^{6c}$ is H or F. In some embodiments, $X^{6c}$ is N, C—H, or C—F.

In some embodiments, the invention relates to a compound of formula (I-C), or a pharmaceutically acceptable salt thereof, wherein $R^{6c}$ is H.

In some embodiments, the invention relates to a compound of formula (I-C), or a pharmaceutically acceptable salt thereof, wherein $X^{2a}$ is N, C—H, C-D, C—($C_1$-$C_6$ alkyl), or C-halo; $X^{4a}$ is N, $N^+$—$O^-$, C—H, or C-halo; $X^{5a}$ is N, C—H, C-D, C-CG-Ce alkyl), or C-halo; $X^{6a}$ is N, C—H, C-D, C-CG-Ce alkyl), or C-halo; each R is H or $CH_3$; $R^{4b1}$ and $R^{4b2}$ are each independently H, $C_1$-$C_6$ alkyl, or $C_3$-$C_6$ cycloalkyl; $R^{5b1}$ and $R^{5b2}$ are each independently H, $C_1$-$C_6$ alkyl, or $C_1$-$C_6$ haloalkyl; $R^{2c}$ is OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo; $X^{3c}$ is C—$R^{3c}$; $R^{3c}$ is H, halo, $C_1$-$C_6$ alkyl, or $C_1$-$C_6$ haloalkyl; $X^{4c}$ is C—$R^{4c}$; $R^{4c}$ is H, halo, or $C_1$-$C_6$ haloalkyl; $X^{5c}$ is C—$R^{5c}$; $R^{5c}$ is H or halo; $X^{6c}$ is C—$R^{6c}$; and $R^{6c}$ is H or halo.

In some embodiments, the invention relates to a compound of formula (I-C), or a pharmaceutically acceptable salt thereof, wherein $X^{4a}$ is N; each R is H; $X^{2a}$ is C—$R^{2a}$;
$R^{2a}$ is H; $X^{5a}$ is C—$R^{5a}$; $R^{5a}$ is H; $X^{6a}$ is C—$R^{6a}$; $R^{6a}$ is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{2a}$ is N, C—H, C-D, C—$CH_3$, or C—F; $X^{4a}$ is N, $N^+$—$O^-$, C—H, or C—F; $X^{5a}$ is N, C—H, C-D, C—$CH_3$, or C—F; $X^{6a}$ is N, C—H, C-D, C—$CH_3$, or C—F; each R is H or $CH_3$; $R^{4b1}$ and $R^{4b2}$ are each independently H, $CH_3$, $CH_2CH_3$, or cyclopropyl; $R^{5b1}$ and $R^{5b2}$ are each independently H, $CH_3$, $CH_2CH_3$, $CH(CH_3)_2$, $C(CH_3)_3$, $CHF_2$, $CF_2CH_3$, $CH_2CF_3$, or $CF_3$; $R^{2c}$ is H, F, $CH_3$, CH=$CH_2$, OH, $OCH_3$, $OCD_3$, $OCH_2CH_3$, $OCH(CH_3)_2$, $OCHF_2$,

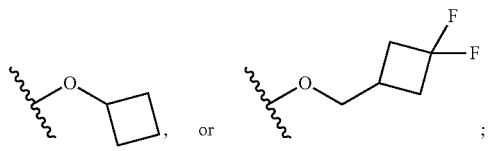 [SMILES: *OC1CCC1 ; *OCC1CC(F)(F)C1]

$X^{3c}$ is N, C—H, C—$CH_3$, C—$CH_2CH_3$, C—$CHF_2$, C—$CF_3$, C—F, or C—Cl; $X^{4c}$ is N, C—H, C—$CHF_2$, C—$CF_3$, or C—F; $X^{5c}$ is N, C—H, C-D, or C—Cl; and $X^{6c}$ is N, C—H, or C—F.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ and $R^{4b2}$ are each independently H or $CH_3$; $R^{5b1}$ and $R^{5b2}$ are each independently H, $CH_3$, or $CF_3$; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is $C_1$-$C_6$ alkyl; $R^{4b2}$ is H; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is H; $R^{4b2}$ is $C_1$-$C_6$ alkyl; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{4b1}$ is $C_1$-$C_6$ alkyl; $R^{4b2}$ is H; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $C_1$-$C_6$ haloalkyl; $R^{5b2}$ is $C_1$-$C_6$ alkyl; $R^{4b1}$ is H; $R^{4b2}$ is $C_1$-$C_6$ alkyl; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CH_3$; $R^{5b2}$ is $CF_3$; $R^{4b1}$ is $CH_3$; $R^{4b2}$ is H; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CH_3$; $R^{5b2}$ is $CF_3$; $R^{4b1}$ is H; $R^{4b2}$ is $CH_3$; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CF_3$; $R^{5b2}$ is $CH_3$; $R^{4b1}$ is $CH_3$; $R^{4b2}$ is H; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C), or a pharmaceutically acceptable salt thereof, wherein $X^{4a}$ is N; each R is H; $X^{2a}$ is C—$R^{2a}$; $R^{2a}$ is H; $X^{5a}$ is C—$R^{5a}$; $R^{5a}$ is H; $X^{6a}$ is C—$R^{6a}$; $R^{6a}$ is H; $R^{5b1}$ is $CF_3$; $R^{5b2}$ is $CH_3$; $R^{4b1}$ is H, and $R^{4b2}$ is $CH_3$; $R^{2c}$ is $C_1$-$C_6$ alkoxy or $C_1$-$C_6$ haloalkoxy; $X^{3c}$ is C—$R^{3c}$; $R^{3c}$ is H, halo, or $C_1$-$C_6$ alkyl; $X^{4c}$ is C—$R^{4c}$; $R^{4c}$ is halo; $X^{5c}$ is C—$R^{5c}$; $R^{5c}$ is H; $X^{6c}$ is C—$R^{6c}$; and $R^{6c}$ is H.

In some embodiments, the invention relates to a compound of formula (I-C) (including any of the foregoing embodiments thereof), i.e., the compound in non-salt form.

In some embodiments, the invention relates to a compound of formula (I-C-1)

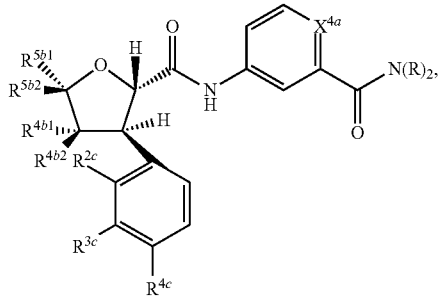

I-C-1 or a pharmaceutically acceptable salt thereof, wherein:
$X^{4a}$ is N, $N^+$—$O^-$, or C—$R^{4a}$;
each R is independently H or $C_1$-$C_6$ alkyl;
$R^{4a}$ is H, halo, $C_1$-$C_6$ alkyl, or $C_1$-$C_6$ haloalkyl;

$R^{4b1}$ and $R^{4b2}$ are each independently H, $C_1$-$C_6$ alkyl, or $C_1$-$C_6$ haloalkyl;
$R^{5b1}$ and $R^{5b2}$ are each independently H, $C_1$-$C_6$ alkyl, or $C_1$-$C_6$ haloalkyl;
$R^{2c}$ is H, OH, halo, $C_1$-$C_6$ alkyl, $C_1$-$C_6$ haloalkyl, $C_1$-$C_6$ alkoxy, or $C_1$-$C_6$ haloalkoxy;
$R^{3c}$ is H, halo, $C_1$-$C_6$ alkyl, or $C_1$-$C_6$ haloalkyl; and
$R^{4c}$ is H, halo, $C_1$-$C_6$ alkyl, or $C_1$-$C_6$ haloalkyl.

In some embodiments, the invention relates to a compound of formula (I-C-1), or a pharmaceutically acceptable salt thereof, wherein $X^{4a}$ is N. In other embodiments, $X^{4a}$ is $N^+$—$O^-$. In other embodiments, $X^{4a}$ is C—$R^{4a}$. In some embodiments, $R^{4a}$ is halo. In other embodiments, $X^{4a}$ is C—F.

In some embodiments, the invention relates to a compound of formula (I-C-1), or a pharmaceutically acceptable salt thereof, wherein each R is H. In other embodiments, each R is independently H or $CH_3$. In other embodiments, $N(R)_2$ is $NHCH_3$.

In some embodiments, the invention relates to a compound of formula (I-C-1), or a pharmaceutically acceptable salt thereof, wherein $R^{4a}$ is halo.

In some embodiments, the invention relates to a compound of formula (I-C-1), or a pharmaceutically acceptable salt thereof, wherein $R^{4b1}$ and $R^{4b2}$ are each independently H or $C_1$-$C_6$ alkyl. In other embodiments, $R^{4b1}$ and $R^{4b2}$ are each independently H or $CH_3$. In other embodiments, $R^{4b1}$ is $C_1$-$C_6$ alkyl, and $R^{4b2}$ is H. In other embodiments, $R^{4b1}$ is H, and $R^{4b2}$ is $C_1$-$C_6$ alkyl. In other embodiments, $R^{4b1}$ is $CH_3$, and $R^{4b2}$ is H. In other embodiments, $R^{4b1}$ is H, and $R^{4b2}$ is $CH_3$.

In some embodiments, the invention relates to a compound of formula (I-C-1), or a pharmaceutically acceptable salt thereof, wherein $R^{5b1}$ and $R^{5b2}$ are each independently $C_1$-$C_6$ alkyl or $C_1$-$C_6$ haloalkyl. In other embodiments, $R^{5b1}$ and $R^{5b2}$ are each independently H, $CH_3$, or $CF_3$. In other embodiments, $R^{5b1}$ is $C_1$-$C_6$ alkyl, and $R^{5b2}$ is $C_1$-$C_6$ haloalkyl. In other embodiments, $R^{5b1}$ is $C_1$-$C_6$ haloalkyl, and $R^{5b2}$ is $C_1$-$C_6$ alkyl. In other embodiments, $R^{5b1}$ is $CH_3$, and $R^{5b2}$ is $CF_3$. In other embodiments, $R^{5b1}$ is $CF_3$, and $R^{5b2}$ is $CH_3$.

In some embodiments, the invention relates to a compound of formula (I-C-1), or a pharmaceutically acceptable salt thereof, wherein $R^{2c}$ is OH, $C_1$-$C_6$ alkoxy, or $C_1$-$C_6$ haloalkoxy. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is OH, $OCH_3$, $OCD_3$, $OCH_2CH_3$, or $OCHF_2$. In other embodiments, $R^{2c}$ is OH. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCHF_2$.

In some embodiments, the invention relates to a compound of formula (I-C-1), or a pharmaceutically acceptable salt thereof, wherein $R^{3c}$ is H, halo, or $C_1$-$C_6$ alkyl. In other embodiments, $R^{3c}$ is halo. In other embodiments, $R^{3c}$ is $C_1$-$C_6$ alkyl. In other embodiments, $R^{3c}$ is H, F, Cl, or $CH_3$. In other embodiments, $R^{3c}$ is H. In other embodiments, $R^{3c}$ is F. In other embodiments, $R^{3c}$ is Cl. In other embodiments, $R^{3c}$ is $CH_3$.

In some embodiments, the invention relates to a compound of formula (I-C-1), or a pharmaceutically acceptable salt thereof, wherein $R^{4c}$ is halo. In other embodiments, $R^{4c}$ is F.

In some embodiments, the invention relates to a compound of formula (I-C-1), or a pharmaceutically acceptable salt thereof, wherein $X^{4a}$ is N; each R is H; $R^{4b1}$ and $R^{4b2}$ are each independently H or $C_1$-$C_6$ alkyl; $R^{5b1}$ and $R^{5b2}$ are each independently $C_1$-$C_6$ alkyl or $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ and $R^{4b2}$ are each independently H or $CH_3$; $R^{5b1}$ and $R^{5b2}$ are each independently H, $CH_3$, or $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is $C_1$-$C_6$ alkyl; $R^{4b2}$ is H; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is H; $R^{4b2}$ is $C_1$-$C_6$ alkyl; $R^{5b1}$ is $C_1$-$C_6$ alkyl; $R^{5b2}$ is $C_1$-$C_6$ haloalkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is $C_1$-$C_6$ alkyl; $R^{4b2}$ is H; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is H; $R^{4b2}$ is $C_1$-$C_6$ alkyl; $R^{5b1}$ is $C_1$-$C_6$ haloalkyl; $R^{5b2}$ is $C_1$-$C_6$ alkyl; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is $CH_3$; $R^{4b2}$ is H; $R^{5b1}$ is $CH_3$; $R^{5b2}$ is $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is H; $R^{4b2}$ is $CH_3$; $R^{5b1}$ is $CH_3$; $R^{5b2}$ is $CF_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is $CH_3$; $R^{4b2}$ is H; $R^{5b1}$ is $CF_3$; $R^{5b2}$ is $CH_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1), or a pharmaceutically acceptable salt thereof, wherein $X^{4a}$ is N; each R is H; $R^{4b1}$ is H, and $R^{4b2}$ is $CH_3$; $R^{5b1}$ is $CF_3$; $R^{5b2}$ is $CH_3$; $R^{2c}$ is OH, $C_1$-$C_6$ alkoxy, or $C_1$-$C_6$ haloalkoxy; $R^{3c}$ is H, halo, or $C_1$-$C_6$ alkyl; and $R^{4c}$ is halo.

In some embodiments, the invention relates to a compound of formula (I-C-1) (including any of the foregoing embodiments thereof), i.e., the compound in non-salt form.

In some embodiments, the invention relates to a compound selected from Table A or a pharmaceutically acceptable salt thereof. In other embodiments, the invention relates to a compound selected from Table A in non-salt form.

TABLE A

Compound Structures and Names.

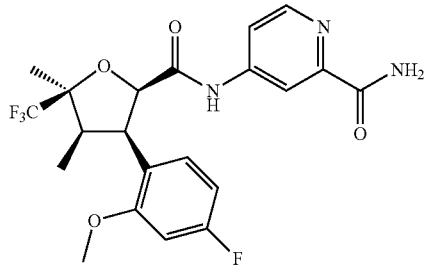 [SMILES: COc1cc(F)ccc1[C@H]1[C@@H](C)[C@@](C)(C(F)(F)F)O[C@H]1C(=O)Nc1ccnc(C(N)=O)c1]

4-((2R,3R,4R,5S)-3-(4-fluoro-2-methoxyphenyl)-4,5-dimethyl-5-(trifluoromethyl)tetrahydrofuran-2-carboxamido)picolinamide

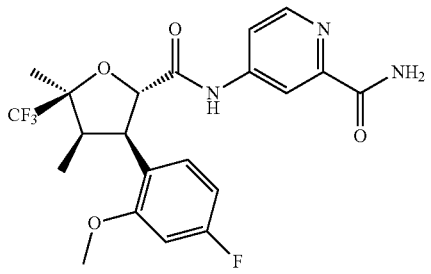 [SMILES: COc1cc(F)ccc1[C@@H]1[C@@H](C(=O)Nc2ccnc(C(N)=O)c2)O[C@](C)(C(F)(F)F)[C@@H]1C]

4-((2S,3R,4R,5S)-3-(4-fluoro-2-methoxyphenyl)-4,5-dimethyl-5-(trifluoromethyl)tetrahydrofuran-2-carboxamido)picolinamide

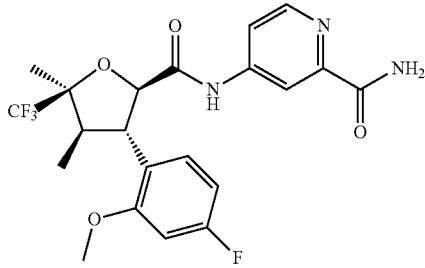 [SMILES: COc1cc(F)ccc1[C@@H]1[C@@H](C)[C@@](C)(C(F)(F)F)O[C@H]1C(=O)Nc1ccnc(C(N)=O)c1]

4-((2R,3S,4R,5S)-3-(4-fluoro-2-methoxyphenyl)-4,5-dimethyl-5-(trifluoromethyl)tetrahydrofuran-2-carboxamido)picolinamide

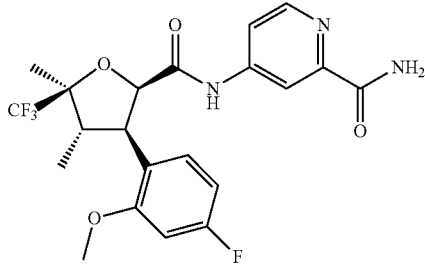 [SMILES: COc1cc(F)ccc1[C@@H]1[C@H](C(=O)Nc2ccnc(C(N)=O)c2)O[C@](C)(C(F)(F)F)[C@H]1C]

4-((2R,3R,4S,5S)-3-(4-fluoro-2-methoxyphenyl)-4,5-dimethyl-5-(trifluoromethyl)tetrahydrofuran-2-carboxamido)picolinamide TABLE A-continued Compound Structures and Names.


4-((2R,3R,4R,5R)-3-(4-fluoro-2-
methoxyphenyl)-4,5-dimethyl-5-
(trifluoromethyl)tetrahydrofuran-
2-carboxamido)picolinamide


4-((2S,3S,4R,5S)-3-(4-fluoro-2-
methoxyphenyl)-4,5-dimethyl-5-
(trifluoromethyl)tetrahydrofuran-2-
carboxamido)picolinamide


4-((2S,3R,4S,5S)-3-(4-fluoro-2-
methoxyphenyl)-4,5-dimethyl-5-
(trifluoromethyl)tetrahydrofuran-
2-carboxamido)picolinamide

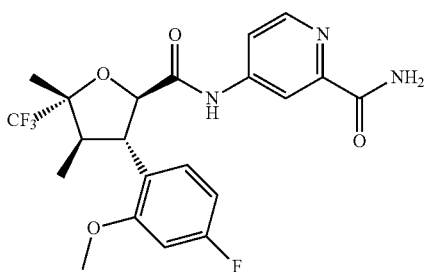 [SMILES: COc1cc(F)ccc1[C@@H]1[C@@H](C)[C@](C)(C(F)(F)F)O[C@H]1C(=O)Nc1ccnc(C(N)=O)c1]

4-((2S,3R,4R,5R)-3-(4-fluoro-2-
methoxyphenyl)-4,5-dimethyl-5-
(trifluoromethyl)tetrahydrofuran-
2-carboxamido)picolinamide TABLE A-continued Compound Structures and Names.

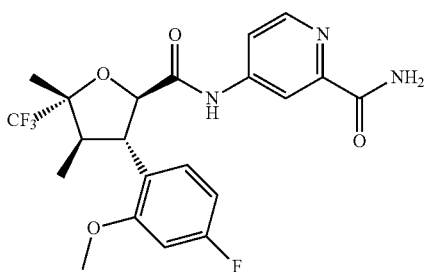 [SMILES: COc1cc(F)ccc1[C@@H]1[C@@H](C)[C@](C)(C(F)(F)F)O[C@H]1C(=O)Nc1ccnc(C(N)=O)c1]

4-((2R,3S,4S,5S)-3-(4-fluoro-2-methoxyphenyl)-4,5-
dimethyl-5-(trifluoromethyl)tetrahydrofuran-2-
carboxamido)picolinamide


4-((2R,3S,4R,5R)-3-(4-fluoro-2-
methoxyphenyl)-4,5-dimethyl-5-
(trifluoromethyl)tetrahydrofuran-
2-carboxamido)picolinamide


4-((2R,3R,4S,5R)-3-(4-fluoro-2-methoxyphenyl)-4,5-
dimethyl-5-(trifluoromethyl)tetrahydrofuran-2-
carboxamido)picolinamide 4-((2S,3S,4S,5S)-3-(4-fluoro-2-
methoxyphenyl)-4,5-dimethyl-5-
(trifluoromethyl)tetrahydrofuran-
2-carboxamido)picolinamide TABLE A-continued Compound Structures and Names.

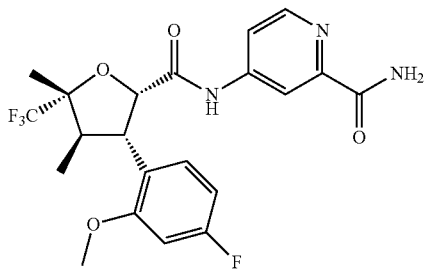 [SMILES: COc1cc(F)ccc1[C@H]1[C@@H](C(=O)Nc2ccnc(C(N)=O)c2)O[C@@](C)(C(F)(F)F)[C@@H]1C]

4-((2S,3S,4R,5R)-3-(4-fluoro-2-methoxyphenyl)-4,5-dimethyl-5-(trifluoromethyl)tetrahydrofuran-2-carboxamido)picolinamide

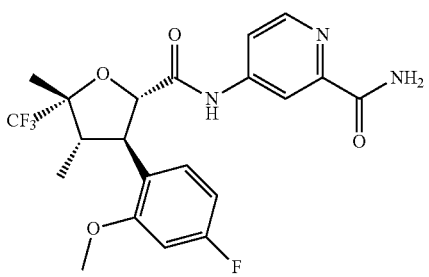 [SMILES: COc1cc(F)ccc1[C@@H]1[C@@H](C(=O)Nc2ccnc(C(N)=O)c2)O[C@@](C)(C(F)(F)F)[C@H]1C]

4-((2S,3R,4S,5R)-3-(4-fluoro-2-methoxyphenyl)-4,5-dimethyl-5-(trifluoromethyl)tetrahydrofuran-2-carboxamido)picolinamide

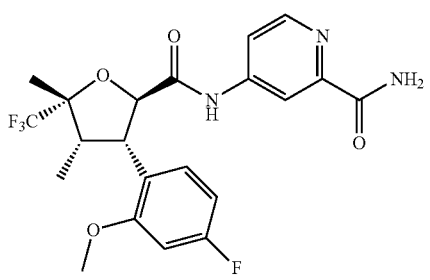 [SMILES: COc1cc(F)ccc1[C@H]1[C@H](C(=O)Nc2ccnc(C(N)=O)c2)O[C@@](C)(C(F)(F)F)[C@H]1C]

4-((2R,3S,4S,5R)-3-(4-fluoro-2-methoxyphenyl)-4,5-dimethyl-5-(trifluoromethyl)tetrahydrofuran-2-carboxamido)picolinamide

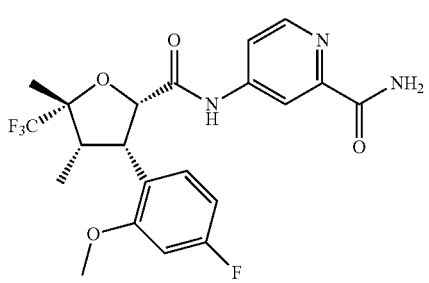 [SMILES: COc1cc(F)ccc1[C@H]1[C@@H](C(=O)Nc2ccnc(C(N)=O)c2)O[C@@](C)(C(F)(F)F)[C@H]1C]

4-((2S,3S,4S,5R)-3-(4-fluoro-2-methoxyphenyl)-4,5-dimethyl-5-(trifluoromethyl)tetrahydrofuran-2-carboxamido)picolinamide TABLE A-continued Compound Structures and Names.

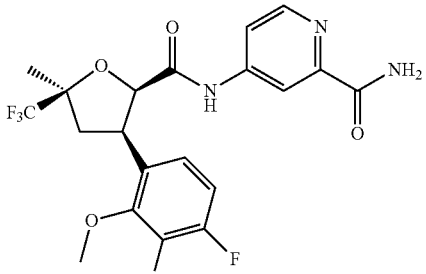

4-((2R,3R,5S)-3-(3,4-difluoro-2-methoxyphenyl)-5-methyl-5-(trifluoromethyl)tetrahydrofuran-2-carboxamido)picolinamide

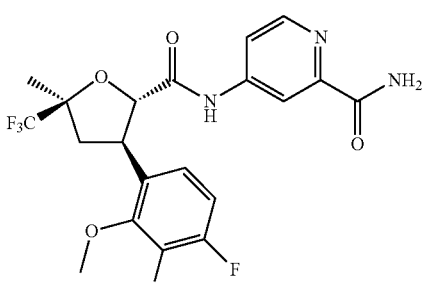

4-((2S,3R,5S)-3-(3,4-difluoro-2-methoxyphenyl)-5-methyl-5-(trifluoromethyl)tetrahydrofuran-2-carboxamido)picolinamide

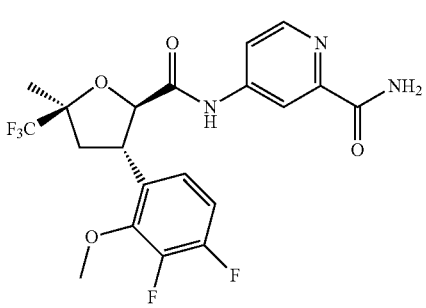 [SMILES: COc1c([C@@H]2C[C@@](C)(C(F)(F)F)O[C@H]2C(=O)Nc2ccnc(C(N)=O)c2)ccc(F)c1F]

4-((2R,3R,5R)-3-(3,4-difluoro-2-methoxyphenyl)-5-methyl-5-(trifluoromethyl)tetrahydrofuran-2-carboxamido)picolinamide

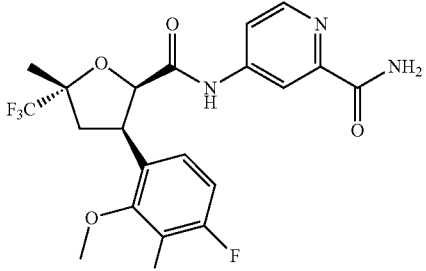

4-((2R,3S,5S)-3-(3,4-difluoro-2-methoxyphenyl)-5-methyl-5-(trifluoromethyl)tetrahydrofuran-2-carboxamido)picolinamide TABLE A-continued Compound Structures and Names.

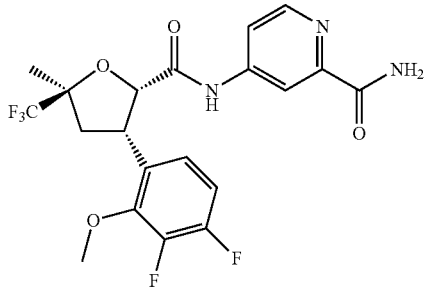 [SMILES: COc1c([C@@H]2C[C@@](C)(C(F)(F)F)O[C@@H]2C(=O)Nc2ccnc(C(N)=O)c2)ccc(F)c1F]

4-((2S,3S,5S)-3-(3,4-difluoro-2-methoxyphenyl)-5-methyl-5-(trifluoromethyl)tetrahydrofuran-2-carboxamido)picolinamide

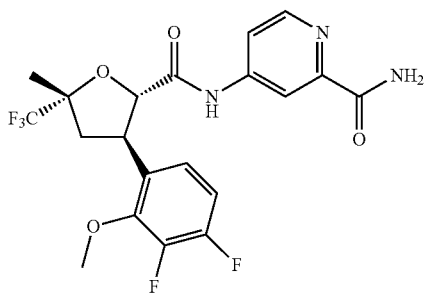 [SMILES: COc1c([C@H]2C[C@](C)(C(F)(F)F)O[C@@H]2C(=O)Nc2ccnc(C(N)=O)c2)ccc(F)c1F]

4-((2S,3R,5R)-3-(3,4-difluoro-2-methoxyphenyl)-5-methyl-5-(trifluoromethyl)tetrahydrofuran-2-carboxamido)picolinamide

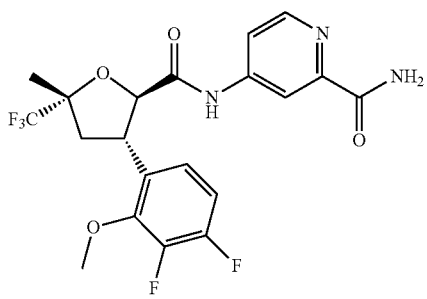 [SMILES: COc1c([C@@H]2C[C@](C)(C(F)(F)F)O[C@H]2C(=O)Nc2ccnc(C(N)=O)c2)ccc(F)c1F]

4-((2R,3S,5R)-3-(3,4-difluoro-2-methoxyphenyl)-5-methyl-5-(trifluoromethyl)tetrahydrofuran-2-carboxamido)picolinamide

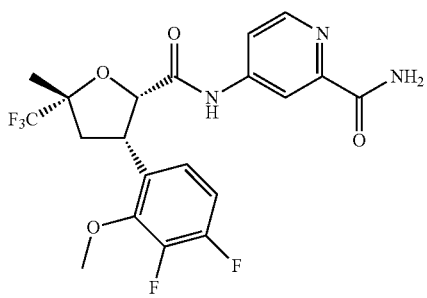 [SMILES: COc1c([C@@H]2C[C@](C)(C(F)(F)F)O[C@@H]2C(=O)Nc2ccnc(C(N)=O)c2)ccc(F)c1F]

4-((2S,3S,5R)-3-(3,4-difluoro-2-methoxyphenyl)-5-methyl-5-(trifluoromethyl)tetrahydrofuran-2-carboxamido)picolinamide

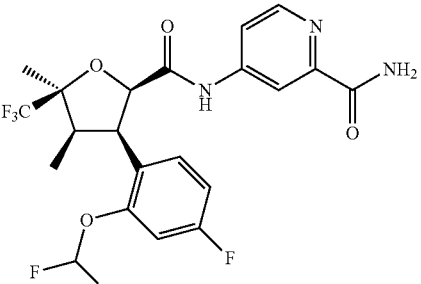

4-((2R,3R,4R,5S)-3-(2-(difluoromethoxy)-4-fluorophenyl)-4,5-dimethyl-5-(trifluoromethyl)tetrahydrofuran-2-carboxamido)picolinamide

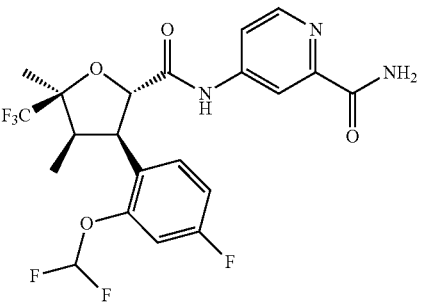

4-((2S,3R,4R,5S)-3-(2-(difluoromethoxy)-4-fluorophenyl)-4,5-dimethyl-5-(trifluoromethyl)tetrahydrofuran-2-carboxamido)picolinamide

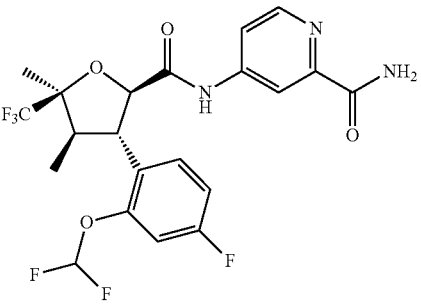 [SMILES: C[C@@H]1[C@@H](c2ccc(F)cc2OC(F)F)[C@H](C(=O)Nc2ccnc(C(N)=O)c2)O[C@]1(C)C(F)(F)F]

4-((2R,3S,4R,5S)-3-(2-(difluoromethoxy)-4-fluorophenyl)-4,5-dimethyl-5-(trifluoromethyl)tetrahydrofuran-2-carboxamido)picolinamide TABLE A-continued Compound Structures and Names.

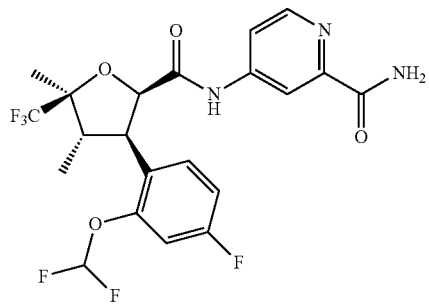 [SMILES: C[C@H]1[C@H](c2ccc(F)cc2OC(F)F)[C@H](C(=O)Nc2ccnc(C(N)=O)c2)O[C@]1(C)C(F)(F)F]

4-((2R,3R,4S,5S)-3-(2-(difluoromethoxy)-4-
fluorophenyl)-4,5-dimethyl-5-
(trifluoromethyl)tetrahydrofuran-2-
carboxamido)picolinamide

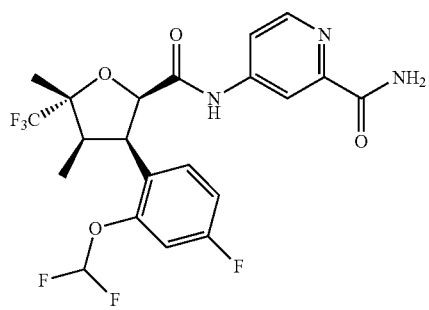 [SMILES: C[C@@H]1[C@H](c2ccc(F)cc2OC(F)F)[C@H](C(=O)Nc2ccnc(C(N)=O)c2)O[C@@]1(C)C(F)(F)F]

4-((2R,3R,4R,5R)-3-(2-(difluoromethoxy)-4-
fluorophenyl)-4,5-dimethyl-5-
(trifluoromethyl)tetrahydrofuran-2-
carboxamido)picolinamide

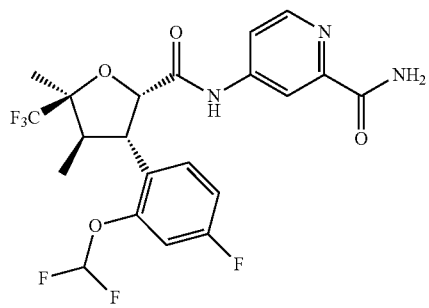 [SMILES: C[C@@H]1[C@@H](c2ccc(F)cc2OC(F)F)[C@@H](C(=O)Nc2ccnc(C(N)=O)c2)O[C@]1(C)C(F)(F)F]

4-((2S,3S,4R,5S)-3-(2-(difluoromethoxy)-4-
fluorophenyl)-4,5-dimethyl-5-
(trifluoromethyl)tetrahydrofuran-2-
carboxamido)picolinamide

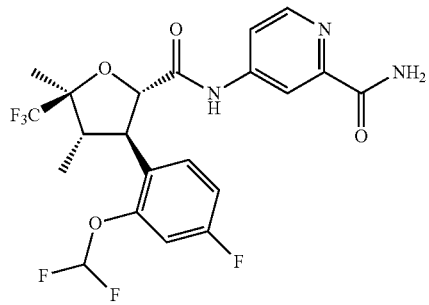 [SMILES: C[C@H]1[C@H](c2ccc(F)cc2OC(F)F)[C@@H](C(=O)Nc2ccnc(C(N)=O)c2)O[C@]1(C)C(F)(F)F]

4-((2S,3R,4S,5S)-3-(2-(difluoromethoxy)-4-
fluorophenyl)-4,5-dimethyl-5-
(trifluoromethyl)tetrahydrofuran-2-
carboxamido)picolinamide

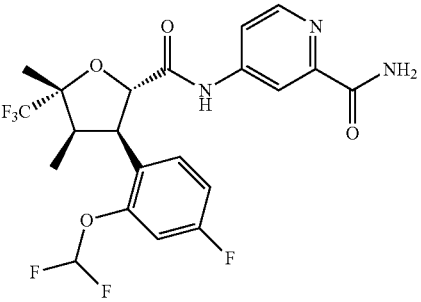 [SMILES: C[C@@H]1[C@H](c2ccc(F)cc2OC(F)F)[C@@H](C(=O)Nc2ccnc(C(N)=O)c2)O[C@@]1(C)C(F)(F)F]

4-((2S,3R,4R,5R)-3-(2-(difluoromethoxy)-4-
fluorophenyl)-4,5-dimethyl-5-
(trifluoromethyl)tetrahydrofuran-2-
carboxamido)picolinamide

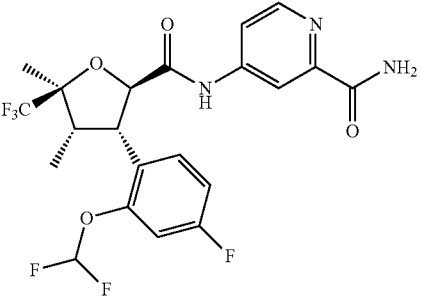 [SMILES: C[C@H]1[C@@H](c2ccc(F)cc2OC(F)F)[C@H](C(=O)Nc2ccnc(C(N)=O)c2)O[C@]1(C)C(F)(F)F]

4-((2R,3S,4S,5S)-3-(2-(difluoromethoxy)-4-
fluorophenyl)-4,5-dimethyl-5-
(trifluoromethyl)tetrahydrofuran-2-
carboxamido)picolinamide

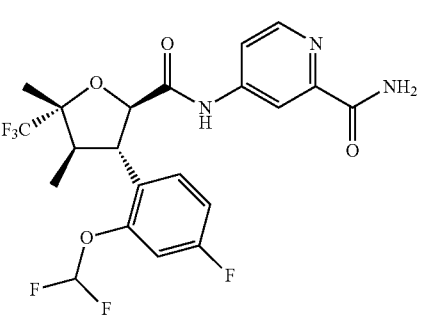 [SMILES: C[C@@H]1[C@@H](c2ccc(F)cc2OC(F)F)[C@H](C(=O)Nc2ccnc(C(N)=O)c2)O[C@@]1(C)C(F)(F)F]

4-((2R,3S,4R,5R)-3-(2-(difluoromethoxy)-4-
fluorophenyl)-4,5-dimethyl-5-
(trifluoromethyl)tetrahydrofuran-2-
carboxamido)picolinamide TABLE A-continued Compound Structures and Names.

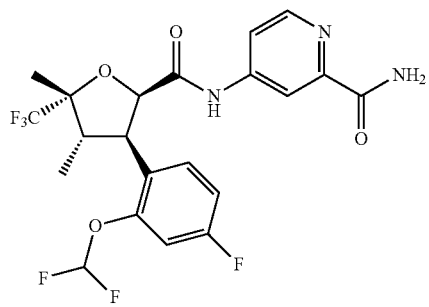 [SMILES: C[C@H]1[C@H](c2ccc(F)cc2OC(F)F)[C@H](C(=O)Nc2ccnc(C(N)=O)c2)O[C@@]1(C)C(F)(F)F]

4-((2R,3R,4S,5R)-3-(2-(difluoromethoxy)-4-
fluorophenyl)-4,5-dimethyl-5-
(trifluoromethyl)tetrahydrofuran-2-
carboxamido)picolinamide

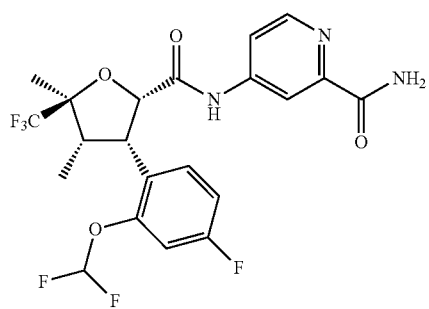 [SMILES: C[C@H]1[C@@H](c2ccc(F)cc2OC(F)F)[C@@H](C(=O)Nc2ccnc(C(N)=O)c2)O[C@]1(C)C(F)(F)F]

4-((2S,3S,4S,5S)-3-(2-(difluoromethoxy)-4-
fluorophenyl)-4,5-dimethyl-5-
(trifluoromethyl)tetrahydrofuran-2-
carboxamido)picolinamide

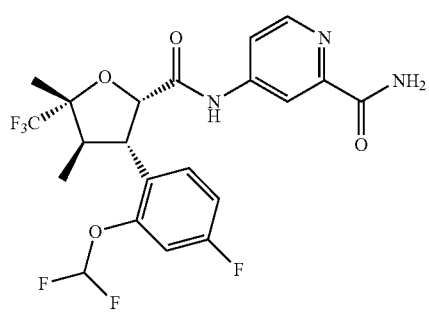 [SMILES: C[C@@H]1[C@@H](c2ccc(F)cc2OC(F)F)[C@@H](C(=O)Nc2ccnc(C(N)=O)c2)O[C@@]1(C)C(F)(F)F]

4-((2S,3S,4R,5R)-3-(2-(difluoromethoxy)-4-
fluorophenyl)-4,5-dimethyl-5-
(trifluoromethyl)tetrahydrofuran-2-
carboxamido)picolinannide

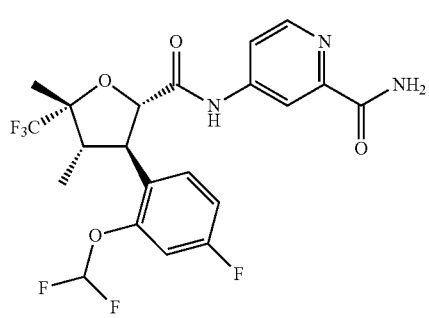 [SMILES: C[C@H]1[C@H](c2ccc(F)cc2OC(F)F)[C@@H](C(=O)Nc2ccnc(C(N)=O)c2)O[C@@]1(C)C(F)(F)F]

4-((2S,3R,4S,5R)-3-(2-(difluoromethoxy)-4-
fluorophenyl)-4,5-dimethyl-5-
(trifluoromethyl)tetrahydrofuran-2-
carboxamido)picolinamide

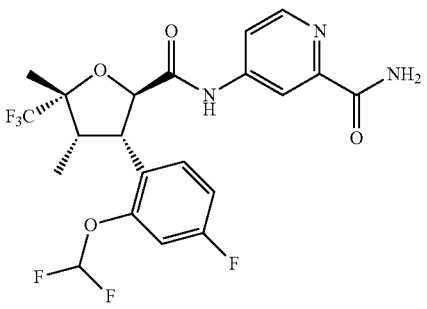 [SMILES: C[C@H]1[C@@H](c2ccc(F)cc2OC(F)F)[C@H](C(=O)Nc2ccnc(C(N)=O)c2)O[C@@]1(C)C(F)(F)F]

4-((2R,3S,4S,5R)-3-(2-(difluoromethoxy)-4-
fluorophenyl)-4,5-dimethyl-5-
(trifluoromethyl)tetrahydrofuran-2-
carboxamido)picolinamide

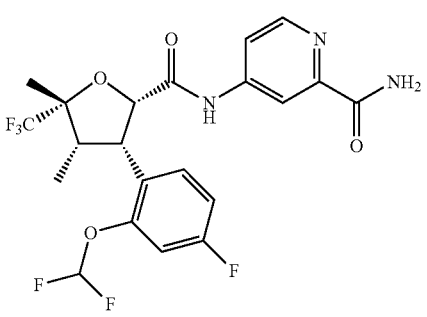

4-((2S,3S,4S,5R)-3-(2-(difluoromethoxy)-4-
fluorophenyl)-4,5-dimethyl-5-
(trifluoromethyl)tetrahydrofuran-2-
carboxamido)picolinamide

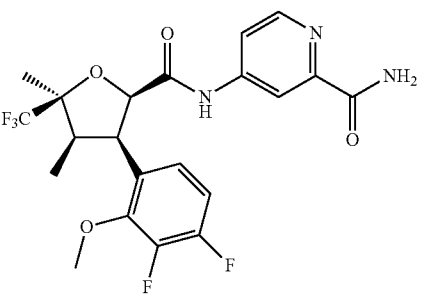 [SMILES: COc1c([C@H]2[C@@H](C)[C@@](C)(C(F)(F)F)O[C@H]2C(=O)Nc2ccnc(C(N)=O)c2)ccc(F)c1F]

4-((2R,3R,4R,5S)-3-(3,4-difluoro-2-
methoxyphenyl)-4,5-dimethyl-5-
(trifluoromethyl)tetrahydrofuran-2-
carboxamido)picolinamide TABLE A-continued Compound Structures and Names.

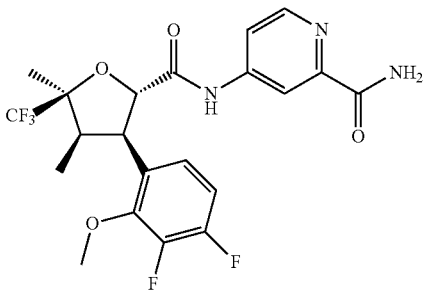 [SMILES: COc1c([C@@H]2[C@@H](C(=O)Nc3ccnc(C(N)=O)c3)O[C@](C)(C(F)(F)F)[C@@H]2C)ccc(F)c1F]

4-((2S,3R,4R,5S)-3-(3,4-difluoro-
2-methoxyphenyl)-4,5-dimethyl-5-
(trifluoromethyl)tetrahydrofuran-2-
carboxamido)picolinamide

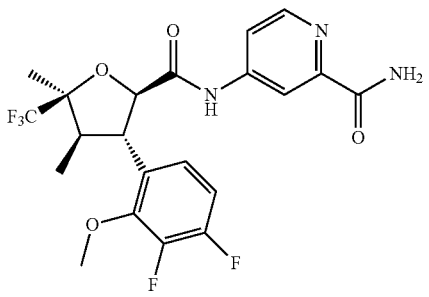 [SMILES: COc1c([C@@H]2[C@@H](C)[C@@](C)(C(F)(F)F)O[C@H]2C(=O)Nc2ccnc(C(N)=O)c2)ccc(F)c1F]

4-((2R,3S,4R,5S)-3-(3,4-difluoro-2-methoxyphenyl)-
4,5-dimethyl-5-(trifluoromethyl)tetrahydrofuran-2-
carboxamido)picolinamide

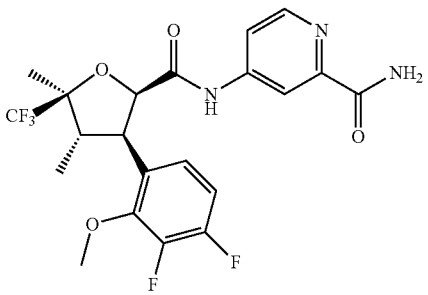 [SMILES: COc1c([C@@H]2[C@H](C(=O)Nc3ccnc(C(N)=O)c3)O[C@](C)(C(F)(F)F)[C@H]2C)ccc(F)c1F]

4-((2R,3R,4S,5S)-3-(3,4-difluoro-
2-methoxyphenyl)-4,5-dimethyl-5-
(trifluoromethyl)tetrahydrofuran-2-
carboxamido)picolinamide

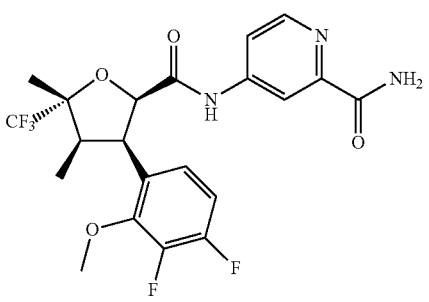 [SMILES: COc1c([C@H]2[C@@H](C)[C@](C)(C(F)(F)F)O[C@H]2C(=O)Nc2ccnc(C(N)=O)c2)ccc(F)c1F]

4-((2R,3R,4R,5R)-3-(3,4-difluoro-
2-methoxyphenyl)-4,5-dimethyl-5-
(trifluoromethyl)tetrahydrofuran-2-
carboxamido)picolinamide TABLE A-continued Compound Structures and Names.

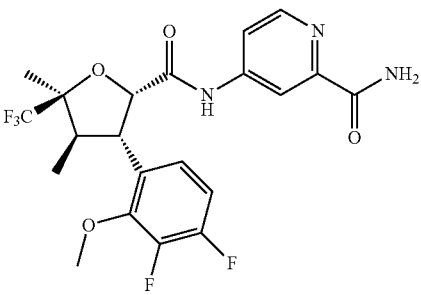 [SMILES: COc1c([C@H]2[C@@H](C(=O)Nc3ccnc(C(N)=O)c3)O[C@](C)(C(F)(F)F)[C@@H]2C)ccc(F)c1F]

4-((2S,3S,4R,5S)-3-(3,4-difluoro-2-
methoxyphenyl)-4,5-dimethyl-5-
(trifluoromethyl)tetrahydrofuran-2-
carboxamido)picolinamide

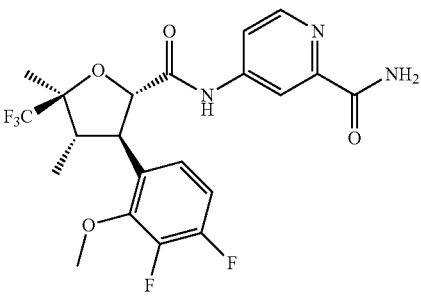 [SMILES: COc1c([C@@H]2[C@@H](C(=O)Nc3ccnc(C(N)=O)c3)O[C@](C)(C(F)(F)F)[C@H]2C)ccc(F)c1F]

4-((2S,3R,4S,5S)-3-(3,4-difluoro-2-
methoxyphenyl)-4,5-dimethyl-5-
(trifluoromethyl)tetrahydrofuran-2-
carboxamido)picolinamide

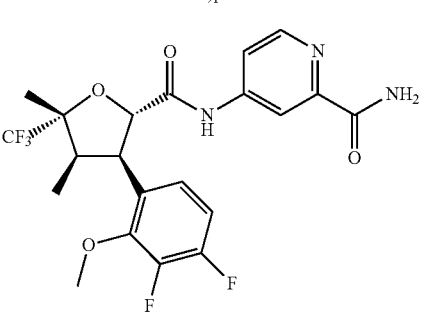

4-((2S,3R,4R,5R)-3-(3,4-difluoro-
2-methoxyphenyl)-4,5-dimethyl-5-
(trifluoromethyl)tetrahydrofuran-2-
carboxamido)picolinamide

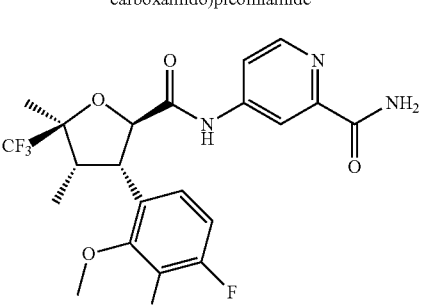

4-((2R,3S,4S,5S)-3-(3,4-difluoro-2-
methoxyphenyl)-4,5-dimethyl-5-
(trifluoromethyl)tetrahydrofuran-2-
carboxamido)picolinamide TABLE A-continued Compound Structures and Names.

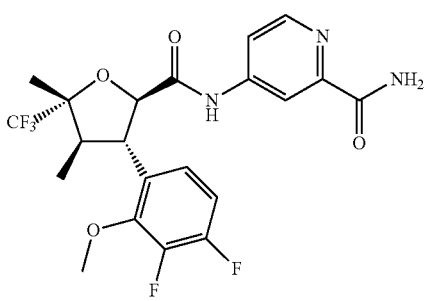 [SMILES: COc1c([C@@H]2[C@@H](C)[C@](C)(C(F)(F)F)O[C@H]2C(=O)Nc2ccnc(C(N)=O)c2)ccc(F)c1F]

4-((2R,3S,4R,5R)-3-(3,4-difluoro-2-
methoxyphenyl)-4,5-dimethyl-5-
(trifluoromethyl)tetrahydrofuran-2-
carboxamido)picolinamide

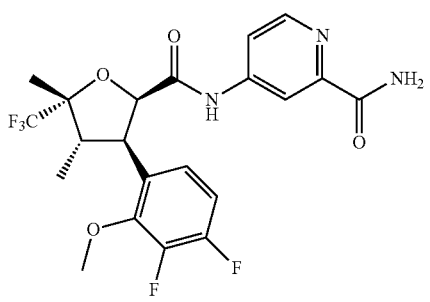 [SMILES: COc1c([C@@H]2[C@H](C(=O)Nc3ccnc(C(N)=O)c3)O[C@@](C)(C(F)(F)F)[C@H]2C)ccc(F)c1F]

4-((2R,3R,4S,5R)-3-(3,4-difluoro-2-methoxyphenyl)-
4,5-dimethyl-5-(trifluoromethyl)tetrahydrofuran-2-
carboxamido)picolinamide

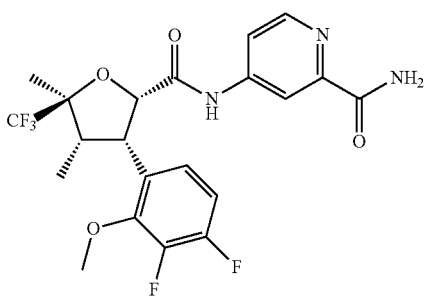 [SMILES: COc1c([C@H]2[C@@H](C(=O)Nc3ccnc(C(N)=O)c3)O[C@](C)(C(F)(F)F)[C@H]2C)ccc(F)c1F]

4-((2S,3S,4S,5S)-3-(3,4-difluoro-2-
methoxyphenyl)-4,5-dimethyl-5-
(trifluoromethyl)tetrahydrofuran-2-
carboxamido)picolinamide

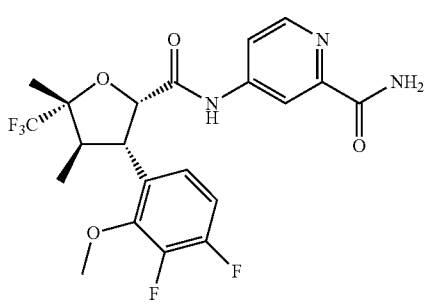 [SMILES: COc1c([C@H]2[C@@H](C(=O)Nc3ccnc(C(N)=O)c3)O[C@@](C)(C(F)(F)F)[C@@H]2C)ccc(F)c1F]

4-((2S,3S,4R,5R)-3-(3,4-difluoro-2-methoxyphenyl)-
4,5-dimethyl-5-(trifluoromethyl)tetrahydrofuran-2-
carboxamido)picolinamide TABLE A-continued Compound Structures and Names.

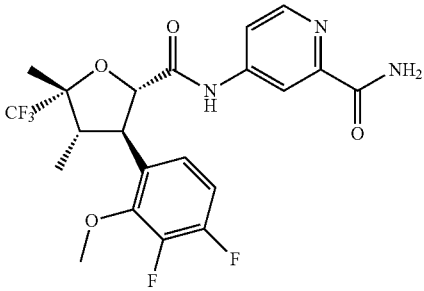 [SMILES: COc1c([C@@H]2[C@@H](C(=O)Nc3ccnc(C(N)=O)c3)O[C@@](C)(C(F)(F)F)[C@H]2C)ccc(F)c1F]

4-((2S,3R,4S,5R)-3-(3,4-difluoro-
2-methoxyphenyl)-4,5-dimethyl-5-
(trifluoromethyl)tetrahydrofuran-2-
carboxamido)picolinamide

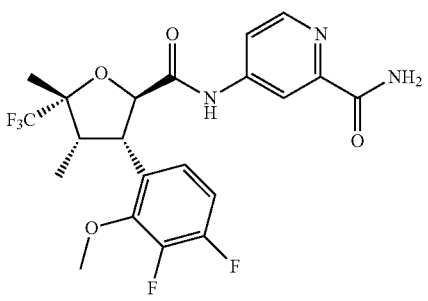 [SMILES: COc1c([C@H]2[C@H](C(=O)Nc3ccnc(C(N)=O)c3)O[C@@](C)(C(F)(F)F)[C@H]2C)ccc(F)c1F]

4-((2R,3S,4S,5R)-3-(3,4-difluoro-2-nnethoxyphenyl)-
4,5-dimethyl-5-(trifluoromethyl)tetrahydrofuran-2-
carboxamido)picolinamide

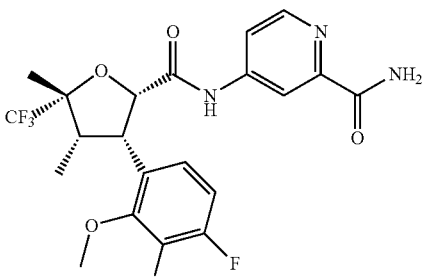

4-((2S,3S,4S,5R)-3-(3,4-difluoro-2-
methoxyphenyl)-4,5-dimethyl-5-
(trifluoromethyl)tetrahydrofuran-2-
carboxamido)picolinamide

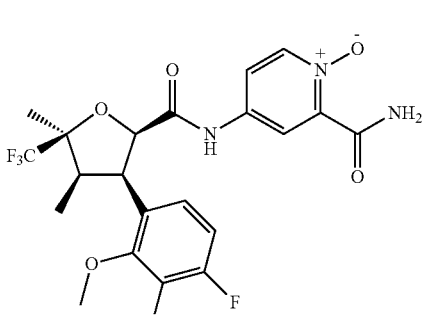

2-carbamoyl-4-((2R,3R,4R,5S)-3-(3,4-difluoro-2-
methoxyphenyl)-4,5-dimethyl-5-
(trifluoromethyl)tetrahydrofuran-2-
carboxamido)pyridine 1-oxide TABLE A-continued Compound Structures and Names.

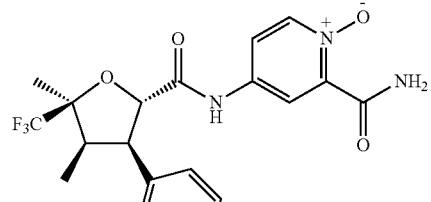

2-carbamoyl-4-((2S,3R,4R,5S)-3-(3,4-difluoro-2-
methoxyphenyl)-4,5-dimethyl-5-
(trifluoromethyl)tetrahydrofuran-2-
carboxamido)pyridine 1-oxide

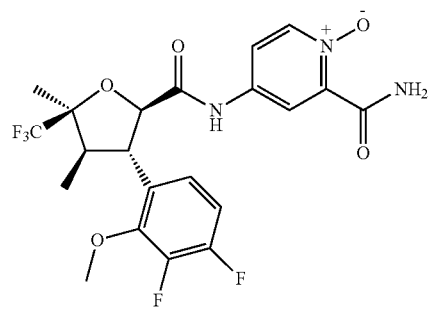

2-carbamoyl-4-((2R,3S,4R,5S)-3-(3,4-difluoro-2-
methoxyphenyl)-4,5-dimethyl-5-
(trifluoromethyl)tetrahydrofuran-2-
carboxamido)pyridine 1-oxide

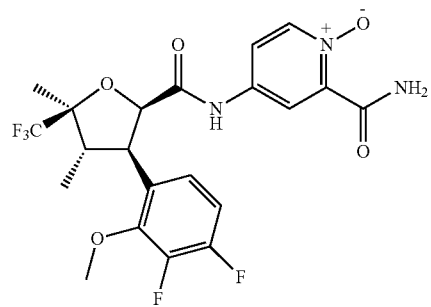

2-carbamoyl-4-((2R,3R,4S,5S)-3-(3,4-difluoro-2-
methoxyphenyl)-4,5-dimethyl-5-
(trifluoromethyl)tetrahydrofuran-2-
carboxamido)pyridine 1-oxide

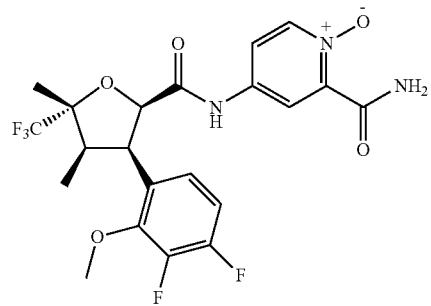

TABLE A-continued

Compound Structures and Names.

2-carbamoyl-4-((2R,3R,4R,5R)-3-(3,4-difluoro-2-
methoxyphenyl)-4,5-dimethyl-5-
(trifluoromethyl)tetrahydrofuran-2-
carboxamido)pyridine 1-oxide

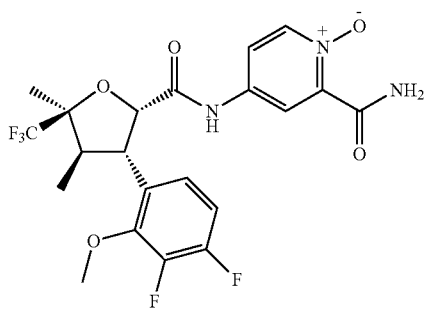

2-carbamoyl-4-((2S,3S,4R,5S)-3-(3,4-difluoro-2-
methoxyphenyl)-4,5-dimethyl-5-
(trifluoromethyl)tetrahydrofuran-2-
carboxamido)pyridine 1-oxide

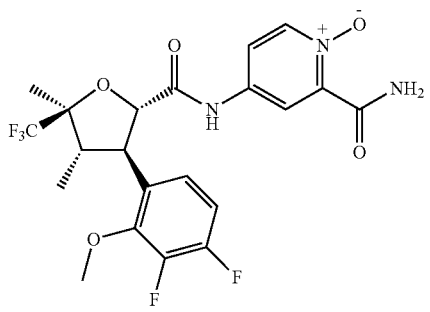

2-carbamoyl-4-((2S,3R,4S,5S)-3-(3,4-
difluoro-2-methoxyphenyl)-4,5-dimethyl-5-
(trifluoromethyl)tetrahydrofuran-2-
carboxamido)pyridine 1-oxide

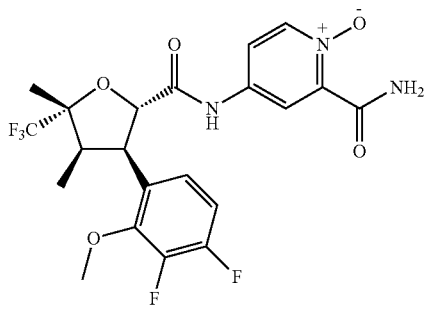

2-carbamoyl-4-((2S,3R,4R,5R)-3-(3,4-
difluoro-2-methoxyphenyl)-4,5-dimethyl-5-
(trifluoromethyl)tetrahydrofuran-2-
carboxamido)pyridine 1-oxide TABLE A-continued Compound Structures and Names.

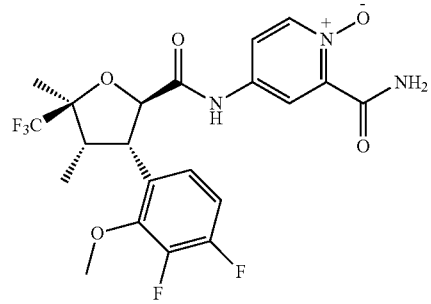

2-carbamoyl-4-((2R,3S,4S,5S)-3-(3,4-difluoro-
2-methoxyphenyl)-4,5-dimethyl-5-
(trifluoromethyl)tetrahydrofuran-2-
carboxamido)pyridine 1-oxide

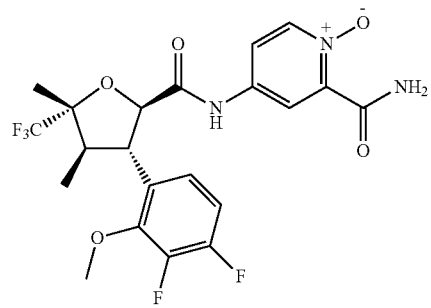

2-carbamoyl-4-((2R,3S,4R,5R)-3-(3,4-difluoro-2-
methoxyphenyl)-4,5-dimethyl-5-
(trifluoromethyl)tetrahydrofuran-2-
carboxamido)pyridine 1-oxide

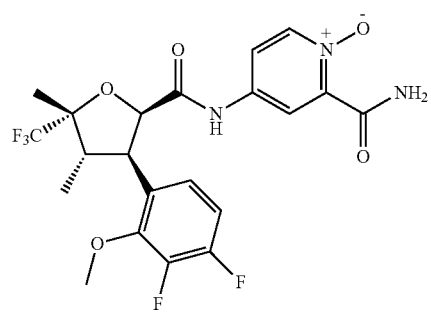

2-carbamoyl-4-((2R,3R,4S,5R)-3-(3,4-
difluoro-2-methoxyphenyl)-4,5-dimethyl-5-
(trifluoromethyl)tetrahydrofuran-2-
carboxamido)pyridine 1-oxide

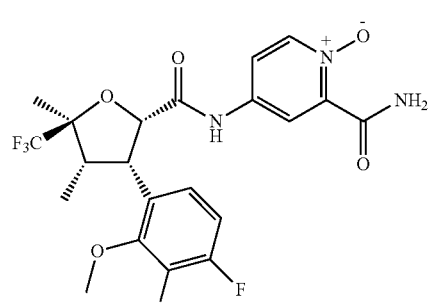

TABLE A-continued

Compound Structures and Names.

2-carbamoyl-4-((2S,3S,4S,5S)-3-(3,4-difluoro-2-
methoxyphenyl)-4,5-dimethyl-5-
(trifluoromethyl)tetrahydrofuran-2-
carboxamido)pyridine 1-oxide

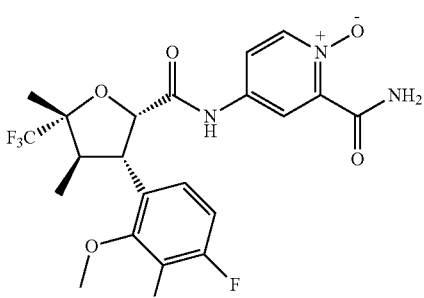

2-carbamoyl-4-((2S,3S,4R,5R)-3-(3,4-difluoro-
2-methoxyphenyl)-4,5-dimethyl-5-
(trifluoromethyl)tetrahydrofuran-2-
carboxamido)pyridine 1-oxide

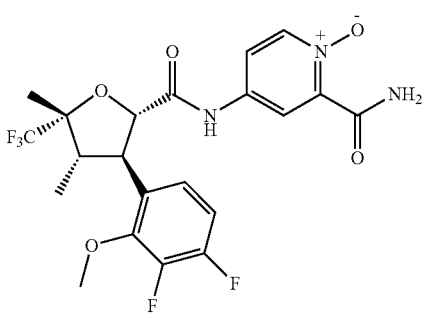

2-carbamoyl-4-((2S,3R,4S,5R)-3-(3,4-difluoro-2-
methoxyphenyl)-4,5-dimethyl-5-
(trifluoromethyl)tetrahydrofuran-2-
carboxamido)pyridine 1-oxide

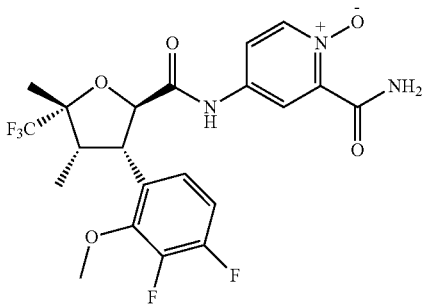

2-carbamoyl-4-((2R,3S,4S,5R)-3-(3,4-
difluoro-2-methoxyphenyl)-4,5-dimethyl-5-
(trifluoromethyl)tetrahydrofuran-2-
carboxamido)pyridine 1-oxide TABLE A-continued Compound Structures and Names.

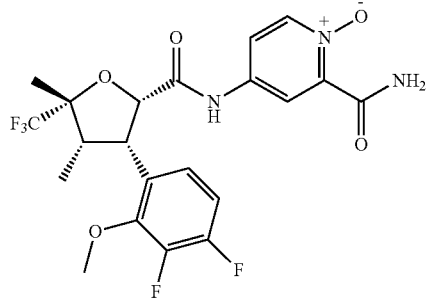

2-carbamoyl-4-((2S,3S,4S,5R)-3-(3,4-difluoro-2-methoxyphenyl)-4,5-dimethyl-5-(trifluoromethyl)tetrahydrofuran-2-carboxamido)pyridine 1-oxide

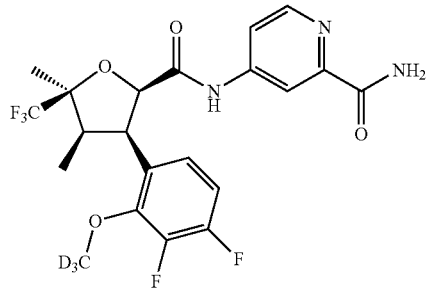 [SMILES: [2H]C([2H])([2H])Oc1c([C@H]2[C@@H](C)[C@@](C)(C(F)(F)F)O[C@H]2C(=O)Nc2ccnc(C(N)=O)c2)ccc(F)c1F]

4-((2R,3R,4R,5S)-3-(3,4-difluoro-2-(methoxy-d₃)phenyl)-4,5-dimethyl-5-(trifluoromethyl)tetrahydrofuran-2-carboxamido)picolinamide

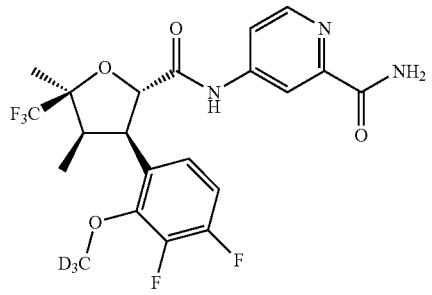 [SMILES: [2H]C([2H])([2H])Oc1c([C@@H]2[C@@H](C(=O)Nc3ccnc(C(N)=O)c3)O[C@](C)(C(F)(F)F)[C@@H]2C)ccc(F)c1F]

4-((2S,3R,4R,5S)-3-(3,4-difluoro-2-(methoxy-d₃)phenyl)-4,5-dimethyl-5-(trifluoromethyl)tetrahydrofuran-2-carboxamido)picolinamide

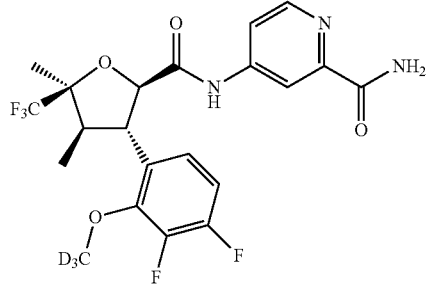 [SMILES: [2H]C([2H])([2H])Oc1c([C@@H]2[C@@H](C)[C@@](C)(C(F)(F)F)O[C@H]2C(=O)Nc2ccnc(C(N)=O)c2)ccc(F)c1F]

TABLE A-continued

Compound Structures and Names.

4-((2R,3S,4R,5S)-3-(3,4-difluoro-2-(methoxy-d₃)phenyl)-4,5-dimethyl-5-(trifluoromethyl)tetrahydrofuran-2-carboxamido)picolinamide

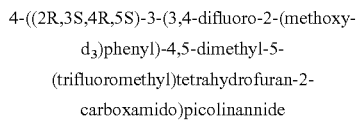
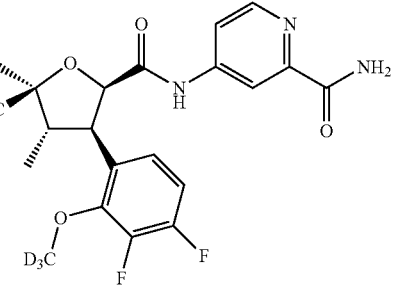

4-((2R,3R,4S,5S)-3-(3,4-difluoro-2-(methoxy-d₃)phenyl)-4,5-dimethyl-5-(trifluoromethyl)tetrahydrofuran-2-carboxamido)picolinamide

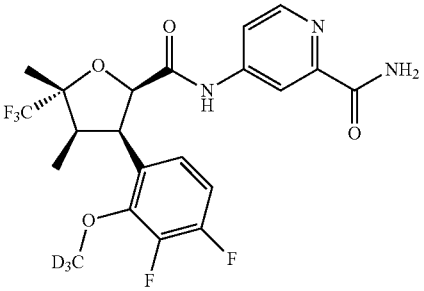 [SMILES: [2H]C([2H])([2H])Oc1c([C@H]2[C@@H](C)[C@](C)(C(F)(F)F)O[C@H]2C(=O)Nc2ccnc(C(N)=O)c2)ccc(F)c1F]

4-((2R,3R,4R,5R)-3-(3,4-difluoro-2-(methoxy-d₃)phenyl)-4,5-dimethyl-5-(trifluoromethyl)tetrahydrofuran-2-carboxamido)picolinamide

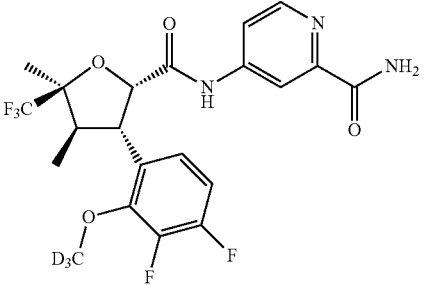 [SMILES: [2H]C([2H])([2H])Oc1c([C@H]2[C@@H](C(=O)Nc3ccnc(C(N)=O)c3)O[C@](C)(C(F)(F)F)[C@@H]2C)ccc(F)c1F]

4-((2S,3S,4R,5S)-3-(3,4-difluoro-2-(methoxy-d₃)phenyl)-4,5-dimethyl-5-(trifluoromethyl)tetrahydrofuran-2-carboxamido)picolinamide TABLE A-continued Compound Structures and Names.

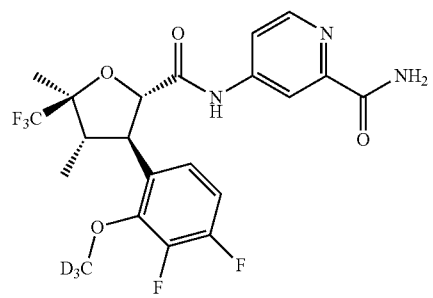 [SMILES: [2H]C([2H])([2H])Oc1c([C@@H]2[C@@H](C(=O)Nc3ccnc(C(N)=O)c3)O[C@](C)(C(F)(F)F)[C@H]2C)ccc(F)c1F]

4-((2S,3R,4S,5S)-3-(3,4-difluoro-2-(methoxy-d₃)phenyl)-4,5-dimethyl-5-(trifluoromethyl)tetrahydrofuran-2-carboxamido)picolinamide

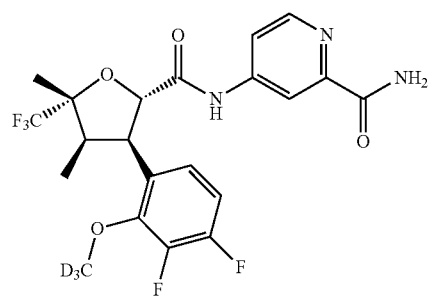 [SMILES: [2H]C([2H])([2H])Oc1c([C@@H]2[C@@H](C(=O)Nc3ccnc(C(N)=O)c3)O[C@@](C)(C(F)(F)F)[C@@H]2C)ccc(F)c1F]

4-((2S,3R,4R,5R)-3-(3,4-difluoro-2-(methoxy-d₃)phenyl)-4,5-dimethyl-5-(trifluoromethyl)tetrahydrofuran-2-carboxamido)picolinamide

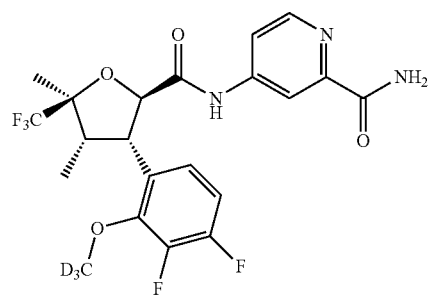 [SMILES: [2H]C([2H])([2H])Oc1c([C@H]2[C@H](C(=O)Nc3ccnc(C(N)=O)c3)O[C@](C)(C(F)(F)F)[C@H]2C)ccc(F)c1F]

4-((2R,3S,4S,5S)-3-(3,4-difluoro-2-(methoxy-d₃)phenyl)-4,5-dimethyl-5-(trifluoromethyl)tetrahydrofuran-2-carboxamido)picolinamide

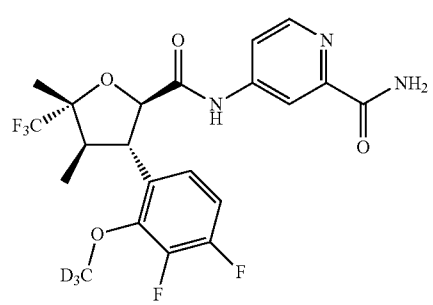 [SMILES: [2H]C([2H])([2H])Oc1c([C@@H]2[C@@H](C)[C@](C)(C(F)(F)F)O[C@H]2C(=O)Nc2ccnc(C(N)=O)c2)ccc(F)c1F]

4-((2R,3S,4R,5R)-3-(3,4-difluoro-2-(methoxy-d₃)phenyl)-4,5-dimethyl-5-(trifluoromethyl)tetrahydrofuran-2-carboxamido)picolinamide TABLE A-continued Compound Structures and Names.

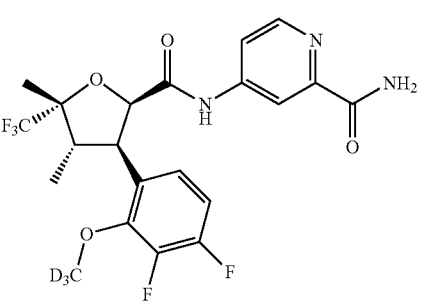 [SMILES: [2H]C([2H])([2H])Oc1c([C@@H]2[C@H](C(=O)Nc3ccnc(C(N)=O)c3)O[C@@](C)(C(F)(F)F)[C@H]2C)ccc(F)c1F]

4-((2R,3R,4S,5R)-3-(3,4-difluoro-2-(methoxy-d₃)phenyl)-4,5-dimethyl-5-(trifluoromethyl)tetrahydrofuran-2-carboxamido)picolinamide

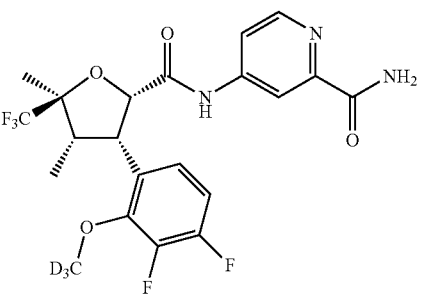 [SMILES: [2H]C([2H])([2H])Oc1c([C@H]2[C@@H](C(=O)Nc3ccnc(C(N)=O)c3)O[C@](C)(C(F)(F)F)[C@H]2C)ccc(F)c1F]

4-((2S,3S,4S,5S)-3-(3,4-difluoro-2-(methoxy-d₃)phenyl)-4,5-dimethyl-5-(trifluoromethyl)tetrahydrofuran-2-carboxamido)picolinamide

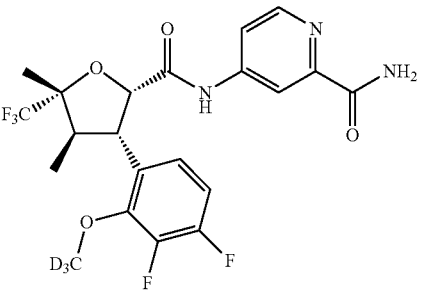 [SMILES: [2H]C([2H])([2H])Oc1c([C@H]2[C@@H](C(=O)Nc3ccnc(C(N)=O)c3)O[C@@](C)(C(F)(F)F)[C@@H]2C)ccc(F)c1F]

4-((2S,3S,4R,5R)-3-(3,4-difluoro-2-(methoxy-d₃)phenyl)-4,5-dimethyl-5-(trifluoromethyl)tetrahydrofuran-2-carboxamido)picolinamide

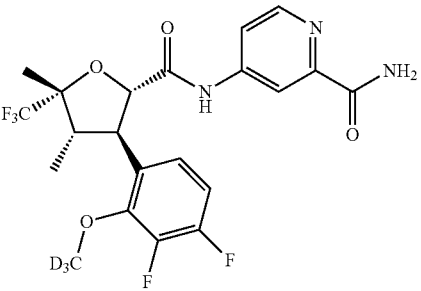 [SMILES: [2H]C([2H])([2H])Oc1c([C@@H]2[C@@H](C(=O)Nc3ccnc(C(N)=O)c3)O[C@@](C)(C(F)(F)F)[C@H]2C)ccc(F)c1F]

TABLE A-continued

Compound Structures and Names.

4-((2S,3R,4S,5R)-3-(3,4-difluoro-2-(methoxy-d₃)phenyl)-4,5-dimethyl-5-(trifluoromethyl)tetrahydrofuran-2-carboxamido)picolinamide 4-((2R,3S,4S,5R)-3-(3,4-difluoro-2-(methoxy-d₃)phenyl)-4,5-dimethyl-5-(trifluoromethyl)tetrahydrofuran-2-carboxamido)picolinamide 4-((2S,3S,4S,5R)-3-(3,4-difluoro-2-(methoxy-d₃)phenyl)-4,5-dimethyl-5-(trifluoromethyl)tetrahydrofuran-2-carboxamido)picolinamide 4-((2R,3R,4R,5S)-3-(2-(difluoromethoxy)-3,4-difluorophenyl)-4,5-dimethyl-5-(trifluoromethyl)tetrahydrofuran-2-carboxamido)picolinamide 4-((2S,3R,4R,5S)-3-(2-(difluoromethoxy)-3,4-difluorophenyl)-4,5-dimethyl-5-(trifluoromethyl)tetrahydrofuran-2-carboxamido)picolinamide 4-((2R,3S,4R,5S)-3-(2-(difluoromethoxy)-3,4-difluorophenyl)-4,5-dimethyl-5-(trifluoromethyl)tetrahydrofuran-2-carboxamido)picolinamide 4-((2R,3R,4S,5S)-3-(2-(difluoromethoxy)-3,4-difluorophenyl)-4,5-dimethyl-5-(trifluoromethyl)tetrahydrofuran-2-carboxamido)picolinamide 4-((2R,3R,4R,5R)-3-(2-(difluoromethoxy)-3,4-difluorophenyl)-4,5-dimethyl-5-

TABLE A-continued

Compound Structures and Names.

(trifluoromethyl)tetrahydrofuran-2-carboxamido)picolinamide 4-((2S,3S,4R,5S)-3-(2-(difluoromethoxy)-3,4-difluorophenyl)-4,5-dimethyl-5-(trifluoromethyl)tetrahydrofuran-2-carboxamido)picolinamide 4-((2S,3R,4S,5S)-3-(2-(difluoromethoxy)-3,4-difluorophenyl)-4,5-dimethyl-5-(trifluoromethyl)tetrahydrofuran-2-carboxamido)picolinamide 4-((2S,3R,4R,5R)-3-(2-(difluoromethoxy)-3,4-difluorophenyl)-4,5-dimethyl-5-(trifluoromethyl)tetrahydrofuran-2-carboxamido)picolinamide 4-((2R,3S,4S,5S)-3-(2-(difluoromethoxy)-3,4-difluorophenyl)-4,5-dimethyl-5-(trifluoromethyl)tetrahydrofuran-2-carboxamido)picolinamide 4-((2R,3S,4R,5R)-3-(2-(difluoromethoxy)-3,4-difluorophenyl)-4,5-dimethyl-5-(trifluoromethyl)tetrahydrofuran-2-carboxamido)picolinamide 4-((2R,3R,4S,5R)-3-(2-(difluoromethoxy)-3,4-difluorophenyl)-4,5-dimethyl-5-(trifluoromethyl)tetrahydrofuran-2-carboxamido)picolinamide 4-((2S,3S,4S,5S)-3-(2-(difluoromethoxy)-3,4-difluorophenyl)-4,5-dimethyl-5-(trifluoromethyl)tetrahydrofuran-2-carboxamido)picolinamide TABLE A-continued Compound Structures and Names.

4-((2S,3S,4R,5R)-3-(2-(difluoromethoxy)-3,4-difluorophenyl)-4,5-dimethyl-5-(trifluoromethyl)tetrahydrofuran-2-carboxamido)picolinamide 4-((2S,3R,4S,5R)-3-(2-(difluoromethoxy)-3,4-difluorophenyl)-4,5-dimethyl-5-(trifluoromethyl)tetrahydrofuran-2-carboxamido)picolinamide 4-((2R,3S,4S,5R)-3-(2-(difluoromethoxy)-3,4-difluorophenyl)-4,5-dimethyl-5-(trifluoromethyl)tetrahydrofuran-2-carboxamido)picolinamide 4-((2S,3S,4S,5R)-3-(2-(difluoromethoxy)-3,4-difluorophenyl)-4,5-dimethyl-5-(trifluoromethyl)tetrahydrofuran-2-carboxamido)picolinamide 2-carbamoyl-4-((2R,3R,4R,5S)-3-(2-(difluoromethoxy)-3,4-difluorophenyl)-4,5-dimethyl-5-(trifluoromethyl)tetrahydrofuran-2-carboxamido)pyridine 1-oxide 2-carbamoyl-4-((2S,3R,4R,5S)-3-(2-(difluoromethoxy)-3,4-difluorophenyl)-4,5-dimethyl-5-(trifluoromethyl)tetrahydrofuran-2-carboxamido)pyridine 1-oxide 2-carbamoyl-4-((2R,3S,4R,5S)-3-(2-(difluoromethoxy)-3,4-difluorophenyl)-4,5-dimethyl-5-(trifluoromethyl)tetrahydrofuran-2-carboxamido)pyridine 1-oxide TABLE A-continued Compound Structures and Names.

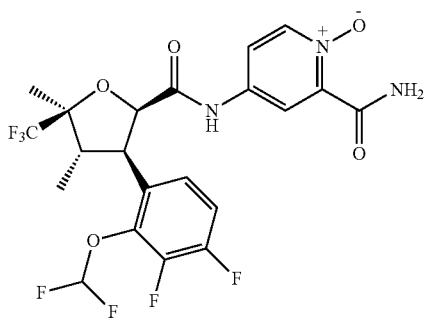

2-carbamoyl-4-((2R,3R,4S,5S)-3-(2-(difluoromethoxy)-3,4-difluorophenyl)-4,5-dimethyl-5-(trifluoromethyl)tetrahydrofuran-2-carboxamido)pyridine 1-oxide

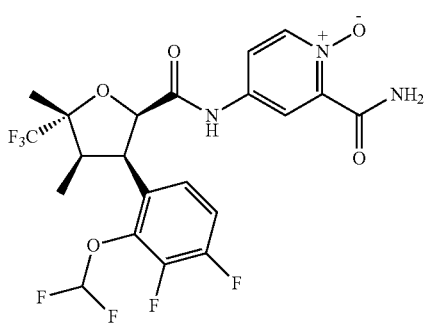

2-carbamoyl-4-((2R,3R,4R,5R)-3-(2-(difluoromethoxy)-3,4-difluorophenyl)-4,5-dimethyl-5-(trifluoromethyl)tetrahydrofuran-2-carboxamido)pyridine 1-oxide

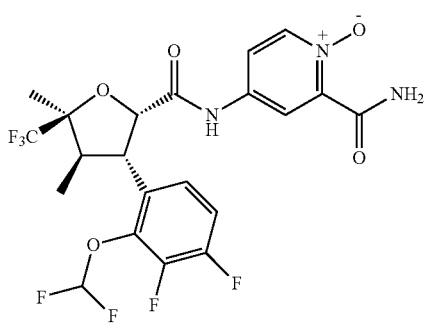

2-carbamoyl-4-((2S,3S,4R,5S)-3-(2-(difluoromethoxy)-3,4-difluorophenyl)-4,5-dimethyl-5-(trifluoromethyl)tetrahydrofuran-2-carboxamido)pyridine 1-oxide TABLE A-continued Compound Structures and Names.

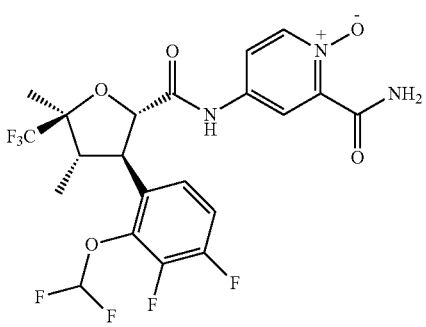

2-carbamoyl-4-((2S,3R,4S,5S)-3-(2-(difluoromethoxy)-3,4-difluorophenyl)-4,5-dimethyl-5-(trifluoromethyl)tetrahydrofuran-2-carboxamido)pyridine 1-oxide

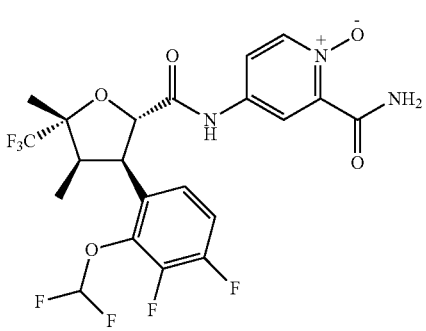

2-carbamoyl-4-((2S,3R,4R,5R)-3-(2-(difluoromethoxy)-3,4-difluorophenyl)-4,5-dimethyl-5-(trifluoromethyl)tetrahydrofuran-2-carboxamido)pyridine 1-oxide

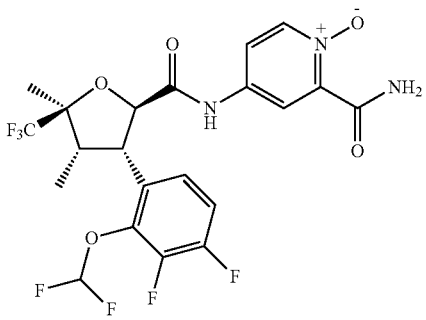

2-carbamoyl-4-((2R,3S,4S,5S)-3-(2-(difluoromethoxy)-3,4-difluorophenyl)-4,5-dimethyl-5-(trifluoromethyl)tetrahydrofuran-2-carboxamido)pyridine 1-oxide TABLE A-continued Compound Structures and Names.

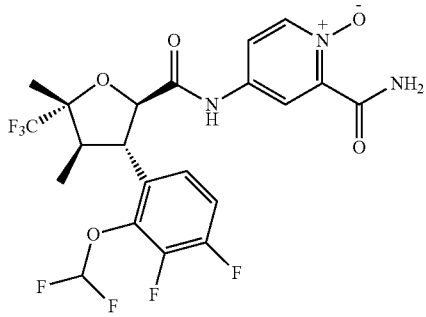

2-carbamoyl-4-((2R,3S,4R,5R)-3-(2-
(difluoromethoxy)-3,4-difluorophenyl)-4,5-
dimethyl-5-
(trifluoromethyl)tetrahydrofuran-2-
carboxamido)pyridine 1-oxide

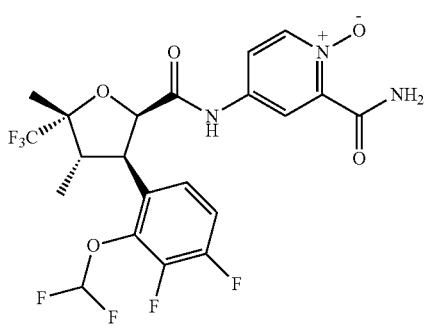

2-carbamoyl-4-((2R,3R,4S,5R)-3-(2-
(difluoromethoxy)-3,4-difluorophenyl)-4,5-
dimethyl-5-
(trifluoromethyl)tetrahydrofuran-2-
carboxamido)pyridine 1-oxide

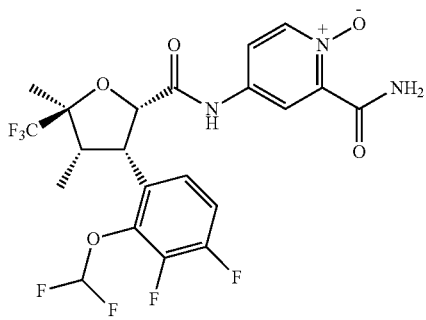

2-carbamoyl-4-((2S,3S,4S,5S)-3-(2-
(difluoromethoxy)-3,4-difluorophenyl)-4,5-
dimethyl-5-(trifluoromethyl)tetrahydrofuran-
2-carboxamido)pyridine 1-oxide TABLE A-continued Compound Structures and Names.

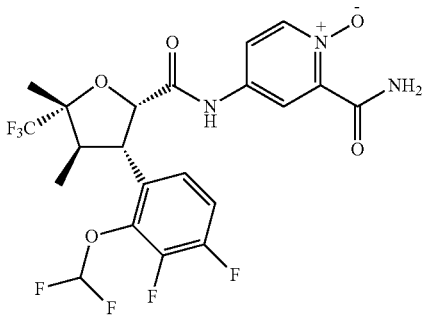

2-carbamoyl-4-((2S,3S,4R,5R)-3-(2-
(difluoromethoxy)-3,4-difluorophenyl)-4,5-
dimethyl-5-(trifluoromethyl)tetrahydrofuran-
2-carboxamido)pyridine 1-oxide

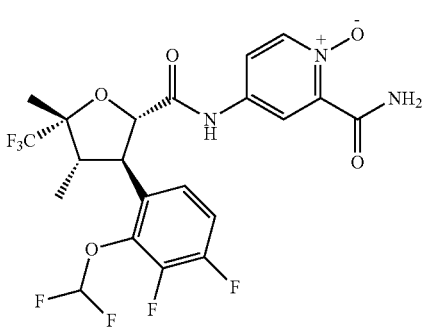

2-carbamoyl-4-((2S,3R,4S,5R)-3-(2-
(difluoromethoxy)-3,4-difluorophenyl)-4,5-
dimethyl-5-(trifluoromethyl)tetrahydrofuran-
2-carboxamido)pyridine 1-oxide

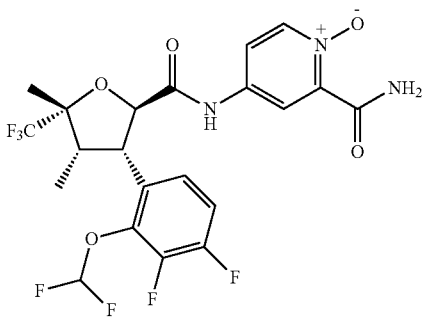

2-carbamoyl-4-((2R,3S,4S,5R)-3-(2-
(difluoromethoxy)-3,4-difluorophenyl)-4,5-
dimethyl-5-(trifluoromethyl)tetrahydrofuran-
2-carboxamido)pyridine 1-oxide TABLE A-continued Compound Structures and Names.

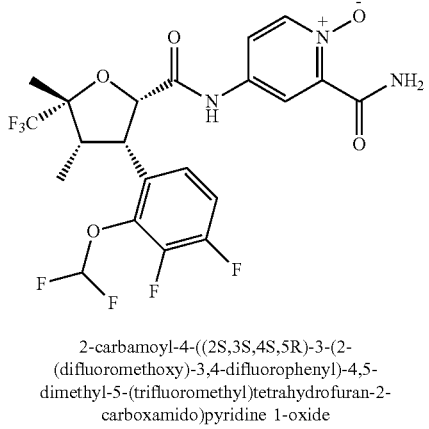

2-carbamoyl-4-((2S,3S,4S,5R)-3-(2-
(difluoromethoxy)-3,4-difluorophenyl)-4,5-
dimethyl-5-(trifluoromethyl)tetrahydrofuran-2-
carboxamido)pyridine 1-oxide

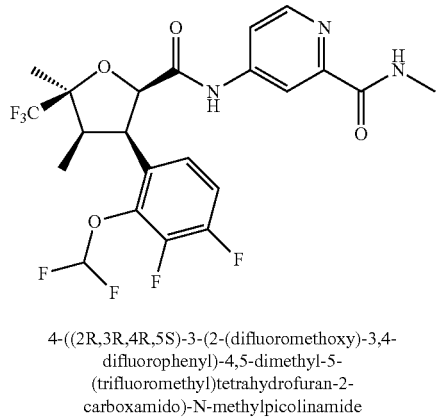

4-((2R,3R,4R,5S)-3-(2-(difluoromethoxy)-3,4-
difluorophenyl)-4,5-dimethyl-5-
(trifluoromethyl)tetrahydrofuran-2-
carboxamido)-N-methylpicolinamide

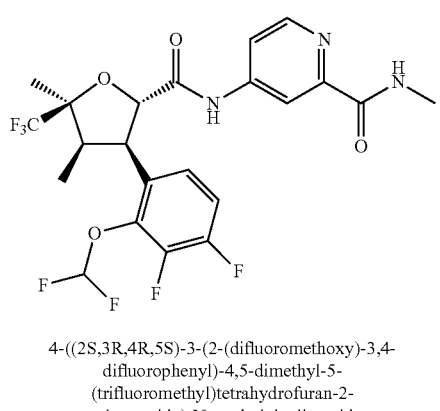

4-((2S,3R,4R,5S)-3-(2-(difluoromethoxy)-3,4-
difluorophenyl)-4,5-dimethyl-5-
(trifluoromethyl)tetrahydrofuran-2-
carboxamido)-N-methylpicolinamide

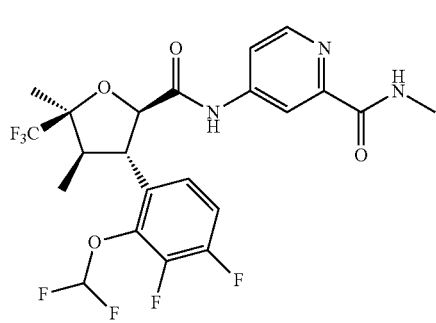 [SMILES: CNC(=O)c1cc(NC(=O)[C@@H]2O[C@](C)(C(F)(F)F)[C@H](C)[C@H]2c2ccc(F)c(F)c2OC(F)F)ccn1]

TABLE A-continued

Compound Structures and Names.

4-((2R,3S,4R,5S)-3-(2-(difluoromethoxy)-3,4-
difluorophenyl)-4,5-dimethyl-5-
(trifluoromethyl)tetrahydrofuran-2-
carboxamido)-N-rnethylpicolinamide

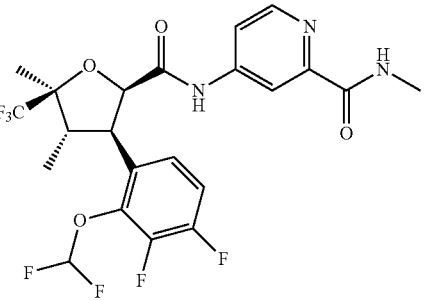

4-((2R,3R,4S,5S)-3-(2-(difluoromethoxy)-3,4-
difluorophenyl)-4,5-dimethyl-5-
(trifluoromethyl)tetrahydrofuran-2-
carboxamido)-N-rnethylpicolinamide

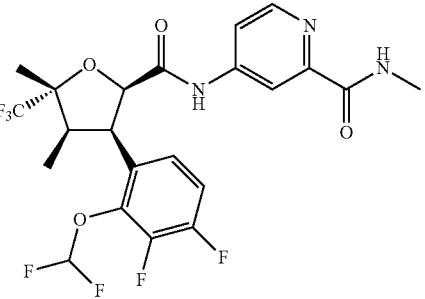

4-((2R,3R,4R,5R)-3-(2-(difluoromethoxy)-3,4-
difluorophenyl)-4,5-dimethyl-5-
(trifluoromethyl)tetrahydrofuran-2-
carboxamido)-N-methylpicolinamide

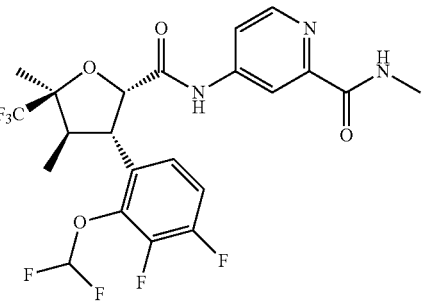

4-((2S,3S,4R,5S)-3-(2-(difluoromethoxy)-
3,4-difluorophenyl)-4,5-dimethyl-5-
(trifluoromethyl)tetrahydrofuran-2-
carboxamido)-N-methylpicolinamide

TABLE A-continued

Compound Structures and Names.

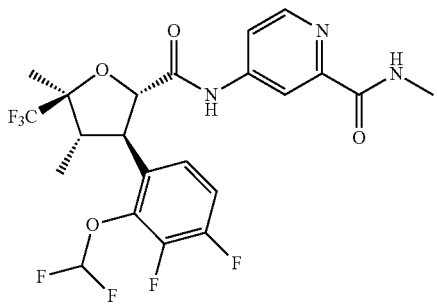 [SMILES: CNC(=O)c1cc(NC(=O)[C@H]2O[C@](C)(C(F)(F)F)[C@@H](C)[C@@H]2c2ccc(F)c(F)c2OC(F)F)ccn1]

4-((2S,3R,4S,5S)-3-(2-(difluoromethoxy)-
3,4-difluorophenyl)-4,5-dimethyl-5-
(trifluoromethyl)tetrahydrofuran-2-
carboxamido)-N-methylpicolinamide

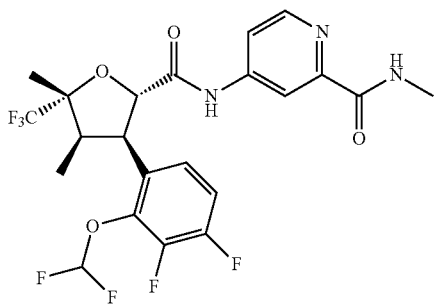 [SMILES: CNC(=O)c1cc(NC(=O)[C@H]2O[C@@](C)(C(F)(F)F)[C@H](C)[C@@H]2c2ccc(F)c(F)c2OC(F)F)ccn1]

4-((2S,3R,4R,5R)-3-(2-(difluoromethoxy)-
3,4-difluorophenyl)-4,5-dimethyl-5-
(trifluoromethyl)tetrahydrofuran-2-
carboxamido)-N-methylpicolinamide

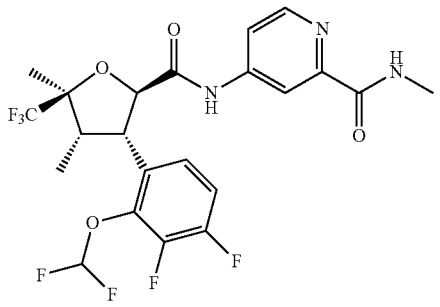 [SMILES: CNC(=O)c1cc(NC(=O)[C@@H]2O[C@](C)(C(F)(F)F)[C@@H](C)[C@H]2c2ccc(F)c(F)c2OC(F)F)ccn1]

4-((2R,3S,4S,5S)-3-(2-(difluoromethoxy)-3,4-
difluorophenyl)-4,5-dimethyl-5-
(trifluoromethyl)tetrahydrofuran-2-
carboxamido)-N-methylpicolinamide

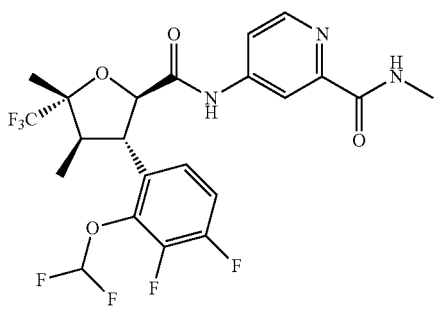 [SMILES: CNC(=O)c1cc(NC(=O)[C@@H]2O[C@@](C)(C(F)(F)F)[C@H](C)[C@H]2c2ccc(F)c(F)c2OC(F)F)ccn1]

4-((2R,3S,4R,5R)-3-(2-(difluoromethoxy)-3,4-
difluorophenyl)-4,5-dimethyl-5-

TABLE A-continued

Compound Structures and Names.

(trifluoromethyl)tetrahydrofuran-2-
carboxamido)-N-methylpicolinamide

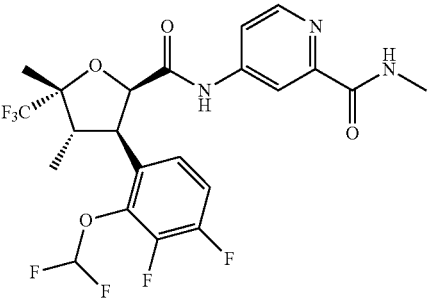 [SMILES: CNC(=O)c1cc(NC(=O)[C@@H]2O[C@@](C)(C(F)(F)F)[C@@H](C)[C@@H]2c2ccc(F)c(F)c2OC(F)F)ccn1]

4-((2R,3R,4S,5R)-3-(2-(difluoromethoxy)-3,4-
difluorophenyl)-4,5-dimethyl-5-
(trifluoromethyl)tetrahydrofuran-2-
carboxamido)-N-methylpicolinamide

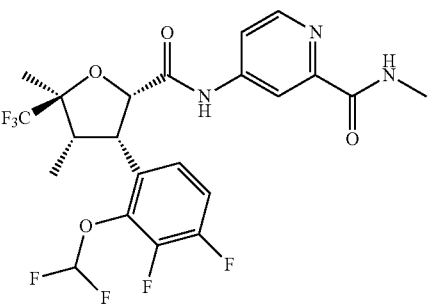 [SMILES: CNC(=O)c1cc(NC(=O)[C@H]2O[C@](C)(C(F)(F)F)[C@@H](C)[C@H]2c2ccc(F)c(F)c2OC(F)F)ccn1]

4-((2S,3S,4S,5S)-3-(2-(difluoromethoxy)-3,4-
difluorophenyl)-4,5-dimethyl-5-
(trifluoromethyl)tetrahydrofuran-2-
carboxamido)-N-methylpicolinamide

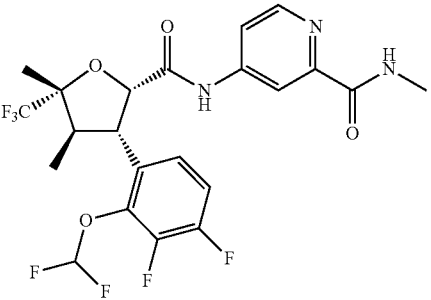 [SMILES: CNC(=O)c1cc(NC(=O)[C@H]2O[C@@](C)(C(F)(F)F)[C@H](C)[C@H]2c2ccc(F)c(F)c2OC(F)F)ccn1]

4-((2S,3S,4R,5R)-3-(2-(difluoromethoxy)-3,4-
difluorophenyl)-4,5-dimethyl-5-
(trifluoromethyl)tetrahydrofuran-2-
carboxamido)-N-nnethylpicolinamide

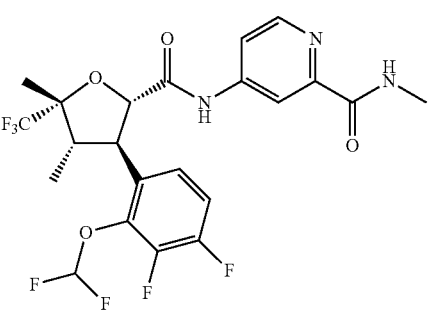 [SMILES: CNC(=O)c1cc(NC(=O)[C@H]2O[C@@](C)(C(F)(F)F)[C@@H](C)[C@@H]2c2ccc(F)c(F)c2OC(F)F)ccn1]

TABLE A-continued

Compound Structures and Names.

4-((2S,3R,4S,5R)-3-(2-(difluoromethoxy)-3,4-difluorophenyl)-4,5-dimethyl-5-(trifluoromethyl)tetrahydrofuran-2-carboxamido)-N-methylpicolinamide 4-((2R,3S,4S,5R)-3-(2-(difluoromethoxy)-3,4-difluorophenyl)-4,5-dimethyl-5-(trifluoromethyl)tetrahydrofuran-2-carboxamido)-N-methylpicolinamide 4-((2S,3S,4S,5R)-3-(2-(difluoromethoxy)-3,4-difluorophenyl)-4,5-dimethyl-5-(trifluoromethyl)tetrahydrofuran-2-carboxamido)-N-methylpicolinamide 4-((2R,3R,5S)-3-(3-chloro-4-fluoro-2-methoxyphenyl)-5-methyl-5-(trifluoromethyl)tetrahydrofuran-2-carboxamido)picolinamide 4-((2S,3R,5S)-3-(3-chloro-4-fluoro-2-methoxyphenyl)-5-methyl-5-(trifluoromethyl)tetrahydrofuran-2-carboxamido)picolinamide 4-((2R,3S,5S)-3-(3-chloro-4-fluoro-2-methoxyphenyl)-5-methyl-5-(trifluoromethyl)tetrahydrofuran-2-carboxamido)picolinamide 4-((2R,3R,5R)-3-(3-chloro-4-fluoro-2-methoxyphenyl)-5-methyl-5-(trifluoromethyl)tetrahydrofuran-2-carboxamido)picolinamide 4-((2S,3S,5S)-3-(3-chloro-4-fluoro-2-methoxyphenyl)-5-methyl-5-(trifluoromethyl)tetrahydrofuran-2-carboxamido)picolinamide TABLE A-continued Compound Structures and Names.

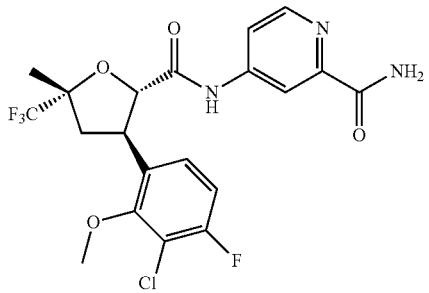 [SMILES: COc1c([C@H]2C[C@](C)(C(F)(F)F)O[C@@H]2C(=O)Nc2ccnc(C(N)=O)c2)ccc(F)c1Cl]

4-((2S,3R,5R)-3-(3-chloro-4-fluoro-2-
methoxyphenyl)-5-methyl-5-
(trifluoromethyl)tetrahydrofuran-2-
carboxamido)picolinamide

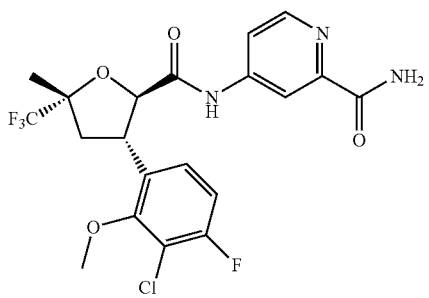 [SMILES: COc1c([C@@H]2C[C@](C)(C(F)(F)F)O[C@H]2C(=O)Nc2ccnc(C(N)=O)c2)ccc(F)c1Cl]

4-((2R,3S,5R)-3-(3-chloro-4-fluoro-2-
methoxyphenyl)-5-methyl-5-
(trifluoromethyl)tetrahydrofuran-2-
carboxamido)picolinamide

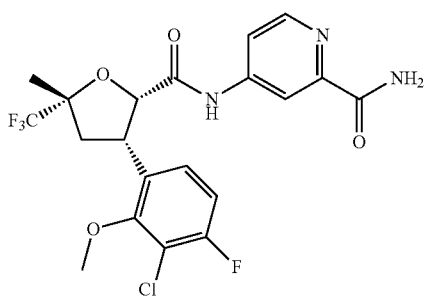 [SMILES: COc1c([C@@H]2C[C@](C)(C(F)(F)F)O[C@@H]2C(=O)Nc2ccnc(C(N)=O)c2)ccc(F)c1Cl]

4-((2S,3S,5R)-3-(3-chloro-4-fluoro-2-
methoxyphenyl)-5-methyl-5-
(trifluoromethyl)tetrahydrofuran-2-
carboxamido)picolinamide

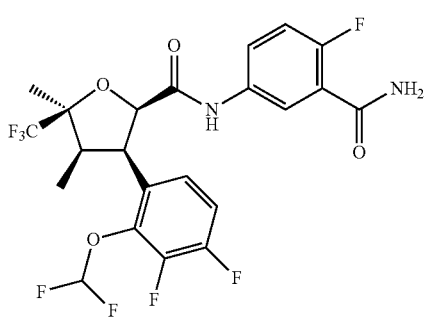 [SMILES: C[C@@H]1[C@H](c2ccc(F)c(F)c2OC(F)F)[C@H](C(=O)Nc2ccc(F)c(C(N)=O)c2)O[C@]1(C)C(F)(F)F]

(2R,3R,4R,5S)-N-(3-carbamoyl-4-
fluorophenyl)-3-(2-(difluoromethoxy)-3,4-

TABLE A-continued

Compound Structures and Names.

difluorophenyl)-4,5-dimethyl-5-
(trifluoromethyl)tetrahydrofuran-2-
carboxamide

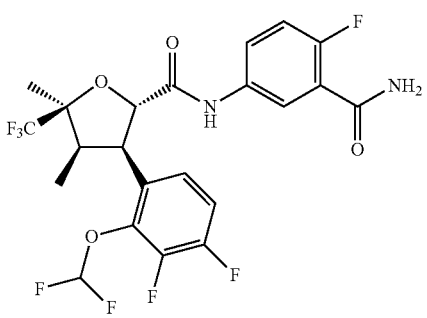 [SMILES: C[C@@H]1[C@H](c2ccc(F)c(F)c2OC(F)F)[C@@H](C(=O)Nc2ccc(F)c(C(N)=O)c2)O[C@]1(C)C(F)(F)F]

(2S,3R,4R,5S)-N-(3-carbamoyl-4-fluorophenyl)-
3-(2-(difluoromethoxy)-3,4-difluorophenyl)-4,5-
dimethyl-5-(trifluoromethyl)tetrahydrofuran-2-
carboxamide

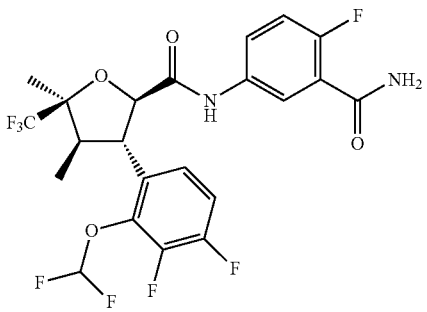 [SMILES: C[C@@H]1[C@@H](c2ccc(F)c(F)c2OC(F)F)[C@H](C(=O)Nc2ccc(F)c(C(N)=O)c2)O[C@]1(C)C(F)(F)F]

(2R,3S,4R,5S)-N-(3-carbamoyl-4-fluorophenyl)-
3-(2-(difluoromethoxy)-3,4-difluorophenyl)-4,5-
dimethyl-5-(trifluoromethyl)tetrahydrofuran-2-
carboxamide

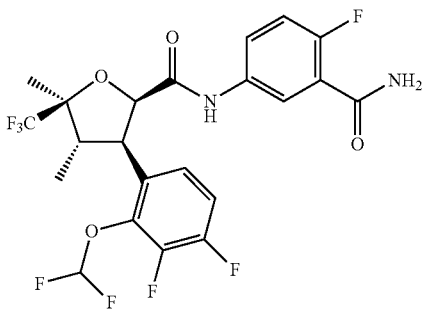 [SMILES: C[C@H]1[C@H](c2ccc(F)c(F)c2OC(F)F)[C@H](C(=O)Nc2ccc(F)c(C(N)=O)c2)O[C@]1(C)C(F)(F)F]

(2R,3R,4S,5S)-N-(3-carbamoyl-4-fluorophenyl)-
3-(2-(difluoromethoxy)-3,4-difluorophenyl)-4,5-
dimethyl-5-(trifluoromethyl)tetrahydrofuran-2-
carboxamide TABLE A-continued Compound Structures and Names.

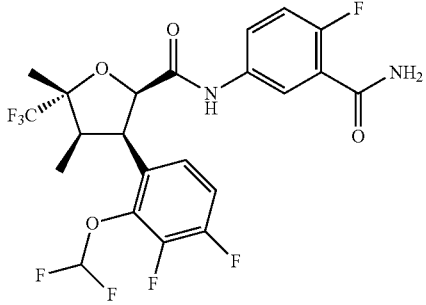 [SMILES: C[C@@H]1[C@H](c2ccc(F)c(F)c2OC(F)F)[C@H](C(=O)Nc2ccc(F)c(C(N)=O)c2)O[C@@]1(C)C(F)(F)F]

(2R,3R,4R,5R)-N-(3-carbamoyl-4-fluorophenyl)-3-(2-(difluoromethoxy)-3,4-difluorophenyl)-4,5-dimethyl-5-(trifluoromethyl)tetrahydrofuran-2-carboxamide

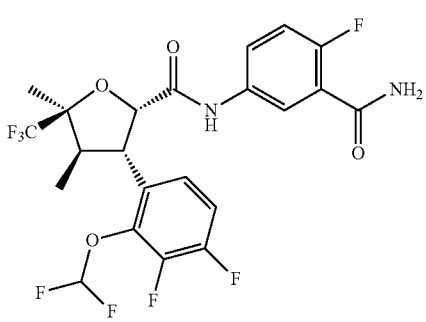 [SMILES: C[C@@H]1[C@@H](c2ccc(F)c(F)c2OC(F)F)[C@@H](C(=O)Nc2ccc(F)c(C(N)=O)c2)O[C@]1(C)C(F)(F)F]

(2S,3S,4R,5S)-N-(3-carbamoyl-4-fluorophenyl)-3-(2-(difluoromethoxy)-3,4-difluorophenyl)-4,5-dimethyl-5-(trifluoromethyl)tetrahydrofuran-2-carboxamide

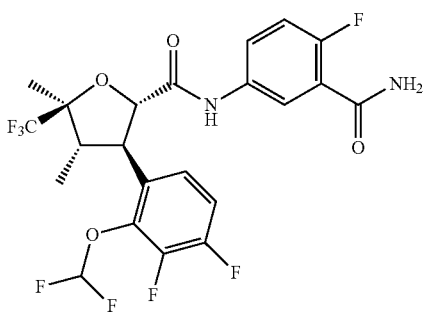 [SMILES: C[C@H]1[C@H](c2ccc(F)c(F)c2OC(F)F)[C@@H](C(=O)Nc2ccc(F)c(C(N)=O)c2)O[C@]1(C)C(F)(F)F]

(2S,3R,4S,5S)-N-(3-carbamoyl-4-fluorophenyl)-3-(2-(difluoromethoxy)-3,4-difluorophenyl)-4,5-dimethyl-5-(trifluoromethyl)tetrahydrofuran-2-carboxamide TABLE A-continued Compound Structures and Names.

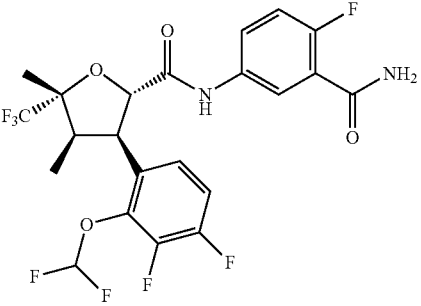 [SMILES: C[C@@H]1[C@H](c2ccc(F)c(F)c2OC(F)F)[C@@H](C(=O)Nc2ccc(F)c(C(N)=O)c2)O[C@@]1(C)C(F)(F)F]

(2S,3R,4R,5R)-N-(3-carbamoyl-4-fluorophenyl)-3-(2-(difluoromethoxy)-3,4-difluorophenyl)-4,5-dimethyl-5-(trifluoromethyl)tetrahydrofuran-2-carboxamide

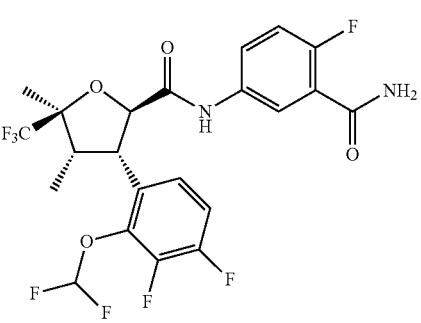 [SMILES: C[C@H]1[C@@H](c2ccc(F)c(F)c2OC(F)F)[C@H](C(=O)Nc2ccc(F)c(C(N)=O)c2)O[C@]1(C)C(F)(F)F]

(2R,3S,4S,5S)-N-(3-carbamoyl-4-fluorophenyl)-3-(2-(difluoromethoxy)-3,4-difluorophenyl)-4,5-dimethyl-5-(trifluoromethyl)tetrahydrofuran-2-carboxamide

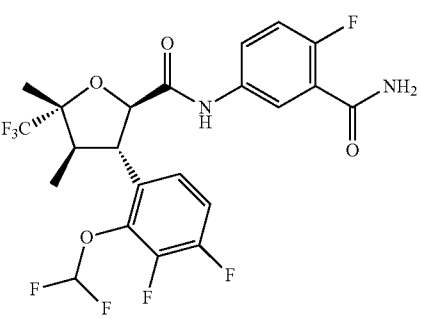 [SMILES: C[C@@H]1[C@@H](c2ccc(F)c(F)c2OC(F)F)[C@H](C(=O)Nc2ccc(F)c(C(N)=O)c2)O[C@@]1(C)C(F)(F)F]

(2R,3S,4R,5R)-N-(3-carbamoyl-4-fluorophenyl)-3-(2-(difluoromethoxy)-3,4-difluorophenyl)-4,5-dimethyl-5-(trifluoromethyl)tetrahydrofuran-2-carboxamide TABLE A-continued Compound Structures and Names.

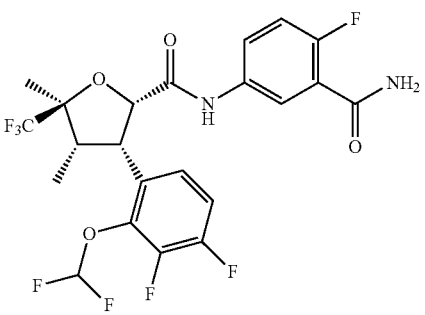 [SMILES: C[C@H]1[C@@H](c2ccc(F)c(F)c2OC(F)F)[C@@H](C(=O)Nc2ccc(F)c(C(N)=O)c2)O[C@]1(C)C(F)(F)F]

(2R,3R,4S,5R)-N-(3-carbamoyl-4-
fluorophenyl)-3-(2-(difluoromethoxy)-3,4-
difluorophenyl)-4,5-dimethyl-5-
(trifluoromethyl)tetrahydrofuran-2-
carboxamide

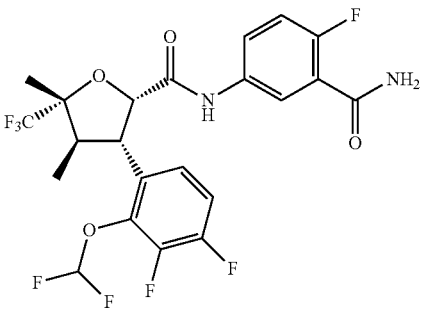 [SMILES: C[C@@H]1[C@@H](c2ccc(F)c(F)c2OC(F)F)[C@@H](C(=O)Nc2ccc(F)c(C(N)=O)c2)O[C@@]1(C)C(F)(F)F]

(2S,3S,4S,5S)-N-(3-carbamoyl-4-
fluorophenyl)-3-(2-(difluoromethoxy)-3,4-
difluorophenyl)-4,5-dimethyl-5-
(trifluoromethyl)tetrahydrofuran-2-
carboxamide

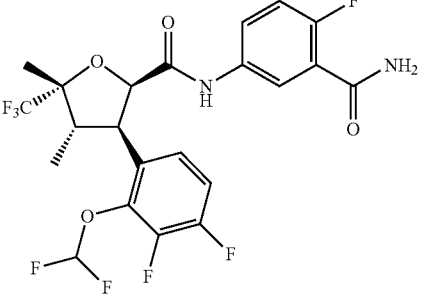

(2S,3S,4R,5R)-N-(3-carbamoyl-4-
fluorophenyl)-3-(2-(difluoromethoxy)-3,4-
difluorophenyl)-4,5-dimethyl-5-
(trifluoromethyl)tetrahydrofuran-2-
carboxamide TABLE A-continued Compound Structures and Names.

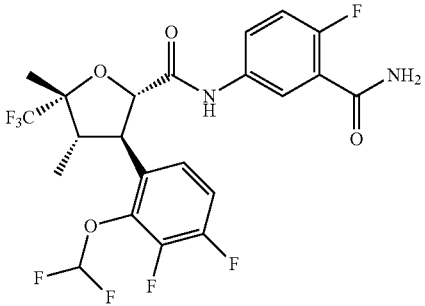 [SMILES: C[C@H]1[C@H](c2ccc(F)c(F)c2OC(F)F)[C@@H](C(=O)Nc2ccc(F)c(C(N)=O)c2)O[C@@]1(C)C(F)(F)F]

(2S,3R,4S,5R)-N-(3-carbamoyl-4-
fluorophenyl)-3-(2-(difluoromethoxy)-3,4-
difluorophenyl)-4,5-dimethyl-5-
(trifluoromethyl)tetrahydrofuran-2-
carboxamide

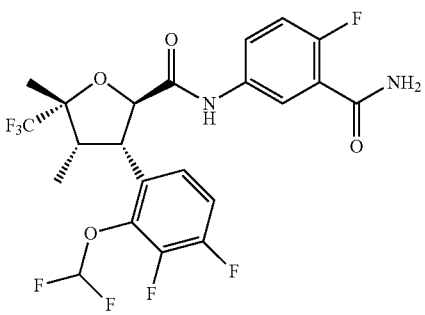 [SMILES: C[C@H]1[C@@H](c2ccc(F)c(F)c2OC(F)F)[C@H](C(=O)Nc2ccc(F)c(C(N)=O)c2)O[C@@]1(C)C(F)(F)F]

(2R,3S,4S,5R)-N-(3-carbamoyl-4-
fluorophenyl)-3-(2-(difluoromethoxy)-3,4-
difluorophenyl)-4,5-dimethyl-5-
(trifluoromethyl)tetrahydrofuran-2-
carboxamide

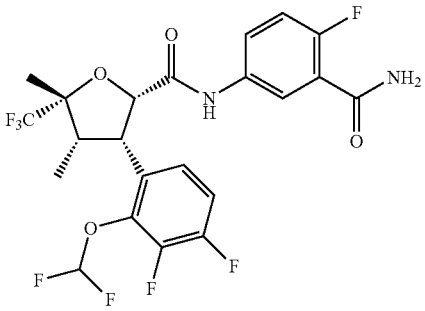 [SMILES: C[C@H]1[C@@H](c2ccc(F)c(F)c2OC(F)F)[C@@H](C(=O)Nc2ccc(F)c(C(N)=O)c2)O[C@@]1(C)C(F)(F)F]

(2S,3S,4S,5R)-N-(3-carbamoyl-4-
fluorophenyl)-3-(2-(difluoromethoxy)-3,4-
difluorophenyl)-4,5-dimethyl-5-
(trifluoromethyl)tetrahydrofuran-2-
carboxamide

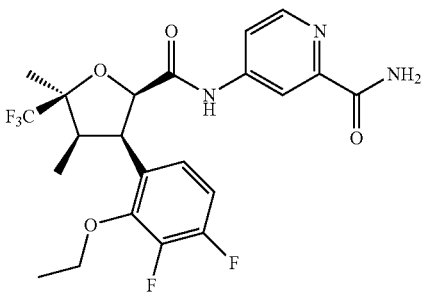 [SMILES: CCOc1c([C@H]2[C@@H](C)[C@@](C)(C(F)(F)F)O[C@H]2C(=O)Nc2ccnc(C(N)=O)c2)ccc(F)c1F]

TABLE A-continued

Compound Structures and Names.

4-((2R,3R,4R,5S)-3-(2-ethoxy-3,4-difluorophenyl)-4,5-dimethyl-5-(trifluoromethyl)tetrahydrofuran-2-carboxamido)picolinamide 4-((2S,3R,4R,5S)-3-(2-ethoxy-3,4-difluorophenyl)-4,5-dimethyl-5-(trifluoromethyl)tetrahydrofuran-2-carboxamido)picolinamide 4-((2R,3S,4R,5S)-3-(2-ethoxy-3,4-difluorophenyl)-4,5-dimethyl-5-(trifluoromethyl)tetrahydrofuran-2-carboxamido)picolinamide 4-((2R,3R,4S,5S)-3-(2-ethoxy-3,4-difluorophenyl)-4,5-dimethyl-5-(trifluoromethyl)tetrahydrofuran-2-carboxamido)picolinamide 4-((2R,3R,4R,5R)-3-(2-ethoxy-3,4-difluorophenyl)-4,5-dimethyl-5-(trifluoromethyl)tetrahydrofuran-2-carboxamido)picolinamide 4-((2S,3S,4R,5S)-3-(2-ethoxy-3,4-difluorophenyl)-4,5-dimethyl-5-(trifluoromethyl)tetrahydrofuran-2-carboxamido)picolinamide 4-((2S,3R,4S,5S)-3-(2-ethoxy-3,4-difluorophenyl)-4,5-dimethyl-5-(trifluoromethyl)tetrahydrofuran-2-carboxamido)picolinamide 4-((2S,3R,4R,5R)-3-(2-ethoxy-3,4-difluorophenyl)-4,5-dimethyl-5-(trifluoromethyl)tetrahydrofuran-2-carboxamido)picolinamide TABLE A-continued Compound Structures and Names.

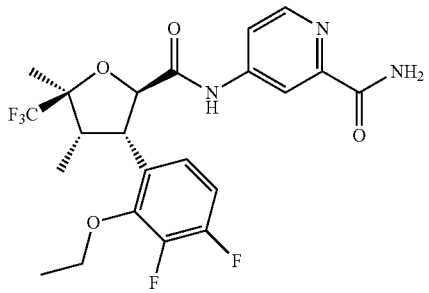 [SMILES: CCOc1c([C@H]2[C@H](C(=O)Nc3ccnc(C(N)=O)c3)O[C@](C)(C(F)(F)F)[C@H]2C)ccc(F)c1F]

4-((2R,3S,4S,5S)-3-(2-ethoxy-3,4-difluorophenyl)-
4,5-dimethyl-5-(trifluoromethyl)tetrahydrofuran-2-
carboxamido)picolinamide

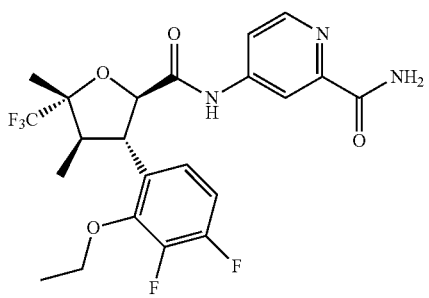 [SMILES: CCOc1c([C@@H]2[C@@H](C)[C@](C)(C(F)(F)F)O[C@H]2C(=O)Nc2ccnc(C(N)=O)c2)ccc(F)c1F]

4-((2R,3S,4R,5R)-3-(2-ethoxy-3,4-difluorophenyl)-
4,5-dimethyl-5-(trifluoromethyl)tetrahydrofuran-2-
carboxamido)picolinamide

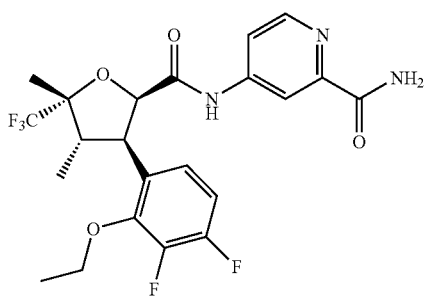 [SMILES: CCOc1c([C@@H]2[C@H](C(=O)Nc3ccnc(C(N)=O)c3)O[C@@](C)(C(F)(F)F)[C@H]2C)ccc(F)c1F]

4-((2R,3R,4S,5R)-3-(2-ethoxy-3,4-difluorophenyl)-
4,5-dimethyl-5-(trifluoromethyl)tetrahydrofuran-2-
carboxamido)picolinamide

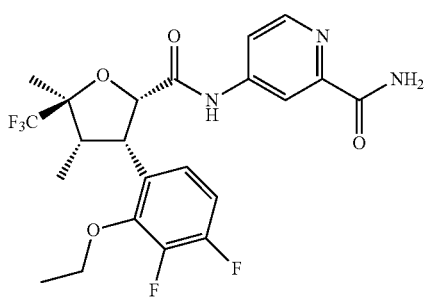 [SMILES: CCOc1c([C@H]2[C@@H](C(=O)Nc3ccnc(C(N)=O)c3)O[C@](C)(C(F)(F)F)[C@H]2C)ccc(F)c1F]

4-((2S,3S,4S,5S)-3-(2-ethoxy-3,4-difluorophenyl)-
4,5-dimethyl-5-(trifluoromethyl)tetrahydrofuran-2-
carboxamido)picolinamide TABLE A-continued Compound Structures and Names.

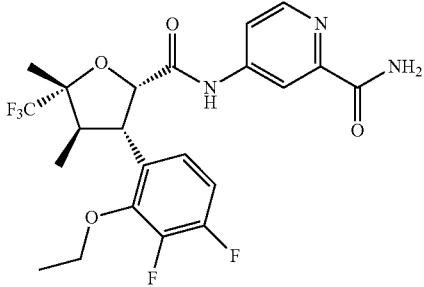 [SMILES: CCOc1c([C@H]2[C@@H](C(=O)Nc3ccnc(C(N)=O)c3)O[C@@](C)(C(F)(F)F)[C@@H]2C)ccc(F)c1F]

4-((2S,3S,4R,5R)-3-(2-ethoxy-3,4-difluorophenyl)-
4,5-dimethyl-5-(trifluoromethyl)tetrahydrofuran-2-
carboxamido)picolinamide

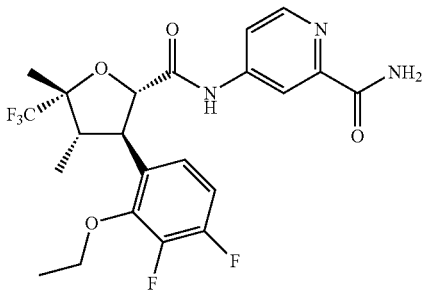 [SMILES: CCOc1c([C@@H]2[C@@H](C(=O)Nc3ccnc(C(N)=O)c3)O[C@@](C)(C(F)(F)F)[C@H]2C)ccc(F)c1F]

4-((2S,3R,4S,5R)-3-(2-ethoxy-3,4-
difluorophenyl)-4,5-dimethyl-5-
(trifluoromethyl)tetrahydrofuran-2-
carboxamido)picolinamide

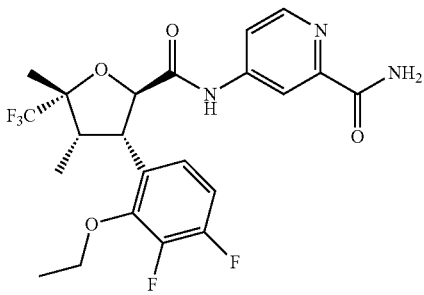 [SMILES: CCOc1c([C@H]2[C@H](C(=O)Nc3ccnc(C(N)=O)c3)O[C@@](C)(C(F)(F)F)[C@H]2C)ccc(F)c1F]

4-((2R,3S,4S,5R)-3-(2-ethoxy-3,4-difluorophenyl)-
4,5-dimethyl-5-(trifluoromethyl)tetrahydrofuran-2-
carboxamido)picolinamide

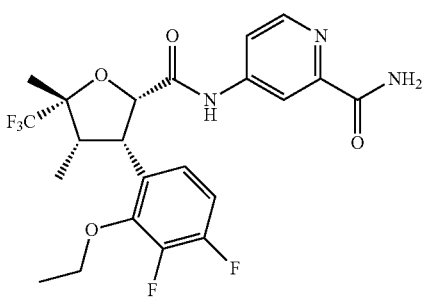 [SMILES: CCOc1c([C@H]2[C@@H](C(=O)Nc3ccnc(C(N)=O)c3)O[C@@](C)(C(F)(F)F)[C@H]2C)ccc(F)c1F]

4-((2S,3S,4S,5R)-3-(2-ethoxy-3,4-difluorophenyl)-
4,5-dimethyl-5-(trifluoromethyl)tetrahydrofuran-2-
carboxamido)picolinamide TABLE A-continued Compound Structures and Names.

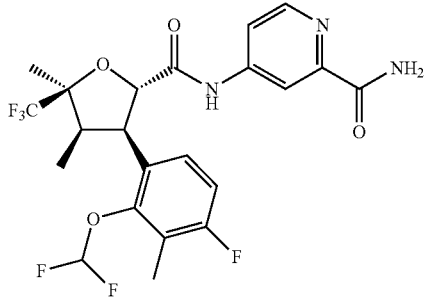 [SMILES: Cc1c(F)ccc([C@@H]2[C@@H](C(=O)Nc3ccnc(C(N)=O)c3)O[C@](C)(C(F)(F)F)[C@@H]2C)c1OC(F)F]

4-((2R,3R,4R,5S)-3-(2-(difluoronnethoxy)-4-fluoro-3-
methylphenyl)-4,5-dimethyl-5-
(trifluoromethyl)tetrahydrofuran-2-
carboxamido)picolinamide


4-((2S,3R,4R,5S)-3-(2-(difluoromethoxy)-4-
fluoro-3-methylphenyl)-4,5-dimethyl-5-
(trifluoromethyl)tetrahydrofuran-2-
carboxamido)picolinamide


4-((2R,3S,4R,5S)-3-(2-(difluoromethoxy)-4-
fluoro-3-methylphenyl)-4,5-dimethyl-5-
(trifluoromethyl)tetrahydrofuran-2-
carboxamido)picolinamide

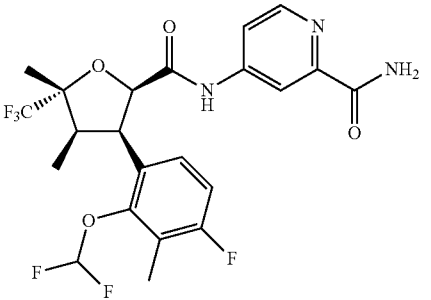 [SMILES: Cc1c(F)ccc([C@H]2[C@@H](C)[C@](C)(C(F)(F)F)O[C@H]2C(=O)Nc2ccnc(C(N)=O)c2)c1OC(F)F]

4-((2R,3R,4S,5S)-3-(2-(difluoromethoxy)-4-fluoro-3-
methylphenyl)-4,5-dimethyl-5-
(trifluoromethyl)tetrahydrofuran-2-
carboxamido)picolinamide TABLE A-continued Compound Structures and Names.

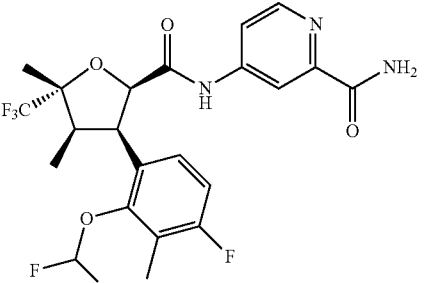

4-((2R,3R,4R,5R)-3-(2-(difluoromethoxy)-4-fluoro-
3-methylphenyl)-4,5-dimethyl-5-
(trifluoromethyl)tetrahydrofuran-2-
carboxamido)picolinamide

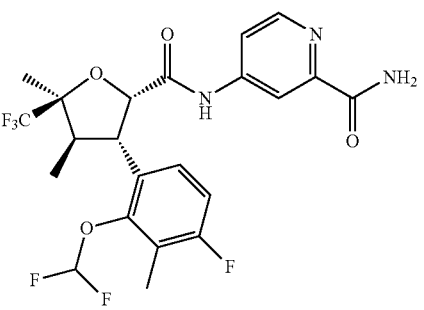 [SMILES: Cc1c(F)ccc([C@H]2[C@@H](C(=O)Nc3ccnc(C(N)=O)c3)O[C@](C)(C(F)(F)F)[C@@H]2C)c1OC(F)F]

4-((2S,3S,4R,5S)-3-(2-(difluoromethoxy)-4-
fluoro-3-methylphenyl)-4,5-dimethyl-5-
(trifluoromethyl)tetrahydrofuran-2-
carboxamido)picolinamide

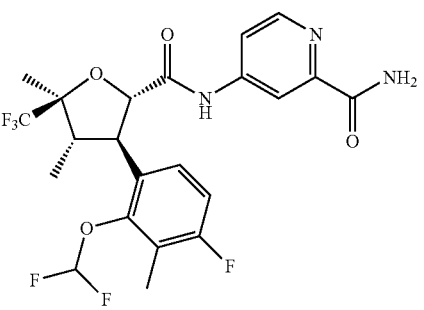 [SMILES: Cc1c(F)ccc([C@@H]2[C@@H](C(=O)Nc3ccnc(C(N)=O)c3)O[C@](C)(C(F)(F)F)[C@H]2C)c1OC(F)F]

4-((2S,3R,4S,5S)-3-(2-(difluoromethoxy)-4-fluoro-
3-nnethylphenyl)-4,5-dimethyl-5-
(trifluoromethyl)tetrahydrofuran-2-
carboxamido)picolinamide

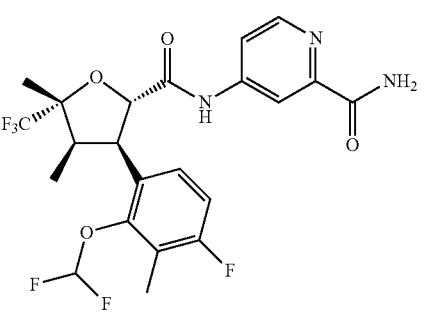 [SMILES: Cc1c(F)ccc([C@@H]2[C@@H](C(=O)Nc3ccnc(C(N)=O)c3)O[C@@](C)(C(F)(F)F)[C@@H]2C)c1OC(F)F]

TABLE A-continued

Compound Structures and Names.

4-((2S,3R,4R,5R)-3-(2-(difluoromethoxy)-4-fluoro-3-methylphenyl)-4,5-dimethyl-5-(trifluoromethyl)tetrahydrofuran-2-carboxamido)picolinamide 4-((2R,3S,4S,5S)-3-(2-(difluoromethoxy)-4-fluoro-3-methylphenyl)-4,5-dimethyl-5-(trifluoromethyl)tetrahydrofuran-2-carboxamido)picolinamide 4-((2R,3S,4R,5R)-3-(2-(difluoromethoxy)-4-fluoro-3-methylphenyl)-4,5-dimethyl-5-(trifluoromethyl)tetrahydrofuran-2-carboxamido)picolinamide 4-((2R,3R,4S,5R)-3-(2-(difluoromethoxy)-4-fluoro-3-methylphenyl)-4,5-dimethyl-5-(trifluoromethyl)tetrahydrofuran-2-carboxamido)picolinamide 4-((2S,3S,4S,5S)-3-(2-(difluoromethoxy)-4-fluoro-3-methylphenyl)-4,5-dimethyl-5-(trifluoromethyl)tetrahydrofuran-2-carboxamido)picolinamide 4-((2S,3S,4R,5R)-3-(2-(difluoromethoxy)-4-fluoro-3-methylphenyl)-4,5-dimethyl-5-(trifluoromethyl)tetrahydrofuran-2-carboxamido)picolinamide 4-((2S,3R,4S,5R)-3-(2-(difluoromethoxy)-4-fluoro-3-methylphenyl)-4,5-dimethyl-5-(trifluoromethyl)tetrahydrofuran-2-carboxamido)picolinamide 4-((2R,3S,4S,5R)-3-(2-(difluoromethoxy)-4-fluoro-3-methylphenyl)-4,5-dimethyl-5-

TABLE A-continued

Compound Structures and Names.

(trifluoromethyl)tetrahydrofuran-2-carboxamido)picolinamide 4-((2S,3S,4S,5R)-3-(2-(difluoromethoxy)-4-fluoro-3-methylphenyl)-4,5-dimethyl-5-(trifluoromethyl)tetrahydrofuran-2-carboxamido)picolinamide 4-((2R,3R,4R,5S)-3-(3,4-difluoro-2-methoxyphenyl)-4-methyl-5-(trifluoromethyl)tetrahydrofuran-2-carboxamido)picolinamide 4-((2S,3R,4R,5S)-3-(3,4-difluoro-2-methoxyphenyl)-4-methyl-5-(trifluoromethyl)tetrahydrofuran-2-carboxamido)picolinamide 4-((2R,3S,4R,5S)-3-(3,4-difluoro-2-methoxyphenyl)-4-methyl-5-(trifluoromethyl)tetrahydrofuran-2-carboxamido)picolinamide 4-((2R,3R,4S,5S)-3-(3,4-difluoro-2-methoxyphenyl)-4-methyl-5-(trifluoromethyl)tetrahydrofuran-2-carboxamido)picolinamide 4-((2R,3R,4R,5R)-3-(3,4-difluoro-2-methoxyphenyl)-4-methyl-5-(trifluoromethyl)tetrahydrofuran-2-carboxamido)picolinamide 4-((2S,3S,4R,5S)-3-(3,4-difluoro-2-methoxyphenyl)-4-methyl-5-(trifluoromethyl)tetrahydrofuran-2-carboxamido)picolinamide TABLE A-continued Compound Structures and Names.

4-((2S,3R,4S,5S)-3-(3,4-difluoro-2-methoxyphenyl)-4-methyl-5-(trifluoromethyl)tetrahydrofuran-2-carboxamido)picolinamide 4-((2S,3R,4R,5R)-3-(3,4-difluoro-2-methoxyphenyl)-4-methyl-5-(trifluoromethyl)tetrahydrofuran-2-carboxamido)picolinamide 4-((2R,3S,4S,5S)-3-(3,4-difluoro-2-methoxyphenyl)-4-methyl-5-(trifluoromethyl)tetrahydrofuran-2-carboxamido)picolinamide 4-((2R,3S,4R,5R)-3-(3,4-difluoro-2-methoxyphenyl)-4-methyl-5-(trifluoromethyl)tetrahydrofuran-2-carboxamido)picolinamide TABLE A-continued Compound Structures and Names.

4-((2R,3R,4S,5R)-3-(3,4-difluoro-2-methoxyphenyl)-4-methyl-5-(trifluoromethyl)tetrahydrofuran-2-carboxamido)picolinamide 4-((2S,3S,4S,5S)-3-(3,4-difluoro-2-methoxyphenyl)-4-methyl-5-(trifluoromethyl)tetrahydrofuran-2-carboxamido)picolinamide 4-((2S,3S,4R,5R)-3-(3,4-difluoro-2-methoxyphenyl)-4-methyl-5-(trifluoromethyl)tetrahydrofuran-2-carboxamido)picolinamide 4-((2S,3R,4S,5R)-3-(3,4-difluoro-2-methoxyphenyl)-4-methyl-5-(trifluoromethyl)tetrahydrofuran-2-carboxamido)picolinamide TABLE A-continued Compound Structures and Names.

4-((2R,3S,4S,5R)-3-(3,4-difluoro-2-methoxyphenyl)-4-methyl-5-(trifluoromethyl)tetrahydrofuran-2-carboxamido)picolinamide

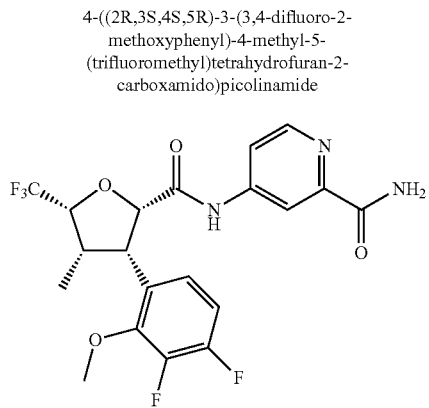

4-((2S,3S,4S,5R)-3-(3,4-difluoro-2-methoxyphenyl)-4-methyl-5-(trifluoromethyl)tetrahydrofuran-2-carboxamido)picolinamide

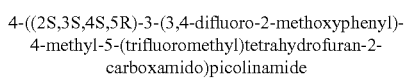

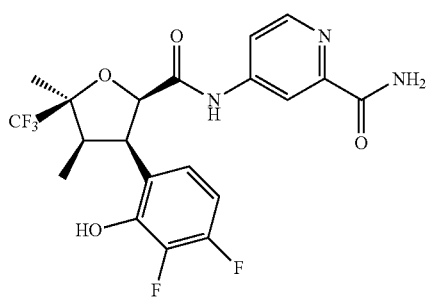 [SMILES: C[C@@H]1[C@H](c2ccc(F)c(F)c2O)[C@H](C(=O)Nc2ccnc(C(N)=O)c2)O[C@]1(C)C(F)(F)F]

4-((2R,3R,4R,5S)-3-(3,4-difluoro-2-hydroxyphenyl)-4,5-dimethyl-5-(trifluoromethyl)tetrahydrofuran-2-carboxamido)picolinamide

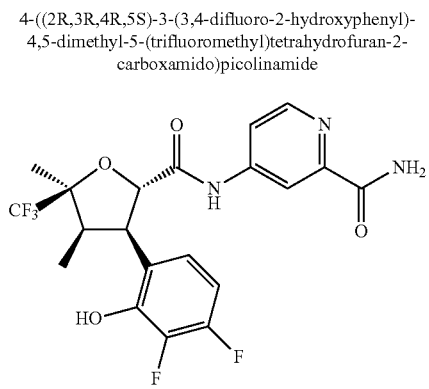

4-((2S,3R,4R,5S)-3-(3,4-difluoro-2-hydroxyphenyl)-4,5-dimethyl-5-(trifluoromethyl)tetrahydrofuran-2-carboxamido)picolinamide

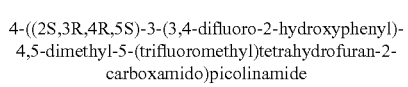

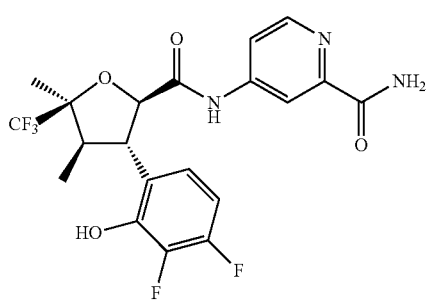 [SMILES: C[C@@H]1[C@@H](c2ccc(F)c(F)c2O)[C@H](C(=O)Nc2ccnc(C(N)=O)c2)O[C@]1(C)C(F)(F)F]

TABLE A-continued

Compound Structures and Names.

4-((2R,3S,4R,5S)-3-(3,4-difluoro-2-hydroxyphenyl)-4,5-dimethyl-5-(trifluoromethyl)tetrahydrofuran-2-carboxamido)picolinamide

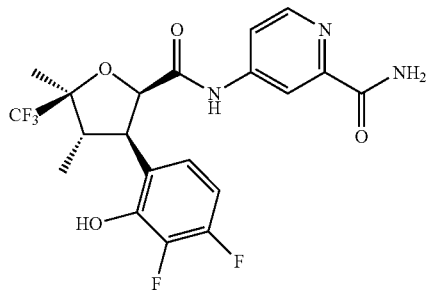 [SMILES: C[C@H]1[C@H](c2ccc(F)c(F)c2O)[C@H](C(=O)Nc2ccnc(C(N)=O)c2)O[C@]1(C)C(F)(F)F]

4-((2R,3R,4S,5S)-3-(3,4-difluoro-2-hydroxyphenyl)-4,5-dimethyl-5-(trifluoromethyl)tetrahydrofuran-2-carboxamido)picolinamide

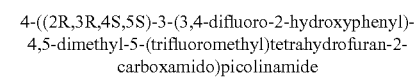

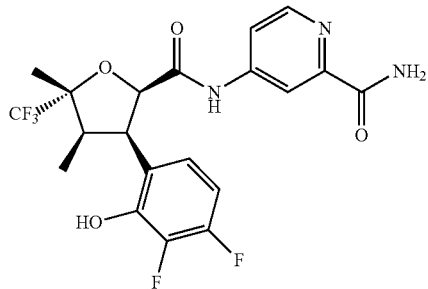 [SMILES: C[C@@H]1[C@H](c2ccc(F)c(F)c2O)[C@H](C(=O)Nc2ccnc(C(N)=O)c2)O[C@@]1(C)C(F)(F)F]

4-((2R,3R,4R,5R)-3-(3,4-difluoro-2-hydroxyphenyl)-4,5-dimethyl-5-(trifluoromethyl)tetrahydrofuran-2-carboxamido)picolinamide

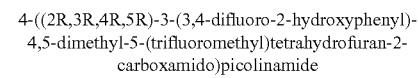

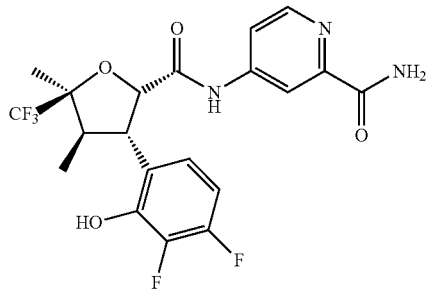

4-((2S,3S,4R,5S)-3-(3,4-difluoro-2-hydroxyphenyl)-4,5-dimethyl-5-(trifluoromethyl)tetrahydrofuran-2-carboxamido)picolinamide

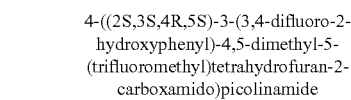

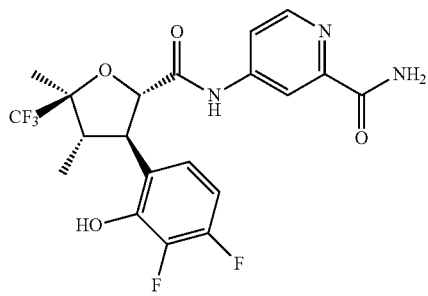 [SMILES: C[C@H]1[C@H](c2ccc(F)c(F)c2O)[C@@H](C(=O)Nc2ccnc(C(N)=O)c2)O[C@]1(C)C(F)(F)F]

TABLE A-continued

Compound Structures and Names.

4-((2S,3R,4S,5S)-3-(3,4-difluoro-2-hydroxyphenyl)-
4,5-dimethyl-5-(trifluoromethyl)tetrahydrofuran-2-
carboxamido)picolinamide

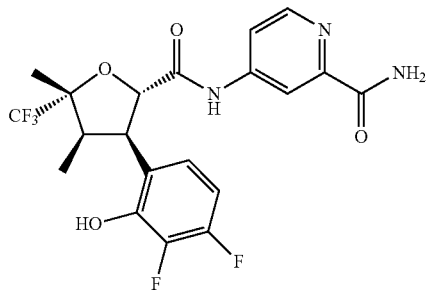 [SMILES: C[C@@H]1[C@H](c2ccc(F)c(F)c2O)[C@@H](C(=O)Nc2ccnc(C(N)=O)c2)O[C@@]1(C)C(F)(F)F]

4-((2S,3R,4R,5R)-3-(3,4-difluoro-2-hydroxyphenyl)-
4,5-dimethyl-5-(trifluoromethyl)tetrahydrofuran-2-
carboxamido)picolinamide

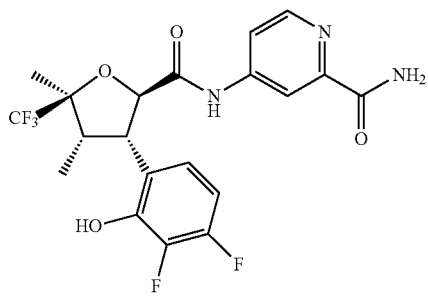 [SMILES: C[C@H]1[C@@H](c2ccc(F)c(F)c2O)[C@H](C(=O)Nc2ccnc(C(N)=O)c2)O[C@]1(C)C(F)(F)F]

4-((2R,3S,4S,5S)-3-(3,4-difluoro-2-hydroxyphenyl)-
4,5-dimethyl-5-(trifluoromethyl)tetrahydrofuran-2-
carboxamido)picolinamide

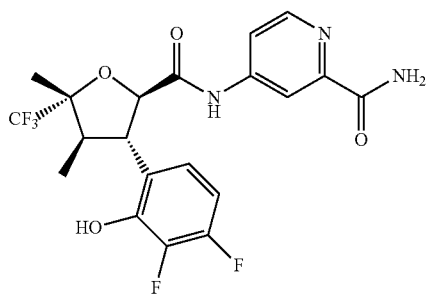 [SMILES: C[C@@H]1[C@@H](c2ccc(F)c(F)c2O)[C@H](C(=O)Nc2ccnc(C(N)=O)c2)O[C@@]1(C)C(F)(F)F]

4-((2R,3S,4R,5R)-3-(3,4-difluoro-2-hydroxyphenyl)-
4,5-dimethyl-5-(trifluoromethyl)tetrahydrofuran-2-
carboxamido)picolinamide

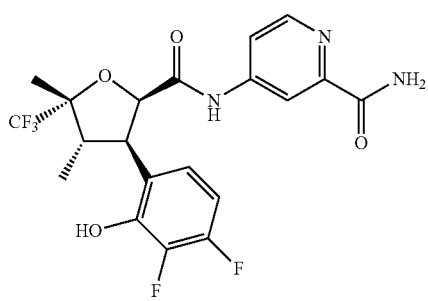 [SMILES: C[C@H]1[C@H](c2ccc(F)c(F)c2O)[C@H](C(=O)Nc2ccnc(C(N)=O)c2)O[C@@]1(C)C(F)(F)F]

TABLE A-continued

Compound Structures and Names.

4-((2R,3R,4S,5R)-3-(3,4-difluoro-2-hydroxyphenyl)-
4,5-dimethyl-5-(trifluoromethyl)tetrahydrofuran-2-
carboxamido)picolinamide

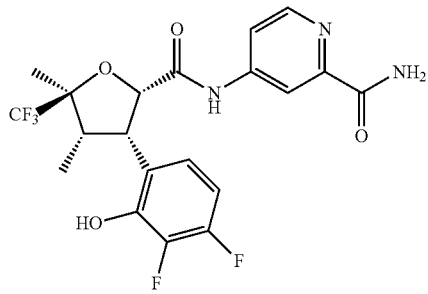 [SMILES: C[C@H]1[C@@H](c2ccc(F)c(F)c2O)[C@@H](C(=O)Nc2ccnc(C(N)=O)c2)O[C@]1(C)C(F)(F)F]

4-((2S,3S,4S,5S)-3-(3,4-difluoro-2-hydroxyphenyl)-
4,5-dimethyl-5-(trifluoromethyl)tetrahydrofuran-2-
carboxamido)picolinamide

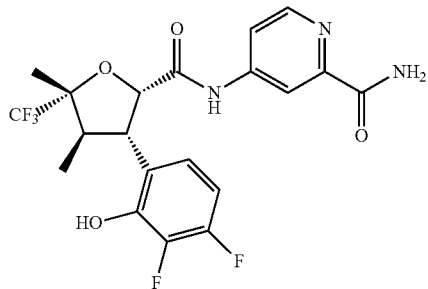 [SMILES: C[C@@H]1[C@@H](c2ccc(F)c(F)c2O)[C@@H](C(=O)Nc2ccnc(C(N)=O)c2)O[C@@]1(C)C(F)(F)F]

4-((2S,3S,4R,5R)-3-(3,4-difluoro-2-hydroxyphenyl)-
4,5-dimethyl-5-(trifluoromethyl)tetrahydrofuran-2-
carboxamido)picolinamide

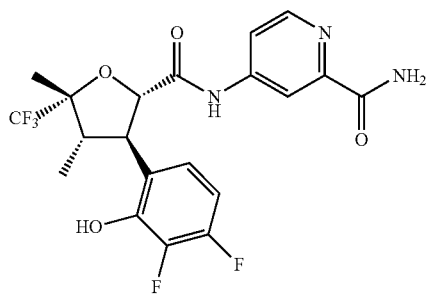 [SMILES: C[C@H]1[C@H](c2ccc(F)c(F)c2O)[C@@H](C(=O)Nc2ccnc(C(N)=O)c2)O[C@@]1(C)C(F)(F)F]

4-((2S,3R,4S,5R)-3-(3,4-difluoro-2-hydroxyphenyl)-
4,5-dimethyl-5-(trifluoromethyl)tetrahydrofuran-2-
carboxamido)picolinamide

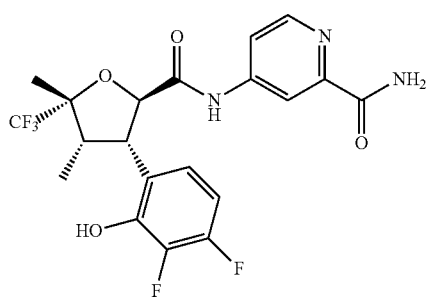 [SMILES: C[C@H]1[C@@H](c2ccc(F)c(F)c2O)[C@H](C(=O)Nc2ccnc(C(N)=O)c2)O[C@@]1(C)C(F)(F)F]

TABLE A-continued

Compound Structures and Names.

4-((2R,3S,4S,5R)-3-(3,4-difluoro-2-hydroxyphenyl)-
4,5-dimethyl-5-(trifluoromethyl)tetrahydrofuran-2-
carboxamido)picolinamide

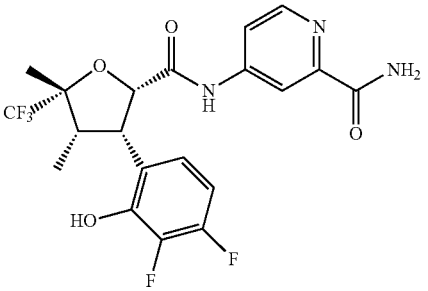 [SMILES: C[C@H]1[C@@H](c2ccc(F)c(F)c2O)[C@@H](C(=O)Nc2ccnc(C(N)=O)c2)O[C@@]1(C)C(F)(F)F]

4-((2S,3S,4S,5R)-3-(3,4-difluoro-2-hydroxyphenyl)-
4,5-dimethyl-5-(trifluoromethyl)tetrahydrofuran-2-
carboxamido)picolinamide In some embodiments, the invention relates to a compound selected from Table B or a pharmaceutically acceptable salt thereof. In other embodiments, the invention relates to a compound selected from Table B in non-salt form.

TABLE B

Compound Structures and Names.

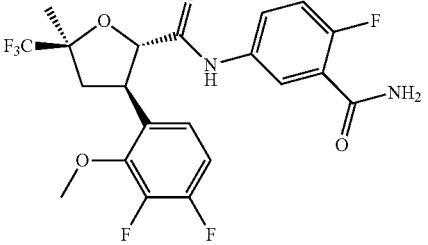

(2S,3R,5S)-N-(3-carbamoyl-4-fluorophenyl)-3-(3,4-
difluoro-2-methoxyphenyl)-5-methyl-5-
(trifluoromethyl)tetrahydrofuran-2-carboxamide

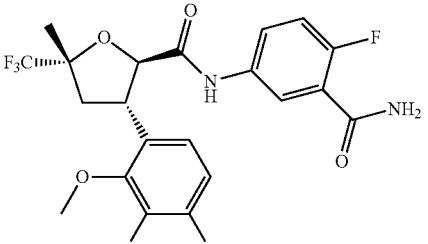

(2R,3S,5R)-N-(3-carbamoyl-4-fluorophenyl)-3-(3,4-
difluoro-2-methoxyphenyl)-5-methyl-5-
(trifluoromethyl)tetrahydrofuran-2-carboxamide

TABLE B-continued

Compound Structures and Names.

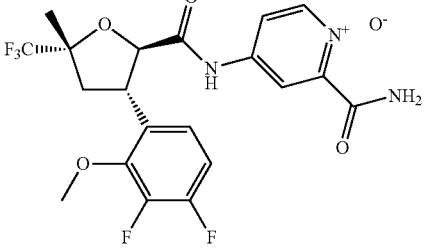

2-carbamoyl-4-((2R,3S,5R)-3-(3,4-difluoro-2-
methoxyphenyl)-5-methyl-5-
(trifluoromethyl)tetrahydrofuran-2-
carboxamido)pyridine 1-oxide

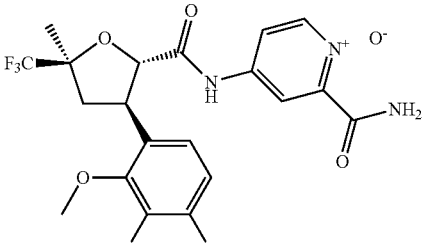

2-carbamoyl-4-((2S,3R,5S)-3-(3,4-difluoro-2-
methoxyphenyl)-5-methyl-5-
(trifluoromethyl)tetrahydrofuran-2-
carboxamido)pyridine 1-oxide

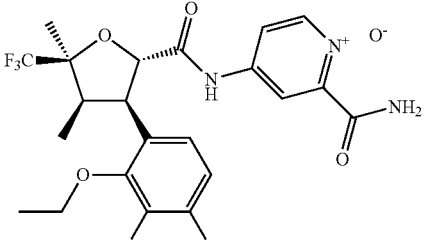

2-carbamoyl-4-((2S,3R,4R,5S)-3-(2-ethoxy-3,4-
difluorophenyl)-4,5-dimethyl-5-
(trifluoromethyl)tetrahydrofuran-2-
carboxamido)pyridine 1-oxide

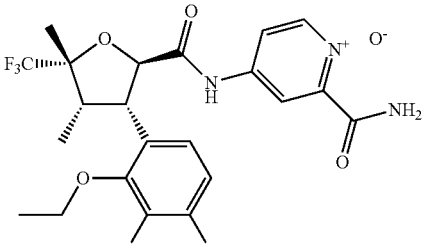

2-carbamoyl-4-((2R,3S,4S,5R)-3-(2-ethoxy-3,4-
difluorophenyl)-4,5-dimethyl-5-
(trifluoromethyl)tetrahydrofuran-2-
carboxamido)pyridine 1-oxide TABLE B-continued Compound Structures and Names.

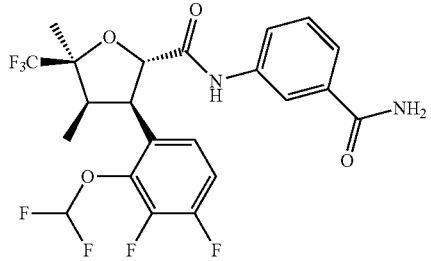

(2S,3R,4R,5S)-N-(3-carbamoylphenyl)-3-(2-
(difluoromethoxy)-3,4-difluorophenyl)-4,5-
dimethyl-5-(trifluoromethyl)tetrahydrofuran-2-
carboxamide

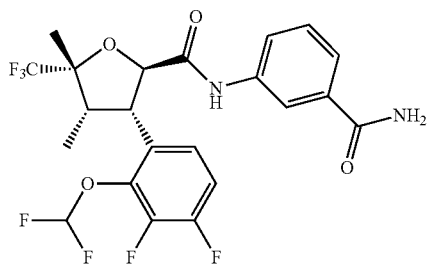

(2R,3S,4S,5R)-N-(3-carbamoylphenyl)-3-(2-
(difluoromethoxy)-3,4-difluorophenyl)-4,5-
dimethyl-5-(trifluoromethyl)tetrahydrofuran-2-
carboxamide

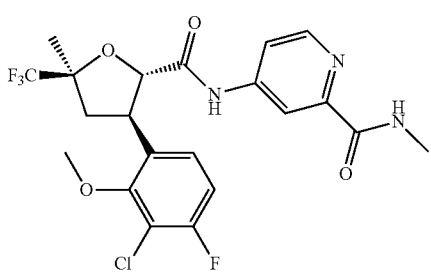

4-((2S,3R,5S)-3-(3-chloro-4-fluoro-2-
methoxyphenyl)-5-methyl-5-
(trifluoromethyl)tetrahydrofuran-2-
carboxamido)-N-methylpicolinamide

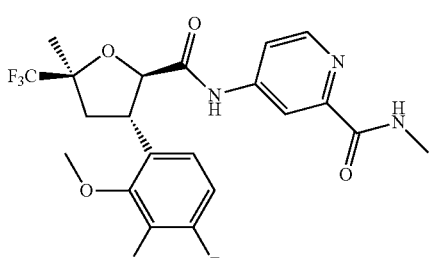

4-((2R,3S,5S)-3-(3-chloro-4-fluoro-2-
methoxyphenyl)-5-methyl-5-
(trifluoromethyl)tetrahydrofuran-2-carboxamido)-
N-methylpicolinamide TABLE B-continued Compound Structures and Names.

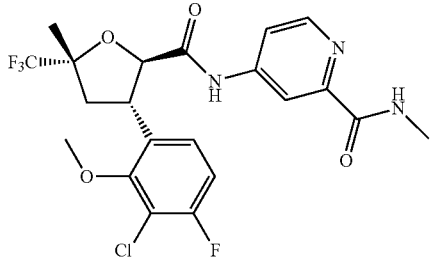

4-((2R,3S,5R)-3-(3-chloro-4-fluoro-2-
methoxyphenyl)-5-methyl-5-
(trifluoromethyl)tetrahydrofuran-2-
carboxamido)-N-methylpicolinamide

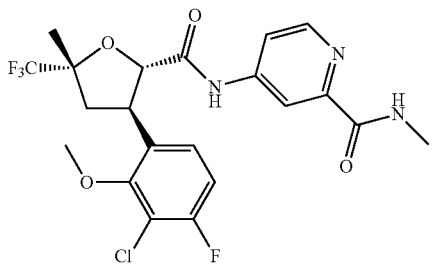

4-((2S,3R,5R)-3-(3-chloro-4-fluoro-2-
methoxyphenyl)-5-methyl-5-
(trifluoromethyl)tetrahydrofuran-2-
carboxamido)-N-methylpicolinamide

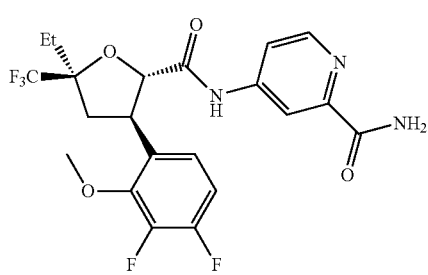

4-((2S,3R,5S)-3-(3,4-difluoro-2-
methoxyphenyl)-5-ethyl-5-
(trifluoromethyl)tetrahydrofuran-2-
carboxamido)picolinamide

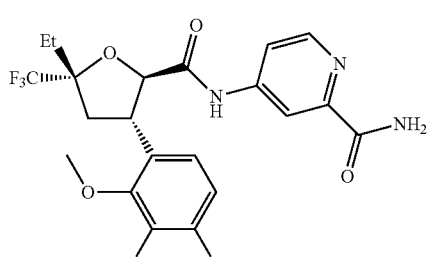

4-((2R,3S,5R)-3-(3,4-difluoro-2-
methoxyphenyl)-5-ethyl-5-
(trifluoromethyl)tetrahydrofuran-2-
carboxamido)picolinamide TABLE B-continued Compound Structures and Names.

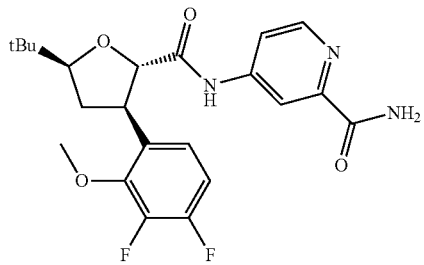

4-((2S,3R,5S)-5-(tert-butyl)-3-(3,4-difluoro-
2-methoxyphenyl)tetrahydrofuran-2-
carboxamido)picolinamide

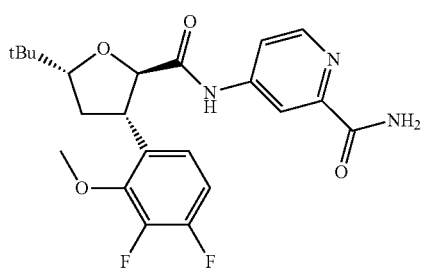

4-((2R,3S,5R)-5-(tert-butyl)-3-(3,4-difluoro-
2-methoxyphenyl)tetrahydrofuran-2-
carboxamido)picolinamide

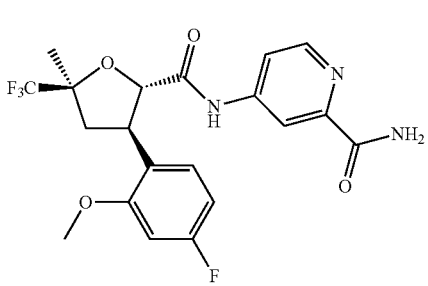

4-((2S,3R,5S)-3-(4-fluoro-2-methoxyphenyl)-
5-methyl-5-(trifluoromethyl)tetrahydrofuran-
2-carboxamido)picolinamide

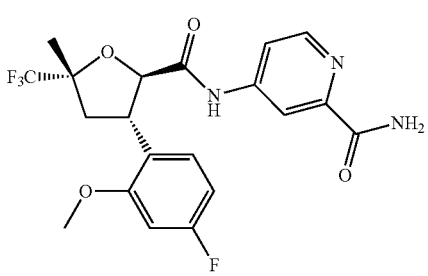

4-((2R,3S,5R)-3-(4-fluoro-2-methoxyphenyl)-
5-methyl-5-(trifluoromethyl)tetrahydrofuran-
2-carboxamido)picolinamide TABLE B-continued Compound Structures and Names.

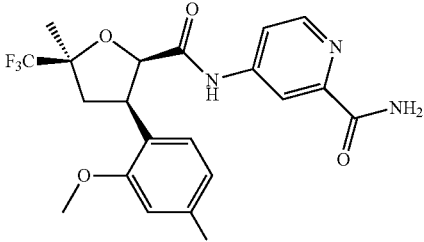

4-((2R,3R,5S)-3-(4-fluoro-2-methoxyphenyl)-
5-methyl-5-(trifluoromethyl)tetrahydrofuran-
2-carboxamido)picolinamide

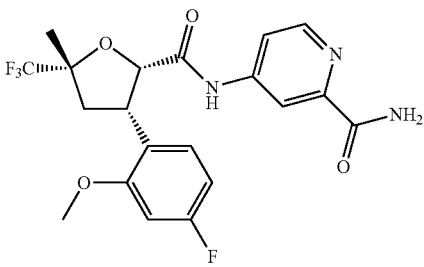

4-((2S,3S,5R)-3-(4-fluoro-2-methoxyphenyl)-
5-methyl-5-(trifluoromethyl)tetrahydrofuran-
2-carboxamido)picolinamide

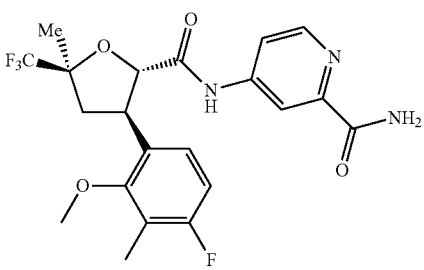

4-((2S,3R,5S)-3-(4-fluoro-2-methoxy-3-
methylphenyl)-5-methyl-5-
(trifluoromethyl)tetrahydrofuran-2-
carboxamido)picolinamide

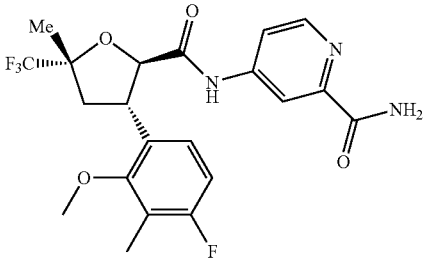

4-((2R,3S,5R)-3-(4-fluoro-2-methoxy-3-
methylphenyl)-5-methyl-5-
(trifluoromethyl)tetrahydrofuran-2-
carboxamido)picolinamide TABLE B-continued Compound Structures and Names.

4-((2S,3R,5S)-3-(2-(difluoromethoxy)-4-fluorophenyl)-5-methyl-5-(trifluoromethyl)tetrahydrofuran-2-carboxamido)picolinamide 4-((2R,3S,5R)-3-(2-(difluoromethoxy)-4-fluorophenyl)-5-methyl-5-(trifluoromethyl)tetrahydrofuran-2-carboxamido)picolinamide 4-((2S,3R,5S)-3-(3-ethyl-4-fluoro-2-methoxyphenyl)-5-methyl-5-(trifluoromethyl)tetrahydrofuran-2-carboxamido)picolinamide 4-((2R,3S,5R)-3-(3-ethyl-4-fluoro-2-methoxyphenyl)-5-methyl-5-(trifluoromethyl)tetrahydrofuran-2-carboxamido)picolinamide 4-((2S,3R,5S)-3-(2,4-difluoro-3-methylphenyl)-5-methyl-5-(trifluoromethyl)tetrahydrofuran-2-carboxamido)picolinamide 4-((2R,3S,5R)-3-(2,4-difluoro-3-methylphenyl)-5-methyl-5-(trifluoromethyl)tetrahydrofuran-2-carboxamido)picolinamide 4-((2S,3R,5S)-3-(2-fluoro-6-methoxyphenyl)-5-methyl-5-(trifluoromethyl)tetrahydrofuran-2-carboxamido)picolinamide 4-((2R,3S,5R)-3-(2-fluoro-6-methoxyphenyl)-5-methyl-5-(trifluoromethyl)tetrahydrofuran-2-carboxamido)picolinamide TABLE B-continued Compound Structures and Names.

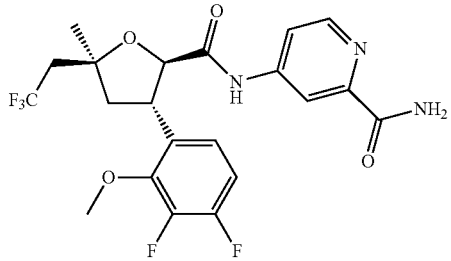

4-((2R,3S,5S)-3-(3,4-difluoro-2-
methoxyphenyl)-5-methyl-5-(2,2,2-
trifluoroethyl)tetrahydrofuran-2-
carboxamido)picolinamide

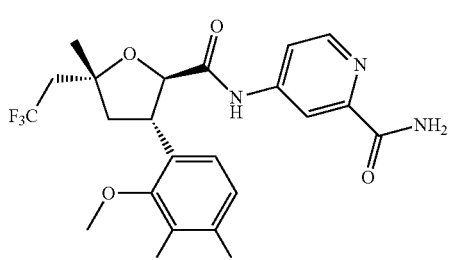

4-((2R,3S,5R)-3-(3,4-difluoro-2-
methoxyphenyl)-5-methyl-5-(2,2,2-
trifluoroethyl)tetrahydrofuran-2-
carboxamido)picolinamide

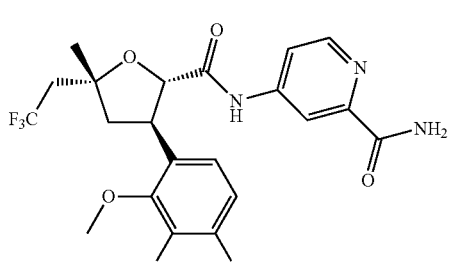

4-((2S,3R,5R)-3-(3,4-difluoro-2-
methoxyphenyl)-5-methyl-5-(2,2,2-
trifluoroethyl)tetrahydrofuran-2-
carboxamido)picolinamide

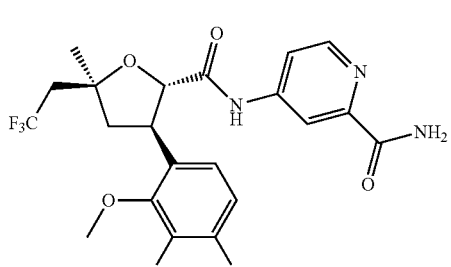

4-((2S,3R,5S)-3-(3,4-difluoro-2-
methoxyphenyl)-5-methyl-5-(2,2,2-
trifluoroethyl)tetrahydrofuran-2-
carboxamido)picolinamide

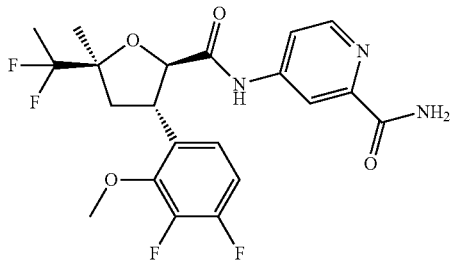

4-((2R,3S,5S)-3-(3,4-difluoro-2-methoxyphenyl)-
5-(1,1-difluoroethyl)-5-methyltetrahydrofuran-2-
carboxamido)picolinamide

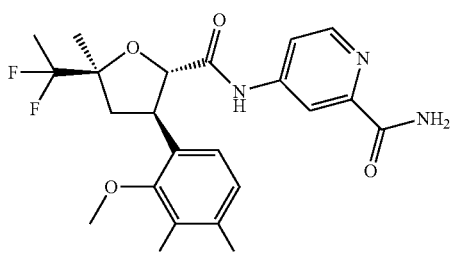

4-((2S,3R,5S)-3-(3,4-difluoro-2-methoxyphenyl)-
5-(1,1-difluoroethyl)-5-methyltetrahydrofuran-2-
carboxamido)picolinamide

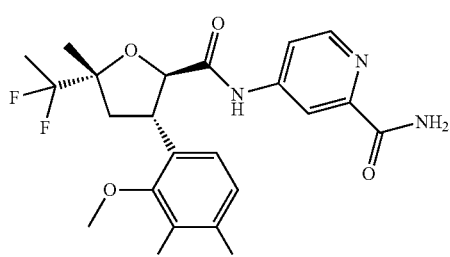

4-((2R,3S,5R)-3-(3,4-difluoro-2-
methoxyphenyl)-5-(1,1-difluoroethyl)-5-
methyltetrahydrofuran-2-
carboxamido)picolinamide

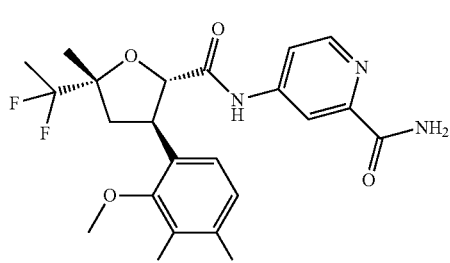

4-((2S,3R,5R)-3-(3,4-difluoro-2-methoxyphenyl)-
5-(1,1-difluoroethyl)-5-methyltetrahydrofuran-2-
carboxamido)picolinamide TABLE B-continued Compound Structures and Names.

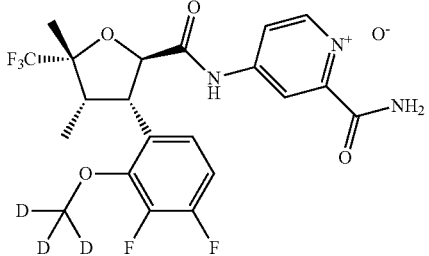

2-carbamoyl-4-((2R,3S,4S,5R)-3-(3,4-difluoro-2-
(methoxy-d₃)phenyl)-4,5-dimethyl-5-
(trifluoromethyl)tetrahydrofuran-2-
carboxamido)pyridine 1-oxide

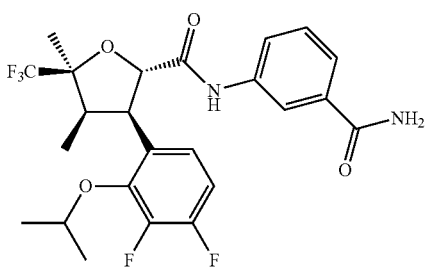

(2S,3R,4R,5S)-N-(3-carbamoylphenyl)-3-
(3,4-difluoro-2-isopropoxyphenyl)-4,5-
dimethyl-5-(trifluoromethyl)tetrahydrofuran-2-
carboxamide

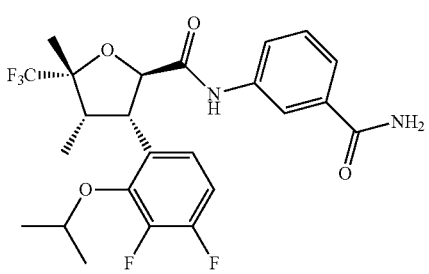

(2R,3S,4S,5R)-N-(3-carbamoylphenyl)-3-
(3,4-difluoro-2-isopropoxyphenyl)-4,5-
dimethyl-5-(trifluoromethyl)tetrahydrofuran-2-
carboxamide

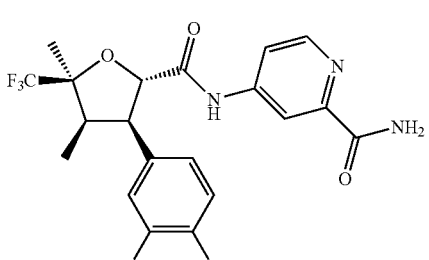

4-((2S,3R,4R,5S)-3-(3,4-difluorophenyl)-
4,5-dimethyl-5-
(trifluoromethyl)tetrahydrofuran-2-
carboxamido)picolinamide TABLE B-continued Compound Structures and Names.

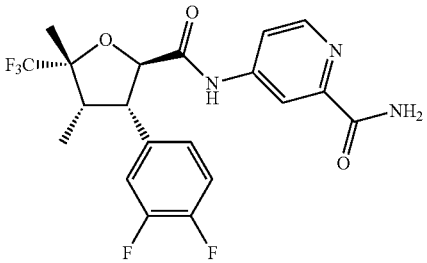

4-((2R,3S,4S,5R)-3-(3,4-difluorophenyl)-
4,5-dimethyl-5-
(trifluoromethyl)tetrahydrofuran-2-
carboxamido)picolinamide

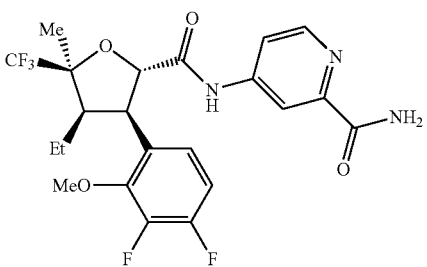

4-((2S,3R,4R,5S)-3-(3,4-difluoro-2-
methoxyphenyl)-4-ethyl-5-methyl-5-
(trifluoromethyl)tetrahydrofuran-2-
carboxamido)picolinamide

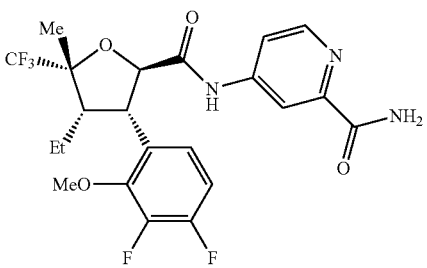

4-((2R,3S,4S,5R)-3-(3,4-difluoro-2-
methoxyphenyl)-4-ethyl-5-methyl-5-
(trifluoromethyl)tetrahydrofuran-2-
carboxamido)picolinamide

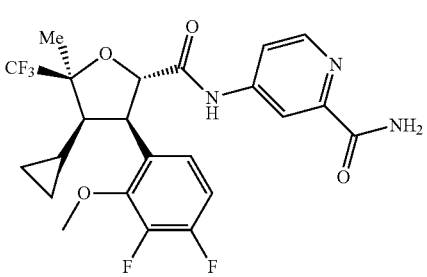

4-((2S,3R,4R,5S)-4-cyclopropyl-3-(3,4-
difluoro-2-methoxyphenyl)-5-methyl-5-
(trifluoromethyl)tetrahydrofuran-2-
carboxamido)picolinamide TABLE B-continued Compound Structures and Names.

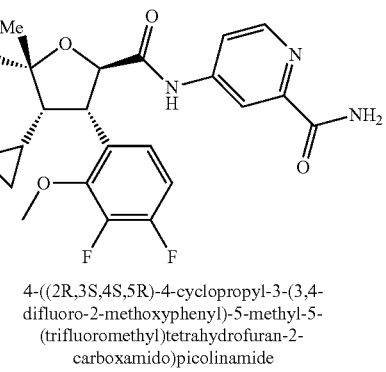

4-((2R,3S,4S,5R)-4-cyclopropyl-3-(3,4-difluoro-2-methoxyphenyl)-5-methyl-5-(trifluoromethyl)tetrahydrofuran-2-carboxamido)picolinamide

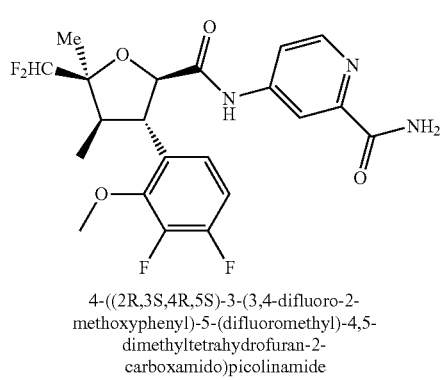 [SMILES: COc1c([C@@H]2[C@@H](C)[C@@](C)(C(F)F)O[C@H]2C(=O)Nc2ccnc(C(N)=O)c2)ccc(F)c1F]

4-((2R,3S,4R,5S)-3-(3,4-difluoro-2-methoxyphenyl)-5-(difluoromethyl)-4,5-dimethyltetrahydrofuran-2-carboxamido)picolinamide

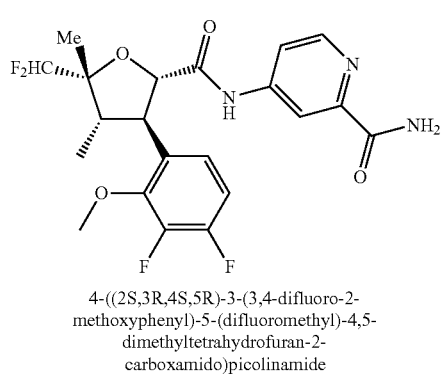 [SMILES: COc1c([C@@H]2[C@@H](C(=O)Nc3ccnc(C(N)=O)c3)O[C@@](C)(C(F)F)[C@H]2C)ccc(F)c1F]

4-((2S,3R,4S,5R)-3-(3,4-difluoro-2-methoxyphenyl)-5-(difluoromethyl)-4,5-dimethyltetrahydrofuran-2-carboxamido)picolinamide

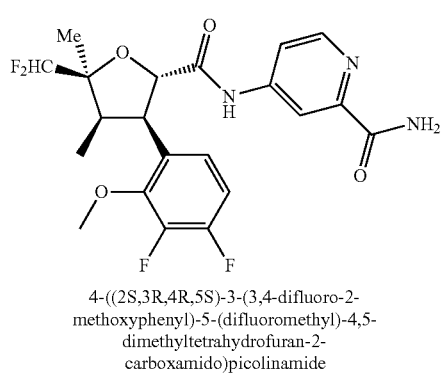 [SMILES: COc1c([C@@H]2[C@@H](C(=O)Nc3ccnc(C(N)=O)c3)O[C@](C)(C(F)F)[C@@H]2C)ccc(F)c1F]

4-((2S,3R,4R,5S)-3-(3,4-difluoro-2-methoxyphenyl)-5-(difluoromethyl)-4,5-dimethyltetrahydrofuran-2-carboxamido)picolinamide TABLE B-continued Compound Structures and Names.

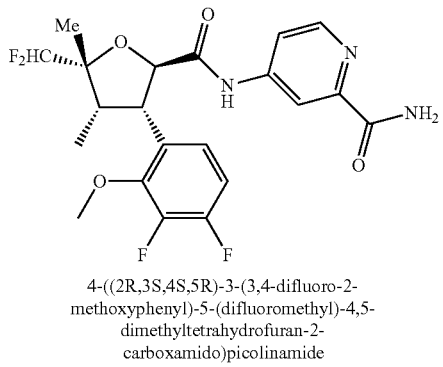 [SMILES: COc1c([C@H]2[C@H](C(=O)Nc3ccnc(C(N)=O)c3)O[C@@](C)(C(F)F)[C@H]2C)ccc(F)c1F]

4-((2R,3S,4S,5R)-3-(3,4-difluoro-2-methoxyphenyl)-5-(difluoromethyl)-4,5-dimethyltetrahydrofuran-2-carboxamido)picolinamide

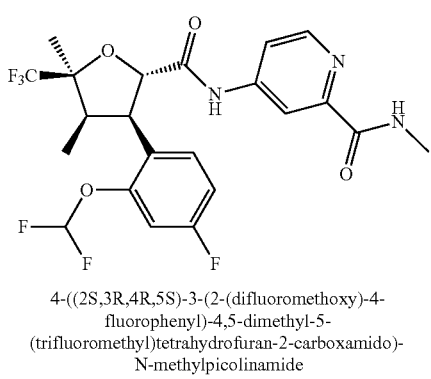 [SMILES: CNC(=O)c1cc(NC(=O)[C@H]2O[C@](C)(C(F)(F)F)[C@H](C)[C@@H]2c2ccc(F)cc2OC(F)F)ccn1]

4-((2S,3R,4R,5S)-3-(2-(difluoromethoxy)-4-fluorophenyl)-4,5-dimethyl-5-(trifluoromethyl)tetrahydrofuran-2-carboxamido)-N-methylpicolinamide

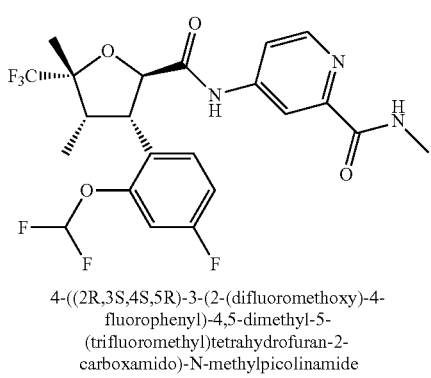 [SMILES: CNC(=O)c1cc(NC(=O)[C@@H]2O[C@@](C)(C(F)(F)F)[C@@H](C)[C@H]2c2ccc(F)cc2OC(F)F)ccn1]

4-((2R,3S,4S,5R)-3-(2-(difluoromethoxy)-4-fluorophenyl)-4,5-dimethyl-5-(trifluoromethyl)tetrahydrofuran-2-carboxamido)-N-methylpicolinamide

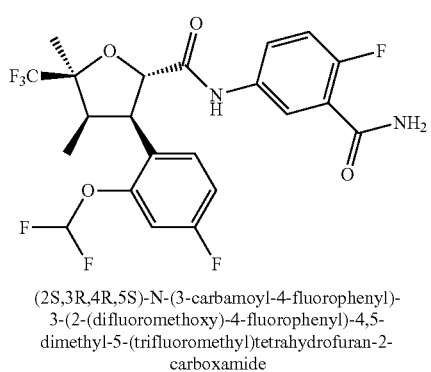 [SMILES: C[C@@H]1[C@H](c2ccc(F)cc2OC(F)F)[C@@H](C(=O)Nc2ccc(F)c(C(N)=O)c2)O[C@]1(C)C(F)(F)F]

(2S,3R,4R,5S)-N-(3-carbamoyl-4-fluorophenyl)-3-(2-(difluoromethoxy)-4-fluorophenyl)-4,5-dimethyl-5-(trifluoromethyl)tetrahydrofuran-2-carboxamide TABLE B-continued Compound Structures and Names.

(2R,3S,4S,5R)-N-(3-carbamoyl-4-fluorophenyl)-3-(2-(difluoromethoxy)-4-fluorophenyl)-4,5-dimethyl-5-(trifluoromethyl)tetrahydrofuran-2-carboxamide 4-((2S,3S,4R)-3-(3,4-difluoro-2-methoxyphenyl)-4,5,5-trimethyltetrahydrofuran-2-carboxamido)picolinamide 4-((2R,3R,4S)-3-(3,4-difluoro-2-methoxyphenyl)-4,5,5-trimethyltetrahydrofuran-2-carboxamido)picolinamide 4-((2S,3R,4S)-3-(3,4-difluoro-2-methoxyphenyl)-4,5,5-trimethyltetrahydrofuran-2-carboxamido)picolinamide TABLE B-continued Compound Structures and Names.

4-((2R,3S,4R)-3-(3,4-difluoro-2-methoxyphenyl)-4,5,5-trimethyltetrahydrofuran-2-carboxamido)picolinamide 4-((2S,3R,4R)-3-(3,4-difluoro-2-methoxyphenyl)-4,5,5-trimethyltetrahydrofuran-2-carboxamido)picolinamide 4-((2R,3S,4S)-3-(3,4-difluoro-2-methoxyphenyl)-4,5,5-trimethyltetrahydrofuran-2-carboxamido)picolinamide 4-((2S,3R,4R,5R)-3-(3,4-difluoro-2-methoxyphenyl)-4,5-dimethyltetrahydrofuran-2-carboxamido)picolinamide TABLE B-continued Compound Structures and Names.

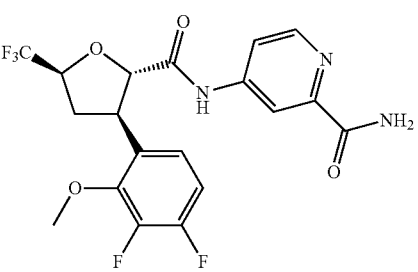

4-((2R,3S,4S,5S)-3-(3,4-difluoro-2-methoxyphenyl)-4,5-dimethyltetrahydrofuran-2-carboxamido)picolinamide

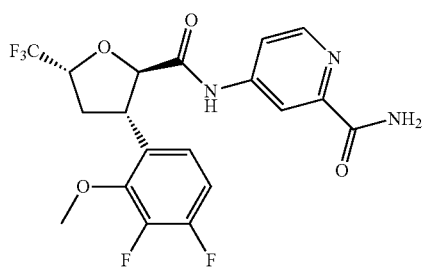

4-((2S,3R,5S)-3-(3,4-difluoro-2-methoxyphenyl)-5-(trifluoromethyl)tetrahydrofuran-2-carboxamido)picolinamide

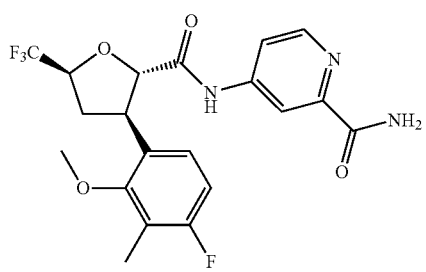

4-((2R,3S,5R)-3-(3,4-difluoro-2-methoxyphenyl)-5-(trifluoromethyl)tetrahydrofuran-2-carboxamido)picolinamide

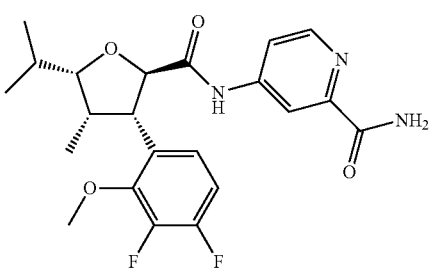

4-((2S,3R,5S)-3-(4-fluoro-2-methoxy-3-methylphenyl)-5-(trifluoromethyl)tetrahydrofuran-2-carboxamido)picolinamide TABLE B-continued Compound Structures and Names.

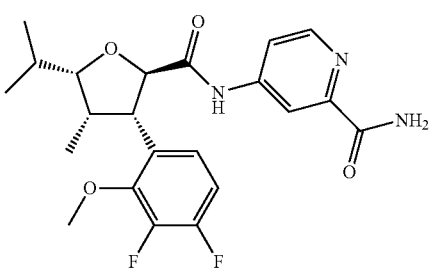

4-((2R,3S,5R)-3-(4-fluoro-2-methoxy-3-methylphenyl)-5-(trifluoromethyl)tetrahydrofuran-2-carboxamido)picolinamide

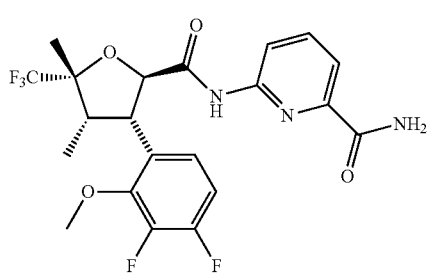

4-((2R,3S,4S,5S)-3-(3,4-difluoro-2-methoxyphenyl)-5-isopropyl-4-methyltetrahydrofuran-2-carboxamido)picolinamide

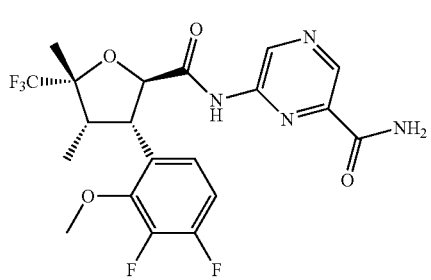

6-((2R,3S,4S,5R)-3-(3,4-difluoro-2-methoxyphenyl)-4,5-dimethyl-5-(trifluoromethyl)tetrahydrofuran-2-carboxamido)picolinamide 6-((2R,3S,4S,5R)-3-(3,4-difluoro-2-methoxyphenyl)-4,5-dimethyl-5-(trifluoromethyl)tetrahydrofuran-2-carboxamido)pyrazine-2-carboxamide TABLE B-continued Compound Structures and Names.

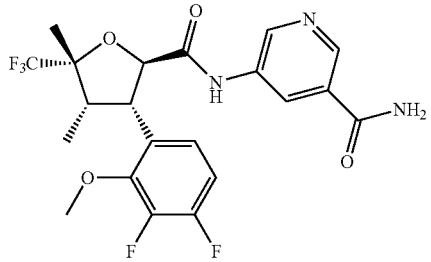

5-((2R,3S,4S,5R)-3-(3,4-difluoro-2-
methoxyphenyl)-4,5-dimethyl-5-
(trifluoromethyl)tetrahydrofuran-2-
carboxamido)nicotinamide

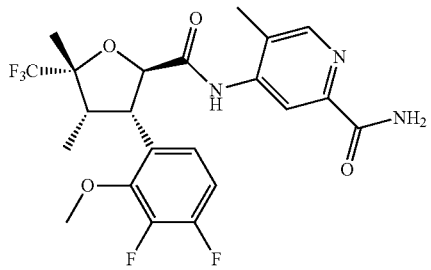

4-((2R,3S,4S,5R)-3-(3,4-difluoro-2-
methoxyphenyl)-4,5-dimethyl-5-
(trifluoromethyl)tetrahydrofuran-2-
carboxamido)-5-methylpicolinamide

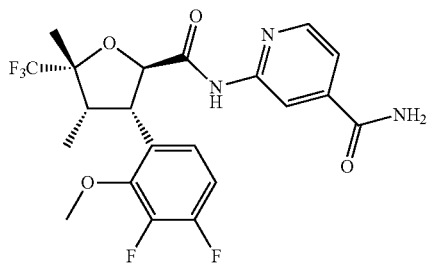

2-((2R,3S,4S,5R)-3-(3,4-difluoro-2-
methoxyphenyl)-4,5-dimethyl-5-
(trifluoromethyl)tetrahydrofuran-2-
carboxamido)isonicotinamide

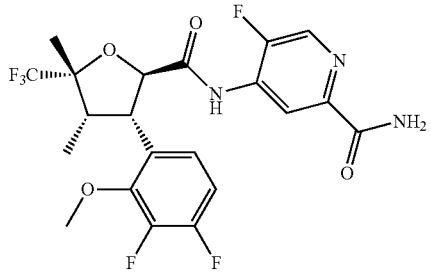

4-((2R,3S,4S,5R)-3-(3,4-difluoro-2-
methoxyphenyl)-4,5-dimethyl-5-
(trifluoromethyl)tetrahydrofuran-2-
carboxamido)-5-fluoropicolinamide TABLE B-continued Compound Structures and Names.

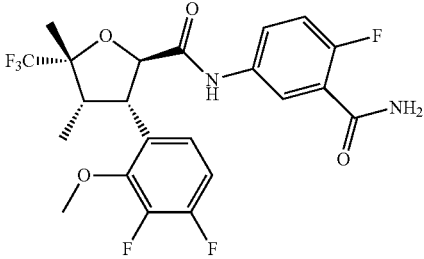

(2R,3S,4S,5R)-N-(3-carbamoyl-4-fluorophenyl)-
3-(3,4-difluoro-2-methoxyphenyl)-4,5-dimethyl-
5-(trifluoromethyl)tetrahydrofuran-2-
carboxamide

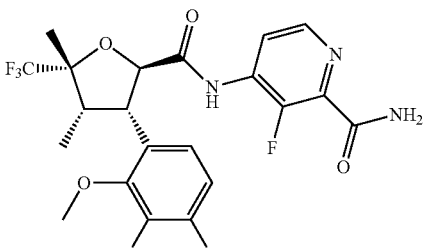

4-((2R,3S,4S,5R)-3-(3,4-difluoro-2-
methoxyphenyl)-4,5-dimethyl-5-
(trifluoromethyl)tetrahydrofuran-2-
carboxamido)-3-fluoropicolinamide

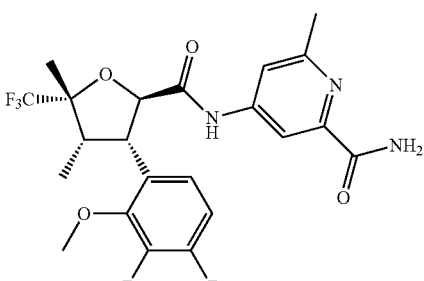

4-((2R,3S,4S,5R)-3-(3,4-difluoro-2-
methoxyphenyl)-4,5-dimethyl-5-
(trifluoromethyl)tetrahydrofuran-2-
carboxamido)-6-methylpicolinamide

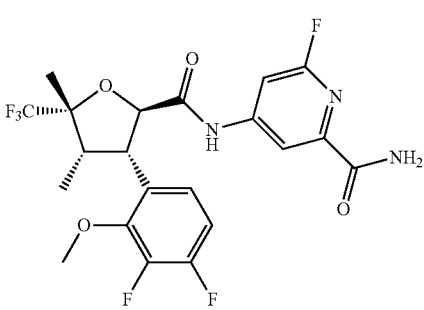

4-((2R,3S,4S,5R)-3-(3,4-difluoro-2-
methoxyphenyl)-4,5-dimethyl-5-
(trifluoromethyl)tetrahydrofuran-2-
carboxamido)-6-fluoropicolinamide TABLE B-continued Compound Structures and Names.

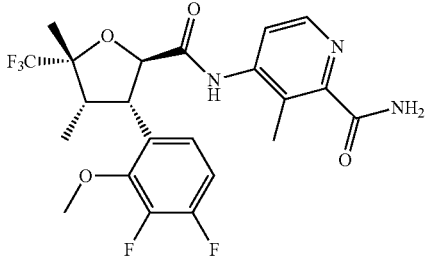

4-((2R,3S,4S,5R)-3-(3,4-difluoro-2-methoxyphenyl)-4,5-dimethyl-5-(trifluoromethyl)tetrahydrofuran-2-carboxamido)-3-methylpicolinamide

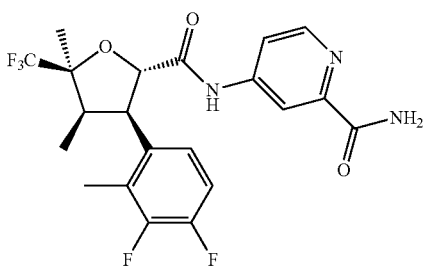

4-((2S,3R,4R,5S)-3-(3,4-difluoro-2-methylphenyl)-4,5-dimethyl-5-(trifluoromethyl)tetrahydrofuran-2-carboxamido)picolinamide

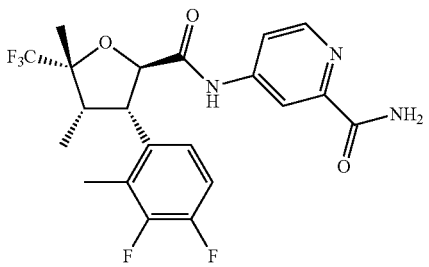

4-((2R,3S,4S,5R)-3-(3,4-difluoro-2-methylphenyl)-4,5-dimethyl-5-(trifluoromethyl)tetrahydrofuran-2-carboxamido)picolinamide

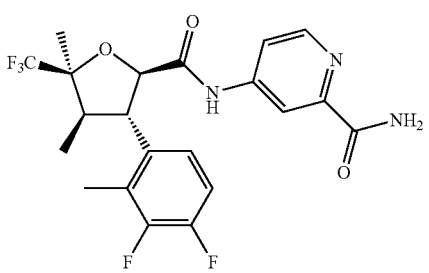

4-((2R,3S,4R,5S)-3-(3,4-difluoro-2-methylphenyl)-4,5-dimethyl-5-(trifluoromethyl)tetrahydrofuran-2-carboxamido)picolinamide

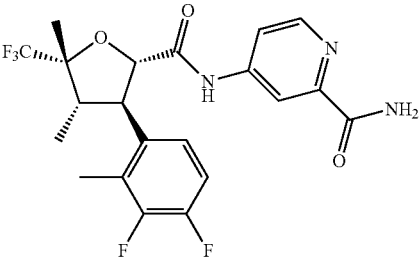

4-((2S,3R,4S,5R)-3-(3,4-difluoro-2-methylphenyl)-4,5-dimethyl-5-(trifluoromethyl)tetrahydrofuran-2-carboxamido)picolinamide

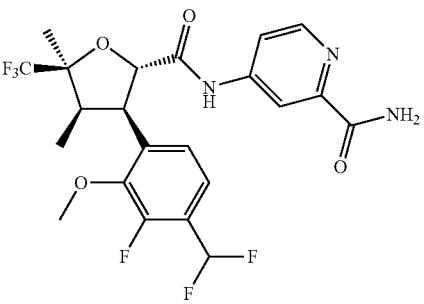

4-((2S,3R,4R,5S)-3-(4-(difluoromethyl)-3-fluoro-2-methoxyphenyl)-4,5-dimethyl-5-(trifluoromethyl)tetrahydrofuran-2-carboxamido)picolinamide

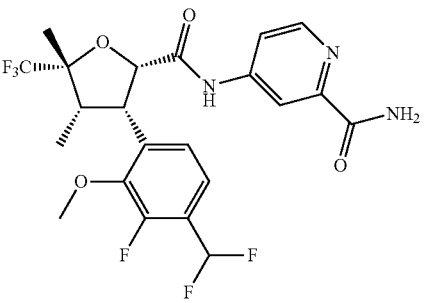

4-((2R,3S,4S,5R)-3-(4-(difluoromethyl)-3-fluoro-2-methoxyphenyl)-4,5-dimethyl-5-(trifluoromethyl)tetrahydrofuran-2-carboxamido)picolinamide

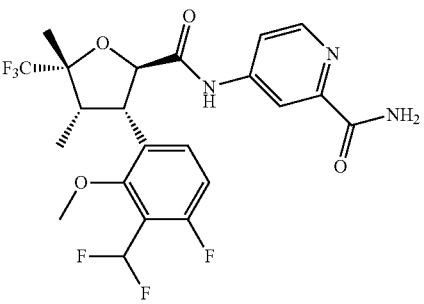

4-((2R,3S,4S,5R)-3-(3-(difluoromethyl)-4-fluoro-2-methoxyphenyl)-4,5-dimethyl-5-(trifluoromethyl)tetrahydrofuran-2-carboxamido)picolinamide TABLE B-continued Compound Structures and Names.

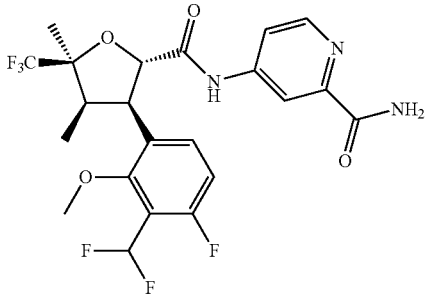

4-((2S,3R,4R,5S)-3-(3-(difluoromethyl)-4-
fluoro-2-methoxyphenyl)-4,5-dimethyl-5-
(trifluoromethyl)tetrahydrofuran-2-
carboxamido)picolinamide

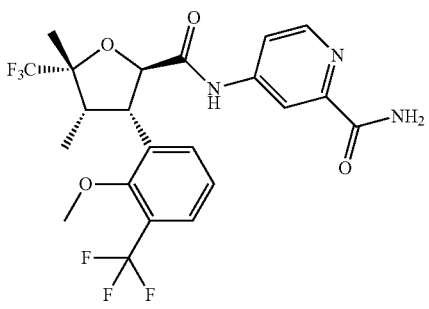

4-((2R,3S,4S,5R)-3-(2-methoxy-3-
(trifluoromethyl)phenyl)-4,5-dimethyl-5-
(trifluoromethyl)tetrahydrofuran-2-
carboxamido)picolinamide

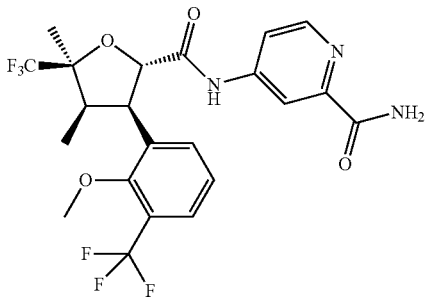

4-((2S,3R,4R,5S)-3-(2-methoxy-3-
(trifluoromethyl)phenyl)-4,5-dimethyl-5-
(trifluoromethyl)tetrahydrofuran-2-
carboxamido)picolinamide

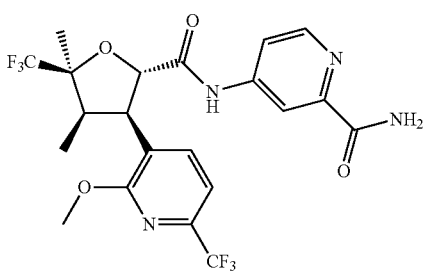

4-((2S,3R,4R,5S)-3-(2-methoxy-6-
(trifluoromethyl)pyridin-3-yl)-4,5-dimethyl-5-
(trifluoromethyl)tetrahydrofuran-2-
carboxamido)picolinamide TABLE B-continued Compound Structures and Names.

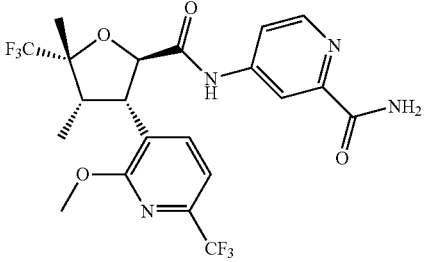

4-((2R,3S,4S,5R)-3-(2-methoxy-6-
(trifluoromethyl)pyridin-3-yl)-4,5-dimethyl-5-
(trifluoromethyl)tetrahydrofuran-2-
carboxamido)picolinamide

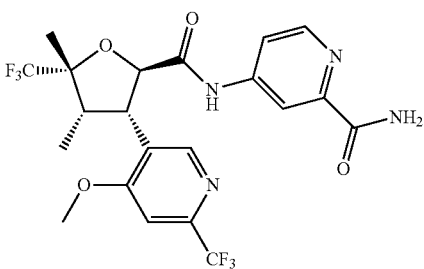

4-((2R,3S,4S,5R)-3-(4-methoxy-6-
(trifluoromethyl)pyridin-3-yl)-4,5-dimethyl-5-
(trifluoromethyl)tetrahydrofuran-2-
carboxamido)picolinamide

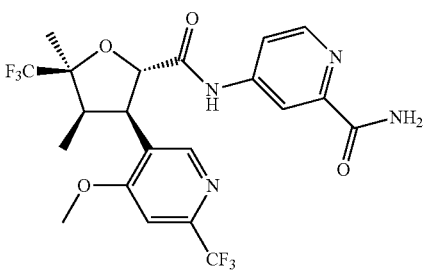

4-((2S,3R,4R,5S)-3-(4-methoxy-6-
(trifluoromethyl)pyridin-3-yl)-4,5-dimethyl-5-
(trifluoromethyl)tetrahydrofuran-2-
carboxamido)picolinamide

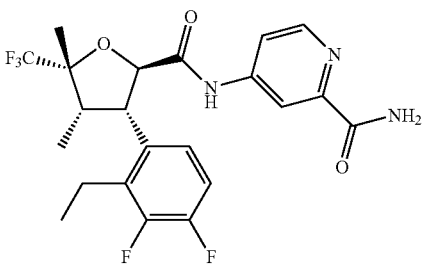

4-((2R,3S,4S,5R)-3-(2-ethyl-3,4-
difluorophenyl)-4,5-dimethyl-5-
(trifluoromethyl)tetrahydrofuran-2-
carboxamido)picolinamide TABLE B-continued Compound Structures and Names.

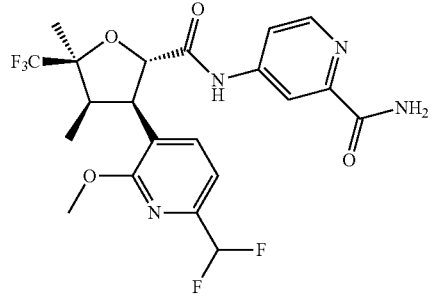

4-((2S,3R,4R,5S)-3-(6-(difluoromethyl)-2-
methoxypyridin-3-yl)-4,5-dimethyl-5-
(trifluoromethyl)tetrahydrofuran-2-
carboxamido)picolinamide

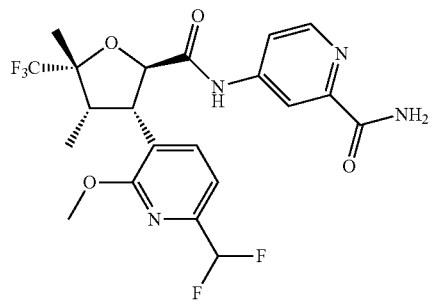

4-((2R,3S,4S,5R)-3-(6-(difluoromethyl)-2-
methoxypyridin-3-yl)-4,5-dimethyl-5-
(trifluoromethyl)tetrahydrofuran-2-
carboxamido)picolinamide

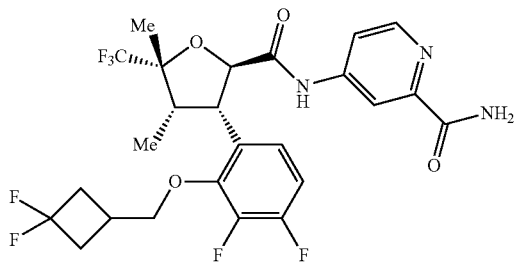

4-((2R,3S,4S,5R)-3-(2-((3,3-
difluorocyclobutyl)methoxy)-3,4-difluorophenyl)-4,5-
dimethyl-5-(trifluoromethyl)tetrahydrofuran-2-
carboxamido)picolinamide

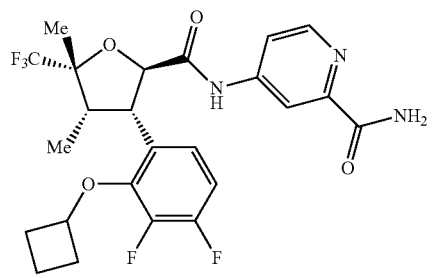

4-((2R,3S,4S,5R)-3-(2-cyclobutoxy-3,4-
difluorophenyl)-4,5-dimethyl-5-
(trifluoromethyl)tetrahydrofuran-2-
carboxamido)picolinamide

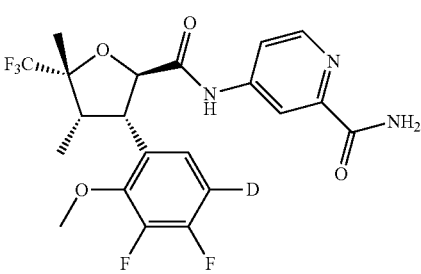

4-((2R,3S,4S,5R)-3-(3,4-difluoro-2-
methoxyphenyl-5-d)-4,5-dimethyl-5-
(trifluoromethyl)tetrahydrofuran-2-
carboxamido)picolinamide

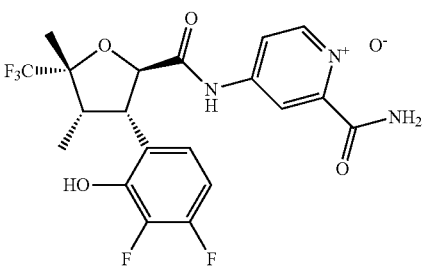

2-carbamoyl-4-((2R,3S,4S,5R)-3-(3,4-
difluoro-2-hydroxyphenyl)-4,5-dimethyl-5-
(trifluoromethyl)tetrahydrofuran-2-
carboxamido)pyridine 1-oxide

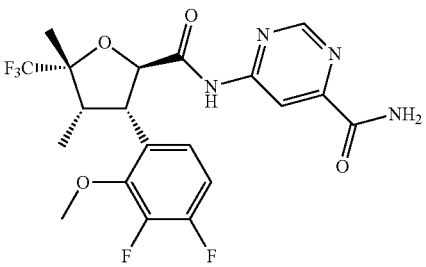

6-((2R,3S,4S,5R)-3-(3,4-difluoro-2-
methoxyphenyl)-4,5-dimethyl-5-
(trifluoromethyl)tetrahydrofuran-2-
carboxamido)pyrimidine-4-carboxamide

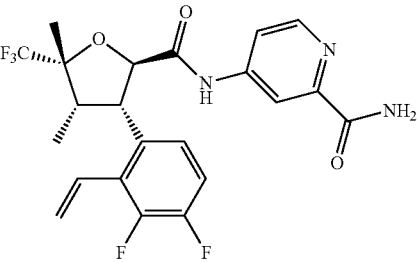

4-((2R,3S,4S,5R)-3-(3,4-difluoro-2-
vinylphenyl)-4,5-dimethyl-5-
(trifluoromethyl)tetrahydrofuran-2-
carboxamido)picolinamide TABLE B-continued Compound Structures and Names.

4-((2R,3S,4S,5R)-3-(2-(difluoromethoxy)-3,4-difluorophenyl)-4,5-dimethyl-5-(trifluoromethyl)tetrahydrofuran-2-carboxamido)-5-methylpicolinamide 4-((2S,3R,4R,5S)-3-(2-(difluoromethoxy)-3,4-difluorophenyl)-4,5-dimethyl-5-(trifluoromethyl)tetrahydrofuran-2-carboxamido)-5-methylpicolinamide 4-((2R,3S,4S,5R)-3-(5-chloro-3,4-difluoro-2-methoxyphenyl)-4,5-dimethyl-5-(trifluoromethyl)tetrahydrofuran-2-carboxamido)picolinamide 4-((2R,3S,4S,5R)-3-(4-fluoro-2-hydroxyphenyl)-4,5-dimethyl-5-(trifluoromethyl)tetrahydrofuran-2-carboxamido)picolinamide TABLE B-continued Compound Structures and Names.

4-((2R,3S,4S,5R)-3-(3,4-difluoro-2-methoxyphenyl)-4,5-dimethyl-5-(trifluoromethyl)tetrahydrofuran-2-carboxamido)picolinamide-5-d 4-((2R,3S,4S,5R)-3-(3,4-difluoro-2-methoxyphenyl)-4,5-dimethyl-5-(trifluoromethyl)tetrahydrofuran-2-carboxamido)picolinamide-3-d 4-((2R,3S,4S,5R)-3-(3,4-difluoro-2-methoxyphenyl)-4,5-dimethyl-5-(trifluoromethyl)tetrahydrofuran-2-carboxamido)picolinamide-6-d 4-((2S,3R,4R,5S)-3-(3-methoxypyridin-2-yl)-4,5-dimethyl-5-(trifluoromethyl)tetrahydrofuran-2-carboxamido)picolinamide TABLE B-continued Compound Structures and Names.

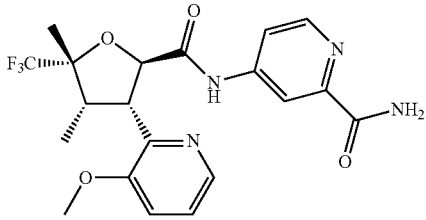

4-((2R,3S,4S,5R)-3-(3-methoxypyridin-2-yl)-4,5-dimethyl-5-(trifluoromethyl)tetrahydrofuran-2-carboxamido)picolinamide

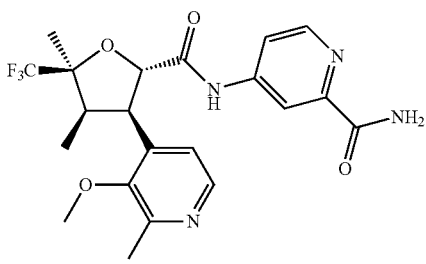

4-((2S,3R,4R,5S)-3-(3-methoxy-2-methylpyridin-4-yl)-4,5-dimethyl-5-(trifluoromethyl)tetrahydrofuran-2-carboxamido)picolinamide TABLE B-continued Compound Structures and Names.

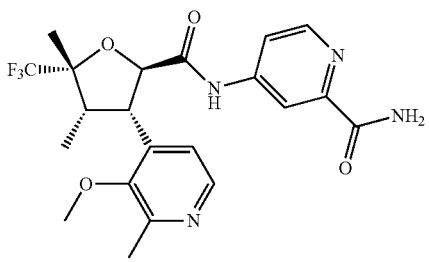

4-((2R,3S,4S,5R)-3-(3-methoxy-2-methylpyridin-4-yl)-4,5-dimethyl-5-(trifluoromethyl)tetrahydrofuran-2-carboxamido)picolinamide In some embodiments, the invention relates to a compound selected from Table C or a pharmaceutically acceptable salt thereof. In other embodiments, the invention relates to a compound selected from Table C in non-salt form.

TABLE C

Compound Names.

(2R,3R,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3R,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3R,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3S,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3R,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3R,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3S,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3R,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3S,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3R,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3S,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3S,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3R,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3S,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3S,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2S,3S,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide
(2R,3R,4R,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3R,4R,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3R,4S,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide

TABLE C-continued

Compound Names.

(2R,3S,4R,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3R,4R,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3R,4S,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3R,4R,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3R,4R,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3S,4S,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3R,4S,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3S,4R,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3S,4S,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3R,4S,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3S,4R,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3S,4S,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2S,3S,4S,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide
(2R,3R,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3R,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3R,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3S,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3R,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3R,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3S,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3R,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3S,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3R,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3S,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3S,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3R,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3S,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3S,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2S,3S,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide
(2R,3R,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3R,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3R,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3S,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3R,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3R,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3S,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3R,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3S,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3R,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide TABLE C-continued Compound Names.

(2S,3S,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3S,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3R,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3S,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3S,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2S,3S,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide
(2R,3R,5R)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2R,3R,5S)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2R,3S,5R)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2S,3R,5R)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2R,3S,5S)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2S,3R,5S)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2S,3S,5R)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2S,3S,5S)-N-(3-carbamoyl-4-fluoro-phenyl)-3-(3,4-difluoro-2-methoxy-phenyl)-5-methyl-5-(trifluoromethyl)tetrahydrofuran-2-carboxamide
(2R,3R,4R,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3R,4R,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3R,4S,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3S,4R,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3R,4R,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3R,4S,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3S,4R,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3R,4R,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3S,4S,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3R,4S,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3S,4R,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3S,4S,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3R,4S,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3S,4R,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3S,4S,5R)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2S,3S,4S,5S)-N-(3-carbamoylphenyl)-3-[2-(difluoromethoxy)-3,4-difluoro-phenyl]-4,5-dimethyl-5-(trifluoromethyl)tetrahydrofuran-2-carboxamide
(2R,3R,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2R,3R,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2R,3S,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2S,3R,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2R,3S,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2S,3R,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2S,3S,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2S,3S,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide
(2R,3R,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide

TABLE C-continued

Compound Names.

(2R,3R,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2R,3R,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2R,3S,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3R,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2R,3R,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2R,3S,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3R,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2R,3S,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3R,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3S,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2R,3S,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3R,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3S,4R,5S)-4-[[3-(2-ethoxv-3,4-difluoro-phenyl)-4,5-dimethyl-5-(trifluoromethyl)tetrahydrofuran-2-carbonyl]amino]-1-oxido-pyridin-1-ium-2-carboxamide
(2S,3S,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
(2S,3S,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide
4-[[[(2R,3R,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3R,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3R,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3S,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3R,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3R,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3S,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3R,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3S,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3R,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3S,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3S,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3R,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3S,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3S,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2S,3S,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide
4-[[[(2R,3R,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[[(2R,3R,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[[(2R,3R,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[[(2R,3S,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[[(2S,3R,4R,5R)-3-(3,4-difluoro-2-hydroxy-phenyl)-4,5-dimethyl-5-(trifluoromethyl)tetrahydrofuran-2-carbonyl]amino]-1-oxido-pyridin- 1-ium-2-carboxamide
4-[[[(2R,3R,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[[(2R,3S,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[[(2S,3R,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide TABLE C-continued Compound Names.

4-[[(2R,3S,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2S,3R,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2S,3S,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2R,3S,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2S,3R,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2S,3S,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2S,3S,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
4-[[(2S,3S,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide
(2R,3R,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3R,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3R,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3S,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3R,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3R,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3S,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3R,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3S,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3R,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3S,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3S,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3R,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3S,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3S,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2S,3S,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide
(2R,3R,4R,5R)-4-[[3-(4-fluoro-2-hydroxy-phenyl)-4,5-dimethyl-5-(trifluoromethyl)tetrahydrofuran-2-carbonyl]amino]pyridme-2-carboxamide
(2R,3R,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3R,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3S,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3R,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3R,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3S,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3R,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3S,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3R,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3S,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3S,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3R,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3S,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2S,3S,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide

TABLE C-continued

Compound Names.

(2S,3S,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide
(2R,3R,5R)-4-[[3-(3,4-difluoro-2-methoxy-phenyl)-5-ethyl-5-(trifluoromethyl)tetrahydrofuran-2-carbonyl]amino]pyridine-2-carboxamide
(2R,3R,5S)-4-[[3-(3,4-difluoro-2-methoxy-phenyl)-5-ethyl-5-(trifluoromethyl)tetrahydrofuran-2-carbonyl]amino]pyridine-2-carboxamide
(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxamide
(2S,3R,5R)-4-[[3-(3,4-difluoro-2-methoxy-phenyl)-5-ethyl-5-(trifluoromethyl)tetrahydrofuran-2-carbonyl]amino]pyridine-2-carboxamide
(2R,3S,5S)-4-[[3-(3,4-difluoro-2-methoxy-phenyl)-5-ethyl-5-(trifluoromethyl)tetrahydrofuran-2-carbonyl]amino]pyridine-2-carboxamide
(2S,3R,5S)-4-[[3-(3,4-difluoro-2-methoxy-phenyl)-5-ethyl-5-(trifluoromethyl)tetrahydrofuran-2-carbonyl]amino]pyridine-2-carboxamide
(2S,3S,5R)-4-[[3-(3,4-difluoro-2-methoxy-phenyl)-5-ethyl-5-(trifluoromethyl)tetrahydrofuran-2-carbonyl]amino]pyridine-2-carboxamide
(2S,3S,5S)-4-[[3-(3,4-difluoro-2-methoxy-phenyl)-5-ethyl-5-(trifluoromethyl)tetrahydrofuran-2-carbonyl]amino]pyridine-2-carboxamide
(2R,3R,5R)-4-[[5-tert-butyl-3-(3,4-difluoro-2-methoxy-phenyl)tetrahydrofuran-2-carbonyl]amino]pyridine-2-carboxamide
(2R,3R,5S)-4-[[5-tert-butyl-3-(3,4-difluoro-2-methoxy-phenyl)tetrahydrofuran-2-carbonyl]amino]pyridine-2-carboxamide
(2R,3S,5R)-4-[[5-tert-butyl-3-(3,4-difluoro-2-methoxy-phenyl)tetrahydrofuran-2-carbonyl]amino]pyridine-2-carboxamide
(2S,3R,5R)-4-[[5-teri-butyl-3-(3,4-difluoro-2-methoxy-phenyl)tetrahydrofuran-2-carbonyl]amino]pyridine-2-carboxamide
(2R,3S,5S)-4-[[5-tert-butyl-3-(3,4-difluoro-2-methoxy-phenyl)tetrahydrofuran-2-carbonyl]amino]pyridine-2-carboxamide
(2S,3R,5S)-4-[[5-tert-butyl-3-(3,4-difluoro-2-methoxy-phenyl)tetrahydrofuran-2-carbonyl]amino]pyridine-2-carboxamide
(2S,3S,5R)-4-[[5-tert-butyl-3-(3,4-difluoro-2-methoxy-phenyl)tetrahydrofuran-2-carbonyl]amino]pyridine-2-carboxamide
(2S,3S,5S)-4-[[5-tert-butyl-3-(3,4-difluoro-2-methoxy-phenyl)tetrahydrofuran-2-carbonyl]amino]pyridine-2-carboxamide
(2R,3R,5R)-4-[[3-(4-fluoro-2-methoxy-phenyl)-5-methyl-5-(trifluoromethyl)tetrahydrofuran-2-carbonyl]amino]pyridine-2-carboxamide
(2R,3R,5S)-4-[[3-(4-fluoro-2-methoxy-phenyl)-5-methyl-5-(trifluoromethyl)tetrahydrofuran-2-carbonyl]amino]pyridine-2-carboxamide
(2R,3S,5R)-4-[[3-(4-fluoro-2-methoxy-phenyl)-5-methyl-5-(trifluoromethyl)tetrahydrofuran-2-carbonyl]amino]pyridine-2-carboxamide
(2S,3R,5R)-4-[[3-(4-fluoro-2-methoxy-phenyl)-5-methyl-5-(trifluoromethyl)tetrahydrofuran-2-carbonyl]amino]pyridine-2-carboxamide
(2R,3S,5S)-4-[[3-(4-fluoro-2-methoxy-phenyl)-5-methyl-5-(trifluoromethyl)tetrahydrofuran-2-carbonyl]amino]pyridine-2-carboxamide
(2S,3R,5S)-4-[[3-(4-fluoro-2-methoxy-phenyl)-5-methyl-5-(trifluoromethyl)tetrahydrofuran-2-carbonyl]amino]pyridine-2-carboxamide
(2S,3S,5R)-4-[[3-(4-fluoro-2-methoxy-phenyl)-5-methyl-5-(trifluoromethyl)tetrahydrofuran-2-carbonyl]amino]pyridine-2-carboxamide
(2S,3S,5S)-4-[[3-(4-fluoro-2-methoxy-phenyl)-5-methyl-5-(trifluoromethyl)tetrahydrofuran-2-carbonyl]amino]pyridine-2-carboxamide
(2R,3R,5R)-4-[[3-(4-fluoro-2-methoxy-3-methyl-phenyl)-5-methyl-5-(trifluoromethyl)tetrahydrofuran-2-carbonyl]amino]pyridine-2-carboxamide
(2R,3R,5S)-4-[[3-(4-fluoro-2-methoxy-3-methyl-phenyl)-5-methyl-5-(trifluoromethyl)tetrahydrofuran-2-carboxamide
(2R,3S,5R)-4-[[3-(4-fluoro-2-methoxy-3-methyl-phenyl)-5-methyl-5-(trifluoromethyl)tetrahydrofuran-2-carbonyl]amino]pyridine-2-carboxamide
(2S,3R,5R)-4-[[3-(4-fluoro-2-methoxy-3-methyl-phenyl)-5-methyl-5-(trifluoromethyl)tetrahydrofuran-2-carbonyl]amino]pyridine-2-carboxamide
(2R,3S,5S)-4-[[3-(4-fluoro-2-methoxy-3-methyl-phenyl)-5-methyl-5-(trifluoromethyl)tetrahydrofuran-2-carbonyl]amino]pyridine-2-carboxamide
(2S,3R,5S)-4-[[3-(4-fluoro-2-methoxy-3-methyl-phenyl)-5-methyl-5-(trifluoromethyl)tetrahydrofuran-2-carbonyl]amino]pyridine-2-carboxamide
(2S,3S,5R)-4-[[3-(4-fluoro-2-methoxy-3-methyl-phenyl)-5-methyl-5-(trifluoromethyl)tetrahydrofuran-2-carbonyl]amino]pyridine-2-carboxamide
(2S,3S,5S)-4-[[3-(4-fluoro-2-methoxy-3-methyl-phenyl)-5-methyl-5-(trifluoromethyl)tetrahydrofuran-2-carbonyl]amino]pyridine-2-carboxamide
(2R,3R,5R)-4-[[3-[2-(difluoromethoxy)-4-fluoro-phenyl]-5-methyl-5-(trifluoromethyl)tetrahydrofuran-2-carbonyl]amino]pyridine-2-carboxamide
(2R,3R,5S)-4-[[3-[2-(difluoromethoxy)-4-fluoro-phenyl]-5-methyl-5-(trifluoromethyl)tetrahydrofuran-2-carbonyl]amino]pyridine-2-carboxamide
(2R,3S,5R)-4-[[3-[2-(difluoromethoxy)-4-fluoro-phenyl]-5-methyl-5-(trifluoromethyl)tetrahydrofuran-2-carbonyl]amino]pyridine-2-carboxamide
(2S,3R,5R)-4-[[3-[2-(difluoromethoxy)-4-fluoro-phenyl]-5-methyl-5-(trifluoromethyl)tetrahydrofuran-2-carbonyl]amino]pyridine-2-carboxamide
(2R,3S,5S)-4-[[3-[2-(difluoromethoxy)-4-fluoro-phenyl]-5-methyl-5-(trifluoromethyl)tetrahydrofuran-2-carbonyl]amino]pyridine-2-carboxamide
(2S,3R,5S)-4-[[3-[2-(difluoromethoxy)-4-fluoro-phenyl]-5-methyl-5-(trifluoromethyl)tetrahydrofuran-2-carbonyl]amino]pyridine-2-carboxamide TABLE C-continued Compound Names.

(2S,3S,5R)-4-[[3-[2-(difluoromethoxy)-4-fluoro-phenyl]-5-methyl-5-(trifluoromethyl)tetrahydrofuran-2-carbonyl]amino]pyridine-2-carboxamide
(2S,3S,5S)-4-[[3-[2-(difluoromethoxy)-4-fluoro-phenyl]-5-methyl-5-(trifluoromethyl)tetrahydrofuran-2-carbonyl]amino]pyridine-2-carboxamide
(2R,3R,5R)-4-[[3-(2,4-difluoro-3-methyl-phenyl)-5-methyl-5-(trifluoromethyl)tetrahydrofuran-2-carbonyl]amino]pyridine-2-carboxamide
(2R,3R,5S)-4-[[3-(2,4-difluoro-3-methyl-phenyl)-5-methyl-5-(trifluoromethyl)tetrahydrofuran-2-carbonyl]amino]pyridine-2-carboxamide
(2R,3S,5R)-4-[[3-(2,4-difluoro-3-methyl-phenyl)-5-methyl-5-(trifluoromethyl)tetrahydrofuran-2-carbonyl]amino]pyridine-2-carboxamide
(2S,3R,5R)-4-[[3-(2,4-difluoro-3-methyl-phenyl)-5-methyl-5-(trifluoromethyl)tetrahydrofuran-2-carbonyl]amino]pyridine-2-carboxamide
(2R,3S,5S)-4-[[3-(2,4-difluoro-3-methyl-phenyl)-5-methyl-5-(trifluoromethyl)tetrahydrofuran-2-carbonyl]amino]pyridine-2-carboxamide
(2S,3R,5S)-4-[[3-(2,4-difluoro-3-methyl-phenyl)-5-methyl-5-(trifluoromethyl)tetrahydrofuran-2-carbonyl]amino]pyridine-2-carboxamide
(2S,3S,5R)-4-[[3-(2,4-difluoro-3-methyl-phenyl)-5-methyl-5-(trifluoromethyl)tetrahydrofuran-2-carbonyl]amino]pyridine-2-carboxamide
(2S,3S,5S)-4-[[3-(2,4-difluoro-3-methyl-phenyl)-5-methyl-5-(trifluoromethyl)tetrahydrofuran-2-carbonyl]amino]pyridine-2-carboxamide
(2R,3R,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2R,3R,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2S,3R,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2R,3S,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2S,3R,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2S,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2S,3S,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide
(2R,3R,5R)-4-[[3-(2-fluoro-6-methoxy-phenyl)-5-methyl-5-(trifluoromethyl)tetrahydrofuran-2-carbonyl]amino]pyridine-2-carboxamide
(2R,3R,5S)-4-[[3-(2-fluoro-6-methoxy-phenyl)-5-methyl-5-(trifluoromethyl)tetrahydrofuran-2-carbonyl]amino]pyridine-2-carboxamide
(2R,3S,5R)-4-[[3-(2-fluoro-6-methoxy-phenyl)-5-methyl-5-(trifluoromethyl)tetrahydrofuran-2-carbonyl]amino]pyridine-2-carboxamide
(2S,3R,5R)-4-[[3-(2-fluoro-6-methoxy-phenyl)-5-methyl-5-(trifluoromethyl)tetrahydrofuran-2-carbonyl]amino]pyridine-2-carboxamide
(2R,3S,5S)-4-[[3-(2-fluoro-6-methoxy-phenyl)-5-methyl-5-(trifluoromethyl)tetrahydrofuran-2-carbonyl]amino]pyridine-2-carboxamide
(2S,3R,5S)-4-[[3-(2-fluoro-6-methoxy-phenyl)-5-methyl-5-(trifluoromethyl)tetrahydrofuran-2-carbonyl]amino]pyridine-2-carboxamide
(2S,3S,5R)-4-[[3-(2-fluoro-6-methoxy-phenyl)-5-methyl-5-(trifluoromethyl)tetrahydrofuran-2-carbonyl]amino]pyridine-2-carboxamide
(2S,3S,5S)-4-[[3-(2-fluoro-6-methoxy-phenyl)-5-methyl-5-(trifluoromethyl)tetrahydrofuran-2-carbonyl]amino]pyridine-2-carboxamide
(2R,3R,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2R,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2S,3R,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2S,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2S,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2S,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide
(2R,3R,5R)-4-[[5-(1,1-difluoroethyl)-3-(3,4-difluoro-2-methoxy-phenyl)-5-methyl-tetrahydrofuran-2-carbonyl]amino]pyridine-2-carboxamide
(2R,3R,5S)-4-[[5-(1,1-difluoroethyl)-3-(3,4-difluoro-2-methoxy-phenyl)-5-methyl-tetrahydrofuran-2-carbonyl]amino]pyridine-2-carboxamide
(2R,3S,5R)-4-[[5-(1,1-difluoroethyl)-3-(3,4-difluoro-2-methoxy-phenyl)-5-methyl-tetrahydrofuran-2-carbonyl]amino]pyridine-2-carboxamide
(2S,3R,5R)-4-[[5-(1,1-difluoroethyl)-3-(3,4-difluoro-2-methoxy-phenyl)-5-methyl-tetrahydrofuran-2-carbonyl]amino]pyridine-2-carboxamide
(2R,3S,5S)-4-[[5-(1,1-difluoroethyl)-3-(3,4-difluoro-2-methoxy-phenyl)-5-methyl-tetrahydrofuran-2-carbonyl]amino]pyridine-2-carboxamide TABLE C-continued Compound Names.

(2S,3R,5S)-4-[[5-(1,1-difluoroethyl)-3-(3,4-difluoro-2-methoxy-phenyl)-5-methyl-tetrahydrofuran-2-carbonyl]amino]pyridine-2-carboxamide
(2S,3S,5R)-4-[[5-(1,1-difluoroethyl)-3-(3,4-difluoro-2-methoxy-phenyl)-5-methyl-tetrahydrofuran-2-carbonyl]amino]pyridine-2-carboxamide
(2S,3S,5S)-4-[[5-(1,1-difluoroethyl)-3-(3,4-difluoro-2-methoxy-phenyl)-5-methyl-tetrahydrofuran-2-carbonyl]amino]pyridine-2-carboxamide
(2R,3R,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3R,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3R,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3S,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3R,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3R,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3S,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3R,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3R,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3S,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3S,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3R,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3S,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2S,3S,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide
(2R,3R,4R,5R)-4-[[3-(3,4-difluorophenyl)-4,5-dimethyl-5-(trifluoromethyl)tetrahydrofuran-2-carbonyl]amino]pyridine-2-carboxamide
(2R,3R,4R,5S)-4-[[3-(3,4-difluorophenyl)-4,5-dimethyl-5-(trifluoromethyl)tetrahydrofuran-2-carbonyl]amino]pyridine-2-carboxamide
(2R,3R,4S,5R)-4-[[3-(3,4-difluorophenyl)-4,5-dimethyl-5-(trifluoromethyl)tetrahydrofuran-2-carbonyl]amino]pyridine-2-carboxamide
(2R,3S,4R,5R)-4-[[3-(3,4-difluorophenyl)-4,5-dimethyl-5-(trifluoromethyl)tetrahydrofuran-2-carbonyl]amino]pyridine-2-carboxamide
(2S,3R,4R,5R)-4-[[3-(3,4-difluorophenyl)-4,5-dimethyl-5-(trifluoromethyl)tetrahydrofuran-2-carbonyl]amino]pyridine-2-carboxamide
(2R,3R,4S,5S)-4-[[3-(3,4-difluorophenyl)-4,5-dimethyl-5-(trifluoromethyl)tetrahydrofuran-2-carbonyl]amino]pyridine-2-carboxamide
(2R,3S,4R,5S)-4-[[3-(3,4-difluorophenyl)-4,5-dimethyl-5-(trifluoromethyl)tetrahydrofuran-2-carbonyl]amino]pyridine-2-carboxamide
(2S,3R,4R,5S)-4-[[3-(3,4-difluorophenyl)-4,5-dimethyl-5-(trifluoromethyl)tetrahydrofuran-2-carbonyl]amino]pyridine-2-carboxamide
(2R,3S,4S,5R)-4-[[3-(3,4-difluorophenyl)-4,5-dimethyl-5-(trifluoromethyl)tetrahydrofuran-2-carbonyl]amino]pyridine-2-carboxamide
(2S,3R,4S,5R)-4-[[3-(3,4-difluorophenyl)-4,5-dimethyl-5-(trifluoromethyl)tetrahydrofuran-2-carbonyl]amino]pyridine-2-carboxamide
(2S,3S,4R,5R)-4-[[3-(3,4-difluorophenyl)-4,5-dimethyl-5-(trifluoromethyl)tetrahydrofuran-2-carbonyl]amino]pyridine-2-carboxamide
(2R,3S,4S,5S)-4-[[3-(3,4-difluorophenyl)-4,5-dimethyl-5-(trifluoromethyl)tetrahydrofuran-2-carbonyl]amino]pyridine-2-carboxamide
(2S,3R,4S,5S)-4-[[3-(3,4-difluorophenyl)-4,5-dimethyl-5-(trifluoromethyl)tetrahydrofuran-2-carbonyl]amino]pyridine-2-carboxamide
(2S,3S,4R,5S)-4-[[3-(3,4-difluorophenyl)-4,5-dimethyl-5-(trifluoromethyl)tetrahydrofuran-2-carbonyl]amino]pyridine-2-carboxamide
(2S,3S,4S,5R)-4-[[3-(3,4-difluorophenyl)-4,5-dimethyl-5-(trifluoromethyl)tetrahydrofuran-2-carbonyl]amino]pyridine-2-carboxamide
(2S,3S,4S,5S)-4-[[3-(3,4-difluorophenyl)-4,5-dimethyl-5-(trifluoromethyl)tetrahydrofuran-2-carbonyl]amino]pyridine-2-carboxamide
(2R,3R,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3R,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3R,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3S,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide TABLE C-continued Compound Names.

(2S,3R,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3R,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3S,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3R,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3R,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3S,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3S,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3R,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3S,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2S,3S,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide
(2R,3R,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3R,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3R,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3S,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3R,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3R,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3S,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3R,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3S,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3R,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3S,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3S,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3R,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3S,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3S,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2S,3S,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide
(2R,3R,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3R,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3R,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3S,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3R,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3R,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3S,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3R,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3S,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3R,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3S,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide TABLE C-continued Compound Names.

(2R,3S,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3R,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3S,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3S,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide
(2S,3S,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide
(2R,3R,5R)-4-[[3-(3,4-difluoro-2-methoxy-phenyl)-4,5,5-trimethyl-tetrahydrofuran-2-carbonyl]amino]pyridine-2-carboxamide
(2R,3R,5S)-4-[[3-(3,4-difluoro-2-methoxy-phenyl)-4,5,5-trimethyl-tetrahydrofuran-2-carbonyl]amino]pyridine-2-carboxamide
(2R,3S,5R)-4-[[3-(3,4-difluoro-2-methoxy-phenyl)-4,5,5-trimethyl-tetrahydrofuran-2-carbonyl]amino]pyridine-2-carboxamide
(2S,3R,5R)-4-[[3-(3,4-difluoro-2-methoxy-phenyl)-4,5,5-trimethyl-tetrahydrofuran-2-carbonyl]amino]pyridine-2-carboxamide
(2R,3S,5S)-4-[[3-(3,4-difluoro-2-methoxy-phenyl)-4,5,5-trimethyl-tetrahydrofuran-2-carbonyl]amino]pyridine-2-carboxamide
(2S,3R,5S)-4-[[3-(3,4-difluoro-2-methoxy-phenyl)-4,5,5-trimethyl-tetrahydrofuran-2-carbonyl]amino]pyridine-2-carboxamide
(2S,3S,5R)-4-[[3-(3,4-difluoro-2-methoxy-phenyl)-4,5,5-trimethyl-tetrahydrofuran-2-carbonyl]amino]pyridine-2-carboxamide
(2S,3S,5S)-4-[[3-(3,4-difluoro-2-methoxy-phenyl)-4,5,5-trimethyl-tetrahydrofuran-2-carbonyl]amino]pyridine-2-carboxamide
(2R,3R,4R,5R)-4-[[3-(3,4-difluoro-2-methoxy-phenyl)-4,5-dimethyl-tetrahydrofuran-2-carbonyl]amino]pyridine-2-carboxamide
(2R,3R,4R,5S)-4-[[3-(3,4-difluoro-2-methoxy-phenyl)-4,5-dimethyl-tetrahydrofuran-2-carbonyl]amino]pyridine-2-carboxamide
(2R,3R,4S,5R)-4-[[3-(3,4-difluoro-2-methoxy-phenyl)-4,5-dimethyl-tetrahydrofuran-2-carbonyl]amino]pyridine-2-carboxamide
(2R,3S,4R,5R)-4-[[3-(3,4-difluoro-2-methoxy-phenyl)-4,5-dimethyl-tetrahydrofuran-2-carbonyl]amino]pyridine-2-carboxamide
(2S,3R,4R,5R)-4-[[3-(3,4-difluoro-2-methoxy-phenyl)-4,5-dimethyl-tetrahydrofuran-2-carbonyl]amino]pyridine-2-carboxamide
(2R,3R,4S,5S)-4-[[3-(3,4-difluoro-2-methoxy-phenyl)-4,5-dimethyl-tetrahydrofuran-2-carbonyl]amino]pyridine-2-carboxamide
(2R,3S,4R,5S)-4-[[3-(3,4-difluoro-2-methoxy-phenyl)-4,5-dimethyl-tetrahydrofuran-2-carbonyl]amino]pyridine-2-carboxamide
(2S,3R,4R,5S)-4-[[3-(3,4-difluoro-2-methoxy-phenyl)-4,5-dimethyl-tetrahydrofuran-2-carbonyl]amino]pyridine-2-carboxamide
(2R,3S,4S,5R)-4-[[3-(3,4-difluoro-2-methoxy-phenyl)-4,5-dimethyl-tetrahydrofuran-2-carbonyl]amino]pyridine-2-carboxamide
(2S,3R,4S,5R)-4-[[3-(3,4-difluoro-2-methoxy-phenyl)-4,5-dimethyl-tetrahydrofuran-2-carbonyl]amino]pyridine-2-carboxamide
(2S,3S,4R,5R)-4-[[3-(3,4-difluoro-2-methoxy-phenyl)-4,5-dimethyl-tetrahydrofuran-2-carbonyl]amino]pyridine-2-carboxamide
(2R,3S,4S,5S)-4-[[3-(3,4-difluoro-2-methoxy-phenyl)-4,5-dimethyl-tetrahydrofuran-2-carbonyl]amino]pyridine-2-carboxamide
(2S,3R,4S,5S)-4-[[3-(3,4-difluoro-2-methoxy-phenyl)-4,5-dimethyl-tetrahydrofuran-2-carbonyl]amino]pyridine-2-carboxamide
(2S,3S,4R,5S)-4-[[3-(3,4-difluoro-2-methoxy-phenyl)-4,5-dimethyl-tetrahydrofuran-2-carbonyl]amino]pyridine-2-carboxamide
(2S,3S,4S,5R)-4-[[3-(3,4-difluoro-2-methoxy-phenyl)-4,5-dimethyl-tetrahydrofuran-2-carbonyl]amino]pyridine-2-carboxamide
(2S,3S,4S,5S)-4-[[3-(3,4-difluoro-2-methoxy-phenyl)-4,5-dimethyl-tetrahydrofuran-2-carbonyl]amino]pyridine-2-carboxamide
(2R,3R,5R)-4-[[3-(3,4-difluoro-2-methoxy-phenyl)-5-(trifluoromethyl)tetrahydrofuran-2-carbonyl]amino]pyridine-2-carboxamide
(2R,3R,5S)-4-[[3-(3,4-difluoro-2-methoxy-phenyl)-5-(trifluoromethyl)tetrahydrofuran-2-carbonyl]amino]pyridine-2-carboxamide
(2R,3S,5R)-4-[[3-(3,4-difluoro-2-methoxy-phenyl)-5-(trifluoromethyl)tetrahydrofuran-2-carbonyl]amino]pyridine-2-carboxamide
(2S,3R,5R)-4-[[3-(3,4-difluoro-2-methoxy-phenyl)-5-(trifluoromethyl)tetrahydrofuran-2-carbonyl]amino]pyridine-2-carboxamide
(2R,3S,5S)-4-[[3-(3,4-difluoro-2-methoxy-phenyl)-5-(trifluoromethyl)tetrahydrofuran-2-carbonyl]amino]pyridine-2-carboxamide
(2S,3R,5S)-4-[[3-(3,4-difluoro-2-methoxy-phenyl)-5-(trifluoromethyl)tetrahydrofuran-2-carbonyl]amino]pyridine-2-carboxamide
(2S,3S,5R)-4-[[3-(3,4-difluoro-2-methoxy-phenyl)-5-(trifluoromethyl)tetrahydrofuran-2-carbonyl]amino]pyridine-2-carboxamide
(2S,3S,5S)-4-[[3-(3,4-difluoro-2-methoxy-phenyl)-5-(trifluoromethyl)tetrahydrofuran-2-carbonyl]amino]pyridine-2-carboxamide
(2R,3R,5R)-4-[[3-(4-fluoro-2-methoxy-3-methyl-phenyl)-5-(trifluoromethyl)tetrahydrofuran-2-carbonyl]amino]pyridine-2-carboxamide
(2R,3R,5S)-4-[[3-(4-fluoro-2-methoxy-3-methyl-phenyl)-5-(trifluoromethyl)tetrahydrofuran-2-carbonyl]amino]pyridine-2-carboxamide

TABLE C-continued

Compound Names.

(2R,3S,5R)-4-[[3-(4-fluoro-2-methoxy-3-methyl-phenyl)-5-(trifluoromethyl)tetrahydrofuran-2-carbonyl]amino]pyridine-2-carboxamide
(2S,3S,5R)-4-[[3-(4-fluoro-2-methoxy-3-methyl-phenyl)-5-(trifluoromethyl)tetrahydrofuran-2-carbonyl]amino]pyridine-2-carboxamide
(2R,3S,5S)-4-[[3-(4-fluoro-2-methoxy-3-methyl-phenyl)-5-(trifluoromethyl)tetrahydrofuran-2-carbonyl]amino]pyridine-2-carboxamide
(2S,3R,5S)-4-[[3-(4-fluoro-2-methoxy-3-methyl-phenyl)-5-(trifluoromethyl)tetrahydrofuran-2-carbonyl]amino]pyridine-2-carboxamide
(2S,3S,5R)-4-[[3-(4-fluoro-2-methoxy-3-methyl-phenyl)-5-(trifluoromethyl)tetrahydrofuran-2-carbonyl]amino]pyridine-2-carboxamide
(2S,3S,5S)-4-[[3-(4-fluoro-2-methoxy-3-methyl-phenyl)-5-(trifluoromethyl)tetrahydrofuran-2-carbonyl]amino]pyridine-2-carboxamide
(2R,3R,4R,5R)-3-(3,4-difluoro-2-methoxy-phenyl)-5-isopropyl-4-methyl-tetrahydrofuran-2-carbonyl]amino]pyridine-2-carboxamide
(2R,3R,4R,5S)-3-(3,4-difluoro-2-methoxy-phenyl)-5-isopropyl-4-methyl-tetrahydrofuran-2-carbonyl]amino]pyridine-2-carboxamide
(2R,3R,4S,5R)-3-(3,4-difluoro-2-methoxy-phenyl)-5-isopropyl-4-methyl-tetrahydrofuran-2-carbonyl]amino]pyridine-2-carboxamide
(2R,3S,4R,5R)-3-(3,4-difluoro-2-methoxy-phenyl)-5-isopropyl-4-methyl-tetrahydrofuran-2-carbonyl]amino]pyridine-2-carboxamide
(2S,3R,4R,5R)-3-(3,4-difluoro-2-methoxy-phenyl)-5-isopropyl-4-methyl-tetrahydrofuran-2-carbonyl]amino]pyridine-2-carboxamide
(2R,3R,4S,5S)-3-(3,4-difluoro-2-methoxy-phenyl)-5-isopropyl-4-methyl-tetrahydrofuran-2-carbonyl]amino]pyridine-2-carboxamide
(2R,3S,4R,5S)-3-(3,4-difluoro-2-methoxy-phenyl)-5-isopropyl-4-methyl-tetrahydrofuran-2-carbonyl]amino]pyridine-2-carboxamide
(2S,3R,4R,5S)-3-(3,4-difluoro-2-methoxy-phenyl)-5-isopropyl-4-methyl-tetrahydrofuran-2-carbonyl]amino]pyridine-2-carboxamide
(2R,3S,4S,5R)-3-(3,4-difluoro-2-methoxy-phenyl)-5-isopropyl-4-methyl-tetrahydrofuran-2-carbonyl]amino]pyridine-2-carboxamide
(2S,3R,4S,5R)-3-(3,4-difluoro-2-methoxy-phenyl)-5-isopropyl-4-methyl-tetrahydrofuran-2-carbonyl]amino]pyridine-2-carboxamide
(2S,3S,4R,5R)-3-(3,4-difluoro-2-methoxy-phenyl)-5-isopropyl-4-methyl-tetrahydrofuran-2-carbonyl]amino]pyridine-2-carboxamide
(2R,3S,4S,5S)-3-(3,4-difluoro-2-methoxy-phenyl)-5-isopropyl-4-methyl-tetrahydrofuran-2-carbonyl]amino]pyridine-2-carboxamide
(2S,3R,4S,5S)-3-(3,4-difluoro-2-methoxy-phenyl)-5-isopropyl-4-methyl-tetrahydrofuran-2-carbonyl]amino]pyridine-2-carboxamide
(2S,3S,4R,5S)-3-(3,4-difluoro-2-methoxy-phenyl)-5-isopropyl-4-methyl-tetrahydrofuran-2-carbonyl]amino]pyridine-2-carboxamide
(2S,3S,4S,5R)-3-(3,4-difluoro-2-methoxy-phenyl)-5-isopropyl-4-methyl-tetrahydrofuran-2-carbonyl]amino]pyridine-2-carboxamide
(2S,3S,4S,5S)-3-(3,4-difluoro-2-methoxy-phenyl)-5-isopropyl-4-methyl-tetrahydrofuran-2-carbonyl]amino]pyridine-2-carboxamide
6-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-[[[(2R,3R,4R,5R)-3-(3,4-difluoro-2-methoxy-phenyl)-4,5-dimethyl-5-(trifluoromethyl)tetrahydrofuran-2-carbonyl]amino]pyrazine-2-carboxamide

TABLE C-continued

Compound Names.

6-[[[(2R,3R,4R,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2R,3R,4S,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2R,3S,4R,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3R,4R,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2R,3R,4S,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2R,3S,4R,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3R,4R,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2R,3S,4S,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3R,4S,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3S,4R,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2R,3S,4S,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3R,4S,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3S,4R,5S)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3S,4S,5R)-3-(3,4-difluoro-2-methoxy-phenyl)-4,5-dimethyl-5-(trifluoromethyl)tetrahydrofuran-2-carbonyl]amino]pyrazine-2-carboxamide
6-[[[(2S,3S,4S,5S)-3-(3,4-difluoro-2-methoxy-phenyl)-4,5-dimethyl-5-(trifluoromethyl)tetrahydrofuran-2-carbonyl]amino]pyrazine-2-carboxamide
5-[[[(2R,3R,4R,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3R,4R,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3R,4S,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3S,4R,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3R,4R,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3R,4S,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3S,4R,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3R,4R,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3S,4S,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3R,4S,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3S,4R,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2R,3S,4S,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3R,4S,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3S,4R,5S)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3S,4S,5R)-3-(3,4-difluoro-2-methoxy-phenyl)-4,5-dimethyl-5-(trifluoromethyl)tetrahydrofuran-2-carbonyl]amino]pyridine-3-carboxamide
5-[[[(2S,3S,4S,5S)-3-(3,4-difluoro-2-methoxy-phenyl)-4,5-dimethyl-5-(trifluoromethyl)tetrahydrofuran-2-carbonyl]amino]pyridine-3-carboxamide
4-[[[(2R,3R,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2R,3R,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2R,3R,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2R,3S,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2S,3R,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2R,3R,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2R,3S,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[[(2S,3R,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide TABLE C-continued Compound Names.

4-[[(2R,3S,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2S,3R,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2S,3S,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2R,3S,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2S,3S,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2S,3S,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide
2-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-4-carboxamide
2-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-4-carboxamide
6-[[(2R,3R,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3R,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3R,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3S,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3R,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3R,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3S,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3R,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3S,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3R,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3S,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2R,3S,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3R,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3S,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide
6-[[(2S,3S,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide TABLE C-continued Compound Names.

6-[[(2S,3S,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide
4-[[(2R,3R,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3R,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3R,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3S,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3R,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3R,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3S,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3R,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3S,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3R,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3S,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2R,3S,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3R,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3S,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3S,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide
(2R,3R,4R,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3R,4R,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3R,4S,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3S,4R,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3R,4R,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3R,4S,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3S,4R,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3R,4R,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3S,4S,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3R,4S,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3S,4R,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2R,3S,4S,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3R,4S,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3S,4R,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3S,4S,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
(2S,3S,4S,5S)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide
5-deuterio-4-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide TABLE C-continued Compound Names.

5-deuterio-4-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
5-deuterio-4-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3R,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3R,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3S,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3R,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3R,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3S,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3R,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3R,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3S,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3S,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3R,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3S,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide
4-[[(2R,3R,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3R,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3R,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3S,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3R,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3R,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3S,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3R,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3S,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3R,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3S,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3S,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3R,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide

TABLE C-continued

Compound Names.

4-[[(2S,3S,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3S,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide
4-[[(2R,3R,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3R,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3R,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3S,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3R,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3R,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3S,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3R,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3S,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3R,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3S,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3S,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3R,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3S,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3S,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide
4-[[(2R,3R,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3R,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3R,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3S,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3R,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3R,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3S,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3R,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3S,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3R,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3S,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2R,3S,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3R,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3S,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3S,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
4-[[(2S,3S,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide
3-deuterio-4-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide TABLE C-continued Compound Names.

3-deuterio-4-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
3-deuterio-4-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide
6-deuterio-4-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide
(2R,3R,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3R,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3R,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3S,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3R,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3R,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3S,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3R,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3R,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3S,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide TABLE C-continued Compound Names.

(2R,3S,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3R,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3S,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide
(2S,3S,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide
(2R,3R,4R,5R)-4-[[3-[4-(difluoromethyl)-3-fluoro-2-methoxy-phenyll-4,5-dimethyl-5-(trifluoromethyl)tetrahydrofuran-2-carbonyl]amino]pyridine-2-carboxamide
(2R,3R,4R,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3R,4S,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3S,4R,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3R,4R,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3R,4S,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3S,4R,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3R,4R,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3S,4S,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3R,4S,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3S,4R,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3S,4S,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3R,4S,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3S,4R,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3S,4S,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2S,3S,4S,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide
(2R,3R,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide TABLE C-continued Compound Names.

(2R,3R,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3S,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3R,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2S,3S,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide
(2R,3R,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3R,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3R,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3S,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3R,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3R,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3S,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3R,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3R,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3S,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3S,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3R,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3S,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2S,3S,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide
(2R,3R,4R,5R)-4-[[3-(3-methoxy-2-pyridyl)-4,5-dimethyl-5-(trifluoromethyl)tetrahydrofuran-2-carbonyl]amino]pyridine-2-carboxamide
(2R,3R,4R,5S)-4-[[3-(3-methoxy-2-pyridyl)-4,5-dimethyl-5-(trifluoromethyl)tetrahydrofuran-2-carbonyl]amino]pyridine-2-carboxamide
(2R,3R,4S,5R)-4-[[3-(3-methoxy-2-pyridyl)-4,5-dimethyl-5-(trifluoromethyl)tetrahydrofuran-2-carbonyl]amino]pyridine-2-carboxamide
(2R,3S,4R,5R)-4-[[3-(3-methoxy-2-pyridyl)-4,5-dimethyl-5-(trifluoromethyl)tetrahydrofuran-2-carbonyl]amino]pyridine-2-carboxamide
(2S,3R,4R,5R)-4-[[3-(3-methoxy-2-pyridyl)-4,5-dimethyl-5-(trifluoromethyl)tetrahydrofuran-2-carbonyl]amino]pyridine-2-carboxamide
(2R,3R,4S,5S)-4-[[3-(3-methoxy-2-pyridyl)-4,5-dimethyl-5-(trifluoromethyl)tetrahydrofuran-2-carbonyl]amino]pyridine-2-carboxamide
(2R,3S,4R,5S)-4-[[3-(3-methoxy-2-pyridyl)-4,5-dimethyl-5-(trifluoromethyl)tetrahydrofuran-2-carbonyl]amino]pyridine-2-carboxamide
(2S,3R,4R,5S)-4-[[3-(3-methoxy-2-pyridyl)-4,5-dimethyl-5-(trifluoromethyl)tetrahydrofuran-2-carbonyl]amino]pyridine-2-carboxamide
(2R,3S,4S,5R)-4-[[3-(3-methoxy-2-pyridyl)-4,5-dimethyl-5-(trifluoromethyl)tetrahydrofuran-2-carbonyl]amino]pyridine-2-carboxamide TABLE C-continued Compound Names.

(2S,3R,4S,5R)-4-[[3-(3-methoxy-2-pyridyl)-4,5-dimethyl-5-(trifluoromethyl)tetrahydrofuran-2-carbonyl]amino]pyridine-2-carboxamide
(2S,3S,4R,5R)-4-[[3-(3-methoxy-2-pyridyl)-4,5-dimethyl-5-(trifluoromethyl)tetrahydrofuran-2-carbonyl]amino]pyridine-2-carboxamide
(2R,3S,4S,5S)-4-[[3-(3-methoxy-2-pyridyl)-4,5-dimethyl-5-(trifluoromethyl)tetrahydrofuran-2-carbonyl]amino]pyridine-2-carboxamide
(2S,3R,4S,5S)-4-[[3-(3-methoxy-2-pyridyl)-4,5-dimethyl-5-(trifluoromethyl)tetrahydrofuran-2-carbonyl]amino]pyridine-2-carboxamide
(2S,3S,4R,5S)-4-[[3-(3-methoxy-2-pyridyl)-4,5-dimethyl-5-(trifluoromethyl)tetrahydrofuran-2-carbonyl]amino]pyridine-2-carboxamide
(2S,3S,4S,5R)-4-[[3-(3-methoxy-2-pyridyl)-4,5-dimethyl-5-(trifluoromethyl)tetrahydrofuran-2-carbonyl]amino]pyridine-2-carboxamide
(2S,3S,4S,5S)-4-[[3-(3-methoxy-2-pyridyl)-4,5-dimethyl-5-(trifluoromethyl)tetrahydrofuran-2-carbonyl]amino]pyridine-2-carboxamide
(2R,3R,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3R,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3R,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3S,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3R,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3R,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3S,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3R,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3S,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3R,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3S,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2R,3S,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3R,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3S,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3S,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide
(2S,3S,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide
4-[[(2R,3R,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3R,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3R,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3S,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3R,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3R,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3S,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3R,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3S,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2R,3S,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3R,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3S,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide
4-[[(2S,3S,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide

TABLE C-continued

Compound Names.

4-[[(2R,3R,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3R,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3R,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3S,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3R,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3R,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3S,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3R,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3R,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3S,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3S,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3R,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3S,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2S,3S,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide
4-[[(2R,3R,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4R,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3R,4R,5S)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3R,4S,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3S,4R,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3R,4R,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3R,4S,5S)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3S,4R,5S)-3-(3,4-difluoro-2-vinyl-phenyl)-4,5-dimethyl-5-(trifluoromethyl)tetrahydrofuran-2-carbonyl]amino]pyridine-2-carboxamide

TABLE C-continued

Compound Names.

4-[[(2S,3R,4R,5S)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3S,4S,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3R,4S,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3S,4R,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2R,3S,4S,5S)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3R,4S,5S)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3S,4R,5S)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3S,4S,5R)-3-(3,4-difluoro-2-vinyl-phenyl)-4,5-dimethyl-5-(trifluoromethyl)tetrahydrofuran-2-carbonyl]amino]pyridine-2-carboxamide
4-[[(2S,3S,4S,5S)-3-(3,4-difluoro-2-vinyl-phenyl)-4,5-dimethyl-5-(trifluoromethyl)tetrahydrofuran-2-carbonyl]amino]pyridine-2-carboxamide
(2R,3R,4R,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3R,4R,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3R,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3S,4R,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3R,4R,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3R,4S,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3S,4R,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3R,4R,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3R,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3S,4R,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2R,3S,4S,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3R,4S,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3S,4R,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
(2S,3S,4S,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide
4-[[(2R,3R,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3S,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3R,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide TABLE C-continued Compound Names.

4-[[(2S,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2S,3S,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide
4-[[(2R,3R,4R,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3R,4R,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3R,4S,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3S,4R,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3R,4R,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3R,4S,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3S,4R,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3R,4R,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3S,4S,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3R,4S,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3S,4R,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2R,3S,4S,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3R,4S,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3S,4R,5S)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3S,4S,5R)-3-(2-ethyl-3,4-difluoro-phenyl)-4,5-dimethyl-5-(trifluoromethyl)tetrahydrofuran-2-carbonyl]amino]pyridine-2-carboxamide
4-[[(2S,3S,4S,5S)-3-(2-ethyl-3,4-difluoro-phenyl)-4,5-dimethyl-5-(trifluoromethyl)tetrahydrofuran-2-carbonyl]amino]pyridine-2-carboxamide In some embodiments, the invention relates to a compound of formula

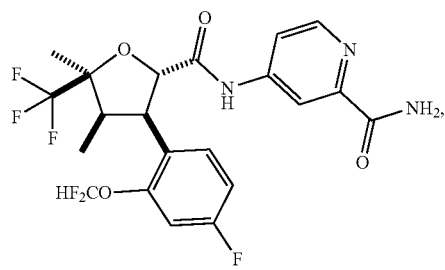

or a pharmaceutically acceptable salt thereof, wherein the compound has the absolute stereochemistry of the first eluting isomer when a racemic mixture of enantiomers is separated by SFC as described in Example 1, Step 6. Such compound is considered to be a "compound of the invention," as that term is used herein.

In some embodiments, the invention relates to a compound of formula

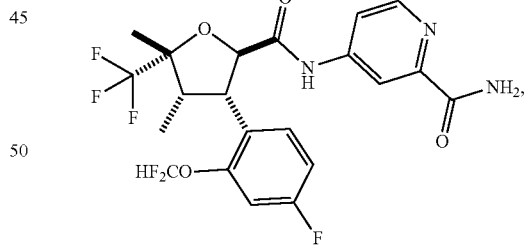

or a pharmaceutically acceptable salt thereof, wherein the compound has the absolute stereochemistry of the second eluting isomer when a racemic mixture of enantiomers is separated by SFC as described in Example 1, Step 6. Such compound is considered to be a "compound of the invention," as that term is used herein.

In some embodiments, the invention relates to a compound of formula

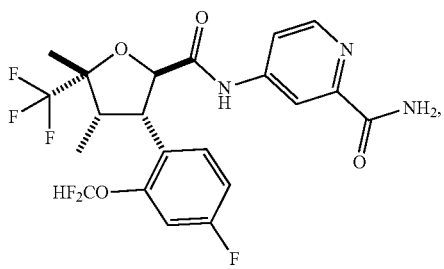

or a pharmaceutically acceptable salt thereof, wherein the compound has the absolute stereochemistry of the first eluting isomer when a racemic mixture of enantiomers is separated by SFC as described in Example 1 (Chiralpak AS-H column). Such compound is considered to be a "compound of the invention," as that term is used herein.

In some embodiments, the invention relates to a compound of formula

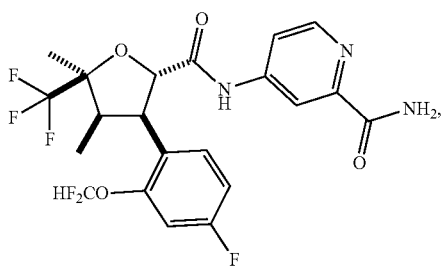

or a pharmaceutically acceptable salt thereof, wherein the compound has the absolute stereochemistry of the second eluting isomer when a racemic mixture of enantiomers is separated by SFC as described in Example 1 (Chiralpak AS-H column). Such compound is considered to be a "compound of the invention," as that term is used herein.

In some embodiments, the invention relates to a compound of formula

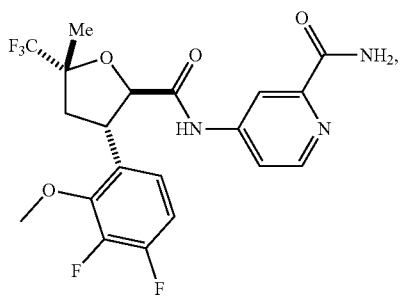

or a pharmaceutically acceptable salt thereof, wherein the compound has the absolute stereochemistry of the first eluting isomer when a racemic mixture of enantiomers is separated by SFC as described in Example 2, Step 10. Such compound is considered to be a "compound of the invention," as that term is used herein.

In some embodiments, the invention relates to a compound of formula

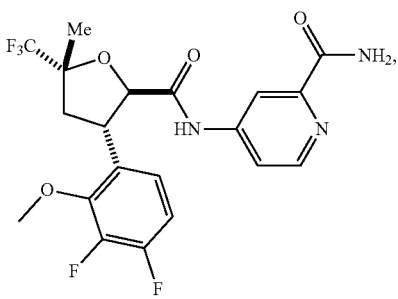

or a pharmaceutically acceptable salt thereof, wherein the compound has the absolute stereochemistry of the second eluting isomer when a racemic mixture of enantiomers is separated by SFC as described in Example 2, Step 10. Such compound is considered to be a "compound of the invention," as that term is used herein.

In some embodiments, the invention relates to a compound of formula

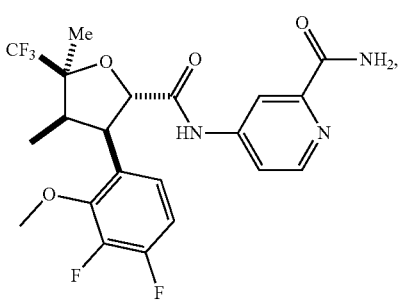

or a pharmaceutically acceptable salt thereof, wherein the compound has the absolute stereochemistry of the first eluting isomer when a racemic mixture of enantiomers is separated by SFC as described in Example 3, Step 13. Such compound is considered to be a "compound of the invention," as that term is used herein.

In some embodiments, the invention relates to a compound of formula

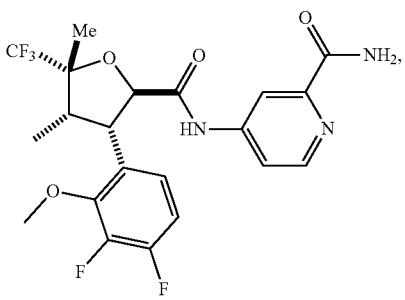 [SMILES: COc1c([C@H]2[C@H](C(=O)Nc3ccnc(C(N)=O)c3)O[C@@](C)(C(F)(F)F)[C@H]2C)ccc(F)c1F]

or a pharmaceutically acceptable salt thereof, wherein the compound has the absolute stereochemistry of the second eluting isomer when a racemic mixture of enantiomers is separated by SFC as described in Example 3, Step 13. Such compound is considered to be a "compound of the invention," as that term is used herein.

In some embodiments, the invention relates to a compound of formula

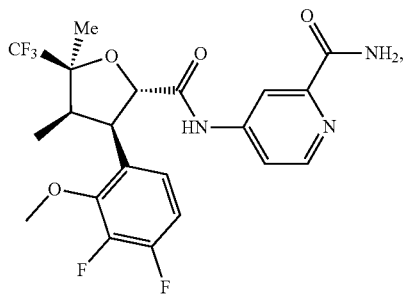

or a pharmaceutically acceptable salt thereof. Such compound is considered to be a "compound of the invention," as that term is used herein.

In some embodiments, the invention relates to a compound of formula

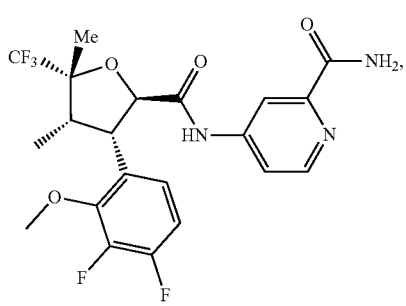

or a pharmaceutically acceptable salt thereof. Such compound is considered to be a "compound of the invention," as that term is used herein.

In some embodiments, the invention relates to a compound of formula

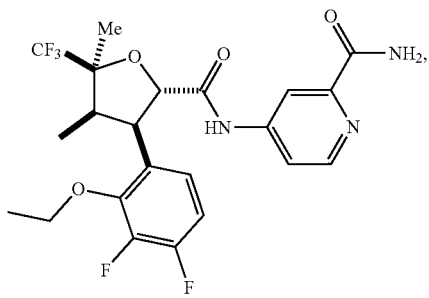 [SMILES: CCOc1c([C@@H]2[C@@H](C(=O)Nc3ccnc(C(N)=O)c3)O[C@](C)(C(F)(F)F)[C@@H]2C)ccc(F)c1F]

or a pharmaceutically acceptable salt thereof, wherein the compound has the absolute stereochemistry of the first eluting isomer when a racemic mixture of enantiomers is separated by SFC as described in Example 3. Such compound is considered to be a "compound of the invention," as that term is used herein.

In some embodiments, the invention relates to a compound of formula

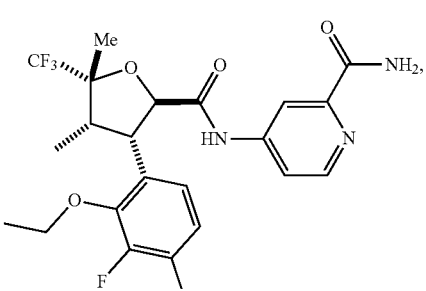

or a pharmaceutically acceptable salt thereof, wherein the compound has the absolute stereochemistry of the second eluting isomer when a racemic mixture of enantiomers is separated by SFC as described in Example 3. Such compound is considered to be a "compound of the invention," as that term is used herein.

In some embodiments, the invention relates to a compound of formula

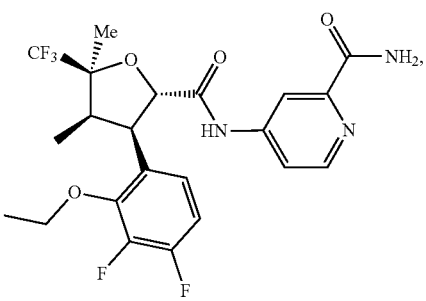

or a pharmaceutically acceptable salt thereof. Such compound is considered to be a "compound of the invention," as that term is used herein.

In some embodiments, the invention relates to a compound of formula

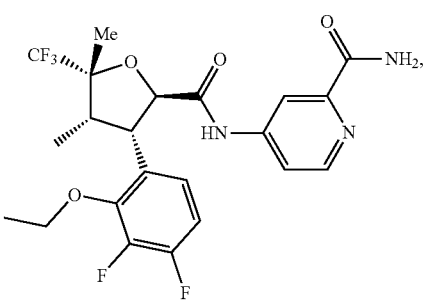

or a pharmaceutically acceptable salt thereof. Such compound is considered to be a "compound of the invention," as that term is used herein.

In some embodiments, the invention relates to a compound of formula

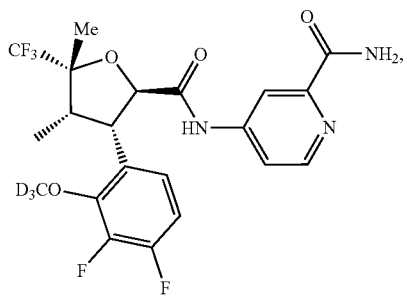

or a pharmaceutically acceptable salt thereof. Such compound is considered to be a "compound of the invention," as that term is used herein.

In some embodiments, the invention relates to a compound of formula

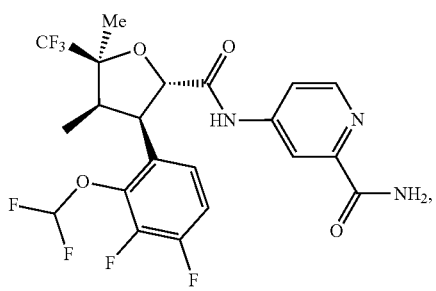

or a pharmaceutically acceptable salt thereof. Such compound is considered to be a "compound of the invention," as that term is used herein.

In some embodiments, the invention relates to a compound of formula

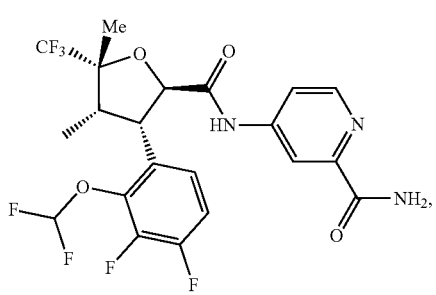

or a pharmaceutically acceptable salt thereof. Such compound is considered to be a "compound of the invention," as that term is used herein.

In some embodiments, the invention relates to a compound of formula

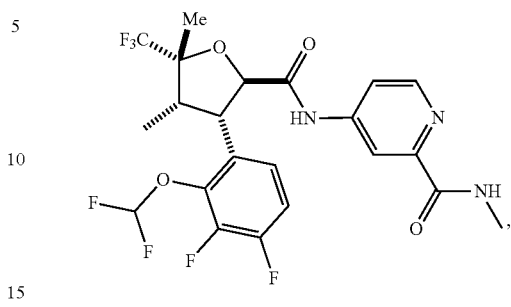

or a pharmaceutically acceptable salt thereof, wherein the compound has the absolute stereochemistry of the first eluting isomer when a racemic mixture of enantiomers is separated by SFC as described in Example 1 (Chiralpak AS-H column). Such compound is considered to be a "compound of the invention," as that term is used herein.

In some embodiments, the invention relates to a compound of formula

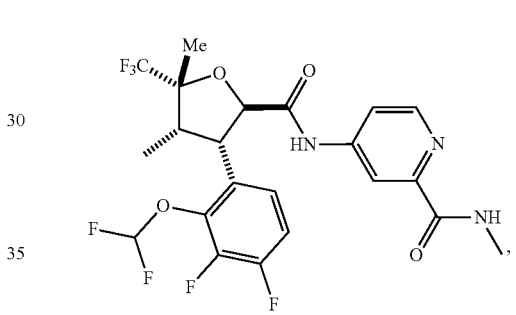

or a pharmaceutically acceptable salt thereof, wherein the compound has the absolute stereochemistry of the second eluting isomer when a racemic mixture of enantiomers is separated by SFC as described in Example 1 (Chiralpak AS-H column). Such compound is considered to be a "compound of the invention," as that term is used herein.

In some embodiments, the invention relates to a compound of formula

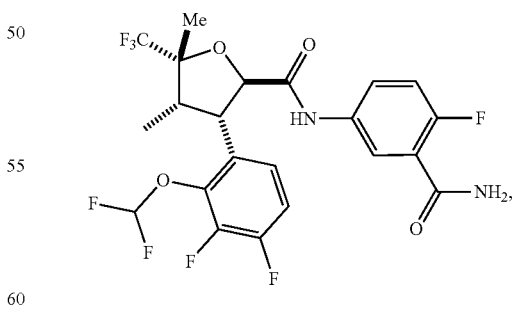

or a pharmaceutically acceptable salt thereof, wherein the compound has the absolute stereochemistry of the first eluting isomer when a racemic mixture of enantiomers is separated by SFC as described in Example 4, Step 4. Such compound is considered to be a "compound of the invention," as that term is used herein.

In some embodiments, the invention relates to a compound of formula

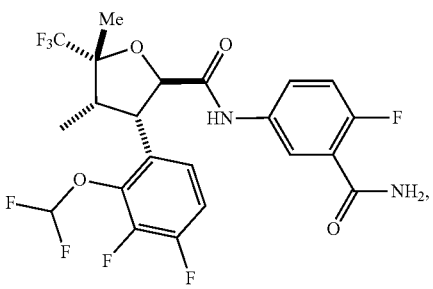 [SMILES: C[C@H]1[C@@H](c2ccc(F)c(F)c2OC(F)F)[C@H](C(=O)Nc2ccc(F)c(C(N)=O)c2)O[C@@]1(C)C(F)(F)F]

or a pharmaceutically acceptable salt thereof, wherein the compound has the absolute stereochemistry of the second eluting isomer when a racemic mixture of enantiomers is separated by SFC as described in Example 4, Step 4. Such compound is considered to be a "compound of the invention," as that term is used herein.

In some embodiments, the invention relates to a compound of formula

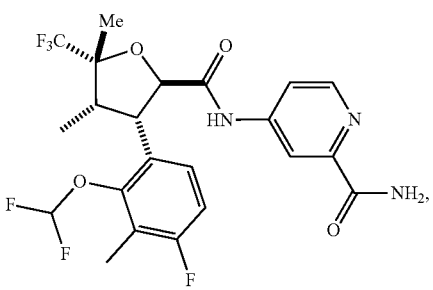 [SMILES: Cc1c(F)ccc([C@H]2[C@H](C(=O)Nc3ccnc(C(N)=O)c3)O[C@@](C)(C(F)(F)F)[C@H]2C)c1OC(F)F]

or a pharmaceutically acceptable salt thereof, wherein the compound has the absolute stereochemistry of the first eluting isomer when a racemic mixture of enantiomers is separated by SFC as described in Example 4, Step 4 (Chiralpak AS-H column). Such compound is considered to be a "compound of the invention," as that term is used herein.

In some embodiments, the invention relates to a compound of formula

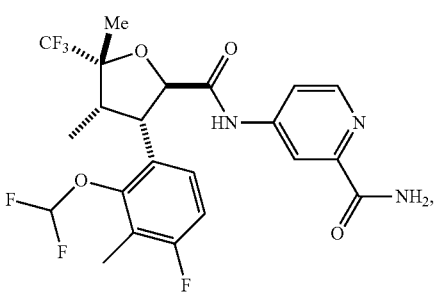 [SMILES: Cc1c(F)ccc([C@H]2[C@H](C(=O)Nc3ccnc(C(N)=O)c3)O[C@@](C)(C(F)(F)F)[C@H]2C)c1OC(F)F]

or a pharmaceutically acceptable salt thereof, wherein the compound has the absolute stereochemistry of the second eluting isomer when a racemic mixture of enantiomers is separated by SFC as described in Example 4, Step 4 (Chiralpak AS-H column). Such compound is considered to be a "compound of the invention," as that term is used herein.

In some embodiments, the invention relates to a compound of formula

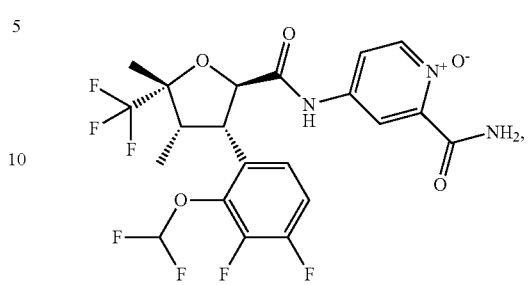

or a pharmaceutically acceptable salt thereof. Such compound is considered to be a "compound of the invention," as that term is used herein.

In some embodiments, the invention relates to a compound of formula

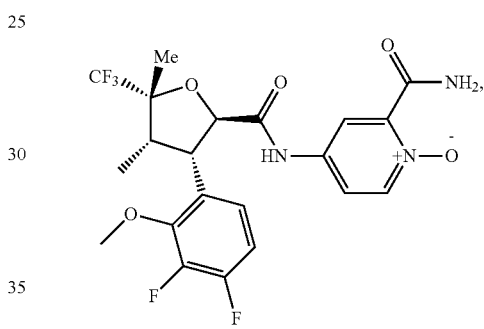

or a pharmaceutically acceptable salt thereof. Such compound is considered to be a "compound of the invention," as that term is used herein.

In some embodiments, the invention relates to a compound of formula

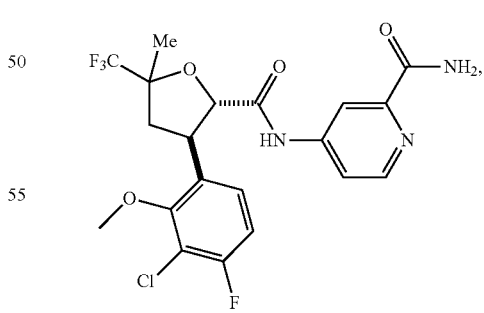

or a pharmaceutically acceptable salt thereof, wherein the compound has the absolute stereochemistry of the first eluting isomer when a mixture of racemic diastereomers (epimeric at the 5-position) is separated by SFC as described in Example 6, Step 7. Such compound is considered to be a "compound of the invention," as that term is used herein.

In some embodiments, the invention relates to a compound of formula

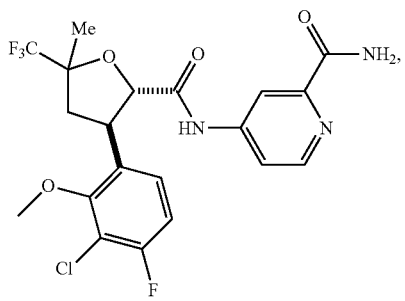 [SMILES: COc1c([C@H]2CC(C)(C(F)(F)F)O[C@@H]2C(=O)Nc2ccnc(C(N)=O)c2)ccc(F)c1Cl]

or a pharmaceutically acceptable salt thereof, wherein the compound has the absolute stereochemistry of the second eluting isomer when a mixture of racemic diastereomers (epimeric at the 5-position) is separated by SFC as described in Example 6, Step 7. Such compound is considered to be a "compound of the invention," as that term is used herein.

In some embodiments, the invention relates to a compound of formula

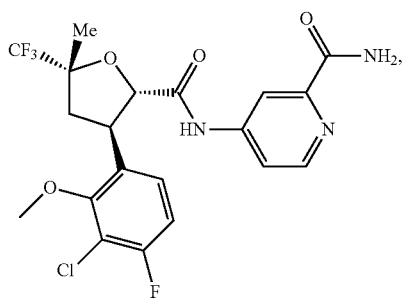 [SMILES: COc1c([C@H]2C[C@](C)(C(F)(F)F)O[C@@H]2C(=O)Nc2ccnc(C(N)=O)c2)ccc(F)c1Cl]

or a pharmaceutically acceptable salt thereof. Such compound is considered to be a "compound of the invention," as that term is used herein.

In some embodiments, the invention relates to a compound of formula

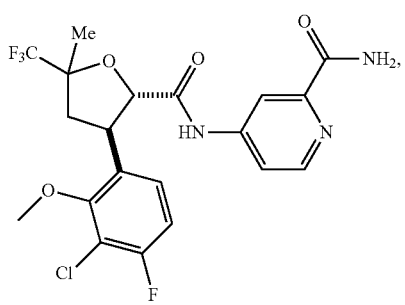 [SMILES: COc1c([C@H]2CC(C)(C(F)(F)F)O[C@@H]2C(=O)Nc2ccnc(C(N)=O)c2)ccc(F)c1Cl]

or a pharmaceutically acceptable salt thereof, wherein the compound has the absolute stereochemistry of the third eluting isomer when a mixture of racemic diastereomers (epimeric at the 5-position) is separated by SFC as described in Example 6, Step 7. Such compound is considered to be a "compound of the invention," as that term is used herein.

In some embodiments, the invention relates to a compound of formula

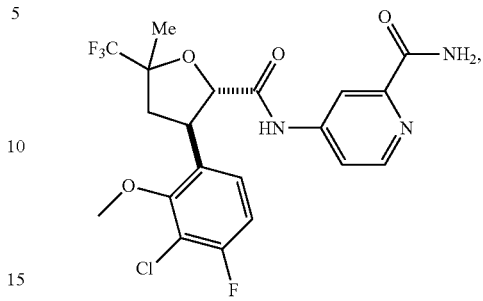

or a pharmaceutically acceptable salt thereof, wherein the compound has the absolute stereochemistry of the fourth eluting isomer when a mixture of racemic diastereomers (epimeric at the 5-position) is separated by SFC as described in Example 6, Step 7. Such compound is considered to be a "compound of the invention," as that term is used herein.

In some embodiments, the invention relates to a compound of formula

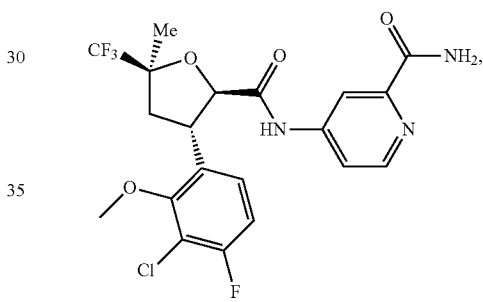

or a pharmaceutically acceptable salt thereof. Such compound is considered to be a "compound of the invention," as that term is used herein.

In some embodiments, the invention relates to a compound of formula

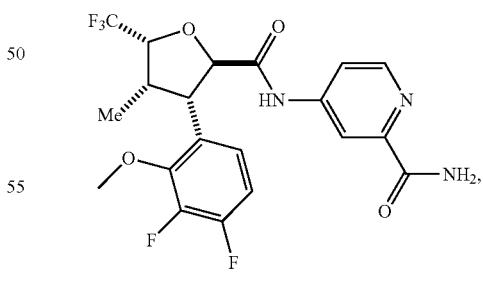

or a pharmaceutically acceptable salt thereof, wherein the compound has the absolute stereochemistry of the first eluting isomer when a racemic mixture of enantiomers is separated by SFC as described in Example 7, Step 11. Such compound is considered to be a "compound of the invention," as that term is used herein.

In some embodiments, the invention relates to a compound of formula

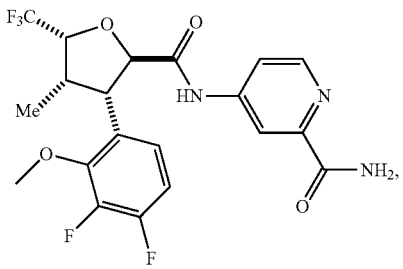 [SMILES: COc1c([C@@H]2[C@H](C)[C@H](C(F)(F)F)O[C@H]2C(=O)Nc2ccnc(C(N)=O)c2)ccc(F)c1F]

or a pharmaceutically acceptable salt thereof, wherein the compound has the absolute stereochemistry of the second eluting isomer when a racemic mixture of enantiomers is separated by SFC as described in Example 7, Step 11. Such compound is considered to be a "compound of the invention," as that term is used herein.

In some embodiments, the invention relates to a compound of formula

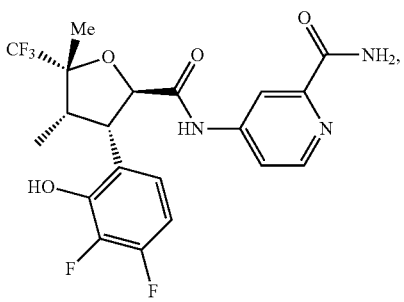 [SMILES: C[C@H]1[C@@H](c2ccc(F)c(F)c2O)[C@H](C(=O)Nc2ccnc(C(N)=O)c2)O[C@@]1(C)C(F)(F)F]

or a pharmaceutically acceptable salt thereof. Such compound is considered to be a "compound of the invention," as that term is used herein.

Solid Forms of Compounds of the Invention

In another aspect, the invention relates to a compound of the invention, or a pharmaceutically acceptable salt thereof, in solid form. In some embodiments, the compound of the invention, or pharmaceutically acceptable salt thereof, is in crystalline solid form.

Solid Forms of Compound 7

In some embodiments, the invention relates to a compound of formula

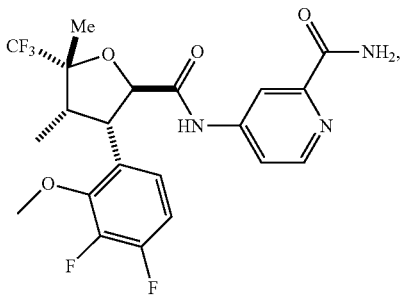 [SMILES: COc1c([C@H]2[C@H](C(=O)Nc3ccnc(C(N)=O)c3)O[C@@](C)(C(F)(F)F)[C@H]2C)ccc(F)c1F]

wherein the compound has the absolute stereochemistry of the second eluting isomer when a racemic mixture of enantiomers is separated by SFC as described in Example 3, Step 13, wherein the compound is in crystalline solid form.

In some embodiments, the crystalline solid form is Form A.

In some embodiments, Form A is characterized by an XRPD pattern having diffractions at angles (degrees 2 theta±0.2) of 9.9, 13.9, 15.7, and 19.0. In other embodiments, Form A is characterized by an XRPD pattern having at least one, at least two, or at least three diffractions at angles (degrees 2 theta±0.2) of 9.9, 13.9, 15.7, and 19.0. In other embodiments, Form A is characterized by an XRPD pattern having diffractions at angles (degrees 2 theta±0.2) of 7.3, 9.9, 13.9, 15.7, 19.0, 20.1, 20.3, and 25.4. In other embodiments, Form A is characterized by an XRPD pattern having at least one, at least two, at least three, at least four, at least five, at least six, or at least seven diffractions at angles (degrees 2 theta±0.2) of 7.3, 9.9, 13.9, 15.7, 19.0, 20.1, 20.3, and 25.4. In other embodiments, Form A is characterized by an XRPD pattern substantially similar to FIG. 1.

In some embodiments, Form A is characterized by a DSC thermogram having a melting onset of 186° C. with a peak at 187° C.

In some embodiments, Form A is obtainable by crystallization from methanol at 60° C.

In some embodiments, the crystalline solid form is Form B.

In some embodiments, Form B is characterized by an XRPD pattern having diffractions at angles (degrees 2 theta±0.2) of 12.8, 14.1, 15.2, 18.5, and 20.3. In other embodiments, Form B is characterized by an XRPD pattern having at least one, at least two, at least three, or at least four diffractions at angles (degrees 2 theta±0.2) of 12.8, 14.1, 15.2, 18.5, and 20.3. In other embodiments, Form B is characterized by an XRPD pattern having diffractions at angles (degrees 2 theta±0.2) of 12.0, 12.8, 14.1, 15.2, 16.9, 18.4, 18.5, 18.7, 19.3, and 20.3. In other embodiments, Form B is characterized by an XRPD pattern having at least one, at least two, at least three, at least four, at least five, at least six, at least seven, at least eight, or at least nine diffractions at angles (degrees 2 theta±0.2) of 12.0, 12.8, 14.1, 15.2, 16.9, 18.4, 18.5, 18.7, 19.3, and 20.3. In other embodiments, Form B is characterized by an XRPD pattern having diffractions at angles (degrees 2 theta±0.2) of 7.6, 9.2, 12.0, 12.8, 14.1, 15.1, 15.2, 16.2, 16.9, 17.6, 18.4, 18.5, 18.7, 19.3, 20.3, 21.7, 22.0, 22.2, 22.9, 23.6, 24.0, 24.2, 25.2, 26.9, 27.0, 27.4, 28.6, and 28.9. In other embodiments, Form B is characterized by an XRPD pattern having at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, or at least twenty-seven diffractions at angles (degrees 2 theta±0.2) of 7.6, 9.2, 12.0, 12.8, 14.1, 15.1, 15.2, 16.2, 16.9, 17.6, 18.4, 18.5, 18.7, 19.3, 20.3, 21.7, 22.0, 22.2, 22.9, 23.6, 24.0, 24.2, 25.2, 26.9, 27.0, 27.4, 28.6, and 28.9. In other embodiments, Form B is characterized by an XRPD pattern substantially similar to FIG. 4.

In some embodiments, Form B is characterized by a solid state $^{13}C$ NMR spectrum having peaks at chemical shifts of 172.5, 172.1, 168.5, 168.3, 168.0, 151.5, 148.3, 147.8, 127.7, 122.7, 116.6, 115.1, 110.6, 86.5, 80.2, 63.2, 44.3, 23.0, and 13.1 ppm. In some embodiments, Form B is characterized by a solid state $^{13}$C NMR spectrum substantially similar to FIG. 5.

In some embodiments, Form B is characterized by a solid state $^{19}$F NMR spectrum having peaks at chemical shifts of −137.1 and −152.8 ppm. In some embodiments, Form B is characterized by a solid state $^{19}$F NMR spectrum substantially similar to FIG. 6.

In some embodiments, Form B is characterized by a DSC thermogram having a melting onset of 182° C. with a peak at 183° C.

In some embodiments, Form B is characterized by an IR spectrum having peaks at 3501, 3356, 1684, 1565, 1505, and 1122 cm$^{-1}$. In some embodiments, Form B is characterized by an IR spectrum substantially similar to FIG. 9.

In some embodiments, Form B is characterized by an orthorhombic crystal system, as determined by single-crystal X-ray analysis. In other embodiments, Form B is characterized by a P2$_1$2$_1$2$_1$ space group, as determined by single-crystal X-ray analysis. In other embodiments, Form B is characterized by a unit cell, as determined by single-crystal X-ray analysis, of the following dimensions: a=7.3929(2) Å; b=14.5827(4) Å; c=18.9312(6) Å; α=90°; β=90°; and γ=90°.

In some embodiments, Form B is obtainable by dissolving the compound in ethyl acetate and then crystallizing the compound by adding n-heptane as an antisolvent. In other embodiments, Form B is obtainable by the procedure described in Example 3.

In some embodiments, the invention relates to a compound of formula

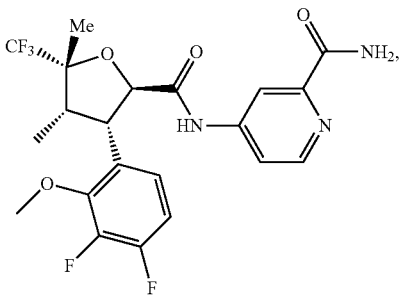 [SMILES: COc1c([C@H]2[C@H](C(=O)Nc3ccnc(C(N)=O)c3)O[C@@](C)(C(F)(F)F)[C@H]2C)ccc(F)c1F]

wherein the compound is in crystalline solid form.

In some embodiments, the crystalline solid form is Form A.

In some embodiments, Form A is characterized by an XRPD pattern having diffractions at angles (degrees 2 theta±0.2) of 9.9, 13.9, 15.7, and 19.0. In other embodiments, Form A is characterized by an XRPD pattern having at least one, at least two, or at least three diffractions at angles (degrees 2 theta±0.2) of 9.9, 13.9, 15.7, and 19.0. In other embodiments, Form A is characterized by an XRPD pattern having diffractions at angles (degrees 2 theta±0.2) of 7.3, 9.9, 13.9, 15.7, 19.0, 20.1, 20.3, and 25.4. In other embodiments, Form A is characterized by an XRPD pattern having at least one, at least two, at least three, at least four, at least five, at least six, or at least seven diffractions at angles (degrees 2 theta±0.2) of 7.3, 9.9, 13.9, 15.7, 19.0, 20.1, 20.3, and 25.4. In other embodiments, Form A is characterized by an XRPD pattern substantially similar to FIG. 1.

In some embodiments, Form A is characterized by a DSC thermogram having a melting onset of 186° C. with a peak at 187° C.

In some embodiments, Form A is obtainable by crystallization from methanol at 60° C.

In some embodiments, the crystalline solid form is Form B.

In some embodiments, Form B is characterized by an XRPD pattern having diffractions at angles (degrees 2 theta±0.2) of 12.8, 14.1, 15.2, 18.5, and 20.3. In other embodiments, Form B is characterized by an XRPD pattern having at least one, at least two, at least three, or at least four diffractions at angles (degrees 2 theta±0.2) of 12.8, 14.1, 15.2, 18.5, and 20.3. In other embodiments, Form B is characterized by an XRPD pattern having diffractions at angles (degrees 2 theta±0.2) of 12.0, 12.8, 14.1, 15.2, 16.9, 18.4, 18.5, 18.7, 19.3, and 20.3. In other embodiments, Form B is characterized by an XRPD pattern having at least one, at least two, at least three, at least four, at least five, at least six, at least seven, at least eight, or at least nine diffractions at angles (degrees 2 theta±0.2) of 12.0, 12.8, 14.1, 15.2, 16.9, 18.4, 18.5, 18.7, 19.3, and 20.3. In other embodiments, Form B is characterized by an XRPD pattern having diffractions at angles (degrees 2 theta±0.2) of 7.6, 9.2, 12.0, 12.8, 14.1, 15.1, 15.2, 16.2, 16.9, 17.6, 18.4, 18.5, 18.7, 19.3, 20.3, 21.7, 22.0, 22.2, 22.9, 23.6, 24.0, 24.2, 25.2, 26.9, 27.0, 27.4, 28.6, and 28.9. In other embodiments, Form B is characterized by an XRPD pattern having at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, or at least twenty-seven diffractions at angles (degrees 2 theta±0.2) of 7.6, 9.2, 12.0, 12.8, 14.1, 15.1, 15.2, 16.2, 16.9, 17.6, 18.4, 18.5, 18.7, 19.3, 20.3, 21.7, 22.0, 22.2, 22.9, 23.6, 24.0, 24.2, 25.2, 26.9, 27.0, 27.4, 28.6, and 28.9. In other embodiments, Form B is characterized by an XRPD pattern substantially similar to FIG. 4.

In some embodiments, Form B is characterized by a solid state $^{13}$C NMR spectrum having peaks at chemical shifts of 172.5, 172.1, 168.5, 168.3, 168.0, 151.5, 148.3, 147.8, 127.7, 122.7, 116.6, 115.1, 110.6, 86.5, 80.2, 63.2, 44.3, 23.0, and 13.1 ppm. In other embodiments, Form B is characterized by a solid state $^{13}$C NMR spectrum substantially similar to FIG. 5.

In some embodiments, Form B is characterized by a solid state $^{19}$F NMR spectrum having peaks at chemical shifts of −137.1 and −152.8 ppm. In other embodiments, Form B is characterized by a solid state $^{19}$F NMR spectrum substantially similar to FIG. 6.

In some embodiments, Form B is characterized by a DSC thermogram having a melting onset of 182° C. with a peak at 183° C.

In some embodiments, Form B is characterized by an IR spectrum having peaks at 3501, 3356, 1684, 1565, 1505, and 1122 cm$^{-1}$. In other embodiments, Form B is characterized by an IR spectrum substantially similar to FIG. 9.

In some embodiments, Form B is characterized by an orthorhombic crystal system, as determined by single-crystal X-ray analysis. In other embodiments, Form B is characterized by a P2$_1$2$_1$2$_1$ space group, as determined by single-crystal X-ray analysis. In other embodiments, Form B is characterized by a unit cell, as determined by single-crystal X-ray analysis, of the following dimensions: a=7.3929(2) Å; b=14.5827(4) Å; c=18.9312(6) Å; α=90°; β=90°; and γ=90°.

In some embodiments, Form B is obtainable by dissolving the compound in ethyl acetate and then crystallizing the compound by adding n-heptane as an antisolvent. In other embodiments, Form B is obtainable by the procedure described in Example 3.

Solid Forms of Compound 9

In some embodiments, the invention relates to a compound of formula

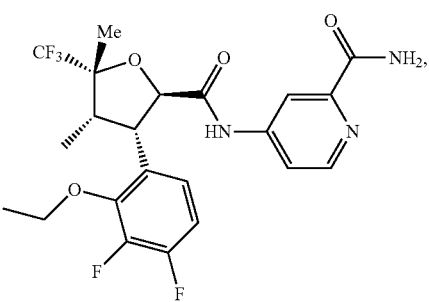 [SMILES: CCOc1c([C@H]2[C@H](C(=O)Nc3ccnc(C(N)=O)c3)O[C@@](C)(C(F)(F)F)[C@H]2C)ccc(F)c1F]

wherein the compound is in crystalline solid form.

In some embodiments, the crystalline solid form is Form A.

In some embodiments, Form A is characterized by an orthorhombic crystal system, as determined by single-crystal X-ray analysis. In other embodiments, Form A is characterized by an 1222 space group, as determined by single-crystal X-ray analysis. In other embodiments, Form A is characterized by a unit cell, as determined by single-crystal X-ray analysis, of the following dimensions: a=12.0172(5) Å; b=15.6682(6) Å; c=24.1406(11) Å; α=90°; β=90°; and γ=90°.

In some embodiments, Form A is obtainable by dissolving the compound in a 10/90 dichloromethane/dichloroethane solution, followed by vapor diffusion of pentane. In some embodiments, Form A is obtainable by the procedure described in Example 3.

Solid Forms of Compound 11

In some embodiments, the invention relates to a compound of formula

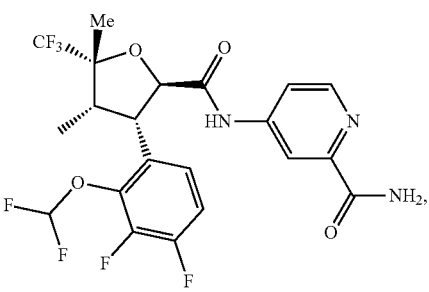 [SMILES: C[C@H]1[C@@H](c2ccc(F)c(F)c2OC(F)F)[C@H](C(=O)Nc2ccnc(C(N)=O)c2)O[C@@]1(C)C(F)(F)F]

wherein the compound is in crystalline solid form.

In some embodiments, the crystalline solid form is Form A.

In some embodiments, Form A is characterized by an XRPD pattern having diffractions at angles (degrees 2 theta±0.2) of 10.1, 13.7, 14.1, 16.3, and 20.0. In other embodiments, Form A is characterized by an XRPD pattern having at least one, at least two, at least three, or at least four diffractions at angles (degrees 2 theta±0.2) of 10.1, 13.7, 14.1, 16.3, and 20.0. In other embodiments, Form A is characterized by an XRPD pattern having diffractions at angles (degrees 2 theta±0.2) of 7.3, 10.1, 13.7, 14.1, 16.0, 16.3, 20.0, 20.4, 23.7, and 24.8. In other embodiments, Form A is characterized by an XRPD pattern having at least one, at least two, at least three, at least four, at least five, at least six, at least seven, at least eight, or at least nine diffractions at angles (degrees 2 theta±0.2) of 7.3, 10.1, 13.7, 14.1, 16.0, 16.3, 20.0, 20.4, 23.7, and 24.8. In other embodiments, Form A is characterized by an XRPD pattern having diffractions at angles (degrees 2 theta±0.2) of 7.1, 7.3, 10.1, 13.7, 14.1, 16.0, 16.3, 17.6, 18.5, 18.9, 20.0, 20.4, 21.5, 23.7, 24.8, 25.7, and 26.1. In other embodiments, Form A is characterized by an XRPD pattern having at least one, at least two, at least three, at least four, at least five, at least six, at least seven, at least eight, at least nine, at least ten, at least eleven, at least twelve, at least thirteen, at least fourteen, at least fifteen, or at least sixteen diffractions at angles (degrees 2 theta±0.2) of 7.1, 7.3, 10.1, 13.7, 14.1, 16.0, 16.3, 17.6, 18.5, 18.9, 20.0, 20.4, 21.5, 23.7, 24.8, 25.7, and 26.1. In other embodiments, Form A is characterized by an XRPD pattern substantially similar to FIG. 12.

In some embodiments, Form A is obtainable by suspending the compound in water. In other embodiments, Form A is obtainable by the procedure described in Example 4.

In some embodiments, the crystalline solid form is Form B.

In some embodiments, Form B is characterized by an XRPD pattern having diffractions at angles (degrees 2 theta±0.2) of 6.8, 13.2, 16.1, 20.6, and 21.3. In other embodiments, Form B is characterized by an XRPD pattern having at least one, at least two, at least three, or at least four diffractions at angles (degrees 2 theta±0.2) of 6.8, 13.2, 16.1, 20.6, and 21.3. In other embodiments, Form B is characterized by an XRPD pattern having diffractions at angles (degrees 2 theta±0.2) of 6.8, 11.5, 13.2, 13.6, 14.4, 16.1, 16.3, 18.8, 20.6, and 21.3. In other embodiments, Form B is characterized by an XRPD pattern having at least one, at least two, at least three, at least four, at least five, at least six, at least seven, at least eight, or at least nine diffractions at angles (degrees 2 theta±0.2) of 6.8, 11.5, 13.2, 13.6, 14.4, 16.1, 16.3, 18.8, 20.6, and 21.3. In other embodiments, Form B is characterized by an XRPD pattern having diffractions at angles (degrees 2 theta±0.2) of 6.8, 11.5, 13.2, 13.6, 14.4, 15.6, 16.1, 16.3, 17.6, 18.0, 18.8, 19.4, 20.6, 21.3, 22.3, 23.3, 24.2, and 27.4. In other embodiments, Form B is characterized by an XRPD pattern having at least one, at least two, at least three, at least four, at least five, at least six, at least seven, at least eight, at least nine, at least ten, at least eleven, at least twelve, at least thirteen, at least fourteen, at least fifteen, at least sixteen, or at least seventeen diffractions at angles (degrees 2 theta±0.2) of 6.8, 11.5, 13.2, 13.6, 14.4, 15.6, 16.1, 16.3, 17.6, 18.0, 18.8, 19.4, 20.6, 21.3, 22.3, 23.3, 24.2, and 27.4. In other embodiments, Form B is characterized by an XRPD pattern substantially similar to FIG. 13.

In some embodiments, Form A is characterized by a monoclinic crystal system, as determined by single-crystal X-ray analysis. In other embodiments, Form A is characterized by a P2$_1$ space group, as determined by single-crystal X-ray analysis. In other embodiments, Form A is characterized by a unit cell, as determined by single-crystal X-ray analysis, of the following dimensions: a=12.0863(2) Å; b=7.48310(10) Å; c=23.9904(4) Å; α=90°; β=90.0130(10)°; and γ=90°.

In some embodiments, Form B is obtainable by recrystallization from acetonitrile. In other embodiments, Form B is obtainable by the procedure described in Example 4.

Solid Form of Compound 19

In some embodiments, the invention relates to a compound of formula

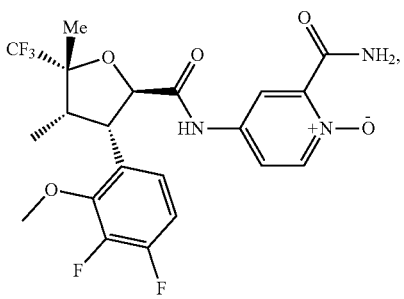

wherein the compound is in crystalline solid form.

In some embodiments, the crystalline solid form is Form A.

In some embodiments, Form A is characterized by an XRPD pattern having diffractions at angles (degrees 2 theta±0.2) of 13.7, 15.2, and 18.2. In other embodiments, Form A is characterized by an XRPD pattern having at least one or at least two diffractions at angles (degrees 2 theta±0.2) of 13.7, 15.2, and 18.2. In other embodiments, Form A is characterized by an XRPD pattern having diffractions at angles (degrees 2 theta±0.2) of 13.7, 15.2, 18.2, 18.3, 20.8, and 23.8. In other embodiments, Form A is characterized by an XRPD pattern having at least one, at least two, at least three, at least four, or at least five diffractions at angles (degrees 2 theta±0.2) of 13.7, 15.2, 18.2, 18.3, 20.8, and 23.8. In other embodiments, Form A is characterized by an XRPD pattern having diffractions at angles (degrees 2 theta±0.2) of 13.7, 14.3, 15.2, 18.2, 18.3, 20.8, 22.5, 23.8, and 25.8. In other embodiments, Form A is characterized by an XRPD pattern having at least one, at least two, at least three, at least four, at least five, at least six, at least seven, or at least eight diffractions at angles (degrees 2 theta±0.2) of 13.7, 14.3, 15.2, 18.2, 18.3, 20.8, 22.5, 23.8, and 25.8. In other embodiments, Form A is characterized by an XRPD pattern having diffractions at angles (degrees 2 theta±0.2) of 6.8, 13.7, 14.3, 15.2, 16.1, 18.2, 18.3, 19.1, 20.6, 20.8, 22.5, 23.8, 24.0, 25.8, 26.3, and 26.6. In other embodiments, Form A is characterized by an XRPD pattern having at least one, at least two, at least three, at least four, at least five, at least six, at least seven, at least eight, at least nine, at least ten, at least eleven, at least twelve, at least thirteen, at least fourteen, or at least fifteen diffractions at angles (degrees 2 theta±0.2) of 6.8, 13.7, 14.3, 15.2, 16.1, 18.2, 18.3, 19.1, 20.6, 20.8, 22.5, 23.8, 24.0, 25.8, 26.3, and 26.6. In other embodiments, Form A is characterized by an XRPD pattern substantially similar to FIG. 15.

In some embodiments, Form A is characterized by a solid state $^{13}$C NMR spectrum having peaks at chemical shifts of 171.4, 141.6, 118.0, 112.2, 23.0, and 11.6 ppm. In other embodiments, Form A is characterized by a solid state $^{13}$C NMR spectrum having peaks at chemical shifts of 171.4, 164.2, 151.8, 149.5, 148.4, 146.6, 144.0, 141.6, 138.7, 126.2, 123.8, 118.0, 112.2, 86.4, 78.8, 63.3, 47.6, 43.8, 23.0, and 11.6 ppm. In other embodiments, Form A is characterized by a solid state $^{13}$C NMR spectrum substantially similar to FIG. 16.

In some embodiments, Form A is characterized by a solid state $^{19}$F NMR spectrum having peaks at chemical shifts of −74.6, −141.5, and −154.6 ppm. In other embodiments, Form A is characterized by a solid state $^{19}$F NMR spectrum substantially similar to FIG. 17.

In some embodiments, Form A is characterized by a monoclinic crystal system, as determined by single-crystal X-ray analysis. In other embodiments, Form A is characterized by a P2$_1$ space group, as determined by single-crystal X-ray analysis. In other embodiments, Form A is characterized by a unit cell, as determined by single-crystal X-ray analysis, of the following dimensions: a=11.2266(3) Å; b=7.3948(2) Å; c=13.1432(4) Å; α=90°; β=100.3980(1)°; and γ=90°.

In some embodiments, Form A is obtainable by precipitation from methanol via addition of heptane antisolvent. In other embodiments, Form A is obtainable from a suspension of the compound in ethanol, acetonitrile, and water by lyophilization. In other embodiments, Form A is obtainable by dissolving the compound in methanol and allowing slow diffusion of heptane antisolvent. In other embodiments, Form A is obtainable by the procedure described in Example 5.

Solid Form of Compound 22

In some embodiments, the invention relates to a compound of formula

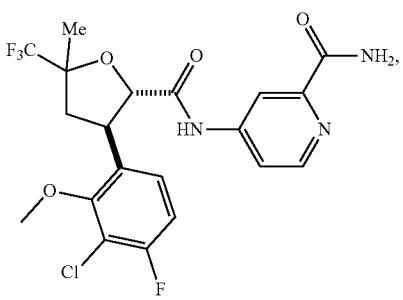 [SMILES: COc1c([C@H]2CC(C)(C(F)(F)F)O[C@@H]2C(=O)Nc2ccnc(C(N)=O)c2)ccc(F)c1Cl]

wherein the compound has the absolute stereochemistry of the third eluting isomer when a mixture of racemic diastereomers (epimeric at the 5-position) is separated by SFC as described in Example 6, Step 7, wherein the compound is in crystalline solid form.

In some embodiments, the crystalline solid form is Form A.

In some embodiments, Form A is characterized by an XRPD pattern having diffractions at angles (degrees 2 theta±0.2) of 9.2, 10.4, and 15.7. In other embodiments, Form A is characterized by an XRPD pattern having at least one or at least two diffractions at angles (degrees 2 theta±0.2) of 9.2, 10.4, and 15.7. In other embodiments, Form A is characterized by an XRPD pattern having diffractions at angles (degrees 2 theta±0.2) of 7.7, 9.2, 10.4, 12.9, 15.7, and 18.4. In other embodiments, Form A is characterized by an XRPD pattern having at least one, at least two, at least three, at least four, or at least five diffractions at angles (degrees 2 theta±0.2) of 7.7, 9.2, 10.4, 12.9, 15.7, and 18.4. In other embodiments, Form A is characterized by an XRPD pattern having diffractions at angles (degrees 2 theta±0.2) of 7.7, 9.2, 10.4, 12.9, 15.7, 18.4, 19.8, 21.7, and 24.0. In other embodiments, Form A is characterized by an XRPD pattern having at least one, at least two, at least three, at least four, at least five, at least six, at least seven, or at least eight diffractions at angles (degrees 2 theta±0.2) of 7.7, 9.2, 10.4, 12.9, 15.7, 18.4, 19.8, 21.7, and 24.0. In other embodiments, Form A is characterized by an XRPD pattern having diffractions at angles (degrees 2 theta±0.2) of 7.7, 9.2, 10.4, 12.9, 13.8, 14.7, 15.7, 16.1, 18.4, 19.8, 21.7, 22.3, and 24.0. In other embodiments, Form A is characterized by an XRPD pattern having at least one, at least two, at least three, at least four, at least five, at least six, at least seven, at least eight, at least nine, at least ten, at least eleven, or at least twelve diffractions at angles (degrees 2 theta±0.2) of 7.7, 9.2, 10.4, 12.9, 13.8, 14.7, 15.7, 16.1, 18.4, 19.8, 21.7, 22.3, and 24.0. In other embodiments, Form A is characterized by an XRPD pattern substantially similar to FIG. 19.

In some embodiments, Form A is characterized by a solid state $^{13}$C NMR spectrum having peaks at chemical shifts of 167.7, 126.0, 115.9, 43.5, and 20.3 ppm. In other embodiments, Form A is characterized by a solid state $^{13}$C NMR spectrum having peaks at chemical shifts of 172.6, 167.7, 158.7, 156.8, 151.8, 148.7, 128.6, 126.0, 115.9, 113.1, 112.3, 88.0, 85.5, 62.0, 60.5, 55.6, 43.5, 37.7, 29.6, 21.1, and 20.3 ppm. In other embodiments, Form A is characterized by a solid state $^{13}$C NMR spectrum substantially similar to FIG. 20.

In some embodiments, Form A is characterized by a solid state $^{19}$F NMR spectrum having peaks at chemical shifts of −82.2, −83.1, −111.7, and −114.4 ppm. In other embodiments, Form A is characterized by a solid state $^{19}$F NMR spectrum substantially similar to FIG. 21.

In some embodiments, Form A is obtainable by slow evaporation of a 1:1 2-methyltetrahydrofuran/heptane solution. In other embodiments, Form A is obtainable by the procedure described in Example 6.

Solid Form of Compound 23

In some embodiments, the invention relates to a compound of formula

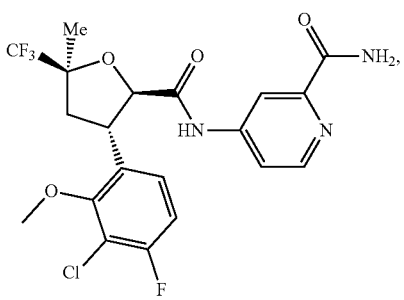 [SMILES: COc1c([C@@H]2C[C@@](C)(C(F)(F)F)O[C@H]2C(=O)Nc2ccnc(C(N)=O)c2)ccc(F)c1Cl]

wherein the compound is in crystalline solid form.

In some embodiments, the crystalline solid form is Form A.

In some embodiments, Form A is characterized by an XRPD pattern having diffractions at angles (degrees 2 theta±0.2) of 17.2, 19.3, and 22.3. In other embodiments, Form A is characterized by an XRPD pattern having at least one or at least two diffractions at angles (degrees 2 theta±0.2) of 17.2, 19.3, and 22.3. In other embodiments, Form A is characterized by an XRPD pattern having diffractions at angles (degrees 2 theta±0.2) of 14.2, 15.8, 17.2, 19.3, 22.3, and 30.6. In other embodiments, Form A is characterized by an XRPD pattern having at least one, at least two, at least three, at least four, or at least five diffractions at angles (degrees 2 theta±0.2) of 14.2, 15.8, 17.2, 19.3, 22.3, and 30.6. In other embodiments, Form A is characterized by an XRPD pattern having diffractions at angles (degrees 2 theta±0.2) of 12.2, 14.2, 15.8, 17.2, 19.3, 22.3, 25.0, 25.1, and 30.6. In other embodiments, Form A is characterized by an XRPD pattern having at least one, at least two, at least three, at least four, at least five, at least six, at least seven, or at least eight diffractions at angles (degrees 2 theta±0.2) of 12.2, 14.2, 15.8, 17.2, 19.3, 22.3, 25.0, 25.1, and 30.6. In other embodiments, Form A is characterized by an XRPD pattern having diffractions at angles (degrees 2 theta±0.2) of 11.3, 12.2, 13.2, 14.2, 15.2, 15.8, 16.6, 17.2, 19.3, 21.1, 22.3, 22.8, 23.7, 24.6, 25.0, 25.1, 25.9, 27.1, 27.9, 30.6, 34.4, and 39.4. In other embodiments, Form A is characterized by an XRPD pattern having at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or at least twenty-one diffractions at angles (degrees 2 theta±0.2) of 11.3, 12.2, 13.2, 14.2, 15.2, 15.8, 16.6, 17.2, 19.3, 21.1, 22.3, 22.8, 23.7, 24.6, 25.0, 25.1, 25.9, 27.1, 27.9, 30.6, 34.4, and 39.4. In other embodiments, Form A is characterized by an XRPD pattern substantially similar to FIG. 22.

In some embodiments, Form A is characterized by a solid state $^{13}$C NMR spectrum having peaks at chemical shifts of 171.1, 149.3, 123.3, 41.6, and 20.0 ppm. In other embodiments, Form A is characterized by a solid state $^{13}$C NMR spectrum having peaks at chemical shifts of 171.1, 166.7, 156.8, 155.5, 151.9, 149.3, 147.3, 131.5, 123.3, 119.0, 114.2, 112.8, 86.0, 85.0, 61.7, 61.0, 44.4, 41.6, and 20.0 ppm. In other embodiments, Form A is characterized by a solid state $^{13}$C NMR spectrum substantially similar to FIG. 23.

In some embodiments, Form A is characterized by a solid state $^{19}$F NMR spectrum having peaks at chemical shifts of −78.2, −113.5, and −115.1 ppm. In other embodiments, Form A is characterized by a solid state $^{19}$F NMR spectrum substantially similar to FIG. 24.

In some embodiments, Form A is characterized by a monoclinic crystal system, as determined by single-crystal X-ray analysis. In other embodiments, Form A is characterized by a P2$_1$ space group, as determined by single-crystal X-ray analysis. In other embodiments, Form A is characterized by a unit cell, as determined by single-crystal X-ray analysis, of the following dimensions: a=7.8661(3) Å; b=7.9167(3) Å; c=16.8777(7) Å; α=90°; (β=98.487(2)°; and γ=90°.

In some embodiments, Form A is obtainable by slow evaporation of a 1:1 2-methyltetrahydrofuran/heptane solution. In other embodiments, Form A is obtainable by dissolving the compound in methanol and allowing slow diffusion of heptane vapor. In other embodiments, Form A is obtainable by the procedure described in Example 6.

Solid Form of Compound 25

In some embodiments, the invention relates to a compound of formula

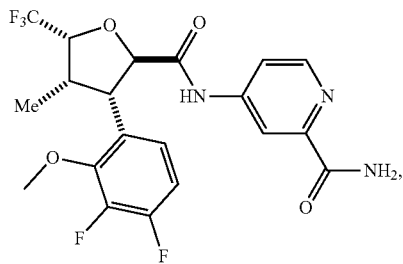 [SMILES: COc1c([C@@H]2[C@H](C)[C@H](C(F)(F)F)O[C@H]2C(=O)Nc2ccnc(C(N)=O)c2)ccc(F)c1F]

wherein the compound has the absolute stereochemistry of the second eluting isomer when a racemic mixture of enantiomers is separated by SFC as described in Example 7, Step 11, wherein the compound is in crystalline solid form.

In some embodiments, the crystalline solid form is Form A.

In some embodiments, Form A is characterized by an XRPD pattern having diffractions at angles (degrees 2 theta±0.2) of 6.8, 7.9, and 13.8. In other embodiments, Form A is characterized by an XRPD pattern having at least one or at least two diffractions at angles (degrees 2 theta±0.2) of 6.8, 7.9, and 13.8. In other embodiments, Form A is characterized by an XRPD pattern having diffractions at angles (degrees 2 theta±0.2) of 6.8, 7.9, 11.0, 13.7, 13.8, and 27.4. In other embodiments, Form A is characterized by an XRPD pattern having at least one, at least two, at least three, at least four, or at least five diffractions at angles (degrees 2 theta±0.2) of 6.8, 7.9, 11.0, 13.7, 13.8, and 27.4. In other embodiments, Form A is characterized by an XRPD pattern having diffractions at angles (degrees 2 theta±0.2) of 6.8, 7.9, 11.0, 13.7, 13.8, 15.9, 16.3, 23.2, and 27.4. In other embodiments, Form A is characterized by an XRPD pattern having at least one, at least two, at least three, at least four, at least five, at least six, at least seven, or at least eight diffractions at angles (degrees 2 theta±0.2) of 6.8, 7.9, 11.0, 13.7, 13.8, 15.9, 16.3, 23.2, and 27.4. In other embodiments, Form A is characterized by an XRPD pattern having diffractions at angles (degrees 2 theta±0.2) of 3.2, 6.8, 7.9, 11.0, 11.8, 13.7, 13.8, 15.1, 15.9, 16.3, 17.5, 18.6, 19.0, 19.5, 21.6, 21.9, 23.2, 27.0, 27.4, 29.4, and 30.3. In other embodiments, Form A is characterized by an XRPD pattern having at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty diffractions at angles (degrees 2 theta±0.2) of 3.2, 6.8, 7.9, 11.0, 11.8, 13.7, 13.8, 15.1, 15.9, 16.3, 17.5, 18.6, 19.0, 19.5, 21.6, 21.9, 23.2, 27.0, 27.4, 29.4, and 30.3. In other embodiments, Form A is characterized by an XRPD pattern substantially similar to FIG. 26.

In some embodiments, Form A is obtainable by slow evaporation of a 1:1 2-methyltetrahydrofuran/heptane solution. In other embodiments, Form A is obtainable by the procedure described in Example 7.

Salts, Compositions, Uses, Formulation, Administration and Additional Agents

Pharmaceutically Acceptable Salts and Compositions

As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. The salt may be in pure form, in a mixture (e.g., solution, suspension, or colloid) with one or more other substances, or in the form of a hydrate, solvate, or co-crystal. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is $Na_V1.8$.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, bunionectomy pain, herniorrhaphy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia, small fiber neuropathy or idiopathic small-fiber neuropathy. As used herein, the phrase "idiopathic small-fiber neuropathy" shall be understood to include any small fiber neuropathy. In some aspects, the neuropathic pain comprises diabetic neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., bunionectomy pain, herniorrhaphy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of herniorrhaphy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method of treating or lessening the severity in a subject of a neurodegenerative disease comprising administering an effective amount of a compound of the invention, a pharmaceutically acceptable salt thereof or a pharmaceutical composition thereof. In some aspects, the neurodegenerative disease comprises multiple sclerosis. In some aspects, the neurodegenerative disease comprises Pitt Hopkins Syndrome (PTHS).

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain, herniorrhaphy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is $Na_v1.8$.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain, bunionectomy pain, herniorrhaphy pain, multiple sclerosis, Charcot-Marie-Tooth syndrome, incontinence, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia, small fiber neuropathy or idiopathic small-fiber neuropathy. As used herein, the phrase "idiopathic small-fiber neuropathy" shall be understood to include any small fiber neuropathy. In some aspects, the neuropathic pain comprises diabetic neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute post-operative pain.

In another aspect, the invention features a compound of the invention, or a pharmaceutically acceptable salt or pharmaceutical composition thereof, for use in a method of treating or lessening the severity in a subject of postsurgical pain (e.g., bunionectomy pain, herniorrhaphy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In another aspect, the invention features a compound of the invention, or a pharmaceutically acceptable salt or pharmaceutical composition thereof, for use in a method of treating or lessening the severity in a subject of herniorrhaphy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method of treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain, herniorrhaphy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is $Na_V1.8$.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, bunionectomy pain, herniorrhaphy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia, small fiber neuropathy or idiopathic small-fiber neuropathy. In some aspects, the neuropathic pain comprises diabetic neuropathy.

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., bunionectomy pain, herniorrhaphy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of herniorrhaphy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for the manufacture of a medicament for use in treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition. In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain, herniorrhaphy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence; pathological cough; hyperactive bladder; painful bladder syndrome; interstitial cystitis (IC); prostatitis; complex regional pain syndrome (CRPS) type I; complex regional pain syndrome (CRPS) type II; widespread pain, paroxysmal extreme pain, pruritus, tinnitus, or angina-induced pain. Administration of Pharmaceutically Acceptable Salts and Compositions.

In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder; the activity of the specific compound or salt employed; the specific composition employed; the age, body weight, general health, sex and diet of the subject; the time of administration, route of administration, and rate of excretion of the specific compound or salt employed; the duration of the treatment; drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 100 mg/kg, or about 0.01 mg/kg to about 50 mg/kg, of subject body weight per day, one or more times a day, effective to obtain the desired therapeutic effect.

Liquid dosage forms for oral administration include, but are not limited to, pharmaceutically acceptable emulsions, microemulsions, solutions, suspensions, syrups and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in International Publication No. WO 2014/120808 A9 and U.S. Publication No. 2014/0213616 A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine, or difelikefalin;

(2) a nonsteroidal antiinflammatory drug (NSAID), e.g. aspirin, diclofenac, diflunisal, etodolac, fenbufen, fenoprofen, flufenisal, flurbiprofen, ibuprofen (including without limitation intravenous ibuprofen (e.g., Caldolor®)), indomethacin, ketoprofen, ketorolac (including without limitation ketorolac tromethamine (e.g., Toradol®)), meclofenamic acid, mefenamic acid, meloxicam, IV meloxicam (e.g., Anjeso®), nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine (HO antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anesthetic such as mexiletine;

(20) a corticosteroid such as dexamethasone;

(21) a 5-HT receptor agonist or antagonist, particularly a 5-HT$_{1B/1D}$ agonist such as eletriptan, sumatriptan, naratriptan, zolmitriptan or rizatriptan;

(22) a 5-HT$_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®, Tramadol ER (Ultram ER®), IV Tramadol, Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',T: 6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(l-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H- pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0] hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxa-diazol-5-one, C-[1-(1H-tetrazol-5-ylmethyl)-cycloheptyl]-methylamine, (3S,4S)-(1-aminomethyl-3,4-dimethyl-cyclo-pentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGuR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethyl-venlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(R,3S)-3-amino-4-hydroxy-1-(5-thiazolyl)-butyl]thio]-S-chloro-S-pyridinecarbonitrile; 2-[[(R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzene-sulfonamide or 4-[(15)-1-({[5-chloro-2-(3-fluorophenoxy) pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarbox-ylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) a $Na_v1.7$ blocker, such as XEN-402, XEN403, TV-45070, PF-05089771, CNV1014802, GDC-0276, RG7893, BIIB-074 (Vixotrigine), BIIB-095, ASP-1807, DSP-3905, OLP-1002, RQ-00432979, FX-301, DWP-17061, IMB-110, IMB-111, IMB-112 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883,840, 8,466,188, or WO2013/109521 (US2015005304), the entire contents of each application hereby incorporated by reference.

(38a) a $Na_v1.7$ blocker such as (2-benzylspiro[3,4-dihy-dropyrrolo[1,2-a]pyrazine-1,4'-piperidine]-1'-yl)-(4-iso-propoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl) methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl] methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl) spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro [3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl] ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl] ethanone, 2,2,2-trifluoro-1-[1'-(5-isopentyloxypyridine-2-carbonyl)-2-methyl-spiro[3,4-dihydropyrrolo[1,2-a] pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl] methanone, 2,2,2-trifluoro-1-[1'-(5-isopentyloxypyridine-2-carbonyl)-2,4-dimethyl-spiro[3,4-dihydropyrrolo[1,2-a] pyrazine-1,4'-piperidine]-6-yl]ethanone, 1-[(3S)-2,3-dimethyl-1'-[4-(3,3,3-trifluoropropoxymethyl)benzoyl] spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy] phenyl]methanone, 2,2,2-trifluoro-1-[1'-(5-isopropoxy-6- methyl-pyridine-2-carbonyl)-2,4-dimethyl-spiro[3,4-dihydropyrrolo[1,2-a]pyrazine-1,4'-piperidine]-6-yl] ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl] methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) a $Na_v1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), WO2015/089361 (US20150166589), WO2019014352 (US20190016671), WO2018/213426, WO2020/146682, WO2020/146612, WO2020/014243, WO2020/014246, WO2020/092187, and WO2020/092667 (US2020140411), the entire contents of each application hereby incorporated by reference.

(39a) a $Na_v1.8$ blocker such as 4,5-dichloro-2-(4-fluoro-2-methoxyphenoxy)-N-(2-oxo-1,2-dihydropyridin-4-yl) benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl) benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy) phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl) benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl) benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl) benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, 2-(4-fluoro-2-methyl-phenoxy)-N-(2-oxo-1H-pyridin-4-yl)-4-(trifluoromethyl)benzamide, [4-[[2-(4-fluoro-2-methyl-phenoxy)-4-(trifluoromethyl)benzoyl]amino]-2-oxo-1-pyridyl]methyl dihydrogen phosphate, 2-(4-fluoro-2-(methyl-$d_3$)phenoxy)-N-(2-oxo-1,2-dihydropyridin-4-yl)-4-(trifluoromethyl)benzamide, (4-(2-(4-fluoro-2-(methyl-$d_3$) phenoxy)-4-(trifluoromethyl)benzamido)-2-oxopyridin-1 (2H)-yl)methyl dihydrogen phosphate, 3-(4-fluoro-2-methoxyphenoxy)-N-(3-(methylsulfonyl)phenyl) quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl) quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy) quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy) quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy) quinoxaline-2-carboxamido)picolinic acid, 3-(4-fluoro-2-methoxyphenoxy)-N-(2-oxo-2,3-dihydro-1H-benzo[d] imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl) quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy) quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido) picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido) picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl) benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl) benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methoxyphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido) benzoic acid, 5-(4,5-dichloro-2-(2,4-difluorophenoxy) benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl) benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl) benzamide, 2-(2-chloro-4-fluorophenoxy)-N-(3-sulfamoylphenyl)-6-(trifluoromethyl)benzamide, 2-(2- chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis(trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl)benzamide, N-(3-sulfamoylphenyl)-2-(4-(trifluoromethoxy)phenoxy)-4-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethyl)benzamide, N-(3-carbamoyl-4-fluoro-phenyl)-2-fluoro-6-[2-methoxy-4-(trifluoromethoxy)phenoxy]-3-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethoxy)benzamide, 4-[[2-fluoro-6-[2-methoxy-4-(trifluoromethoxy)phenoxy]-3-(trifluoromethyl)benzoyl]amino]pyridine-2-carboxamide, 4-[[3-chloro-2-fluoro-6-[2-methoxy-4-(trifluoromethoxy)phenoxy]benzoyl]amino]pyridine-2-carboxamide, 4-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-3-(difluoromethyl)-2-fluoro-6-[2-methoxy-4-(trifluoromethoxy)phenoxy]benzamide, 4-[[2-fluoro-6-[2-(trideuteriomethoxy)-4-(trifluoromethoxy)phenoxy]-3-(trifluoromethoxy)benzoyl]amino]pyridine-2-carboxamide, N-(3-carbamoyl-4-fluoro-phenyl)-6-[2-chloro-4-(trifluoromethoxy)phenoxy]-2-fluoro-3-(trifluoromethyl)benzamide, N-(3-carbamoyl-4-fluoro-phenyl)-2-fluoro-6-[2-methyl-4-(trifluoromethoxy)phenoxy]-3-(trifluoromethyl)benzamide, N-(3-carbamoyl-4-fluoro-phenyl)-2,3,4-trifluoro-6-[2-methoxy-4-(trifluoromethoxy)phenoxy]benzamide, N-(2-carbamoyl-4-pyridyl)-3-fluoro-5-[2-methoxy-4-(trifluoromethoxy)phenoxy]-2-(trifluoromethyl)pyridine-4-carboxamide, 4-[[6-[2-(difluoromethoxy)-4-(trifluoromethoxy)phenoxy]-2-fluoro-3-(trifluoromethyl)benzoyl]amino]pyridine-2-carboxamide, N-(3-carbamoyl-4-fluoro-phenyl)-6-[3-chloro-4-(trifluoromethoxy)phenoxy]-2-fluoro-3-(trifluoromethyl)benzamide, N-(3-carbamoyl-4-fluoro-phenyl)-2-fluoro-6-[4-(trifluoromethoxy)phenoxy]-3-(trifluoromethyl)benzamide, N-(4-carbamoyl-3-fluoro-phenyl)-2-fluoro-6-[2-methoxy-4-(trifluoromethoxy)phenoxy]-3-(trifluoromethyl)benzamide, 4-[[2-fluoro-6-[2-(trideuteriomethoxy)-4-(trifluoromethoxy)phenoxy]-4-(trifluoromethyl)benzoyl]amino]pyridine-2-carboxamide, N-(3-carbamoyl-4-fluoro-phenyl)-2-fluoro-6-[3-fluoro-4-(trifluoromethoxy)phenoxy]-3-(trifluoromethyl)benzamide, N-(3-carbamoyl-4-fluoro-phenyl)-2-[2-methoxy-4-(trifluoromethoxy)phenoxy]-5-(1,1,2,2,2-pentafluoroethyl)benzamide, 4-[[4-(difluoromethoxy)-2-fluoro-6-[2-methoxy-4-(trifluoromethoxy)phenoxy]benzoyl]amino]pyridine-2-carboxamide, N-(3-carbamoyl-4-fluoro-phenyl)-2-fluoro-6-[2-fluoro-4-(trifluoromethoxy)phenoxy]-3-(trifluoromethyl)benzamide, 4-[[4-cyclopropyl-2-fluoro-6-[2-methoxy-4-(trifluoromethoxy)phenoxy]benzoyl]amino]pyridine-2-carboxamide, N-(3-carbamoyl-4-fluoro-phenyl)-5-fluoro-2-[2-methoxy-4-(trifluoromethoxy)phenoxy]-4-(trifluoromethyl)benzamide, 5-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-2-fluoro-6-(4-fluorophenoxy)-3-(trifluoromethyl)benzamide, or 4-[[2-fluoro-6-[3-fluoro-2-methoxy-4-(trifluoromethoxy)phenoxy]-3-(trifluoromethyl)benzoyl]amino]pyridine-2-carboxamide;

(40) a combined $Na_V1.7$ and $Na_V1.8$ blocker, such as DSP-2230, Lohocla201 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof;

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

(48) acetaminophen (including without limitation intravenous acetaminophen (e.g., Ofirmev®));

(49) bupivacaine (including without limitation bupivacaine liposome injectable suspension (e.g., Exparel®), bupivacaine ER (Posimir), bupivacaine collagen (Xaracoll) and transdermal bupivacaine (Eladur®)); and

(50) bupivacaine and meloxicam combination (e.g., HTX-011).

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is selected from a GlyT2/5HT2 inhibitor, such as Operanserin (VVZ149), a TRPV modulator such as CA008, CMX-020, NE06860, FTABS, CNTX4975, MCP101, MDR16523, or MDR652, a EGRI inhibitor such as Brivoglide (AYX1), an NGF inhibitor such as Tanezumab, Fasinumab, ASP6294, MEDI7352, a Mu opioid agonist such as Cebranopadol, NKTR181 (oxycodegol), a CB-1 agonist such as NEO1940 (AZN1940), an imidazoline 12 agonist such as CR4056 or a p75NTR-Fc modulator such as LEVI-04.

In another embodiment, the additional therapeutic agent is oliceridine or ropivacaine (TLC590).

In another embodiment, the additional therapeutic agent is a $Na_V1.7$ blocker such as ST-2427 and those disclosed in WO2010129864, WO2015157559, WO2017059385, WO2018183781, WO2018183782, and WO2020072835 the entire contents of each application hereby incorporated by reference.

In another embodiment, the additional therapeutic agent is ASP18071, CC-8464, ANP-230, ANP-231, NOC-100, NTX-1175, ASN008, NW3509, AM-6120, AM-8145, AM-0422, BL-017881, NTM-006, Opiranserin (Unafrar™), brivoligide, SR419, NRD.E1, LX9211, LY3016859, ISC-17536, NFX-88, LAT-8881, AP-235, NYX 2925, CNTX-6016, S-600918, S-637880, RQ-00434739, KLS-2031, MEDI 7352, or XT-150.

In another embodiment, the additional therapeutic agent is a sodium channel inhibitor (also known as a sodium channel blocker), such as the $Na_V1.7$ and $Na_V1.8$ blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof, biopsied material obtained from a mammal or extracts thereof, and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

Synthesis of the Compounds of the Invention

The compounds of the invention can be prepared from known materials by the methods described in the Examples, other similar methods, and other methods known to one skilled in the art. As one skilled in the art would appreciate, the functional groups of the intermediate compounds may need to be protected by suitable protecting groups. Protecting groups may be added or removed in accordance with standard techniques, which are well-known to those skilled in the art. The use of protecting groups is described in detail in T. G. M. Wuts et al., *Greene's Protective Groups in Organic Synthesis* (4th ed. 2006).

Radiolabeled Analogs of the Compounds of the Invention

In another aspect, the invention relates to radiolabeled analogs of the compounds of the invention. As used herein, the term "radiolabeled analogs of the compounds of the invention" refers to compounds that are identical to the compounds of the invention, as described herein (including all embodiments thereof), except that one or more atoms has been replaced with a radioisotope of the atom present in the compounds of the invention.

As used herein, the term "radioisotope" refers to an isotope of an element that is known to undergo spontaneous radioactive decay. Examples of radioisotopes include $^3$H, $^4$C, $^{32}$P, $^{35}$S, $^{18}$F, $^{36}$Cl, and the like, as well as the isotopes for which a decay mode is identified in V. S. Shirley & C. M. Lederer, Isotopes Project, Nuclear Science Division, Lawrence Berkeley Laboratory, Table of Nuclides (January 1980).

The radiolabeled analogs can be used in a number of beneficial ways, including in various types of assays, such as substrate tissue distribution assays. For example, tritium ($^3$H)- and/or carbon-14 ($^4$C)-labeled compounds may be useful for various types of assays, such as substrate tissue distribution assays, due to relatively simple preparation and excellent detectability.

In another aspect, the invention relates to pharmaceutically acceptable salts of the radiolabeled analogs, in accordance with any of the embodiments described herein in connection with the compounds of the invention.

In another aspect, the invention relates to pharmaceutical compositions comprising the radiolabeled analogs, or pharmaceutically acceptable salts thereof, and a pharmaceutically acceptable carrier, adjuvant or vehicle, in accordance with any of the embodiments described herein in connection with the compounds of the invention.

In another aspect, the invention relates to methods of inhibiting voltage-gated sodium channels and methods of treating or lessening the severity of various diseases and disorders, including pain, in a subject comprising administering an effective amount of the radiolabeled analogs, pharmaceutically acceptable salts thereof, and pharmaceutical compositions thereof, in accordance with any of the embodiments described herein in connection with the compounds of the invention.

In another aspect, the invention relates to radiolabeled analogs, pharmaceutically acceptable salts thereof, and pharmaceutical compositions thereof, for use, in accordance with any of the embodiments described herein in connection with the compounds of the invention.

In another aspect, the invention relates to the use of the radiolabeled analogs, or pharmaceutically acceptable salts thereof, and pharmaceutical compositions thereof, for the manufacture of medicaments, in accordance with any of the embodiments described herein in connection with the compounds of the invention.

In another aspect, the radiolabeled analogs, pharmaceutically acceptable salts thereof, and pharmaceutical compositions thereof, can be employed in combination therapies, in accordance with any of the embodiments described herein in connection with the compounds of the invention.

EXAMPLES

General methods. $^1$H NMR (400 MHz) spectra were obtained as solutions in an appropriate deuterated solvent such as dimethyl sulfoxide-$d_6$ (DMSO-$d_6$).

Analytical supercritical fluid chromatography (SFC) separation of various isomeric mixtures was accomplished using a Waters UPC2-SFC instrument comprising a convergence manager, a sample manager, a binary solvent manager, a column manager-30S, a PDA detector, an isocratic solvent manager and a QDa detector. Columns used include those by manufactured by Regis Technologies (e.g., R'R Whelk 0-1, 3.5 μm particle size, 5.0 cm×3.0 mm size) with a mobile phase of Solvent A: liquid $CO_2$ (58-60 bar/40° C.) Solvent B: methanol HPLC grade with 20 mM $NH_3$ at a flow rate of 2 ml/min and an injection volume of 2 μl. Gradient: at 0 min (95:5) A:B, at 3.5 min (50:50) A:B, at 3.55 min (40:60) A:B, at 3.95 min (40:60) A:B and at 4.0 min (95:5) A:B. Samples for analytical SFC were dissolved in methanol at approximately 0.5 mg/ml concentration.

Preparative SFC used the same stationary and mobile phases as those described above for analytical SFC but the samples were purified using a different instrument and gradient method as follows. Preparative SFC separation of various isomeric mixtures was accomplished using a Waters Prep-100 SFC instrument comprising a Back Pressure Regulator, a 2767 Sample Manager, a 2545 Quarternary Gradient Module, a Column Oven, a 2998 PDA detector, an Isocratic Solvent Manager, a P-200 CO2 pump, SFC Flow Splitter-100, 3 Heat exchangers, a Series III LC pump and a QDa detector. Columns used include those manufactured by Regis Technologies (e.g., R'R Whelk 0-1, 5.0 μm particle size, 25.0 cm×21.1 mm size) with a mobile phase of Solvent A: liquid $CO_2$ (58-60 bar/40° C.) Solvent B: methanol HPLC grade with 20 mM $NH_3$ at a flow rate of 100 ml/min and an injection volume of 500 μl (50 mg crude loading), 2:1 ratio of methanol to dichloroethane was used for solubilization and SFC injection of crude compound. For injection 500 μl/50 mg loading the following method was used: Isocratic: at 0 min to 7.6 min (80:20) A:B, Gradient: at 8.1 min (75:25) A:B, Isocratic at 8.2 to 10.6 min (75:25) (A:B), Gradient: at 10.7 min (80:20) A:B and Isocratic: at 11 min (80:20) (A:B). For injection 1500 μl/150 mg loading the following method was used: Isocratic: at 0 min to 7.5 min (80:20) A:B, Gradient: at 7.6 min (75:25) A:B, Gradient: at 8.1 min (60:40) A:B, Isocratic: at 8.7 min to 10.6 min (60:40) A:B, Gradient: at 10.7 min (80:20) A:B and Isocratic: at 12 min (80:20) A:B.

LC/MS Method: LC/MS analysis was conducted using an Acquity UPLC BEH $C_8$ column (50×2.1 mm, 1.7 μm particle) made by Waters (pn: 186002877) with a (2.1×5 mm, 1.7 μm particle) guard column (pn: 186003978), and a dual gradient run from 2-98% mobile phase B over 4.45 minutes. Mobile phase A=$H_2O$ (10 mM ammonium formate with 0.05% ammonium hydroxide). Mobile phase B=acetonitrile. Flow rate=0.6 mL/min, injection volume=2 μL, and column temperature=45° C.

X-ray powder diffraction (XRPD) analysis was performed at room temperature in transmission mode using a PANalytical Empyrean system equipped with a sealed tube source and a PIXcel 1D Medipix-3 detector (Malvern Pa. Nalytical Inc, Westborough, Mass.). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49 s per step.

Solid state NMR analysis was conducted on a Bruker-Biospin 400 MHz wide-bore spectrometer equipped with Bruker-Biospin 4 mm HFX probe was used. Samples were packed into 4 mm $ZrO_2$ rotors and spun under Magic Angle Spinning (MAS) condition with spinning speed typically set to 12.5 kHz. The proton relaxation time was measured using $^1$H MAS $T_1$ saturation recovery relaxation experiment in order to set up proper recycle delay of the $^{13}$C cross-polarization (CP) MAS experiment. The fluorine relaxation time was measured using $^{19}$F MAS $T_1$ saturation recovery relaxation experiment in order to set up proper recycle delay of the $^{19}$F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

Thermogravimetric analysis (TGA) data were collected on a TA Discovery Thermogravimetric Analyzer or equivalent instrumentation. A sample with weight of approximately 1-5 mg was scanned from 25° C. to 350° C. at a heating rate of 10° C./min. Data were collected by Thermal Advantage Q Series™ software and analyzed by Trios and/or Universal Analysis software (TA Instruments, New Castle, Del.).

Differential scanning calorimetry (DSC) data were acquired using a TA Instruments Q2000 or equivalent instrumentation. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 300° C. When the run was completed, the data were analyzed by Trios and/or Universal Analysis software (TA Instruments, New Castle, Del.).

Infrared (IR) spectra were collected using a Thermo Scientific Nicolet iS50 Spectrometer equipped with a diamond ATR sampling accessory.

X-ray diffraction data were acquired on a Bruker diffractometer equipped with Cu $K_\alpha$ radiation (=1.5478 Å) and a CCD detector. The structure was solved and refined using SHELX programs (Sheldrick, G. M., Acta Cryst., (2008) A64, 112-122).

Abbreviations

Unless otherwise noted, or where the context dictates otherwise, the following abbreviations shall be understood to have the following meanings:

| Abbreviation | Meaning |
| --- | --- |
| NMR | Nuclear magnetic resonance |
| ESI-MS | Electrospray mass spectrometry |
| LC/MS | Liquid chromatography-mass spectrometry |
| UPLC | Ultra performance liquid chromatography |
| HPLC/MS/MS | High performance liquid chromatography/tandem mass spectrometry |
| IS | Internal standard |
| HPLC | High performance liquid chromatography |
| SFC | Supercritical fluid chromatography |

-continued

| Abbreviation | Meaning |
|---|---|
| MDAP | Mass directed auto purification |
| ESI | Electrospray ionization |
| LED | Light-emitting diode |
| g | grams |
| mg | milligrams |
| L | Liter(s) |
| mL | Milliliters |
| μL | Microliters |
| nL | nanoliters |
| mmol | millimoles |
| hr, h | hours |
| min | Minutes |
| ms | millisecond |
| mm | Millimeters |
| μm | Micrometers |
| nm | nanometer |
| MHz | Megahertz |
| Hz | Hertz |
| N | Normal (concentration) |
| M | Molar (concentration) |
| mM | Millimolar (concentration) |
| μM | Micromolar (concentration) |
| ppm | Parts per million |
| % w/v | Weight-volume concentration |
| ArBPin | 2-[2-(difluoromethoxy)-4-fluoro-phenyl]-4,4,5,5-tetramethyl-1,3,2-dioxaborolane |
| t-BuOH | tert-butyl alcohol |
| DAST | Diethylaminosulfur trifluoride |
| DCM | Dichloromethane |
| DCE | Dichloroethane |
| DIEA, DIPEA | N, N-Diisopropyl ethyl amine |
| DMA | N,N-Dimethylacetamide |
| DMF | N,N-Dimethylformamide |
| DMSO | Dimethyl sulfoxide |
| DRG | Dorsal root ganglia |
| EtOH | Ethanol |
| EtOAc | Ethyl acetate |
| HATU | 1-[Bis(dimethylamino)methylene]-1H-1,2,3-triazolo[4,5-b]pyridinium 3-oxide hexafluorophosphate |
| EDCI | 1-Ethyl-3-(3-dimethylaminopropyl)carbodiimide |
| T3P | Propylphosphonic anhydride, i.e., 2,4,6-tripropyl-1,3,5,2,4,6-trioxatriphosphinane 2,4,6-trioxide |
| TCFH | N,N,N',N'-Tetramethylchloroformamidinium hexafluorophosphate |
| MeOH | Methanol |
| MTBE | Methyl tert-butyl ether |
| NMP | N-Methylpyrrolidone |
| THF | Tetrahydrofuran |
| TEA | triethylamine |
| RB | Round bottom (flask) |
| RT | Room temperature |
| ca. | Circa (approximately) |
| E-VIPR | Electrical stimulation voltage ion probe reader |
| HEK | Human embryonic kidney |
| KIR2.1 | Inward-rectifier potassium ion channel 2.1 |
| DMEM | Dulbecco's Modified Eagle's Medium |
| FBS | Fetal bovine serum |
| NEAA | Non-essential amino acids |
| HEPES | 2-[4-(2-hydroxyethyl)piperazin-1-yl]ethanesulfonic acid |
| DiSBAC$_6$(3) | Bis-(1,3-dihexyl-thiobarbituric acid) trimethine oxonol |
| CC2-DMPE | Chlorocoumarin-2-dimyristoyl phosphatidylethanolamine |
| VABSC-1 | Voltage Assay Background Suppression Compound |
| HS | Human serum |
| BSA | Bovine Serum Albumin |

Example 1 rel-(2S,3R,4R,5S)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide (1) and rel-(2R,3S,4S,5R)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide (2)

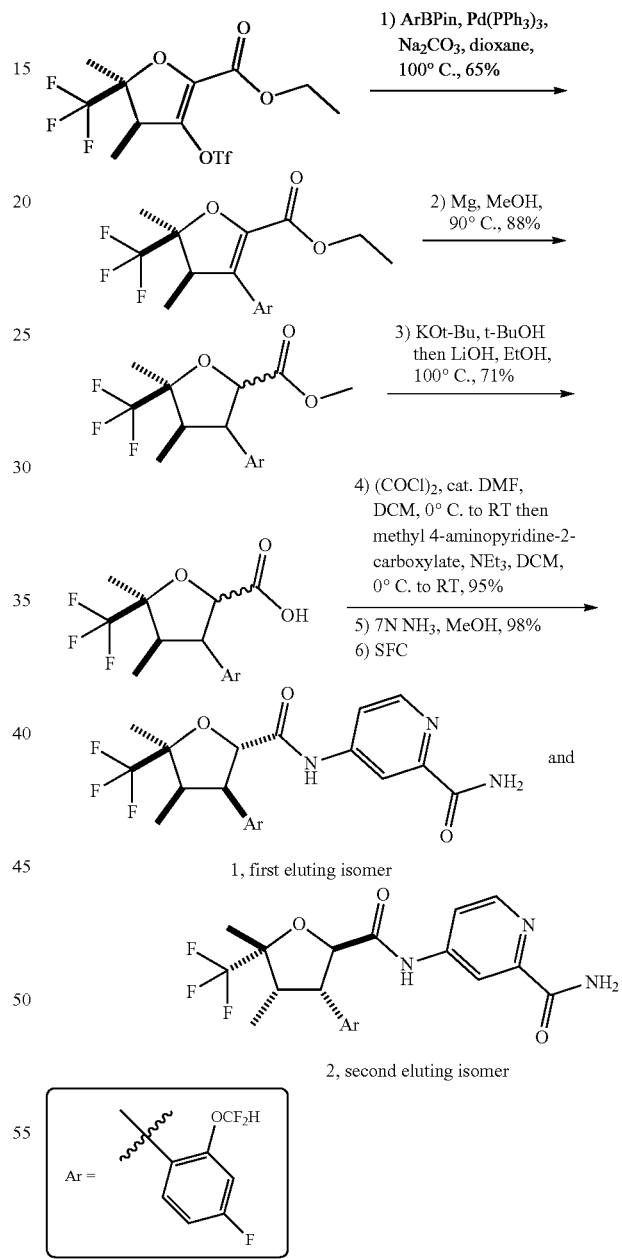

Step 1:

A mixture of ethyl rac-(2S,3R)-2,3-dimethyl-2-(trifluoromethyl)-4-(trifluoromethylsulfonyloxy)-3H-furan-5-carboxylate (3.0 g, 7.77 mmol), 2-[2-(difluoromethoxy)-4-fluoro-phenyl]-4,4,5,5-tetramethyl-1,3,2-dioxaborolane ("ArBPin", 2.33 g, 8.09 mmol), Pd(PPh$_3$)$_4$ (380 mg, 0.33 mmol), and sodium carbonate (16 mL of 2 M, 32.00 mmol) in dioxane (60 mL) was heated at 100° C. for 1 hour. The solution was diluted in EtOAc and water, the layers separated and the organic layer washed with brine, dried (MgSO$_4$), filtered and concentrated in vacuo. Purification by flash chromatography (220 g SiO$_2$, 0 to 30% EtOAc in petroleum ether) gave ethyl rac-(2S,3R)-4-[2-(difluoromethoxy)-4-fluoro-phenyl]-2,3-dimethyl-2-(trifluoromethyl)-3H-furan-5-carboxylate (2.0 g, 65%). $^1$H NMR (500 MHz, Chloroform-d) δ 7.19 (dd, J=8.5, 6.4 Hz, 1H), 6.99-6.89 (m, 2H), 6.44 (t, J=73.3 Hz, 1H), 4.14 (qd, J=7.1, 1.7 Hz, 2H), 3.45 (q, J=7.4 Hz, 1H), 1.72-1.65 (m, 3H), 1.14 (t, J=7.1 Hz, 3H), 1.12-1.08 (m, 3H) ppm. ESI-MS m/z calc. 398.09528, found 399.0 (M+1)$^+$.

Step 2:

Magnesium filings (3.5 g, 144.0 mmol) were ground in a mortar and added to a solution of ethyl rac-(2S,3R)-4-[2-(difluoromethoxy)-4-fluoro-phenyl]-2,3-dimethyl-2-(trifluoromethyl)-3H-furan-5-carboxylate (2.0 g, 5.02 mmol) in MeOH (60 mL). The flask was purged with nitrogen and the reaction was stirred at ambient temperature until the observed exotherm finished (30 mins). The reaction was then heated at 90° C. for 3 hours before being cooled to 0° C. and quenched and acidified by careful addition of 2 M HCl. The mixture was concentrated in vacuo and extracted with DCM (3×100 mL). The combined organic layers were dried (MgSO$_4$), filtered and concentrated in vacuo to give methyl rac-(3R,4R,5S)-3-[2-(difluoromethoxy)-4-fluoro-phenyl]-4,5-dimethyl-5-(trifluoromethyl)tetrahydrofuran-2-carboxylate (1.7 g, 88%) as a mixture of epimers at the position adjacent to the ester (stereochemical assignments tentative). ESI-MS m/z calc. 386.09528, found 387.0 (M+1)$^+$.

Step 3:

To a solution of methyl rac-(3R,4R,5S)-3-[2-(difluoromethoxy)-4-fluoro-phenyl]-4,5-dimethyl-5-(trifluoromethyl)tetrahydrofuran-2-carboxylate (3.2 g, 8.28 mmol) in t-BuOH (80 mL) was added KOt-Bu (4.25 g, 37.87 mmol). The reaction was stirred at ambient temperature overnight then quenched by addition of saturated aqueous NH$_4$Cl solution and diluted with EtOAc. The aqueous layer was separated and extracted with EtOAc and the combined organic layers were dried (MgSO$_4$), filtered and concentrated in vacuo. The residue was dissolved in EtOH (20 mL) and LiOH (15 mL of 2 M, 30.00 mmol) and the mixture stirred at 110° C. for 1 hour. The reaction was quenched by addition of saturated aqueous NH$_4$Cl solution and diluted with EtOAc. The aqueous layer was separated and extracted with EtOAc and the combined organic layers were dried over MgSO$_4$, filtered, and concentrated in vacuo. Purification by flash chromatography (80 g SiO$_2$, 0 to 100% EtOAc in heptanes) gave rac-(3R,4R,5S)-3-[2-(difluoromethoxy)-4-fluoro-phenyl]-4,5-dimethyl-5-(trifluoromethyl)tetrahydrofuran-2-carboxylic acid (2.2 g, 71%) as a mixture of epimers at the position adjacent to the ester (stereochemical assignments tentative). ESI-MS m/z calc. 372.07962, found 371.2 (M–1)$^-$.

Step 4:

To a solution of rac-(3R,4R,5S)-3-[2-(difluoromethoxy)-4-fluoro-phenyl]-4,5-dimethyl-5-(trifluoromethyl)tetrahydrofuran-2-carboxylic acid (650 mg, 1.75 mmol) in DCM (24 mL) stirring at 0° C. was added DMF (50 μL, 0.65 mmol) and oxalyl chloride (400 μL, 4.59 mmol). The reaction was warmed to ambient temperature over 30 mins then concentrated in vacuo. The residue was further dried on a high-vacuum apparatus for 5 mins to give a white foam, which was dissolved in DCM (24 mL) and added dropwise to a solution of methyl 4-aminopyridine-2-carboxylate (305 mg, 2.01 mmol) and NEt$_3$ (800 μL, 5.74 mmol) in DCM (9 mL) with stirring at 0° C. The reaction was warmed to ambient temperature over 4 hours, then quenched by addition of MeOH (2 mL) and concentrated in vacuo. Purification by flash chromatography (12 g SiO$_2$, 0 to 70% EtOAc in heptane, loaded in DCM) gave methyl rac-(3R,4R,5S)-4-[[3-[2-(difluoromethoxy)-4-fluoro-phenyl]-4,5-dimethyl-5-(trifluoromethyl)tetrahydrofuran-2-carbonyl]amino]pyridine-2-carboxylate (840 mg, 95%), as a 85:15 mixture of epimers at the position adjacent to the amide (stereochemical assignments tentative). ESI-MS m/z calc. 506.12766, found 507.9 (M+1)$^+$.

Step 5:

A solution of methyl rac-(3R,4R,5S)-4-[[3-[2-(difluoromethoxy)-4-fluoro-phenyl]-4,5-dimethyl-5-(trifluoromethyl)tetrahydrofuran-2-carbonyl]amino]pyridine-2-carboxylate (740 mg, 1.46 mmol) in methanolic ammonia (15 mL of 7 M, 105.0 mmol) was stirred in a sealed vessel at 100° C. for 16 hours. The solution was concentrated in vacuo to give rac-(3R,4R,5S)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide (700 mg, 98%) as a mixture of epimers at the position adjacent to the amide (stereochemical assignments tentative). ESI-MS m/z calc. 491.12796, found 491.7 (M+1)$^+$.

Step 6:

Purification of rac-(3R,4R,5S)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide (400 mg, 0.81 mmol) by chiral SFC using a Chiralpak IC column, 5 um particle size, 25 cm×20 mm from Daicel gave:

First Eluting Isomer (rt=3.40 min): rel-(2S,3R,4R,5S)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide (1, 150 mg, 74%) (stereochemical assignments tentative). $^1$H NMR (500 MHz, Methanol-d$_4$) δ 8.48 (d, J=5.5 Hz, 1H), 8.25 (d, J=2.2 Hz, 1H), 7.90 (dd, J=5.5, 2.2 Hz, 1H), 7.49 (dd, J=9.0, 6.3 Hz, 1H), 7.01 (dd, J=9.0, 6.7 Hz, 2H), 7.14-6.74 (m, 1H), 5.14 (d, J=10.3 Hz, 1H), 4.33 (dd, J=10.3, 7.9 Hz, 1H), 2.83 (p, J=7.6 Hz, 1H), 1.66 (s, 3H), 0.83 (dd, J=7.7, 2.3 Hz, 3H) ppm. ESI-MS m/z calc. 491.12796, found 492.2 (M+1)$^+$; 490.3 (M–1)$^-$.

Second Eluting Isomer (rt=4.28 min): The second eluting isomer was purified further by reverse phase preparative HPLC (basic eluent) to give rel-(2R,3S,4S,5R)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide (2, 100 mg, 50%) (stereochemical assignments tentative). $^1$H NMR (500 MHz, Methanol-d$_4$) δ 8.49 (d, J=5.5 Hz, 1H), 8.27-8.23 (m, 1H), 7.90 (dd, J=5.5, 2.2 Hz, 1H), 7.49 (dd, J=9.1, 6.4 Hz, 1H), 7.06-6.99 (m, 2H), 7.16-6.69 (m, 1H), 5.14 (d, J=10.3 Hz, 1H), 4.33 (dd, J=10.3, 7.9 Hz, 1H), 2.83 (p, J=7.6 Hz, 1H), 1.66 (d, J=1.3 Hz, 3H), 0.83 (dd, J=7.6, 2.3 Hz, 3H) ppm. ESI-MS m/z calc. 491.12796, found 492.1 (M+1)$^+$.

The following compound was made using a similar method to that described in Example 1, but no SFC separation step 6 was carried out at the end of the synthesis, and the compound was isolated as a racemate:

| Cmpd No. | Compound Name | LC/MS | NMR (shifts in ppm) |
|---|---|---|---|
| 28 | rac-(2S,3R,4R,5R)-4-[[3-[2-(difluoromethoxy)-4-fluoro-phenyl]-4,5-dimethyl-5-(trifluoromethyl)tetrahydrofuran-2-carbonyl]amino]pyridine-2-carboxamide | ESI-MS m/z calc. 491.12796, found 492.0 (M + 1)⁺; Retention time: 3.12 minutes | $^1$H NMR (500 MHz, Chloroform-d) δ 8.46 (d, J = 5.5 Hz, 1H), 8.05 (dd, J = 5.6, 2.2 Hz, 1H), 7.96 (d, J = 2.2 Hz, 1H), 7.82 (s, 1H), 7.44 (dd, J = 8.7, 6.1 Hz, 1H), 6.99 (td, J = 8.3, 2.6 Hz, 1H), 6.90 (dd, J = 9.5, 2.5 Hz, 1H), 6.54 (t, J = 72.8 Hz, 1H), 5.61 (s, 1H), 5.00 (d, J = 9.3 Hz, 1H), 4.26 (t, J = 8.7 Hz, 1H), 3.08-2.93 (m, 1H), 1.43 (s, 3H), 0.74 (d, J = 7.4 Hz, 3H) ppm. |

The following compounds were made using a similar method to that described in Example 1, but using methylamine at 40° C. in step 5. The conditions used for the epimerization/hydrolysis step 3 followed the conditions described in Example 11 step 5. The purification in step 6 was conducted by chiral SFC using a Chiralpak AS-H column, 5 μm particle size, 25 cm×10 mm from Daicel on a Minigram SFC instrument from Berger Instruments:

| Cmpd No. | Compound Name | LC/MS | NMR (shifts in ppm) |
|---|---|---|---|
| 29 | rel-(2S,3R,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide (first eluting peak by SFC on Chiralpak AS-H column, rt = 2.00 min) | ESI-MS m/z calc. 505.14362, found 506.5 (M + 1)⁺; 504.5 (M − 1)⁻; Retention time: 3.28 minutes | $^1$H NMR (500 MHz, Chloroform-d) δ 8.60 (s, 1H), 8.43 (d, J = 5.5 Hz, 1H), 8.12 (dd, J = 5.5, 2.2 Hz, 1H), 8.07-7.98 (m, 1H), 7.88 (d, J = 2.2 Hz, 1H), 7.48 (dd, J = 8.8, 6.2 Hz, 1H), 7.00 (td, J = 8.3, 2.6 Hz, 1H), 6.87 (dd, J = 9.3, 2.5 Hz, 1H), 6.53 (d, J = 74.0 Hz, 1H), 5.05 (d, J = 11.0 Hz, 1H), 4.09 (dd, J = 11.1, 8.0 Hz, 1H), 3.04 (d, J = 5.1 Hz, 3H), 2.80 (p, J = 7.6 Hz, 1H), 1.70 (s, 3H), 0.86-0.75 (m, 3H) ppm. |
| 30 | rel-(2R,3S,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide (second eluting peak by SFC on Chiralpak AS-H column, rt = 3.23 min) | ESI-MS m/z calc. 505.14362, found 506.5 (M + 1)⁺; 504.5 (M − 1)⁻; Retention time: 3.28 minutes | $^1$H NMR (500 MHz, Chloroform-d) δ 8.61 (s, 1H), 8.43 (d, J = 5.6 Hz, 1H), 8.13 (dd, J = 5.6, 2.2 Hz, 1H), 8.04 (s, 1H), 7.88 (d, J = 2.3 Hz, 1H), 7.48 (dd, J = 8.8, 6.2 Hz, 1H), 7.00 (td, J = 8.3, 2.5 Hz, 1H), 6.87 (dd, J = 9.2, 2.5 Hz, 1H), 6.53 (d, J = 72.7 Hz, 1H), 5.05 (d, J = 11.1 Hz, 1H), 4.09 (dd, J = 11.1, 8.0 Hz, 1H), 3.04 (d, J = 5.0 Hz, 3H), 2.80 (p, J = 7.6 Hz, 1H), 1.72-1.68 (m, 3H), 0.86-0.75 (m, 3H) ppm. |

The following compounds were made using a similar method to that described in Example 1, except that 5-amino-2-fluorobenzamide was used as coupling partner in step 4, and step 5 was omitted. The conditions used for the epimerization/hydrolysis step 3 followed the conditions described in Example 11 step 5. The purification in step 6 was conducted by chiral SFC using a Chiralpak AS-H column, 5um particle size, 25 cm×10 mm from Daicel on a Minigram SFC instrument from Berger Instruments:

| Cmpd No. | Compound Name | LC/MS | NMR (shifts in ppm) |
|---|---|---|---|
| 31 | rel-(2S,3R,4R,5S)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide (first eluting peak by SFC on Chiralpak AS-H column, rt = 1.79 min) | ESI-MS m/z calc. 508.1233, found 507.1 (M − 1)⁻; Retention time: 3.22 minutes | $^1$H NMR (500 MHz, Chloroform-d) δ 8.51 (s, 1H), 8.13 (ddd, J = 9.0, 4.5, 2.9 Hz, 1H), 7.90 (dd, J = 6.6, 2.9 Hz, 1H), 7.49 (dd, J = 8.8, 6.1 Hz, 1H), 7.10 (dd, J = 11.3, 9.0 Hz, 1H), 6.98 (td, J = 8.3, 2.6 Hz, 1H), 6.86 (dd, J = 9.3, 2.6 Hz, 1H), 6.70 (d, J = 12.2 Hz, 1H), 6.68-6.35 (m, 1H), 5.88 (s, 1H), 5.05 (d, J = 11.0 Hz, 1H), 4.09 (dd, J = 11.0, 7.9 Hz, 1H), 2.79 (p, J = 7.6 Hz, 1H), 1.69 (d, J = 1.1 Hz, 3H), 0.84-0.75 (m, 3H) ppm. |
| 32 | rel-(2R,3S,4S,5R)-N-(3-carbamoyl-4-fluoro-phenyl)-3-[2-(difluoromethoxy)-4-fluoro-phenyl]-4,5-dimethyl-5-(trifluoromethyl)tetrahydrofuran-2-carboxamide (second eluting peak by SFC on Chiralpak AS-H column, rt = 3.07 min) | ESI-MS m/z calc. 508.1233, found 507.1 (M − 1)⁻; Retention time: 3.22 minutes | $^1$H NMR (500 MHz, Chloroform-d) δ 8.50 (s, 1H), 8.13 (ddd, J = 9.0, 4.4, 2.9 Hz, 1H), 7.90 (dd, J = 6.6, 2.9 Hz, 1H), 7.49 (dd, J = 8.8, 6.2 Hz, 1H), 7.10 (dd, J = 11.2, 9.0 Hz, 1H), 6.98 (ddd, J = 8.8, 7.9, 2.6 Hz, 1H), 6.86 (dd, J = 9.2, 2.5 Hz, 1H), 6.70 (d, J = 12.0 Hz, 1H), 6.68-6.32 (m, 1H), 5.86 (s, 1H), 5.05 (d, J = 11.0 Hz, 1H), 4.09 (dd, J = 11.0, 7.9 Hz, 1H), 2.79 (p, J = 7.6 Hz, 1H), 1.69 (d, J = 1.1 Hz, 3H), 0.83-0.76 (m, 3H) ppm. |

The following compounds were made using a similar method to that described in Example 1, but using catalytic 1,2-dibromoethane to activate the magnesium in step 2 and without the separation of the racemate by chiral SFC in step 6:

| Cmpd No. | Compound Name | LC/MS | NMR (shifts in ppm) |
|---|---|---|---|
| 33 | rac-(2S,3R,4R,5R)-4-[[3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 473.1374, found 474.0 (M + 1)⁺; Retention time: 3.19 minutes | $^1$H NMR (500 MHz, Chloroform-d) δ 8.55 (s, 1H), 8.46 (d, J = 5.5 Hz, 1H), 8.07 (dd, J = 5.5, 2.1 Hz, 1H), 7.96 (d, J = 2.2 Hz, 1H), 7.82 (s, 1H), 7.10-7.01 (m, 1H), 6.90 (q, J = 8.7 Hz, 1H), 5.51 (s, 1H), 4.96 (d, J = 9.0 Hz, 1H), 4.24 (t, J = 8.5 Hz, 1H), 4.00 (d, J = 2.7 Hz, 3H), 2.97 (q, J = 7.5 Hz, 1H), 1.42 (s, 3H), 0.72 (d, J = 7.4 Hz, 3H) ppm. |
| 34 | rac-(2S,3R,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 473.1374, found 474.1 (M + 1)⁺; Retention time: 3.15 minutes | $^1$H NMR (500 MHz, Chloroform-d) δ 8.55 (s, 1H), 8.46 (d, J = 5.5 Hz, 1H), 8.08 (dd, J = 5.5, 2.2 Hz, 1H), 7.94 (d, J = 2.2 Hz, 1H), 7.83 (s, 1H), 7.01-6.86 (m, 2H), 5.55 (s, 1H), 4.74 (d, J = 9.7 |

| Cmpd No. | Compound Name | LC/MS | NMR (shifts in ppm) |
|---|---|---|---|
| 35 | rac-(2R,3S,4R,5R)-4-[[3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 473.1374, found 474.0 (M + 1)+; Retention time: 3.22 minutes | Hz, 1H), 3.99 (d, J = 2.3 Hz, 3H), 3.68 (t, J = 11.0 Hz, 1H), 2.52 (dd, J = 12.1, 6.9 Hz, 1H), 1.63-1.58 (m, 3H), 1.03 (dd, J = 7.2, 2.1 Hz, 3H) ppm. $^1$H NMR (500 MHz, Methanol-d$_4$) δ 8.48 (dd, J = 5.5, 0.6 Hz, 1H), 8.24 (dd, J = 2.2, 0.6 Hz, 1H), 7.86 (dd, J = 5.5, 2.2 Hz, 1H), 7.12 (ddd, J = 8.2, 5.6, 2.2 Hz, 1H), 7.02 (ddd, J = 9.8, 8.9, 7.5 Hz, 1H), 4.63 (d, J = 10.4 Hz, 1H), 3.91 (d, J = 2.2 Hz, 3H), 3.62 (dd, J = 12.0, 10.4 Hz, 1H), 3.35 (s, 1H), 2.91 (dq, J = 11.9, 6.9 Hz, 1H), 1.51 (d, J = 1.1 Hz, 3H), 0.99 (d, J = 6.9 Hz, 3H) ppm. |

The following compounds were made using a method similar to that described in Example 1, but using catalytic 1,2-dibromoethane to activate the magnesium in step 2, and without the addition of LiOH/EtOH in step 3. The purification in step 6 was conducted by SFC using a DEAP column, 5 μm particle size, 25 cm×21.2 mm from Princeton Chromatography Inc. on an SFC 100 instrument from Waters Corp., followed by chiral SFC using a Chiralpak AS-H column, 5 μm particle size, 25 cm×10 mm from Daicel on a Minigram SFC instrument from Berger Instruments. Compound 3a was purified further by chiral SFC using a Chiralpak OD-H column, 5 μm particle size, 25 cm×10 mm from Daicel on a Minigram SFC instrument from Berger Instruments. Compounds 38 and 39 were separated by chiral SFC using a (RR)-Whelk-O1 column, 5 μm particle size, 25 cm×21.2 mm from Regis Technologies:

| Cmpd No. | Compound Name | LC/MS | NMR (shifts in ppm) |
|---|---|---|---|
| 3a | rel-(2R,3S,4S,5R)-4-[[3-(4-fluoro-2-methoxy-phenyl)-4,5-dimethyl-5-(trifluoromethyl)tetrahydrofuran-2-carbonyl]amino]pyridine-2-carboxamide (first eluting isomer by SFC on Chiralpak AS-H column, rt = 1.77 min) | ESI-MS m/z calc. 455.14682, found 456.6 (M + 1)+; 454.7 (M − 1)−; Retention time: 3.16 minutes | $^1$H NMR (500 MHz, Chloroform-d) δ 8.71 (s, 1H), 8.44 (d, J = 5.6 Hz, 1H), 8.18 (dd, J = 5.6, 2.2 Hz, 1H), 7.93 (d, J = 2.2 Hz, 1H), 7.85 (s, 1H), 7.35 (dd, J = 8.6, 6.4 Hz, 1H), 6.71 (td, J = 8.4, 2.5 Hz, 1H), 6.61 (dd, J = 10.7, 2.5 Hz, 1H), 5.62 (s, 1H), 5.08 (d, J = 11.3 Hz, 1H), 4.10 (dd, J = 11.2, 7.7 Hz, 1H), 3.81 (s, 3H), 2.81 (p, J = 7.5 Hz, 1H), 1.70 (d, J = 1.2 Hz, 3H), 0.75 (dq, J = 7.4, 2.4 Hz, 3H) ppm. |
| 3b | rel-(2S,3R,4R,5S)-4-[[3-(4-fluoro-2-methoxy-phenyl)-4,5-dimethyl-5-(trifluoromethyl)tetrahydrofuran-2-carbonyl]amino]pyridine-2-carboxamide (second eluting isomer by SFC on Chiralpak AS-H column, rt = 2.79 min) | ESI-MS m/z calc. 455.14682, found 456.6 (M + 1)+; 454.7 (M − 1)−; Retention time: 3.16 minutes | |
| 36 | rel-(2R,3S,4R,5S)-4-[[3-(4-fluoro-2-methoxy-phenyl)-4,5-dimethyl-5-(trifluoromethyl)tetrahydrofuran-2-carbonyl]amino]pyridine-2-carboxamide (first eluting isomer by SFC on Chiralpak AS-H column, rt = 2.94 min) | ESI-MS m/z calc. 455.14682, found 456.6 (M + 1)+; 454.6 (M − 1)−; Retention time: 3.06 minutes | $^1$H NMR (500 MHz, Methanol-d$_4$) δ 8.49 (d, J = 5.5 Hz, 1H), 8.18 (d, J = 2.1 Hz, 1H), 7.84 (dd, J = 5.5, 2.2 Hz, 1H), 7.30 (dd, J = 8.5, 6.6 Hz, 1H), 6.79 (dd, J = 11.0, 2.5 Hz, 1H), 6.71 (td, J = 8.3, 2.5 Hz, 1H), 4.80 (s, 1H), 3.78 (s, 3H), 3.77-3.71 (m, 1H), 2.84-2.70 (m, 1H), 1.60 (d, J = 1.1 Hz, |

-continued

| Cmpd No. | Compound Name | LC/MS | NMR (shifts in ppm) |
|---|---|---|---|
| 37 | rel-(2S,3R,4S,5R)-4-[[3-(4-fluoro-2-methoxy-phenyl)-4,5-dimethyl-5-(trifluoromethyl)tetrahydrofuran-2-carbonyl]amino]pyridine-2-carboxamide (second eluting isomer by SFC on Chiralpak AS-H column, rt = 3.66 min) | ESI-MS m/z calc. 455.14682, found 456.6 (M + 1)+; 454.6 (M − 1)−; Retention time: 3.06 minutes | 3H), 1.05-0.97 (m, 3H) ppm.<br>$^1$H NMR (500 MHz, Chloroform-d) δ 8.56 (s, 1H), 8.45 (d, J = 5.5 Hz, 1H), 8.09 (dd, J = 5.5, 2.2 Hz, 1H), 7.92 (d, J = 2.1 Hz, 1H), 7.83 (d, J = 4.3 Hz, 1H), 7.13 (dd, J = 8.3, 6.5 Hz, 1H), 6.71-6.63 (m, 2H), 5.58 (s, 1H), 4.92 (d, J = 9.6 Hz, 1H), 3.82 (s, 3H), 3.54 (t, J = 10.9 Hz, 1H), 2.80-2.67 (m, 1H), 1.62-1.58 (m, 3H), 1.01 (dt, J = 7.0, 1.9 Hz, 3H) ppm. |
| 38 | rel-(2S,3R,4S,5S)-4-[[3-(4-fluoro-2-methoxy-phenyl)-4,5-dimethyl-5-(trifluoromethyl)tetrahydrofuran-2-carbonyl]amino]pyridine-2-carboxamide (first eluting isomer by SFC on Whelk01 column, rt = 3.29 min) | ESI-MS m/z calc. 455.14682, found 456.6 (M + 1)+; 454.7 (M − 1)−; Retention time: 3.13 minutes | $^1$H NMR (500 MHz, Chloroform-d) δ 8.58 (s, 1H), 8.45 (d, J = 5.5 Hz, 1H), 8.17 (dd, J = 5.5, 2.2 Hz, 1H), 7.92 (d, J = 2.2 Hz, 1H), 7.86 (s, 1H), 7.14 (dd, J = 8.4, 6.4 Hz, 1H), 6.72-6.62 (m, 2H), 5.64 (s, 1H), 4.80 (d, J = 10.6 Hz, 1H), 3.78 (s, 3H), 3.30 (t, J = 11.2 Hz, 1H), 3.06 (dq, J = 13.4, 6.8 Hz, 1H), 1.51 (s, 3H), 0.96 (d, J = 6.8 Hz, 3H) ppm. |
| 39 | rel-(2R,3S,4R,5R)-4-[[3-(4-fluoro-2-methoxy-phenyl)-4,5-dimethyl-5-(trifluoromethyl)tetrahydrofuran-2-carbonyl]amino]pyridine-2-carboxamide (second eluting isomer by SFC on Whelk01 column, rt = 4.09 min) | ESI-MS m/z calc. 455.14682, found 456.6 (M + 1)+; 454.6 (M − 1)−; Retention time: 3.13 minutes | $^1$H NMR (500 MHz, Chloroform-d) δ 8.59 (s, 1H), 8.47 (d, J = 5.5 Hz, 1H), 8.18 (dd, J = 5.5, 2.2 Hz, 1H), 7.94 (d, J = 2.2 Hz, 1H), 7.87 (s, 1H), 7.16 (dd, J = 8.4, 6.5 Hz, 1H), 6.75-6.64 (m, 2H), 5.66-5.61 (m, 1H), 4.83 (d, J = 10.6 Hz, 1H), 3.81 (s, 3H), 3.32 (t, J = 11.2 Hz, 1H), 3.09 (dq, J = 11.8, 6.9 Hz, 1H), 1.53 (s, 3H), 0.99 (d, J = 6.8 Hz, 3H) ppm. |
| 40 | rel-(2R,3S,4S,5S)-4-[[3-(4-fluoro-2-methoxy-phenyl)-4,5-dimethyl-5-(trifluoromethyl)tetrahydrofuran-2-carbonyl]amino]pyridine-2-carboxamide (first eluting isomer by SFC on Chiralpak AS-H column, rt = 1.87 min) | ESI-MS m/z calc. 455.14682, found 456.6 (M + 1)+; 454.6 (M − 1)−; Retention time: 3.09 minutes | $^1$H NMR (500 MHz, Chloroform-d) δ 8.45 (s, 1H), 8.45 (d, J = 5.5 Hz, 1H), 8.09 (dd, J = 5.4, 2.2 Hz, 1H), 7.94 (d, J = 2.2 Hz, 1H), 7.83 (s, 1H), 7.34-7.27 (m, 1H), 6.70 (td, J = 8.3, 2.5 Hz, 1H), 6.62 (dd, J = 10.8, 2.5 Hz, 1H), 5.60-5.56 (m, 1H), 5.01 (d, J = 9.1 Hz, 1H), 4.26 (t, J = 8.6 Hz, 1H), 3.82 (s, 3H), 3.01 (p, J = 7.5 Hz, 1H), 1.41 (s, 3H), 0.68 (d, J = 7.4 Hz, 3H) ppm. |
| 41 | rel-(2S,3R,4R,5R)-4-[[3-(4-fluoro-2-methoxy-phenyl)-4,5-dimethyl-5-(trifluoromethyl)tetrahydrofuran-2-carbonyl]amino]pyridine-2-carboxamide (second eluting isomer by SFC on Chiralpak AS-H column, rt = 2.96 min) | ESI-MS m/z calc. 455.14682, found 456.6 (M + 1)+; 454.7 (M − 1)−; Retention time: 3.09 minutes | $^1$H NMR (500 MHz, Chloroform-d) δ 8.57 (s, 1H), 8.45 (d, J = 5.5 Hz, 1H), 8.09 (dd, J = 5.6, 2.2 Hz, 1H), 7.94 (d, J = 2.4 Hz, 1H), 7.85-7.80 (m, 1H), 7.30 (dd, J = 8.5, 6.4 Hz, 1H), 6.70 (td, J = 8.3, 2.5 Hz, 1H), 6.62 (dd, J = 10.7, 2.5 Hz, 1H), 5.56 (s, 1H), 5.01 (d, J = 9.1 Hz, 1H), 4.26 (t, J = 8.6 Hz, 1H), 3.82 (s, 3H), 3.01 (p, J = 7.5 Hz, 1H), 1.41 (s, |

| Cmpd No. | Compound Name | LC/MS | NMR (shifts in ppm) |
|---|---|---|---|
| | | | 3H), 0.68 (d, J = 7.4 Hz, 3H) ppm. |

The following compounds were made using a method similar to that described in Example 1, but using catalytic 1,2-dibromoethane to activate the magnesium in step 2, and without the addition of LiOH/EtOH in step 3. The purification in step 6 was conducted by SFC using a Lux Cellulose-2 column, 5 μm particle size, 25 cm×10 mm from Phenomenex on an SFC 100 instrument from Waters Corp., on a Minigram SFC instrument from Berger Instruments:

| Cmpd No. | Compound Name | LC/MS | NMR (shifts in ppm) |
|---|---|---|---|
| 42 | rel-(2R,3S,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide (first eluting isomer by SFC on Lux Cellulose-2 column, rt = 4.18 min) | ESI-MS m/z calc. 505.14362, found 506.1 (M + 1)$^+$; 504.1 (M − 1)$^-$; Retention time: 3.37 minutes | $^1$H NMR (400 MHz, DMSO-d$_6$) δ 10.73 (s, 1H), 8.49 (d, J = 5.6 Hz, 1H), 8.29 (d, J = 2.1 Hz, 1H), 8.06 (s, 1H), 7.83 (dd, J = 5.5, 2.2 Hz, 1H), 7.71 (d, J = 7.8 Hz, 1H), 7.64 (dd, J = 8.1, 1.5 Hz, 1H), 7.61 (s, 1H), 7.38 (t, J = 7.8 Hz, 1H), 5.15 (d, J = 10.2 Hz, 1H), 4.38 (dd, J = 10.2, 7.8 Hz, 1H), 3.84 (s, 3H), 2.91-2.83 (m, 1H), 1.65 (s, 3H), 0.74 (d, J = 7.3 Hz, 3H) ppm. |
| 43 | rel-(2S,3R,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide (second eluting isomer by SFC on Lux Cellulose-2 column, rt = 4.18 min) | ESI-MS m/z calc. 505.14362, found 506.1 (M + 1)$^+$; 504.1 (M − 1)$^-$; Retention time: 3.37 minutes | $^1$H NMR (400 MHz, DMSO-d$_6$) δ 10.73 (s, 1H), 8.48 (d, J = 5.4 Hz, 1H), 8.29 (d, J = 2.1 Hz, 1H), 8.05 (s, 1H), 7.83 (dd, J = 5.5, 2.2 Hz, 1H), 7.71 (d, J = 7.8 Hz, 1H), 7.67-7.58 (m, 2H), 7.37 (t, J = 7.8 Hz, 1H), 5.15 (d, J = 10.2 Hz, 1H), 4.38 (dd, J = 10.2, 7.8 Hz, 1H), 3.84 (s, 3H), 2.88 (q, J = 7.6 Hz, 1H), 1.65 (s, 3H), 0.74 (d, J = 7.2 Hz, 3H) ppm. |

The following compounds were made using a method similar to that described in Example 1, but without the addition of LiOH/EtOH in step 3. The amide coupling step 4 was cared out using T3P as an activating agent rather than oxalyl chloride. The purification in step 6 was conducted by SFC using a Lux i-Cellulose-S column, 5 μm particle size, 25 cm×10 mm from Phenomenex on an SFC 100 instrument from Waters Corp., on a Minigram SFC instrument from Berger Instruments:

| Cmpd No. | Compound Name | LC/MS | NMR (shifts in ppm) |
|---|---|---|---|
| 44 | rel-(2R,3S,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide (first eluting isomer by SFC on Lux i-Cellulose-5 column, rt = 2.65 min) | ESI-MS m/z calc. 505.14362, found 506.2 (M + 1)$^+$; 504.2 (M − 1)$^-$; Retention time: 3.16 minutes | $^1$H NMR (400 MHz, DMSO-d$_6$) δ 10.68 (s, 1H), 8.48 (d, J = 5.5 Hz, 1H), 8.28 (d, J = 2.2 Hz, 1H), 8.05 (s, 1H), 7.83 (dd, J = 5.5, 2.2 Hz, 1H), 7.65-7.57 (m, 2H), 7.37-7.01 (m, 2H), 5.11 (d, J = 10.1 Hz, 1H), 4.29-4.22 (m, 1H), 3.81 (s, 3H), 2.78 (q, J = 7.5 Hz, 1H), 1.63 (s, 3H), 0.74 (d, J = 7.2 Hz, 3H) ppm. |
| 45 | rel-(2S,3R,4R,5S)-4-[[3-[3-(difluoromethyl)-4-fluoro-2-methoxy-phenyl]-4,5-dimethyl- | ESI-MS m/z calc. 505.14362, found 506.1 (M + 1)$^+$; 504.2 (M − 1)$^-$; | $^1$H NMR (400 MHz, DMSO-d$_6$) δ 10.67 (s, 1H), 8.48 (d, J = 5.5 Hz, |

| Cmpd No. | Compound Name | LC/MS | NMR (shifts in ppm) |
|---|---|---|---|
| | 5-(trifluoromethyl)tetrahydrofuran-2-carbonyl]amino]pyridine-2-carboxamide (second eluting isomer by SFC on Lux i-Cellulose-5 column, rt = 3.16 min) | Retention time: 3.16 minutes | 1H), 8.28 (d, J = 2.2 Hz, 1H), 8.05 (s, 1H), 7.82 (dd, J = 5.5, 2.2 Hz, 1H), 7.60 (s, 2H), 7.35-7.03 (m, 2H), 5.11 (d, J = 10.2 Hz, 1H), 4.32-4.22 (m, 1H), 3.81 (s, 3H), 2.78 (dt, J = 14.9, 7.5 Hz, 1H), 1.63 (s, 3H), 0.74 (d, J = 7.4 Hz, 3H) ppm. |

The following compounds were made using a method similar to that described in Example 1, except that methylamine was used in place of ammonia in Step 5. In step 6, purification was performed by chiral SFC using a Chiralpak AS-H column, 5 μm particle size, 25 cm×10 mm from Daicel on a Minigram SFC instrument from Berger Instruments:

| Cmpd No. | Compound Name | LC/MS | NMR (shifts in ppm) |
|---|---|---|---|
| 12 | rel-(2R,3S,4S,5S)-4-[[3-[2-(difluoromethoxy)-3,4-difluoro-phenyl]-4,5-dimethyl-5-(trifluoromethyl)tetrahydrofuran-2-carbonyl]amino]-N-methyl-pyridine-2-carboxamide (first eluting isomer by SFC) | ESI-MS m/z found 524.5 (M + 1)+; Retention time: 3.33 minutes | $^1$H NMR (500 MHz, Methanol-$d_4$) δ 8.51 (d, J = 5.5 Hz, 1H), 8.27 (d, J = 2.1 Hz, 1H), 7.91 (dd, J = 5.5, 2.2 Hz, 1H), 7.37-7.26 (m, 2H), 6.97 (td, J = 73.1, 1.1 Hz, 1H), 5.14 (d, J = 10.4 Hz, 1H), 4.41 (dd, J = 10.4, 8.1 Hz, 1H), 2.99 (s, 3H), 2.87 (p, J = 7.6 Hz, 1H), 1.71 (d, J = 1.2 Hz, 3H), 0.97-0.84 (m, 3H) ppm. |
| 13 | rel-(2S,3R,4R,5R)-4-[[3-[2-(difluoromethoxy)-3,4-difluoro-phenyl]-4,5-dimethyl-5-(trifluoromethyl)tetrahydrofuran-2-carbonyl]amino]-N-methyl-pyridine-2-carboxamide (second eluting isomer by SFC) | ESI-MS m/z found 524.5 (M + 1)+; Retention time: 3.33 minutes | $^1$H NMR (500 MHz, Methanol-$d_4$) δ 8.54-8.49 (m, 1H), 8.27 (d, J = 2.0 Hz, 1H), 7.91 (dd, J = 5.5, 2.2 Hz, 1H), 7.37-7.25 (m, 2H), 6.97 (td, J = 73.1, 1.1 Hz, 1H), 5.14 (d, J = 10.3 Hz, 1H), 4.41 (dd, J = 10.4, 8.0 Hz, 1H), 2.99 (s, 3H), 2.87 (p, J = 7.7 Hz, 1H), 1.71 (d, J = 1.2 Hz, 3H), 0.93-0.86 (m, 3H) ppm. |

Example 2 rel-(2S,3R,5S)-4-[[3-(3,4-difluoro-2-methoxy-phenyl)-5-methyl-5-(trifluoromethyl)tetrahydrofuran-2-carbonyl]amino]pyridine-2-carboxamide (4) and rel-(2R,3S,5R)-4-[[3-(3,4-difluoro-2-methoxy-phenyl)-5-methyl-5-(trifluoromethyl)tetrahydrofuran-2-carbonyl]amino]pyridine-2-carboxamide (5)

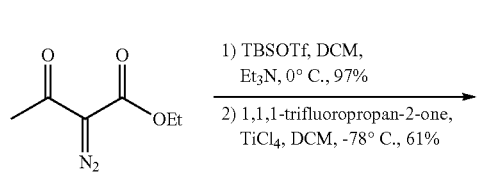

1) TBSOTf, DCM, Et₃N, 0° C., 97%
2) 1,1,1-trifluoropropan-2-one, TiCl₄, DCM, -78° C., 61%

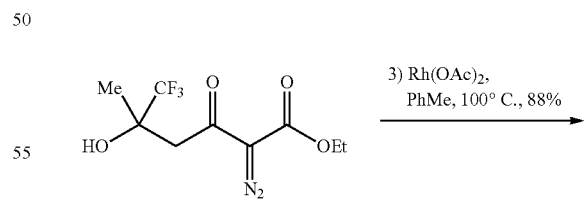

3) Rh(OAc)₂, PhMe, 100° C., 88%

4) Tf₂O, DIPEA, DCM, -78° C., 100%

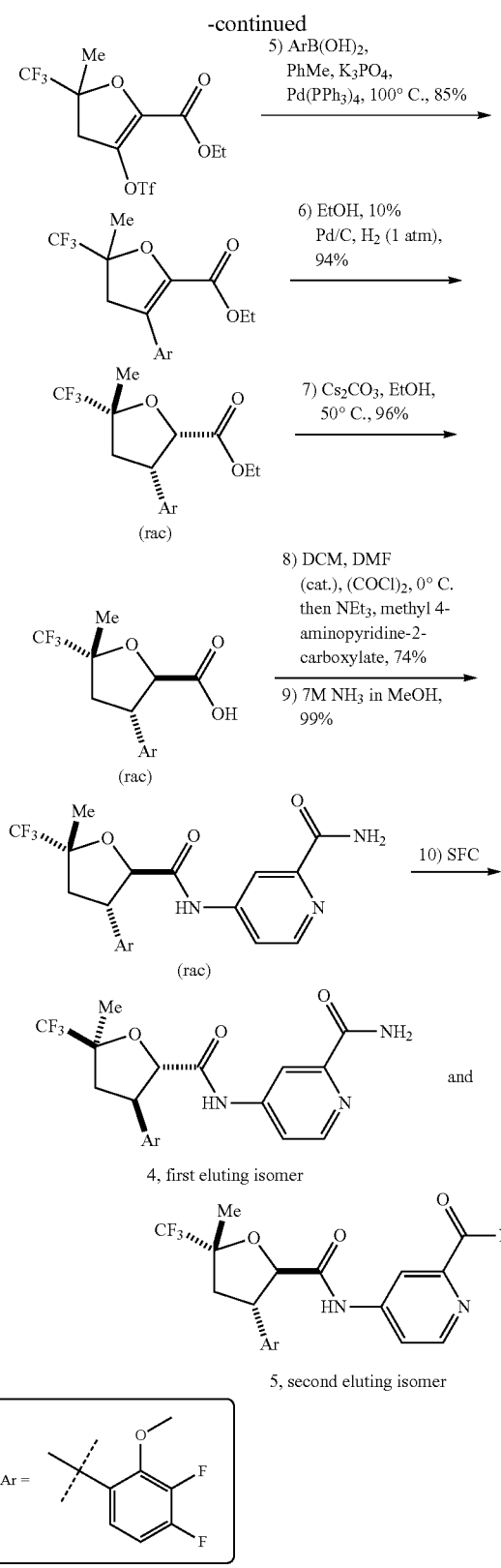

triethylamine (8.05 g, 11.2 mL, 78.8 mmol). TBSOTf (9.24 g, 8.2 mL, 34.3 mmol) was added slowly and the reaction mixture was stirred for 30 mins at 0° C. The reaction mixture was washed with 30% NaHCO$_3$ solution (200 mL). The organic layer was separated and washed with water (500 mL) then dried over MgSO$_4$. The solvent was evaporated to give ethyl 3-[tert-butyl(dimethyl)silyl]oxy-2-diazo-but-3-enoate (8.22 g, 97%) which was used in the next step without further purification.

Step 2

A solution of 1,1,1-trifluoropropan-2-one (33.8 g, 27 mL, 301.2 mmol) in DCM (150 mL) was stirred at −78° C. and TiCl$_4$ (56.8 g, 33 mL, 299.2 mmol) was added dropwise. The reaction was kept at −78° C. for 10 min before a solution of ethyl 3-[tert-butyl(dimethyl)silyl]oxy-2-diazo-but-3-enoate (64 g, 236.7 mmol) in DCM (150 mL) was added dropwise. The reaction was kept at −78° C. for 1 hour then a saturated solution of NaHCO$_3$ was added and the mixture diluted with DCM. The organic layer was dried over MgSO$_4$, concentrated in vacuo and the residue purified by column chromatography (0 to 30% EtOAc in hexane) to give ethyl 2-diazo-6,6,6-trifluoro-5-hydroxy-5-methyl-3-oxo-hexanoate (39 g, 61%) as a pale yellow liquid. $^1$H NMR (400 MHz, Chloroform-d) δ 4.92 (s, 1H), 4.32 (q, J=7.1 Hz, 2H), 3.63 (d, J=15.5 Hz, 1H), 2.84 (d, J=15.5 Hz, 1H), 1.41 (s, 3H), 1.33 (t, J=7.1 Hz, 3H) ppm.

Step 3

Rhodium (II) acetate (643 mg, 1.45 mmol) was charged into an oven dried two necked flask. Toluene (970 mL) was added and the solution was stirred at 100° C. for 10 mins. The solution was briefly lifted out of the oil bath whilst a solution of ethyl 2-diazo-6,6,6-trifluoro-5-hydroxy-5-methyl-3-oxo-hexanoate (39 g, 145.4 mmol) in a toluene (200 mL) was added dropwise, and the reaction was heated at reflux for 1 hr. The reaction mixture was filtered through filter paper and the filtrate was concentrated in vacuo to give ethyl 5-methyl-3-oxo-5-(trifluoromethyl)tetrahydrofuran-2-carboxylate (30.89 g, 88%). $^1$H NMR (400 MHz, Chloroform-d) δ 4.68 (s, 1H), 4.35-4.17 (m, 2H), 2.89 (d, J=18.8, 1H), 2.58 (d, J=18.8, 1H), 1.70 (s, 3H), 1.30 (t, J=7.2, Hz, 3H) ppm.

Step 4

Trifluoromethanesulfonic anhydride (6.0 mL, 35.7 mmol) was added dropwise to a solution of ethyl 5-methyl-3-oxo-5-(trifluoromethyl)tetrahydrofuran-2-carboxylate (6.5 g, 27.1 mmol) and DIPEA (14 mL, 80.4 mmol) in DCM (150 mL) at −78° C. and the reaction stirred for 2.5 hours before saturated aqueous NH$_4$Cl (75 mL) was added. The mixture was warmed to ambient temperature, the layers separated, and the aqueous layer extracted with DCM (2×30 mL). The combined organic extracts were dried (MgSO$_4$), filtered and concentrated in vacuo to give ethyl 2-methyl-2-(trifluoromethyl)-4-(trifluoromethylsulfonyloxy)-3H-furan-5-carboxylate (10.1 g, 100%) which was used directly in the next reaction.

Step 5

To a stirred solution of (3,4-difluoro-2-methoxy-phenyl) boronic acid (2.0 g, 10.6 mmol) and ethyl 2-methyl-2-(trifluoromethyl)-4-(trifluoromethylsulfonyloxy)-3H-furan- Step 1

To a solution of ethyl 2-diazo-3-oxo-butanoate (5.0 g, 31.4 mmol) in DCM (50 mL) stirring at 0° C. was added 5-carboxylate (3 g, 7.90 mmol) in toluene (80 mL) was added K$_3$PO$_4$ (13 mL of 2 M aq., 26.0 mmol). The mixture was degassed with N$_2$ for 20 mins before Pd(PPh$_3$)$_4$ (466 mg, 0.40 mmol) was added and then heated to 100° C. for 1 h. The mixture was filtered by celite pad, the filtrate diluted with water (50 mL) and the aqueous layer extracted with EtOAc (50×2 mL). The organic layer was dried (MgSO$_4$), filtered and evaporated. The residue was purified by column chromatography (SiO$_2$, 0-2% EtOAc in hexane) to give ethyl 4-(3,4-difluoro-2-methoxy-phenyl)-2-methyl-2-(trifluoromethyl)-3H-furan-5-carboxylate (2.5 g, 85%) as a light-yellow liquid. $^1$H NMR (400 MHz, Chloroform-d) δ 6.87 (pd, J=8.8, 6.2 Hz, 2H), 4.15 (q, J=7.1 Hz, 2H), 3.89 (s, 3H), 3.42 (d, J=17.4 Hz, 1H), 2.93 (d, J=17.4 Hz, 1H), 1.65 (s, 3H), 1.14 (t, J=7.1 Hz, 3H) ppm. ESI-MS m/z calc. 366.089, found 367.2 (M+1)$^+$.

Step 6

EtOH (200 mL) was added to ethyl 4-(3,4-difluoro-2-methoxy-phenyl)-2-methyl-2-(trifluoromethyl)-3H-furan-5-carboxylate (5.51 g, 15.0 mmol) and Pd/C (10 wt. % loading, 2.2 g, 2.067 mmol). The mixture was degassed and stirred under a balloon of H$_2$ for 96 hours. The catalyst was removed by filtration, the solids washed with EtOH (50 mL) and the filtrate concentrated in vacuo. A further portion of Pd/C (10 wt. % loading, 2.2 g, 2.07 mmol) was added to the residue followed by EtOH (200 mL) and the reaction mixture stirred under a balloon of H$_2$ at ambient temperature for 24 hours. The catalyst was removed by filtration, the solids washed with EtOH (50 mL) and the filtrate concentrated in vacuo. A further portion of Pd/C (10 wt. % loading, 2.2 g, 2.07 mmol) was added to the residue followed by EtOH (200 mL) and the reaction mixture stirred under a balloon of H$_2$ at ambient temperature for 4 days. The catalyst was removed by filtration, the solids washed with EtOH (50 mL) and the filtrate concentrated in vacuo to give ethyl rac-(2S,3S,5R)-3-(3,4-difluoro-2-methoxy-phenyl)-5-methyl-5-(trifluoromethyl)tetrahydrofuran-2-carboxylate (5.19 g, 94%) as a white solid, and as a single diastereomer. $^1$H NMR (500 MHz, Chloroform-d) δ 6.89-6.86 (m, 1H), 6.82-6.77 (m, 1H), 4.93 (d, J=8.9 Hz, 1H), 4.23 (dt, J=13.0, 7.6 Hz, 1H), 4.08 (d, J=2.9 Hz, 3H), 3.85-3.71 (m, 2H), 2.82 (t, J=12.5 Hz, 1H), 2.04 (dd, J=12.0, 6.7 Hz, 1H), 1.53 (s, 3H), 0.94 (t, J=7.1 Hz, 3H) ppm; $^{19}$F NMR (471 MHz, Chloroform-d) δ−80.15, −136.84 (d, J=19.4 Hz), −154.77 (d, J=19.6 Hz) ppm.

Step 7

Ethyl rac-(2S,3S,5R)-3-(3,4-difluoro-2-methoxy-phenyl)-5-methyl-5-(trifluoromethyl)tetrahydrofuran-2-carboxylate (5.19 g, 14.09 mmol) was dissolved in ethanol (100 mL). Cesium carbonate (7.1 g, 21.8 mmol) was added and the suspension stirred at 50° C. for 2 hours. The reaction mixture was concentrated in vacuo and the residue partitioned between 1M HCl and MTBE. The layers were separated and the aqueous layer was extracted twice with MTBE. The combined organic extracts were dried (MgSO$_4$), filtered and concentrated in vacuo to give rac-(2R,3S,5R)-3-(3,4-difluoro-2-methoxy-phenyl)-5-methyl-5-(trifluoromethyl)tetrahydrofuran-2-carboxylic acid (5.11 g, 96%) as a colourless oil, as a single diastereomer. $^1$H NMR (500 MHz, Chloroform-d) δ 6.99-6.96 (m, 1H), 6.92-6.87 (m, 1H), 4.68 (d, J=10.5 Hz, 1H), 4.00 (d, J=2.7 Hz, 3H), 3.90 (ddd, J=12.0, 10.6, 8.2 Hz, 1H), 2.58 (t, J=12.5 Hz, 1H), 2.31 (dd, J=13.0, 8.2 Hz, 1H), 1.60 (s, 3H) ppm; $^{19}$F NMR (471 MHz, Chloroform-d) δ−81.56, −136.40 (d, J=19.6 Hz), −153.60 (d, J=19.5 Hz) ppm. ESI-MS m/z calc. 340.0734, found 339.5 (M−1)$^-$.

Step 8

To a solution of rac-(2R,3S,5R)-3-(3,4-difluoro-2-methoxy-phenyl)-5-methyl-5-(trifluoromethyl)tetrahydrofuran-2-carboxylic acid (1.5 g, 4.41 mmol) in DCM (30 mL) cooled to −10° C. was added DMF (5 μL, 0.065 mmol) followed by oxalyl chloride (620 μL, 7.11 mmol). The reaction was stirred for 4 hours, allowing it to warm to ambient temperature before further oxalyl chloride (300 μL, 3.55 mmol) was added. The reaction was stirred for a further hour before being concentrated in vacuo. The residue was dissolved in DCM (30 mL) and the solution cooled in an ice bath. TEA (600 μL, 4.31 mmol) and methyl 4-aminopyridine-2-carboxylate (663.7 mg, 4.36 mmol) were added sequentially and the resultant mixture stirred for 30 mins before being quenched with MeOH and concentrated in vacuo. Purification by flash chromatography (40 g SiO$_2$, 0 to 60% ethyl acetate in heptane, loaded in DCM) gave methyl rac-(2R,3S,5R)-4-[[3-(3,4-difluoro-2-methoxy-phenyl)-5-methyl-5-(trifluoromethyl)tetrahydrofuran-2-carbonyl]amino]pyridine-2-carboxylate (827.6 mg, 74%). $^1$H NMR (500 MHz, Chloroform-d) δ 8.63 (d, J=5.5 Hz, 1H), 8.46 (s, 1H), 8.07 (d, J=2.1 Hz, 1H), 7.94 (dd, J=5.5, 2.2 Hz, 1H), 7.00 (ddd, J=8.0, 5.5, 2.1 Hz, 1H), 6.90 (td, J=9.1, 7.3 Hz, 1H), 4.75 (d, J=10.7 Hz, 1H), 4.01 (s, 3H), 3.99 (d, J=2.6 Hz, 3H), 3.83 (td, J=11.4, 8.3 Hz, 1H), 2.61 (t, J=12.5 Hz, 1H), 2.34 (dd, J=13.1, 8.2 Hz, 1H), 1.65 (s, 3H) ppm. ESI-MS m/z calc. 474.1214, found 474.7 (M+1)$^+$ and 473.2 (M−1)$^-$.

Step 9

Methyl rac-(2R,3S,5R)-4-[[3-(3,4-difluoro-2-methoxy-phenyl)-5-methyl-5-(trifluoromethyl)tetrahydrofuran-2-carbonyl]amino]pyridine-2-carboxylate (1.9 g, 4.01 mmol) was dissolved in methanolic ammonia (20 mL of 7 M, 140.0 mmol) and the reaction stirred at ambient temperature overnight. Additional methanolic ammonia (5 mL of 7 M, 35.0 mmol) was added and reaction stirred at ambient temperature for a further 3 hrs before being concentrated in vacuo to give rac-(2R,3S,5R)-4-[[3-(3,4-difluoro-2-methoxy-phenyl)-5-methyl-5-(trifluoromethyl)tetrahydrofuran-2-carbonyl]amino]pyridine-2-carboxamide (1.94 g, 99%). $^1$H NMR (500 MHz, Methanol-d$_4$) δ 8.49 (dd, J=5.5, 0.6 Hz, 1H), 8.26 (dd, J=2.2, 0.6 Hz, 1H), 7.88 (dd, J=5.5, 2.2 Hz, 1H), 7.14 (ddd, J=8.3, 5.7, 2.3 Hz, 1H), 6.99 (ddd, J=9.9, 8.9, 7.5 Hz, 1H), 4.67 (d, J=10.3 Hz, 1H), 4.10-4.01 (m, 1H), 3.92 (d, J=2.3 Hz, 3H), 3.35 (s, 3H), 2.62 (t, J=12.4 Hz, 1H), 2.40 (dd, J=12.8, 8.2 Hz, 1H), 1.63 (s, 3H) ppm. ESI-MS m/z calc. 459.12173, found 460.2 (M+1)$^+$ and 458.3 (M−1)$^-$.

Step 10 rac-(2R,3S,5R)-4-[[3-(3,4-Difluoro-2-methoxy-phenyl)-5-methyl-5-(trifluoromethyl)tetrahydrofuran-2-carbonyl]amino]pyridine-2-carboxamide (1.9 g, 3.89 mmol) was separated by chiral SFC using a (R,R)-Whelk-O1 column, 5 μm particle size, 25 cm×21.2 mm from Regis Technologies to give two single isomers of unknown absolute configuration:

First Eluting Isomer (rt=5.05 min): rel-(2S,3R,5S)-4-[[3-(3,4-difluoro-2-methoxy-phenyl)-5-methyl-5-(trifluoromethyl)tetrahydrofuran-2-carbonyl]amino]pyridine-2-carboxamide (4, 724 mg, 38%); ESI-MS m/z calc. 459.12173, found 460.2 (M+1)⁺ and 458.3 (M−1)⁻. ¹H NMR (500 MHz, Methanol-d₄) δ 8.36 (d, J=5.5 Hz, 1H), 8.13 (d, J=2.1 Hz, 1H), 7.75 (dd, J=5.5, 2.2 Hz, 1H), 7.00 (ddd, J=8.2, 5.6, 2.2 Hz, 1H), 6.86 (td, J=9.3, 7.5 Hz, 1H), 4.55 (d, J=10.3 Hz, 1H), 3.92 (ddd, J=12.2, 10.4, 8.2 Hz, 1H), 3.79 (d, J=2.3 Hz, 3H), 3.22 (s, 1H), 2.49 (t, J=12.4 Hz, 1H), 2.27 (dd, J=12.8, 8.2 Hz, 1H), 1.50 (s, 3H) ppm.

Second Eluting Isomer (rt=7.36 min): rel-(2R,3S,5R)-4-[[3-(3,4-difluoro-2-methoxy-phenyl)-5-methyl-5-(trifluoromethyl)tetrahydrofuran-2-carbonyl]amino]pyridine-2-carboxamide (5, 749 mg, 39%); ESI-MS m/z calc. 459.12173, found 460.2 (M+1)⁺ and 458.3 (M−1)⁻. ¹H NMR (500 MHz, Methanol-d₄) δ 8.36 (d, J=5.5 Hz, 1H), 8.13 (d, J=2.2 Hz, 1H), 7.75 (dd, J=5.5, 2.2 Hz, 1H), 7.01 (ddd, J=8.3, 5.6, 2.2 Hz, 1H), 6.86 (td, J=9.4, 7.5 Hz, 1H), 4.55 (d, J=10.2 Hz, 1H), 3.92 (ddd, J=12.0, 10.4, 8.2 Hz, 1H), 3.79 (d, J=2.3 Hz, 3H), 3.22 (s, 3H), 2.49 (t, J=12.4 Hz, 1H), 2.27 (dd, J=12.9, 8.2 Hz, 1H), 1.50 (s, 3H) ppm.

The following compounds were made using a method similar to that described Example 2, except that 5-amino-2-fluorobenzamide was used as coupling partner in step 8, and step 9 was omitted:

Example 3

(2S,3R,4R,5S)-4-[[3-(3,4-difluoro-2-methoxy-phenyl)-4,5-dimethyl-5-(trifluoromethyl)tetrahydrofuran-2-carbonyl]amino]pyridine-2-carboxamide (6) and (2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide (7)

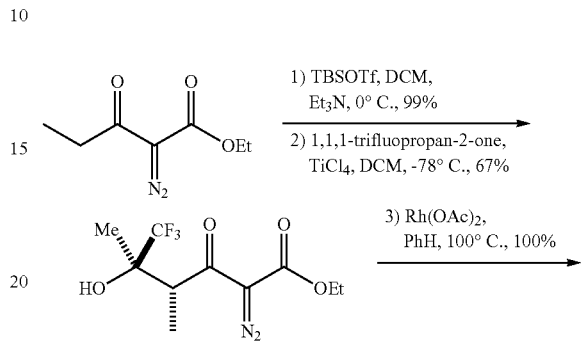

| Cmpd No. | Compound Name | LC/MS | NMR (shifts in ppm) |
| --- | --- | --- | --- |
| 46 | rel-(2S,3R,5S)-N-(3-carbamoyl-4-fluoro-phenyl)-3-(3,4-difluoro-2-methoxy-phenyl)-5-methyl-5-(trifluoromethyl)tetrahydrofuran-2-carboxamide (first eluting isomer by SFC on Whelk01 column, rt = 0.90 min) | ESI-MS m/z calc. 476.11707, found 477.1 (M + 1)⁺; 475.3 (M − 1)⁻; Retention time: 3.09 minutes | ¹H NMR (500 MHz, Chloroform-d) δ 8.44 (s, 1H), 8.18 (ddd, J = 9.0, 4.4, 2.9 Hz, 1H), 7.89 (dd, J = 6.6, 2.9 Hz, 1H), 7.10 (dd, J = 11.3, 9.0 Hz, 1H), 7.01 (ddd, J = 8.8, 5.6, 2.2 Hz, 1H), 6.89 (td, J = 9.2, 7.3 Hz, 1H), 6.71 (d, J = 11.8 Hz, 1H), 5.91 (s, 1H), 4.73 (d, J = 10.7 Hz, 1H), 3.97 (d, J = 2.5 Hz, 3H), 3.82 (td, J = 11.4, 8.3 Hz, 1H), 3.49 (d, J = 4.4 Hz, 1H), 2.57 (t, J = 12.5 Hz, 1H), 2.32 (dd, J = 13.0, 8.2 Hz, 1H), 1.64 (s, 3H) ppm. |
| 47 | rel-(2R,3S,5R)-N-(3-carbamoyl-4-fluoro-phenyl)-3-(3,4-difluoro-2-methoxy-phenyl)5-methyl-5-(trifluoromethyl)tetrahydrofuran-2-carboxamide (second eluting isomer by SFC on Whelk01 column, rt = 1.35 min) | ESI-MS m/z calc. 476.11707, found 477.1 (M + 1)⁺; 475.3 (M − 1)⁻; Retention time: 3.09 minutes | ¹H NMR (500 MHz, Chloroform-d) δ 8.42 (s, 1H), 8.18 (ddd, J = 9.0, 4.4, 2.9 Hz, 1H), 7.89 (dd, J = 6.6, 2.9 Hz, 1H), 7.11 (dd, J = 11.2, 9.0 Hz, 1H), 7.01 (ddd, J = 8.1, 5.5, 2.2 Hz, 1H), 6.89 (td, J = 9.1, 7.3 Hz, 1H), 6.71 (d, J = 11.8 Hz, 1H), 5.88 (s, 1H), 4.73 (d, J = 10.7 Hz, 1H), 3.97 (d, J = 2.5 Hz, 3H), 3.82 (td, J = 11.4, 8.3 Hz, 1H), 2.57 (t, J = 12.5 Hz, 1H), 2.32 (dd, J = 13.1, 8.2 Hz, 1H), 1.64 (s, 3H) ppm. |

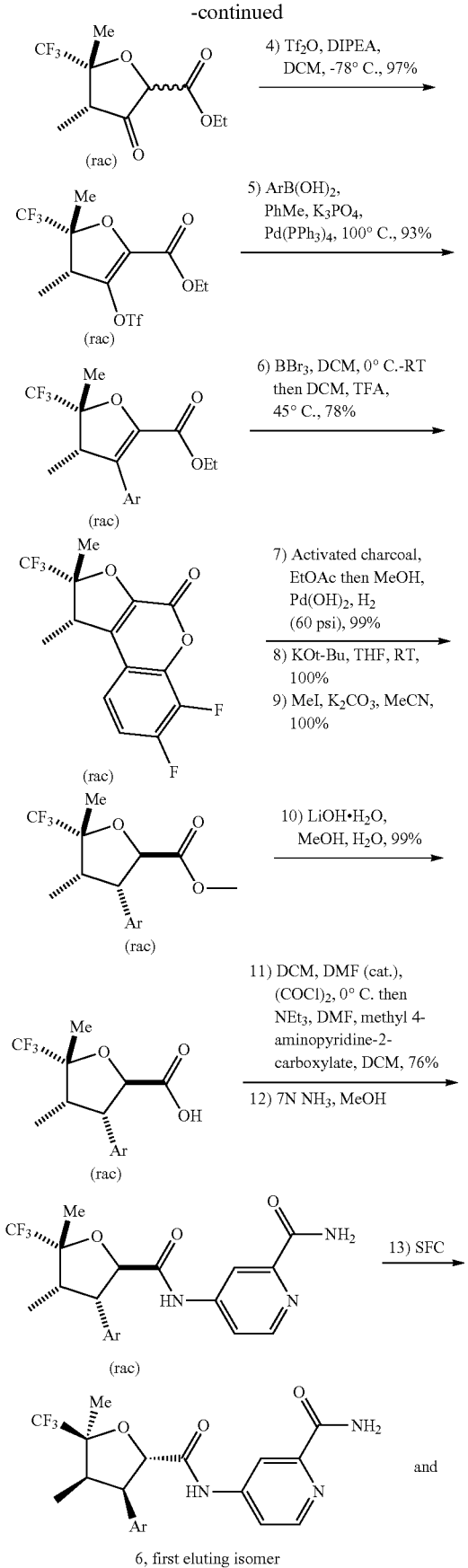

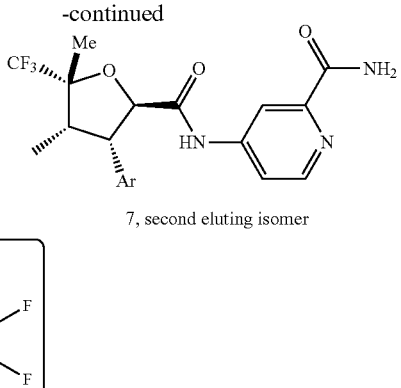

Step 1

NEt$_3$ (7.7 mL, 55.2 mmol) was added to a solution of ethyl 2-diazo-3-oxo-pentanoate (6.69 g, 39.3 mmol) in DCM (80 mL) with stirring at 0° C. under nitrogen. Trimethylsilyl trifluoromethanesulfonate (8.5 mL, 47.0 mmol) was added dropwise over 5 mins and the mixture was stirred for a further 30 mins at 0° C. The reaction mixture was diluted with pentane (100 mL), the layers separated and the organic phase washed with dilute aqueous sodium bicarbonate (100 mL) and brine (100 mL). The organic layer was dried (MgSO$_4$), and concentrated in vacuo to give ethyl (Z)-2-diazo-3-trimethylsilyloxy-pent-3-enoate (9.4 g, 99%) as a red oil. $^1$H NMR (500 MHz, Chloroform-d) δ 5.33 (q, J=7.0 Hz, 1H), 4.25 (q, J=7.1 Hz, 2H), 1.67 (d, J=7.0 Hz, 3H), 1.29 (t, J=7.1 Hz, 3H), 0.22 (s, 9H) ppm.

Step 2:

To a solution of 1,1,1-trifluoropropan-2-one (8 mL, 89.4 mmol) in DCM (80 mL) stirring at −78° C. was added TiCl$_4$ (70 mL of 1 M in DCM, 70.00 mmol) via cannula. To the resulting solution, a solution of ethyl (Z)-2-diazo-3-trimethylsilyloxy-pent-3-enoate (36.1 g of 31.3% w/w, 46.6 mmol) in 40 mL of DCM was added dropwise over 15 mins. After 100 mins the reaction was carefully quenched with water, allowing the temperature to rise slowly, and then extracted with DCM. The combined organic layers were dried (MgSO$_4$), filtered, and concentrated in vacuo. Purification by flash chromatography (330 g SiO$_2$, 0 to 20% EtOAc in heptane) gave ethyl 2-diazo-6,6,6-trifluoro-5-hydroxy-4,5-dimethyl-3-oxo-hexanoate (8.82 g, 67%), which was stored as a solution in toluene. $^1$H NMR (500 MHz, Chloroform-d) δ 4.33 (q, J=7.1 Hz, 2H), 4.14 (q, J=7.0 Hz, 1H), 3.98 (s, 1H), 1.43 (q, J=1.2 Hz, 3H), 1.35 (t, J=7.1 Hz, 3H), 1.31 (dq, J=7.0, 1.4 Hz, 3H) ppm. ESI-MS m/z calc. 282.08273, found 283.1 (M+1)$^+$; 281.0 (M−1)$^-$.

Step 3

A solution of rhodium tetraacetate (245 mg, 0.55 mmol) in benzene (32 mL) was heated at reflux for 10 min before a solution of ethyl 2-diazo-6,6,6-trifluoro-5-hydroxy-4,5-dimethyl-3-oxo-hexanoate (10 g, 35.4 mmol) in benzene (13 mL) was added slowly via addition funnel while refluxing for 60 mins. The mixture was then concentrated in vacuo to give ethyl rac-(4R,5R)-4,5-dimethyl-3-oxo-5-(trifluoromethyl)tetrahydrofuran-2-carboxylate (9.0 g, 100%) as a green coloured residue containing residual catalyst, and as a mixture of epimers at the position next to the ester. This material was used without further purification. $^1$H NMR (500 MHz, Chloroform-d) δ 4.83-4.57 (m, 1H), 4.38-4.16 (m, 2H), 2.60 (dddd, J=9.3, 8.2, 5.6, 1.4 Hz, 1H), 1.73-1.63 (m, 3H), 1.30 (t, J=7.1 Hz, 3H), 1.24 (ddq, J=6.4, 4.1, 1.9 Hz, 3H) ppm.

Step 4

To a stirred solution of ethyl rac-(4R,5R)-4,5-dimethyl-3-oxo-5-(trifluoromethyl)tetrahydrofuran-2-carboxylate (48 g, 188.83 mmol) in DCM (400 mL) stirring at −78° C. was added DIPEA (29.680 g, 40 mL, 229.64 mmol). A solution of trifluoromethylsulfonyl trifluoromethanesulfonate (53.440 g, 32 mL, 189.41 mmol) in DCM (200 mL) was added to the reaction mixture at the same temperature over 1 h. The reaction mixture was stirred for 30 mins at 0° C. before being quenched with 100 mL saturated aqueous NaHCO$_3$ solution. The organic layer was separated and aqueous layer extracted with DCM (160 mL). The combined organic layers were dried (MgSO$_4$) and concentrated in vacuo to give ethyl rac-(4R,5R)-2,3-dimethyl-2-(trifluoromethyl)-4-(trifluoromethylsulfonyloxy)-3H-furan-5-carboxylate (71 g, 97%). $^1$H NMR (400 MHz, Chloroform-d) δ 4.38-4.32 (m, 2H), 3.29-3.23 (m, 1H), 1.64 (s, 3H), 1.37-1.33 (m, 6H) ppm.

Step 5

To stirred a solution of ethyl rac-(4R,5R)-2,3-dimethyl-2-(trifluoromethyl)-4-(trifluoromethylsulfonyloxy)-3H-furan-5-carboxylate (26 g, 67.311 mmol) in toluene (130.00 mL) was added (3,4-difluoro-2-methoxy-phenyl)boronic acid (14 g, 74.5 mmol) followed by K$_3$PO$_4$ (100 mL of 2 M, 200.00 mmol) under an argon atmosphere. The reaction was degassed before tetrakis(triphenylphosphine)palladium(0) (4 g, 3.46 mmol) was added. After further degassing, the reaction was heated at 100° C. for 2 hours. The reaction was diluted in water and the aqueous layer extracted with EtOAc (2×100 mL). The combined organic layers were concentrated in vacuo. Purification by flash chromatography (SiO$_2$, 0 to 10% EtOAc in heptane) gave ethyl 4-(3,4-difluoro-2-methoxy-phenyl)-2,3-dimethyl-2-(trifluoromethyl)-3H-furan-5-carboxylate (24.4 g, 93%) as a 6:1 diastereomeric mixture, with the major isomer believed to be ethyl rac-(4R,5R)-4-(3,4-difluoro-2-methoxy-phenyl)-2,3-dimethyl-2-(trifluoromethyl)-3H-furan-5-carboxylate. Major isomer: $^1$H NMR (400 MHz, Chloroform-d) δ 6.88-6.79 (m, 2H), 4.17-4.09 (m, 2H), 3.90 (s, 3H), 3.46 (q, J=7.4 Hz, 1H), 1.67 (s, 3H), 1.12 (t, J=7.4 Hz, 3H), 1.06 (dd, J=5.4, 2.7 Hz, 3H) ppm. Minor isomer $^1$H NMR (400 MHz, Chloroform-d) δ 6.88-6.79 (m, 2H), 4.17-4.09 (m, 2H), 3.88 (s, 3H), 3.76-3.71 (m, 1H), 1.51 (s, 3H), 1.12 (t, J=7.4 Hz, 3H), 0.99 (dd, J=5.4, 2.7 Hz, 3H) ppm. ESI-MS m/z calc. 380.1047, found 381.02 (M+1)$^+$.

Step 6

To an ice-cooled solution of ethyl 4-(3,4-difluoro-2-methoxy-phenyl)-2,3-dimethyl-2-(trifluoromethyl)-3H-furan-5-carboxylate (110 g, 243.0 mmol) in DCM (360 mL) was added BBr$_3$ (370 mL of 1 M, 370.0 mmol) dropwise. Upon completion the mixture was quenched by addition of water and aqueous sodium bicarbonate solution, the aqueous layer extracted with DCM and the combined organic layers dried (MgSO$_4$) and concentrated in vacuo. The residue was dissolved in DCM (430 mL) at ambient temperature and TFA (40 mL, 519.2 mmol) was added, then the reaction was heated to 45° C. Upon completion, the mixture was quenched by addition of aqueous sodium bicarbonate solution and the aqueous layer extracted with DCM, dried (MgSO$_4$) and concentrated in vacuo to give the desired product in a 5:1 mixture of diastereomers. Recrystallization was carried out by solubilizing the crude in the smallest possible amount of DCM and adding a layer of heptane on top of this solution (liquid-liquid diffusion). After approx. 1 hour, 56.5 g (d.r. 97:3 syn:anti) from the first and second crystallization was obtained, and a further 4.6 g (d.r. 96:4 syn:anti) from the third crystallization was obtained. The first to third batches were combined to give 6,7-difluoro-1,2-dimethyl-2-(trifluoromethyl)-1H-furo[2,3-c]chromen-4-one (61 g, 78%), with the major isomer believed to be rac-(1S,2R)-6,7-difluoro-1,2-dimethyl-2-(trifluoromethyl)-1H-furo[2,3-c]chromen-4-one. ESI-MS m/z calc. 320.04718, found 321.5 (M+1)$^+$; 319.6 (M−1)$^−$.

Step 7 rac-(1S,2R)-6,7-Difluoro-1,2-dimethyl-2-(trifluoromethyl)-1H-furo[2,3-c]chromen-4-one (30 g, 93.69 mmol) was dissolved in EtOAc (400 mL) and stirred with activated charcoal (6 g, 499.6 mmol) (0.2 g/g of substrate) at ambient temperature for 4 hours and 30 minutes. The mixture was filtered through a pad of celite, washing with EtOAc. The filtrate was concentrated in vacuo to give a white solid. The white solid was suspended in MeOH (600 mL) and added to a suspension of Pd(OH)$_2$ (13.62 g of 20% w/w, 19.40 mmol) in MeOH (150 mL) in a 2.25 L Parr bottle. The resulting mixture was shaken in the Parr hydrogenator under a hydrogen pressure of 60 psi overnight. The suspension was filtered through celite under a nitrogen atmosphere, rinsed with MeOH and then with EtOAc, and the resulting filtrate was concentrated in vacuo to give methyl rac-(2R,3S,4S,5R)-3-(3,4-difluoro-2-hydroxy-phenyl)-4,5-dimethyl-5-(trifluoromethyl)tetrahydrofuran-2-carboxylate (32.75 g, 99%). $^1$H NMR (400 MHz, Methanol-d4) δ 7.05 (ddq, J=9.4, 5.9, 1.9 Hz, 1H), 6.57 (ddd, J=10.0, 9.0, 7.6 Hz, 1H), 5.01 (d, J=6.0 Hz, 1H), 4.34 (dd, J=8.4, 6.0 Hz, 1H), 3.49 (s, 3H), 3.01-2.86 (m, 1H), 1.50 (q, J=1.2 Hz, 3H), 0.89 (dq, J=7.6, 1.9 Hz, 3H) ppm. ESI-MS m/z calc. 354.08905, found 353.3 (M−1)$^−$.

Step 8

A solution of methyl rac-(2R,3S,4S,5R)-3-(3,4-difluoro-2-hydroxy-phenyl)-4,5-dimethyl-5-(trifluoromethyl)tetrahydrofuran-2-carboxylate (60.8 g, 171.6 mmol) in THF (620 mL) was cooled to 1° C., and potassium tert-butoxide (65.0472 g, 579.7 mmol) was added over 10 mins, keeping the internal temperature below 10° C. The mixture was stirred at 0° C. for a further 5 min, and then the mixture was warmed slightly. When the temperature had reached 13° C., the reaction was cooled down again with an ice bath before adding 2 M HCl (365 mL, to pH 1), keeping the internal temperature below 15° C. Water (300 mL) was added, the layers were separated, and the aqueous layer was extracted with EtOAc (110 mL). The combined organic extracts were washed with brine (300 mL), dried (MgSO$_4$), filtered and concentrated in vacuo to give rac-(2R,3S,4S,5R)-3-(3,4-difluoro-2-hydroxy-phenyl)-4,5-dimethyl-5-(trifluoromethyl)tetrahydrofuran-2-carboxylic acid (58.22 g, 100%). $^1$H NMR (400 MHz, Methanol-d$_4$) δ 7.00 (ddd, J=8.4, 5.6, 2.3 Hz, 1H), 6.69 (ddd, J=10.1, 8.8, 7.5 Hz, 1H), 4.98 (d, J=10.5 Hz, 1H), 4.18 (dd, J=10.5, 7.6 Hz, 1H), 2.83 (p, J=7.5 Hz, 1H), 1.59 (q, J=1.2 Hz, 3H), 0.76 (dq, J=7.2, 2.2 Hz, 3H) ppm. ESI-MS m/z calc. 340.0734, found 339.0 (M−1)⁻.

Step 9

To a solution of rac-(2R,3S,4S,5R)-3-(3,4-difluoro-2-hydroxy-phenyl)-4,5-dimethyl-5-(trifluoromethyl)tetrahydrofuran-2-carboxylic acid (58.39 g, 171.6 mmol) in acetonitrile (300 mL) was added K₂CO₃ (82.6 g, 597.7 mmol) and MeI (37 mL, 594.3 mmol). The reaction was heated to 80° C. (internally temperature reached 61° C.) for 5 hours before being cooled to ambient temperature and diluted with DCM (350 mL). The mixture was filtered, washing the filter cake with more DCM (350 mL) and the filtrate was concentrated in vacuo to give methyl rac-(2R,3S,4S,5R)-3-(3,4-difluoro-2-methoxy-phenyl)-4,5-dimethyl-5-(trifluoromethyl)tetrahydrofuran-2-carboxylate (64.7 g, 100%) as an orange oil containing some residual K₂CO₃. This material was used in the next step without further purification. ¹H NMR (400 MHz, Chloroform-d) δ 6.91 (ddd, J=7.6, 5.7, 1.9 Hz, 1H), 6.85 (td, J=9.1, 7.2 Hz, 1H), 4.91 (d, J=10.2 Hz, 1H), 4.13 (dd, J=10.2, 8.0 Hz, 1H), 4.00 (d, J=2.7 Hz, 3H), 3.71 (s, 3H), 2.72 (p, J=7.7 Hz, 1H), 1.62 (q, J=1.2 Hz, 3H), 0.76 (dq, J=7.5, 2.4 Hz, 3H) ppm.

Step 10

Methyl rac-(2R,3S,4S,5R)-3-(3,4-difluoro-2-methoxy-phenyl)-4,5-dimethyl-5-(trifluoromethyl)tetrahydrofuran-2-carboxylate (63.2 g, 171.6 mmol) was dissolved in MeOH (500 mL) and water (300 mL). LiOH—H₂O (14.8882 g, 354.8 mmol) was added and the resultant mixture stirred at ambient temperature for 2 hours. The MeOH was removed in vacuo and the mixture was diluted in MTBE (320 mL). 2 M HCl (440 mL) was added to reach pH 1, the layers were separated and the aqueous layer extracted twice with MTBE (100 mL). The combined organic layers were dried (MgSO₄), filtered and concentrated in vacuo to give rac-(2R,3S,4S,5R)-3-(3,4-difluoro-2-methoxy-phenyl)-4,5-dimethyl-5-(trifluoromethyl)tetrahydrofuran-2-carboxylic acid (60.3 g, 99%) as an orange oil. ¹H NMR (400 MHz, DMSO-d₆) δ 12.96 (s, 1H), 7.40-6.82 (m, 2H), 4.96 (dd, J=15.5, 10.5 Hz, 1H), 4.08 (dd, J=10.4, 7.6 Hz, 1H), 3.93 (d, J=2.2 Hz, 3H), 2.67 (p, J=7.7 Hz, 1H), 1.59-1.49 (m, 3H), 0.77-0.63 (m, 3H) ppm. ESI-MS m/z calc. 354.08905, found 353.1 (M−1)⁻.

Step 11

To a solution of rac-(2R,3S,4S,5R)-3-(3,4-difluoro-2-methoxy-phenyl)-4,5-dimethyl-5-(trifluoromethyl)tetrahydrofuran-2-carboxylic acid (158.6 g, 447.7 mmol) and DMF (135 μL, 1.74 mmol) in DCM (1.5 L) stirring at 0° C. under nitrogen was added oxalyl chloride (79 mL, 905.6 mmol) via dropping funnel, over 30 mins. Halfway through addition the ice bath was removed and the mixture allowed to warm ambient temperature over the remainder of the addition. The mixture was stirred at ambient temperature for a further 1 hour before being evaporated in vacuo. The residue was dissolved in DCM (700 mL) and added via dropping funnel to a solution of methyl 4-aminopyridine-2-carboxylate (81.5 g, 535.7 mmol), DMF (135 μL, 1.744 mmol) and Et₃N (95 mL, 681.6 mmol) in DCM (780 mL) stirring at −10° C. The rate of addition was controlled so as to keep internal temperature below 5° C. (15 mins). Following addition, the mixture was diluted in water (600 mL), the layers were separated and the aqueous phase was further extracted with DCM (100 mL). Solid formed at the interface between the layers and was collected by filtration to provide filtered desired product (43.2 g). The filtrate was washed further with water (600 mL), dried (MgSO₄), filtered and concentrated in vacuo. The residue was suspended in MeOH (360 mL) and stirred rapidly for 20 mins. The mixture was filtered and the solid washed with MeOH and dried under vacuum for 30 mins. This material was combined with the previously obtained product to give methyl rac-(2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxylate (166.2 g, 76%) as a white solid. H NMR (500 MHz, DMSO-d₆) δ 10.74 (s, 1H), 8.57 (d, J=5.4 Hz, 1H), 8.36 (d, J=2.0 Hz, 1H), 7.85 (dd, J=5.5, 2.2 Hz, 1H), 7.16 (qd, J=9.2, 6.3 Hz, 2H), 5.11 (d, J=10.1 Hz, 1H), 4.25 (dd, J=10.2, 7.7 Hz, 1H), 3.95 (d, J=2.0 Hz, 3H), 3.87 (s, 3H), 2.77 (p, J=7.6 Hz, 1H), 1.61 (s, 3H), 0.81-0.65 (m, 3H) ppm. ESI-MS m/z calc. 488.13705, found 489.6 (M+1)⁺; 487.6 (M−1)⁻.

Step 12

Methanolic ammonia (3 L of 7 M, 21.00 mol) was added to methyl rac-(2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxylate (166 g, 339.9 mmol) and the reaction stirred at ambient temperature overnight. The mixture was concentrated in vacuo to give rac-(2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide (173 g) as an off-white solid, which was used in the next step without further purification. ESI-MS m/z calc. 473.1374, found 474.6 (M+1)⁺; 472.6 (M−1)⁻.

Step 13 rac-(2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide (670 mg, 1.415 mmol) was purified by chiral SFC (using a (R'R) Whelk 0-1 column, 3-5 μm particle size, 5.0 cm×3.0 mm from Regis Technologies with Solvent A: liquid CO₂ [58-60 bar/40° C.; Solvent B: methanol HPLC grade with 20 mM NH₃ on a UPC2-SFC instrument from Waters Corp.) to give:

First Eluting Isomer: (2S,3R,4R,5S)-4-[[3-(3,4-difluoro-2-methoxy-phenyl)-4,5-dimethyl-5-(trifluoromethyl)tetrahydrofuran-2-carbonyl]amino]pyridine-2-carboxamide (6, 198 mg): ¹H NMR (500 MHz, Methanol-d₄) δ 8.52 (d, J=5.5 Hz, 1H), 8.30 (d, J=2.0 Hz, 1H), 7.94 (dd, J=5.5, 2.2 Hz, 1H), 7.16 (ddd, J=8.2, 5.6, 2.3 Hz, 1H), 7.02 (ddd, J=9.9, 8.9, 7.5 Hz, 1H), 5.12 (d, J=10.4 Hz, 1H), 4.37 (dd, J=10.4, 8.0 Hz, 1H), 4.03 (d, J=2.2 Hz, 3H), 2.84 (p, J=7.6 Hz, 1H), 1.70 (d, J=1.1 Hz, 3H), 0.86 (dq, J=7.4, 2.4 Hz, 3H) ppm. ESI-MS m/z calc. 473.1374, found 474.6 (M+1)⁺; 472.7 (M−1)⁻.

Second Eluting Isomer: (2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide (7, 195 mg): ¹H NMR (500 MHz, Methanol-d₄) δ 8.39 (d, J=5.5 Hz, 1H), 8.16 (d, J=2.0 Hz, 1H), 7.80 (dd, J=5.5, 2.0 Hz, 1H), 7.02 (ddd, J=8.2, 5.7, 2.4 Hz, 1H), 6.88 (ddd, J=9.9, 8.8, 7.5 Hz, 1H), 4.98 (d, J=10.4 Hz, 1H), 4.23 (dd, J=10.4, 7.9 Hz, 1H), 3.89 (d, J=2.2 Hz, 3H), 2.70 (p, J=7.6 Hz, 1H), 1.56 (d, J=1.1 Hz, 3H), 0.72 (dq, J=7.6, 2.4 Hz, 3H) ppm. ESI-MS m/z calc. 473.1374, found 474.6 (M+1)⁺; 472.8 (M−1)⁻.

The absolute stereochemistry of 6 and 7 was determined by single-crystal X-ray crystallography of 7.

Compound 7—Solid Form A

Crystallization of Compound 7 in methanol at 60° C. produced a crystalline form of Compound 7, which is referred to herein as Form A. Form A was characterized by XRPD, TGA, and DSC analysis.

The XRPD pattern of Form A is depicted in FIG. 1, and the corresponding data are summarized in the following table:

| Angle (°2θ ± 0.2) | Rel. Intensity (%) |
|---|---|
| 7.3 | 19.9 |
| 9.9 | 28.3 |
| 13.9 | 100.0 |
| 15.7 | 20.1 |
| 19.0 | 50.4 |
| 20.1 | 31.8 |
| 20.3 | 19.3 |
| 25.4 | 14.7 |

Figure 2:
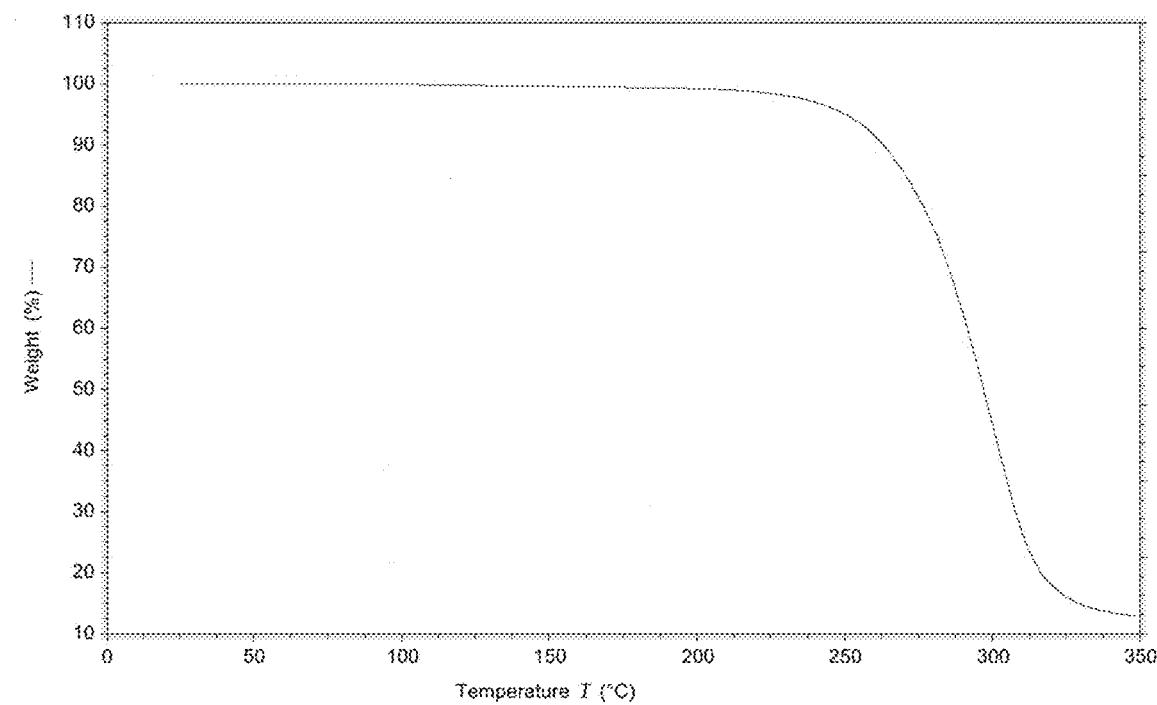
FIG. 2 depicts TGA thermogram characteristic of Compound 7, Form A.

The TGA thermogram of Form A is depicted in FIG. 2 and shows negligible weight loss from ambient temperature up until thermal degradation.

Figure 3:
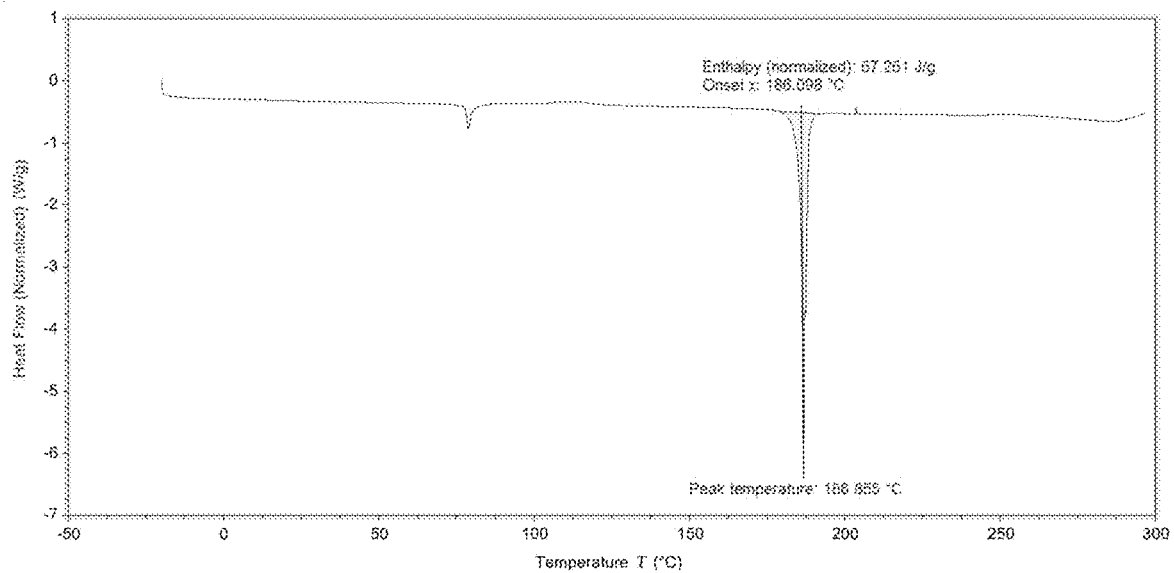
FIG. 3 depicts DSC thermogram characteristic of Compound 7, Form A.

The DSC thermogram of Form A is depicted in FIG. 3 and shows a melting onset of 186° C. with a peak at 187° C.

Compound 7—Solid Form B

Compound 7 was dissolved in ethyl acetate (6 volumes) at 68° C. The mixture was cooled to 50° C. over 1 hour, and n-heptane (6 volumes) was added over 5 hours. The mixture was then cooled to 20° C. over a further 5 hours and held overnight. The resulting solid material was filtered, washed with heptane (3 volumes), and dried to produce a crystalline form of Compound 7, which is referred to herein as Form B. Form B was characterized by XRPD, solid state NMR ($^{13}$C and $^{19}$F), TGA, DSC, IR, and single-crystal X-ray analysis.

Figure 4:
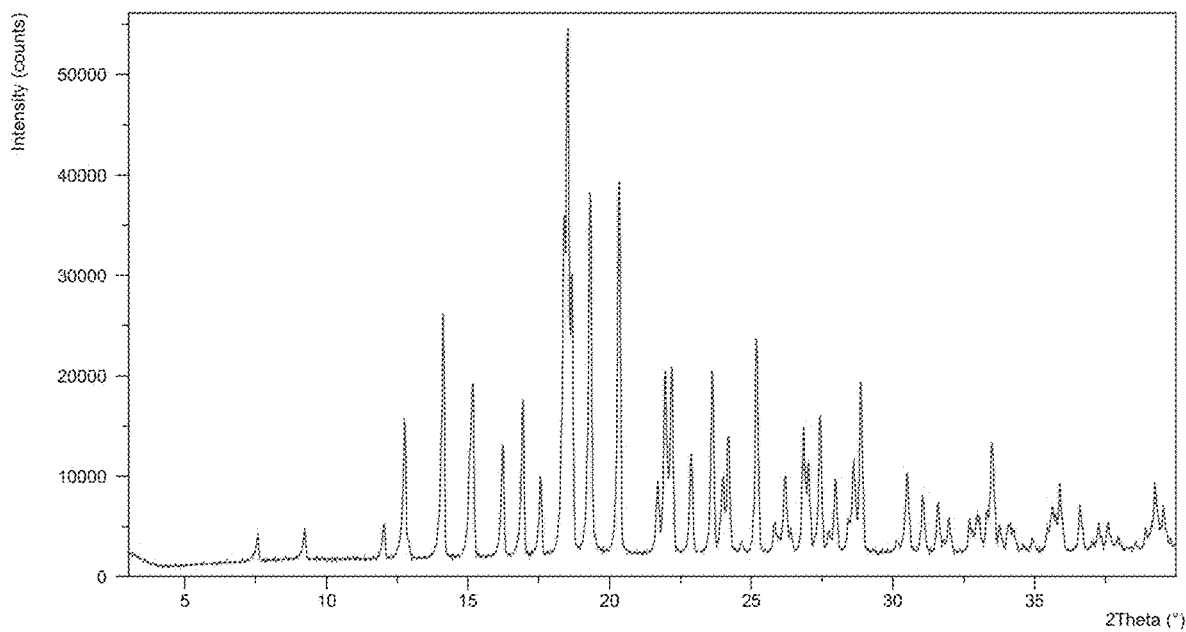
FIG. 4 depicts an XRPD pattern characteristic of Compound 7, Form B.

The XRPD pattern of Form B is depicted in FIG. 4, and the corresponding data are summarized in the following table:

| Angle (°2θ ± 0.2) | Rel. Intensity (%) |
|---|---|
| 7.6 | 11.3 |
| 9.2 | 10.5 |
| 12.0 | 10.0 |
| 12.8 | 36.7 |
| 14.1 | 59.3 |
| 15.1 | 24.0 |
| 15.2 | 39.4 |
| 16.2 | 23.9 |
| 16.9 | 31.9 |
| 17.6 | 51.1 |
| 18.4 | 63.1 |
| 18.5 | 100.0 |
| 18.7 | 51.7 |
| 19.3 | 64.2 |
| 20.3 | 64.6 |
| 21.7 | 11.6 |
| 22.0 | 29.3 |
| 22.2 | 29.7 |
| 22.9 | 15.1 |
| 23.6 | 27.3 |
| 24.0 | 10.9 |
| 24.2 | 16.8 |
| 25.2 | 30.0 |
| 26.9 | 15.6 |
| 27.0 | 10.7 |
| 27.4 | 17.0 |
| 28.6 | 10.8 |
| 28.9 | 20.9 |

Figure 5:
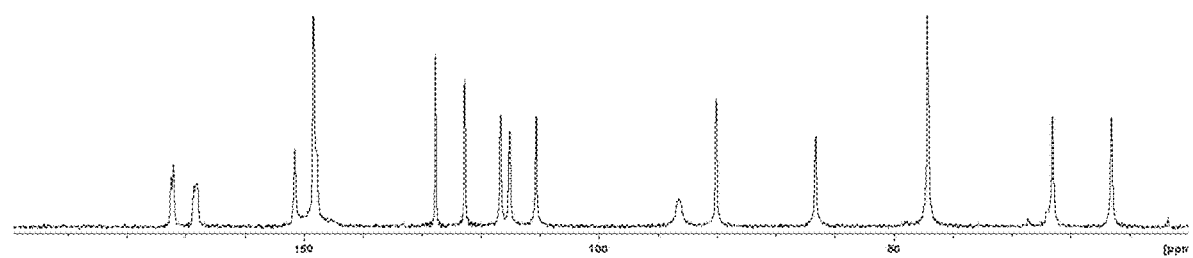
FIG. 5 depicts a solid state $^{13}$C NMR spectrum characteristic of Compound 7, Form B.

The solid state $^{13}$C NMR spectrum of Form B is depicted in FIG. 5, and the corresponding data are summarized in the following table:

| Chemical Shift [ppm] | Rel. Intensity (%) |
|---|---|
| 172.5 | 23.1 |
| 172.1 | 29.4 |
| 168.5 | 18.8 |
| 168.3 | 17.8 |
| 168.0 | 20.1 |
| 151.5 | 36.8 |
| 148.3 | 100.0 |
| 147.8 | 35.0 |
| 127.7 | 83.3 |
| 122.7 | 70.4 |
| 116.6 | 53.1 |
| 115.1 | 44.5 |
| 110.6 | 51.6 |
| 86.5 | 13.0 |
| 80.2 | 60.4 |
| 63.2 | 42.3 |
| 44.3 | 99.1 |
| 23.0 | 51.8 |
| 13.1 | 51.7 |

Figure 6:
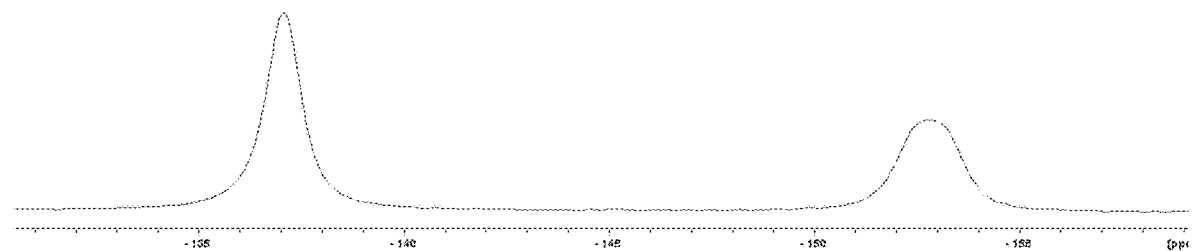
FIG. 6 depicts a solid state $^{19}$F NMR spectrum characteristic of Compound 7, Form B.

The solid state $^{19}$F NMR spectrum of Form B is depicted in FIG. 6, and the corresponding data are summarized in the following table:

| Chemical Shift [ppm] | Rel. Intensity |
|---|---|
| −137.1 | 12.5 |
| −152.8 | 5.8 |

Figure 7:
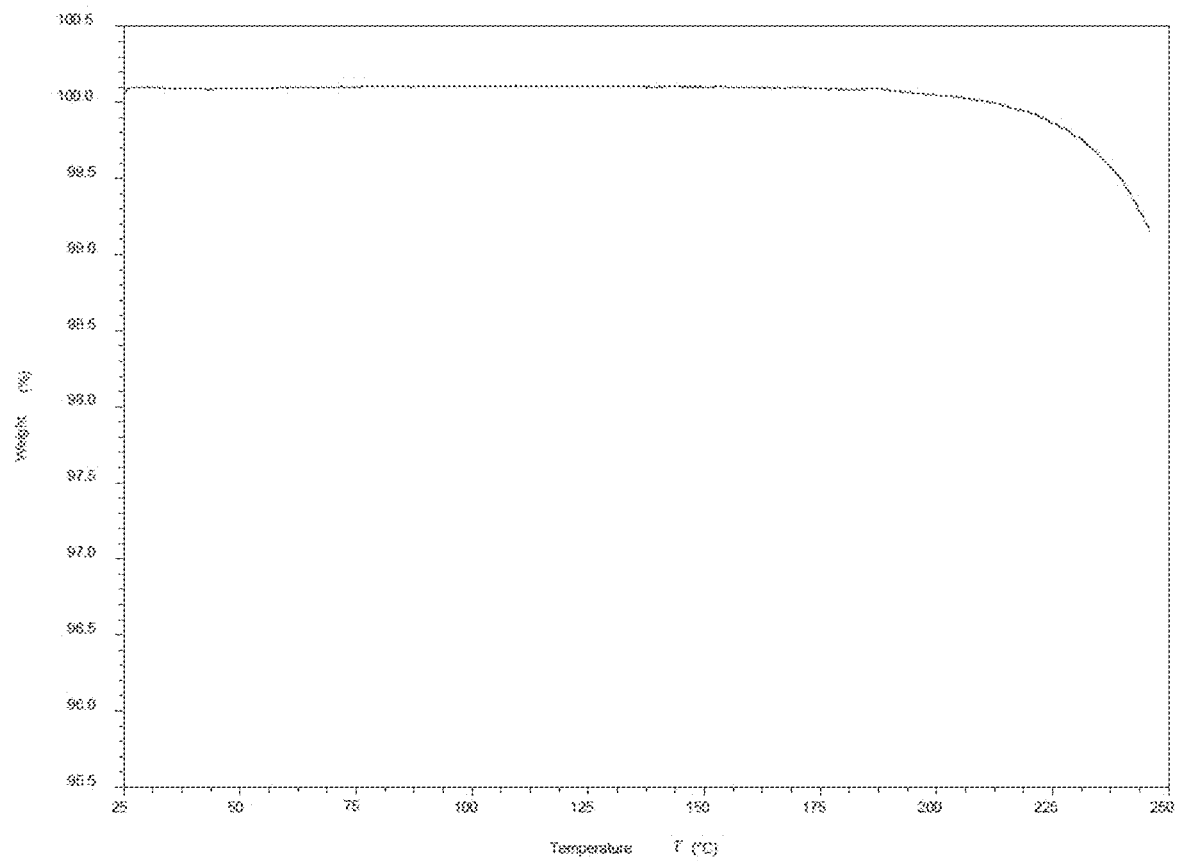
FIG. 7 depicts a TGA thermogram characteristic of Compound 7, Form B.

The TGA thermogram of Form B is depicted in FIG. 7 and shows negligible weight loss from ambient temperature up until thermal degradation.

Figure 8:
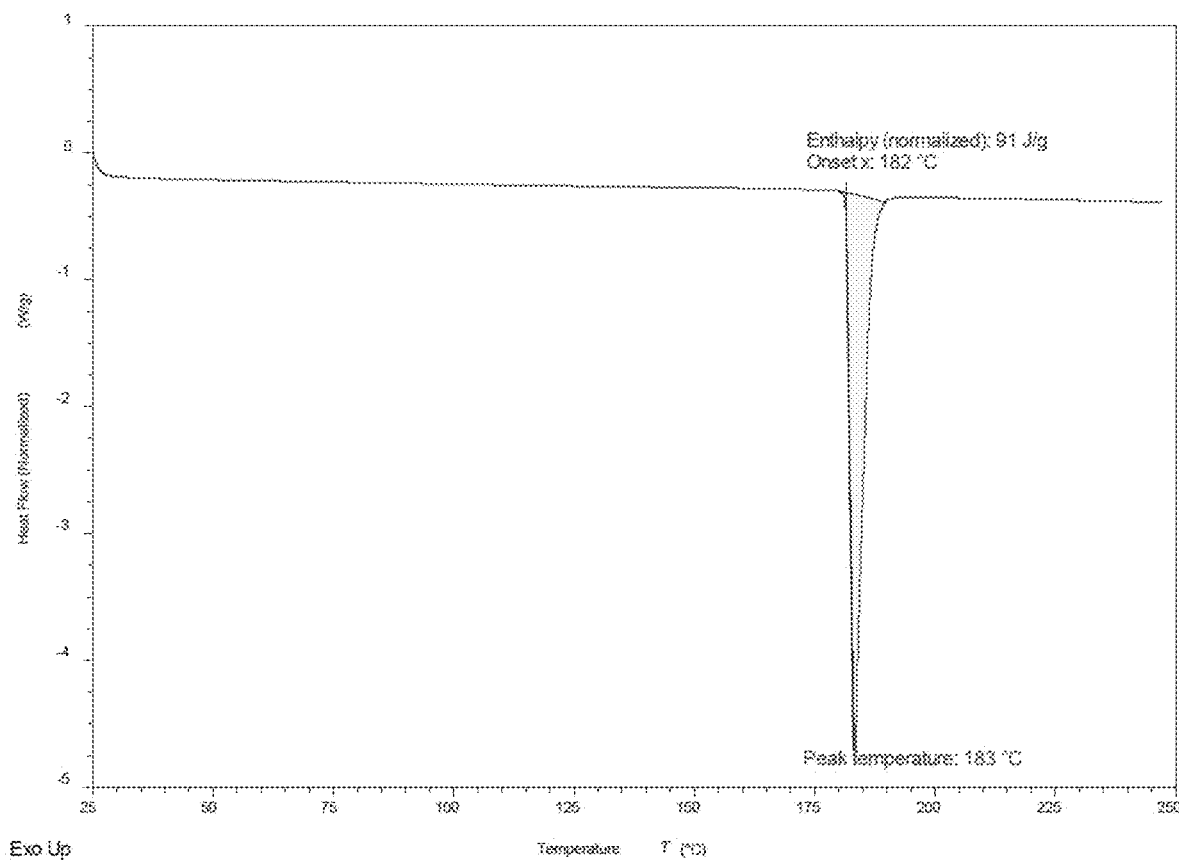
FIG. 8 depicts a DSC thermogram characteristic of Compound 7, Form B.

The DSC thermogram of Form B is depicted in FIG. 8 and shows a melting onset of 182° C. with a peak at 183° C.

Figure 9:
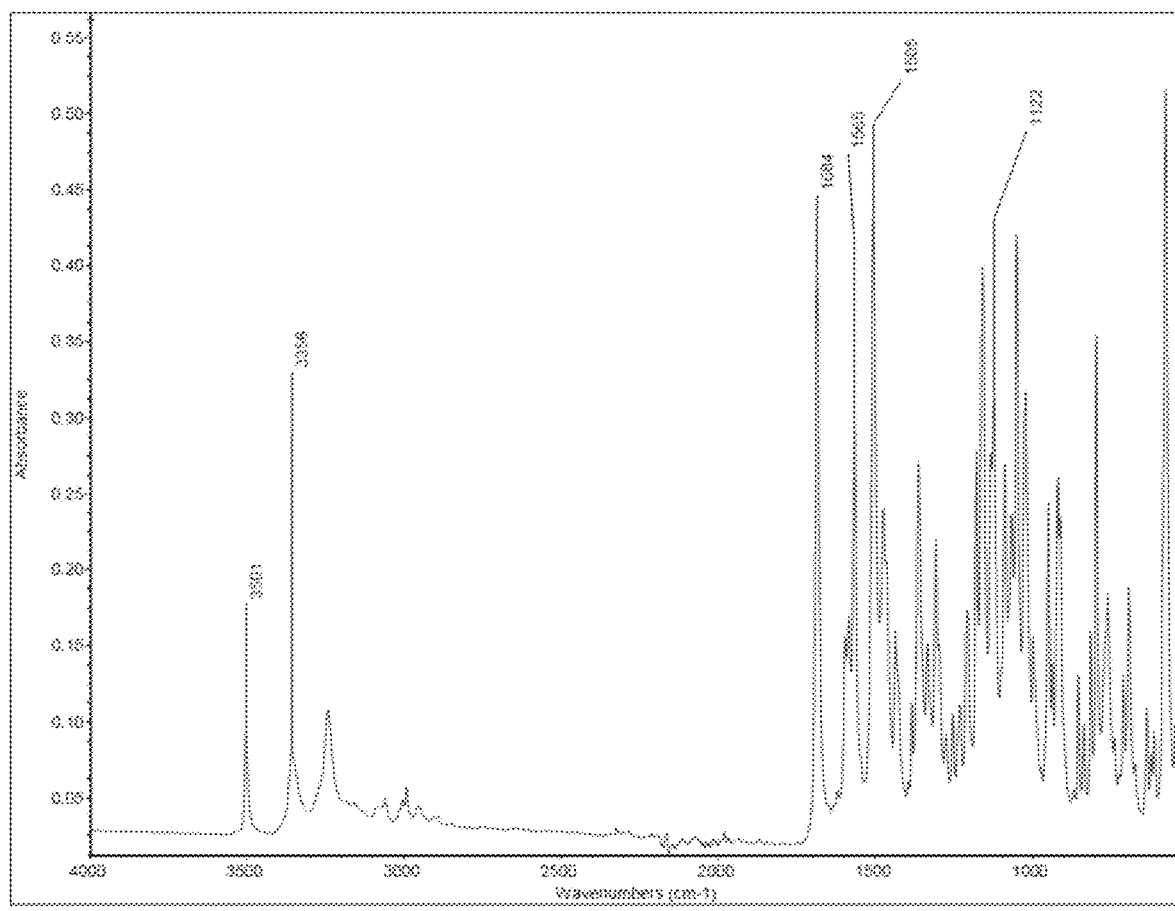
FIG. 9 depicts an IR spectrum characteristic of Compound 7, Form B.

The IR spectrum of Form B is depicted in FIG. 9 and includes peaks at 3501, 3356, 1684, 1565, 1505, and 1122 cm$^{-1}$.

Figure 10:
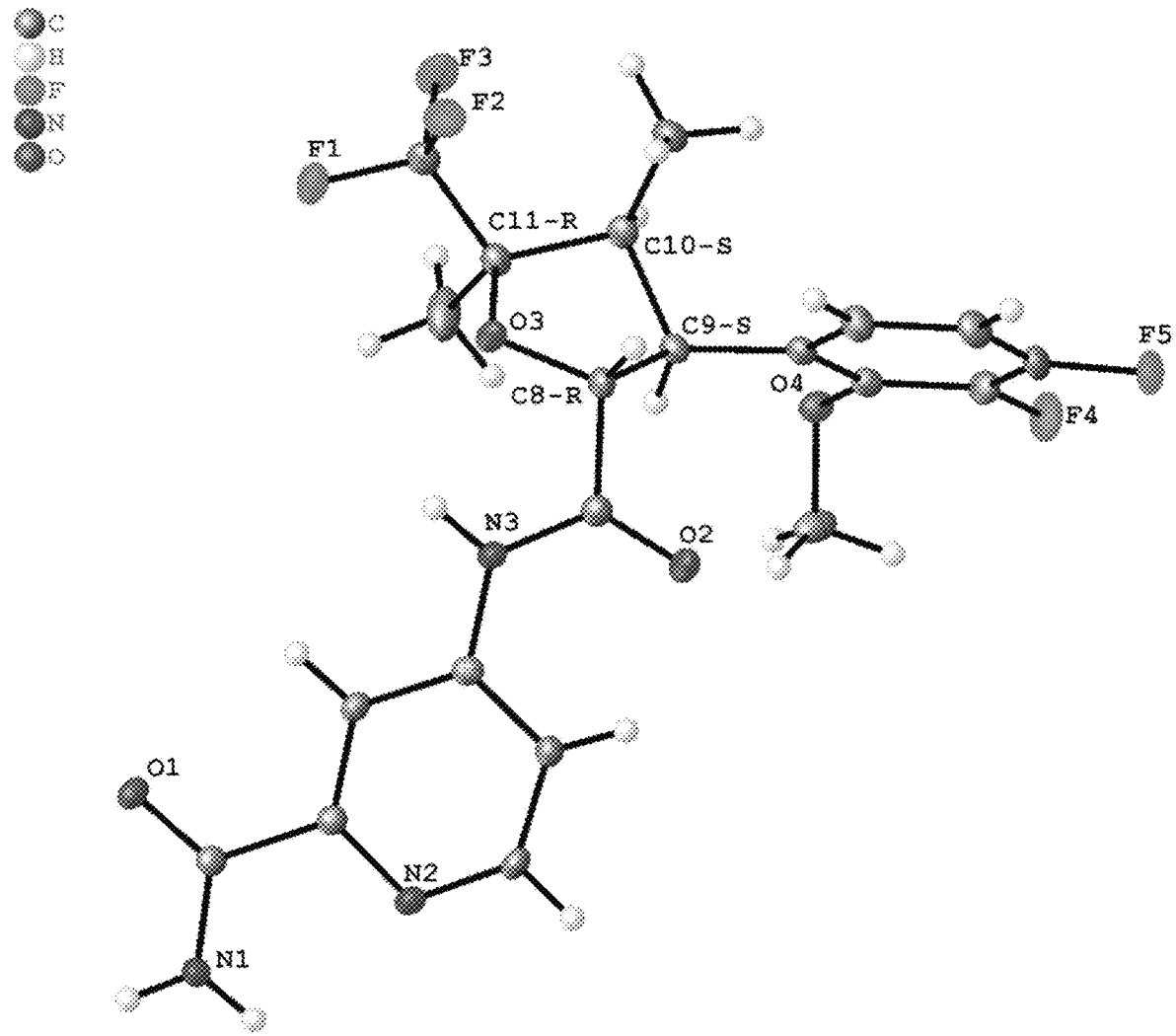
FIG. 10 depicts a thermal ellipsoid plot characteristic of Compound 7, Form B.

Crystals having Form B were grown for single-crystal X-ray analysis by dissolving 1 mg of Compound 7 material in 500 µL of ethanol, which was allowed to evaporate slowly over several days. The thermal ellipsoid plot, at 50% probability, is depicted in FIG. 10, and the unit cell parameters are reported in the following table:

| | |
|---|---|
| Crystal System: | Orthorhombic |
| Space Group: | P2$_1$2$_1$2$_1$ |
| a (Å) | 7.3929 (2) |
| b (Å) | 14.5827 (4) |
| c (Å) | 18.9312 (6) |
| α (°) | 90 |
| β (°) | 90 |
| γ (°) | 90 |
| V (Å$^3$) | 2040.94 (10) |
| Z | 4 |
| Temperature | 100K |

The following compounds were made using a similar method to that of Example 3 and were separated by chiral SFC using a (R,R)-Whelk-O1 column, 5 µm particle size, 25 cm×21.2 mm from Regis Technologies:

| Cmpd No. | Compound Name | LC/MS | NMR (shifts in ppm) |
|---|---|---|---|
| 8 | (2S,3R,4R,5S)-4-[[3-(2-ethoxy-3,4-difluoro-phenyl)-4,5-dimethyl-5-(trifluoromethyl)tetrahydrofuran-2-carbonyl]amino]pyridine-2-carboxamide (first eluting isomer by SFC, rt = 3.76 min) | ESI-MS m/z found 488.35 (M + 1)+; Retention time: 3.355 minutes | $^1$H NMR (500 MHz, DMSO-d$_6$) δ 10.73 (s, 1H), 8.50 (dd, J = 5.5, 0.6 Hz, 1H), 8.28 (dd, J = 2.2, 0.6 Hz, 1H), 8.06 (d, J = 2.8 Hz, 1H), 7.83 (dd, J = 5.5, 2.2 Hz, 1H), 7.62 (d, J = 2.8 Hz, 1H), 7.20-7.15 (m, 2H), 5.11 (d, J = 10.4 Hz, 1H), 4.30 (dd, J = 10.4, 7.5 Hz, 1H), 4.24-4.12 (m, 2H), 2.76 (p, J = 7.5 Hz, 1H), 1.62 (s, 3H), 1.36 (t, J = 7.0 Hz, 3H), 0.74 (dd, J = 7.6, 2.4 Hz, 3H) ppm. |
| 9 | (2R,3S,4S,5R)-4-[[3-(2-ethoxy-3,4-difluoro-phenyl)-4,5-dimethyl-5-(trifluoromethyl)tetrahydrofuran-2-carbonyl]amino]pyridine-2-carboxamide (second eluting isomer by SFC, rt = 8.22 min) | ESI-MS m/z found 488.35 (M + 1)+; Retention time: 3.355 minutes | $^1$H NMR (500 MHz, DMSO-d$_6$) δ 10.73 (s, 1H), 8.50 (dd, J = 5.5, 0.6 Hz, 1H), 8.28 (dd, J = 2.2, 0.7 Hz, 1H), 8.06 (d, J = 2.8 Hz, 1H), 7.83 (dd, J = 5.5, 2.2 Hz, 1H), 7.61 (d, J = 2.8 Hz, 1H), 7.20-7.14 (m, 2H), 5.11 (d, J = 10.4 Hz, 1H), 4.30 (dd, J = 10.4, 7.6 Hz, 1H), 4.24-4.12 (m, 2H), 2.76 (p, J = 7.5 Hz, 1H), 1.62 (s, 3H), 1.36 (t, J = 7.0 Hz, 3H), 0.74 (dd, J = 7.6, 2.4 Hz, 3H) ppm. |

Compound 9—Solid Form A

Figure 11:
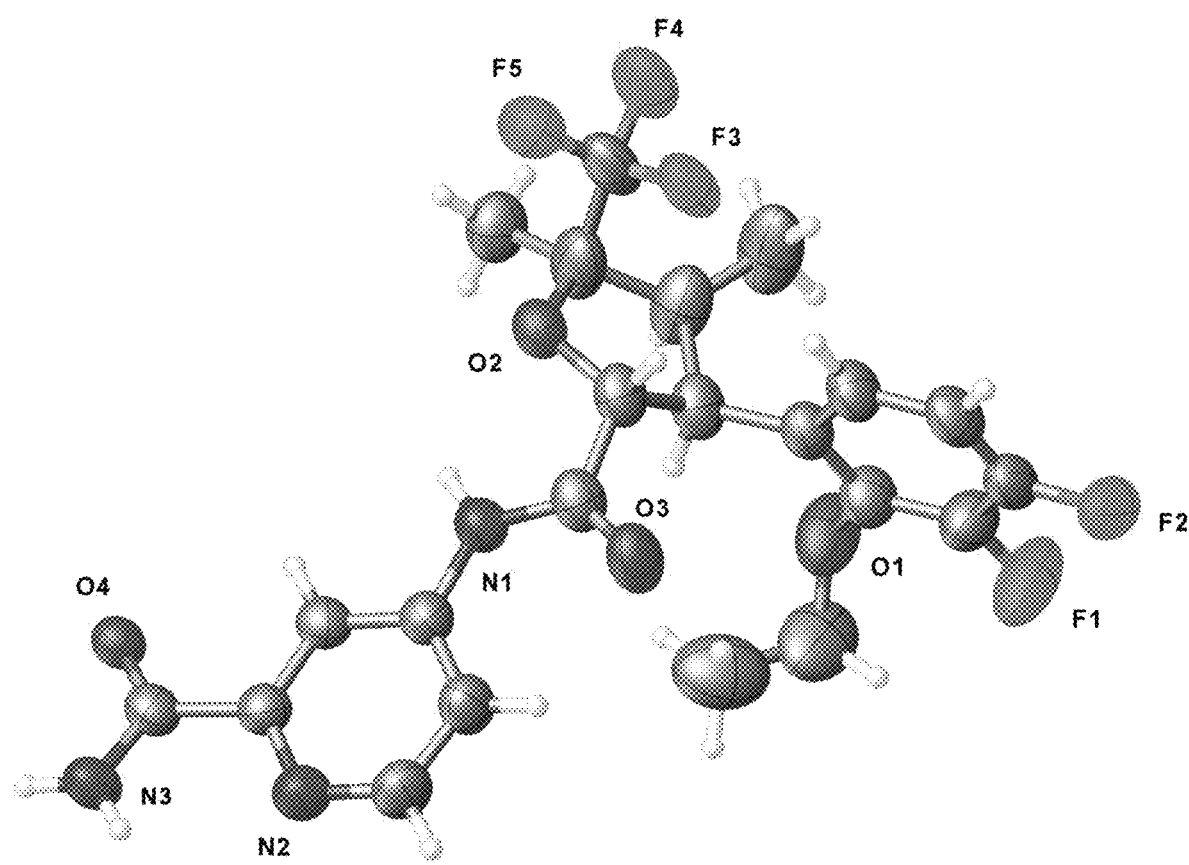
FIG. 11 depicts a thermal ellipsoid plot characteristic of Compound 9, Form A.

A crystalline form of Compound 9, referred to herein as Form A, was obtained and was characterized by single-crystal X-ray analysis. Crystals having Form A were grown for single-crystal X-ray analysis by dissolving ~1 mg of Compound 9 material in 350 μL of 10/90 dichloromethane/dichloroethane solution, which was then vapor diffused with pentane over several days. The thermal ellipsoid plot, at 50% probability, is depicted in FIG. 11, and the unit cell parameters are reported in the following table:

| | |
|---|---|
| Crystal System: | Orthorhombic |
| Space Group: | I222 |
| a (Å) | 12.0172 (5) |
| b (Å) | 15.6682 (6) |
| c (Å) | 24.1406 (11) |
| α (°) | 90 |
| β (°) | 90 |
| γ (°) | 90 |
| V (Å$^3$) | 4545.4 (3) |
| Z | 8 |
| Temperature | 100K |

The following compound was made from (2R,3S,4S,5R)-3-(3,4-difluoro-2-hydroxy-phenyl)-4,5-dimethyl-5-(trifluoromethyl)tetrahydrofuran-2-carboxylic acid, which can be obtained by separating the enantiomers of the 6,7-difluoro-1,2-dimethyl-2-(trifluoromethyl)-1H-furo[2,3-c]chromen-4-one obtained in Step 6 using the SFC conditions described in Step 1 of Example 23, and using the resulting optically pure material in steps 7 and 8 of Example 3, by a method similar to that described in Steps 9-12 of Example 3, using CD$_3$I in place of MeI in Step 9:

| Cmpd No. | Compound Name | LC/MS | NMR (shifts in ppm) |
|---|---|---|---|
| 26 | 4-[[(2R,3S,4S,5R)-3-[3,4-difluoro-2-(trideuteriomethoxy)phenyl]-4,5-dimethyl-5-(trifluoromethyl)tetrahydrofuran- | ESI-MS m/z found 477.6 (M + 1)+; Retention time: 3.24 minutes | $^1$H NMR (500 MHz, DMSO-d$_6$) δ 10.71 (s, 1H), 8.49 (d, J = 5.5 Hz, 1H), 8.28 (d, J = 2.2 Hz, 1H), 8.05 (s, 1H), 7.83 |

| Cmpd No. | Compound Name | LC/MS | NMR (shifts in ppm) |
| --- | --- | --- | --- |
| | 2-carbonyl]amino]pyridine-2-carboxamide | | (dd, J = 5.5, 2.2 Hz, 1H), 7.60 (s, 1H), 7.17 (dd, J = 9.6, 6.2 Hz, 2H), 5.10 (d, J = 10.2 Hz, 1H), 4.26 (dd, J = 10.2, 7.7 Hz, 1H), 2.78 (p, J = 7.6 Hz, 1H), 1.61 (s, 3H), 0.73 (d, J = 7.5 Hz, 3H) ppm. |

The following compounds were prepared by methods similar to the methods described herein:

| Cmpd No. | Compound Name | LC/MS | NMR (shifts in ppm) |
| --- | --- | --- | --- |
| 48 | 4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide | | $^1$H NMR (400 MHz, DMSO-$d_6$) δ 10.29 (s, 1H), 8.42 (d, J = 5.5 Hz, 1H), 8.20 (d, J = 1.5 Hz, 1H), 8.02 (br s, 1H), 7.70 (dd, J = 5.4, 1.9 Hz, 1H), 7.58 (br s, 1H), 7.24-7.17 (m, 1H), 6.99 (q, J = 9.1 Hz, 1H), 5.12 (d, J = 5.9 Hz, 1H), 4.37-4.25 (m, 1H), 3.89 (s, 3H), 2.98 (quin, J = 7.5 Hz, 1H), 1.54 (s, 3H), 0.75 (brd, J = 6.7 Hz, 3H) ppm. |
| 49 | 4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide | | $^1$H NMR (400 MHz, DMSO-$d_6$) δ 10.20 (s, 1H), 8.39 (d, J = 5.5 Hz, 1H), 8.02 (br d, J = 2.1 Hz, 1H), 7.98 (d, J = 2.0 Hz, 1H), 7.65-7.53 (m, 1H), 7.48 (dd, J = 2.2, 5.5 Hz, 1H), 7.00-6.90 (m, 2H), 4.85 (d, J = 8.9 Hz, 1H), 3.98 (d, J = 2.0 Hz, 3H), 3.93 (dd, J = 9.1, 13.0 Hz, 1H), 2.99 (br qd, J = 6.7, 12.7 Hz, 1H), 1.68 (s, 3H), 0.98 (br d, J = 6.5 Hz, 3H) ppm. |
| 50 | 4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 473.4, found 474.2 (M + H)$^+$; Retention time: 8.9 minutes | $^1$H NMR (400 MHz, Chloroform-d) δ 8.83 (s, 1H), 8.45 (d, J = 5.6 Hz, 1H), 8.19 (dd, J = 5.6, 2.3 Hz, 1H), 8.03 (dd, J = 2.2, 0.4 Hz, 1H), 7.84 (br d, J = 3.8 Hz, 1H), 6.98-6.88 (m, 2H), 5.80 (br d, J = 3.9 Hz, 1H), 4.68 (d, J = 10.6 Hz, 1H), 3.94 (d, J = 2.4 Hz, 3H), 3.41 (t, J = 11.3 Hz, 1H), 2.93-2.84 (m, 1H), 1.53 (s, 3H), 0.98 (d, J = 6.8 Hz, 3H) ppm. |

Example 4

(2S,3R,4R,5S)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (10) and (2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (11)

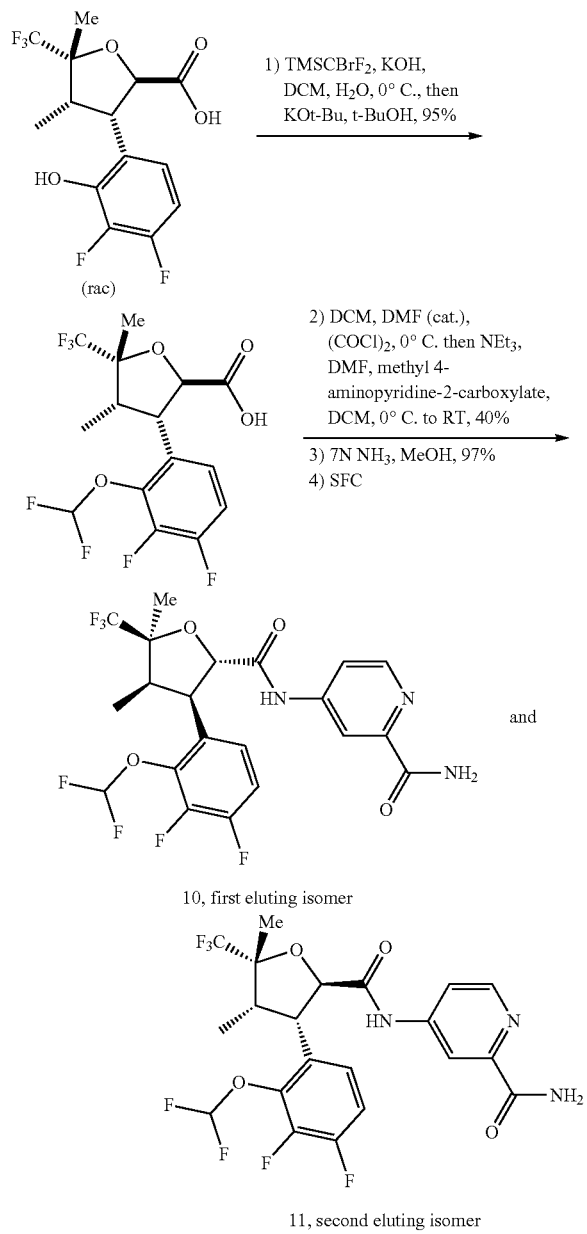

Step 1

To a solution of rac-(2R,3S,4S,5R)-3-(3,4-difluoro-2-hydroxy-phenyl)-4,5-dimethyl-5-(trifluoromethyl)tetrahydrofuran-2-carboxylic acid (9.30 g, 27.33 mmol, prepared as described in Example 3, Step 8) in DCM (50 mL) stirring at 0° C. was added a solution of KOH (18.4 g, 328.0 mmol) in $H_2O$ (50 mL) and the solution stirred vigorously. [Bromo(difluoro)methyl]-trimethyl-silane (22.5 g, 110.8 mmol) was added and stirring continued at this temperature. Upon complete consumption of starting material, the mixture was acidified by addition of 1 N HCl, extracted with DCM and concentrated in vacuo. The resultant oil was dissolved in tert-butanol (50 mL) at ambient temperature and KOt-Bu (7.5 g, 66.84 mmol) was added. After complete conversion the mixture was acidified with 1 N HCl, diluted with DCM, the layers separated and the aqueous layer extracted. The organic phase was washed with water concentrated in vacuo to give rac-(2R,3S,4S,5R)-3-[2-(difluoromethoxy)-3,4-difluoro-phenyl]-4,5-dimethyl-5-(trifluoromethyl)tetrahydrofuran-2-carboxylic acid (10.10 g, 95%) which was used without further purification.

Step 2

To an ice-cooled solution of rac-(2R,3S,4S,5R)-3-[2-(difluoromethoxy)-3,4-difluoro-phenyl]-4,5-dimethyl-5-(trifluoromethyl)tetrahydrofuran-2-carboxylic acid (10.10 g, 25.88 mmol) in DCM (100 mL) stirring at 0° C., DMF (400 μL, 5.17 mmol) and oxalyl chloride (4.85 mL, 55.60 mmol) were added. The mixture was warmed to ambient temperature over 30 min before being concentrated in vacuo. The solids were dissolved in DCM (80 mL) and DMF (400 μL, 5.17 mmol) and the solution added to an ice cooled solution of methyl 4-aminopyridine-2-carboxylate (4.05 g, 26.62 mmol) and $NEt_3$ (4.5 mL, 32.29 mmol) in DCM (80 mL). The reaction was warmed to ambient temperature over 2 hours then quenched by addition of water (1 drop) and MeOH (2 mL) and concentrated in vacuo. Purification by flash chromatography (4 g $SiO_2$, 0 to 100% EtOAc in petroleum ether) gave methyl rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxylate (5.4 g, 40%). ESI-MS m/z calc. 524.1182, found 523.6 (M−1)⁻.

Step 3

Methyl rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxylate (5.50 g, 10.49 mmol) was dissolved in MeOH (300 mL) and methanolic ammonia (300 mL of 3.37 M, 1.01 mol) and stirred at ambient temperature overnight before the reaction mixture was concentrated in vacuo to afford rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (115, 5.18 g, 97%). ¹H NMR (500 MHz, Methanol-d₄) δ 8.38 (d, J=5.6 Hz, 1H), 8.15 (d, J=2.1 Hz, 1H), 7.79 (dd, J=5.5, 2.2 Hz, 1H), 7.23-7.10 (m, 2H), 6.83 (td, J=73.1, 1.0 Hz, 1H), 4.99 (d, J=10.3 Hz, 1H), 4.27 (dd, J=10.4, 8.1 Hz, 1H), 2.73 (p, J=7.7 Hz, 1H), 1.56 (d, J=1.2 Hz, 3H), 0.78-0.72 (m, 3H) ppm. ESI-MS m/z calc. 509.11856, found 510.5 (M+1)⁺; 508.6 (M−1)⁻.

Step 4

Purification of rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (82 mg, 0.1562 mmol) by chiral SFC [System: (R,R)-Whelk-O1 column, 5 μm particle size, 25 cm×21.2 mm from Regis Technologies, MeOH, 20 mM $NH_3$] gave:

First Eluting Isomer: (2S,3R,4R,5S)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (10, 23 mg). $^1$H NMR (500 MHz, Methanol-d$_4$) δ 8.53 (d, J=5.5 Hz, 1H), 8.30 (dd, J=2.2, 0.6 Hz, 1H), 7.93 (dd, J=5.5, 2.2 Hz, 1H), 7.40-7.23 (m, 2H), 6.97 (td, J=73.1, 1.0 Hz, 1H), 5.14 (d, J=10.4 Hz, 1H), 4.41 (dd, J=10.3, 8.1 Hz, 1H), 2.87 (p, J=7.7 Hz, 1H), 1.71 (d, J=1.3 Hz, 3H), 0.94-0.81 (m, 3H) ppm. ESI-MS m/z calc. 509.11856, found 510.4 (M+1)$^+$; 508.4 (M−1)$^−$.

Second Eluting Isomer: (2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (11, 28 mg, 70%). $^1$H NMR (500 MHz, Methanol-d$_4$) δ 8.53 (d, J=5.5 Hz, 1H), 8.30 (dd, J=2.2, 0.6 Hz, 1H), 7.93 (dd, J=5.5, 2.2 Hz, 1H), 7.40-7.23 (m, 2H), 6.97 (td, J=73.1, 1.0 Hz, 1H), 5.14 (d, J=10.4 Hz, 1H), 4.41 (dd, J=10.3, 8.1 Hz, 1H), 2.87 (p, J=7.7 Hz, 1H), 1.71 (d, J=1.3 Hz, 3H), 0.94-0.81 (m, 3H) ppm. ESI-MS m/z calc. 509.11856, found 510.4 (M+1)$^+$, 508.4 (M−1)$^−$.

The absolute stereochemistry of 10 and 11 was determined by single-crystal X-ray crystallography of 11.

Compound 11—Solid Form A

Compound 11 was suspended in distilled water, the suspension was stirred at 37° C. for 24 hours, at which time the suspension was filter-centrifuged. The resulting solid was dried at 60° C. overnight in a vacuum oven to afford a crystalline form of Compound 11, which is referred to herein as Form A. Form A was characterized by XRPD analysis.

Figure 12:
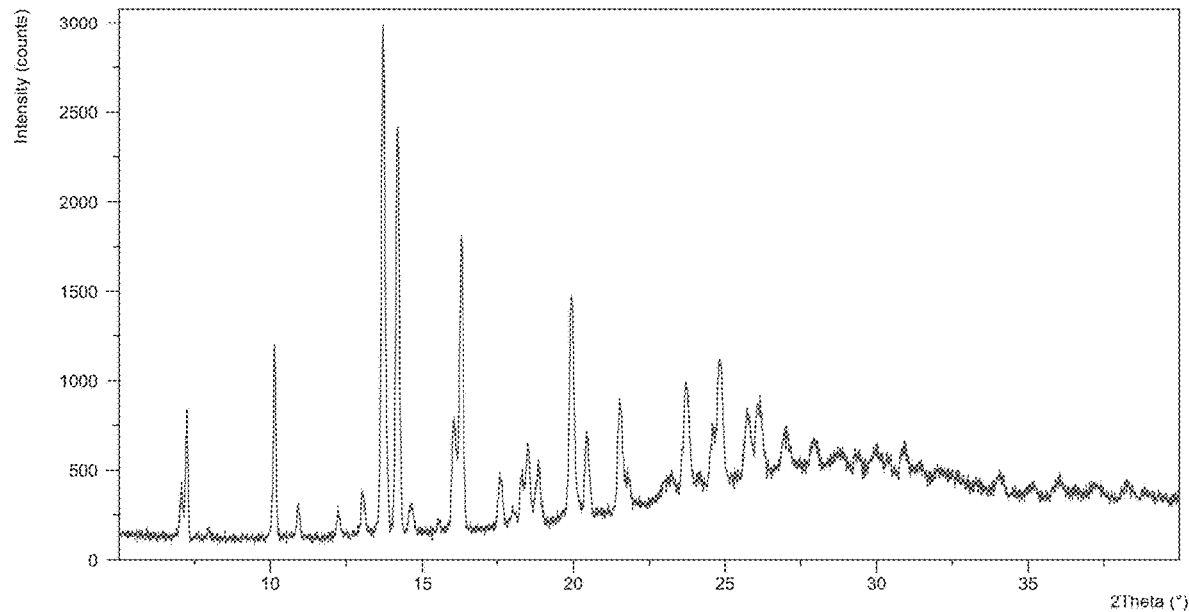
FIG. 12 depicts an XRPD pattern characteristic of Compound 11, Form A.

The XRPD pattern of Form A is depicted in FIG. 12, and the corresponding data are summarized in the following table:

| Angle (°2θ ± 0.2) | Rel. Intensity (%) |
|---|---|
| 7.1 | 12.0 |
| 7.3 | 29.0 |
| 10.1 | 43.2 |
| 13.7 | 100.0 |
| 14.1 | 76.7 |
| 16.0 | 23.0 |
| 16.3 | 65.6 |
| 17.6 | 10.3 |
| 18.5 | 17.0 |
| 18.9 | 11.5 |
| 20.0 | 46.5 |
| 20.4 | 18.5 |
| 21.5 | 15.2 |
| 23.7 | 22.9 |
| 24.8 | 27.3 |
| 25.7 | 12.7 |
| 26.1 | 13.9 |

Compound 11—Solid Form B

Compound 11 was recrystallized from acetonitrile and dried overnight to produce a crystalline form of Compound 11, which is referred to herein as Form B. Form B was characterized by XRPD and single-crystal X-ray analysis.

Figure 13:
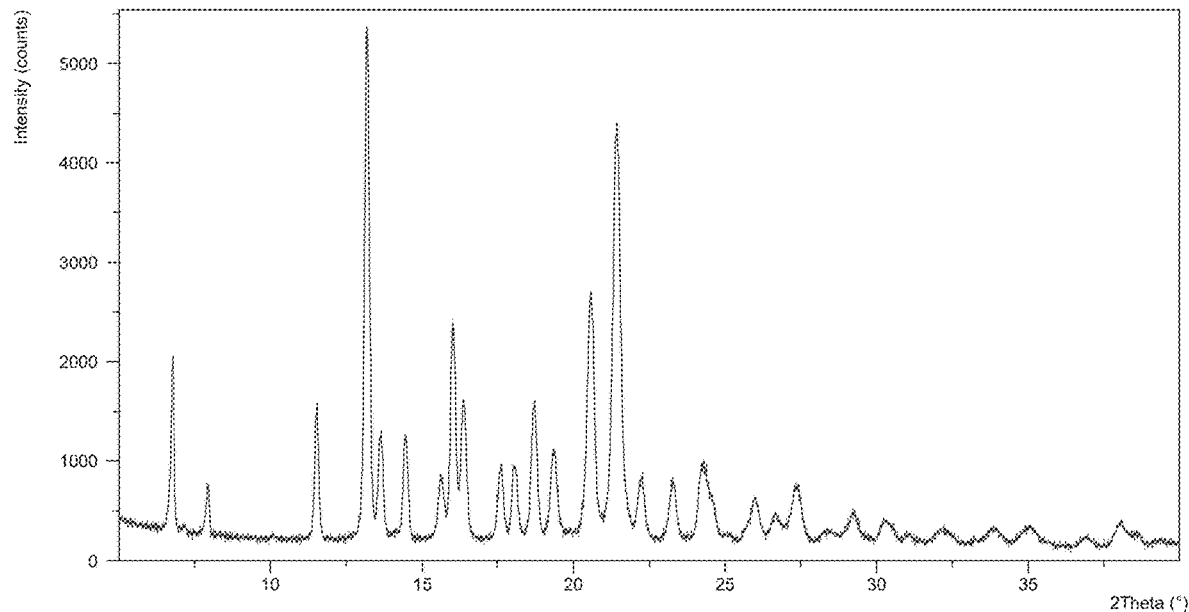
FIG. 13 depicts an XRPD pattern characteristic of Compound 11, Form B.

The XRPD pattern of Form B is depicted in FIG. 13, and the corresponding data are summarized in the following table:

| Angle (°2θ ± 0.2) | Rel. Intensity (%) |
|---|---|
| 6.8 | 36.4 |
| 11.5 | 26.7 |
| 13.2 | 100.0 |
| 13.6 | 18.3 |
| 14.4 | 19.8 |
| 15.6 | 12.0 |
| 16.1 | 40.5 |
| 16.3 | 28.2 |
| 17.6 | 14.0 |
| 18.0 | 13.2 |
| 18.8 | 23.9 |
| 19.4 | 16.6 |
| 20.6 | 48.1 |
| 21.3 | 67.5 |
| 22.3 | 11.2 |
| 23.3 | 10.8 |
| 24.2 | 12.1 |
| 27.4 | 9.8 |

Figure 14:
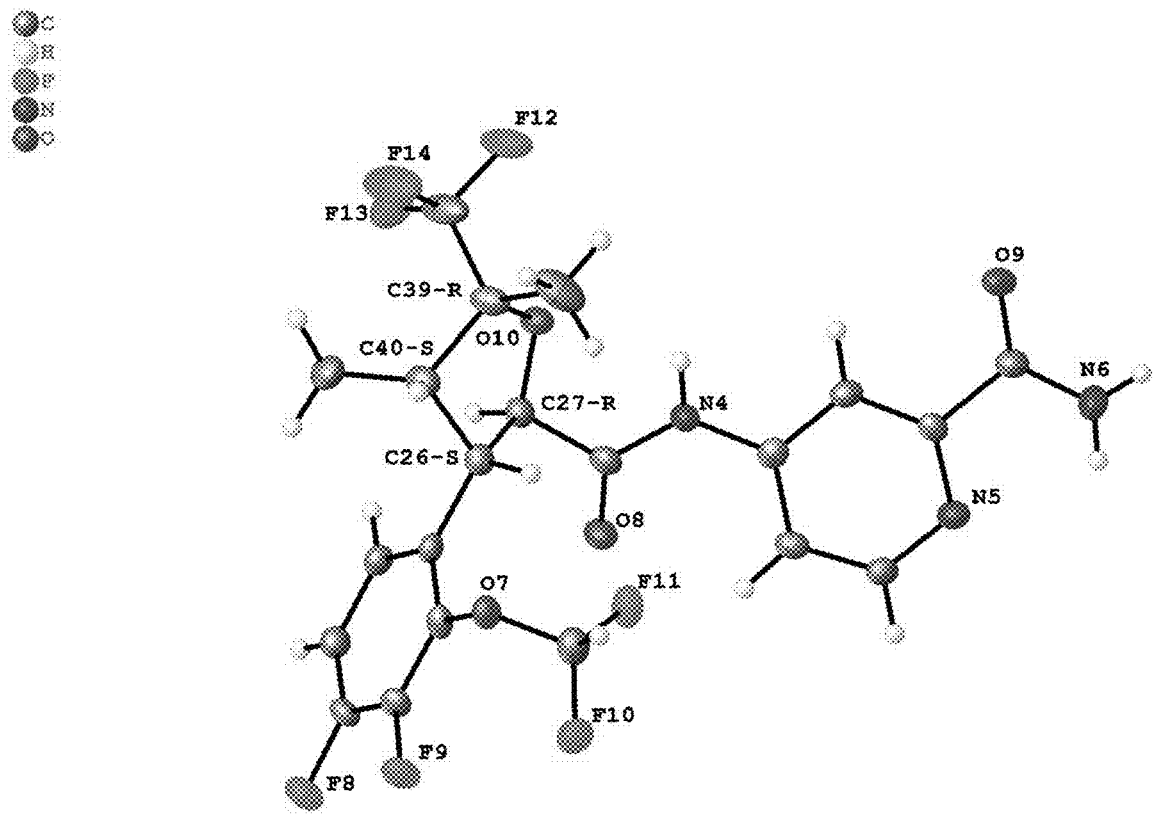
FIG. 14 depicts a thermal ellipsoid plot characteristic of Compound 11, Form A.

Crystals having Form A were grown for single-crystal X-ray analysis by concentration of a toluene solution of Compound 11. The thermal ellipsoid plot, at 50% probability, is depicted in FIG. 14, and the unit cell parameters are reported in the following table:

| Crystal System: | Monoclinic |
|---|---|
| Space Group: | P2$_1$ |
| a (Å) | 12.0863(2) |
| b (Å) | 7.48310(10) |
| c (Å) | 23.9904(4) |
| α (°) | 90 |
| β (°) | 90.0130(10) |
| γ (°) | 90 |
| V (Å$^3$) | 2169.76(6) |
| Z/Z' | 2/0.5 |
| Temperature | 100(2)K |

The following compounds were made using a method similar to that described in Example 4, except that 5-amino-2-fluorobenzamide was used in place of methyl 4-aminopyridine-2-carboxylate in Step 2, and Step 3 was omitted. In step 4, purification was performed by chiral SFC using a (R,R)-Whelk-O1 column, 5 μm particle size, 25 cm×21.2 mm from Regis Technologies:

| Cmpd No. | Compound Name | LC/MS | NMR (shifts in ppm) |
|---|---|---|---|
| 14 | rel-(2R,3S,4S,5R)-N-(3-carbamoyl-4-fluoro-phenyl)-3-[2-(difluoromethoxy)-3,4-difluoro-phenyl]-4,5-dimethyl-5-(trifluoromethyl)tetrahydrofuran-2-carboxamide (first eluting isomer by SFC) | ESI-MS m/z found 527.1 (M + 1)$^+$; Retention time: 3.23 minutes | $^1$H NMR (500 MHz, Methanol-d$_4$) δ 7.96 (dd, J = 6.5, 2.8 Hz, 1H), 7.77 (ddd, J = 9.0, 4.4, 2.8 Hz, 1H), 7.35-7.24 (m, 2H), 7.19 (dd, J = 10.5, 9.0 Hz, 1H), 6.94 (td, J = 73.1, 1.1 Hz, 1H), 5.08 (d, J = 10.5 Hz, 1H), 4.36 (dd, J = 10.5, 8.0 Hz, 1H), 2.83 (p, J = 7.6 Hz, 1H), 1.73-1.65 (m, 3H), 0.87 (dq, J = 7.4, 2.3 Hz, 3H) ppm. |

-continued

| Cmpd No. | Compound Name | LC/MS | NMR (shifts in ppm) |
|---|---|---|---|
| 15 | rel-(2R,3S,4S,5R)-N-(3-carbamoyl-4-fluoro-phenyl)-3-[2-(difluoromethoxy)-3,4-difluoro-phenyl]-4,5-dimethyl-5-(trifluoromethyl)tetrahydrofuran-2-carboxamide (second eluting isomer by SFC) | ESI-MS m/z found 527.1 (M + 1)$^+$; Retention time: 3.23 minutes | $^1$H NMR (500 MHz, Methanol-d$_4$) δ 7.97 (dd, J = 6.5, 2.8 Hz, 1H), 7.78 (ddd, J = 9.0, 4.4, 2.8 Hz, 1H), 7.37-7.24 (m, 2H), 7.20 (dd, J = 10.5, 9.0 Hz, 1H), 6.95 (td, J = 73.1, 1.0 Hz, 1H), 5.09 (d, J = 10.5 Hz, 1H), 4.37 (dd, J = 10.5, 8.0 Hz, 1H), 2.84 (p, J = 7.7 Hz, 1H), 1.69 (d, J = 1.2 Hz, 3H), 0.88 (dt, J = 7.4, 2.4 Hz, 3H) ppm. |

The following compounds were made using a method similar to that described in Example 4, except that 3-aminobenzamide was used in place of methyl 4-aminopyridine-2-carboxylate in Step 2, and Step 3 was omitted. In step 4, purification was performed by chiral SFC using a Lux Cellulose-2 column, 5 μm particle size, 25 cm×10 mm from Phenomenex, Inc.:

| Cmpd No. | Compound Name | LC/MS | NMR (shifts in ppm) |
|---|---|---|---|
| 51 | rel-(2S,3R,4R,5S)-N-(3-carbamoylpheny1)-3-[2-(difluoromethoxy)-3,4-difluoro-phenyl]-4,5-dimethyl-5-(trifluoromethyl)tetrahydrofuran-2-carboxamide (first eluting isomer by SFC on Lux Cellulose-2 column, rt = 2.97 min) | ESI-MS m/z calc. 508.1233, found 509.1 (M + 1)$^+$; 507.2 (M − 1)$^-$; Retention time: 3.19 minutes | $^1$H NMR (500 MHz, DMSO-d$_6$) δ 10.32 (s, 1H), 8.06 (t, J = 1.9 Hz, 1H), 7.93 (s, 1H), 7.77-7.74 (m, 1H), 7.58 (dt, J = 7.8, 1.3 Hz, 1H), 7.51-7.41 (m, 1H), 7.38 (t, J = 7.9 Hz, 1H), 7.34-7.32 (m, 2H), 7.29 (t, J = 72.2 Hz, 1H), 5.12 (d, J = 10.4 Hz, 1H), 4.28 (dd, J = 10.4, 7.6 Hz, 1H), 2.76 (p, J = 7.3 Hz, 1H), 1.60 (s, 3H), 0.76 (d, J = 6.4 Hz, 3H) ppm. |
| 52 | rel-(2R,3S,4S,5R)-N-(3-carbamoylpheny1)-3-[2-(difluoromethoxy)-3,4-difluoro-phenyl]-4,5-dimethyl-5-(trifluoromethyl)tetrahydrofuran-2-carboxamide (second eluting isomer by SFC on Lux Cellulose-2 column, rt = 3.51 min) | ESI-MS m/z calc. 508.1233, found 509.1 (M + 1)$^+$; 507.2 (M − 1)$^-$; Retention time: 3.18 minutes | $^1$H NMR (500 MHz, DMSO-d$_6$) δ 8.06 (t, J = 2.0 Hz, 1H), 7.93 (s, 1H), 7.75 (ddd, J = 8.3, 2.3, 1.0 Hz, 1H), 7.58 (dt, J = 7.6, 1.3 Hz, 1H), 7.51-7.46 (m, 1H), 7.38 (t, J = 7.9 Hz, 1H), 7.35-7.31 (m, 2H), 7.29 (t, J = 71.9 Hz, 1H), 5.12 (d, J = 10.3 Hz, 1H), 4.28 (dd, J = 10.4, 7.6 Hz, 1H), 2.76 (p, J = 7.6 Hz, 1H), 1.60 (s, 3H), 0.76 (d, J = 6.2 Hz, 3H) ppm. Amide NH not observed. |

The following compound was made using a method similar to that described in Example 4, except that rac-(2R,3S,4S,5R)-3-(2-(difluoromethoxy)-4-fluoro-3-methylphenyl)-4,5-dimethyl-5-(trifluoromethyl)tetrahydrofuran-2-carboxylic acid was used as the starting material for step 2. Rac-(2R,3S,4S,5R)-3-(2-(difluoromethoxy)-4-fluoro-3-methylphenyl)-4,5-dimethyl-5-(trifluoromethyl)tetrahydrofuran-2-carboxylic acid was prepared using methods analogous to those described for other intermediates of this application. The separation of the racemates at step 4 was not carried out and the compound was isolated as a racemate:

| Cmpd No. | Compound Name | LC/MS | NMR (shifts in ppm) |
|---|---|---|---|
| 53 | rac-(2S,3R,4R,5S)-4-[[3-[2-(difluoromethoxy)-4-fluoro-3-methyl-phenyl]-4,5-dimethyl-5-(trifluoromethyl)tetrahydrofuran-2-carbonyl]amino]pyridine-2-carboxamide | ESI-MS m/z calc. 505.14362, found 506.1 (M + 1)$^+$; 504.2 (M − 1)$^-$; Retention time: 3.36 minutes | $^1$H NMR (500 MHz, DMSO-d$_6$) δ 10.70 (s, 1H), 8.49 (d, J = 5.5 Hz, 1H), 8.33-8.22 (m, 1H), 8.06 (d, J = 2.6 Hz, 1H), 7.82 (dd, J = 5.5, 2.2 Hz, 1H), 7.61 (d, J = 2.8 Hz, 1H), 7.36 (dd, J = 8.8, 6.2 Hz, 1H), 7.26-6.90 (m, 2H), 5.10 (d, J = 10.4 Hz, 1H), 4.32 (dd, J = 10.5, 7.5 Hz, 1H), 2.75 (p, J = 7.4 Hz, 1H), 2.18 (d, J = 2.0 Hz, 3H), 1.60 (s, 3H), 0.79-0.70 (m, 3H) ppm. |

The following compounds were made by separating 53 by chiral SFC (Example 4, Step 4) using a Chiralpak AS-H column, 5 μm particle size, 25 cm×10 mm from Daicel on a Minigram SFC instrument from Berger Instruments:

| Cmpd No. | Compound Name | LC/MS | NMR (shifts in ppm) |
|---|---|---|---|
| 16 | rel-(2R,3S,4S,5R)-4-[[3-[2-(difluoromethoxy)-4-fluoro-3-methyl-phenyl]-4,5-dimethyl-5-(trifluoromethyl)tetrahydrofuran-2-carbonyl]amino]pyridine-2-carboxamide (first eluting isomer by SFC) | ESI-MS m/z found 506 (M + 1)$^+$; Retention time: 3.34 minutes | $^1$H NMR (500 MHz, Chloroform-d) δ 8.60 (s, 1H), 8.46 (d, J = 5.5 Hz, 1H), 8.10 (dd, J = 5.6, 2.3 Hz, 1H), 7.94 (d, J = 2.1 Hz, 1H), 7.83 (s, 1H), 7.31 (dd, J = 8.8, 6.1 Hz, 1H), 7.06 (t, J = 8.7 Hz, 1H), 5.56 (s, 1H), 4.97 (d, J = 11.1 Hz, 1H), 4.18 (dd, J = 11.1, 8.0 Hz, 1H), 2.79 (p, J = 7.7 Hz, 1H), 2.25 (d, J = 2.2 Hz, 3H), 1.69 (d, J = 1.1 Hz, 3H), 0.86-0.79 (m, 3H) ppm. |
| 17 | rel-(2R,3S,4S,5R)-4-[[3-[2-(difluoromethoxy)-4-fluoro-3-methyl-phenyl]-4,5-dimethyl-5-(trifluoromethyl)tetrahydrofuran-2-carbonyl]amino]pyridine-2-carboxamide (second eluting isomer by SFC) | ESI-MS m/z found 507 (M + 1)$^+$; Retention time: 3.34 minutes | $^1$H NMR (500 MHz, Chloroform-d) δ 8.59 (s, 1H), 8.46 (d, J = 5.5 Hz, 1H), 8.09 (dd, J = 5.5, 2.3 Hz, 1H), 7.93 (d, J = 2.2 Hz, 1H), 7.83 (s, 1H), 7.34-7.29 (m, 1H), 5.54 (s, 1H), 4.96 (d, J = 11.1 Hz, 1H), 4.18 (dd, J = 11.2, 8.1 Hz, 1H), 2.78 (p, J = 7.7 Hz, 1H), 2.24 (d, J = 2.2 Hz, 3H), 1.69 (d, J = 1.1 Hz, 3H), 0.86-0.76 (m, 3H) ppm. |

Example 5

(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-1-oxido-pyridin-1-ium-2-carboxamide (18)

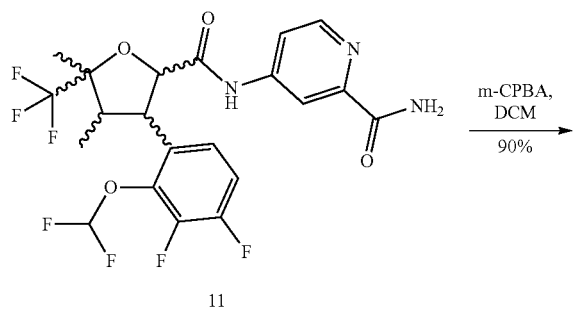

11 m-CPBA, DCM
90%

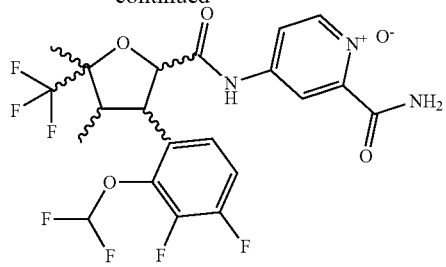

18

To a solution of (2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]pyridine-2-carboxamide (11, 35 mg, 0.06802 mmol) in DCM (1 mL) was added m-CPBA (50 mg, 0.2028 mmol) in one portion at ambient temperature. After 16 hours a further portion of m-CPBA (50 mg, 0.2028 mmol) was added and the reaction stirred for 4 days. The mixture was concentrated in vacuo and the remaining solid purified by silica gel chromatography (4 g, 0 to 100% EA in heptane) to afford (2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-1-oxido-pyridin-1-ium-2-carboxamide (18, 33 mg, 90%). $^1$H NMR (500 MHz, Methanol-$d_4$) δ 8.47 (d, J=3.2 Hz, 1H), 8.18 (d, J=7.3 Hz, 1H), 7.93 (dd, J=7.3, 3.2 Hz, 1H), 7.23-7.12 (m, 2H), 6.83 (td, J=73.1, 1.1 Hz, 1H), 5.00 (d, J=10.4 Hz, 1H), 4.26 (dd, J=10.5, 8.1 Hz, 1H), 2.72 (p, J=7.6 Hz, 1H), 1.56 (s, 3H), 0.75 (dq, J=4.7, 2.4 Hz, 3H) ppm. ESI-MS m/z calc. 525.11346, found 526.6 (M+1)$^+$; 524.7 (M−1)$^−$.

The following compounds were made using a method similar to Example 5, using 5, 7, 9, 26, and 27, respectively, as the starting materials:

| Cmpd No. | Compound Name | LC/MS | NMR (shifts in ppm) |
|---|---|---|---|
| 19 | (2R,3S,4S,5R)-4-[[3-(3,4-difluoro-2-methoxy-phenyl)-4,5-dimethyl-5-(trifluoromethyl)tetrahydrofuran-2-carbonyl]amino]-1-oxido-pyridin-1-ium-2-carboxamide | ESI-MS m/z found 490.5 (M + 1)$^+$; Retention time: 3.014 minutes | $^1$H NMR (500 MHz, DMSO-$d_6$) δ 10.79 (s, 1H), 10.58 (d, J = 4.6 Hz, 1H), 8.52 (d, J = 3.3 Hz, 1H), 8.31 (d, J = 7.2 Hz, 1H), 8.21 (d, J = 4.7 Hz, 1H), 7.87 (dd, J = 7.2, 3.3 Hz, 1H), 7.16 (dd, J = 9.7, 6.5 Hz, 2H), 5.08 (d, J = 10.2 Hz, 1H), 4.24 (dd, J = 10.2, 7.7 Hz, 1H), 3.94 (d, J = 2.1 Hz, 3H), 2.76 (p, J = 7.6 Hz, 1H), 1.60 (s, 3H), 0.72 (dd, J = 7.6, 2.3 Hz, 3H) ppm. |
| 54 | rel-(2R,3S,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide | ESI-MS m/z calc. 475.11667, found 476.1 (M + 1)$^+$; 474.0 (M − 1)$^−$; Retention time: 2.82 minutes | $^1$H NMR (500 MHz, Chloroform-d) δ 11.10 (d, J = 5.2 Hz, 1H), 8.84 (s, 1H), 8.29 (dd, J = 7.2, 3.3 Hz, 1H), 8.25-8.14 (m, 2H), 6.99 (ddd, J = 8.0, 5.6, 1.9 Hz, 1H), 6.94-6.86 (m, 1H), 6.15 (s, 1H), 4.77 (d, J = 10.7 Hz, 1H), 3.99 (d, J = 2.6 Hz, 3H), 3.88-3.76 (m, 1H), 2.61 (t, J = 12.5 Hz, 1H), 2.34 (dd, J = 13.1, 8.2 Hz, 1H), 1.65 (s, 3H) ppm. |
| 55 | (2R,3S,4S,5R)-4-[[3-(2-ethoxy-3,4-difluoro-phenyl)-4,5-dimethyl-5-(trifluoromethyl)tetrahydrofuran- | ESI-MS m/z calc. 503.14795, found 504.5 (M + 1)$^+$; 502.5 (M − 1)$^−$; Retention time: 3.17 | $^1$H NMR (500 MHz, DMSO-$d_6$) δ 10.82 (s, 1H), 10.59 (d, J = 4.7 Hz, 1H), 8.53 (d, J = 3.2 Hz, |

-continued

| Cmpd No. | Compound Name | LC/MS | NMR (shifts in ppm) |
|---|---|---|---|
| | 2-carbonyl]amino]-1-oxido-pyridin-1-ium-2-carboxamide | minutes | 1H), 8.32 (d, J = 7.2 Hz, 1H), 8.22 (d, J = 4.6 Hz, 1H), 7.88 (dd, J = 7.2, 3.2 Hz, 1H), 7.22-7.09 (m, 2H), 5.09 (d, J = 10.4 Hz, 1H), 4.28 (dd, J = 10.5, 7.6 Hz, 1H), 4.25-4.11 (m, 2H), 2.75 (p, J = 7.4 Hz, 1H), 1.61 (s, 3H), 1.35 (t, J = 7.0 Hz, 3H), 0.73 (d, J = 7.1 Hz, 3H) ppm. |
| 56 | 4-[[(2R,3S,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide | ESI-MS m/z calc. 492.15115, found 493.6 (M + 1)$^+$; 491.6 (M − 1)$^-$; Retention time: 3.02 minutes | |
| 57 | 4-[[(2R,3S,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide | ESI-MS m/z calc. 475.11667, found 476.6 (M + 1)$^+$; 474.4 (M − 1)$^-$; Retention time: 2.35 minutes | $^1$H NMR (500 MHz, Methanol-d$_4$) δ 8.58 (d, J = 3.2 Hz, 1H), 8.30 (d, J = 7.2 Hz, 1H), 8.07 (dd, J = 7.2, 3.2 Hz, 1H), 7.03 (ddd, J = 8.4, 5.7, 2.1 Hz, 1H), 6.72 (ddd, J = 10.1, 8.8, 7.4 Hz, 1H), 5.12 (d, J = 10.4 Hz, 1H), 4.34 (dd, J = 10.5, 7.8 Hz, 2H), 2.92 (p, J = 7.6 Hz, 1H), 1.68 (s, 2H), 0.83 (dt, J = 7.5, 2.3 Hz, 3H) ppm; Amide NH and NH$_2$; alcohol OH not observed. |

Compound 19—Solid Form A

A crystalline form of Compound 19, referred to herein as Form A, was obtained from a suspension of Compound 19 in ethanol, acetonitrile, and water by lyophilization. Form A can also be obtained by precipitation from a methanol solution via addition of heptane antisolvent. Form A was characterized by XRPD, solid state NMR ($^{13}$C and $^{19}$F), and single-crystal X-ray analysis.

Figure 15:
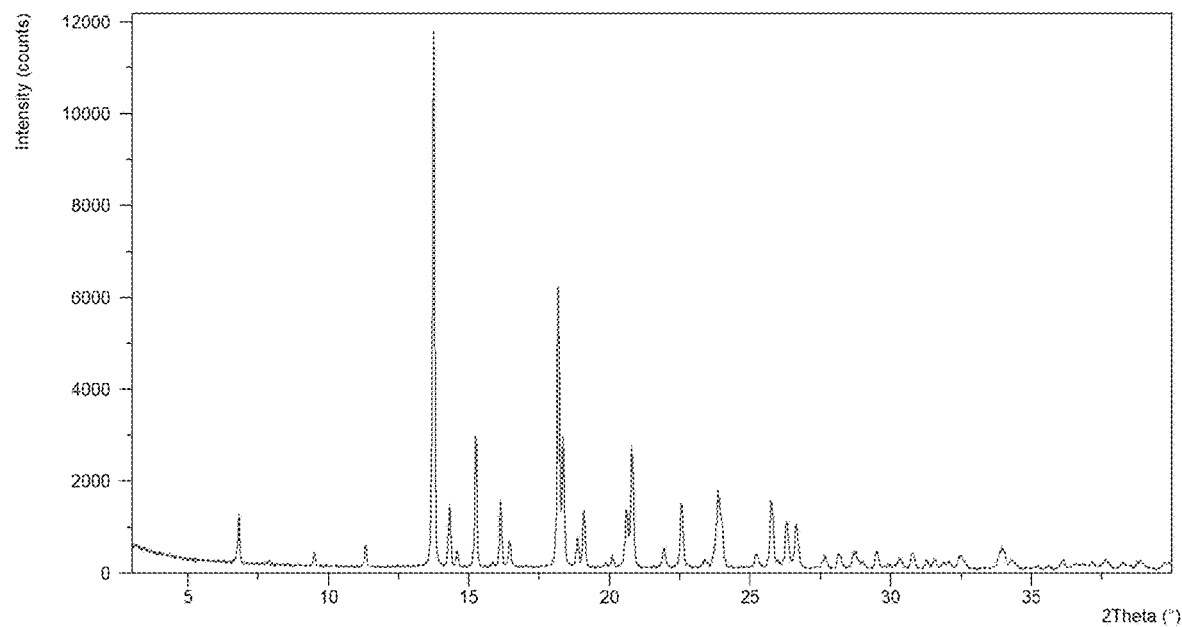
FIG. 15 depicts an XRPD pattern characteristic of Compound 19, Form A.

The XRPD pattern of Form A is depicted in FIG. 15, and the corresponding data are summarized in the following table:

| Angle (° 2θ ± 0.2) | Rel. Intensity (%) |
|---|---|
| 6.8 | 8.8 |
| 13.7 | 100 |
| 14.3 | 11.1 |
| 15.2 | 24.1 |
| 16.1 | 12.2 |
| 18.2 | 51.5 |
| 18.3 | 23.5 |
| 19.1 | 10.0 |
| 20.6 | 10.4 |
| 20.8 | 22.0 |
| 22.5 | 11.6 |
| 23.8 | 13.6 |
| 24.0 | 7.5 |
| 25.8 | 11.8 |
| 26.3 | 7.9 |
| 26.6 | 7.7 |

Figure 16:
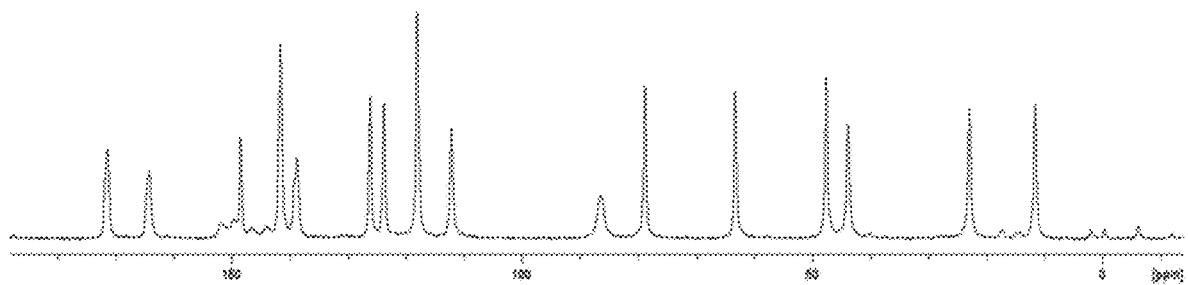
FIG. 16 depicts a solid state $^{13}$C NMR spectrum characteristic of Compound 19, Form A.

The solid state $^{13}$C NMR spectrum of Form A is depicted in FIG. 16, and the corresponding data are summarized in the following table:

| Chemical Shift [ppm] | Rel. Intensity (%) |
|---|---|
| 171.4 | 39.1 |
| 164.2 | 29.2 |
| 151.8 | 6.3 |
| 149.5 | 8.2 |
| 148.4 | 44.8 |
| 146.6 | 4.3 |
| 144.0 | 5.4 |
| 141.6 | 86.1 |
| 138.7 | 35.3 |
| 126.2 | 62.8 |
| 123.8 | 59.1 |
| 118.0 | 100.0 |
| 112.2 | 49.2 |
| 86.4 | 19.1 |
| 78.8 | 67.1 |
| 63.3 | 65.2 |
| 47.6 | 71.9 |
| 43.8 | 50.2 |
| 23.0 | 56.9 |
| 11.6 | 58.6 |

Figure 17:
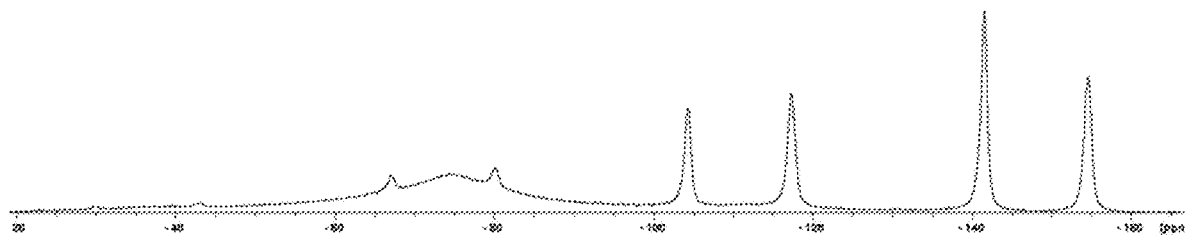
FIG. 17 depicts a solid state $^{19}$F NMR spectrum characteristic of Compound 19, Form A.

The solid state $^{19}$F NMR spectrum of Form A is depicted in FIG. 17, and the corresponding data are summarized in the following table:

| Chemical Shift [ppm] | Rel. Intensity |
|---|---|
| −74.6 | 2.4 |
| −141.5 | 12.5 |
| −154.6 | 8.4 |

Figure 18:
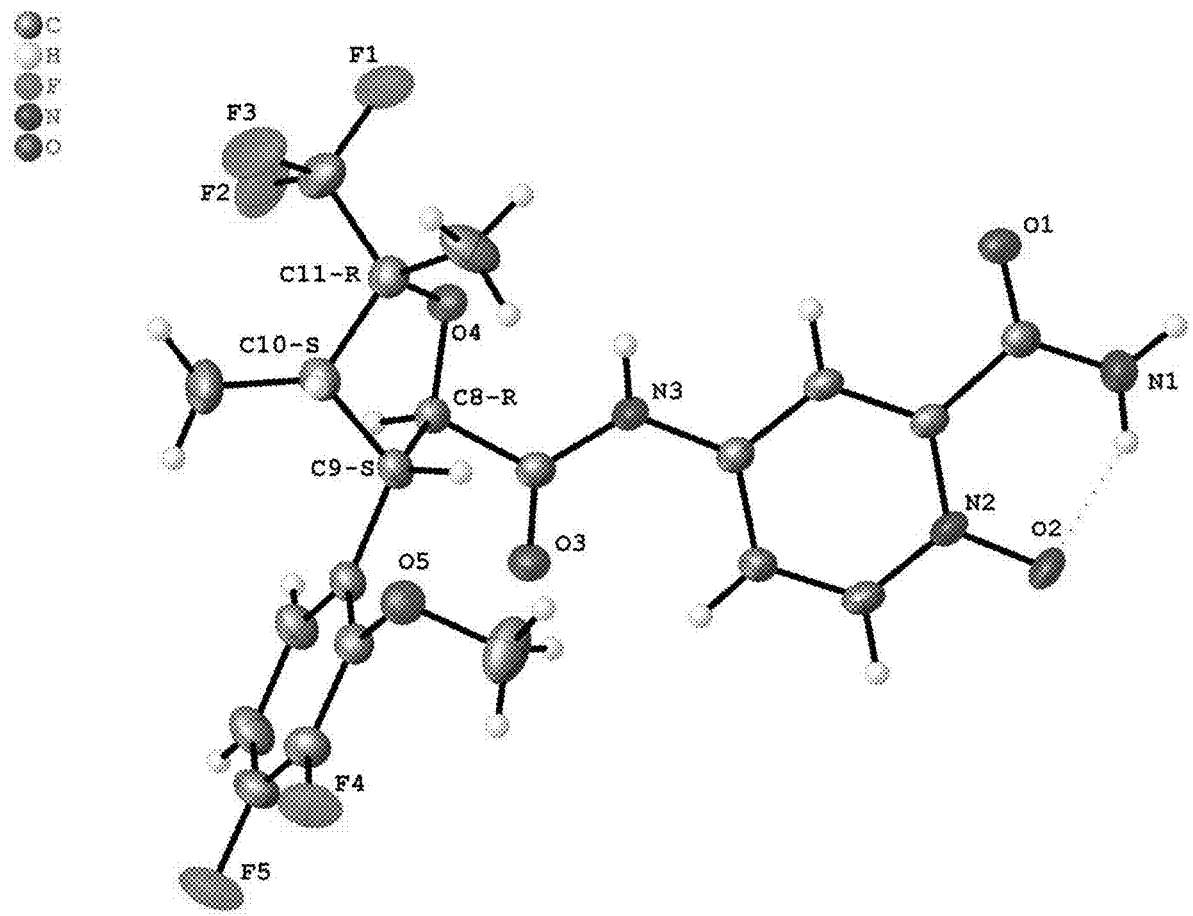
FIG. 18 depicts a thermal ellipsoid plot characteristic of Compound 19, Form A.

The absolute stereochemistry of Compound 19 was confirmed by single crystal X-ray crystallographic analysis. Crystals having Form A were grown for single-crystal X-ray analysis by dissolving ~1 mg of Compound 19 material in 150 μL of methanol and allowing slow diffusion of heptane antisolvent over several days. The thermal ellipsoid plot, at 50% probability, is depicted in FIG. 18, and the unit cell parameters are reported in the following table:

| Crystal System: | Monoclinic |
|---|---|
| Space Group: | P2$_1$ |
| a (Å) | 11.2266 (3) |
| b (Å) | 7.3948 (2) |
| c (Å) | 13.1432 (4) |
| α (°) | 90 |
| β (°) | 100.3980 (10) |
| γ (°) | 90 |
| V (Å$^3$) | 1073.21 (5) |
| Z/Z' | 2/0.5 |
| Temperature | 173 (2)K |

Example 6 rel-(2S,3R,5S)-4-[[3-(3-chloro-4-fluoro-2-methoxy-phenyl)-5-methyl-5-(trifluoromethyl)tetrahydro-furan-2-carbonyl]amino]pyridine-2-carboxamide (20), (2S,3R,5R)-4-[[3-(3-chloro-4-fluoro-2-methoxy-phenyl)-5-methyl-5-(trifluoromethyl)tetrahydrofuran-2-carbonyl]amino]pyridine-2-carboxamide (21), rel-(2R,3S,5R)-4-[[3-(3-chloro-4-fluoro-2-methoxy-phenyl)-5-methyl-5-(trifluoromethyl)tetrahydrofuran-2-carbonyl]amino]pyridine-2-carboxamide (22), and (2R,3S,5S)-4-[[3-(3-chloro-4-fluoro-2-methoxy-phenyl)-5-methyl-5-(trifluoromethyl)tetrahydrofuran-2-carbonyl]amino]pyridine-2-carboxamide (23)

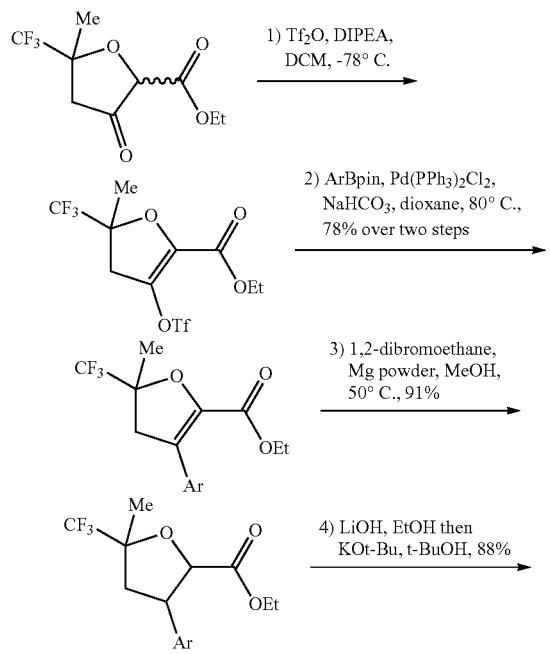

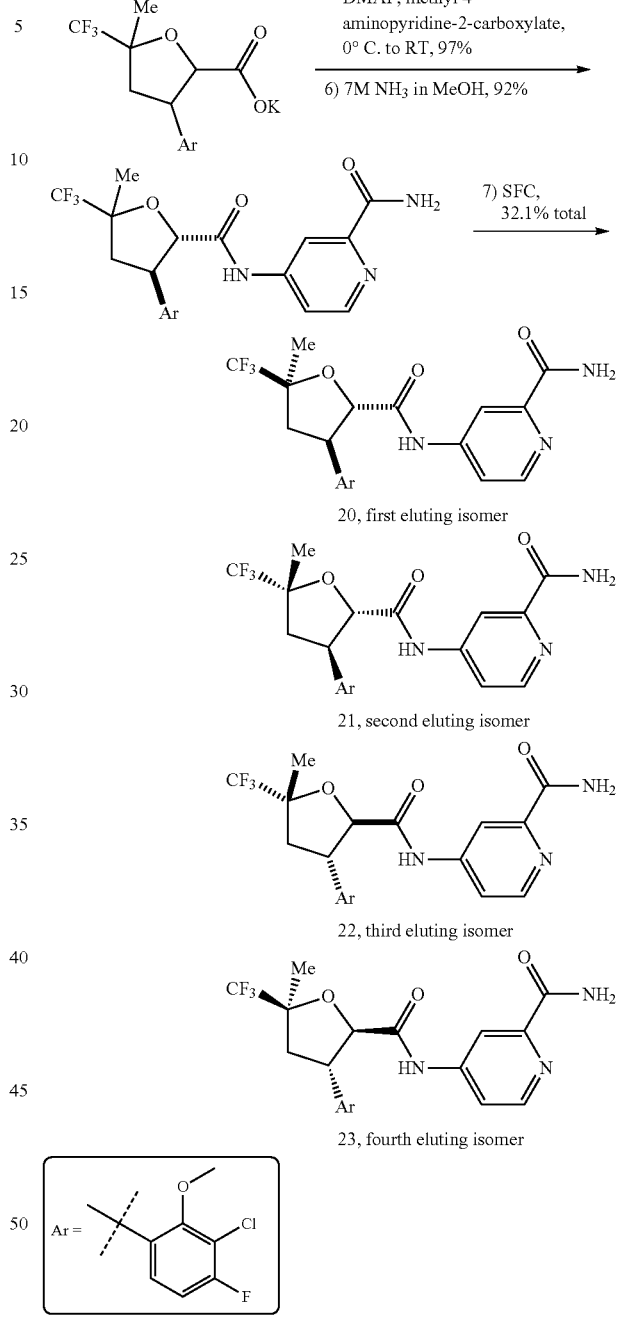

Step 1

Trifluoromethylsulfonyl trifluoromethanesulfonate (1.53 g, 5.42 mmol) was added dropwise to a solution of ethyl 5-methyl-3-oxo-5-(trifluoromethyl)tetrahydrofuran-2-carboxylate (1000 mg, 4.16 mmol) and triethylamine (1.26 g, 12.45 mmol) in DCM (40 mL) stirring at −78° C. After 2 h, the reaction was quenched by addition of saturated aqueous NaHCO$_3$ solution, the layers were separated and the aqueous layer extracted with DCM. The combined organic layers were passed through a phase separator cartridge, filtered and concentrated in vacuo to give ethyl 2-methyl-2-(trifluoromethyl)-4-(trifluoromethylsulfonyloxy)-3H-furan-5-carboxylate (2.7 g, 87% yield) at 50% purity (containing 1 eq. $NEt_3$), which was used without further purification. ESI-MS m/z calc. 372.01022, found 373.0 $(M+1)^+$.

Step 2

A mixture of ethyl 2-methyl-2-(trifluoromethyl)-4-(trifluoromethylsulfonyloxy)-3H-furan-5-carboxylate (2 g, 50% purity with 1 eq. $NEt_3$, 2.686 mmol), 2-(3-chloro-4-fluoro-2-methoxy-phenyl)-4,4,5,5-tetramethyl-1,3,2-dioxaborolane (925.8 mg, 3.231 mmol) and $Pd(PPh_3)_2Cl_2$ (97.63 mg, 0.14 mmol) in dioxane (25 mL) and saturated aqueous $NaHCO_3$ (excess) was degassed, refilled with $N_2$ (three times before catalyst addition, then three times after catalyst addition), and heated at 80° C. for 4 hours. The reaction mixture was cooled to ambient temperature and filtered through a celite cartridge, eluting with EtOAc, then the filtrate concentrated in vacuo. Purification by flash chromatography (40 g $SiO_2$ 0 to 20% EtOAc in heptane) gave ethyl 4-(3-chloro-4-fluoro-2-methoxy-phenyl)-2-methyl-2-(trifluoromethyl)-3H-furan-5-carboxylate (800 mg, 78%) as a clear oil. $^1$H NMR (400 MHz, Chloroform-d) δ 7.12 (dd, J=8.7, 6.1 Hz, 1H), 6.96 (t, J=8.5 Hz, 1H), 4.19 (q, J=7.1 Hz, 2H), 3.80 (s, 3H), 3.52 (d, J=17.6 Hz, 1H), 2.96 (dt, J=17.6, 0.9 Hz, 1H), 1.69 (d, J=1.0 Hz, 3H), 1.17 (t, J=7.1 Hz, 3H) ppm. ESI-MS m/z calc. 382.0595, found 383.3 $(M+1)^+$.

Step 3

A pressure tube was loaded with magnesium powder (770 mg, 31.68 mmol) and purged with nitrogen. To the reaction vessel was added MeOH (12 mL) followed by a solution of ethyl 4-(3-chloro-4-fluoro-2-methoxy-phenyl)-2-methyl-2-(trifluoromethyl)-3H-furan-5-carboxylate (600 mg, 1.57 mmol) in MeOH (12 mL) and the resulting solution was degassed with nitrogen. A few drops of 1,2-dibromoethane (12 μL, 0.14 mmol) were added and the reaction mixture was stirred vigorously at 50° C. After 5 hours the reaction mixture was cooled and quenched by pouring slowly onto a cooled 1M solution of HCl. The mixture was stirred for 30 mins until clear. TBME was added to solution while stirring, the layers separated and the aqueous layer extracted with TBME (×3). The combined organic layers were passed through a phase separator cartridge and the filtrate concentrated in vacuo to give ethyl 3-(3-chloro-4-fluoro-2-methoxy-phenyl)-5-methyl-5-(trifluoromethyl)tetrahydrofuran-2-carboxylate (550 mg, 91%), which was used without further purification. ESI-MS m/z calc. 384.07516, found 385.2 $(M+1)^+$.

Step 4

Ethyl 3-(3-chloro-4-fluoro-2-methoxy-phenyl)-5-methyl-5-(trifluoromethyl)tetrahydrofuran-2-carboxylate (550 mg, 1.43 mmol) was dissolved in ethanol (25 mL) and LiOH (5 mL of 2 M, 10.00 mmol) was added. The resulting white suspension was stirred at ambient temperature overnight before being concentrated in vacuo and then partitioned between EtOAc and 1M aqueous HCl. The layers were separated and the organic layer passed through a phase separator cartridge). The filtrate was concentrated in vacuo to give a yellow oil which was dissolved in tert-butanol (20 mL). Potassium tert-butoxide (800 mg, 7.129 mmol) was added and the mixture stirred at ambient temperature overnight. The reaction mixture was evaporated in vacuo to give potassium 3-(3-chloro-4-fluoro-2-methoxy-phenyl)-5-methyl-5-(trifluoromethyl)tetrahydrofuran-2-carboxylate (500 mg, 88%). ESI-MS m/z calc. 356.04385, found 355.2 $(M-1)^-$.

Step 5

To a solution of potassium 3-(3-chloro-4-fluoro-2-methoxy-phenyl)-5-methyl-5-(trifluoromethyl)tetrahydrofuran-2-carboxylate (500 mg, 1.40 mmol) in DCM (20 mL) stirring at ambient temperature was added DMF (25 μL, 0.32 mmol) and oxalyl chloride (415 μL, 4.76 mmol). After 15 mins the reaction mixture was concentrated in vacuo then the residue diluted in DCM (10 mL) and added dropwise over 5 mins to a solution of methyl 4-aminopyridine-2-carboxylate (334 mg, 2.20 mmol), DMAP (16.55 mg, 0.14 mmol) and $Et_3N$ (1.2 mL, 8.61 mmol) in DCM (10 mL) stirring at 0° C. After 10 mins the reaction was warmed to ambient temperature and after 40 mins the reaction mixture was diluted with DCM (50 mL) and washed with 2 M HCl solution (50 mL). The organic layer was passed through a phase separator cartridge and the filtrate was concentrated in vacuo to give methyl 4-[[3-(3-chloro-4-fluoro-2-methoxy-phenyl)-5-methyl-5-(trifluoromethyl)tetrahydrofuran-2-carbonyl]amino]pyridine-2-carboxylate (670 mg, 97%), which was used without further purification. ESI-MS m/z calc. 490.09186, found 491.1 $(M+1)^+$.

Step 6

Methyl 4-[[3-(3-chloro-4-fluoro-2-methoxy-phenyl)-5-methyl-5-(trifluoromethyl)tetrahydrofuran-2-carbonyl]amino]pyridine-2-carboxylate (470 mg, 0.96 mmol) was dissolved in methanolic ammonia (10.00 mL of 2 M, 20.00 mmol) and stirred overnight at ambient temperature. The reaction mixture was evaporated in vacuo to give 4-[[3-(3-chloro-4-fluoro-2-methoxy-phenyl)-5-methyl-5-(trifluoromethyl)tetrahydrofuran-2-carbonyl]amino]pyridine-2-carboxamide (420 mg, 92%), which was used without further purification. ESI-MS m/z calc. 475.0922, found 476.4 $(M+1)^+$.

Step 7

(4-[[3-(3-Chloro-4-fluoro-2-methoxy-phenyl)-5-methyl-5-(trifluoromethyl)tetrahydrofuran-2-carbonyl]amino]pyridine-2-carboxamide (420 mg, 0.8827 mmol) was separated by chiral SFC [(R,R)-Whelk-O1 column, 5 μm particle size, 25 cm×21.2 mm from Regis Technologies, MeOH, 20 mM $NH_3$], followed by further purification of one or more of the fractions by chiral SFC using a Chiralpak IC column, 5 μm particle size, 25 cm×20 mm from Daicel or a Chiralpak ID column, 5 μm particle size, 25 cm×20 mm from Daicel to give:

First Eluting Isomer: rel-(2S,3R,5S)-4-[[3-(3-chloro-4-fluoro-2-methoxy-phenyl)-5-methyl-5-(trifluoromethyl)tetrahydrofuran-2-carbonyl]amino]pyridine-2-carboxamide (20, 30 mg, 7.1%) (further purified by chiral SFC using Chiralpak IC column). $^1$H NMR (500 MHz, Chloroform-d) δ 8.92 (s, 1H), 8.47 (d, J=5.5 Hz, 1H), 8.21 (dd, J=5.6, 2.1 Hz, 1H), 8.09 (d, J=2.2 Hz, 1H), 7.87 (d, J=4.1 Hz, 1H), 7.26 (dd, J=8.8, 5.8 Hz, 1H), 7.03 (t, J=8.4 Hz, 1H), 5.87-5.82 (m, 1H), 4.77 (d, J=10.6 Hz, 1H), 3.98 (td, J=11.2, 8.3 Hz, 1H), 3.88 (s, 3H), 2.51 (dd, J=13.2, 11.7 Hz, 1H), 2.42 (dd, J=13.2, 8.3 Hz, 1H), 1.69 (s, 3H) ppm. ESI-MS m/z calc. 475.0922, found 476.4 $(M+1)^+$; 474.4 $(M-1)^-$.

Second Eluting Isomer: (2S,3R,5R)-4-[[3-(3-chloro-4-fluoro-2-methoxy-phenyl)-5-methyl-5-(trifluoromethyl)tetrahydrofuran-2-carbonyl]amino]pyridine-2-carboxamide (21, 29 mg, 6.7%) (further purified by chiral SFC using Chiralpak ID column). $^1$H NMR (500 MHz, Chloroform-d) δ 8.56 (s, 1H), 8.48 (d, J=5.5 Hz, 1H), 8.08 (dd, J=5.5, 2.2 Hz, 1H), 7.98 (d, J=2.1 Hz, 1H), 7.86 (d, J=4.4 Hz, 1H), 7.23 (dd, J=8.8, 5.8 Hz, 1H), 7.01 (t, J=8.4 Hz, 1H), 5.86 (d, J=4.2 Hz, 1H), 4.80 (d, J=9.7 Hz, 1H), 4.10-4.00 (m, 1H), 3.93 (s, 3H), 3.52-3.48 (m, 1H), 2.86 (dd, J=13.9, 8.4 Hz, 1H), 2.16-2.07 (m, 1H), 1.64 (s, 2H) ppm. ESI-MS m/z calc. 475.0922, found 476.4 (M+1)$^+$; 474.4 (M−1)$^−$.

Third Eluting Isomer: rel-(2R,3S,5R)-4-[[3-(3-chloro-4-fluoro-2-methoxy-phenyl)-5-methyl-5-(trifluoromethyl)tetrahydrofuran-2-carbonyl]amino]pyridine-2-carboxamide (22, 42 mg, 9.5%). $^1$H NMR (500 MHz, Chloroform-d) δ 8.87 (s, 1H), 8.33 (d, J=5.6 Hz, 1H), 8.08 (dd, J=5.6, 2.2 Hz, 1H), 7.98 (d, J=2.2 Hz, 1H), 7.74 (d, J=4.5 Hz, 1H), 7.12 (dd, J=8.8, 5.8 Hz, 1H), 6.89 (t, J=8.4 Hz, 1H), 5.79 (d, J=4.5 Hz, 1H), 4.63 (d, J=10.7 Hz, 1H), 3.85 (td, J=11.2, 8.4 Hz, 1H), 3.74 (s, 3H), 2.37 (dd, J=13.2, 11.7 Hz, 1H), 2.28 (dd, J=13.1, 8.4 Hz, 1H), 1.55 (s, 3H) ppm. ESI-MS m/z calc. 475.0922, found 476.4 (M+1)$^+$; 474.4 (M−1)$^−$.

Fourth Eluting Isomer: (2R,3S,5S)-4-[[3-(3-chloro-4-fluoro-2-methoxy-phenyl)-5-methyl-5-(trifluoromethyl)tetrahydrofuran-2-carbonyl]amino]pyridine-2-carboxamide (23, 40 mg, 8.8%). $^1$H NMR (500 MHz, Chloroform-d) δ 8.43 (s, 1H), 8.35 (d, J=5.5 Hz, 1H), 7.95 (dd, J=5.5, 2.2 Hz, 1H), 7.85 (d, J=2.2 Hz, 1H), 7.73 (d, J=4.3 Hz, 1H), 7.10 (dd, J=8.8, 5.9 Hz, 1H), 6.87 (t, J=8.4 Hz, 1H), 5.76-5.71 (m, 1H), 4.67 (d, J=9.7 Hz, 1H), 3.97-3.87 (m, 1H), 3.80 (s, 3H), 2.73 (dd, J=13.9, 8.4 Hz, 1H), 1.98 (dd, J=13.9, 11.6 Hz, 1H), 1.51 (s, 3H) ppm. ESI-MS m/z calc. 475.0922, found 476.4 (M+1)$^+$; 474.4 (M−1)$^−$.

Compound 22—Solid Form A

A crystalline form of Compound 22, referred to herein as Form A, was generated by slow evaporation of a 1:1 2-methyltetrahydrofuran/heptane solution. Form A was characterized by XRPD and solid state NMR ($^{13}$C and $^{19}$F) analysis.

Figure 19:
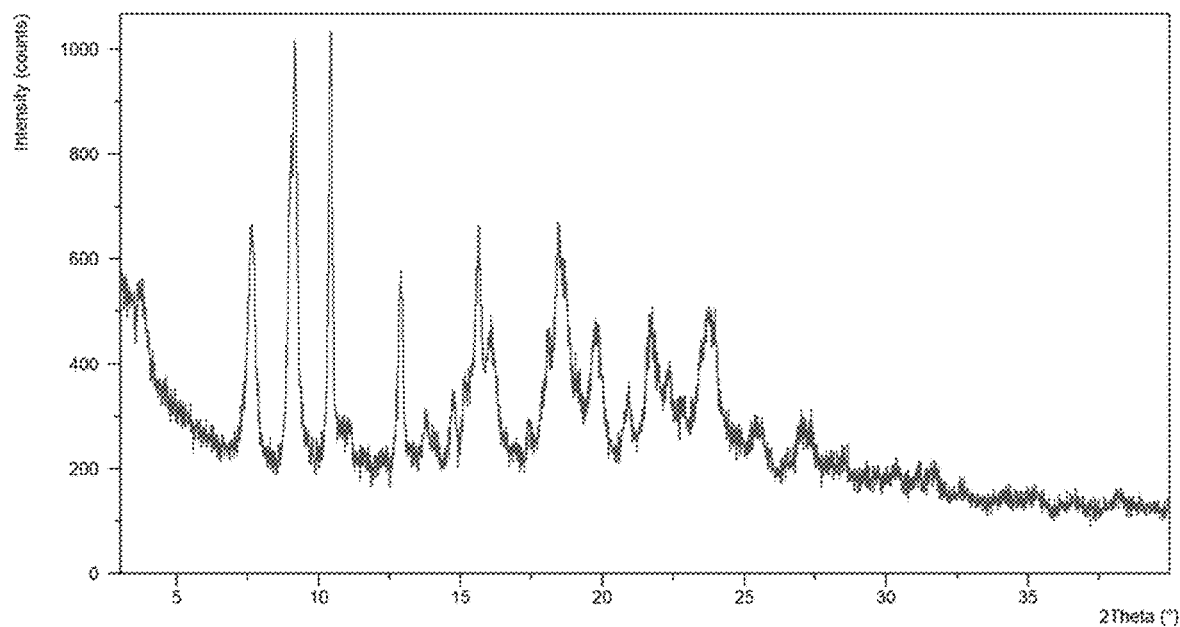
FIG. 19 depicts an XRPD pattern characteristic of Compound 22, Form A.

The XRPD pattern of Form A is depicted in FIG. 19, and the corresponding data are summarized in the following table:

| Angle (° 2θ ± 0.2) | Rel. Intensity (%) |
|---|---|
| 7.7 | 48.9 |
| 9.2 | 95.9 |
| 10.4 | 100 |
| 12.9 | 44.8 |
| 13.8 | 9.9 |
| 14.7 | 13.4 |
| 15.7 | 46.2 |
| 16.1 | 27.4 |
| 18.4 | 46.0 |
| 19.8 | 26.5 |
| 21.7 | 23.6 |
| 22.3 | 13.6 |
| 24.0 | 23.8 |

Figure 20:
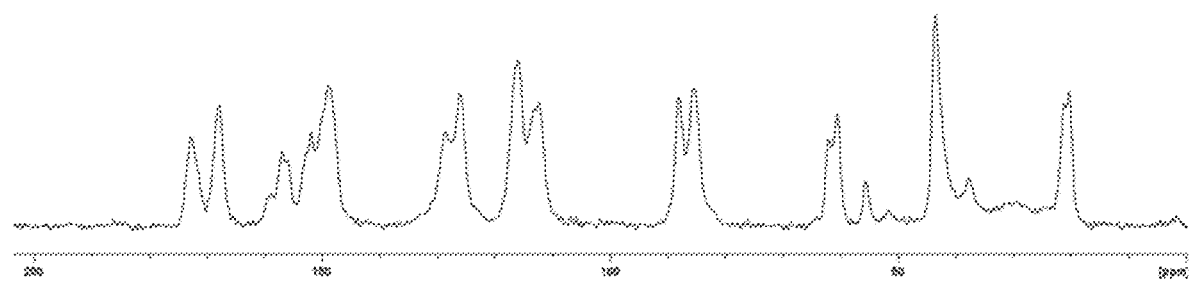
FIG. 20 depicts a solid state $^{13}$C NMR spectrum characteristic of Compound 22, Form A.

The solid state $^{13}$C NMR spectrum of Form A is depicted in FIG. 20, and the corresponding data are summarized in the following table:

| Chemical Shift [ppm] | Rel. Intensity (%) |
|---|---|
| 172.6 | 41.8 |
| 167.7 | 56.7 |
| 158.7 | 14.5 |
| 156.8 | 34.9 |
| 151.8 | 43.8 |
| 148.7 | 65.9 |
| 128.6 | 44.0 |
| 126.0 | 62.1 |
| 115.9 | 77.5 |
| 113.1 | 54.9 |
| 112.3 | 58.0 |
| 88.0 | 60.7 |
| 85.5 | 64.1 |
| 62.0 | 40.7 |
| 60.5 | 52.3 |
| 55.6 | 21.3 |
| 43.5 | 100.0 |
| 37.7 | 22.1 |
| 29.6 | 11.0 |
| 21.1 | 57.3 |
| 20.3 | 62.9 |

Figure 21:
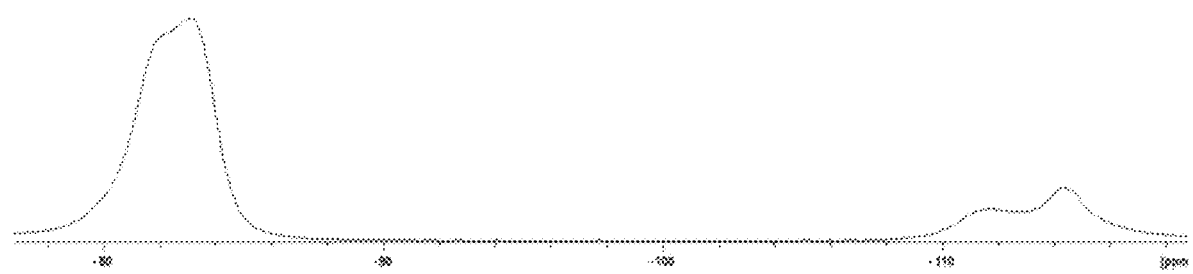
FIG. 21 depicts a solid state $^{19}$F NMR spectrum characteristic of Compound 22, Form A.

The solid state $^{19}$F NMR spectrum of Form A is depicted in FIG. 21, and the corresponding data are summarized in the following table:

| Chemical Shift [ppm] | Rel. Intensity |
|---|---|
| −82.2 | 11.7 |
| −83.1 | 12.5 |
| −111.7 | 1.8 |
| −114.4 | 3.0 |

Compound 23—Solid Form A

A crystalline form of Compound 23, referred to herein as Form A, was generated by slow evaporation of a 1:1 2-methyltetrahydrofuran/heptane solution. Form A was characterized by XRPD, solid state NMR ($^{13}$C and $^{19}$F), and single-crystal X-ray analysis.

Figure 22:
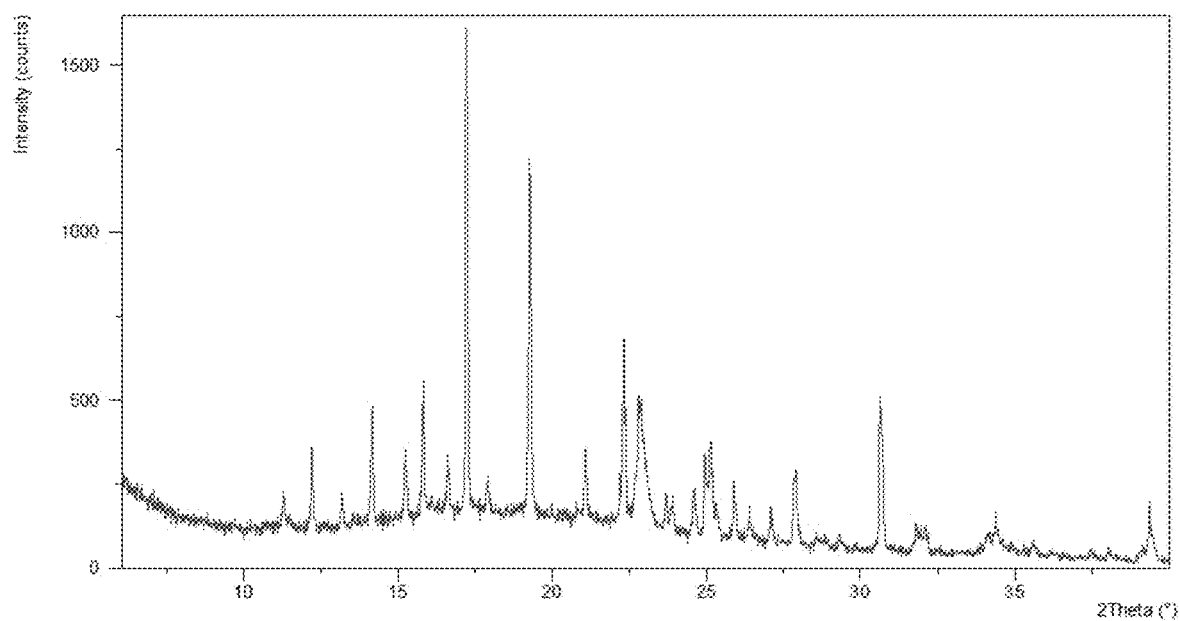
FIG. 22 depicts an XRPD pattern characteristic of Compound 23, Form A.

The XRPD pattern of Form A is depicted in FIG. 22, and the corresponding data are summarized in the following table:

| Angle (° 2θ ± 0.2) | Rel. Intensity (%) |
|---|---|
| 11.3 | 5.8 |
| 12.2 | 16.8 |
| 13.2 | 6.9 |
| 14.2 | 22.2 |
| 15.2 | 13.1 |
| 15.8 | 25.5 |
| 16.6 | 10.2 |
| 17.2 | 100 |
| 19.3 | 71.7 |
| 21.1 | 14.4 |
| 22.3 | 37.3 |
| 22.8 | 24.9 |
| 23.7 | 7.0 |
| 24.6 | 8.7 |
| 25.0 | 16.7 |
| 25.1 | 19.7 |
| 25.9 | 10.9 |
| 27.1 | 5.3 |
| 27.9 | 13.2 |
| 30.6 | 31.6 |
| 34.4 | 6.7 |
| 39.4 | 11.5 |

Figure 23:
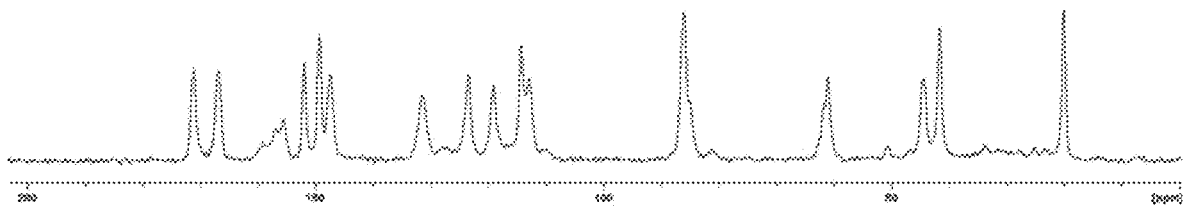
FIG. 23 depicts a solid state $^{13}$C NMR spectrum characteristic of Compound 23, Form A.

The solid state $^{13}$C NMR spectrum of Form A is depicted in FIG. 23, and the corresponding data are summarized in the following table:

| Chemical Shift [ppm] | Rel. Intensity (%) |
| --- | --- |
| 171.1 | 60.6 |
| 166.7 | 59.9 |
| 156.8 | 19.4 |
| 155.5 | 27.1 |
| 151.9 | 64.5 |
| 149.3 | 83.3 |
| 147.3 | 56.5 |
| 131.5 | 42.1 |
| 123.3 | 56.1 |
| 119.0 | 49.1 |
| 114.2 | 76.6 |
| 112.8 | 54.0 |
| 86.0 | 98.6 |
| 85.0 | 39.0 |
| 61.7 | 36.4 |
| 61.0 | 54.8 |
| 44.4 | 53.9 |
| 41.6 | 88.6 |
| 20.0 | 100.0 |

Figure 24:
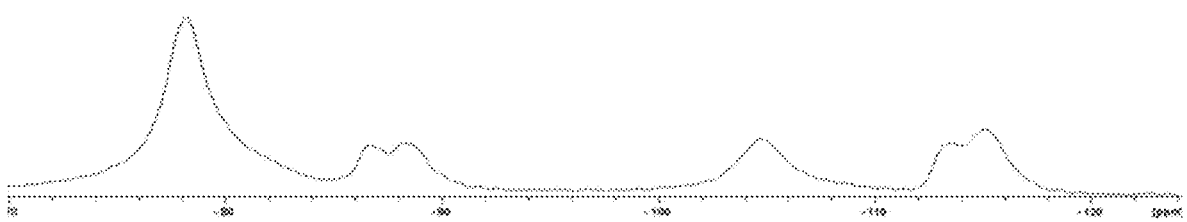
FIG. 24 depicts a solid state $^{19}$F NMR spectrum characteristic of Compound 23, Form A.

The solid state $^{19}$F NMR spectrum of Form A is depicted in FIG. 24, and the corresponding data are summarized in the following table:

| Chemical Shift [ppm] | Rel. Intensity |
| --- | --- |
| −78.2 | 12.5 |
| −113.5 | 3.7 |
| −115.1 | 4.7 |

Figure 25:
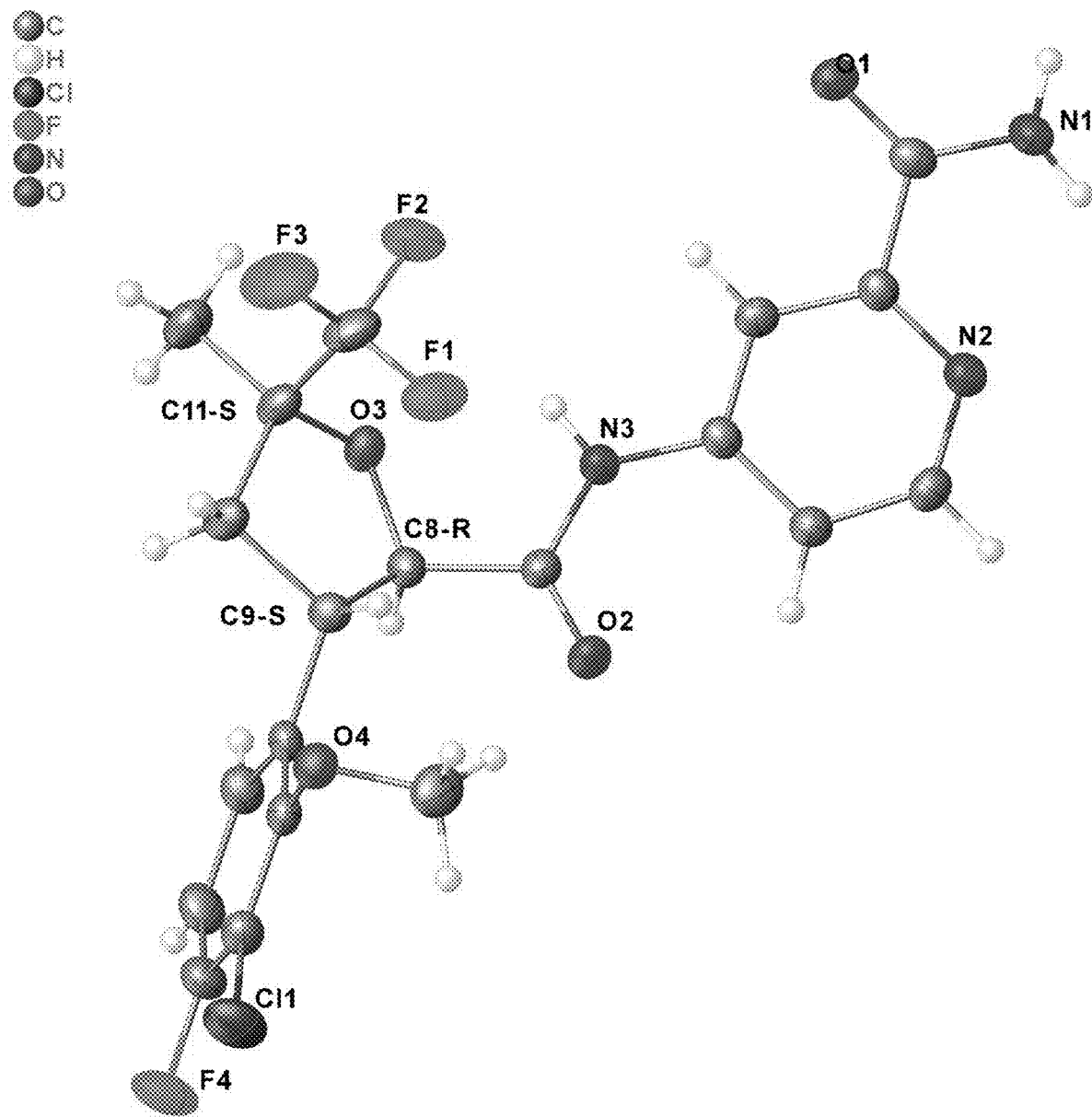
FIG. 25 depicts a thermal ellipsoid plot characteristic of Compound 23, Form A.

Crystals having Form A were grown for single-crystal X-ray analysis by dissolving A-mg of Compound 23 material in 150 μL of methanol and allowing diffusion of heptane vapor over several days. The thermal ellipsoid plot, at 50% probability, is depicted in FIG. 25, and the unit cell parameters are reported in the following table:

| | |
| --- | --- |
| Crystal System: | Monoclinic |
| Space Group: | P2$_1$ |
| a (Å) | 7.8661 (3) |
| b (Å) | 7.9167 (3) |
| c (Å) | 16.8777 (7) |
| α (°) | 90 |
| β (°) | 98.487 (2) |
| γ (°) | 90 |
| V (Å$^3$) | 1039.52 (7) |
| Z | 2 |
| Temperature | 173 (2)K |

The following compounds were made using a method similar to that described in Example 6, except that methylamine was used in place of ammonia in Step 7. In step 4, purification was performed by chiral SFC using a (R,R)-Whelk-O1 column, 5 μm particle size, 25 cm×21.2 mm from Reis Technologies on a Minigram SFC instrument from Berger Instruments:

| Cmpd No. | Compound Name | LC/MS | NMR (shifts in ppm) |
| --- | --- | --- | --- |
| 58 | rel-(2S,3R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide (first eluting isomer by SFC on Whelk01 column, rt = 3.41 min) | ESI-MS m/z calc. 489.10785, found 490.4 (M + 1)$^+$; 488.4 (M − 1)$^-$; Retention time: 3.21 minutes | $^1$H NMR (500 MHz, Chloroform-d) δ 8.62 (s, 1H), 8.46 (d, J = 5.5 Hz, 1H), 8.18 (dd, J = 5.6, 2.2 Hz, 1H), 8.13 (s, 1H), 7.93 (d, J = 2.2 Hz, 1H), 7.25 (dd, J = 8.8, 5.8 Hz, 1H), 7.07-6.95 (m, 1H), 4.75 (d, J = 10.7 Hz, 1H), 3.99-3.85 (m, 1H), 3.89 (s, 3H), 3.06 (d, J = 5.0 Hz, 3H), 2.51 (dd, J = 13.2, 11.7 Hz, 1H), 2.42 (dd, J = 13.2, 8.3 Hz, 1H), 1.68 (s, 3H) ppm. |
| 59 | rel-(2R,3S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide (second eluting isomer by SFC on Whelk01 column, rt = 3.81 min) | ESI-MS m/z calc. 489.10785, found 490.4 (M + 1)$^+$; 488.4 (M − 1)$^-$; Retention time: 3.17 minutes | $^1$H NMR (500 MHz, Chloroform-d) δ 8.48 (s, 1H), 8.36 (d, J = 5.5 Hz, 1H), 8.08-8.00 (m, 2H), 7.86 (d, J = 2.2 Hz, 1H), 7.14 (dd, J = 8.8, 5.9 Hz, 1H), 6.92 (dd, J = 8.8, 8.1 Hz, 1H), 4.71 (d, J = 9.7 Hz, 1H), 4.01-3.91 (m, 1H), 3.84 (s, 3H), 2.97 (d, J = 5.1 Hz, 3H), 2.77 (dd, J = 13.9, 8.4 Hz, 1H), 2.03 (dd, J = 13.8, 11.7 Hz, 1H), 1.56 (s, 2H) ppm. |
| 60 | rel-(2R,3S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide (third eluting isomer by SFC on Whelk01 column, rt = 4.32 min) | ESI-MS m/z calc. 489.10785, found 490.4 (M + 1)$^+$; 488.4 (M − 1)$^-$; Retention time: 3.22 minutes | $^1$H NMR (500 MHz, Chloroform-d) δ 8.54 (s, 1H), 8.36 (d, J = 5.5 Hz, 1H), 8.09 (dd, J = 5.6, 2.2 Hz, 1H), 8.05 (s, 1H), 7.84 (d, J = 2.1 Hz, 1H), 7.16 (dd, J = 8.8, 5.9 Hz, 1H), 6.93 (t, J = 8.4 Hz, 1H), 4.66 (d, J = 10.7 Hz, 1H), 3.85 (td, J = 11.3, |

| Cmpd No. | Compound Name | LC/MS | NMR (shifts in ppm) |
|---|---|---|---|
| | | | 8.4 Hz, 1H), 3.79 (s, 3H), 2.97 (d, J = 5.0 Hz, 3H), 2.41 (dd, J = 13.2, 11.7 Hz, 1H), 2.32 (dd, J = 13.2, 8.4 Hz, 1H), 1.59 (s, 3H) ppm. |
| 61 | rel-(2S,3R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide (fourth eluting isomer by SFC on Whelk01 column, rt = 4.93 min) | ESI-MS m/z calc. 489.10785, found 490.4 (M + 1)$^+$; 488.4 (M − 1)$^-$; Retention time: 3.16 minutes | $^1$H NMR (500 MHz, Chloroform-d) δ 8.59 (s, 1H), 8.45 (d, J = 5.6 Hz, 1H), 8.12 (dd, J = 5.6, 2.2 Hz, 1H), 7.95 (d, J = 2.2 Hz, 1H), 7.23 (dd, J = 8.8, 5.8 Hz, 1H), 7.01 (dd, J = 8.7, 8.1 Hz, 1H), 4.80 (d, J = 9.7 Hz, 1H), 4.11-4.01 (m, 1H), 3.93 (s, 3H), 3.06 (d, J = 5.0 Hz, 3H), 2.91-2.82 (m, 1H), 2.16-2.07 (m, 1H), 1.64 (d, J = 1.1 Hz, 3H) ppm. |

Example 7 rel-(2R,3S,4S,5R)-4-[[3-(3,4-difluoro-2-methoxy-phenyl)-4-methyl-5-(trifluoromethyl)tetrahydrofuran-2-carbonyl]amino]pyridine-2-carboxamide (24) and rel-(2S,3R,4R,5S)-4-[[3-(3,4-difluoro-2-methoxy-phenyl)-4-methyl-5-(trifluoromethyl)tetrahydrofuran-2-carbonyl]amino]pyridine-2-carboxamide (25)

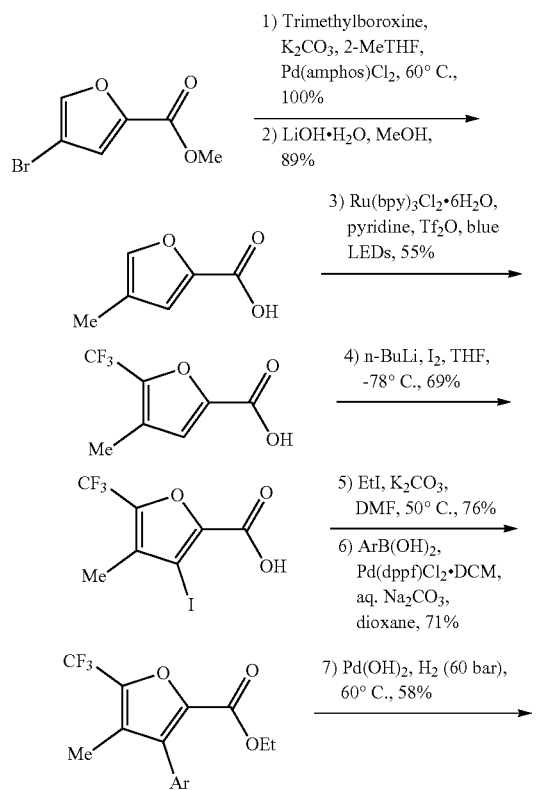

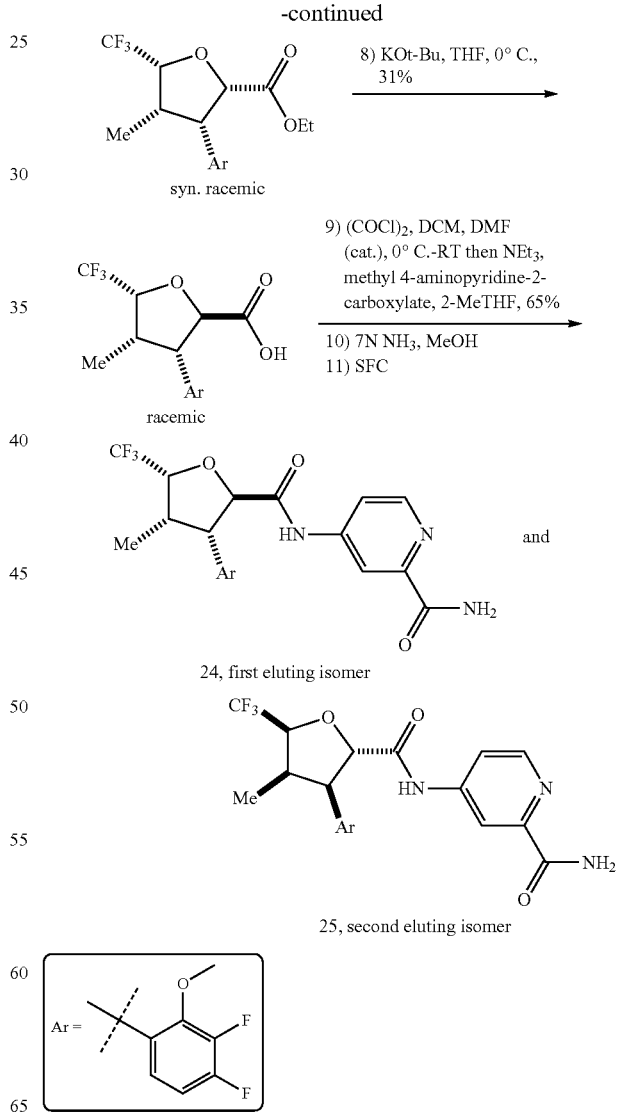

Step 1:

A solution of 2,4,6-trimethyl-1,3,5,2,4,6-trioxatriborinane (25 g of 50% w/w, 99.57 mmol) and potassium carbonate (21.5 g, 155.6 mmol) in water (40 mL) were added to a solution of methyl 4-bromofuran-2-carboxylate (10 g, 48.78 mmol) in 2-methyltetrahydrofuran (200 mL) and the reaction mixture degassed for 10 mins. Pd(amphos)Cl$_2$ (1.5 g, 2.12 mmol) was added and the reaction mixture further degassed for 5 mins before the reaction was heated at 60° C. for 4 hours. The reaction was then cooled to ambient temperature, filtered through a small pad of celite and washed with MTBE (200 mL). The layers were separated and the aqueous layer extracted with MTBE (2×20 mL). The combined organic extracts were dried (Na$_2$SO$_4$) and carefully concentrated in vacuo (approximately 90 mBar, no heating) to give methyl 4-methylfuran-2-carboxylate (6.836 g, 100%) which was used without any further purification.

Step 2

To a solution of methyl 4-methylfuran-2-carboxylate (10 g, 48.78 mmol) in THF (40 mL), water (40 mL) and MeOH (10 mL) stirring at ambient temperature was added LiOH H$_2$O (12.3 g, 293.11 mmol). The reaction was stirred for 2 hours before MTBE (100 mL) and water (100 mL) were added. The aqueous layer was isolated and treated with 6 N HCl solution to adjust the pH to about 3-4, then extracted with MTBE (2×50 mL). The combined organic layers were concentrated in vacuo to afford 4-methylfuran-2-carboxylic acid (5.5 g, 89%) as an off-white solid. $^1$H NMR (400 MHz, DMSO-d$_6$) δ 12.92 (s, 1H), 7.65 (s, 1H), 7.07 (s, 1H), 2.00 (s, 3H) ppm.

Step 3

To a solution of 4-methylfuran-2-carboxylic acid (150 mg, 1.19 mmol) in DCE (25 mL) was added tris(2,2'-bipyridyl)dichlororuthenium(II) hexahydrate (17 mg, 0.023 mmol) and pyridine (288 μL, 3.56 mmol) then triflic anhydride (599 μL, 3.56 mmol) dropwise over 5 mins. The mixture was irradiated with blue LEDs for 2 hours at ambient temperature stirring at 800 rpm, using a PennPhD Photoreactor m2 (using 450 nm blue LED lights) and an EvoluChemm PhotoRedOx Box device (using 455 nm blue LED lights) used in parallel. This process was repeated in 5 batches and the crude material combined for purification. The combined reaction mixtures were washed with 1M NaCO$_3$ (2×80 mL) and the organic layer discarded. The combined aqueous layers were acidified to pH 2 using 1M HCl and extracted with MTBE (2×50 mL). The combined organic layers were washed with brine (20 mL), dried (MgSO$_4$) and concentrated in vacuo. The residue was redissolved in a small amount of diethyl ether and slowly triturated by addition of petroleum ether and allowed to stir. The liquid was decanted to afford 4-methyl-5-(trifluoromethyl)furan-2-carboxylic acid (700 mg at 90% purity, 55%) as an off-white solid. $^1$H NMR (400 MHz, DMSO-d$_6$) δ 13.75 (brs, 1H), 7.29 (d, J=1.2 Hz, 1H), 2.19 (q, J=2.0 Hz, 3H) ppm. ESI-MS m/z calc. 194.01907, found 193.3 (M−1)$^−$.

Step 4

To a solution of 4-methyl-5-(trifluoromethyl)furan-2-carboxylic acid (2.8 g, 14.03 mmol) in THF (40 mL) stirring at −78° C. was added n-BuLi (14 mL of 2.5 M in hexanes, 35.00 mmol). The solution was stirred at −78° C. for 20 mins before a solution of iodine (3.9 g, 15.37 mmol) in THF (5 mL) was added. The mixture was allowed to warm to ambient temperature, then partitioned between MTBE (80 mL) and water (100 mL). The organic layer was discarded and the aqueous layer acidified to pH 2 with 1 M HCl and extracted with MTBE (2×40 mL). The combined organic fractions were washed with brine (20 mL), dried (MgSO$_4$) and concentrated in vacuo. Purification by flash chromatography (40 g SiO$_2$, 0 to 100% MTBE in petroleum ether) gave 3-iodo-4-methyl-5-(trifluoromethyl)furan-2-carboxylic acid (3.1 g, 69%) as an oil. ESI-MS m/z calc. 319.9157, found 319.3 (M−1)$^−$.

Step 5

To a solution of 3-iodo-4-methyl-5-(trifluoromethyl)furan-2-carboxylic acid (300 mg at 71% purity, 0.6656 mmol) in DMF (5 mL) was added potassium carbonate (276 mg, 2.00 mmol) and iodoethane (160 μL, 2.00 mmol). The mixture was heated at 50° C. for 2 hours then cooled to ambient temperature and partitioned between MTBE (40 mL) and water (80 mL). The layers were separated and the aqueous layer further extracted with MTBE (30 mL). The combined organic fractions were washed with brine (1×20 mL), dried (MgSO$_4$) and concentrated in vacuo. Purification by flash chromatography (80 g SiO$_2$, 0 to 100% EtOAc in petroleum ether) gave ethyl 3-iodo-4-methyl-5-(trifluoromethyl)furan-2-carboxylate (220 mg at 80% purity, 76%) as an oil. $^1$H NMR (500 MHz, Chloroform-d) δ 4.42 (dq, J=20.1, 7.1 Hz, 2H), 2.24-2.11 (m, 3H), 1.42 (dt, J=20.2, 7.1 Hz, 3H) ppm.

Step 6

To a solution of ethyl 3-iodo-4-methyl-5-(trifluoromethyl)furan-2-carboxylate (500 mg at 71% purity, 1.01 mmol) in dioxane (2 mL) was added (3,4-difluoro-2-methoxy-phenyl)boronic acid (476 mg, 2.533 mmol), Pd(dppf)Cl$_2$DCM (83 mg, 0.10 mmol) and aqueous sodium carbonate (2 mL of 2 M, 4.00 mmol). The mixture was heated at 80° C. for 1 hour before being cooled to ambient temperature and partitioned between MTBE (30 mL) and water (30 mL). The layers were separated and the aqueous layer further extracted with MTBE (10 mL). The combined organic fractions were washed with brine (1×20 mL), dried (MgSO$_4$) and concentrated in vacuo. Purification by flash chromatography (12 g SiO$_2$, 0 to 100% EtOAc in petroleum ether) gave ethyl 3-(3,4-difluoro-2-methoxy-phenyl)-4-methyl-5-(trifluoromethyl)furan-2-carboxylate (330 mg at 80% purity, 71%) as an oil. ESI-MS m/z calc. 364.0734, found 365.4 (M+1)$^+$.

Step 7

A solution of ethyl 3-(3,4-difluoro-2-methoxy-phenyl)-4-methyl-5-(trifluoromethyl)furan-2-carboxylate (410 mg at 70% purity, 0.7879 mmol) in ethanol (2 mL) was passed through a 70 mm palladium hydroxide (90.52 mg, 0.64 mmol) CatCart® on an H-Cube® at 60° C. and 60 bar pressure of hydrogen. The mixture was recirculated for 30 hours before being concentrated in vacuo to give ethyl rac-(2S,3S,4S,5R)-3-(3,4-difluoro-2-methoxy-phenyl)-4-methyl-5-(trifluoromethyl)tetrahydrofuran-2-carboxylate (300 mg at 75% purity, 58%), which was used in the next step without further purification. ESI-MS m/z calc. 368.1047, found 369.3 (M+1)$^+$.

Step 8

To a solution of ethyl rac-(2S,3S,4S,5R)-3-(3,4-difluoro-2-methoxy-phenyl)-4-methyl-5-(trifluoromethyl)tetrahydrofuran-2-carboxylate (900 mg at 80% purity, 2.44 mmol) in THF (5 mL) stirring at 0° C. was added KOt-Bu (822 mg, 7.33 mmol). The reaction was stirred for 30 mins before being diluted with MTBE (5 mL) and quenched by addition of 1 M HCl. The layers were separated and the aqueous layer was further extracted with MTBE (5 mL). The combined organic layers were dried (MgSO$_4$), filtered and concentrated in vacuo to give rac-(2R,3S,4S,5R)-3-(3,4-difluoro-2-methoxy-phenyl)-4-methyl-5-(trifluoromethyl)tetrahydrofuran-2-carboxylic acid (500 mg at 52% purity, 31%) as an oil, which was used without further purification. ESI-MS m/z calc. 340.0734, found 339.4 (M−1)⁻.

Step 9

To an ice-cooled solution of rac-(2R,3S,4S,5R)-3-(3,4-difluoro-2-methoxy-phenyl)-4-methyl-5-(trifluoromethyl)tetrahydrofuran-2-carboxylic acid (380 mg at 52% purity, 0.58 mmol) in 2-methyltetrahydrofuran (5 mL) was added a solution of DMF (5 mg, 0.068 mmol) in 2-methyltetrahydrofuran and oxalyl chloride (116 μL, 1.330 mmol) dropwise. The mixture was warmed to ambient temperature over 30 mins then concentrated in vacuo. The residue was redissolved in 2-methyltetrahydrofuran (5 mL) and methyl 4-aminopyridine-2-carboxylate (114 mg, 0.75 mmol) and NEt$_3$ (162 μL, 1.16 mmol) were added. The mixture was warmed to ambient temperature over 1 hour before being quenched by the addition of water (10 mL). The layers were separated and the aqueous layer extracted with EtOAc (2×10 mL). The combined organic layers were dried (MgSO$_4$), filtered and concentrated in vacuo to give methyl rac-(2R,3S,4S,5R)-4-[[3-(3,4-difluoro-2-methoxy-phenyl)-4-methyl-5-(trifluoromethyl)tetrahydrofuran-2-carbonyl]amino]pyridine-2-carboxylate (210 mg at 86% purity, 65%). ESI-MS m/z calc. 474.1214, found 475.5 (M+1)⁺.

Step 10 and 11

To a solution of methyl rac-(2R,3S,4S,5R)-4-[[3-(3,4-difluoro-2-methoxy-phenyl)-4-methyl-5-(trifluoromethyl)tetrahydrofuran-2-carbonyl]amino]pyridine-2-carboxylate (200 mg at 86% purity, 0.42 mmol) in MeOH (2 mL) was added methanolic ammonia (322 μL of 7 M, 2.25 mmol). The mixture was stirred at ambient temperature for 6 hours before being concentrated in vacuo to afford rac-(2R,3S,4S,5R)-4-[[3-(3,4-difluoro-2-methoxy-phenyl)-4-methyl-5-(trifluoromethyl)tetrahydrofuran-2-carbonyl]amino]pyridine-2-carboxamide. The residue was purified by chiral SFC using a Chiralpak AS-H column, 5 μm particle size, 25 cm×10 mm from Daicel on a Minigram SFC instrument from Berger Instruments to give:

First Eluting Isomer: rel-(2R,3S,4S,5R)-4-[[3-(3,4-difluoro-2-methoxy-phenyl)-4-methyl-5-(trifluoromethyl)tetrahydrofuran-2-carbonyl]amino]pyridine-2-carboxamide (24, 60 mg). ¹H NMR (500 MHz, Chloroform-d) δ 8.75 (s, 1H), 8.49 (d, J=5.6 Hz, 1H), 8.14 (dd, J=5.5, 2.2 Hz, 1H), 8.02 (d, J=2.2 Hz, 1H), 7.85 (s, 1H), 7.10 (ddd, J=7.9, 5.4, 2.0 Hz, 1H), 6.94 (td, J=9.2, 7.5 Hz, 1H), 5.60 (s, 1H), 5.07 (d, J=10.7 Hz, 1H), 4.78-4.65 (m, 1H), 4.08-3.94 (m, 4H), 3.09-2.94 (m, 1H), 0.83 (dt, J=7.3, 2.0 Hz, 3H) ppm. ESI-MS m/z calc. 459.12173, found 460.2 (M+1)⁺.

Second Eluting Isomer: rel-(2S,3R,4R,5S)-4-[[3-(3,4-difluoro-2-methoxy-phenyl)-4-methyl-5-(trifluoromethyl)tetrahydrofuran-2-carbonyl]amino]pyridine-2-carboxamide (25, 68 mg). ¹H NMR (500 MHz, Chloroform-d) δ 8.75 (s, 1H), 8.49 (d, J=5.6 Hz, 1H), 8.14 (dd, J=5.5, 2.2 Hz, 1H), 8.02 (d, J=2.2 Hz, 1H), 7.85 (s, 1H), 7.10 (ddd, J=7.9, 5.4, 2.0 Hz, 1H), 6.94 (td, J=9.2, 7.5 Hz, 1H), 5.60 (s, 1H), 5.07 (d, J=10.7 Hz, 1H), 4.78-4.65 (m, 1H), 4.08-3.94 (m, 4H), 3.09-2.94 (m, 1H), 0.83 (dt, J=7.3, 2.0 Hz, 3H) ppm. ESI-MS m/z calc. 459.12173, found 460.2 (M+1)⁺.

Compound 25—Solid Form A

Compound 25 was dissolved in a 1:1 mixture of 2-methyltetrahydrofuran and heptane, and the mixture was subjected to slow evaporation of the solvent, producing a crystalline form of Compound 25, which is referred to herein as Form A. Form A was characterized by XRPD and solid state NMR (¹³C and ¹⁹F) analysis.

Figure 26:
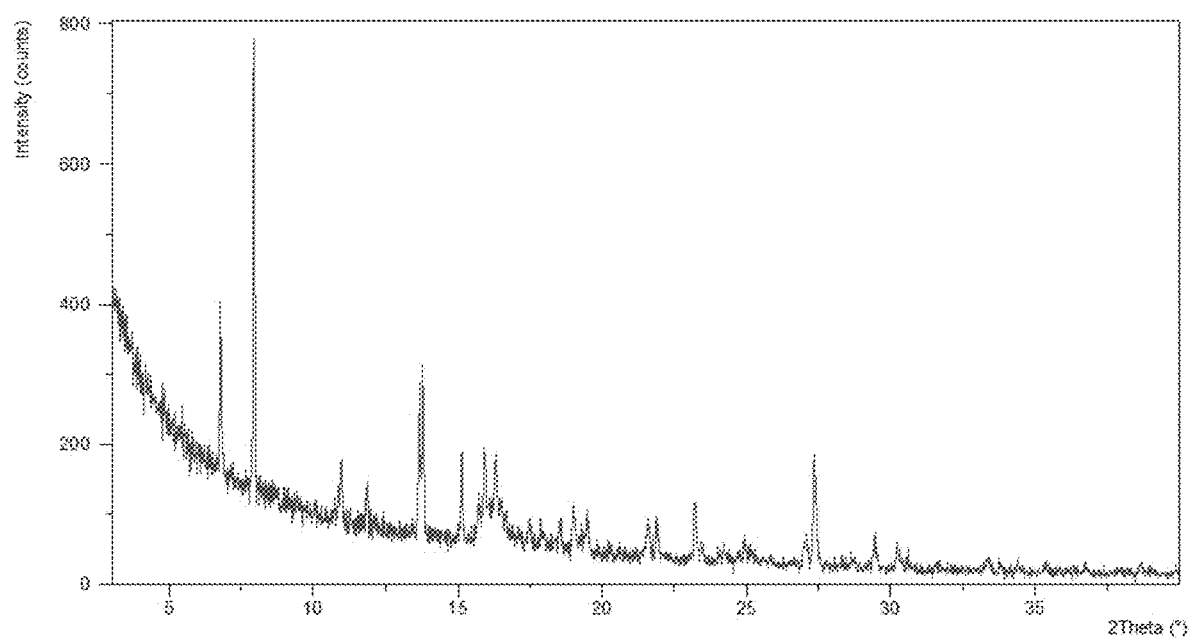
FIG. 26 depicts an XRPD pattern characteristic of Compound 25, Form A.

The XRPD pattern of Form A is depicted in FIG. 26, and the corresponding data are summarized in the following table:

| Angle (° 2θ ± 0.2) | Rel. Intensity (%) |
| --- | --- |
| 3.2 | 5.43 |
| 6.8 | 29.74 |
| 7.9 | 100 |
| 11.0 | 13.22 |
| 11.8 | 4.16 |
| 13.7 | 26.93 |
| 13.8 | 36.08 |
| 15.1 | 18 |
| 15.9 | 17.42 |
| 16.3 | 16.21 |
| 17.5 | 3.92 |
| 18.6 | 3.77 |
| 19.0 | 8.7 |
| 19.5 | 6.95 |
| 21.6 | 7.98 |
| 21.9 | 6.78 |
| 23.2 | 11.32 |
| 27.0 | 5.04 |
| 27.4 | 24.34 |
| 29.4 | 4.93 |
| 30.3 | 3.29 |

Example 8

(2R,3S,4S,5R)-4-[[3-(3,4-difluoro-2-hydroxy-phenyl)-4,5-dimethyl-5-(trifluoromethyl)tetrahydrofuran-2-carbonyl]amino]pyridine-2-carboxamide (27)

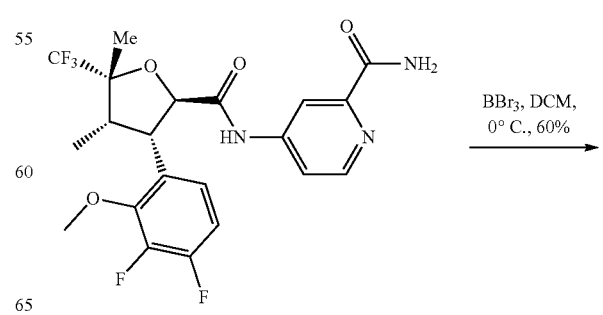

7

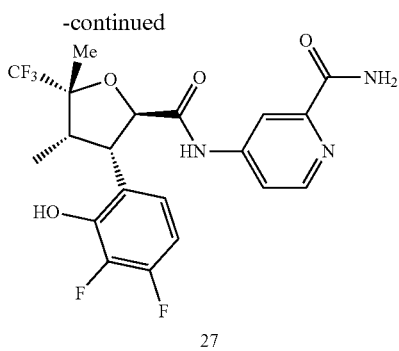

27

To a solution of (2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide (7, 280 mg, 0.59 mmol) in DCM (6 mL) stirring at 0° C. was added boron tribromide (830.0 µL of 1 M, 0.83 mmol). The mixture was warmed slowly to ambient temperature and stirred for 24 hours. The mixture was then cooled to 0° C. and additional boron tribromide (400 µL of 1 M, 0.40 mmol) was added. An additional portion of boron tribromide (400 µL of 1 M, 0.40 mmol) was added at 0° C., after which the mixture was warmed to and stirred at ambient temperature for 16 hours. Subsequently, water and saturated aqueous sodium bicarbonate solution were added and the mixture was stirred for 30 mins. The aqueous layer was isolated and extracted with DCM, and the combined organic layers were dried and concentrated in vacuo. Purification by flash chromatography (12 g SiO$_2$, 0 to 70% EtOAc in heptane) gave (2R,3S,4S,5R)-4-[[3-(3,4-difluoro-2-hydroxy-phenyl)-4,5-dimethyl-5-(trifluoromethyl)tetrahydrofuran-2-carbonyl]amino]pyridine-2-carboxamide (162 mg, 60%) (27). ESI-MS m/z calc. 459.12, found 460.7 (M+1)$^+$; 458.8 (M−1)$^-$. $^1$H NMR (500 MHz, DMSO-d$_6$) δ 10.73 (s, 1H), 10.46 (s, 1H), 8.50 (d, J=5.6 Hz, 1H), 8.27 (s, 1H), 8.06 (s, 1H), 7.86-7.82 (m, 1H), 7.61 (s, 1H), 7.06-7.00 (m, 1H), 6.89-6.83 (m, 1H), 5.15-5.08 (m, 1H), 4.29-4.22 (m, 1H), 2.86-2.80 (m, 1H), 1.61 (s, 3H), 0.72 (d, J=7.2 Hz, 3H) ppm.

The following compound was made using a method similar to that described in Example 8, except that (2R,3S,4S,5R)-4-[[3-(4-fluoro-2-methoxy-phenyl)-4,5-dimethyl-5-(trifluoromethyl)tetrahydrofuran-2-carbonyl]amino]pyridine-2-carboxamide was used as the starting material in place of (2R,3S,4S,5R)-4-[[3-(3,4-difluoro-2-methoxy-phenyl)-4,5-dimethyl-5-(trifluoromethyl)tetrahydrofuran-2-carbonyl]amino]pyridine-2-carboxamide:

Example 9 rel-(2S,3R,5S)-4-[[3-(3,4-difluoro-2-methoxy-phenyl)-5-ethyl-5-(trifluoromethyl)tetrahydrofuran-2-carbonyl]amino]pyridine-2-carboxamide (63) and rel-(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxamide (64)

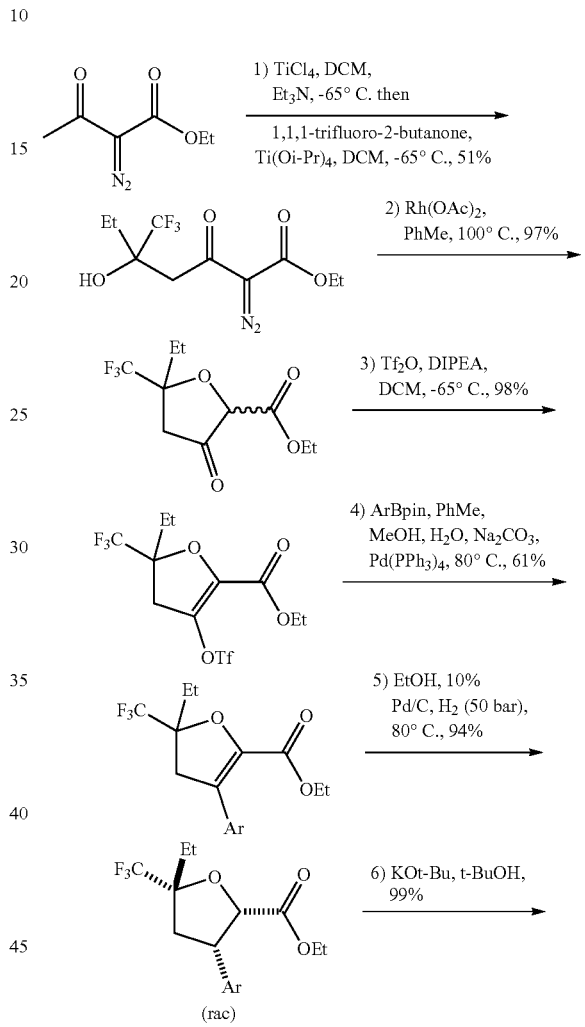

| Cmpd No. | Compound Name | LC/MS | NMR (shifts in ppm) |
|---|---|---|---|
| 62 | (2R,3S,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide | ESI-MS m/z calc. 489.10785, found 490.4 (M + 1)$^+$; 488.4 (M − 1)$^-$; Retention time: 3.21 minutes | $^1$H NMR (500 MHz, DMSO-d$_6$) δ: 10.80 (s, 1H), 8.50 (d, J = 5.5 Hz, 1H), 8.26 (d, J = 2.1 Hz, 1H), 8.07 (d, J = 2.9 Hz, 1H), 7.84 (dd, J = 2.2, 5.5 Hz, 1H), 7.62 (d, J = 2.9 Hz, 1H), 7.20 (t, J = 8.5 Hz, 1H), 6.62 (m, 2H), 5.10 (d, J = 10.4 Hz, 1H), 4.20 (dd, J = 7.5, 10.5 Hz, 1H), 2.83 (p, J = 7.4 Hz, 1H), 1.59 (br s, 3H), 0.70 (dd, J = 2.8, 7.6 Hz, 3H) ppm. Hydroxyl (OH) proton not observed. |

-continued

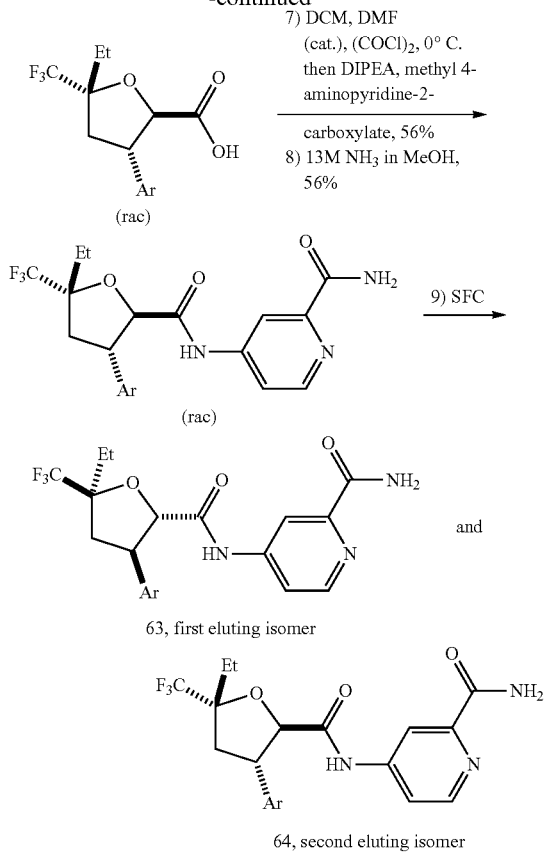

63, first eluting isomer 64, second eluting isomer

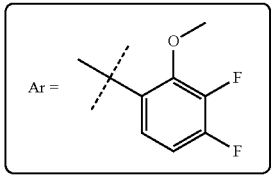

Step 1

To a solution of ethyl 2-diazo-3-oxo-butanoate (12 g, 76.9 mmol) in DCM (420 mL) stirring at −65° C. was added triethylamine (8.71 g, 12 mL, 86.1 mmol) and titanium tetrachloride (85 mL of 1 M, 85.0 mmol). The resulting deep red solution was stirred at −65° C. for 1 hour. A solution of 1,1,1-trifluoro-2-butanone (9.75 g, 10.5 mL, 77.4 mmol) and Ti(Oi-Pr)$_4$ (23.1 g, 24 mL, 81.3 mmol) in DCM (100 mL) was added dropwise and the resulting mixture was stirred at −65° C. for 2 hours then allowed to warm to ambient temperature overnight. The reaction mixture was quenched with saturated NH$_4$Cl solution (200 mL) and extracted with DCM (3×150 mL). The combined organic phases were dried over MgSO$_4$, filtered and concentrated in vacuo. Purification by reverse-phase flash chromatography (C18 silica, acetonitrile/water 0-70%) afforded ethyl 2-diazo-5-hydroxy-3-oxo-5-(trifluoromethyl)heptanoate (11.21 g, 51%) as a yellow liquid. $^1$H NMR (400 MHz, DMSO-d$_6$) δ 5.99 (s, 1H), 4.25 (q, J=7.1 Hz, 2H), 3.28 (d, J=15.4 Hz, 1H), 3.16 (d, J=15.4 Hz, 1H), 1.84 (dp, J=25.7, 7.1 Hz, 2H), 1.26 (t, J=7.1 Hz, 3H), 0.93 (td, J=7.5, 1.2 Hz, 3H) ppm; $^{19}$F NMR (376 MHz, DMSO-d$_6$) δ−78.78 ppm. ESI-MS m/z calc. 282.0827, found 282.95 (M+1)$^+$.

Step 2

To a stirred suspension of rhodium(II) acetate (89 mg, 0.2014 mmol) in toluene (90 mL) at 100° C. was added a solution of ethyl 2-diazo-5-hydroxy-3-oxo-5-(trifluoromethyl)heptanoate (5.8 g, 20.1 mmol) in toluene (200 mL). The reaction mixture was stirred at 100° C. for 1 hour before being cooled to ambient temperature and filtered through a Celite pad, washing with DCM (6×50 mL). The combined filtrates were concentrated in vacuo to afford ethyl 5-ethyl-3-oxo-5-(trifluoromethyl)tetrahydrofuran-2-carboxylate (5.22 g, 97%, mixture of four isomers) as a yellow oil. $^1$H NMR (400 MHz, DMSO-d$_6$) δ 4.99 (d, J=62.3 Hz, 1H), 4.18 (q, J=7.1 Hz, 2H), 3.18-2.98 (m, 1H), 2.90 (dd, J=19.2, 14.4 Hz, 1H), 2.03-1.79 (m, 2H), 1.21 (q, J=7.2 Hz, 3H), 1.05 (td, J=7.4, 0.9 Hz, 3H), 0.97 (td, J=7.5, 1.0 Hz, 1H) ppm; $^{19}$F NMR (376 MHz, DMSO-d$_6$) δ−78.68, −79.35 ppm.

Step 3

To a solution of ethyl 5-ethyl-3-oxo-5-(trifluoromethyl)tetrahydrofuran-2-carboxylate (4.25 g, 14.7 mmol) in DCM (120 mL) stirring at −65° C. was added DIPEA (5.79 g, 7.8 mL, 44.8 mmol) and trifluoromethylsulfonyl trifluoromethanesulfonate (5.37 g, 3.2 mL, 19.0 mmol). The resulting orange solution was stirred at −65° C. for 3 hours before being quenched with saturated aqueous NaHCO$_3$ solution (80 mL) and extracted with DCM (4×60 mL). The combined organic phases were dried over MgSO$_4$, filtered and concentrated in vacuo. The residue was dissolved in EtOAc (500 mL) and washed with 1 M HCl (5×100 mL). The organic phase was dried over Na$_2$SO$_4$, filtered and concentrated to afford ethyl 2-ethyl-2-(trifluoromethyl)-4-(trifluoromethylsulfonyloxy)-3H-furan-5-carboxylate (5.84 g, 98%). $^1$H NMR (300 MHz, Chloroform-d) δ 4.39 (q, J=7.2 Hz, 2H), 3.29 (d, J=17.5 Hz, 1H), 3.09 (d, J=17.5 Hz, 1H), 2.19-2.01 (m, 1H), 1.81 (dd, J=14.6, 7.4 Hz, 1H), 1.39 (t, J=7.2 Hz, 3H), 1.16-1.03 (m, 3H) ppm; $^{19}$F NMR (376 MHz, Chloroform-d) δ−73.84, −82.96 ppm.

Step 4

Ethyl 2-ethyl-2-(trifluoromethyl)-4-(trifluoromethylsulfonyloxy)-3H-furan-5-carboxylate (5.8 g, 14.3 mmol), 2-(3,4-difluoro-2-methoxy-phenyl)-4,4,5,5-tetramethyl-1,3,2-dioxaborolane (5.78 g, 21.4 mmol), sodium carbonate (3.78 g, 35.7 mmol), toluene (45 mL), MeOH (4.5 mL) and water (4.5 mL) were placed in a 120 mL glass pressure reactor. The mixture was degassed and purged with argon three times. Pd(PPh$_3$)$_4$ (1.24 g, 1.07 mmol) was added and the reactor was sealed and the mixture stirred at 80° C. overnight before being cooled to ambient temperature, diluted with EtOAc (50 mL) and filtered through a pad of Celite, washing with EtOAc (6×50 mL). Combined filtrates were concentrated in vacuo. Purification by flash chromatography (SiO$_2$, 0-5% EtOAc in hexane) gave ethyl 4-(3,4-difluoro-2-methoxy-phenyl)-2-ethyl-2-(trifluoromethyl)-3H-furan-5-carboxylate (2.7 g, 45%) as a yellow oil. Repurification of mixed fractions by flash chromatography (SiO$_2$, 0-10% EtOAc in hexane) gave ethyl 4-(3,4-difluoro-2-methoxy-phenyl)-2-ethyl-2-(trifluoromethyl)-3H-furan-5-carboxylate (0.9 g, 16%) as a light-yellow oil. $^1$H NMR (300 MHz, Chloroform-d) δ 6.97-6.82 (m, 2H), 4.18 (q, J=7.1 Hz, 2H), 3.92 (d, J=2.0 Hz, 3H), 3.32 (d, J=17.7 Hz, 1H), 3.09 (dd, J=17.7, 1.0 Hz, 1H), 2.13 (dq, J=14.9, 7.5 Hz, 1H), 1.82 (dq, J=14.7, 7.4 Hz, 1H), 1.15 (dt, J=12.4, 7.4 Hz, 6H) ppm; $^{19}$F NMR (376 MHz, Chloroform-d) δ−82.50, −135.66 (ddd, J=20.2, 9.4, 6.3 Hz), −154.83-−154.95 (m) ppm. ESI-MS m/z calc. 380.1047, found 381.0 (M+1)⁺.

Step 5

A solution of ethyl 4-(3,4-difluoro-2-methoxy-phenyl)-2-ethyl-2-(trifluoromethyl)-3H-furan-5-carboxylate (240 mg, 0.60 mmol) in ethanol (15 mL) was hydrogenated in an H-cube apparatus using a Pd/C catalytic cartridge at 80° C. and 50 bar, with flow rate of 0.5 ml/min. The mixture was concentrated in vacuo to afford ethyl rac-(2S,3S,5R)-3-(3,4-difluoro-2-methoxy-phenyl)-5-ethyl-5-(trifluoromethyl)tetrahydrofuran-2-carboxylate (185 mg, 77%, mixture of four isomers) as a white solid; $^1$H NMR (300 MHz, Chloroform-d) δ 7.06-6.71 (m, 2H), 4.95 (d, J=9.1 Hz, 1H), 4.29-4.15 (m, 1H), 4.09 (d, J=2.9 Hz, 3H), 3.82 (dddd, J=17.9, 10.8, 7.1, 3.7 Hz, 2H), 2.77 (t, J=12.5 Hz, 1H), 2.15 (dd, J=12.4, 7.3 Hz, 1H), 1.93 (dq, J=13.8, 7.3 Hz, 2H), 1.11 (td, J=7.6, 1.3 Hz, 3H), 0.97 (t, J=7.2 Hz, 3H) ppm; $^{19}$F NMR (376 MHz, Chloroform-d) δ−76.93, −79.92, −136.98 (ddd, J=19.4, 9.6, 5.4 Hz), −153.95 (d, J=12.5 Hz), −154.80 (ddt, J=19.5, 6.2, 2.9 Hz) ppm.

Step 6

To a solution of ethyl rac-(2S,3S,5R)-3-(3,4-difluoro-2-methoxy-phenyl)-5-ethyl-5-(trifluoromethyl)tetrahydrofuran-2-carboxylate (100 mg, 0.25 mmol) in tert-butanol (3 mL) at ambient temperature was added potassium 2-methylpropan-2-olate (84 mg, 0.75 mmol). The reaction mixture was stirred for 1 hour before being quenched with saturated aqueous NH₄Cl solution (1 mL) and extracted with EtOAc (3×5 mL). The combined organic layers were dried over Na₂SO₄, filtered and concentrated in vacuo to afford rac-(2R,3S,5R)-3-(3,4-difluoro-2-methoxy-phenyl)-5-ethyl-5-(trifluoromethyl)tetrahydrofuran-2-carboxylic acid (93 mg, 99%, mixture of four isomers) as a yellow oil. $^1$H NMR (300 MHz, Chloroform-d) δ 7.02-6.83 (m, 2H), 4.68 (d, J=10.8 Hz, 1H), 3.98 (d, J=2.6 Hz, 3H), 3.76 (q, J=10.6 Hz, 1H), 2.55-2.33 (m, 2H), 1.95 (dt, J=14.7, 7.3 Hz, 1H), 1.79 (dq, J=14.6, 7.4 Hz, 1H), 1.12 (t, J=7.4 Hz, 3H) ppm; $^{19}$F NMR (376 MHz, Chloroform-d) δ−77.01, −79.71, −79.93, −137.04 (ddd, J=19.3, 9.5, 5.6 Hz), −153.72 (d, J=20.7 Hz), −153.92 (ddd, J=19.5, 5.0, 2.6 Hz), −154.79 (d, J=19.5 Hz) ppm. ESI-MS m/z calc. 354.089, found 353.4 (M−1)⁻.

Step 7

To a solution of rac-(2R,3S,5R)-3-(3,4-difluoro-2-methoxy-phenyl)-5-ethyl-5-(trifluoromethyl)tetrahydrofuran-2-carboxylic acid (290 mg, 0.8186 mmol) in DCM (6 mL) stirring at 0° C. was added a catalytic amount of DMF (15.1 mg, 16 µL, 0.21 mmol) and oxalyl chloride (291 mg, 194 µL, 2.29 mmol). The mixture was stirred at 0° C. for 2 hours then concentrated in vacuo and azeotroped with DCM (3×5 mL). The residue was taken up in DCM (6 mL) and the resulting solution added to ice-cooled solution of methyl 4-aminopyridine-2-carboxylate (137 mg, 0.9004 mmol) and DIPEA (445.20 mg, 0.6 mL, 3.4447 mmol) in DCM (6 mL). The resulting mixture was stirred at 0° C. for 1 hour and then 60 hours at ambient temperature. The mixture was poured into water (10 mL) and extracted with DCM (3×10 mL). The combined organic layers were dried over Na₂SO₄, filtered and concentrated. Purification using flash chromatography (SiO₂, 0 to 60% EtOAc in hexane) gave methyl rac-(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxylate (223 mg, 56%, mixture of four isomers) as a white foam. H NMR (300 MHz, Chloroform-d) δ 8.65 (d, J=5.5 Hz, 1H), 8.53 (s, 1H), 8.10-8.06 (m, 1H), 7.96 (dd, J=5.5, 2.2 Hz, 1H), 7.08-6.86 (m, 2H), 4.82 (d, J=10.9 Hz, 1H), 4.03 (s, 3H), 4.00 (d, J=2.6 Hz, 3H), 3.75 (td, J=11.1, 9.0 Hz, 1H), 2.63-2.38 (m, 2H), 2.18-1.84 (m, 2H), 1.24-1.12 (m, 3H) ppm; $^{19}$F NMR (376 MHz, Chloroform-d) δ −76.90, −79.76, −136.20 (ddd, J=19.2, 9.1, 5.7 Hz), −136.61 (ddd, J=19.3, 9.4, 5.6 Hz), −153.43-−153.56 (m), −153.95-−154.06 (m) ppm. ESI-MS m/z calc. 488.1371, found 489.2 (M+1)⁺; 487.1 (M−1)⁻.

Step 8

Methyl rac-(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxylate (200 mg, 0.41 mmol) was dissolved in methanolic ammonia (2.2 mL of 13 M, 28.6 mmol). The solution was stirred at ambient temperature overnight then concentrated in vacuo and the residue azeotroped with MeOH (3×5 mL) to give rac-(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxamide (108 mg, 56%, mixture of four isomers) as a light-yellow solid. $^1$H NMR (300 MHz, Chloroform-d) δ 8.58 (s, 1H), 8.49 (d, J=5.5 Hz, 1H), 8.19 (dd, J=5.6, 2.3 Hz, 1H), 7.92 (d, J=2.2 Hz, 1H), 7.85 (d, J=8.5 Hz, 1H), 7.09-6.85 (m, 2H), 5.60 (s, 1H), 4.80 (d, J=10.9 Hz, 1H), 4.00 (d, J=2.6 Hz, 3H), 3.74 (q, J=10.8 Hz, 1H), 2.63-2.37 (m, 2H), 1.99 (ddt, J=37.8, 14.5, 7.3 Hz, 2H), 1.18 (t, J=7.5 Hz, 3H) ppm; $^{19}$F NMR (376 MHz, Chloroform-d) δ−76.93, −79.78, −136.32 (ddd, J=19.5, 9.5, 5.8 Hz), −136.69 (ddd, J=19.3, 9.4, 5.6 Hz), −153.54 (dd, J=19.1, 6.3 Hz), −154.05 (d, J=19.6 Hz) ppm. ESI-MS m/z calc. 473.1374, found 474.15 (M+1)⁺; 472.15 (M−1)⁻.

Step 9 rac-(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxamide (108 mg, 0.23 mmol) was separated by chiral SFC using a Lux Cellulose-2 column, 5 um particle size, 25 cm×10 mm from Phenomenex, Inc. to give two single isomers of unknown absolute configuration:

First Eluting Isomer (rt=3.22 min): rel-(2S,3R,5S)-4-[[3-(3,4-difluoro-2-methoxy-phenyl)-5-ethyl-5-(trifluoromethyl)tetrahydrofuran-2-carbonyl]amino]pyridine-2-carboxamide (63, 29 mg, 27%); ESI-MS m/z calc. 473.1374, found 474.4 (M+1)⁺ and 472.4 (M−1)⁻.

Second Eluting Isomer (rt=4.63 min): rel-(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxamide (64, 35 mg, 32%); ESI-MS m/z calc. 473.1374, found 474.4 (M+1)⁺ and 472.4 (M−1)⁻.

The following compounds were made using a method similar to that described in Example 9, except that trimethylacetaldehyde was used as the starting material in place of 1,1,1-trifluoro-2-butanone in step 1. In step 9, purification was performed by chiral SFC using a (R,R)-Whelk-O1 column, 5 µm particle size, 25 cm×21.2 mm from Regis Technologies on a Minigram SFC instrument from Berger Instruments:

| Cmpd No. | Compound Name | LC/MS | NMR (shifts in ppm) |
|---|---|---|---|
| 65 | rel-(2S,3R,5S)-4-[[5-tert-butyl-3-(3,4-difluoro-2-methoxy-phenyl)tetrahydrofuran-2-carbonyl]amino]pyridine-2-carboxamide (first eluting isomer by SFC on Whelk01 column, rt = 1.18 min) | ESI-MS m/z calc. 433.1813, found 434.2 (M + 1)+; 432.3 (M − 1)−; Retention time: 3.23 minutes | $^1$H NMR (500 MHz, Chloroform-d) δ 8.62 (s, 1H), 8.46 (d, J = 5.5 Hz, 1H), 8.18 (dd, J = 5.6, 2.2 Hz, 1H), 8.13 (s, 1H), 7.93 (d, J = 2.2 Hz, 1H), 7.25 (dd, J = 8.8, 5.8 Hz, 1H), 7.07-6.95 (m, 1H), 4.75 (d, J = 10.7 Hz, 1H), 3.99-3.85 (m, 1H), 3.89 (s, 3H), 3.06 (d, J = 5.0 Hz, 3H), 2.51 (dd, J = 13.2, 11.7 Hz, 1H), 2.42 (dd, J = 13.2, 8.3 Hz, 1H), 1.68 (s, 3H) ppm. |
| 66 | rel-(2R,3S,5R)-4-[[5-tert-butyl-3-(3,4-difluoro-2-methoxy-phenyl)tetrahydrofuran-2-carbonyl]amino]pyridine-2-carboxamide (second eluting isomer by SFC on Whelk01 column, rt = 1.68 min) | ESI-MS m/z calc. 433.1813, found 434.2 (M + 1)+; 432.3 (M − 1)−; Retention time: 3.23 minutes | $^1$H NMR (500 MHz, Chloroform-d) δ 8.48 (s, 1H), 8.36 (d, J = 5.5 Hz, 1H), 8.08-8.00 (m, 2H), 7.86 (d, J = 2.2 Hz, 1H), 7.14 (dd, J = 8.8, 5.9 Hz, 1H), 6.92 (dd, J = 8.8, 8.1 Hz, 1H), 4.71 (d, J = 9.7 Hz, 1H), 4.01-3.91 (m, 1H), 3.84 (s, 3H), 2.97 (d, J = 5.1 Hz, 3H), 2.77 (dd, J = 13.9, 8.4 Hz, 1H), 2.03 (dd, J = 13.8, 11.7 Hz, 1H), 1.56 (s, 2H) ppm. |

Example 10 rel-(2S,3R,5S)-4-[[3-(4-fluoro-2-methoxy-phenyl)-5-methyl-5-(trifluoromethyl)tetrahydrofuran-2-carbonyl]amino]pyridine-2-carboxamide (67) and rel-(2R,3S,5R)-4-[[3-(4-fluoro-2-methoxy-phenyl)-5-methyl-5-(trifluoromethyl)tetrahydrofuran-2-carbonyl]amino]pyridine-2-carboxamide (68)

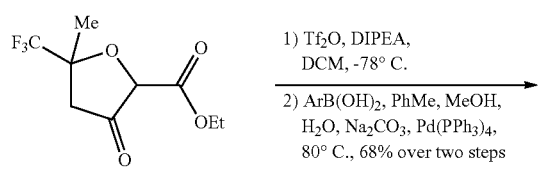

1) Tf$_2$O, DIPEA, DCM, −78° C.
2) ArB(OH)$_2$, PhMe, MeOH, H$_2$O, Na$_2$CO$_3$, Pd(PPh$_3$)$_4$, 80° C., 68% over two steps

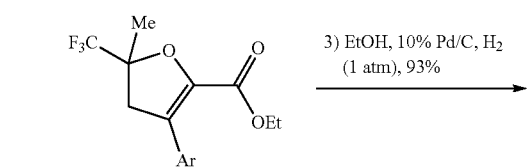

3) EtOH, 10% Pd/C, H$_2$ (1 atm), 93%

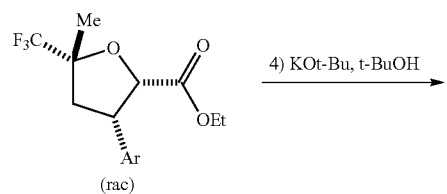

4) KOt-Bu, t-BuOH

-continued

5) DCM, DMF (cat.), (COCl)$_2$ then NEt$_3$, methyl 4-aminopyridine-2-carboxylate, DMAP, DCM, 49%
6) 7M NH$_3$ in MeOH

7) SFC

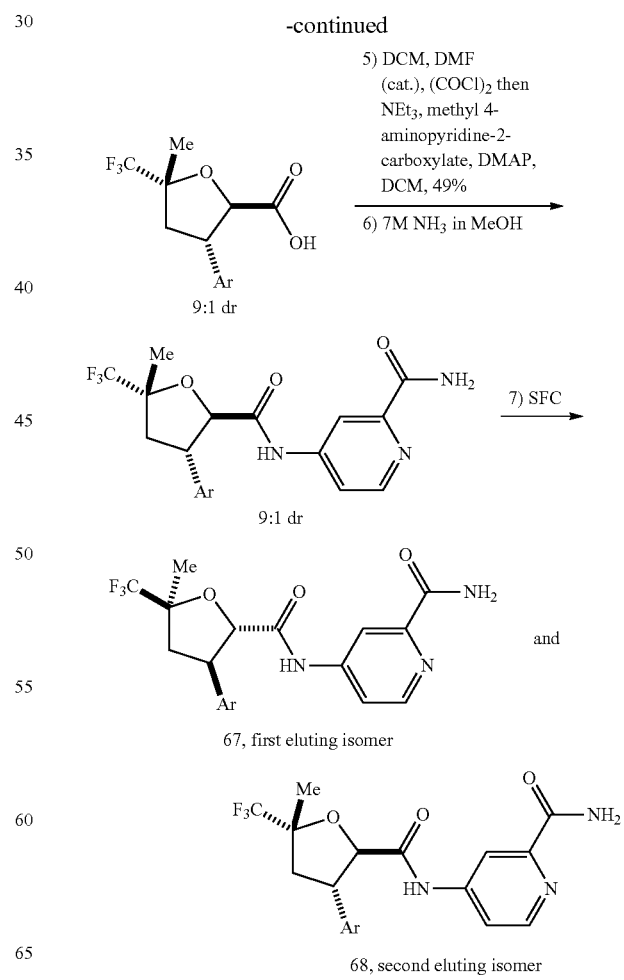

67, first eluting isomer and 68, second eluting isomer

Ar = 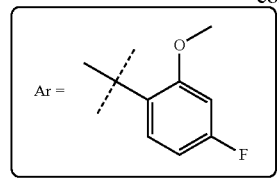

Step 1:

Triflic anhydride (1.5 mL, 8.92 mmol) was added dropwise to a solution of ethyl 5-methyl-3-oxo-5-(trifluoromethyl)tetrahydrofuran-2-carboxylate (1.66 g, 6.91 mmol) and DIPEA (3.6 mL, 20.67 mmol) in DCM (50 mL) stirring at −78° C. After 3 hours saturated aqueous NaHCO$_3$ was added, the layers separated and the aqueous layer extracted with DCM. The combined organic layers were dried (MgSO$_4$), filtered and concentrated in vacuo to give ethyl 2-methyl-2-(trifluoromethyl)-4-(trifluoromethylsulfonyloxy)-3H-furan-5-carboxylate (2.573 g), which was used in the next step without further purification.

Step 2

A solution of ethyl 2-methyl-2-(trifluoromethyl)-4-(trifluoromethylsulfonyloxy)-3H-furan-5-carboxylate (2.573 g, 6.91 mmol), (4-fluoro-2-methoxy-phenyl)boronic acid (1.84 g, 10.83 mmol), Pd(PPh$_3$)$_4$ (600 mg, 0.52 mmol) and Na$_2$CO$_3$ (1.8 g, 16.98 mmol) in PhMe (30 mL), MeOH (3 mL) and H$_2$O (3 mL) was degassed, then heated at 80° C. for 16 hours. The reaction was cooled to ambient temperature, diluted with EtOAc, the layers separated and the organic layer washed with brine, dried (MgSO$_4$), filtered and concentrated in vacuo. Purification by flash chromatography (80 g SiO$_2$, 0 to 20% EtOAc in petrol) gave ethyl 4-(4-fluoro-2-methoxy-phenyl)-2-methyl-2-(trifluoromethyl)-3H-furan-5-carboxylate (1.64 g, 68% over two steps) as a yellow oil. ESI-MS m/z calc. 348.09848, found 349.2 (M+1)$^+$.

Step 3

EtOH (45 mL) was added to a flask containing ethyl 4-(4-fluoro-2-methoxy-phenyl)-2-methyl-2-(trifluoromethyl)-3H-furan-5-carboxylate (1.64 g, 4.71 mmol) and Pd/C (500 mg, 0.47 mmol). The mixture was degassed then stirred under a balloon of hydrogen for 24 hours. The mixture was filtered through Celite, washing with EtOH, and concentrated in vacuo. Pd/C (500 mg, 0.47 mmol) was added to the residue, and the mixture was suspended in EtOH (45 mL). The mixture was degassed then stirred under a balloon of hydrogen for 24 hours. The mixture was filtered through Celite, washing with EtOH, and concentrated in vacuo to give ethyl rac-(2S,3S,5R)-3-(4-fluoro-2-methoxy-phenyl)-5-methyl-5-(trifluoromethyl)tetrahydrofuran-2-carboxylate (1.53 g, 93%) as an off-white solid. ESI-MS m/z calc. 350.11414, found 351.2 (M+1)$^+$.

Step 4

A solution of ethyl rac-(2S,3S,5R)-3-(4-fluoro-2-methoxy-phenyl)-5-methyl-5-(trifluoromethyl)tetrahydrofuran-2-carboxylate (10 mg, 0.029 mmol) and KOt-Bu (192 mg, 1.711 mmol) in tert-butanol (0.3 mL) was stirred at ambient temperature for 20 mins. The reaction was diluted in EtOAc and quenched by addition of saturated aqueous NH4Cl solution. This process was repeated a further 19 times and the 20 reactions combined for the rest of the work-up. The layers were separated and the aqueous layer extracted with EtOAc. The aqueous layer was then acidified with 1 M HCl and extracted again. The combined organic layers were dried (MgSO$_4$), filtered and concentrated in vacuo to give rac-(2R,3S,5R)-3-(4-fluoro-2-methoxy-phenyl)-5-methyl-5-(trifluoromethyl)tetrahydrofuran-2-carboxylic acid (186 mg) as an orange residue, in an 9:1 diastereomeric ratio, which was taken on to the next step without further purification.

Step 5

To a solution of rac-(2R,3S,5R)-3-(4-fluoro-2-methoxy-phenyl)-5-methyl-5-(trifluoromethyl)tetrahydrofuran-2-carboxylic acid (222 mg in 9:1 diastereomeric ratio, 0.69 mmol) in DCM (7.0 mL) was added DMF (10 µL, 0.13 mmol) and oxalyl chloride (200 µL, 2.29 mmol). The reaction was stirred at ambient temperature for 30 mins before being concentrated in vacuo. The residue was diluted in DCM (5 mL) and added dropwise to a solution of methyl 4-aminopyridine-2-carboxylate (160 mg, 1.05 mmol) and Et$_3$N (500 µL, 3.59 mmol) in DCM (2.0 mL) stirring at 0° C. DMAP (8 mg, 0.06548 mmol) was added and the reaction stirred at 0° C. for 10 mins, then warmed to ambient temperature and stirred for a further 16 hours. The reaction mixture was diluted in DCM and washed with 2M HCl solution. The organic layer was dried (MgSO$_4$), filtered and concentrated in vacuo directly onto silica gel. Purification by flash chromatography (40 g SiO$_2$, 0 to 100% EtOAc in petrol) gave methyl rac-(2R,3S,5R)-4-[[3-(4-fluoro-2-methoxy-phenyl)-5-methyl-5-(trifluoromethyl)tetrahydrofuran-2-carbonyl]amino]pyridine-2-carboxylate (154 mg, 49%) as a 9:1 mixture of diastereomers. ESI-MS m/z calc. 456.13083, found 457.3 (M+1)$^+$; 455.2 (M−1)$^−$.

Step 6

Methyl rac-(2R,3S,5R)-4-[[3-(4-fluoro-2-methoxy-phenyl)-5-methyl-5-(trifluoromethyl)tetrahydrofuran-2-carbonyl]amino]pyridine-2-carboxylate (154 mg in a 9:1 mixture of diastereomers, 0.34 mmol) was dissolved in methanolic ammonia (2.0 mL of 7 M, 14.00 mmol) and the solution stirred at ambient temperature overnight, then the mixture was concentrated in vacuo to give rac-(2R,3S,5R)-4-[[3-(4-fluoro-2-methoxy-phenyl)-5-methyl-5-(trifluoromethyl)tetrahydrofuran-2-carbonyl]amino]pyridine-2-carboxamide, as a mixture of diastereomers. ESI-MS m/z calc. 441.13116, found 442.1 (M+1)$^+$; 440.3 (M−1)$^−$.

Step 7

The enantiomers of the major diastereomer of rac-(2R,3S,5R)-4-[[3-(4-fluoro-2-methoxy-phenyl)-5-methyl-5-(trifluoromethyl)tetrahydrofuran-2-carbonyl]amino]pyridine-2-carboxamide (15 mg, 0.03398 mmol) were separated by chiral SFC using a Chiralpak AS-H column, 5 um particle size, 25 cm×21.2 mm from Daicel Corporation to give two single isomers of unknown absolute configuration:

First Eluting Isomer (rt=1.44 min): rel-(2S,3R,5S)-4-[[3-(4-fluoro-2-methoxy-phenyl)-5-methyl-5-(trifluoromethyl)tetrahydrofuran-2-carbonyl]amino]pyridine-2-carboxamide (67, 3.2 mg, 42%); ESI-MS m/z calc. 441.13116, found 442.8 (M+1)$^+$; 440.8 (M−1)$^−$; Retention time: 2.98 mins. $^1$H NMR (500 MHz, DMSO-d$_6$) δ 10.28 (s, 1H), 8.37 (d, J=5.4 Hz, 1H), 8.08-7.94 (m, 2H), 7.56 (s, 1H), 7.54-7.45 (m, 1H), 7.20 (t, J=7.6 Hz, 1H), 6.76 (dd, J=11.3, 2.5 Hz, 1H), 6.64 (td, J=8.6, 2.6 Hz, 1H), 5.10 (d, J=8.4 Hz, 1H), 4.22-4.06 (m, 1H), 3.77 (s, 3H), 2.91 (t, J=12.3 Hz, 1H), 2.24 (dd, J=11.6, 6.7 Hz, 1H), 1.49 (s, 3H) ppm.

Second Eluting Isomer (rt=1.63 min): rel-(2R,3S,5R)-4-[[3-(4-fluoro-2-methoxy-phenyl)-5-methyl-5-(trifluoromethyl)tetrahydrofuran-2-carbonyl]amino]pyridine-2-carboxamide (68, 4.1 mg, 52%). ESI-MS m/z calc. 441.13116, found 442.8 (M+1)$^+$; 440.8 (M−1)$^−$; Retention time: 2.98 mins.

The following compounds were made using the method described in Example 10, taking forward the minor diastereoisomer formed in step 4. In step 7, purification was performed by chiral SFC using a (R,R)-Whelk-O1 column, 5 μm particle size, 25 cm×21.1 mm from Daicel on a Minigram SFC instrument from Berger Instruments:

| Cmpd No. | Compound Name | LC/MS | NMR (shifts in ppm) |
|---|---|---|---|
| 69 | rel-(2R,3R,5S)-4-[[3-(4-fluoro-2-methoxy-phenyl)-5-methyl-5-(trifluoromethyl)tetrahydrofuran-2-carbonyl]amino]pyridine-2-carboxamide (first eluting isomer by SFC on (R,R)-Whelk-O1 column, rt = 1.44 min) | ESI-MS m/z calc. 441.13116, found 442.1 (M + 1)$^+$; 440.2 (M − 1)$^−$; Retention time: 2.85 minutes | $^1$H NMR (500 MHz, DMSO-d$_6$) δ 10.28 (s, 1H), 8.37 (d, J = 5.4 Hz, 1H), 8.08-7.94 (m, 2H), 7.56 (s, 1H), 7.54-7.45 (m, 1H), 7.20 (t, J = 7.6 Hz, 1H), 6.76 (dd, J = 11.3, 2.5 Hz, 1H), 6.64 (td, J = 8.6, 2.6 Hz, 1H), 5.10 (d, J = 8.4 Hz, 1H), 4.22-4.06 (m, 1H), 3.77 (s, 3H), 2.91 (t, J = 12.3 Hz, 1H), 2.24 (dd, J = 11.6, 6.7 Hz, 1H), 1.49 (s, 3H) ppm. |
| 70 | rel-(2S,3S,5R)-4-[[3-(4-fluoro-2-methoxy-phenyl)-5-methyl-5-(trifluoromethyl)tetrahydrofuran-2-carbonyl]amino]pyridine-2-carboxamide (second eluting isomer by SFC on (R,R)-Whelk-O1 column, rt = 1.63 min) | ESI-MS m/z calc. 441.13116, found 442.2 (M + 1)$^+$; 440.7 (M − 1)$^−$; Retention time: 2.85 minutes | |

30

The following compounds were made using the method described in Example 10, except that 2-(4-fluoro-2-methoxy-3-methyl-phenyl)-4,4,5,5-tetramethyl-1,3,2-dioxaborolane was used as coupling partner in the Suzuki coupling step 2. In step 4, THF was used as solvent rather than tert-butanol. In step 7, purification was performed by chiral SFC using a (R,R)-Whelk-O1 column, 5 μm particle size, 25 cm×21.1 mm from Daicel on a Minigram SFC instrument from Berger Instruments:

| Cmpd No. | Compound Name | LC/MS | NMR (shifts in ppm) |
|---|---|---|---|
| 71 | rel-(2S,3R,5S)-4-[[3-(4-fluoro-2-methoxy-3-methyl-phenyl)-5-methyl-5-(trifluoromethyl)tetrahydrofuran-2-carbonyl]amino]pyridine-2-carboxamide (first eluting isomer by SFC on (R,R)-Whelk-O1 column, rt = 1.05 min) | ESI-MS m/z calc. 455.14682, found 456.2 (M + 1)$^+$; 454.2 (M − 1)$^−$; Retention time: 3.05 minutes | |
| 72 | rel-(2R,3S,5R)-4-[[3-(4-fluoro-2-methoxy-3-methyl-phenyl)-5-methyl-5-(trifluoromethyl)tetrahydrofuran-2-carbonyl]amino]pyridine-2-carboxamide (second eluting isomer by SFC on (R,R)-Whelk-O1 column, rt = 1.73 min) | ESI-MS m/z calc. 455.14682, found 456.2 (M + 1)$^+$; 454.2 (M − 1)$^−$; Retention time: 3.06 minutes | $^1$H NMR (500 MHz, DMSO-d$_6$) δ 10.47 (s, 1H), 8.48 (dd, J = 5.5, 0.6 Hz, 1H), 8.24 (dd, J = 2.2, 0.6 Hz, 1H), 8.04 (d, J = 2.8 Hz, 1H), 7.81 (dd, J = 5.5, 2.2 Hz, 1H), 7.65-7.55 (m, 1H), 7.26 (dd, J = 8.7, 6.5 Hz, 1H), 7.02 (t, J = 8.8 Hz, 1H), 4.64 (d, J = 10.1 Hz, 1H), 4.15-4.04 (m, 1H), 3.63 (s, 3H), 2.49-2.46 (m, 1H), 2.33 (t, J = 12.4 Hz, 1H), 2.11 (d, J = 2.0 Hz, 3H), 1.58 (s, 3H) ppm. |

The following compounds were made using the method described in Example 10, except that 2-[2-(difluoromethoxy)-4-fluoro-phenyl]-4,4,5,5-tetramethyl-1,3,2-dioxaborolane was used as coupling partner in the Suzuki coupling step 2 and the conditions used for the epimerization/hydrolysis step 4 are similar to the ones used in Example 2 step 7. In step 7, purification was performed by chiral SFC using a (R,R)-Whelk-O1 column, 5 μm particle size, 25 cm×21.1 mm from Daicel on a Minigram SFC instrument from Berger Instruments:

| Cmpd No. | Compound Name | LC/MS | NMR (shifts in ppm) |
|---|---|---|---|
| 73 | rel-(2S,3R,5S)-4-[[3-[2-(difluoromethoxy)-4-fluoro-phenyl]-5-methyl-5-(trifluoromethyl)tetrahydrofuran-2-carbonyl]amino]pyridine-2-carboxamide (first eluting isomer by SFC on (R,R)-Whelk-O1 column, rt = 2.61 min) | ESI-MS m/z calc. 477.11234, found 478.6 (M + 1)$^+$; 476.6 (M − 1)$^-$; Retention time: 3.03 minutes | $^1$H NMR (500 MHz, DMSO-$d_6$) δ 10.42 (s, 1H), 8.48 (d, J = 5.5 Hz, 1H), 8.25 (d, J = 2.2 Hz, 1H), 8.05 (d, J = 2.8 Hz, 1H), 7.83 (dd, J = 5.5, 2.2 Hz, 1H), 7.59 (d, J = 2.8 Hz, 1H), 7.56-7.49 (m, 1H), 7.42-7.07 (m, 3H), 4.69 (d, J = 10.1 Hz, 1H), 4.05 (ddd, J = 11.8, 10.1, 8.1 Hz, 1H), 2.57-2.51 (m, 1H), 2.43 (dd, J = 12.8, 8.2 Hz, 1H), 1.57 (s, 3H) ppm. |
| 74 | rel-(2R,3S,5R)-4-[[3-[2-(difluoromethoxy)-4-fluoro-phenyl]-5-methyl-5-(trifluoromethyl)tetrahydrofuran-2-carbonyl]amino]pyridine-2-carboxamide (second eluting isomer by SFC on (R,R)-Whelk-O1 column, rt = 3.32 min) | ESI-MS m/z calc. 477.11234, found 478.6 (M + 1)$^+$; 476.6 (M − 1)$^-$; Retention time: 3.04 minutes | |

The following compounds were made using the method described in Example 10, except that (2,4-difluoro-3-methyl-phenyl)boronic acid was used as coupling partner in the Suzuki coupling step 2 and the conditions used for the epimerization/hydrolysis step 4 are similar to the ones used in Example 1 step 3:

| Cmpd No. | Compound Name | LC/MS | NMR (shifts in ppm) |
|---|---|---|---|
| 75 | rel-(2S,3R,5S)-4-[[3-(2,4-difluoro-3-methyl-phenyl)-5-methyl-5-(trifluoromethyl)tetrahydrofuran-2-carbonyl]amino]pyridine-2-carboxamide (first eluting isomer by SFC on Chiralpak AS-H column, rt = 2.89 min) | ESI-MS m/z calc. 443.12683, found 444.6 (M + 1)$^+$; 442.7 (M − 1)$^-$; Retention time: 3.12 minutes | $^1$H NMR (500 MHz, DMSO-$d_6$) δ 10.46 (s, 1H), 8.49 (d, J = 5.5 Hz, 1H), 8.26 (d, J = 2.2 Hz, 1H), 8.11-7.99 (m, 1H), 7.80 (dd, J = 5.5, 2.2 Hz, 1H), 7.60 (d, J = 2.8 Hz, 1H), 7.31 (td, J = 8.5, 6.3 Hz, 1H), 7.05 (d, J = 8.7 Hz, 1H), 4.66 (d, J = 10.1 Hz, 1H), 4.07-3.94 (m, 1H), 2.56-2.44 (m, 2H), 2.12 (s, 3H), 1.57 (s, 3H) ppm |
| 76 | rel-(2R,3S,5R)-4-[[3-(2,4-difluoro-3-methyl-phenyl)-5-methyl-5-(trifluoromethyl)tetrahydrofuran-2-carbonyl]amino]pyridine-2-carboxamide (second eluting isomer by SFC on Chiralpak AS-H column, rt = 3.71 min) | ESI-MS m/z calc. 443.12683, found 444.6 (M + 1)$^+$; 442.7 (M − 1)$^-$; Retention time: 3.12 minutes | |

Example 11 rel-(2S,3R,5S)-4-[[3-(3-ethyl-4-fluoro-2-methoxy-phenyl)-5-methyl-5-(trifluoromethyl)tetrahydro-furan-2-carbonyl]amino]pyridine-2-carboxamide (77) and re-(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide (78)

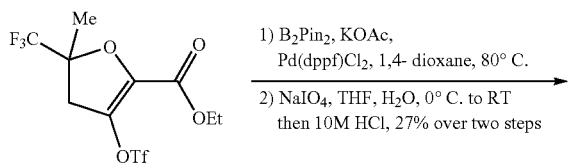

1) B₂Pin₂, KOAc, Pd(dppf)Cl₂, 1,4-dioxane, 80° C.
2) NaIO₄, THF, H₂O, 0° C. to RT then 10M HCl, 27% over two steps

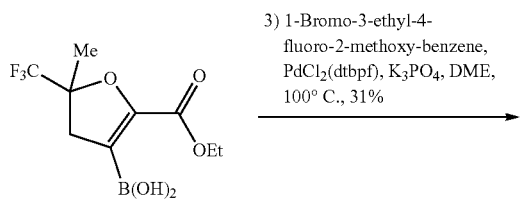

3) 1-Bromo-3-ethyl-4-fluoro-2-methoxy-benzene, PdCl₂(dtbpf), K₃PO₄, DME, 100° C., 31%

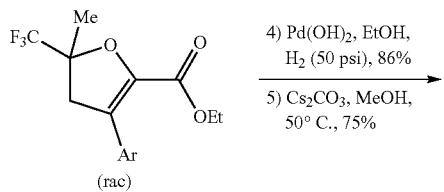

4) Pd(OH)₂, EtOH, H₂ (50 psi), 86%
5) Cs₂CO₃, MeOH, 50° C., 75%

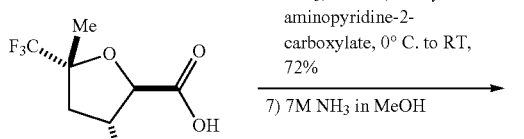

6) DCM, DMF (cat.), (COCl)₂, 0° C. then NEt₃, DMAP, methyl 4-aminopyridine-2-carboxylate, 0° C. to RT, 72%
7) 7M NH₃ in MeOH

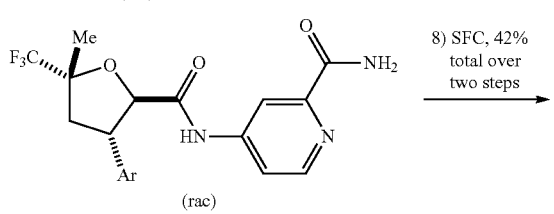

8) SFC, 42% total over two steps

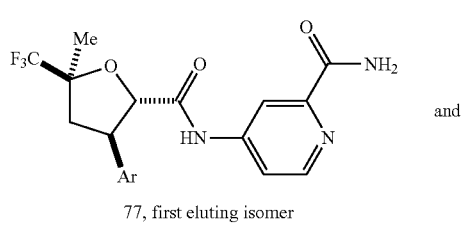

77, first eluting isomer and

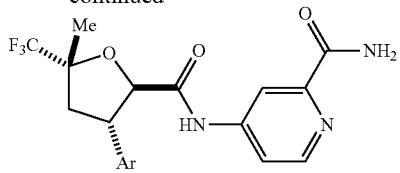

78, second eluting isomer

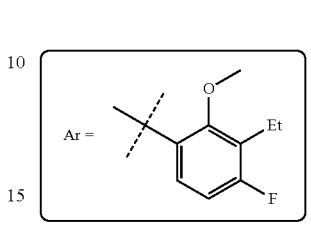

Step 1 and 2

To a stirred solution of ethyl 2-methyl-2-(trifluoromethyl)-4-(trifluoromethylsulfonyloxy)-3H-furan-5-carboxylate (10 g, 26.865 mmol) in 1,4-dioxane (150 mL), Potassium acetate (8 g, 81.514 mmol) and 4,4,5,5-tetramethyl-2-(4,4,5,5-tetramethyl-1,3,2-dioxaborolan-2-yl)-1,3,2-dioxaborolane (27 g, 106.32 mmol) were added. The reaction mixture was de-gassed by argon gas then Pd(dppf)Cl₂ (983 mg, 1.3434 mmol) was added to this reaction mixture and heated to 80° C. under argon for 15 min. Reaction was monitored by TLC. Reaction was allowed to room temperature. Then diluted with EtOAc (500 mL) and water (300 mL). Then filtered through celite bed, two layers were separated and the aqueous layer was extracted with EtOAc (300 mL). The combined organic layers were dried over anhydrous sodium sulfate and concentrated under vacuum.

The crude product was dissolved in THF (30 mL) and H₂O (15 mL), cooled to 0-5° C. NaIO₄ (17 g, 79.479 mmol) was added in the reaction mixture portion wise and stirred it at room temperature for 15 min. Then HCl (10 mL of 1 M, 10.000 mmol) was added and reaction mass was stirred for 4 hours. Then reaction mass was diluted with water (200 mL) and EtOAc (500 mL). Layers were separated. Organic layer was washed with brine solution. Organic layer was dried over anhydrous sodium sulfate and concentrated under reduced pressure. Crude mass was purified by silica gel chromatography using 2-10% EtOAc in hexane to get a yellow solid, this was washed with hexane to get [5-ethoxycarbonyl-2-methyl-2-(trifluoromethyl)-3H-furan-4-yl]boronic acid (2.5 g, 27%) as a white solid. ¹H NMR (400 MHz, DMSO-d₆) δ 8.22 (s, 2H), 4.23 (q, J=7.1 Hz, 2H), 3.11 (d, J=18.2 Hz, 1H), 2.85 (d, J=18.24 Hz, 1H), 1.49 (s, 3H), 1.25 (t, J=7.1 Hz, 3H) ppm.

Step 3

To a stirred solution of 1-bromo-3-ethyl-4-fluoro-2-methoxy-benzene (3 g, 12.87 mmol) and [5-ethoxycarbonyl-2-methyl-2-(trifluoromethyl)-3H-furan-4-yl]boronic acid (3.79 g, 14.16 mmol) in DME (15 mL) was added K₃PO₄ (7.65 g, 36.04 mmol). The mixture was degassed with N₂ gas for 5 mins followed by addition of PdCl₂(dtbpf) (838.86 mg, 1.29 mmol) and heated to 100° C. for 4 h. The reaction mixture was filtered through a celite pad, the filtrate was diluted with water (50 mL) and the aqueous layer extracted with EtOAc (100 mL). The organic layer was dried (MgSO₄), filtered and evaporated in vacuo. Purification by flash chromatography (SiO$_2$, 0 to 3% EtOAc in hexane) gave ethyl 4-(3-ethyl-4-fluoro-2-methoxy-phenyl)-2-methyl-2-(trifluoromethyl)-3H-furan-5-carboxylate (1.5 g, 31%) as light yellow liquid. $^1$H NMR (400 MHz, DMSO-d$_6$) δ 7.1823 (t, J=7 Hz, 1H), 6.9648 (t, J=8.8 Hz, 1H) 4.0401 (q, J=6.9 Hz, 2H), 3.5996 (s, 3H), 3.4321 (d, J=17.6 Hz, 1H), 3.1492 (d, J=17.6 Hz, 1H), 2.6211-2.5858 (m, 2H), 1.614 (s, 3H), 1.1339 (t, J=7.3 Hz, 3H), 1.0159 (t, J=7 Hz, 3H) ppm. ESI-MS m/z calc. 376.1298, found 377.0 (M+1)$^+$.

Step 4

To a stirred solution of ethyl 4-(3-ethyl-4-fluoro-2-methoxy-phenyl)-2-methyl-2-(trifluoromethyl)-3H-furan-5-carboxylate (1.5 g, 3.99 mmol) in ethanol (50 mL) was added Pd(OH)$_2$ (4.5 g, 32.04 mmol). The reaction was stirred at ambient temperature for 16 hours in a Parr shaker under a 50 psi pressure of hydrogen. Reaction mass was filtered through celite bed, filtrate was evaporated under reduced pressure to get crude compound. Purification by flash chromatography (SiO$_2$, 30% EtOAc in hexane) gave ethyl rac-(2S,3S,5R)-3-(3-ethyl-4-fluoro-2-methoxy-phenyl)-5-methyl-5-(trifluoromethyl)tetrahydrofuran-2-carboxylate (1.3 g, 86%) as a white solid. $^1$H NMR (400 MHz, DMSO-d$_6$) δ 7.04 (t, J=6.9 Hz, 1H), 6.92 (t, J=9 Hz, 1H) 4.95 (d, J=8.9 Hz, 1H), 4.35-4.28 (m, 1H), 3.80 (s, 3H), 3.70-3.59 (m, 2H), 2.63-2.54 (m, 3H), 2.31-2.26 (m, 1H), 1.49 (s, 3H), 1.13 (t, J=7.3 Hz, 3H), 0.72 (t, J=7 Hz, 3H) ppm. ESI-MS m/z calc. 378.1454, found 379.0 (M+1)$^+$.

Step 5

To a stirred solution of ethyl rac-(2S,3S,5R)-3-(3-ethyl-4-fluoro-2-methoxy-phenyl)-5-methyl-5-(trifluoromethyl) tetrahydrofuran-2-carboxylate (1.2 g, 3.17 mmol) in MeOH (10 mL) was added cesium carbonate (2.07 g, 6.34 mmol). The reaction was stirred at an ambient temperature for 1 h then it was heated at 50° C. for 16 h. The reaction mixture was concentrated in vacuo then water (5 mL) was added. The aqueous layer was acidified with 1M HCl, to neutral pH. The aqueous layer was extracted in 10% methanol-DCM mixture (2×50 mL) and the organic layer was evaporated in vacuo to give rac-(2R,3S,5R)-3-(3-ethyl-4-fluoro-2-methoxy-phenyl)-5-methyl-5-(trifluoromethyl)tetrahydrofuran-2-carboxylic acid (1 g, 75%) as a colourless liquid, which was used without further purification. $^1$H NMR (400 MHz, DMSO-d$_6$) δ 12.89 (s, 1H), 7.29-7.25 (m, 1H) 6.99 (t, J=9 Hz, 1H), 4.44 (d, J=10.4, 1H), 3.91-3.88 (m, 1H), 3.70 (s, 3H), 2.64-2.58 (m, 2H), 2.49-2.42 (m, 1H), 2.27-1.98 (m, 1H), 1.48 (s, 3H), 1.14 (t, J=7.4 Hz, 3H) ppm. ESI-MS m/z calc. 350.1141, found 351.0 (M+1)$^+$.

Step 6

To a solution of rac-(2R,3S,5R)-3-(3-ethyl-4-fluoro-2-methoxy-phenyl)-5-methyl-5-(trifluoromethyl)tetrahydrofuran-2-carboxylic acid (100 mg, 0.29 mmol) in DCM (2.5 mL) stirring at 0° C. was added DMF (5 µL, 0.065 mmol) and oxalyl chloride (100 µL, 1.15 mmol). After 30 mins the reaction mixture was concentrated in vacuo then diluted in DCM (2.3 mL) and added dropwise to a solution of methyl 4-aminopyridine-2-carboxylate (60 mg, 0.39 mmol), DMAP (4 mg, 0.033 mmol) and Et$_3$N (250 µL, 1.79 mmol) in DCM (2 mL) stirring at 0° C. After 10 mins the reaction was warmed to ambient temperature and stirred for 16 h. The reaction mixture was concentrated onto silica gel and purified by flash chromatography (40 g SiO$_2$, 0 to 100% EtOAc in heptane) to give methyl rac-(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxylate (109 mg, 72%). ESI-MS m/z calc. 484.16214, found 485.8 (M+1)$^+$; 483.1 (M−1)$^-$.

Step 7

Methyl rac-(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxylate (109 mg, 0.20 mmol) and ammonia (10 mL of 7 M, 70.00 mmol) were stirred at ambient temperature overnight. The reaction mixture was concentrated in vacuo to give rac-(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide (105 mg, containing 8% of an undesired minor isomer), which was used without further purification. ESI-MS m/z calc. 469.16248, found 470.2 (M+1)$^+$; 468.2 (M−1)$^-$.

Step 8 rac-(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide (105 mg, 0.22 mmol) was separated by chiral SFC using a Chiralpak AS-H column, 5 um particle size, 25 cm×10 mm from Daicel on a Minigram SFC instrument from Berger Instruments to give two single isomers of unknown absolute configuration:

First Eluting Isomer (rt=3.22 min): rel-(2S,3R,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide (77, 22.6 mg, 22%); ESI-MS m/z calc. 469.16248, found 470.2 (M+1)$^+$; 468.2 (M−1)$^-$ Second Eluting Isomer (rt=4.63 min): rel-(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide (78, 20.7 mg, 20%); ESI-MS m/z calc. 469.16248, found 470.3 (M+1)$^+$; 468.2 (M−1)$^-$.

Example 12 rac-(2R,3S,5R)-4-[[3-(2-fluoro-6-methoxy-phenyl)-5-methyl-5-(trifluoromethyl)tetrahydrofuran-2-carbonyl]amino]pyridine-2-carboxamide (79)

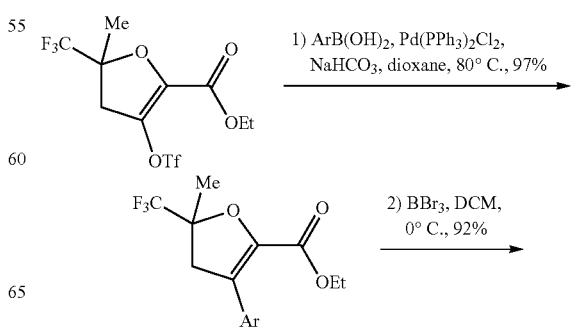

-continued

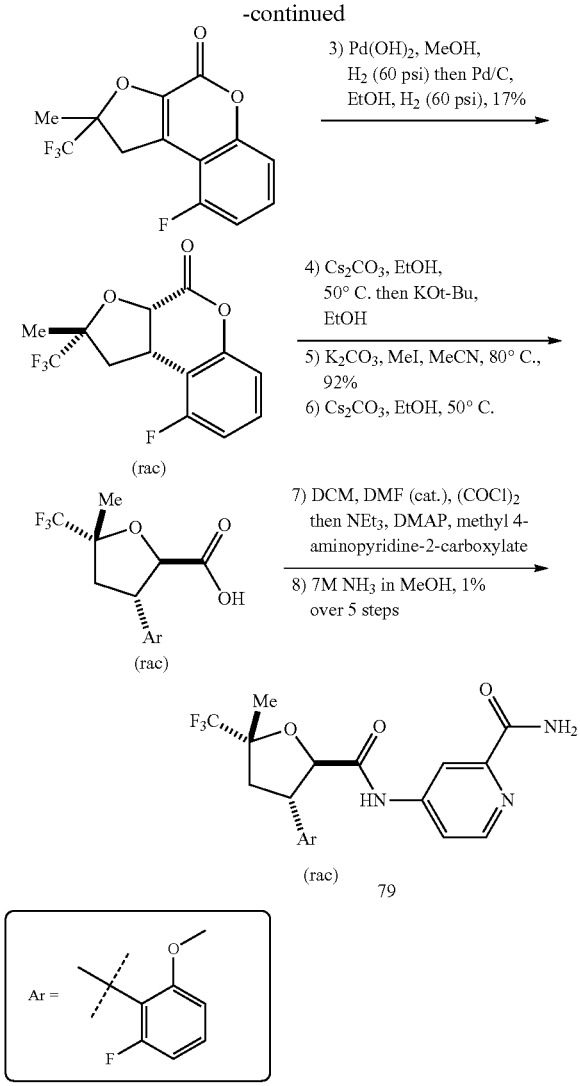

Step 1

A mixture of ethyl 2-methyl-2-(trifluoromethyl)-4-(trifluoromethylsulfonyloxy)-3H-furan-5-carboxylate (1550 mg, 4.16 mmol), (2-fluoro-6-methoxy-phenyl)boronic acid (690 mg, 4.06 mmol) and Pd(PPh$_3$)$_2$Cl$_2$ (160 mg, 0.23 mmol) in dioxane (35 mL) and saturated aqueous NaHCO$_3$ (excess) was degassed and refilled with nitrogen (×3 before catalyst added, then ×3 with catalyst). The reaction mixture was heated at 80° C. for 24 hours before being cooled to ambient temperature and concentrated in vacuo. The residue was redisolved in EtOAc and the solution washed with water/brine. The layers were separated and the organic layer filtered through a celite cartridge (10 g), eluting with EtOAc, then concentrated in vacuo to give ethyl 4-(2-fluoro-6-methoxy-phenyl)-2-methyl-2-(trifluoromethyl)-3H-furan-5-carboxylate (1.40 g, 97%), which was used without further purification. ESI-MS m/z calc. 348.09848, found 349.1 (M+1)$^+$.

Step 2

BBr$_3$ (6.30 mL of 1 M, 6.34 mmol) was added dropwise to an ice-cooled solution of ethyl 4-(2-fluoro-6-methoxy-phenyl)-2-methyl-2-(trifluoromethyl)-3H-furan-5-carboxylate (1450 mg, 4.16 mmol) in DCM (5.65 mL). Upon completion, the mixture was quenched with water and sodium bicarbonate solution. The layers were separated and the aqueous layer extracted with DCM. The organic layer was dried (MgSO$_4$) and concentrated in vacuo. The oil was dissolved in DCM (6.75 mL) and stirred at ambient temperature whilst TFA (1.014 g, 685 µL, 8.90 mmol) was added. The mixture was heated to 45° C. for 30 mins then quenched with sodium bicarbonate solution, extracted with DCM and the organic layer dried (MgSO$_4$) and concentrated in vacuo to give 9-fluoro-2-methyl-2-(trifluoromethyl)-1,2-dihydro-4H-furo[2,3-c]chromen-4-one (1.1 g, 92%) as a brown waxy solid, which was used without any further purification. $^1$H NMR (400 MHz, DMSO-d$_6$) δ 7.57-7.49 (m, 1H), 7.39-7.19 (m, 2H), 3.86-3.59 (m, 2H), 1.72 (d, J=1.0 Hz, 3H) ppm.

Step 3

9-fluoro-2-methyl-2-(trifluoromethyl)-1,2-dihydro-4H-furo[2,3-c]chromen-4-one (1100 mg, 3.82 mmol) was dissolved in MeOH (50 mL) and this solution added to Pd(OH)$_2$ (3 g, 21.4 mmol) in a 250 mL Parr vessel. The mixture was shaken under 60 psi hydrogen at ambient temperature overnight. The reaction mixture was filtered and concentrated in vacuo. The residue was redissolved in ethanol (50 mL) and added to Pd/C (1.1 g), then shaken under 60 psi hydrogen at ambient temperature for 60 hours before being filtered and concentrated in vacuo. Purification by flash chromatography (12 g SiO$_2$, 10 to 40% EtOAc in heptane) gave rac-(2R,3aS,9bS)-9-fluoro-2-methyl-2-(trifluoromethyl)-1,2,3a,9b-tetrahydro-4H-furo[2,3-c]chromen-4-one (190 mg, 17%), which was used without further purification. ESI-MS m/z calc. 290.0566, found 291.1 (M+1)$^+$.

Step 4

Cesium carbonate (430 mg, 1.32 mmol) was added to a stirred suspension of rac-(2R,3aS,9bS)-9-fluoro-2-methyl-2-(trifluoromethyl)-1,2,3a,9b-tetrahydro-4H-furo[2,3-c]chromen-4-one (190 mg, 0.65 mmol) in ethanol (4 mL) and the mixture heated at 50° C. for 2 hours. The reaction was cooled to ambient temperature and concentrated in vacuo. The residue was redissolved in ethanol (4 mL) and potassium tert-butoxide (4 eq.) was added. The reaction was stirred overnight before being quenched with 1M aqueous HCl (5 mL), diluted with EtOAc (10 mL) and the layers separated. The aqueous layer was extracted with EtOAc (3×10 mL), and the combined organic extracts were dried (MgSO$_4$), filtered and concentrated in vacuo to give rac-(2R,3S,5R)-3-(2-fluoro-6-hydroxy-phenyl)-5-methyl-5-(trifluoromethyl)tetrahydrofuran-2-carboxylic acid (200 mg) as a white solid, which was used without further purification.

Step 5

To a solution of rac-(2R,3S,5R)-3-(2-fluoro-6-hydroxy-phenyl)-5-methyl-5-(trifluoromethyl)tetrahydrofuran-2-carboxylic acid (200 mg, 0.65 mmol) in acetonitrile (2 mL) was added K$_2$CO$_3$ (380 mg, 2.75 mmol) and MeI (263 mg, 1.85 mmol). The reaction was heated to 80° C. for 6 hours in a sealed reaction vessel, then cooled to ambient temperature, diluted in DCM and filtered. The filtrate was carefully concentrated in vacuo using a cold water bath to give methyl rac-(2R,3S,5R)-3-(2-fluoro-6-methoxy-phenyl)-5-methyl- 5-(trifluoromethyl)tetrahydrofuran-2-carboxylate (200 mg) as a yellow oil, which was used without further purification.

Step 6

Methyl rac-(2R,3S,5R)-3-(2-fluoro-6-methoxy-phenyl)-5-methyl-5-(trifluoromethyl)tetrahydrofuran-2-carboxylate (200 mg, 0.59 mmol) was added to a stirred suspension of cesium carbonate (390 mg, 1.19 mmol) in ethanol (4 mL) and the mixture heated at 50° C. for 2 hours. The reaction was cooled to ambient temperature and concentrated in vacuo. The residue was dissolved in 1M aqueous HCl (5 mL) and EtOAc (10 mL) and the layers separated. The aqueous layer was extracted with EtOAc (3×10 mL) and the combined organic extracts were dried (MgSO₄), filtered and concentrated in vacuo to give rac-(2R,3S,5R)-3-(2-fluoro-6-methoxy-phenyl)-5-methyl-5-(trifluoromethyl)tetrahydrofuran-2-carboxylic acid (190 mg) as a white solid, which was used in the next step without further purification. ESI-MS m/z calc. 322.08282, found 321.1 (M−1)⁻.

Step 7

To a solution of rac-(2R,3S,5R)-3-(2-fluoro-6-methoxy-phenyl)-5-methyl-5-(trifluoromethyl)tetrahydrofuran-2-carboxylic acid (190 mg, 0.59 mmol) in DCM (10 mL) stirring at ambient temperature was added DMF (4.6 µL, 0.059 mmol) and oxalyl chloride (160 µL, 1.83 mmol). After 15 mins the reaction mixture was concentrated in vacuo, the residue diluted in DCM (3 mL) and added dropwise over 5 mins to an ice-cooled solution of methyl 4-aminopyridine-2-carboxylate (90 mg, 0.59 mmol), DMAP (3.7 mg, 0.030 mmol) and NEt₃ (250 µL, 1.79 mmol) in DCM (5 mL). After warming to ambient temperature overnight the reaction mixture was diluted with DCM (50 mL) and washed with 2M HCl solution (50 mL). The organic layer was passed through a phase separator cartridge and the filtrate concentrated in vacuo to give methyl rac-(2R,3S,5R)-4-[[3-(2-fluoro-6-methoxy-phenyl)-5-methyl-5-(trifluoromethyl)tetrahydrofuran-2-carbonyl]amino]pyridine-2-carboxylate (250 mg), which was used without further purification. ESI-MS m/z calc. 456.13083, found 457.1 (M+1)⁺.

Step 8

Methyl rac-(2R,3S,5R)-4-[[3-(2-fluoro-6-methoxy-phenyl)-5-methyl-5-(trifluoromethyl)tetrahydrofuran-2-carbonyl]amino]pyridine-2-carboxylate (250 mg, 0.55 mmol) was dissolved in methanolic ammonia (10 mL of 7 M, 70.00 mmol) and stirred at ambient temperature for 6 hours. The solution was concentrated in vacuo before being purified fraction lynx (Ammonia shallow 5 gradient, in DMSO loading solvent) to give rac-(2R,3S,5R)-4-[[3-(2-fluoro-6-methoxy-phenyl)-5-methyl-5-(trifluoromethyl)tetrahydrofuran-2-carbonyl]amino]pyridine-2-carboxamide (79, 3.2 mg, 1% over 5 steps). ¹H NMR (400 MHz, Chloroform-d) δ 8.61 (s, 1H), 8.47 (d, J=5.6 Hz, 1H), 8.19 (dd, J=5.6, 2.2 Hz, 1H), 7.97-7.87 (m, 2H), 7.26 (td, J=8.4, 6.6 Hz, 1H), 6.81-6.70 (m, 2H), 5.64 (s, 1H), 5.12 (d, J=10.7 Hz, 1H), 4.05 (td, J=11.5, 8.2 Hz, 1H), 3.87 (s, 3H), 3.10 (t, J=12.4 Hz, 1H), 2.14 (dd, J=12.6, 8.1 Hz, 1H), 1.66 (s, 3H) ppm. ESI-MS m/z calc. 441.13116, found 442.1 (M+1)⁺; 440.3 (M−1)⁻.

Example 13 rel-(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide (80), rel-(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide (81), rel-(2S,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide (82) and rel-(2S,3R,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide (83)

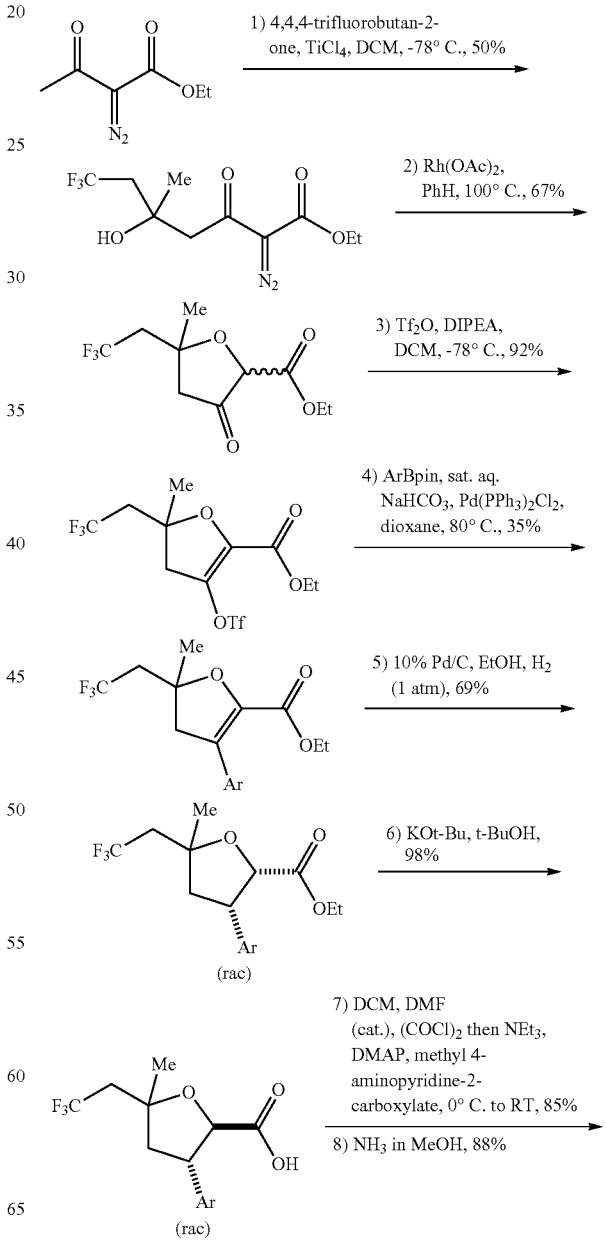

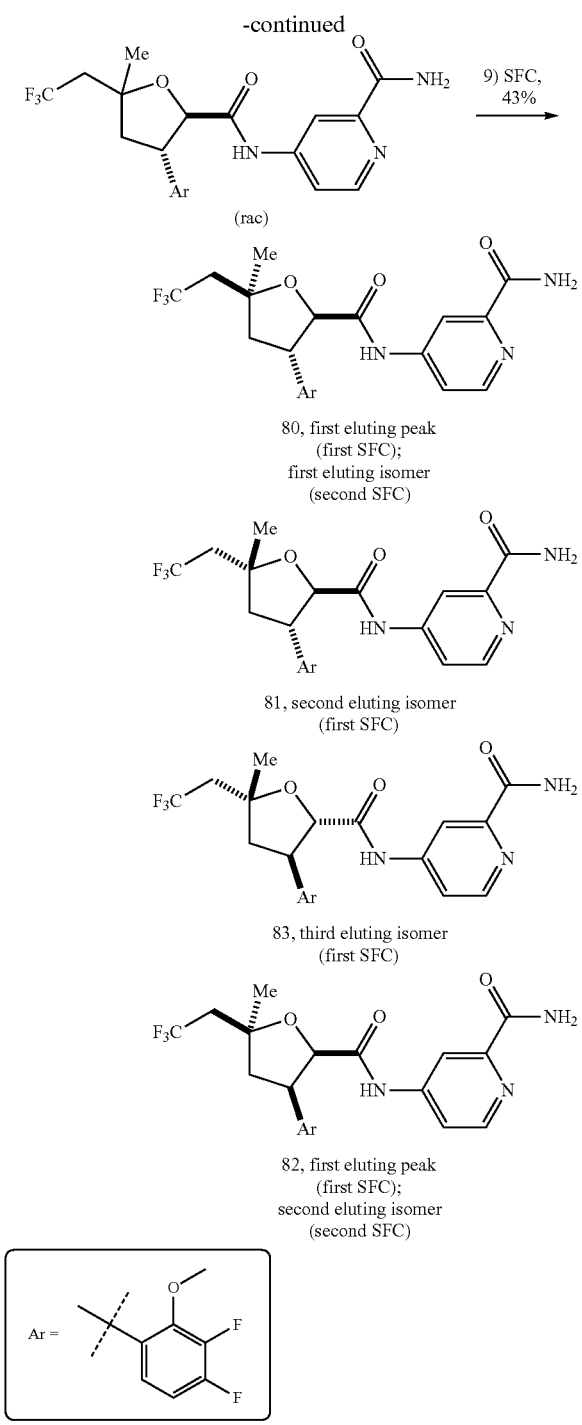

layer was separated and extracted (DCM) and the combined organics washed with brine, dried (MgSO$_4$) and concentrated in vacuo. Purification (80 g SiO$_2$, 0 to 20% EtOAc in heptane) gave ethyl 2-diazo-7,7,7-trifluoro-5-hydroxy-5-methyl-3-oxo-heptanoate (2.5 g, 50%) as a colourless oil. $^1$H NMR (400 MHz, Chloroform-d) δ 4.32 (q, J=7.1 Hz, 2H), 4.17-4.08 (m, 1H), 3.31 (d, J=17.2 Hz, 1H), 3.09 (d, J=17.2 Hz, 1H), 2.63-2.37 (m, 2H), 1.42 (d, J=1.2 Hz, 3H), 1.35 (t, J=7.1 Hz, 3H) ppm.

Step 2

A suspension of rhodium tetraacetate (68 mg, 0.15 mmol) in benzene (60 mL) was heated at 100° C. for 10 mins. A solution of ethyl 2-diazo-7,7,7-trifluoro-5-hydroxy-5-methyl-3-oxo-heptanoate (2500 mg, 8.858 mmol) in benzene (22 mL) was then added dropwise via dropping funnel. After 2 hours the reaction was cooled to ambient temperature, filtered through celite, washing with DCM, and concentrated in vacuo. Purification by flash chromatography (40 g SiO$_2$, 0 to 20% EtOAc in heptane) gave ethyl 5-methyl-3-oxo-5-(2,2,2-trifluoroethyl)tetrahydrofuran-2-carboxylate (1.5 g, 67%) as a colourless oil, in a 1:1 mixture of diastereomers. $^1$H NMR (400 MHz, Chloroform-d) δ 4.67-4.55 (m, 1H), 4.38-4.18 (m, 2H), 2.86-2.66 (m, 2H), 2.65-2.49 (m, 2H), 1.57 (dd, J=52.9, 1.1 Hz, 3H), 1.32 (td, J=7.1, 2.4 Hz, 3H) ppm.

Step 3

Trifluoromethylsulfonyl trifluoromethanesulfonate (2.18 g, 7.72 mmol) was added to a solution of ethyl 5-methyl-3-oxo-5-(2,2,2-trifluoroethyl)tetrahydrofuran-2-carboxylate (1.50 g, 5.90 mmol) and DIPEA (2.3 g, 17.8 mmol) in DCM (50 mL) stirring at −78° C. After 4 hours saturated aq. NaHCO$_3$ solution was added, the layers separated and the aqueous layer extracted with DCM, dried (MgSO$_4$) and concentrated in vacuo to give ethyl 2-methyl-2-(2,2,2-trifluoroethyl)-4-(trifluoromethylsulfonyloxy)-3H-furan-5-carboxylate (2.1 g, 92%), which was used without any further purification.

Step 4

A mixture of ethyl 2-methyl-2-(2,2,2-trifluoroethyl)-4-(trifluoromethylsulfonyloxy)-3H-furan-5-carboxylate (850 mg, 2.20 mmol), 2-(3,4-difluoro-2-methoxy-phenyl)-4,4,5,5-tetramethyl-1,3,2-dioxaborolane (715 mg, 2.647 mmol) and Pd(PPh$_3$)$_2$Cl$_2$ (80 mg, 0.11 mmol) in dioxane (20 mL) and saturated aqueous NaHCO$_3$ (2 mL) was degassed extensively and heated at 80° C. After 4 hours the reaction mixture was cooled to ambient temperature and filtered through a celite cartridge washing with EtOAc, then concentrated in vacuo. The residue was purified by flash chromatography (40 g SiO$_2$, 0 to 20% EtOAc in heptane) to give ethyl 4-(3,4-difluoro-2-methoxy-phenyl)-2-methyl-2-(2,2,2-trifluoroethyl)-3H-furan-5-carboxylate (290 mg, 35%) as a clear oil. ESI-MS m/z calc. 380.1047, found 381.2 (M+1)$^+$.

Step 5

EtOH (10 mL) was added to a mixture of ethyl 4-(3,4-difluoro-2-methoxy-phenyl)-2-methyl-2-(2,2,2-trifluoroethyl)-3H-furan-5-carboxylate (290 mg, 0.7625 mmol) and Pd/C (10 wt. % loading, 1000 mg, 0.94 mmol). The mixture was degassed and stirred under a balloon of hydrogen overnight. Further Pd/C (10 wt. % loading, 1000 mg, 0.94 mmol) was added, the mixture degassed and stirred under a balloon of hydrogen for a further 20 h. The mixture was passed through a celite cartridge rinsing with DCM, and the filtrate concentrated in vacuo and purified by column chromatography (12 g SiO$_2$, 0 to 40% EtOAc/Hexanes) to give ethyl rac-(2S,3S,5R)-3-(3,4-difluoro-2-methoxy-phenyl)-5-methyl-5-(2,2,2-trifluoroethyl)tetrahydrofuran-2-carboxylate (200 mg, 69%). $^1$H NMR (400 MHz, Methanol-d$_4$) δ 6.95-6.81 (m, 2H), 4.86 (d, J=8.5 Hz, 1H), 4.27-4.15 (m, 1H), 4.09 (d, J=2.7 Hz, 3H), 3.84-3.63 (m, 2H), 3.00-2.86 (m, 1H), 2.88-2.73 (m, 1H), 2.51 (t, J=12.8 Hz, 1H), 2.15-2.05 (m, 1H), 1.47 (d, J=1.5 Hz, 3H), 0.85 (t, J=7.1 Hz, 3H) ppm. ESI-MS m/z calc. 382.12036, found 383.3 (M+1)$^+$.

Step 6

A solution of ethyl rac-(2S,3S,5R)-3-(3,4-difluoro-2-methoxy-phenyl)-5-methyl-5-(2,2,2-trifluoroethyl)tetrahydrofuran-2-carboxylate (75 mg, 0.20 mmol) and potassium tert-butoxide (65 mg, 0.58 mmol) in tert-butanol (2.2 mL) were stirred at ambient temperature for 6 h before being quenched with saturated aq. NH$_4$Cl solution and diluted with EtOAc. The layers were separated and the aqueous layer and extracted with EtOAc. The aqueous layer was then acidified with 1M HCl and extracted with further EtOAc. The combined organic layers were dried (MgSO$_4$), filtered and concentrated in vacuo to afford rac-(2R,3S,5R)-3-(3,4-difluoro-2-methoxy-phenyl)-5-methyl-5-(2,2,2-trifluoroethyl)tetrahydrofuran-2-carboxylic acid (68 mg, 98%) which was used without further purification. ESI-MS m/z calc. 354.08905, found 355.0 (M+1)$^+$; 352.9 (M−1)$^-$.

Step 7

To a solution of rac-(2R,3S,5R)-3-(3,4-difluoro-2-methoxy-phenyl)-5-methyl-5-(2,2,2-trifluoroethyl)tetrahydrofuran-2-carboxylic acid (60 mg, 0.17 mmol) in DCM (5 mL) was added DMF (3 µL, 0.04 mmol) and oxalyl chloride (50 µL, 0.57 mmol). After 15 mins at ambient temperature the reaction was concentrated in vacuo. The residue was diluted in DCM (2 mL) and added dropwise to a solution of methyl 4-aminopyridine-2-carboxylate (40 mg, 0.26 mmol), DMAP (2 mg, 0.016 mmol) and Et$_3$N (150 µL, 1.08 mmol) in DCM (1 mL) stirring at 0° C. After 10 mins at this temperature, the reaction was warmed to ambient temperature and stirred for a further 40 mins before being diluted in DCM (50 mL) and washed with 2M HCl solution (50 mL). The organic layer was passed through a phase separator cartridge and concentrated in vacuo to give methyl rac-(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxylate (70 mg, 85%), which was used without further purification. ESI-MS m/z calc. 488.13705, found 489.3 (M+1)$^+$; 487.3 (M−1)$^-$.

Step 8

Methyl rac-(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxylate (70 mg, 0.14 mmol) was stirred in methanolic ammonia (2 mL of 7 M, 14.00 mmol) at ambient temperature overnight. Further methanolic ammonia (2 mL of 7 M, 14.00 mmol) was added and the reaction left for 6 hours before being concentrated in vacuo to give a mixture of rac-(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide and rac-(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide (60 mg, 88%), which was used without further purification. ESI-MS m/z calc. 473.1374, found 474.3 (M+1)$^+$; 472.3 (M−1)$^-$.

Step 9

The mixture of rac-(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide and rac-(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide obtained in Step 8 (60 mg, 0.1267 mmol) was separated by chiral SFC using a (R,R)-Whelk-O1 column, 5 µm particle size, 25 cm×21.2 mm from Regis Technologies on a Minigram SFC instrument from Berger Instruments to give:

First Eluting Isomers (rt=0.91 min): a mixture of both re-(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide (80) and rel-(2S,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide (82), that needed further separation.

Second Eluting Isomer (rt=1.29 min): rel-(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide (81, 9.9 mg, 16.5%). $^1$H NMR (500 MHz, Chloroform-d) δ 8.58 (s, 1H), 8.34 (d, J=5.5 Hz, 1H), 8.06 (dd, J=5.5, 2.2 Hz, 1H), 7.79 (d, J=2.2 Hz, 1H), 7.72 (d, J=4.1 Hz, 1H), 6.87 (ddd, J=8.1, 5.5, 2.1 Hz, 1H), 6.77 (td, J=9.1, 7.2 Hz, 1H), 5.60-5.55 (m, 1H), 4.51 (d, J=10.0 Hz, 1H), 3.87 (d, J=2.4 Hz, 3H), 3.80 (q, J=9.8 Hz, 1H), 2.48 (dddd, J=26.3, 15.2, 11.0, 4.2 Hz, 2H), 2.22 (d, J=9.8 Hz, 2H), 1.45 (s, 3H) ppm. ESI-MS m/z calc. 473.1374, found 474.4 (M+1)$^+$; 472.4 (M−1)$^-$.

Third Eluting Isomer (rt=1.45 min): rel-(2S,3R,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide (83, 4.8 mg, 8%). $^1$H NMR (500 MHz, Chloroform-d) δ 8.59 (s, 1H), 8.33 (d, J=5.5 Hz, 1H), 7.95-7.89 (m, 1H), 7.84 (s, 1H), 7.72 (s, 1H), 6.87 (s, 1H), 6.81-6.72 (m, 1H), 5.46 (s, 1H), 4.53 (d, J=10.3 Hz, 1H), 3.85 (d, J=2.4 Hz, 3H), 3.66 (q, J=10.5 Hz, 1H), 2.50-2.39 (m, 3H), 2.01 (t, J=12.4 Hz, 1H), 1.47 (s, 3H) ppm. ESI-MS m/z calc. 473.1374, found 474.4 (M+1)$^+$; 472.4 (M−1)$^-$.

The first eluting peak was further separated by chiral SFC using a Lux Cellulose-2 column, 5 µm particle size, 25 cm×10 mm from Phenomenex, Inc. to give two single isomers of unknown absolute configuration:

First Eluting Isomer (rt=4.05 min): rel-(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide (80, 3.6 mg, 6%). $^1$H NMR (500 MHz, Chloroform-d) δ 8.76 (s, 1H), 8.48 (d, J=5.5 Hz, 1H), 8.09 (dd, J=5.5, 1.9 Hz, 1H), 7.99 (d, J=2.1 Hz, 1H), 7.93 (s, 1H), 7.02 (ddd, J=8.0, 5.5, 2.1 Hz, 1H), 6.91 (td, J=9.1, 7.3 Hz, 1H), 5.62 (s, 1H), 4.68 (d, J=10.4 Hz, 1H), 4.00 (d, J=2.5 Hz, 3H), 3.81 (td, J=11.0, 8.2 Hz, 1H), 2.65-2.54 (m, 3H), 2.21-2.12 (m, 1H), 1.62 (s, 3H) ppm. ESI-MS m/z calc. 473.1374, found 474.3 (M+1)$^+$; 472.4 (M−1)$^-$.

Second Eluting Isomer (rt=4.39 min): rel-(2S,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide (82, 7 mg, 11.7%). $^1$H NMR (500 MHz, Chloroform-d) δ 8.72 (s, 1H), 8.49 (d, J=5.5 Hz, 1H), 8.21

(dd, J=5.6, 2.0 Hz, 1H), 7.94 (d, J=2.2 Hz, 1H), 7.89 (s, 1H), 7.02 (ddd, J=8.1, 5.5, 2.1 Hz, 1H), 6.91 (td, J=9.1, 7.2 Hz, 1H), 5.68 (s, 1H), 4.66 (d, J=9.9 Hz, 1H), 4.02 (d, J=2.4 Hz, 3H), 4.02-3.90 (m, 1H), 2.63 (dddd, J=26.4, 15.2, 11.0, 4.2 Hz, 2H), 2.36 (d, J=9.7 Hz, 2H), 1.59 (s, 3H) ppm. ESI-MS m/z calc. 473.1374, found 474.4 (M+1)$^+$; 472.4 (M−1)$^-$.

The following compounds were made using a method similar to that described in Example 13, except that 3,3-difluoro-butan-2-one was used as the starting material in place of 4,4,4-trifluorobutan-2-one in step 1. In step 6, ethanol was used as solvent rather than tert-butanol:

| Cmpd No. | Compound Name | LC/MS | NMR (shifts in ppm) |
|---|---|---|---|
| 84 | rel-(2R,3S,5S)-4-[[5-(1,1-difluoroethyl)-3-(3,4-difluoro-2-methoxy-phenyl)-5-methyl-tetrahydrofuran-2-carbonyl]amino]pyridine-2-carboxamide (first eluting peak by SFC on Whelk01 column, rt = 1.18 min; first eluting isomer by SFC on Lux Cellulose-2 column, rt = 2.35 min) | ESI-MS m/z calc. 455.14682, found 456.6 (M + 1)$^+$; 454.7 (M − 1)$^-$; Retention time: 3.01 minutes | $^1$H NMR (500 MHz, Chloroform-d) δ 8.40 (dd, J = 5.4, 2.4 Hz, 1H), 8.21-8.05 (m, 1H), 7.92 (q, J = 2.4 Hz, 1H), 7.01 (td, J = 5.9, 2.9 Hz, 1H), 6.94-6.73 (m, 1H), 4.59 (dd, J = 10.6, 2.8 Hz, 1H), 3.89 (q, J = 2.3 Hz, 3H), 3.85 (dd, J = 8.9, 5.7 Hz, 1H), 2.62-2.49 (m, 1H), 2.16 (dt, J = 12.7, 5.4 Hz, 1H), 1.70 (td, J = 19.0, 2.9 Hz, 3H), 1.51 (d, J = 2.9 Hz, 3H) ppm. |
| 85 | rel-(2S,3R,5S)-4-[[5-(1,1-difluoroethyl)-3-(3,4-difluoro-2-methoxy-phenyl)-5-methyl-tetrahydrofuran-2-carbonyl]amino]pyridine-2-carboxamide (first eluting peak by SFC on Whelk01 column, rt = 1.18 min; second eluting isomer by SFC on Lux Cellulose-2 column, rt = 3.69 min) | ESI-MS m/z calc. 455.14682, found 456.6 (M + 1)$^+$; 454.7 (M − 1)$^-$; Retention time: 2.89 minutes | $^1$H NMR (500 MHz, Chloroform-d) δ 8.30 (dd, J = 5.6, 1.9 Hz, 1H), 7.73 (s, 1H), 7.69-7.64 (m, 1H), 6.75-6.63 (m, 1H), 6.60 (tdd, J = 9.2, 7.1, 2.0 Hz, 1H), 4.80-4.74 (m, 1H), 4.36 (dddd, J = 12.4, 9.5, 7.1, 2.0 Hz, 1H), 4.03 (t, J = 2.6 Hz, 3H), 2.62-2.47 (m, 1H), 1.95 (ddd, J = 12.5, 7.3, 1.7 Hz, 1H), 1.77 (td, J = 19.4, 2.1 Hz, 3H), 1.44 (d, J = 1.9 Hz, 3H) ppm. |
| 86 | rel-(2R,3S,5R)-4-[[5-(1,1-difluoroethyl)-3-(3,4-difluoro-2-methoxy-phenyl)-5-methyl-tetrahydrofuran-2-carbonyl]amino]pyridine-2-carboxamide (second eluting isomer by SFC on Whelk01 column, rt = 1.39 min) | ESI-MS m/z calc. 455.14682, found 456.6 (M + 1)$^+$; 454.7 (M − 1)$^-$; Retention time: 2.89 minutes | $^1$H NMR (500 MHz, Methanol-d$_4$) δ 8.25 (d, J = 5.6 Hz, 1H), 7.69 (d, J = 2.1 Hz, 1H), 7.61 (dd, J = 5.5, 2.2 Hz, 1H), 6.64 (ddd, J = 8.0, 5.6, 1.9 Hz, 1H), 6.55 (td, J = 9.2, 7.2 Hz, 1H), 4.74 (dd, J = 9.9, 1.2 Hz, 1H), 4.34-4.25 (m, 1H), 3.97 (d, J = 2.6 Hz, 3H), 2.50 (t, J = 12.7 Hz, 1H), 1.91 (dd, J = 12.5, 7.1 Hz, 1H), 1.72 (t, J = 19.5 Hz, 3H), 1.39 (s, 3H) ppm. |
| 87 | rel-(2S,3R,5R)-4-[[5-(1,1-difluoroethyl)-3-(3,4-difluoro-2-methoxy-phenyl)-5-methyl-tetrahydrofuran-2-carbonyl]amino]pyridine-2-carboxamide (third eluting isomer by SFC on Whelk01 column, rt = 1.81 min) | ESI-MS m/z calc. 455.14682, found 456.2 (M + 1)$^+$; 454.1 (M − 1)$^-$; Retention time: 2.98 minutes | $^1$H NMR (500 MHz, Chloroform-d) δ 8.33 (d, J = 5.5 Hz, 1H), 8.05 (dq, J = 4.4, 2.3 Hz, 1H), 7.80 (d, J = 2.2 Hz, 1H), 6.93 (ddd, J = 8.1, 5.5, 2.1 Hz, 1H), 6.77 (td, J = 9.2, 7.4 Hz, 1H), 4.51 (d, J = 10.6 Hz, 1H), 3.83-3.67 (m, 4H), 3.14-3.06 (m, 1H), 3.04 (s, 2H), 2.49 (t, J = 12.4 Hz, 1H), 2.12-2.04 (m, 1H), 1.64 (d, J = 19.0 Hz, 2H), 1.43 (s, 3H) ppm. |

Example 14 rel-(2S,3R,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide (88) and rel-(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide (89)

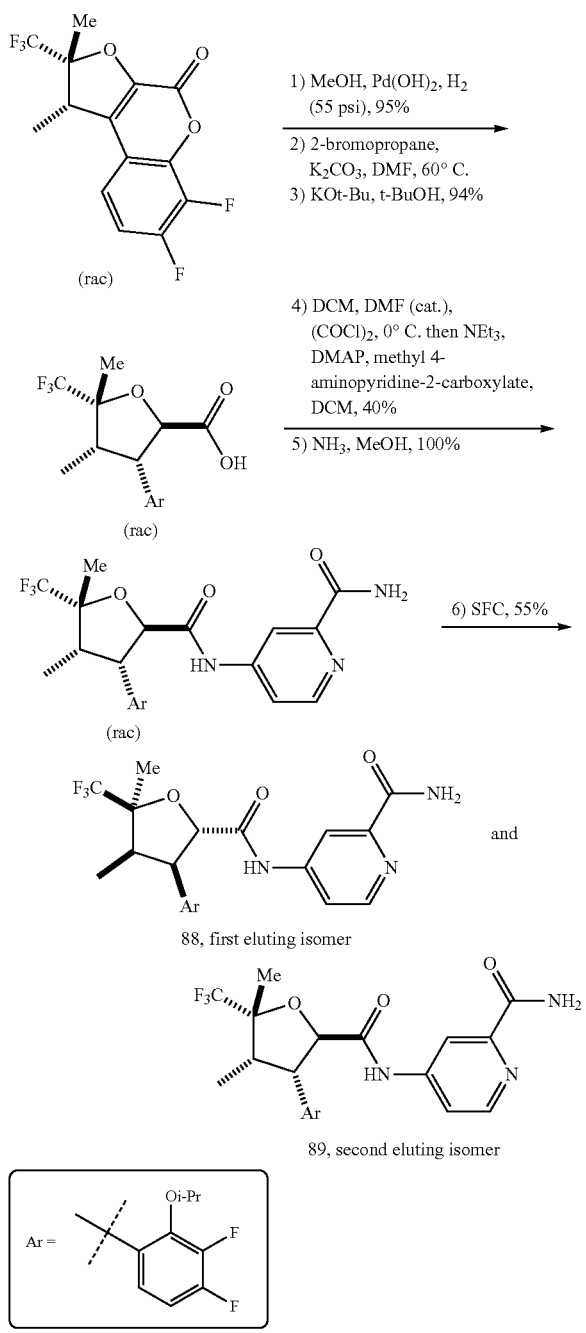

Step 1

MeOH (620 mL) was added into a Parr shaker flask shaker containing rac-(1S,2R)-6,7-difluoro-1,2-dimethyl-2-(trifluoromethyl)-1,2-dihydro-4H-furo[2,3-c]chromen-4-one (32.3 g, 100.9 mmol) and Pd(OH)$_2$ (24 g, 34.18 mmol). The mixture was degassed and repressurised to 55 psi H$_2$, and left to shake for 2 days. The mixture was filtered, washing the catalyst with DCM followed by EtOAc and methanol, and the filtrate concentrated in vacuo to give methyl rac-(2S,3S,4S,5R)-3-(3,4-difluoro-2-hydroxy-phenyl)-4,5-dimethyl-5-(trifluoromethyl)tetrahydrofuran-2-carboxylate (34 g, 95%). $^1$H NMR (500 MHz, Methanol-d$_4$) δ 7.05 (ddt, J=9.1, 7.5, 2.0 Hz, 1H), 6.57 (ddd, J=10.1, 9.0, 7.6 Hz, 1H), 5.01 (d, J=6.0 Hz, 1H), 4.34 (dd, J=8.5, 6.0 Hz, 1H), 3.49 (s, 3H), 2.93 (h, J=7.4 Hz, 1H), 1.50 (d, J=1.2 Hz, 3H), 0.89 (dd, J=7.6, 1.9 Hz, 3H) ppm. ESI-MS m/z calc. 354.08905, found 353.6 (M−1)$^-$.

Step 2

2-bromopropane (210 µL, 2.24 mmol) was added to a solution of methyl rac-(2S,3S,4S,5R)-3-(3,4-difluoro-2-hydroxy-phenyl)-4,5-dimethyl-5-(trifluoromethyl)tetrahydrofuran-2-carboxylate (260 mg, 0.73 mmol) and K$_2$CO$_3$ (305 mg, 2.21 mmol) in DMF (3.7 mL). The reaction was heated at 60° C. for 2 hours before further 2-bromopropane (210 µL, 2.24 mmol) was added. After a further 2 hours stirring at 60° C. the reaction was cooled to ambient temperature and diluted with NH$_4$Cl solution. The layers were separated and the aqueous layer extracted with EtOAc. The combined organic layers were washed with brine, dried (MgSO$_4$), filtered and concentrated in vacuo to afford methyl rac-(2S, 3S,4S,5R)-3-(3,4-difluoro-2-isopropoxy-phenyl)-4,5-dimethyl-5-(trifluoromethyl)tetrahydrofuran-2-carboxylate (271 mg) as an oil which was used without further purification.

Step 3

To a solution of methyl rac-(2S,3S,4S,5R)-3-(3,4-difluoro-2-isopropoxy-phenyl)-4,5-dimethyl-5-(trifluoromethyl)tetrahydrofuran-2-carboxylate (270 mg, 0.68 mmol) in tert-butanol (5 mL) stirring at ambient temperature was added potassium tert-butoxide (155 mg, 1.38 mmol). The reaction was stirred for 2 hours before being diluted in EtOAc and quenched by the addition of 1M HCl. The layers were separated and the aqueous layer extracted with EtOAc. The combined organic layers were dried (MgSO$_4$), filtered and concentrated in vacuo to give rac-(2R,3S,4S,5R)-3-(3, 4-difluoro-2-isopropoxy-phenyl)-4,5-dimethyl-5-(trifluoromethyl)tetrahydrofuran-2-carboxylic acid (246 mg, 94%) as a yellow residue. ESI-MS m/z calc. 382.12036, found 381.6 (M−1)$^-$.

Step 4

To a solution of rac-(2R,3S,4S,5R)-3-(3,4-difluoro-2-isopropoxy-phenyl)-4,5-dimethyl-5-(trifluoromethyl)tetrahydrofuran-2-carboxylic acid (246 mg, 0.64 mmol) in DCM (6 mL) stirring at 0° C. was added DMF (5 µL, 0.065 mmol) and oxalyl chloride (170 µL, 1.95 mmol). After 30 mins the reaction was concentrated in vacuo and the residue diluted in DCM (4 mL). This solution was added dropwise to a solution of methyl 4-aminopyridine-2-carboxylate (145 mg, 0.95 mmol) and Et$_3$N (450 µL, 3.229 mmol) in DCM (2 mL) stirring at 0° C. DMAP (7 mg, 0.057 mmol) was added and the reaction stirred at this temperature for 10 mins before being warmed to ambient temperature and stirred overnight. The reaction mixture was diluted with DCM and washed with 1M HCl solution. The organic layers were dried (MgSO$_4$), filtered and concentrated in vacuo, directly onto silica gel. Purification by flash chromatography (24 g SiO$_2$, 0 to 100% EtOAc in petrol) gave methyl rac-(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxylate (133 mg, 40%). ESI-MS m/z calc. 516.16833, found 517.7 (M+1)$^+$; 515.8 (M−1)$^−$.

Step 5

Methyl rac-(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxylate (133 mg, 0.26 mmol) was stirred in methanolic ammonia (8 mL of 7 M, 56.00 mmol) at ambient temperature overnight. The reaction mixture was concentrated in vacuo to give rac-(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide (130 mg, 100%). ESI-MS m/z calc. 501.1687, found 502.6 (M+1)$^+$.

Step 6 rac-(2R,3S,4S,5R)-(4-[[3-(3,4-difluoro-2-isopropoxy-phenyl)-4,5-dimethyl-5-(trifluoromethyl)tetrahydrofuran-2-carbonyl]amino]pyridine-2-carboxamide (130 mg, 0.26 mmol) was separated by chiral SFC using a (R,R)-Whelk-O1 column, 5 μm particle size, 25 cm×21.2 mm from Regis Technologies on a Minigram SFC instrument from Berger Instruments to give:

First Eluting Isomers (rt=0.84 min): re-(2S,3R,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide (88, 38 mg, 29%). ESI-MS m/z calc. 501.1687, found 502.2 (M+1)$^+$; 500.2 (M−1)$^−$.

Second Eluting Isomer (rt=1.29 min): re-(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide (89, 34.2 mg, 26%). $^1$H NMR (500 MHz, DMSO-d$_6$) δ 10.74 (s, 1H), 8.49 (d, J=5.5 Hz, 1H), 8.26 (d, J=2.2 Hz, 1H), 8.05 (d, J=2.6 Hz, 1H), 7.80 (dd, J=5.5, 2.2 Hz, 1H), 7.61 (d, J=2.8 Hz, 1H), 7.20-7.10 (m, 2H), 5.09 (d, J=10.5 Hz, 1H), 4.62-4.51 (m, 1H), 4.30 (dd, J=10.5, 7.5 Hz, 1H), 2.74 (p, J=7.5 Hz, 1H), 1.61 (s, 3H), 1.35 (d, J=6.1 Hz, 3H), 1.22 (d, J=6.1 Hz, 3H), 0.71 (d, 3H) ppm. ESI-MS m/z calc. 501.1687, found 502.2 (M+1)$^+$; 500.2 (M−1)$^−$.

Example 15 rel-(2S,3R,4R,5S)-4-[[3-(3,4-difluorophenyl)-4,5-dimethyl-5-(trifluoromethyl)tetrahydrofuran-2-carbonyl]amino]pyridine-2-carboxamide (90) and rel-(2R,3S,4S,5R)-4-[[3-(3,4-difluorophenyl)-4,5-dimethyl-5-(trifluoromethyl)tetrahydrofuran-2-carbonyl]amino]pyridine-2-carboxamide (91)

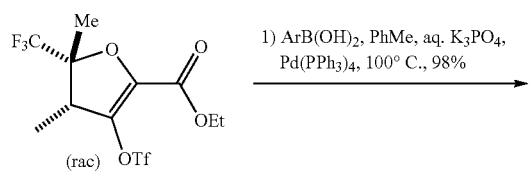

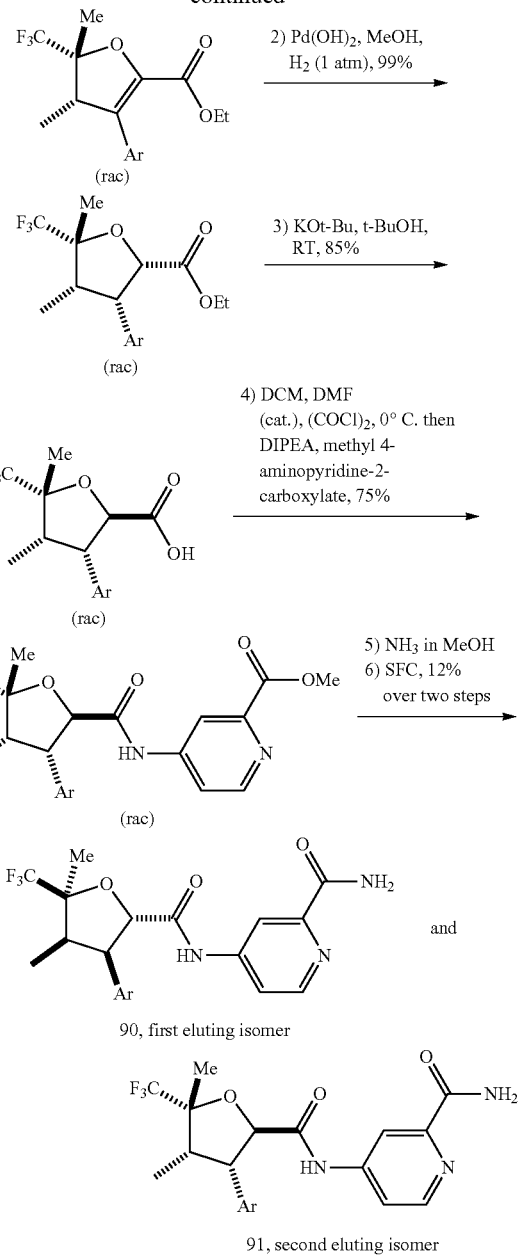

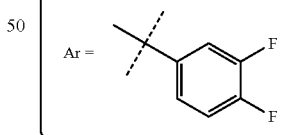

Step 1

To a degassed solution of ethyl rac-(4R,5R)-4,5-dimethyl-5-(trifluoromethyl)-3-(((trifluoromethyl)sulfonyl)oxy)-4,5-dihydrofuran-2-carboxylate (2 g, 4.85 mmol) in toluene (25 mL) was added K$_3$PO$_4$ (8.5 mL of 2 M, 17.00 mmol) and (3,4-difluorophenyl)boronic acid (860 mg, 5.45 mmol). The mixture was further degassed for 10 mins before tetrakis (triphenylphosphine)palladium(0) (285 mg, 0.25 mmol) was added. The reaction was stirred at 100° C. for 2 hours before the solvent was removed in vacuo and the residue diluted with water. The aqueous layer was extracted with EtOAc (3×100 mL) and the combined organic layers were dried (MgSO$_4$) and concentrated in vacuo. Purification by flash chromatography (SiO$_2$, 2 to 5% EtOAc in hexane) gave ethyl rac-(4S,5R)-3-(3,4-difluorophenyl)-4,5-dimethyl-5-(trifluoromethyl)-4,5-dihydrofuran-2-carboxylate (1.7 g, 98%) as a colourless oil. $^1$H NMR (400 MHz, DMSO-d$_6$) δ 7.55-7.38 (m, 2H), 7.21 (ddt, J=8.4, 4.1, 1.6 Hz, 1H), 4.20-3.98 (m, 2H), 3.78 (q, J=7.3 Hz, 1H), 1.63 (s, 3H), 1.08 (t, J=7.1 Hz, 3H), 1.02 (d, J=5.64 Hz, 3H) ppm. ESI-MS m/z calc. 350.0941, found 351.0 (M+1)$^+$.

Step 2

Pd/C (10 wt. % loading, 456 mg, 0.43 mmol) was added to a solution of ethyl rac-(4S,5R)-3-(3,4-difluorophenyl)-4,5-dimethyl-5-(trifluoromethyl)-4,5-dihydrofuran-2-carboxylate (1.00 g, 2.86 mmol) in EtOH (50 mL) and the mixture vacuum degassed. The flask was refilled with hydrogen and a balloon of hydrogen was bubbled through the solution over 5 mins. The reaction was stirred under a balloon of hydrogen at ambient temperature for 3 hours before the balloon was refreshed and the bubbling repeated. The reaction was then left stirring under a balloon of hydrogen for 3 days. The reaction mixture was filtered through celite and the filtrate dried in vacuo to give ethyl rac-(2S,3S,4S,5R)-3-(3,4-difluorophenyl)-4,5-dimethyl-5-(trifluoromethyl)tetrahydrofuran-2-carboxylate (1000 mg, 99%) as a colourless oil which crystallised on standing. $^1$H NMR (500 MHz, Chloroform-d) δ 7.11-7.02 (m, 1H), 6.97 (dt, J=10.0, 8.2 Hz, 1H), 6.94-6.89 (m, 1H), 4.76 (d, J=5.8 Hz, 1H), 3.96 (ttt, J=10.8, 7.1, 3.8 Hz, 2H), 3.60 (dd, J=8.5, 5.8 Hz, 1H), 2.71 (p, J=7.8 Hz, 1H), 1.50-1.40 (m, 3H), 0.89 (t, J=7.1 Hz, 3H), 0.79 (dq, J=7.6, 1.9 Hz, 3H) ppm.

Step 3

A solution of ethyl rac-(2S,3S,4S,5R)-3-(3,4-difluorophenyl)-4,5-dimethyl-5-(trifluoromethyl)tetrahydrofuran-2-carboxylate (1.26 g, 3.58 mmol) and KOt-Bu (801 mg, 7.14 mmol) in tert-butanol (34 mL) was stirred at ambient temperature for 16 hours. The reaction was diluted with EtOAc and acidified to pH 2 with 1 M HCl. The aqueous layer was further extracted with EtOAc. The combined organic layers were dried (MgSO$_4$), filtered and concentrated in vacuo to give rac-(2R,3S,4S,5R)-3-(3,4-difluorophenyl)-4,5-dimethyl-5-(trifluoromethyl)tetrahydrofuran-2-carboxylic acid (1.22 g, 76%) as a pale yellow oil. $^1$H NMR (500 MHz, Chloroform-d) δ 7.17 (dt, J=10.0, 8.3 Hz, 1H), 7.07 (ddd, J=11.3, 7.4, 2.3 Hz, 1H), 6.97 (ddd, J=8.5, 3.9, 1.8 Hz, 1H), 4.93 (d, J=9.6 Hz, 1H), 3.96-3.86 (m, 1H), 2.64 (p, J=7.7 Hz, 1H), 1.29 (s, 3H), 0.85 (dq, J=7.4, 2.3 Hz, 3H) ppm. ESI-MS m/z calc. 324.0785, found 323.1 (M−1)$^-$.

Step 4

Oxalyl chloride (28 μL, 0.32 mmol) was added to a solution of rac-(2R,3S,4S,5R)-3-(3,4-difluorophenyl)-4,5-dimethyl-5-(trifluoromethyl)tetrahydrofuran-2-carboxylic acid (50 mg, 0.13 mmol) in DCM (1 mL) and DMF (5 μL, 0.065 mmol) stirring at 0° C., and the mixture was warmed to ambient temperature over 30 min before being concentrated in vacuo. The residue was azeotroped using toluene and the residue dissolved in DCM (1 mL). To this new solution was added DIPEA (46 μL, 0.26 mmol) and methyl 4-aminopyridine-2-carboxylate (20.4 mg, 0.13 mmol) and the reaction stirred at ambient temperature for 1 hour. The reaction was quenched by addition of MeOH and the mixture evaporated in vacuo. Purification by reverse phase preparative HPLC (basic eluent) gave methyl rac-(2R,3S,4S,5R)-4-[[3-(3,4-difluorophenyl)-4,5-dimethyl-5-(trifluoromethyl)tetrahydrofuran-2-carbonyl]amino]pyridine-2-carboxylate (45 mg, 75%). $^1$H NMR (500 MHz, Chloroform-d) δ 8.66 (d, J=5.5 Hz, 1H), 8.56 (s, 1H), 8.10 (d, J=2.1 Hz, 1H), 7.95 (dd, J=5.5, 2.2 Hz, 1H), 7.20 (dt, J=10.0, 8.3 Hz, 1H), 7.16-7.10 (m, 1H), 7.08-6.98 (m, 1H), 5.00 (d, J=10.4 Hz, 1H), 4.03 (s, 3H), 3.91 (dd, J=10.3, 8.5 Hz, 1H), 2.67 (p, J=7.7 Hz, 1H), 1.71 (d, J=1.1 Hz, 3H), 0.88 (dt, J=7.3, 2.4 Hz, 3H) ppm; $^{19}$F NMR (471 MHz, Chloroform-d) δ−74.42, −136.68 (d, J=21.4 Hz), −138.88 (d, J=21.4 Hz) ppm. ESI-MS m/z calc. 458.1265, found 459.2 (M+1)$^+$.

Step 5

Methyl rac-(2R,3S,4S,5R)-4-[[3-(3,4-difluorophenyl)-4,5-dimethyl-5-(trifluoromethyl)tetrahydrofuran-2-carbonyl]amino]pyridine-2-carboxylate (45 mg, 0.098 mmol) dissolved in methanolic ammonia (3 mL of 7 M, 21.00 mmol) and MeOH (2.5 mL) and stirred at ambient temperature for 2.5 hours. The reaction was heated at 50° C. for 1 hour 40 mins before further methanolic ammonia (3 mL of 7 M, 21.00 mmol) was added. After a further 20 mins the reaction was concentrated in vacuo. Purification by preparative reverse phase HPLC (basic eluent) gave rac-(2R,3S,4S,5R)-4-[[3-(3,4-difluorophenyl)-4,5-dimethyl-5-(trifluoromethyl)tetrahydrofuran-2-carbonyl]amino]pyridine-2-carboxamide (15 mg). ESI-MS m/z calc. 443.12683, found 444.2 (M+1)$^+$; 442.2 (M−1)$^-$.

Step 6 rac-(2R,3S,4S,5R)-4-[[3-(3,4-difluorophenyl)-4,5-dimethyl-5-(trifluoromethyl)tetrahydrofuran-2-carbonyl]amino]pyridine-2-carboxamide was separated by chiral SFC using a (R,R)-Whelk-O1 column, 5 μm particle size, 25 cm×21.2 mm from Regis Technologies to give two single isomers of unknown absolute configuration:

First Eluting Isomer (rt=0.64 min): rel-(2S,3R,4R,5S)-4-[[3-(3,4-difluorophenyl)-4,5-dimethyl-5-(trifluoromethyl)tetrahydrofuran-2-carbonyl]amino]pyridine-2-carboxamide (90, 2 mg, 5%). $^1$H NMR (500 MHz, DMSO-d$_6$) δ 10.63 (s, 1H), 8.49 (d, J=5.5 Hz, 1H), 8.30 (d, J=2.0 Hz, 1H), 8.06 (d, J=2.8 Hz, 1H), 7.84 (dd, J=5.5, 2.2 Hz, 1H), 7.71-7.55 (m, 1H), 7.48 (ddd, J=12.3, 7.8, 2.2 Hz, 1H), 7.42 (dt, J=10.8, 8.6 Hz, 1H), 7.20 (d, J=8.3 Hz, 1H), 5.11 (d, J=9.6 Hz, 1H), 4.18 (dd, J=9.7, 7.6 Hz, 1H), 2.76 (p, J=7.5 Hz, 1H), 1.62 (s, 3H), 0.83-0.64 (m, 3H) ppm. ESI-MS m/z calc. 443.12683, found 444.2 (M+1)$^+$; 442.2 (M−1)$^-$.

Second Eluting Isomer (rt=1.29 min): rel-(2R,3S,4S,5R)-4-[[3-(3,4-difluorophenyl)-4,5-dimethyl-5-(trifluoromethyl)tetrahydrofuran-2-carbonyl]amino]pyridine-2-carboxamide (91, 3 mg, 7%). $^1$H NMR (500 MHz, DMSO-d$_6$) δ 10.65 (s, 1H), 8.49 (d, J=5.5 Hz, 1H), 8.30 (d, J=2.1 Hz, 1H), 8.06 (d, J=2.9 Hz, 1H), 7.84 (dd, J=5.5, 2.2 Hz, 1H), 7.60 (d, J=2.9 Hz, 1H), 7.48 (ddd, J=12.1, 7.7, 1.8 Hz, 1H), 7.42 (dt, J=10.7, 8.6 Hz, 1H), 7.20 (dd, J=9.5, 3.5 Hz, 1H), 5.12 (d, J=9.7 Hz, 1H), 4.18 (dd, J=9.7, 7.7 Hz, 1H), 2.76 (p, J=7.4 Hz, 1H), 1.62 (s, 3H), 0.75 (dd, J=7.4, 2.4 Hz, 3H) ppm. ESI-MS m/z calc. 443.12683, found 444.2 (M+1)$^+$; 442.2 (M−1)$^-$.

Example 16 rel-(2S,3R,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide (92) and rel-(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide (93)

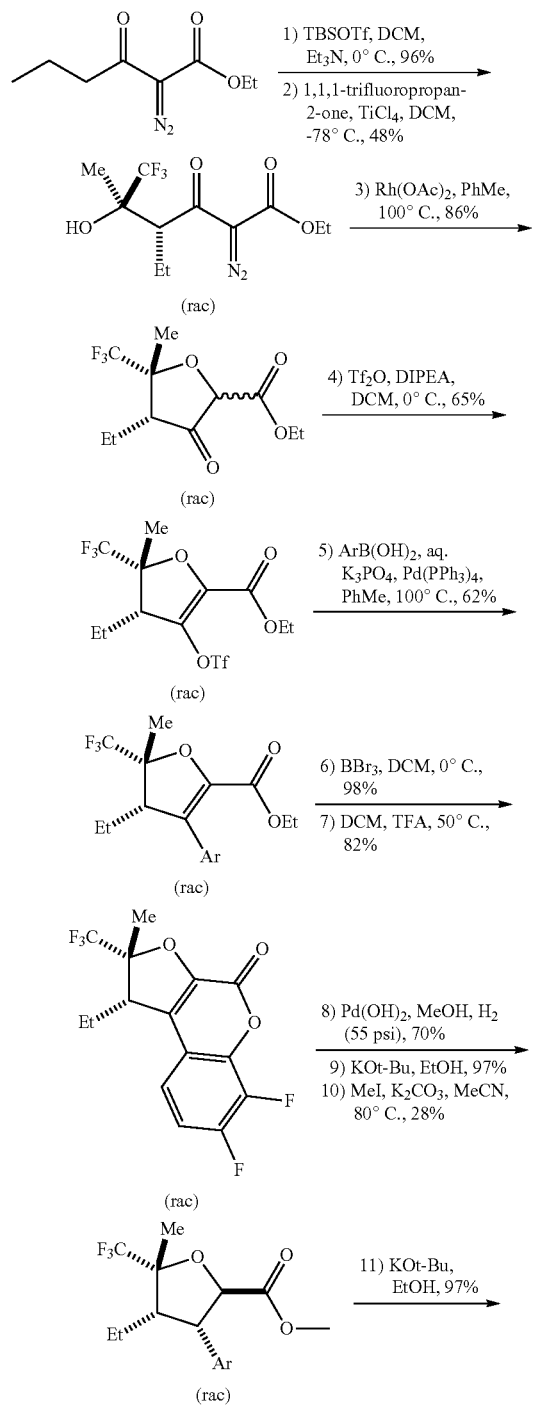

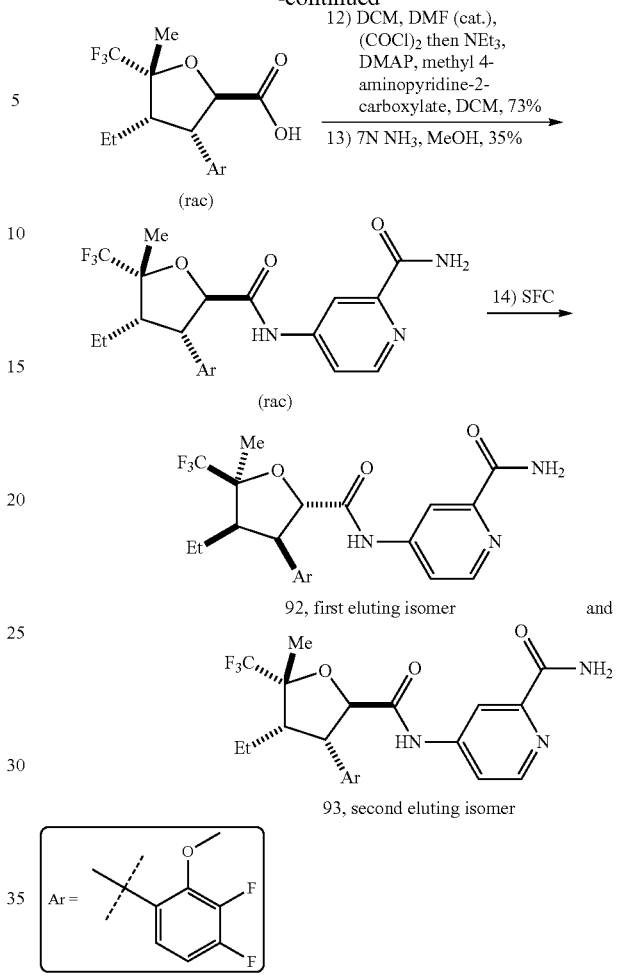

Step 1

To a stirred solution of ethyl 2-diazo-3-oxo-hexanoate (5 g, 24.47 mmol) in DCM (50 mL) stirring at 0° C. was added TEA (6.5340 g, 9 mL, 64.57 mmol). [Tert-butyl(dimethyl)silyl]trifluoromethanesulfonate (8.6250 g, 7.5 mL, 32.63 mmol) was added very slowly and the reaction mixture was stirred for 30 mins at 0° C. The reaction mixture was washed with saturated aqueous $NaHCO_3$ solution (50 mL) and the organic layer dried ($MgSO_4$) and concentrated in vacuo to give ethyl (Z)-3-[tert-butyl(dimethyl)silyl]oxy-2-diazo-hex-3-enoate (7 g, 96%) which was used without further purification. $^1$H NMR (400 MHz, DMSO-$d_6$) δ 5.16 (t, J=7.3 Hz, 1H), 4.18 (q, J=7.1 Hz, 4H), 2.04-2.11 (m, 3H), 1.21 (t, J=8 Hz, 3H), 0.92 (s, 9H), 0.12 (s, 6H) ppm.

Step 2

To a stirred solution of 1,1,1-trifluoropropan-2-one (70 g, 624.72 mmol) in DCM (448 mL) stirring at −78° C. was added $TiCl_4$ (617 mL of 1 M, 617.00 mmol) very slowly. A solution of ethyl (Z)-3-[tert-butyl(dimethyl)silyl]oxy-2-diazo-hex-3-enoate (150 g, 452.33 mmol) in DCM (152 mL, pre-dried over $MgSO_4$) was added and the reaction stirred for 1 hour at this temperature. The reaction mixture was quenched with water (260 mL), the layers separated and the organic layer washed with further water (200 mL), dried (MgSO$_4$) and concentrated in vacuo to give ethyl rac-(4R,5R)-2-diazo-4-ethyl-6,6,6-trifluoro-5-hydroxy-5-methyl-3-oxo-hexanoate (66 g, 48%) as a light reddish liquid which was used without further purification. $^1$H NMR (400 MHz, DMSO-d$_6$) δ 6.17 (s, 1H), 4.21-4.27 (m, 2H), 4.1 (d, J=9.2 Hz, 1H), 1.77-1.82 (m, 1H) 1.64-1.68 (m, 1H), 1.29 (s, 3H), 1.24 (t, J=7 Hz, 3H), 0.83 (t, J=7.4 Hz, 3H) ppm. ESI-MS m/z calc. 296.0984, found 297.1 (M+1)$^+$.

Step 3

To a stirred solution of rhodium(II) acetate (985 mg, 2.23 mmol) in toluene (340 mL) stirring at 100° C. was added a solution of ethyl rac-(4R,5R)-2-diazo-4-ethyl-6,6,6-trifluoro-5-hydroxy-5-methyl-3-oxo-hexanoate (66 g, 219.23 mmol) in toluene (1320 mL) slowly over 1 hour. Upon complete consumption of starting material the reaction mixture was filtered through celite and concentrated in vacuo to afford ethyl rac-(4R,5R)-4-ethyl-5-methyl-3-oxo-5-(trifluoromethyl)tetrahydrofuran-2-carboxylate (53 g, 86%) as a light yellow liquid which was used without further purification. $^1$H NMR (400 MHz, DMSO-d$_6$) δ 4.79 (s, 1H), 4.20-4.13 (m, 2H), 2.95 (t, J=4 Hz, 1H), 1.66 (s, 3H), 1.49-1.41 (m, 2H), 1.20-1.14 (m, 3H), 1.06 (t, J=3.7 Hz, 3H) ppm.

Step 4

To a stirred solution of ethyl rac-(4R,5R)-4-ethyl-5-methyl-3-oxo-5-(trifluoromethyl)tetrahydrofuran-2-carboxylate (53 g, 187.71 mmol) in DCM (340 mL) stirring at 0° C. was added DIPEA (28.196 g, 38 mL, 218.16 mmol) followed by a solution of trifluoromethanesulfonic anhydride (63.840 g, 38 mL, 226.27 mmol) in DCM (190 mL) dropwise over 20 mins. After addition the reaction was quenched by addition of cool water and diluted in hexane. The organic layer was washed with saturated aqueous sodium bicarbonate solution and concentrated in vacuo. Purification by flash chromatography (SiO$_2$, 0 to 1% EtOAc in hexane) gave ethyl rac-(4R,5R)-4-ethyl-5-methyl-5-(trifluoromethyl)-3-(((trifluoromethyl)sulfonyl)oxy)-4,5-dihydrofuran-2-carboxylate (50 g, 65%). $^1$H NMR (400 MHz, Chloroform-d) δ 4.36 (q, J=7.1 Hz, 2H), 3.01 (t, J=6.9 Hz, 1H), 1.92-1.75 (m, J=7.1 Hz, 2H), 1.64 (s, 3H), 1.35 (t, J=7.2 Hz, 3H), 1.07 (t, J=7.5 Hz, 3H) ppm.

Step 5

To a stirred solution of (3,4-difluoro-2-methoxyphenyl)boronic acid (28 g, 148.99 mmol) and ethyl rac-(4R,5R)-4-ethyl-5-methyl-5-(trifluoromethyl)-3-(((trifluoromethyl)sulfonyl)oxy)-4,5-dihydrofuran-2-carboxylate (50 g, 122.41 mmol) in toluene (1000 mL) was added K$_3$PO$_4$ (188 mL of 2 M, 376.00 mmol). The mixture was degassed with N$_2$ gas for 20 mins before Pd(PPh$_3$)$_4$ (7.2 g, 6.23 mmol) was added and the reaction heated to 100° C. for 1 hour. The reaction mixture was filtered through celite, the filtrate was diluted with water (500 mL), and the aqueous layer was extracted with EtOAc (2×750 mL). The combined organic layers were dried (MgSO$_4$) and concentrated in vacuo. Purification by flash chromatography (SiO$_2$, 0 to 2% EtOAc in hexane) gave ethyl rac-(4S,5R)-3-(3,4-difluoro-2-methoxyphenyl)-4-ethyl-5-methyl-5-(trifluoromethyl)-4,5-dihydrofuran-2-carboxylate (30.82 g, 62%) as a light yellow liquid. $^1$H NMR (400 MHz, Chloroform-d) δ 6.91-6.76 (m, 2H), 4.12 (qq, J=6.8, 3.6 Hz, 2H), 3.90 (d, J=2.2 Hz, 3H), 3.32 (t, J=7.0 Hz, 1H), 1.72 (s, 3H), 1.63-1.68 (m, 1H), 1.46 (dq, J=14.6, 7.3 Hz, 1H), 1.11 (t, J=7.1 Hz, 3H), 0.78 (t, J=7.4 Hz, 3H) ppm. ESI-MS m/z calc. 394.1204, found 395.2 (M+1)$^+$.

Step 6

To a solution of ethyl rac-(4S,5R)-3-(3,4-difluoro-2-methoxyphenyl)-4-ethyl-5-methyl-5-(trifluoromethyl)-4,5-dihydrofuran-2-carboxylate (30.8 g, 78.11 mmol) in DCM (275 mL) stirring at 0° C. was added BBr$_3$ (100 mL of 1 M, 100.0 mmol) over 35 mins. The reaction mixture was stirred at this temperature for 1 hour then quenched at this temperature by the slow addition of a mixture of water (110 mL) and satutared aqueous sodium bicarbonate solution (110 mL). The layers were separated and the aqueous layer extracted with DCM (2×100 mL) and the combined organic extracts washed with water (100 mL), dried (MgSO$_4$), filtered and concentrated in vacuo to give ethyl rac-(4S,5R)-3-(3,4-difluoro-2-hydroxyphenyl)-4-ethyl-5-methyl-5-(trifluoromethyl)-4,5-dihydrofuran-2-carboxylate (29.1 g, 98%) as an orangey-brown, powdery solid. $^1$H NMR (500 MHz, Chloroform-d) δ 6.85 (ddd, J=8.8, 5.7, 2.2 Hz, 1H), 6.77 (ddd, J=9.6, 8.8, 7.3 Hz, 1H), 5.87 (s, 1H), 4.30-4.12 (m, 2H), 3.44-3.33 (m, 1H), 1.84-1.74 (m, 3H), 1.74-1.63 (m, 1H), 1.60-1.46 (m, 1H), 1.21 (t, J=7.1 Hz, 3H), 0.82 (t, J=7.4 Hz, 3H) ppm. ESI-MS m/z calc. 380.1047, found 381.2 (M+1)$^+$; 379.0 (M−1)$^-$.

Step 7

TFA (11.8 mL, 153.2 mmol) was added to a solution of ethyl rac-(4S,5R)-3-(3,4-difluoro-2-hydroxyphenyl)-4-ethyl-5-methyl-5-(trifluoromethyl)-4,5-dihydrofuran-2-carboxylate (29.1 g, 76.52 mmol) was dissolved in DCM (200 mL) stirring at ambient temperature. The mixture was heated at 50° C. for 1 hour 45 mins before being cooled to ambient temperature and quenched with saturated aqueous sodium bicarbonate solution (800 mL). The layers were separated, the aqueous layer extracted with DCM (3×200 mL), and the combined organic extracts dried (MgSO$_4$) and concentrated in vacuo. The residue was re-dissolved in DCM (50 mL) and heptane (100 mL) was layered on top. The mixture was allowed to stand at ambient temperature overnight and the resultant solid isolated by filtration, washing with a minimum of heptane. The filtrate was concentrated in vacuo, redissolved in DCM and heptane layered on top. The mixture was allowed to stand at ambient temperature overnight and the resultant second crop of solid isolated by filtration, washing with a minimum of heptane. The crops were combined to give rac-(1S,2R)-1-ethyl-6,7-difluoro-2-methyl-2-(trifluoromethyl)-1H-furo[2,3-c]chromen-4-one (21.0 g, 82%) as a fluffy white solid. $^1$H NMR (500 MHz, Chloroform-d) δ 7.22-7.07 (m, 2H), 3.49 (dd, J=7.3, 4.5 Hz, 1H), 2.16-1.92 (m, 2H), 1.66 (q, J=1.1 Hz, 3H), 1.06-0.96 (m, 3H) ppm; $^{19}$F NMR (471 MHz, Chloroform-d) δ−74.15, −133.57 (d, J=20.1 Hz), −153.89 (d, J=20.1 Hz) ppm. ESI-MS m/z calc. 334.06284, found 335.1 (M+1)$^+$; 333.1 (M−1)$^-$.

Step 8

Pd(OH)$_2$ (27 g of 10% w/w, 19.23 mmol) was added to a Parr vessel containing a solution of rac-(1S,2R)-1-ethyl-6,7-difluoro-2-methyl-2-(trifluoromethyl)-1H-furo[2,3-c]chromen-4-one (21 g, 62.83 mmol) in MeOH (460 mL) that had first been left to sonicate for 15 mins at 45° C. to get material into solution. The flask was evacuated and refilled with H$_2$ three times before being shaken under 55 psi of hydrogen for 24 h. The catalyst was removed by filtration through celite under a blanket of nitrogen, washing with EtOH. The filtrate was concentrated in vacuo to give methyl rac-(2S,3S,4S,5R)-3-(3,4-difluoro-2-hydroxy-phenyl)-4-ethyl-5-methyl-5-(trifluoromethyl)tetrahydrofuran-2-carboxylate (16.2 g, 70%) as a fluffy white solid, in a mixture of diastereomers, also containing 5% of the acid side-product. ESI-MS m/z calc. 368.1047, found 368.9 (M+1)$^+$; 367.2 (M−1)$^−$.

Step 9

Methyl rac-(2S,3S,4S,5R)-3-(3,4-difluoro-2-hydroxy-phenyl)-4-ethyl-5-methyl-5-(trifluoromethyl)tetrahydrofuran-2-carboxylate (1000 mg, 2.616 mmol) was dissolved in ethanol (35 mL) and KOt-Bu (1.21 g, 10.78 mmol) was added. The reaction mixture was stirred at ambient temperature overnight before being concentrated in vacuo and the residue partitioned between EtOAc and 1M HCl. The layers were separated and the organic layer passed through a phase separator cartridge and concentrated in vacuo to give rac-(2R,3S,4S,5R)-3-(3,4-difluoro-2-hydroxy-phenyl)-4-ethyl-5-methyl-5-(trifluoromethyl)tetrahydrofuran-2-carboxylic acid (900 mg, 97%). ESI-MS m/z calc. 354.08905, found 356.3 (M+1)$^+$.

Step 10

To a solution of rac-(2R,3S,4S,5R)-3-(3,4-difluoro-2-hydroxy-phenyl)-4-ethyl-5-methyl-5-(trifluoromethyl)tetrahydrofuran-2-carboxylic acid (1 g, 2.823 mmol) in acetonitrile (6 mL) was added K$_2$CO$_3$ (1.65 g, 11.94 mmol) and MeI (1.6 g, 11.27 mmol). The mixture was heated in a sealed vial at 80° C. for 6 hours before being diluted with DCM, filtered and the filtrate carefully concentrated in vacuo (cold water bath). Purification by flash chromatography (24 g SiO$_2$, 10 to 55% EtOAc in heptane) gave methyl rac-(2R,3S,4S,5R)-3-(3,4-difluoro-2-methoxy-phenyl)-4-ethyl-5-methyl-5-(trifluoromethyl)tetrahydrofuran-2-carboxylate (300 mg, 28%). $^1$H NMR (400 MHz, DMSO-d$_6$) δ 7.17-7.08 (m, 2H), 5.13 (d, J=6.1 Hz, 1H), 4.27 (dd, J=8.7, 6.1 Hz, 1H), 3.89 (d, J=1.5 Hz, 3H), 3.36 (s, 3H), 2.75 (ddd, J=10.5, 8.6, 4.2 Hz, 1H), 1.54-1.48 (m, 3H), 1.52-1.36 (m, 1H), 0.73 (t, J=7.3 Hz, 3H) ppm.

Step 11

To a solution of ethyl rac-(2R,3S,4S,5R)-3-(3,4-difluoro-2-methoxy-phenyl)-4-ethyl-5-methyl-5-(trifluoromethyl)tetrahydrofuran-2-carboxylate (300 mg, 0.78 mmol) in EtOH (10 mL) was added KOt-Bu (363 mg, 3.24 mmol). The reaction was stirred at ambient temperature overnight, then concentrated in vacuo. The residue was partitioned between EtOAc and 1M HCl and the layers separated. The organic layer was passed through a phase separator cartridge and the filtrate evaporated in vacuo to give rac-(2R,3S,4S,5R)-3-(3,4-difluoro-2-methoxy-phenyl)-4-ethyl-5-methyl-5-(trifluoromethyl)tetrahydrofuran-2-carboxylic acid (300 mg), which was used without any further purification. $^1$H NMR (400 MHz, DMSO-d$_6$) δ 7.26-7.10 (m, 2H), 4.79 (d, J=9.0 Hz, 1H), 4.17 (t, J=9.2 Hz, 1H), 3.92 (d, J=1.9 Hz, 3H), 1.58-1.48 (m, 3H), 1.45-1.31 (m, 1H), 1.30-1.02 (m, 2H), 0.50 (t, J=7.3 Hz, 3H) ppm.

Step 12

To a solution of rac-(2R,3S,4S,5R)-3-(3,4-difluoro-2-methoxy-phenyl)-4-ethyl-5-methyl-5-(trifluoromethyl)tetrahydrofuran-2-carboxylic acid (300 mg, 0.81 mmol) in DCM (15 mL) was added DMF (6.4 μL, 0.083 mmol) and oxalyl chloride (216 μL, 2.48 mmol). The mixture was stirred at ambient temperature for 15 mins then concentrated in vacuo. The residue was diluted in DCM (3 mL) and added dropwise to a solution of methyl 4-aminobenzoate (185 mg, 1.22 mmol), DMAP (5 mg, 0.041 mmol) and NEt$_3$ (350 μL, 2.51 mmol) in DCM (5 mL) stirring at ambient temperature. The mixture was stirred for 16 hours then diluted in DCM (50 mL) and washed with 2 M HCl (50 mL). The organic layers were passed through a phase separator cartridge and concentrated in vacuo to give methyl rac-(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxylate (300 mg, 73%), which was used without further purification. ESI-MS m/z calc. 502.1527, found 503.2 (M+1)$^+$.

Step 13

Methyl rac-(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxylate (300 mg, 0.5971 mmol) was dissolved in methanolic ammonia (500 mL of 2 M, 1.00 mol). The reaction was stirred for 16 hours at ambient temperature before being concentrated in vacuo. Purification by flash chromatography (24 g SiO$_2$, 0 to 100% EtOAc in heptane, loaded in DCM) gave rac-(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide (116, 107.1 mg, 35%) as a white solid. $^1$H NMR (500 MHz, DMSO-d$_6$) δ 10.65 (s, 1H), 8.50 (d, J=5.6 Hz, 1H), 8.28 (d, J=2.2 Hz, 1H), 8.06 (d, J=2.5 Hz, 1H), 7.82 (dd, J=5.5, 2.2 Hz, 1H), 7.61 (d, J=2.4 Hz, 1H), 7.25-7.16 (m, 2H), 4.94 (d, J=8.8 Hz, 1H), 4.34 (t, J=9.0 Hz, 1H), 3.91 (d, J=1.8 Hz, 3H), 2.63-2.60 (m, 1H), 1.63 (s, 3H), 1.47-1.41 (m, 1H), 1.27-1.21 (m, 1H), 0.54 (t, J=7.3 Hz, 3H) ppm; $^{19}$F NMR (471 MHz, DMSO-d6) δ−72.26, −138.00 (d, J=21.2 Hz), −154.96 (d, J=21.2 Hz) ppm. ESI-MS m/z calc. 487.15305, found 488.4 (M+1)$^+$.

Step 14 rac-(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide (245 mg, 0.480 mmol) was separated by chiral SFC using a (R,R)-Whelk-O1 column, 5 μm particle size, 25 cm×21.2 mm from Regis Technologies to give two single isomers of unknown absolute configuration:

First Eluting Isomer (rt=0.96 min): rel-(2S,3R,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide (92, 78.6 mg, 67%). $^1$H NMR (500 MHz, DMSO-d$_6$) δ 10.65 (s, 1H), 8.50 (dd, J=5.5, 0.6 Hz, 1H), 8.28 (dd, J=2.2, 0.6 Hz, 1H), 8.06 (d, J=2.7 Hz, 1H), 7.82 (dd, J=5.5, 2.2 Hz, 1H), 7.62-7.61 (m, 1H), 7.25-7.16 (m, 2H), 4.94 (d, J=8.8 Hz, 1H), 4.34 (t, J=9.1 Hz, 1H), 3.91 (d, J=1.8 Hz, 3H), 2.65-2.60 (m, 1H), 1.63 (s, 3H), 1.48-1.39 (m, 1H), 1.28-1.19 (m, 1H), 0.54 (t, J=7.3 Hz, 3H) ppm; $^{19}$F NMR (471 MHz, DMSO-d$_6$) δ−72.26, −138.00 (d, J=21.3 Hz), −154.96 (d, J=21.4 Hz) ppm. ESI-MS m/z calc. 487.15305, found 488.5 (M+1)$^+$.

Second Eluting Isomer (rt=2.07 min): rel-(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide (93, 87.5 mg, 74%). $^1$H NMR (500 MHz, DMSO-$d_6$) δ 10.65 (s, 1H), 8.50 (d, J=5.6 Hz, 1H), 8.28 (d, J=2.1 Hz, 1H), 8.06 (d, J=2.1 Hz, 1H), 7.82 (dd, J=5.5, 2.2 Hz, 1H), 7.61 (d, J=2.9 Hz, 1H), 7.25-7.16 (m, 2H), 4.94 (d, J=8.8 Hz, 1H), 4.34 (t, J=9.0 Hz, 1H), 3.91 (d, J=1.8 Hz, 3H), 2.65-2.60 (m, 1H), 1.63 (s, 3H), 1.48-1.40 (m, 1H), 1.28-1.19 (m, 1H), 0.54 (t, J=7.3 Hz, 3H) ppm; $^{19}$F NMR (471 MHz, DMSO-$d_6$) δ−72.26, −138.00 (d, J=21.2 Hz), −154.96 (d, J=21.4 Hz) ppm. ESI-MS m/z calc. 487.15305, found 488.8 (M+1)$^+$.

The following compounds were made using a method similar to that described in Example 16, except that ethyl 4-cyclopropyl-2-diazo-3-oxo-butanoate was used as the starting material in place of ethyl 2-diazo-3-oxo-hexanoate in step 1. In step 8, 1 atm of pressure of hydrogen was used rather than 55 psi. The conditions used for the saponification step 11 are similar to those used in Example 3 step 10. In step 14, purification was performed by chiral SFC using a Lux Cellulose-2 column, 5 μm particle size, 25 cm×10 mm from Phenomenex, Inc. to give two single isomers of unknown absolute configuration:

| Cmpd No. | Compound Name | LC/MS | NMR (shifts in ppm) |
| --- | --- | --- | --- |
| 94 | rel-(2S,3R,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide (first eluting peak by SFC on Lux Cellulose-2 column, rt = 2.32 min) | ESI-MS m/z calc. 499.15305, found 500.1 (M + 1)$^+$; 498.2 (M − 1)$^-$; Retention time: 3.32 minutes | $^1$H NMR (500 MHz, DMSO-$d_6$) δ 10.69 (s, 1H), 8.49 (d, J = 5.5 Hz, 1H), 8.27 (d, J = 2.1 Hz, 1H), 8.05 (d, J = 2.6 Hz, 1H), 7.83 (dd, J = 5.5, 2.2 Hz, 1H), 7.61 (s, 1H), 7.24 (t, J = 7.5 Hz, 1H), 7.20-7.11 (m, 1H), 5.14 (d, J = 10.4 Hz, 1H), 4.31 (dd, J = 10.3, 8.3 Hz, 1H), 3.92 (d, J = 1.9 Hz, 3H), 1.88 (dd, J = 11.6, 8.2 Hz, 1H), 1.58 (s, 3H), 0.63 (s, 1H), 0.45 (d, J = 13.7 Hz, 1H), 0.20 (q, J = 4.7 Hz, 1H), −0.04−−0.17 (m, 1H), −0.48 (dd, J = 9.6, 5.0 Hz, 1H) ppm. |
| 95 | rel-(2R,3S,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide (second eluting peak by SFC on Lux Cellulose-2 column, rt = 3.59 min) | ESI-MS m/z calc. 499.15305, found 500.6 (M + 1)$^+$; 498.7 (M − 1)$^-$; Retention time: 3.32 minutes | $^1$H NMR (500 MHz, DMSO-$d_6$) δ 10.77 (s, 1H), 8.58 (d, J = 5.5 Hz, 1H), 8.36 (d, J = 2.1 Hz, 1H), 8.14 (d, J = 2.8 Hz, 1H), 7.91 (dd, J = 5.5, 2.2 Hz, 1H), 7.69 (d, J = 2.8 Hz, 1H), 7.32 (ddd, J = 8.1, 5.8, 1.8 Hz, 1H), 7.29-7.20 (m, 1H), 5.23 (d, J = 10.4 Hz, 1H), 4.40 (dd, J = 10.4, 8.2 Hz, 1H), 4.01 (d, J = 1.9 Hz, 3H), 1.96 (dd, J = 11.7, 8.3 Hz, 1H), 1.67 (s, 3H), 0.71 (s, 1H), 0.51 (td, J = 8.6, 4.6 Hz, 1H), 0.28 (dt, J = 10.0, 5.0 Hz, 1H), 0.06−−0.06 (m, 1H), −0.40 (dd, J = 9.7, 4.9 Hz, 1H) ppm. |

Example 17 rel-(2R,3S,4R,5S)-4-[[3-(3,4-difluoro-2-methoxy-phenyl)-5-(difluoromethyl)-4,5-dimethyl-tetrahydro-furan-2-carbonyl]amino]pyridine-2-carboxamide (96), rel-(2S,3R,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide (97), rel-(2S,3R,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide (98) and rel-(2R,3S,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide (99)

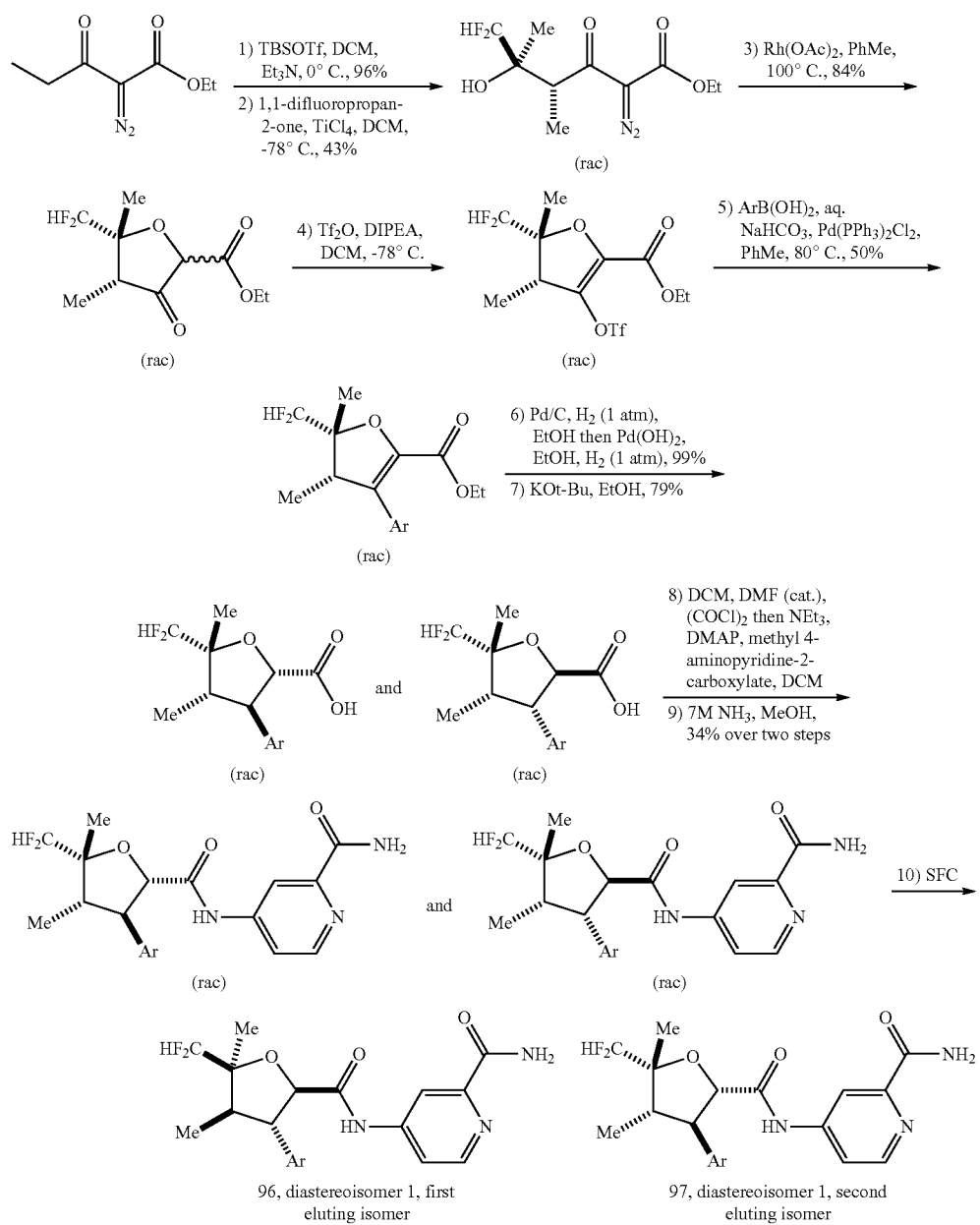

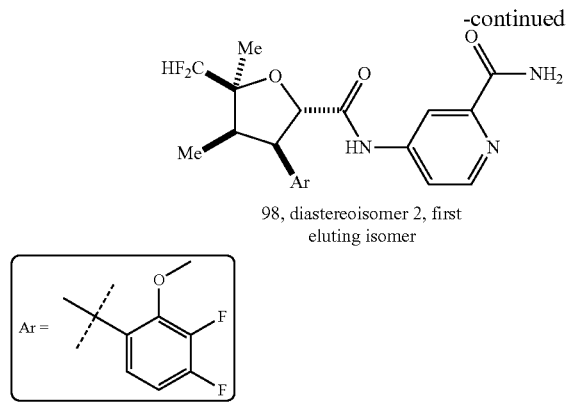

98, diastereoisomer 2, first eluting isomer

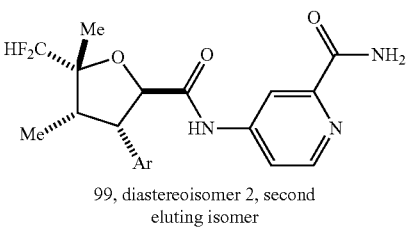

99, diastereoisomer 2, second eluting isomer

Ar =

Step 1

To a solution of ethyl 2-diazo-3-oxo-pentanoate (30 g, 172.77 mmol) in DCM (300 mL) stirring at 0° C. was added $Et_3N$ (45.999 g, 64 mL, 450.03 mmol). TBSOTf (55.223 g, 49 mL, 204.73 mmol) was added slowly and the mixture was stirred for 30 mins at the same temperature. The reaction mixture was diluted with 30% aqueous $NaHCO_3$ solution (200 mL), the layers separated and the organic layer washed with water (500 mL), dried ($MgSO_4$) and concentrated in vacuo to give ethyl rac-(Z)-3-[tert-butyl(dimethyl)silyl]oxy-2-diazo-pent-3-enoate (48 g, 98%), which was used without further purification.

Step 2

To a solution of 1,1-difluoropropan-2-one (14 g, 148.84 mmol) in DCM (100 mL) stirring at −78° C. was added dropwise $TiCl_4$ (28.545 g, 16.5 mL, 150.49 mmol) and ethyl (Z)-3-[tert-butyl(dimethyl)silyl]oxy-2-diazo-pent-3-enoate (20 g, 73.964 mmol). The reaction was stirred at this temperature for 30 mins before diluting in water. The layers were separated and the aqueous layer extracted with DCM (2×100 mL). The combined organic layers were washed with water and brine, nad concentrated in vacuo. Purification by flash chromatography ($SiO_2$) gave ethyl rac-(4R,5R)-2-diazo-6,6-difluoro-5-hydroxy-4,5-dimethyl-3-oxo-hexanoate (8.5 g, 43%) as a liquid. $^1H$ NMR (400 MHz, $CDCl_3$) δ 5.74 (t, J=56.12 Hz, 1H), 4.31 (q, J=14.24 Hz, 2H), 3.97-3.93 (m, 1H), 3.67 (s, 1H), 1.34 (d, J=7.16 Hz, 3H), 1.30 (s, 3H), 1.26-1.23 (m, 3H) ppm.

Step 3

A solution of rhodium(II) acetate (3 mg, 0.0068 mmol) in toluene was stirred at 100° C. for 30 mins before a solution of ethyl rac-(4R,5R)-2-diazo-6,6-difluoro-5-hydroxy-4,5-dimethyl-3-oxo-hexanoate (120 mg, 0.45 mmol) in toluene was added. The mixture was stirred at his temperature for 45 mins then cooled to ambient temperature and filtered. The filtrate was concentrated in vacuo to give ethyl rac-(4R,5R)-5-(difluoromethyl)-4,5-dimethyl-3-oxo-tetrahydrofuran-2-carboxylate (90 mg, 84%) as a light brown liquid, which was used without further purification. $^1H$ NMR (400 MHz, $CDCl_3$) δ 5.66 (t, J=54.62 Hz, 1H), 4.70 (s, 1H), 4.30-4.22 (m, 2H), 2.54-2.46 (m, 1H), 1.71 (s, 3H), 1.38-1.28 (m, 6H) ppm.

Step 4

Triflic anhydride (1.85 mL, 11.00 mmol) was added dropwise to a solution of ethyl rac-(4R,5R)-5-(difluoromethyl)-4,5-dimethyl-3-oxo-tetrahydrofuran-2-carboxylate (2000 mg, 8.47 mmol) and $NEt_3$ (3.55 mL, 25.47 mmol) in DCM (40 mL) with stirring at −78° C. After 2 hours, saturated aqueous $NaHCO_3$ was added, the layers separated and the aqueous layer extracted with DCM. The combined organic layers were passed through a phase separator cartridge and concentrated in vacuo to give ethyl rac-(4R,5R)-5-(difluoromethyl)-4,5-dimethyl-3-(((trifluoromethyl)sulfonyl)oxy)-4,5-dihydrofuran-2-carboxylate (3.8 g), containing some $NEt_3$, which was used as such in the next step, without any further purification. ESI-MS m/z calc. 368.0353, found 369.2 $(M+1)^+$.

Step 5

A mixture of ethyl rac-(4R,5R)-5-(difluoromethyl)-4,5-dimethyl-3-(((trifluoromethyl)sulfonyl)oxy)-4,5-dihydrofuran-2-carboxylate (3250 mg, 8.83 mmol), (3,4-difluoro-2-methoxy-phenyl)boronic acid (2.0 g, 10.64 mmol) and saturated aqueous $NaHCO_3$ (excess) in dioxane (80 mL) was degassed and refilled with nitrogen. $Pd(PPh_3)_2Cl_2$ (321 mg, 0.46 mmol) was added and the mixture further degassed. The reaction was heated at 80° C. for 4 hours then cooled to ambient temperature and concentrated in vacuo. The residue was dissolved in EtOAc, washed with water and brine, and the organic layer filtered through a Celite (10 g), washing with EtOAc, and concentrated in vacuo. Purification by flash chromatography (40 g $SiO_2$, 20 to 40% EtOAc in heptane, loaded in DCM) gave ethyl rac-(4S,5R)-3-(3,4-difluoro-2-methoxyphenyl)-5-(difluoromethyl)-4,5-dimethyl-4,5-dihydrofuran-2-carboxylate (1.6 g, 50%) as a clear oil. $^1H$ NMR (400 MHz, DMSO-$d_6$) δ 7.23-7.10 (m, 1H), 7.10-6.97 (m, 1H), 6.51-6.13 (m, 1H), 4.12-3.95 (m, 2H), 3.82 (dd, J=5.4, 1.8 Hz, 3H), 3.36 (m, 1H), 1.47 (d, J=1.4 Hz, 3H), 1.31-1.14 (m, 3H), 1.08-0.82 (m, 3H) ppm. ESI-MS m/z calc. 362.11414, found 363.3 $(M+1)^+$.

Step 6

EtOH (20 mL) was added to a flask containing ethyl rac-(4S,5R)-3-(3,4-difluoro-2-methoxyphenyl)-5-(difluoromethyl)-4,5-dimethyl-4,5-dihydrofuran-2-carboxylate (300 mg, 0.83 mmol) and Pd/C (900 mg, 0.85 mmol). The mixture was degassed and then stirred under a balloon of hydrogen for 3 days. The reaction mixture was filtered through Celite, washed with EtOH, and the filtrate was concentrated in vacuo. To the residue was added $Pd(OH)_2/C$ (20% wt, 1 equivalent) and EtOH (20 mL) and the mixture degassed and stirred under a balloon of hydrogen overnight.

The mixture was filtered through Celite and the filtrate concentrated in vacuo to give a mixture of isomers of ethyl 3-(3,4-difluoro-2-methoxy-phenyl)-5-(difluoromethyl)-4,5-dimethyl-tetrahydrofuran-2-carboxylate (300 mg, 99%). ESI-MS m/z calc. 364.12976, found 365.1 (M+1)⁺.

Step 7

To a solution of a mixture of isomers of ethyl 3-(3,4-difluoro-2-methoxy-phenyl)-5-(difluoromethyl)-4,5-dimethyl-tetrahydrofuran-2-carboxylate (300 mg, 0.82 mmol) in EtOH (10 mL) was added KOt-Bu (380 mg, 3.39 mmol). The mixture was stirred at ambient temperature overnight then concentrated in vacuo. The residue was partitioned between EtOAc and 1M HCl, the layers separated and the organic layer passed through a phase separator cartridge. The filtrate was concentrated in vacuo to give a mixture of isomers of 3-(3,4-difluoro-2-methoxy-phenyl)-5-(difluoromethyl)-4,5-dimethyl-tetrahydrofuran-2-carboxylic acid (220 mg, 79%) as a colourless oil. ESI-MS m/z calc. 336.09848, found 335.1 (M−1)⁻.

Step 8 and 9

To a solution of a mixture of isomers of 3-(3,4-difluoro-2-methoxy-phenyl)-5-(difluoromethyl)-4,5-dimethyl-tetrahydrofuran-2-carboxylic acid (220 mg, 0.65 mmol) in DCM (6 mL) was added DMF (5 μL, 0.065 mmol) and oxalyl chloride (180 μL, 2.06 mmol). The reaction was stirred at ambient temperature for 2 hours then concentrated in vacuo. The residue was dissolved in DCM (3 mL) and added dropwise over 5 mins to a solution of methyl 4-aminopyridine-2-carboxylate (150 mg, 0.99 mmol), DMAP (4 mg, 0.033 mmol) and NEt₃ (280 μL, 2.01 mmol) in DCM (5 mL) stirring at ambient temperature. The mixture was stirred overnight then evaporated in vacuo. The residue was dissolved in methanolic ammonia (7M, 5 mL) and the solution stirred at ambient temperature overnight before being evaporated in vacuo. Purification by reverse phase preparative HPLC (basic eluent) gave two diastereomers of rac-4-[[3-(3,4-difluoro-2-methoxy-phenyl)-5-(difluoromethyl)-4,5-dimethyl-tetrahydrofuran-2-carbonyl]amino]pyridine-2-carboxamide (100 mg total, 34%) in a 1:1 ratio. ESI-MS m/z calc. 455.14682, found 456.1 (M+1)⁺; 454.1 (M−1)⁻.

Step 10

The two separated diastereomers of rac-4-[[3-(3,4-difluoro-2-methoxy-phenyl)-5-(difluoromethyl)-4,5-dimethyl-tetrahydrofuran-2-carbonyl]amino]pyridine-2-carboxamide (100 mg, 0.2196 mmol) were each further purified by chiral SFC using a (R,R)-Whelk-O1 column, 5 μm particle size, 25 cm×21.2 mm from Regis Technologies to give single isomers of unknown absolute configuration:

First Eluting Isomer of Diastereoisomer 1 (rt=4.45 min): rel-(2R,3S,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide (96, 16.9 mg). ¹H NMR (400 MHz, Chloroform-d) δ 8.86 (s, 1H), 8.41 (d, J=5.6 Hz, 1H), 7.98 (dd, J=5.5, 2.1 Hz, 1H), 7.90 (d, J=2.4 Hz, 2H), 6.79-6.67 (m, 2H), 5.87 (s, 1H), 5.80 (t, 1H), 4.92 (d, J=9.9 Hz, 1H), 4.11 (s, 1H), 4.04 (d, J=2.4 Hz, 3H), 2.55 (dq, J=13.8, 7.1 Hz, 1H), 1.65 (t, J=1.6 Hz, 3H), 1.12 (dd, J=7.0, 1.6 Hz, 3H) ppm. ESI-MS m/z calc. 455.14682, found 456.1 (M+1)⁺; 454.1 (M−1)⁻.

Second Eluting Isomer of Diastereoisomer 1 (rt=5.00 min): rel-(2S,3R,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide (97, 16.5 mg). ¹H NMR (400 MHz, Chloroform-d) δ 8.72 (s, 1H), 8.38 (d, J=5.5 Hz, 1H), 8.03 (dd, J=5.5, 2.2 Hz, 1H), 7.90 (d, J=2.1 Hz, 1H), 7.82-7.76 (m, 1H), 6.91-6.77 (m, 2H), 5.77 (t, J=54.4 Hz, 1H), 5.62 (d, J=4.3 Hz, 1H), 4.62 (d, J=9.7 Hz, 1H), 3.89 (d, J=2.3 Hz, 3H), 3.57 (ddd, J=12.1, 9.7, 2.2 Hz, 1H), 2.38 (dqd, J=14.3, 7.1, 2.8 Hz, 1H), 1.42 (d, J=1.7 Hz, 3H), 0.93 (dd, J=7.2, 1.2 Hz, 3H) ppm. ESI-MS m/z calc. 455.14682, found 456.1 (M+1)⁺; 454.1 (M−1)⁻.

First Eluting Isomer of Diastereoisomer 2 (rt=3.34 min): rel-(2S,3R,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide (98, 17.8 mg). ¹H NMR (400 MHz, Chloroform-d) δ 8.84 (s, 1H), 8.41 (d, J=5.5 Hz, 1H), 7.98 (dd, J=5.8, 2.1 Hz, 1H), 7.90 (d, J=2.2 Hz, 2H), 6.77-6.69 (m, 2H), 5.85 (d, J=4.3 Hz, 1H), 5.80 (t, J=54.5 Hz, 1H), 4.92 (d, J=10.0 Hz, 1H), 4.11 (t, J=11.1 Hz, 1H), 4.03 (d, J=2.4 Hz, 3H), 2.55 (dq, J=14.0, 7.1 Hz, 1H), 1.65 (t, J=1.6 Hz, 3H), 1.16-1.08 (m, 3H) ppm. ESI-MS m/z calc. 455.14682, found 456.1 (M+1)⁺; 454.1 (M−1)⁻.

Second Eluting Isomer of Diastereoisomer 2 (rt=4.00 min): rel-(2R,3S,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide (99, 18.1 mg). ¹H NMR (400 MHz, Chloroform-d) δ 8.81 (s, 1H), 8.47 (d, J=5.5 Hz, 1H), 8.11 (dd, J=5.5, 2.2 Hz, 1H), 7.99 (dd, J=2.3, 0.6 Hz, 1H), 7.87 (d, J=4.4 Hz, 1H), 7.01-6.86 (m, 2H), 5.80 (t, J=54.3 Hz, 1H), 5.74 (s, 1H), 4.71 (d, J=9.7 Hz, 1H), 3.98 (d, J=2.3 Hz, 3H), 3.66 (ddd, J=12.1, 9.7, 2.2 Hz, 1H), 3.50 (s, 3H), 2.54-2.40 (m, 1H), 1.02 (dd, J=7.2, 1.1 Hz, 3H) ppm. ESI-MS m/z calc. 455.14682, found 456.1 (M+1)⁺; 454.1 (M−1)⁻.

Example 18 rac-(2S,3S,4R)-4-[[3-(3,4-difluoro-2-methoxy-phenyl)-4,5,5-trimethyl-tetrahydrofuran-2-carbonyl]amino]pyridine-2-carboxamide (100), rel-(2S,3R,4S)-4-[[3-(3,4-difluoro-2-methoxy-phenyl)-4,5,5-trimethyl-tetrahydrofuran-2-carbonyl]amino]pyridine-2-carboxamide (101) and rel-(2R,3S,4R)-4-[[33-(3,4-difluoro-2-methoxy-phenyl)-4,5,5-trimethyl-tetrahydrofuran-2-carbonyl]amino]pyridine-2-carboxamide (102)

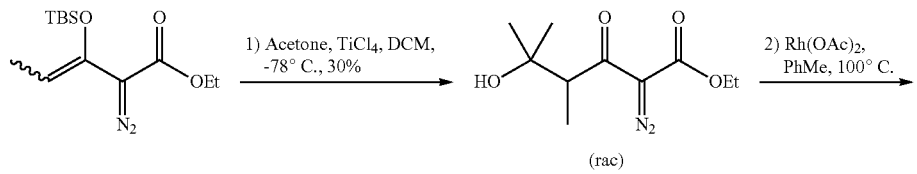

(rac)

-continued

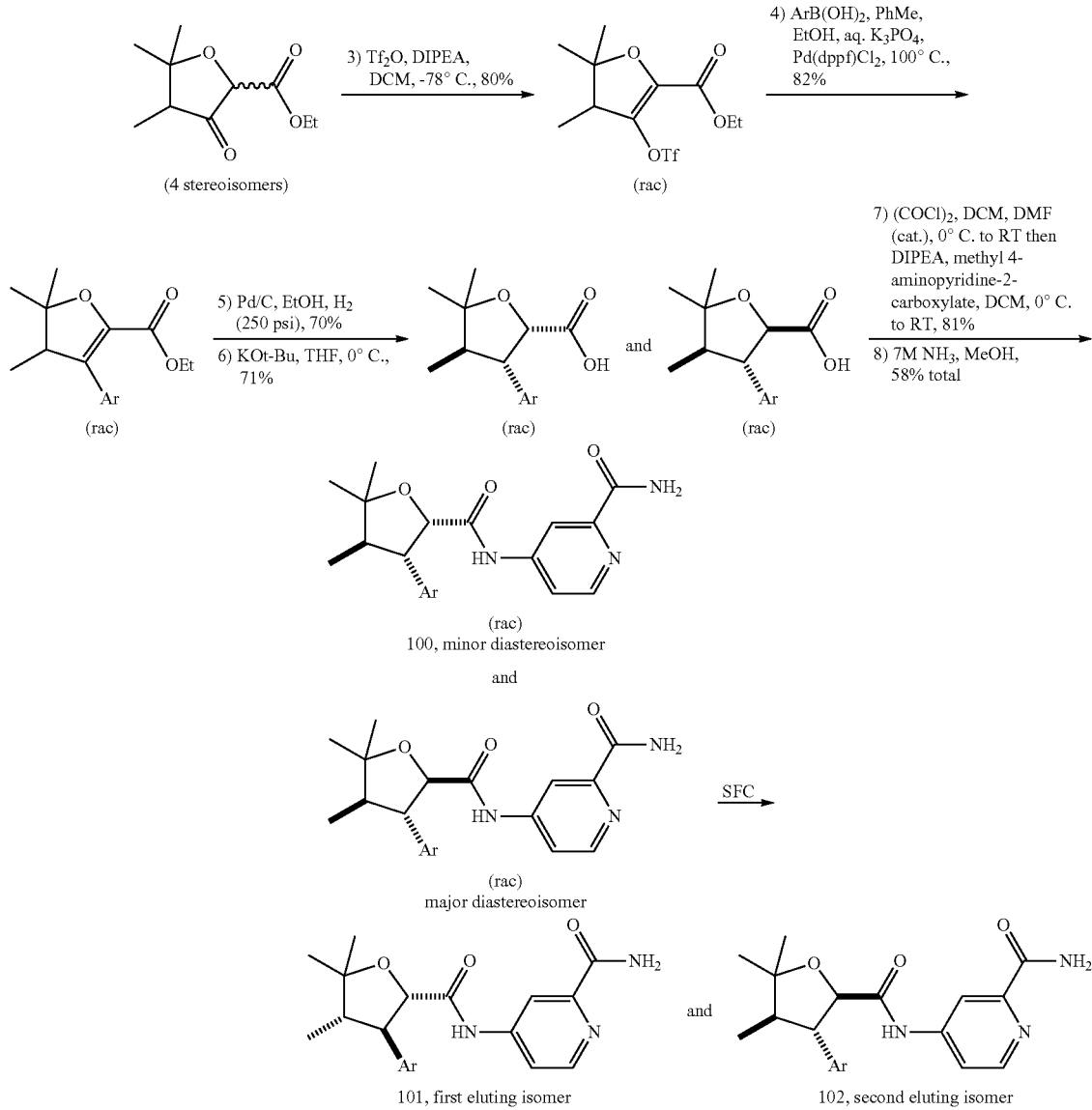

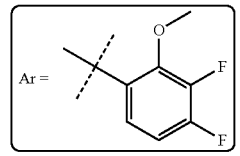

Step 1

To a solution of acetone (5.3 mL, 71.54 mmol) in DCM (100 mL) stirring at −78° C. was added dropwise TiCl$_4$ (12.90 g, 7.5 mL, 68.01 mmol). The reaction was stirred at this temperature for 10 mins before a solution of ethyl (E)-3-[tert-butyl(dimethyl)silyl]oxy-2-diazo-pent-3-enoate (15 g, 52.738 mmol) in DCM (100 mL) was added dropwise. The reaction was stirred at −78° C. for 1 hour then quenched by addition of saturated aqueous NaHCO$_3$. The mixture was diluted with DCM, the layers separated and the organic layer dried (MgSO$_4$) and concentrated in vacuo. Purification by flash chromatography (SiO$_2$, 0 to 30% EtOAc in hexane) gave ethyl rac-2-diazo-5-hydroxy-4,5-dimethyl-3-oxo-hexanoate as a pale yellow liquid. (3.6 g, 30%). $^1$H NMR (400 MHz, Chloroform-d) δ 4.29 (q, J=7.1 Hz, 2H), 3.69 (q, J=7.0 Hz, 1H), 3.46 (br.s, 1H), 1.32 (t, J=7.1 Hz, 3H), 1.26 (s, 3H) 1.24-1.15 (m, 6H) ppm.

Step 2

A solution of rhodium (II) acetate (64 mg, 0.14 mmol) in toluene (36 mL) was heated at 100° C. for 10 minutes, then the heating removed and a solution of ethyl rac-2-diazo-5-hydroxy-4,5-dimethyl-3-oxo-hexanoate (6.58 g, 28.83 mmol) in toluene (95 mL) was added dropwise. The reaction was heated at reflux for 1 hour then filtered through Celite and the filtrate concentrated in vacuo to give ethyl rac-4,5, 5-trimethyl-3-oxo-tetrahydrofuran-2-carboxylate, which was used without further purification.

Step 3

To a solution of ethyl rac-4,5,5-trimethyl-3-oxo-tetrahydrofuran-2-carboxylate (2.83 g, 14.13 mmol) in DCM (5 mL) stirring at −78° C. was added DIPEA (3.1 mL, 17.80 mmol). A solution of triflic anhydride (4.20 g, 2.5 mL, 14.89 mmol) in DCM (5 mL) was added dropwise over 20 mins. Upon complete addition the reaction was diluted with DCM and water, the layers separated and the organic layer dried (MgSO$_4$) and concentrated in vacuo to give ethyl rac-2,2,3-trimethyl-4-(trifluoromethylsulfonyloxy)-3H-furan-5-carboxylate (3.76 g, 80%) as a brown liquid. $^1$H NMR (400 MHz, Chloroform-d) δ 4.33 (q, J=7.1 Hz, 2H), 2.93 (q, J=7.1 Hz, 1H), 1.45 (s, 3H), 1.38-1.30 (m, 6H), 1.14 (d, J=7.1 Hz, 3H) ppm.

Step 4

To a solution of ethyl rac-2,2,3-trimethyl-4-(trifluoromethylsulfonyloxy)-3H-furan-5-carboxylate (3.1 g, 8.03 mmol) in toluene (19 mL) and EtOH (9.5 mL) was added (3,4-difluoro-2-methoxy-phenyl)boronic acid (2.1 g, 11.17 mmol) and K$_3$PO$_4$ (13 mL of 2 M, 26.00 mmol). The reaction was purged with argon for 20 mins before [1,1'-bis(diphenylphosphino)ferrocene]dichloropalladium(II) (197 mg, 0.24 mmol) was added and the mixture stirred at 100° C. for 16 hours. The reaction was concentrated in vacuo and the residue diluted in EtOAc (150 mL). The layers were separated and the organic layer was concentrated in vacuo. Purification by flash chromatography (SiO$_2$, 0 to 50% EtOAc in hexane) gave ethyl rac-4-(3,4-difluoro-2-methoxy-phenyl)-2,2,3-trimethyl-3H-furan-5-carboxylate (2.16 g, 82%) as a light yellow liquid. $^1$H NMR (400 MHz, Chloroform-d) δ 6.89-6.72 (m, 2H), 4.26-4.01 (m, 2H), 3.88 (d, J=1.9 Hz, 3H), 3.07 (q, J=7.2 Hz, 1H), 1.49 (s, 3H), 1.36 (s, 3H), 1.10 (t, J=7.2 Hz, 3H), 0.89 (d, J=7.2 Hz, 3H) ppm.

Step 5

A solution of ethyl rac-4-(3,4-difluoro-2-methoxy-phenyl)-2,2,3-trimethyl-3H-furan-5-carboxylate (1 g, 3.06 mmol) in EtOH (40 mL) was degassed for 10 mins before Pd/C (500 mg, 4.70 mmol) was added. The reaction was stirred under a 250 psi pressure of hydrogen for 16 hours, at ambient temperature, then filtered through Celite and the filtrate concentrated in vacuo. Purification by flash chromatography (SiO$_2$, 5% ethyl acetate in hexane) gave a mixture of isomers of ethyl 3-(3,4-difluoro-2-methoxy-phenyl)-4,5,5-trimethyl-tetrahydrofuran-2-carboxylate (700 mg, 70%) as a white solid. $^1$H NMR (400 MHz, Chloroform-d) δ 6.84-6.73 (m, 2H), 4.70 (d, J=9.2 Hz, 1H), 4.03 (d, J=2.3 Hz, 3H), 3.83-3.70 (m, 2H), 3.45-3.26 (m, 1H), 2.46 (q, J=13.5 Hz, 1H), 1.51 (s, 3H), 1.18 (s, 3H), 0.88-0.76 (m, 6H) ppm.

Step 6

To a solution of a mixture of isomers of ethyl 3-(3,4-difluoro-2-methoxy-phenyl)-4,5,5-trimethyl-tetrahydrofuran-2-carboxylate (600 mg, 1.83 mmol) in THF (10 mL) stirring at 0° C. was added KOt-Bu (862 mg, 7.68 mmol). The reaction was stirred at this temperature for 9 hours then quenched by addition of 2N HCl. The layers were separated and the aqueous layer extracted with EtOAc and water. The organic layer was dried (Na$_2$SO$_4$) and concentrated in vacuo. Purification by flash chromatography (SiO$_2$, 0 to 100% EtOAc in hexane) gave a mixture of isomers of 3-(3,4-difluoro-2-methoxy-phenyl)-4,5,5-trimethyl-tetrahydrofuran-2-carboxylic acid (390 mg, 71%).

Step 7

Oxalyl chloride (105 µL, 1.20 mmol) was added to a solution of a mixture of isomers of 3-(3,4-difluoro-2-methoxy-phenyl)-4,5,5-trimethyl-tetrahydrofuran-2-carboxylic acid (120 mg, 0.40 mmol) and DMF (5 µL, 0.065 mmol) in DCM (3 mL) stirring at 0° C. The mixture was warmed to ambient temperature over 30 mins, then concentrated in vacuo. The residue was dissolved in DCM (2 mL) and the solution cooled to 0° C. before methyl 4-aminopyridine-2-carboxylate (100 mg, 0.66 mmol) and DIPEA (235 µL, 1.35 mmol) were added. The reaction was stirred overnight, allowing to warm to ambient temperature, then quenched with water (20 mL) and the layers separated. The aqueous layer was extracted with EtOAc (2×20 mL) and the combined organics layers were dried (MgSO$_4$), filtered and concentrated in vacuo. Purification by flash chromatography (12 g SiO$_2$, 0 to 15% MeOH in DCM) gave methyl 4-[[3-(3,4-difluoro-2-methoxy-phenyl)-4,5,5-trimethyl-tetrahydrofuran-2-carbonyl]amino]pyridine-2-carboxylate (140 mg, 81%) as a colourless oil, containing an inseperable mixture of diastereomers. ESI-MS m/z calc. 434.1653, found 435.5 (M+1)$^+$; 433.5 (M−1)$^−$.

Step 8 and 9

A solution of a mixture of diastereomers of methyl 4-[[3-(3,4-difluoro-2-methoxy-phenyl)-4,5,5-trimethyl-tetrahydrofuran-2-carbonyl]amino]pyridine-2-carboxylate (140 mg, 0.32 mmol) in methanolic ammonia (9 mL of 7 M, 63.00 mmol) was stirred at ambient temperature overnight, then concentrated in vacuo. Purification by flash chromatography (SiO$_2$, 0-10% MeOH in DCM) followed by reverse phase preparative HPLC (basic eluent) gave two diastereomers:

First Eluting minor diastereoisomer: rac-(2R,3R,4S)-4-[[3-(3,4-difluoro-2-methoxy-phenyl)-4,5,5-trimethyl-tetrahydrofuran-2-carbonyl]amino]pyridine-2-carboxamide (100, 17 mg, 12%). $^1$H NMR (500 MHz, Chloroform-d) δ 8.68 (s, 1H), 8.31 (d, J=5.5 Hz, 1H), 7.83 (s, 1H), 7.78 (s, 1H), 7.67 (d, J=2.2 Hz, 1H), 6.60 (dd, J=9.0, 6.1 Hz, 2H), 5.58 (s, 1H), 4.57 (d, J=10.1 Hz, 1H), 3.98 (s, 3H), 3.85 (d, J=11.0 Hz, 1H), 2.17-2.10 (m, 1H), 1.47 (s, 3H), 1.18 (s, 3H), 0.83 (d, J=6.8 Hz, 3H) ppm. ESI-MS m/z calc. 419.16565, found 420.5 (M+1)$^+$; 418.5 (M−1)$^−$.

Second Eluting major diastereoisomer: rac-(2R,3S,4R)-4-[[3-(3,4-difluoro-2-methoxy-phenyl)-4,5,5-trimethyl-tetrahydrofuran-2-carbonyl]amino]pyridine-2-carboxamide (62 mg, 46%). $^1$H NMR (500 MHz, Chloroform-d) δ 8.80 (s, 1H), 8.37 (d, J=5.5 Hz, 1H), 8.12 (dd, J=5.5, 2.2 Hz, 1H), 7.84 (d, J=2.2 Hz, 1H), 7.81-7.73 (m, 1H), 6.90 (ddd, J=8.8, 5.7, 2.1 Hz, 1H), 6.85 (s, 1H), 5.64 (s, 1H), 4.43 (d, J=9.7 Hz, 1H), 3.91-3.84 (m, 3H), 3.47 (dd, J=11.9, 9.7 Hz, 1H), 2.15 (dq, J=11.9, 6.9 Hz, 1H), 1.37 (s, 3H), 1.20 (s, 3H), 0.75 (d, J=6.9 Hz, 3H) ppm.

The enantiomers of the major diasteromer rac-(2R,3S,4R)-4-[[3-(3,4-difluoro-2-methoxy-phenyl)-4,5,5-trimethyl-tetrahydrofuran-2-carbonyl]amino]pyridine-2-carboxamide (62 mg, 0.15 mmol) were separated by chiral SFC using a Chiralpak AS-H column, 5 um particle size, 25 cm×10 mm from Daicel on a Minigram SFC instrument from Berger Instruments to give two single isomers of unknown absolute configuration:

First Eluting Isomer (rt=2.09 min): rel-(2S,3R,4S)-4-[[3-(3,4-difluoro-2-methoxy-phenyl)-4,5,5-trimethyl-tetrahydrofuran-2-carbonyl]amino]pyridine-2-carboxamide (101, 19 mg, 31%). ¹H NMR (500 MHz, Chloroform-d) δ 8.80 (s, 1H), 8.37 (d, J=5.5 Hz, 1H), 8.12 (dd, J=5.5, 2.2 Hz, 1H), 7.84 (d, J=2.2 Hz, 1H), 7.81-7.73 (m, 1H), 6.90 (ddd, J=8.8, 5.7, 2.1 Hz, 1H), 6.85 (s, 1H), 5.64 (s, 1H), 4.43 (d, J=9.7 Hz, 1H), 3.91-3.84 (m, 3H), 3.47 (dd, J=11.9, 9.7 Hz, 1H), 2.15 (dq, J=11.9, 6.9 Hz, 1H), 1.37 (s, 3H), 1.20 (s, 3H), 0.75 (d, J=6.9 Hz, 3H) ppm. ESI-MS m/z calc. 419.16565, found 420.3 (M+1)⁺; 418.3 (M−1)⁻.

Second Eluting Isomer (rt=2.87 min): rel-(2R,3S,4R)-4-[[3-(3,4-difluoro-2-methoxy-phenyl)-4,5,5-trimethyl-tetrahydrofuran-2-carbonyl]amino]pyridine-2-carboxamide (102, 16 mg, 26%). ¹H NMR (500 MHz, Chloroform-d) δ 8.80 (s, 1H), 8.37 (d, J=5.5 Hz, 1H), 8.12 (dd, J=5.5, 2.2 Hz, 1H), 7.84 (d, J=2.2 Hz, 1H), 7.81-7.73 (m, 1H), 6.90 (ddd, J=8.8, 5.7, 2.1 Hz, 1H), 6.85 (s, 1H), 5.64 (s, 1H), 4.43 (d, J=9.7 Hz, 1H), 3.91-3.84 (m, 3H), 3.47 (dd, J=11.9, 9.7 Hz, 1H), 2.15 (dq, J=11.9, 6.9 Hz, 1H), 1.37 (s, 3H), 1.20 (s, 3H), 0.75 (d, J=6.9 Hz, 3H) ppm. ESI-MS m/z calc. 419.16565, found 420.3 (M+1)⁺; 418.3 (M−1)⁻.

Example 19 rel-(2R,3S,4R)-4-[[3-(3,4-difluoro-2-methoxy-phenyl)-4,5,5-trimethyl-tetrahydrofuran-2-carbonyl]amino]pyridine-2-carboxamide (103), rel-(2S,3R,4S)-4-[[3-(3,4-difluoro-2-methoxy-phenyl)-4,5,5-trimethyl-tetrahydrofuran-2-carbonyl]amino]pyridine-2-carboxamide (104), rel-(2R,3S,4S)-4-[[3-(3,4-difluoro-2-methoxy-phenyl)-4,5,5-trimethyl-tetrahydrofuran-2-carbonyl]amino]pyridine-2-carboxamide (105) and rel-(2S,3R,4R)-4-[[3-(3,4-difluoro-2-methoxy-phenyl)-4,5,5-trimethyl-tetrahydrofuran-2-carbonyl]amino]pyridine-2-carboxamide (106)

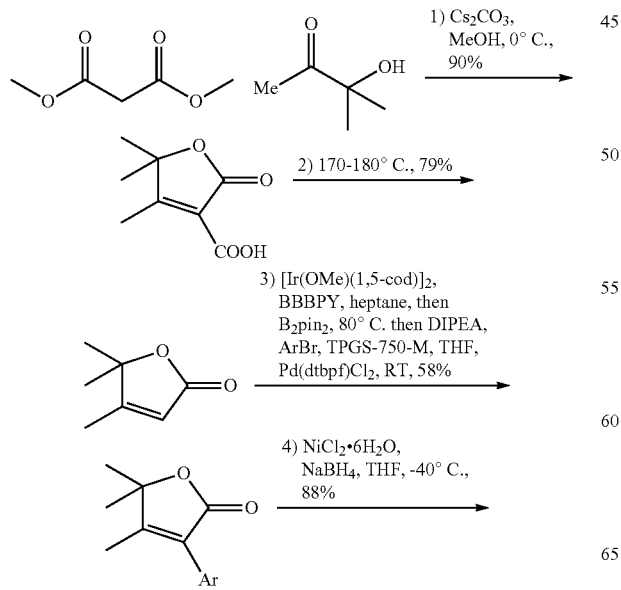

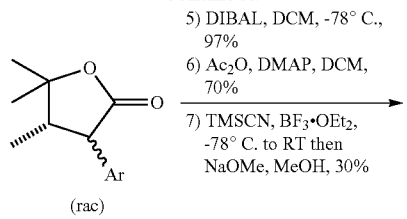

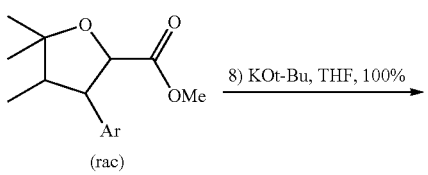

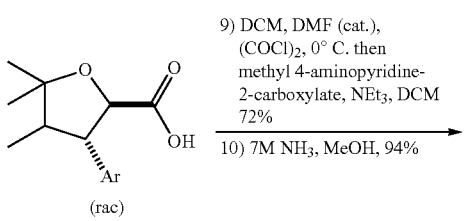

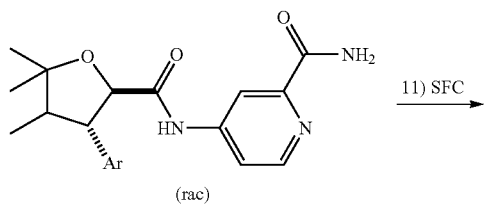

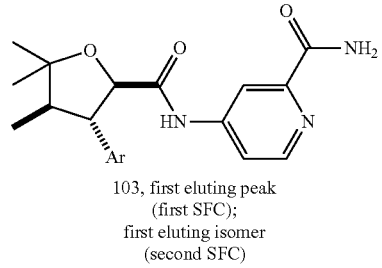

103, first eluting peak (first SFC); first eluting isomer (second SFC)

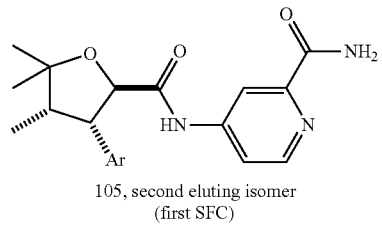

105, second eluting isomer (first SFC)

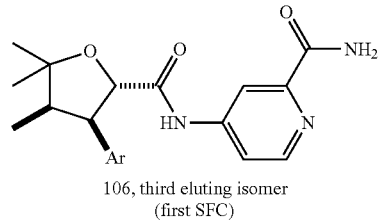

106, third eluting isomer (first SFC)

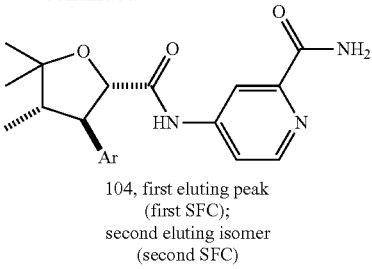

104, first eluting peak (first SFC); second eluting isomer (second SFC)

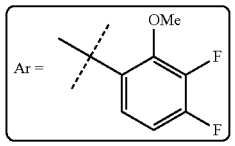

Step 1

A solution of 3-hydroxy-3-methyl-butan-2-one (39 g, 381.86 mmol) and dimethyl propanedioate (25 g, 21.74 mL, 189.23 mmol) in MeOH (550 mL) was cooled to 0° C. and stirred under nitrogen. $Cs_2CO_3$ (127 g, 389.79 mmol) was added and the mixture was stirred overnight. The reaction was then cooled to 0° C. and HCl (630 mL of 1 M, 630.00 mmol) was added. The reaction mixture was concentrated to remove the MeOH, and then EtOAc (800 mL) was added and the layers were separated. The aqueous layer was extracted with EtOAc (2×500 mL) and the combined organic layers dried ($Na_2SO_4$) and concentrated in vacuo. The residue was triturated with n-pentane to give 4,5,5-trimethyl-2-oxo-furan-3-carboxylic acid (29 g, 90%) as a off-white solid. $^1$H NMR (400 MHz, DMSO-$d_6$) δ 13.13 (s, 1H), 2.28 (s, 3H), 1.42 (s, 6H) ppm.

Step 2

4,5,5-trimethyl-2-oxo-furan-3-carboxylic acid (17 g, 99.904 mmol) was heated at 170° C.-180° C. for 4 hours then cooled to ambient temperature. Purification by flash chromatography ($SiO_2$, 15% EtOAc in hexane) gave 4,5,5-trimethylfuran-2-one (10 g, 79%) as an off-white solid. $^1$H NMR (400 MHz, DMSO-$d_6$) δ 5.81 (s, 1H), 2.03 (s, 3H), 1.38 (s, 6H) ppm. ESI-MS m/z calc. 126.0681, found 127.6 (M+1)$^+$.

Step 3

A mixture of (1,5-cyclooctadine)(methoxy)iridium(I) dimer (1.2 g, 1.81 mmol) and 4,4-di-tert-butyl-2,2'-bipyridine (1.6 g, 5.96 mmol) in n-heptane (50 mL) was degassed and stirred for 15 mins under nitrogen. A solution of 4,5,5-trimethylfuran-2-one (15 g, 118.90 mmol) and bis(pinacolato)diboron (31.8 g, 125.23 mmol) in n-heptane (190 mL) was degassed and stirred under nitrogen for 5 mins and then added to the first solution. The resultant reaction mixture was heated at 80° C. for 2 hours then cooled to ambient temperature. DIPEA (46.75 g, 63 mL, 361.69 mmol) was added to a solution of 1-bromo-3,4-difluoro-2-methoxy-benzene (39.8 g, 178.46 mmol) in TPGS-750-M (40.0 g, 40 mL of 2% w/v, 69.59 mmol) and THF (240 mL) and the mixture was degassed and stirred under nitrogen for 10 mins. This was added to the cooled reaction mixture followed by $PdCl_2$(dtbpf) (3 g, 4.60 mmol), and the resultant mixture was stirred overnight at ambient temperature. The mixture was diluted with water (200 mL) and extracted with EtOAc (2×700 mL). The combined organic layers were washed with brine (200 mL), dried ($Na_2SO_4$) and concentrated in vacuo. Purification by flash chromatography (SiO2, 3 to 5% EtOAc in hexane) gave 3-(3,4-difluoro-2-methoxy-phenyl)-4,5,5-trimethyl-furan-2-one (19 g, 58%) as a white solid. $^1$H NMR (400 MHz, DMSO-$d_6$) δ 7.25-7.23 (m, 1H), 7.10-7.07 (m, 1H), 3.81 (d, J=1.72 Hz, 3H), 1.93 (s, 3H), 1.49 (s, 6H) ppm. ESI-MS m/z calc. 268.0911, found 269.2 (M+1)$^+$.

Step 4

To a solution of 3-(3,4-difluoro-2-methoxy-phenyl)-4,5,5-trimethyl-furan-2-one (4.2 g, 15.66 mmol) in MeOH (170 mL) and THF (34 mL) stirring at −40° C. was added $NiCl_2$.$6H_2O$ (3.8 g, 15.99 mmol) and $NaBH_4$ (3 g, 79.30 mmol). The resulting mixture was stirred for 5 mins before further $NiCl_2$.$6H_2O$ (3.8 g, 15.99 mmol) and $NaBH_4$ (3 g, 79.30 mmol) was added. Upon full conversion the reaction was quenched by the addition of saturated aqueous $NH_4Cl$ and the aqueous layer extracted with DCM (2×50 mL). The combined organic extracts were dried ($MgSO_4$) and concentrated in vacuo to give rac-3-(3,4-difluoro-2-methoxy-phenyl)-4,5,5-trimethyl-tetrahydrofuran-2-one (3.72 g, 88%) as a 1:1.4 mixture of diasteromers. ESI-MS m/z calc. 270.10675, found 271.4 (M+1)$^+$.

Step 5

To a solution of rac-3-(3,4-difluoro-2-methoxy-phenyl)-4,5,5-trimethyl-tetrahydrofuran-2-one (3.8 g, 14.06 mmol) in DCM (55 mL) stirring at −78° C. was added DIBAL (17 mL of 1 M, 17.00 mmol). The mixture was stirred at this temperature until complete reaction was observed, then quenched by the addition of saturated ammonium chloride solution (20 mL) and Rochelle's salt (30% w/w solution). The mixture was diluted with DCM (20 mL) and vigorously stirred for 1 h at ambient temperature. The layers were separated and the organic layers dried ($MgSO_4$) and concentrated in vacuo to give rac-3-(3,4-difluoro-2-methoxy-phenyl)-4,5,5-trimethyl-tetrahydrofuran-2-ol (3.70 g, 97%), which was used without further purification.

Step 6

To a solution of rac-3-(3,4-difluoro-2-methoxy-phenyl)-4,5,5-trimethyl-tetrahydrofuran-2-ol (3.7 g, 13.59 mmol) in DCM (40 mL) was added DMAP (850 mg, 6.96 mmol) and acetic anhydride (5.3 mL, 56.17 mmol). The reaction was stirred at ambient temperature overnight then quenched by addition of saturated aqueous sodium bicarbonate solution (50 mL). The mixture was stirred vigorously for 30 mins then the layers were separated. The aqueous layer was extracted with DCM (20 mL) and the combined organic extracts were dried ($MgSO_4$) and concentrated in vacuo. Purification by flash chromatography ($SiO_2$) gave rac-[3-(3,4-difluoro-2-methoxy-phenyl)-4,5,5-trimethyl-tetrahydrofuran-2-yl]acetate (3.0 g, 70%) as a mixture of stereoisomers. Data for desired diastereomer: $^1$H NMR (500 MHz, Chloroform-d) δ 6.91 (d, J=1.4 Hz, 1H), 6.86-6.76 (m, 2H), 3.91 (d, J=1.7 Hz, 3H), 2.92 (qd, J=7.0, 1.4 Hz, 1H), 2.10 (s, 3H), 1.37 (s, 3H), 1.37 (s, 3H), 1.01 (d, J=7.0 Hz, 3H), 0.91-0.86 (m, 1H) ppm. ESI-MS m/z calc. 314.13297, found 256.6 (M-OAc)$^+$.

Step 7

To a solution of rac-[3-(3,4-difluoro-2-methoxy-phenyl)-4,5,5-trimethyl-tetrahydrofuran-2-yl]acetate (3 g, 9.544 mmol) in DCM (90 mL) stirring at −78° C. was added trimethylsilyl cyanide (3.3 mL, 24.75 mmol) and diethyloxonio(trifluoro)boranuide (3.7 mL, 29.98 mmol). The mixture was stirred at this temperature for 30 mins then allowed to warm to ambient temperature. Upon completion the mixture was quenched with saturated aqueous sodium bicarbonate solution, the layers separated and the aqueous layer extracted with DCM (3×30 mL). The combined organic layers were dried ($Na_2SO_4$) and concentrated in vacuo. The residue was dissolved in DCM and filtered through Celite, then concentrated in vacuo. NaOMe (30 mL of 0.5 M in methanol, 15.00 mmol) was added to the residue and the resultant solution stirred at ambient temperature overnight before being quenched by addition of a saturated solution of citric acid. The mixture was stirred at ambient temperature until complete conversion of the amidate was observed, then extracted with DCM (2×30 mL). The combined organic layers were dried ($MgSO4$) and concentrated in vacuo to give methyl rac-3-(3,4-difluoro-2-methoxy-phenyl)-4,5,5-trimethyl-tetrahydrofuran-2-carboxylate (900 mg, 30%), which was used in the next step without further purification. ESI-MS m/z calc. 314.13297, found 315.6 $(M+1)^+$.

Step 8

To a solution of methyl rac-3-(3,4-difluoro-2-methoxy-phenyl)-4,5,5-trimethyl-tetrahydrofuran-2-carboxylate (440 mg, 1.40 mmol) in THF (5.4 mL) was added KOt-Bu (630 mg, 5.61 mmol) and the mixture stirred at ambient temperature. Upon completion, the reaction was quenched by addition of water and the aqueous layer washed with DCM. The aqueous phase was acidified with 1M HCl and extracted with DCM. The organic layer was evaporated in vacuo to give rac-3-(3,4-difluoro-2-methoxy-phenyl)-4,5,5-trimethyl-tetrahydrofuran-2-carboxylic acid (420 mg, 100%) in a 1:1.4 ratio of diastereomers. ESI-MS m/z calc. 300.1173, found 299.6 $(M-1)^-$.

Step 9

To a solution of rac-3-(3,4-difluoro-2-methoxy-phenyl)-4,5,5-trimethyl-tetrahydrofuran-2-carboxylic acid (105 mg, 0.35 mmol) in DCM (1.2 mL) stirring at 0° C. was added DMF (3 μL, 0.039 mmol) and oxalyl chloride (65 μL, 0.75 mmol). The mixture was warmed to ambient temperature over 30 mins then concentrated in vacuo. The residue was dissolved in DCM (600 μL) and the resultant solution added to a solution of methyl 4-aminopyridine-2-carboxylate (64 mg, 0.42 mmol) and $NEt_3$ (68 μL, 0.49 mmol) in DCM (600 μL) stirring at 0° C. The reaction was warmed to ambient temperature over 2 hours, quenched by addition of water (1 drop) and MeOH (2 mL), and the solution concentrated in vacuo. Purification by flash chromatography ($SiO_2$) gave methyl rac-4-[[3-(3,4-difluoro-2-methoxy-phenyl)-4,5,5-trimethyl-tetrahydrofuran-2-carbonyl]amino]pyridine-2-carboxylate (110 mg, 72%). ESI-MS m/z calc. 434.1653, found 435.5 $(M+1)^+$; 433.6 $(M-1)^-$.

Step 10

Methyl rac-4-[[3-(3,4-difluoro-2-methoxy-phenyl)-4,5,5-trimethyl-tetrahydrofuran-2-carbonyl]amino]pyridine-2-carboxylate (110 mg, 0.2532 mmol) was dissolved in methanolic ammonia (6 mL of 4 M, 24.00 mmol) and the solution stirred at ambient temperature. Upon complete conversion the mixture was concentrated in vacuo to give rac-4-[[3-(3,4-difluoro-2-methoxy-phenyl)-4,5,5-trimethyl-tetrahydrofuran-2-carbonyl]amino]pyridine-2-carboxamide (100 mg, 94%) as a mixture of diasteromers. ESI-MS m/z calc. 419.16565, found 420.5 $(M+1)^+$; 418.7 $(M-1)^-$.

Step 11 rac-4-[[3-(3,4-difluoro-2-methoxy-phenyl)-4,5,5-trimethyl-tetrahydrofuran-2-carbonyl]amino]pyridine-2-carboxamide (85 mg, 0.20 mmol) was separated by chiral SFC using a Lux i-Cellulose-5 column, 5 μm particle size, 25 cm×10 mm from Phenomenex, Inc. to give:

First Eluting Isomers (rt=4.84 min): a mixture of both rel-(2R,3S,4R)-4-[[3-(3,4-difluoro-2-methoxy-phenyl)-4,5,5-trimethyl-tetrahydrofuran-2-carbonyl]amino]pyridine-2-carboxamide (103) and rel-(2S,3R,4S)-4-[[3-(3,4-difluoro-2-methoxy-phenyl)-4,5,5-trimethyl-tetrahydrofuran-2-carbonyl]amino]pyridine-2-carboxamide (104), that needed further separation.

Second Eluting Isomer (rt=5.23 min): rel-(2R,3S,4S)-4-[[3-(3,4-difluoro-2-methoxy-phenyl)-4,5,5-trimethyl-tetrahydrofuran-2-carbonyl]amino]pyridine-2-carboxamide (105, 10.2 mg). $^1$H NMR (500 MHz, DMSO-$d_6$) δ 10.46 (s, 1H), 8.47 (d, J=5.6 Hz, 1H), 8.35 (d, J=2.2 Hz, 1H), 8.08-8.05 (m, 1H), 7.87 (dd, J=5.5, 2.2 Hz, 1H), 7.63-7.59 (m, 1H), 7.22-7.11 (m, 2H), 4.87 (d, J=8.5 Hz, 1H), 4.22 (t, J=8.1 Hz, 1H), 3.91 (d, J=1.8 Hz, 3H), 2.35 (p, J=7.4 Hz, 1H), 1.40 (s, 3H), 1.20 (s, 3H), 0.59 (d, J=7.3 Hz, 3H) ppm. ESI-MS m/z calc. 419.16565, found 420.6 $(M+1)^+$; 418.5 $(M-1)^-$.

Third Eluting Isomer (rt=5.67 min): rel-(2S,3R,4R)-4-[[3-(3,4-difluoro-2-methoxy-phenyl)-4,5,5-trimethyl-tetrahydrofuran-2-carbonyl]amino]pyridine-2-carboxamide (106, 14.4 mg). $^1$H NMR (500 MHz, DMSO-$d_6$) δ 10.32 (broad s, 1H), 8.47 (d, J=5.5 Hz, 1H), 8.34 (d, J=2.2 Hz, 1H), 8.04 (d, J=2.7 Hz, 1H), 7.85 (dd, J=5.5, 2.2 Hz, 1H), 7.58 (d, J=2.9 Hz, 1H), 7.26-7.11 (m, 2H), 4.87 (d, J=8.6 Hz, 1H), 4.22 (t, J=8.1 Hz, 1H), 3.91 (d, J=1.8 Hz, 3H), 2.35 (p, J=7.3 Hz, 1H), 1.40 (s, 3H), 1.20 (s, 3H), 0.59 (d, J=7.3 Hz, 3H) ppm. ESI-MS m/z calc. 419.16565, found 420.6 $(M+1)^+$; 418.6 $(M-1)^-$.

The first eluting peak was further separated by chiral SFC using a Chiralpak AS-H column, 5 μm particle size, 25 cm×10 mm from Daicel on a Minigram SFC instrument from Berger Instruments:

First Eluting Isomer (rt=2.27 min): rel-(2R,3S,4R)-4-[[3-(3,4-difluoro-2-methoxy-phenyl)-4,5,5-trimethyl-tetrahydrofuran-2-carbonyl]amino]pyridine-2-carboxamide (103, 6 mg). $^1$H NMR (500 MHz, DMSO-$d_6$) δ 10.24 (s, 1H), 8.47 (d, J=5.6 Hz, 1H), 8.35 (d, J=2.1 Hz, 1H), 8.08 (s, 1H), 7.87 (dd, J=5.5, 2.2 Hz, 1H), 7.65-7.61 (m, 1H), 7.26 (ddd, J=8.3, 5.9, 1.9 Hz, 1H), 7.18 (td, J=9.4, 7.5 Hz, 1H), 4.53-4.44 (m, 1H), 3.83 (d, J=1.4 Hz, 3H), 3.70-3.59 (m, 1H), 2.19 (dq, J=11.8, 6.8 Hz, 1H), 1.37 (s, 3H), 1.20 (s, 3H), 0.78 (d, J=6.8 Hz, 3H) ppm. ESI-MS m/z calc. 419.16565, found 420.6 $(M+1)^+$; 418.5 $(M-1)^-$.

Second Eluting Isomer (rt=3.22 min): rel-(2S,3R,4S)-4-[[3-(3,4-difluoro-2-methoxy-phenyl)-4,5,5-trimethyl-tetrahydrofuran-2-carbonyl]amino]pyridine-2-carboxamide (104, 5.4 mg). $^1$H NMR (500 MHz, DMSO-$d_6$) δ 10.19 (s, 1H), 8.46 (dd, J=5.7, 1.7 Hz, 1H), 8.33 (d, J=2.1 Hz, 1H), 8.04 (s, 1H), 7.86 (dt, J=5.7, 1.9 Hz, 1H), 7.58 (s, 1H), 7.26 (dd, J=8.6, 6.2 Hz, 1H), 7.23-7.14 (m, 1H), 4.46 (dd, J=9.4, 1.6 Hz, 1H), 3.83 (d, J=1.5 Hz, 3H), 3.63 (ddd, J=11.2, 9.3, 1.7 Hz, 1H), 2.19 (dtd, J=12.6, 7.6, 5.9 Hz, 1H), 1.37 (d, J=1.7 Hz, 3H), 1.20 (d, J=1.7 Hz, 3H), 0.77 (dd, J=6.9, 1.7 Hz, 3H) ppm. ESI-MS m/z calc. 419.16565, found 420.6 (M+1)$^+$; 418.5 (M−1)$^-$.

Example 20 rel-(2S,3R,4R,5R)-4-[[3-(3,4-difluoro-2-methoxy-phenyl)-4,5-dimethyl-tetrahydrofuran-2-carbonyl]amino]pyridine-2-carboxamide (107) and rel-(2R,3S,4S,5S)-4-[[3-(3,4-difluoro-2-methoxy-phenyl)-4,5-dimethyl-tetrahydrofuran-2-carbonyl]amino]pyridine-2-carboxamide (108)

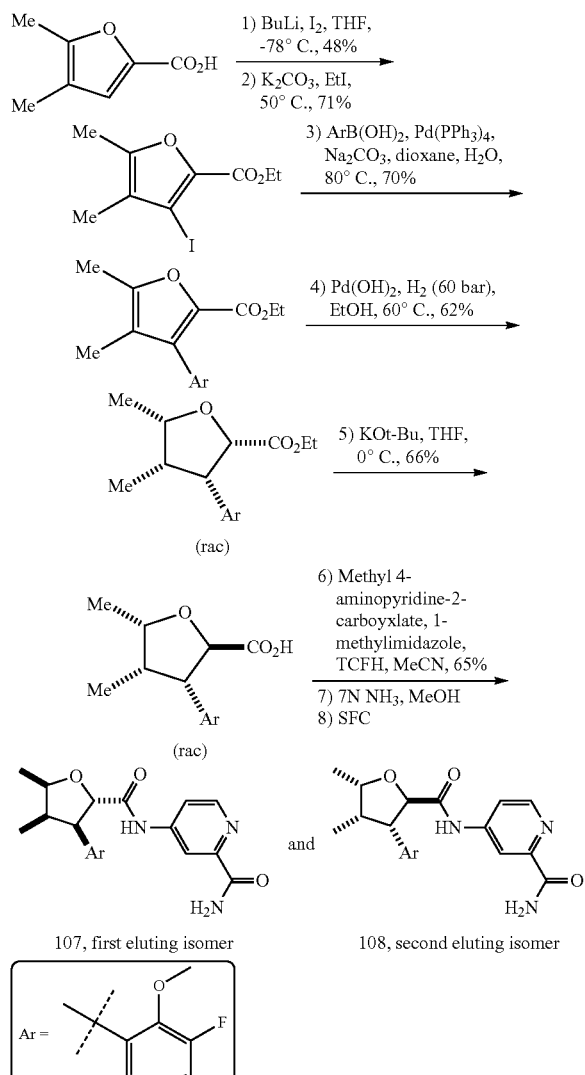

Step 1

To a solution of 4,5-dimethylfuran-2-carboxylic acid (1 g, 7.14 mmol) in THF (15 mL) stirring at −78° C. was added n-BuLi (6.56 mL of 2.5 M, 16.40 mmol) dropwise. The solution was stirred at this temperature for 30 mins before a solution of I$_2$ (2.35 g, 9.26 mmol) in THF (10 mL) was added. The mixture was warmed to ambient temperature then partitioned between MTBE (30 mL) and water (30 mL). The organic layer was discarded, and the aqueous layer acidified to pH 2 by addition of 1 N HCl and extracted with MTBE (2×20 mL). The combined organic layers were washed with brine (10 mL), dried (MgSO$_4$) and concentrated in vacuo to give 3-iodo-4,5-dimethyl-furan-2-carboxylic acid (950 mg, 48%), which was used without further purification. ESI-MS m/z calc. 265.944, found 265.3 (M−1)$^-$.

Step 2

To a solution of 3-iodo-4,5-dimethyl-furan-2-carboxylic acid (900 mg, 3.38 mmol) in DMF (5 mL) was added K$_2$CO$_3$ (1.40 g, 10.13 mmol) and iodoethane (811 μL, 10.14 mmol). The reaction was stirred at 50° C. for 2 hours before being cooled to ambient temperature and partitioned between MTBE (30 mL) and water (30 mL). The aqueous layer was further extracted with MTBE (20 mL) and the combined organic fractions were washed with brine (20 mL), dried (MgSO$_4$) and concentrated in vacuo. Purification by flash chromatography (12 g SiO$_2$, 0 to 100% EtOAc in petroleum ether) gave ethyl 3-iodo-4,5-dimethyl-furan-2-carboxylate (800 mg, 71%) as a white solid. ESI-MS m/z calc. 293.97528, found 295.3 (M+1)$^+$.

Step 3

To a solution of ethyl 3-iodo-4,5-dimethyl-furan-2-carboxylate (700 mg, 2.38 mmol) in dioxane (6 mL) was added (3,4-difluoro-2-methoxy-phenyl)boronic acid (492 mg, 2.62 mmol), Pd(PPh$_3$)$_4$ (343 mg, 0.30 mmol), Na$_2$CO$_3$ (3.57 mL of 2 M, 7.14 mmol) and water (2 mL). The mixture was heated to 80° C. for 2 hours then cooled to ambient temperature and partitioned between EtOAc (30 mL) and water (30 mL). The aqueous layer was further extracted with EtOAc (50 mL) and combined organic layers were washed with brine (20 mL), dried (MgSO$_4$) and concentrated in vacuo. Purification by flash chromatography (12 g SiO$_2$, 0 to 100% EtOAc in petroleum ether) gave ethyl 3-(3,4-difluoro-2-methoxy-phenyl)-4,5-dimethyl-furan-2-carboxylate (520 mg, 70%) as a white solid. $^1$H NMR (500 MHz, Chloroform-d) δ 6.97-6.82 (m, 2H), 4.22 (q, J=7.1 Hz, 2H), 3.81 (d, J=2.0 Hz, 3H), 2.37 (d, J=0.8 Hz, 3H), 1.80 (d, J=0.8 Hz, 3H), 1.19 (t, J=7.1 Hz, 3H) ppm. ESI-MS m/z calc. 310.10165, found 311.4 (M+1)$^+$.

Step 4

A solution of ethyl 3-(3,4-difluoro-2-methoxy-phenyl)-4,5-dimethyl-furan-2-carboxylate (350 mg, 1.128 mmol) in ethanol (2 mL) was circulated through a 70 mm Pd(OH)$_2$ catalyst cartridge on an H-cube apparatus at 60° C. under 60 bar pressure of hydrogen for 48 hours before being concentrated in vacuo to give ethyl rac-(2S,3S,4S,5S)-3-(3,4-difluoro-2-methoxy-phenyl)-4,5-dimethyl-tetrahydrofuran-2-carboxylate (245 mg, 62%). $^1$H NMR (500 MHz, Chloroform-d) δ 7.19-7.08 (m, 1H), 6.72 (td, J=9.3, 7.6 Hz, 1H), 4.55 (d, J=6.1 Hz, 1H), 4.25 (dq, J=9.1, 6.6 Hz, 1H), 4.19-4.02 (m, 1H), 4.02-3.81 (m, 5H), 2.79 (ddt, J=16.4, 8.9, 7.4 Hz, 1H), 1.27-1.04 (m, 3H), 0.86 (t, J=7.1 Hz, 3H), 0.55 (d, J=7.4 Hz, 3H) ppm. ESI-MS m/z calc. 314.13297, found 315.4 (M+1)$^+$.

Step 5

To a solution of ethyl rac-(2S,3S,4S,5S)-3-(3,4-difluoro-2-methoxy-phenyl)-4,5-dimethyl-tetrahydrofuran-2-carboxylate (400 mg, 1.27 mmol) in THF (5 mL) stirring at 0° C. was added KOt-Bu (428 mg, 3.81 mmol). The reaction was stirred for 30 mins before being diluted in MTBE (5 mL) and quenched by addition of 1 M HCl. The aqueous layer was extracted with MTBE (5 mL) and the combined organic layers were dried (MgSO$_4$), filtered and concentrated in vacuo to give rac-(2R,3S,4S,5S)-3-(3,4-difluoro-2-methoxy-phenyl)-4,5-dimethyl-tetrahydrofuran-2-carboxylic acid (270 mg, 66%) as an oil. ESI-MS m/z calc. 286.10165, found 285.4 (M−1)$^-$.

Step 6

To a solution of rac-(2R,3S,4S,5S)-3-(3,4-difluoro-2-methoxy-phenyl)-4,5-dimethyl-tetrahydrofuran-2-carboxylic acid (100 mg, 0.3493 mmol) in MeCN (2 mL) was added methyl 4-aminopyridine-2-carboxylate (63 mg, 0.41 mmol), 1-methylimidazole (100 µL, 1.26 mmol) and TCFH (117 mg, 0.42 mmol). The solution was stirred at ambient temperature for 16 hours then diluted with EtOAc (10 mL) and water (10 mL). The organic layer was dried (MgSO$_4$) and concentrated in vacuo to give methyl rac-(2R,3S,4S,5S)-4-[[3-(3,4-difluoro-2-methoxy-phenyl)-4,5-dimethyl-tetrahydrofuran-2-carbonyl]amino]pyridine-2-carboxylate (95 mg, 65%) as a white solid, which was used without further purification. ESI-MS m/z calc. 420.1497, found 421.5 (M+1)$^+$.

Step 7 and 8

To a solution of methyl rac-(2R,3S,4S,5S)-4-[[3-(3,4-difluoro-2-methoxy-phenyl)-4,5-dimethyl-tetrahydrofuran-2-carbonyl]amino]pyridine-2-carboxylate (95 mg, 0.23 mmol) in MeOH (1 mL) was added methanolic ammonia (322 µL of 7 M, 2.25 mmol). The mixture was stirred at ambient temperature for 6 hours before being concentrated in vacuo to give rac-(2R,3S,4S,5S)-4-[[3-(3,4-difluoro-2-methoxy-phenyl)-4,5-dimethyl-tetrahydrofuran-2-carbonyl]amino]pyridine-2-carboxamide.

rac-(2R,3S,4S,5S)-4-[[3-(3,4-difluoro-2-methoxy-phenyl)-4,5-dimethyl-tetrahydrofuran-2-carbonyl]amino]pyridine-2-carboxamide was separated by chiral SFC using a Chiralpak AS-H column, 5 um particle size, 25 cm×10 mm from Daicel on a Minigram SFC instrument from Berger Instruments:

First Eluting Isomer (rt=1.84 min): rel-(2S,3R,4R,5R)-4-[[3-(3,4-difluoro-2-methoxy-phenyl)-4,5-dimethyl-tetrahydrofuran-2-carbonyl]amino]pyridine-2-carboxamide (107.28 mg, 29%). $^1$H NMR (500 MHz, Chloroform-d) δ 8.96 (s, 1H), 8.48 (d, J=5.5 Hz, 1H), 8.23 (dd, J=5.6, 2.3 Hz, 1H), 7.95 (d, J=2.2 Hz, 1H), 7.89 (s, 1H), 7.12-7.09 (m, 1H), 7.02-6.83 (m, 1H), 5.58 (s, 1H), 4.86 (d, J=9.7 Hz, 1H), 4.57-4.41 (m, 1H), 4.10-3.84 (m, 4H), 2.56 (dt, J=13.5, 6.8 Hz, 1H), 1.35 (d, J=6.4 Hz, 3H), 0.67 (d, J=7.2 Hz, 3H) ppm. ESI-MS m/z calc. 405.15002, found 406.3 (M+1)$^+$.

Second Eluting Isomer (rt=3.28 min): rel-(2R,3S,4S,5S)-4-[[3-(3,4-difluoro-2-methoxy-phenyl)-4,5-dimethyl-tetrahydrofuran-2-carbonyl]amino]pyridine-2-carboxamide (108, 28 mg, 30%). $^1$H NMR (500 MHz, Chloroform-d) δ 8.96 (s, 1H), 8.48 (d, J=5.5 Hz, 1H), 8.23 (dd, J=5.6, 2.3 Hz, 1H), 7.95 (d, J=2.2 Hz, 1H), 7.89 (s, 1H), 7.12-7.09 (m, 1H), 7.02-6.83 (m, 1H), 5.58 (s, 1H), 4.86 (d, J=9.7 Hz, 1H), 4.57-4.41 (m, 1H), 4.10-3.84 (m, 4H), 2.56 (dt, J=13.5, 6.8 Hz, 1H), 1.35 (d, J=6.4 Hz, 3H), 0.67 (d, J=7.2 Hz, 3H) ppm. ESI-MS m/z calc. 405.15002, found 406.3 (M+1)$^+$.

Example 21 rel-(2S,3R,5S)-4-[[3-(3,4-difluoro-2-methoxy-phenyl)-5-(trifluoromethyl)tetrahydrofuran-2-carbonyl]amino]pyridine-2-carboxamide (109) and rel-(2R,3S,5R)-4-[[3-(3,4-difluoro-2-methoxy-phenyl)-5-(trifluoromethyl)tetrahydrofuran-2-carbonyl]amino]pyridine-2-carboxamide (110)

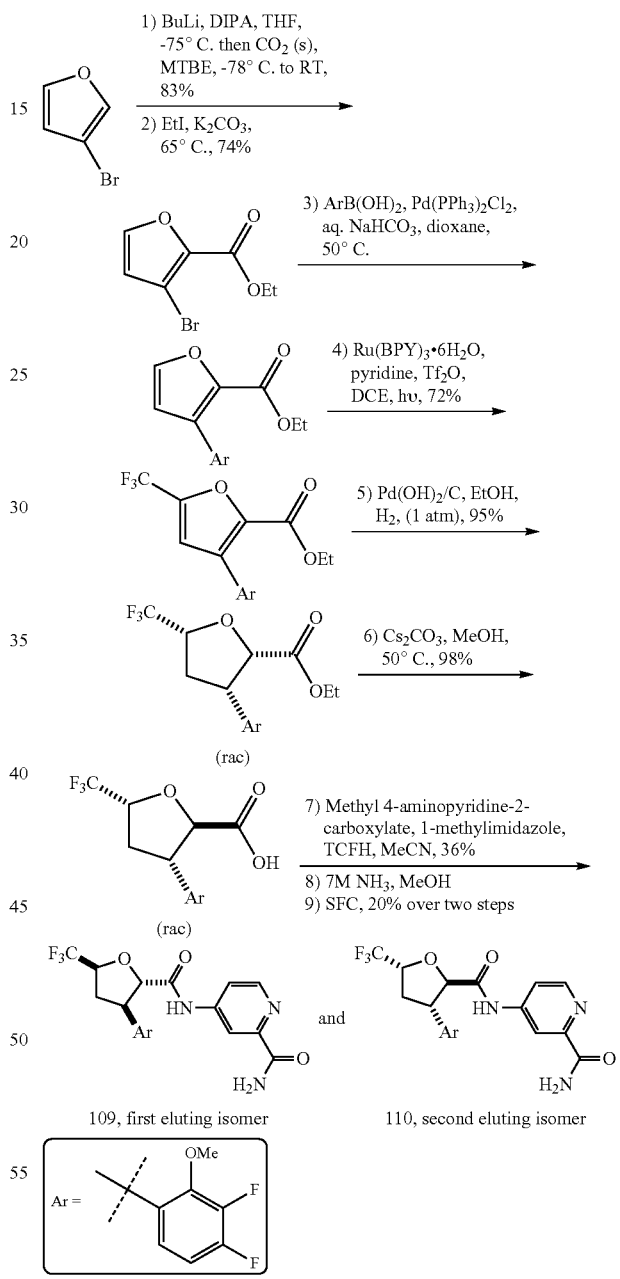

Step 1

To a solution of diisopropylamine (2.3 mL, 16.41 mmol) in THF (15 mL) stirring at −78° C. was added butyllithium (6 mL of 2.5 M, 15.00 mmol), keeping the temperature below −65° C. The reaction mixture was stirred at −75° C.

for 30 mins before a solution of 3-bromofuran (2 g, 13.61 mmol) in THF (10 mL) was added dropwise, again keeping the temperature below −65° C. The mixture was stirred at −78° C. for 30 mins before being added slowly to a pre-cooled (to −78° C.) mixture of dry ice (600 mg, 13.63 mmol) and MTBE (25 mL). Further dry ice was added during the addition. The mixture was allowed to warm to ambient temperature over 2 hours before being carefully added to water (50 mL). The layers were separated and the aqueous phase extracted with MTBE (×2). The aqueous phase was acidified to pH 3 with 1 M HCl and again extracted with MTBE (×3). The combined organic extracts were dried ($Na_2SO_4$), filtered and concentrated in vacuo to give 3-bromofuran-2-carboxylic acid (2.17 g, 83%) as a white solid. $^1$H NMR (500 MHz, Chloroform-d) δ 7.57 (d, J=1.9 Hz, 1H), 6.66 (d, J=1.8 Hz, 1H) ppm.

Step 2

To a solution of 3-bromofuran-2-carboxylic acid (2.17 g, 11.36 mmol) in DMF (25 mL) was added potassium carbonate (4.7 g, 34.01 mmol) and ethyliodide (2.7 mL, 33.76 mmol). The reaction mixture was heated to 65° C. for 40 mins then allowed to cool and stirred over the weekend. The reaction mixture was filtered, washing with EtOAc and then the filtrate diluted with water. The layers were separated and the aqueous layer extracted with EtOAc. The combined organic layers were washed with water (×5) then dried ($Na_2SO_4$), filtered and concentrated in vacuo. The residue was dissolved in EtOAc and adsorbed onto diatomaceous earth (Telos nm). Purification by flash chromatography (24 g $SiO_2$, 0 to 50% EtOAc in heptane) gave ethyl 3-bromofuran-2-carboxylate (1.8322 g, 74%) as a white solid. $^1$H NMR (500 MHz, Chloroform-d) δ 7.50 (d, J=1.9 Hz, 1H), 6.60 (d, J=1.8 Hz, 1H), 4.40 (q, J=7.1 Hz, 2H), 1.41 (t, J=7.1 Hz, 3H) ppm.

Step 3

A mixture of ethyl 3-bromofuran-2-carboxylate (1.55 g, 7.08 mmol), (3,4-difluoro-2-methoxy-phenyl)boronic acid (1.45 g, 7.72 mmol), $Pd(PPh_3)_2Cl_2$ (98 mg, 0.14 mmol) and $NaHCO_3$ (5 mL) in dioxane (20 mL) was heated at 50° C. for 1 hour before being cooled to ambient temperature and diluted with EtOAc and water. The layers were separated and the aqueous phase was extracted with EtOAc (4×). The combined organic extracts were washed with brine, dried ($MgSO_4$), filtered and concentrated in vacuo. The residue was dissolved in EtOAc and adsorbed onto diatomaceous earth (Telos nm). Purification by flash chromatography (24 g $SiO_2$, 0 to 20% EtOAc in heptane) gave ethyl 3-(3,4-difluoro-2-methoxy-phenyl)furan-2-carboxylate (1.5105 g, 76%) as a clear oil. $^1$H NMR (500 MHz, Chloroform-d) δ 7.59 (d, J=1.7 Hz, 1H), 7.07 (ddd, J=8.8, 5.9, 2.3 Hz, 1H), 6.90 (ddd, J=9.6, 8.8, 7.3 Hz, 1H), 6.57 (d, J=1.8 Hz, 1H), 4.27 (q, J=7.1 Hz, 2H), 3.82 (d, J=2.0 Hz, 3H), 1.25 (t, J=7.1 Hz, 3H) ppm. ESI-MS m/z calc. 282.07037, found 283.4 (M+1)$^+$.

Step 4

To a solution of ethyl 3-(3,4-difluoro-2-methoxy-phenyl)furan-2-carboxylate (200 mg, 0.71 mmol) in DCE (25 mL) was added tris(2,2'-bipyridyl)dichlororuthenium(II) hexahydrate (11 mg, 0.015 mmol). The reaction mixture was degassed with nitrogen and pyridine (172 µL, 2.13 mmol) was added followed by trifluoromethylsulfonyl trifluoromethanesulfonate (358 µL, 2.13 mmol) dropwise over 10 mins. The mixture was irradiated with blue LEDs (Penn PhD photoreactor M2 and the Blue LED Hepatochem) for 2 hours stirring at ambient temperature (100 rpm). This process was repeated 13 times, and the crude mixtures combined for work up. The combined mixture was washed with water and brine and the organic layer dried ($MgSO_4$) and concentrated in vacuo. Purification by flash chromatography (24 g $SiO_2$, 0 to 20% EtOAc in heptane) gave ethyl 3-(3,4-difluoro-2-methoxy-phenyl)-5-(trifluoromethyl) furan-2-carboxylate (2.39 g, 72%) as a clear oil that solidifies on standing. $^1$H NMR (500 MHz, Chloroform-d) δ 7.07 (ddd, J=8.8, 5.8, 2.3 Hz, 1H), 6.97-6.87 (m, 2H), 4.31 (q, J=7.1 Hz, 2H), 3.88 (d, J=2.5 Hz, 3H), 1.28 (t, J=7.1 Hz, 3H) ppm. ESI-MS m/z calc. 350.05774, found 351.4 (M+1)$^+$.

Step 5

A solution of ethyl 3-(3,4-difluoro-2-methoxy-phenyl)-5-(trifluoromethyl)furan-2-carboxylate (2.29 g, 6.538 mmol) in ethanol (200 mL) was added to $Pd(OH)_2$/C (920 mg of 20% w/w, 1.310 mmol) and the mixture degassed with nitrogen. The mixture is stirred under a balloon pressure of hydrogen for 18 hours before further $Pd(OH)_2$ (920 mg of 20% w/w, 1.310 mmol) was added, the mixture degassed with nitrogen and then stirred under a balloon pressure of hydrogen for 18 hours. The mixture was filtered through celite, washing with ethanol, and the filtrate concentrated in vacuo to give ethyl rac-(2S,3S,5R)-3-(3,4-difluoro-2-methoxy-phenyl)-5-(trifluoromethyl)tetrahydrofuran-2-carboxylate (3.2 g, 95%). $^1$H NMR (500 MHz, Chloroform-d) δ 6.91-6.75 (m, 2H), 4.88 (d, J=8.8 Hz, 1H), 4.49 (dp, J=11.9, 6.0 Hz, 1H), 4.15-4.03 (m, 4H), 3.88-3.70 (m, 2H), 2.66 (td, J=12.5, 10.7 Hz, 1H), 2.31 (dt, J=11.9, 5.9 Hz, 1H), 0.93 (t, J=7.1 Hz, 3H) ppm. ESI-MS m/z calc. 354.08905, found 355.0 (M+1)$^+$.

Step 6

To a solution of ethyl rac-(2S,3S,5R)-3-(3,4-difluoro-2-methoxy-phenyl)-5-(trifluoromethyl)tetrahydrofuran-2-carboxylate (3.2 g, 6.233 mmol) in MeOH (100 mL) was added cesium carbonate (4 g, 12.28 mmol). The mixture was heated at 50° C. for 16 hours before being concentrated in vacuo. The residue was partitioned between EtOAc and 1M HCl, the layers separated and the organic layer passed through a phase separator and concentrated in vacuo to give rac-(2R,3S,5R)-3-(3,4-difluoro-2-methoxy-phenyl)-5-(trifluoromethyl)tetrahydrofuran-2-carboxylic acid (1.9947 g, 98%) as a yellow oil. $^1$H NMR (500 MHz, Chloroform-d) δ 6.96 (ddd, J=8.8, 5.5, 2.2 Hz, 1H), 6.88 (td, J=9.1, 7.2 Hz, 1H), 4.70-4.59 (m, 2H), 4.00 (d, J=2.7 Hz, 3H), 3.92-3.78 (m, 1H), 2.68-2.54 (m, 1H), 2.35-2.25 (m, 1H) ppm. ESI-MS m/z calc. 326.05774, found 325.0 (M−1)$^-$.

Step 7

To a solution of rac-(2R,3S,5R)-3-(3,4-difluoro-2-methoxy-phenyl)-5-(trifluoromethyl)tetrahydrofuran-2-carboxylic acid (80 mg, 0.25 mmol) in MeCN (3 mL) was added methyl 4-aminopyridine-2-carboxylate (44 mg, 0.29 mmol). 1-methylimidazole (70 mg, 0.8526 mmol) and TCFH (82 mg, 0.29 mmol) were added and the reaction stirred at ambient temperature for 16 hours. The reaction mixture was partitioned between EtOAc (10 mL) and water (10 mL), the layers separated and the aqeuous layer further extracted with EtOAc (10 mL). The combined organic layers were washed with brine (10 mL), dried (MgSO$_4$) and concentrated in vacuo to give methyl rac-(2R,3S,5R)-4-[[3-(3,4-difluoro-2-methoxy-phenyl)-5-(trifluoromethyl)tetrahydrofuran-2-carbonyl]amino]pyridine-2-carboxylate (70 mg, 36%), which was used without further purification. ESI-MS m/z calc. 460.10577, found 461.6 (M+1)$^+$.

Step 8 and 9

To a solution of methyl rac-(2R,3S,5R)-4-[[3-(3,4-difluoro-2-methoxy-phenyl)-5-(trifluoromethyl)tetrahydrofuran-2-carbonyl]amino]pyridine-2-carboxylate (50 mg, 0.11 mmol) in MeOH (1 mL) was added methanolic ammonia (155 μL of 7 M, 1.1 mmol) and the mixture stirred at ambient temperature overnight before being concentrated in vacuo to give rac-(2R,3S,5R)-4-[[3-(3,4-difluoro-2-methoxy-phenyl)-5-(trifluoromethyl)tetrahydrofuran-2-carbonyl]amino]pyridine-2-carboxamide.

rac-(2R,3S,5R)-4-[[3-(3,4-difluoro-2-methoxy-phenyl)-5-(trifluoromethyl)tetrahydrofuran-2-carbonyl]amino]pyridine-2-carboxamide was separated by chiral SFC using a (R,R)-Whelk-O1 column, 5 um particle size, 25 cm×21.2 mm from Regis Technologies to give two single enantiomers of unknown absolute configuration:

First Eluting Isomer (rt=0.75 min): rel-(2S,3R,5S)-4-[[3-(3,4-difluoro-2-methoxy-phenyl)-5-(trifluoromethyl)tetrahydrofuran-2-carbonyl]amino]pyridine-2-carboxamide (109, 5 mg, 10%). $^1$H NMR (500 MHz, Chloroform-d) δ 8.57 (s, 1H), 8.50 (d, J=5.6 Hz, 1H), 8.13 (dd, J=5.5, 2.3 Hz, 1H), 8.00 (d, J=2.2 Hz, 1H), 7.84 (s, 1H), 7.11-7.00 (m, 1H), 6.99-6.84 (m, 1H), 5.56 (s, 1H), 4.76 (d, J=10.2 Hz, 1H), 4.73-4.56 (m, 1H), 4.02 (d, J=2.6 Hz, 3H), 3.83 (q, J=10.4 Hz, 1H), 2.70 (dt, J=13.0, 7.7 Hz, 1H), 2.42 (td, J=12.1, 8.8 Hz, 1H) ppm. ESI-MS m/z calc. 445.1061, found 446.5 (M+1)$^+$.

Second Eluting Isomer (rt=1.15 min): rel-(2R,3S,5R)-4-[[3-(3,4-difluoro-2-methoxy-phenyl)-5-(trifluoromethyl)tetrahydrofuran-2-carbonyl]amino]pyridine-2-carboxamide (110, 5 mg, 10%). $^1$H NMR (500 MHz, Chloroform-d) δ 8.58 (s, 1H), 8.50 (d, J=5.5 Hz, 1H), 8.13 (dd, J=5.5, 2.2 Hz, 1H), 8.00 (d, J=2.5 Hz, 1H), 7.84 (s, 1H), 7.03 (t, J=6.4 Hz, 1H), 6.93 (q, J=8.8 Hz, 1H), 5.56 (s, 1H), 4.76 (d, J=10.2 Hz, 1H), 4.69 (q, J=7.3 Hz, 1H), 4.02 (d, J=2.6 Hz, 3H), 3.91-3.70 (m, 1H), 2.70 (dt, J=13.0, 7.7 Hz, 1H), 2.42 (td, J=12.2, 8.8 Hz, 1H) ppm. ESI-MS m/z calc. 445.1061, found 446.5 (M+1)$^+$.

The following compounds were made using the method described in Example 21, except that (4-fluoro-2-methoxy-3-methyl-phenyl)boronic acid was used as coupling partner in the Suzuki coupling step 3 and the conditions used for the amide formation step 7 are similar to those used in Example 14 step 4:

| Cmpd No. | Compound Name | LC/MS | NMR (shifts in ppm) |
| --- | --- | --- | --- |
| 111 | rel-(2S,3R,5S)-4-[[3-(4-fluoro-2-methoxy-3-methyl-phenyl)-5-(trifluoromethyl)tetrahydrofuran-2-carbonyl]amino]pyridine-2-carboxamide (first eluting isomer by SFC on (R,R)-Whelk-O1 column, rt = 0.82 min) | ESI-MS m/z calc. 441.13116, found 442.5 (M + 1)$^+$; 440.6 (M − 1)$^-$; Retention time: 2.95 minutes | |
| 112 | rel-(2R,3S,5R)-4-[[3-(4-fluoro-2-methoxy-3-methyl-phenyl)-5-(trifluoromethyl)tetrahydrofuran-2-carbonyl]amino]pyridine-2-carboxamide (second eluting isomer by SFC on (R,R)-Whelk-O1 column, rt = 1.38 min) | ESI-MS m/z calc. 441.13116, found 442.3 (M + 1)$^+$; 440.3 (M − 1)$^-$; Retention time: 2.96 minutes | $^1$H NMR (500 MHz. DMSO-d$_6$) δ 10.53 (s, 1H), 8.49 (d, J = 5.5 Hz, 1H), 8.26 (d, J = 2.2 Hz, 1H), 8.05 (d, J = 2.8 Hz, 1H), 7.83 (dd, J = 5.5, 2.2 Hz, 1H), 7.60 (d, J = 2.8 Hz, 1H), 7.31 (dd, J = 8.7, 6.5 Hz, 1H), 7.02 (t, J = 8.8 Hz, 1H), 5.03-4.91 (m, 1H), 4.59 (d, J = 9.4 Hz, 1H), 4.05-3.95 (m, 1H), 3.59 (s, 3H), 2.77 (dt, J = 12.5, 7.4 Hz, 1H), 2.16-2.04 (m, 4H) ppm. |

Example 22

4-[[(2R,3S,4S,5S)-3-(3,4-difluoro-2-methoxy-phenyl)-5-isopropyl-4-methyl-tetrahydrofuran-2-carbonyl]amino]pyridine-2-carboxamide (113)

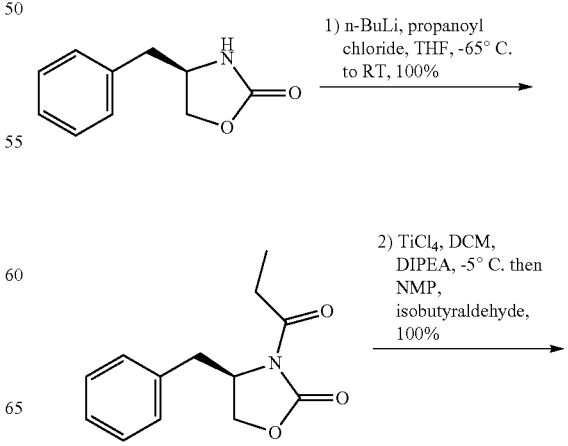

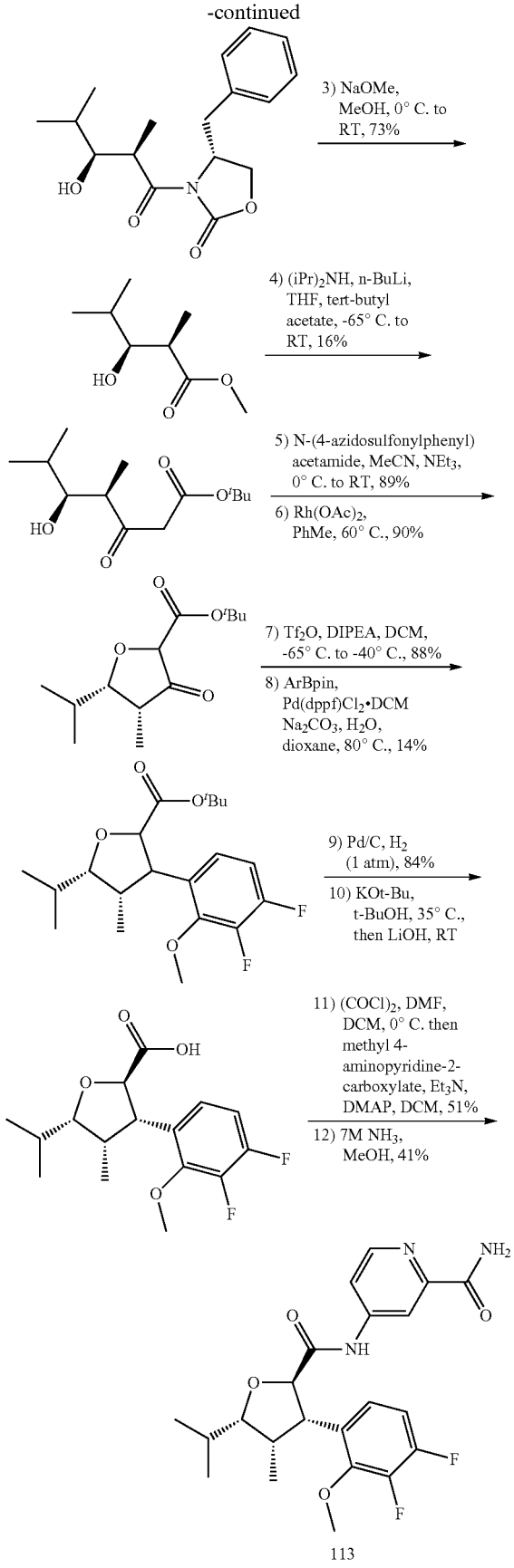

Step 1

To a solution of (4R)-4-benzyloxazolidin-2-one (29.7 g, 164.26 mmol) in THF (297 mL) cooled to −65° C. was added n-BuLi (65.7 mL of 2.5 M, 164.2 mmol) dropwise, keeping the temperature at −65° C. The resulting mixture was stirred at −65° C. for 30 min before propanoyl chloride (17.059 g, 16.247 mL, 180.69 mmol) was added dropwise. The mixture was stirred at −65° C. for 1 hour and then allowed to warm to ambient temperature overnight. The mixture was quenched by addition of saturated aqueous NH$_4$Cl solution (300 mL) and the aqueous layer extracted with EtOAc (2×300 mL). The combined organic layers were washed with saturated aqueous NaHCO$_3$ solution (300 mL) and brine (200 mL), dried (MgSO$_4$), filtered and evaporated in vacuo to give (4R)-4-benzyl-3-propanoyl-oxazolidin-2-one (39 g, 100%) as a colorless oil. $^1$H NMR (300 MHz, Chloroform-d) δ 7.46-7.14 (m, 5H), 4.69 (ddt, J=9.5, 6.9, 3.4 Hz, 1H), 4.27-4.15 (m, 2H), 3.32 (dd, J=13.4, 3.3 Hz, 1H), 2.98 (qd, J=7.3, 5.9 Hz, 2H), 2.80 (dd, J=13.4, 9.6 Hz, 1H), 1.23 (t, J=7.4 Hz, 3H) ppm. ESI-MS m/z calc. mass 233.105, found, 233.95 [M+1]$^+$.

Step 2

To a solution of (4R)-4-benzyl-3-propanoyl-oxazolidin-2-one (13.12 g, 56.25 mmol) in DCM (130 mL) cooled to 0° C. was added titanium tetrachloride (59 mL of 1 M in DCM, 59.00 mmol). The resulting mixture was stirred at 0° C. for 15 mins before DIPEA (8.1620 g, 11 mL, 63.15 mmol) was added and the mixture stirred at this temperature for 40 mins. NMP (5.5512 g, 5.4 mL, 55.999 mmol) was added and the reaction stirred for 10 mins at ambient temperature before isobutyraldehyde (4.2660 g, 5.4 mL, 59.16 mmol) was added and the mixture was stirred at 0° C. for 1 hour and then at ambient temperature overnight. The mixture was quenched with a mixture of water (50 mL) and saturated aqueous NH$_4$Cl solution (50 mL) and extracted with DCM (3×100 mL). The combined organic extracts were dried (Na$_2$SO$_4$), filtered and concentrated in vacuo. Purification by flash chromatography (SiO$_2$, 0 to 20% EtOAc to hexane) gave (4R)-4-benzyl-3-[(2R,3S)-3-hydroxy-2,4-dimethyl-pentanoyl]oxazolidin-2-one (16 g, 86%) as a light yellow oil. $^1$H NMR (300 MHz, Chloroform-d) δ 7.44-7.16 (m, 5H), 4.72 (ddt, J=9.4, 6.9, 3.3 Hz, 1H), 4.30-4.17 (m, 2H), 3.99 (qd, J=7.0, 2.6 Hz, 1H), 3.56 (dd, J=8.6, 2.6 Hz, 1H), 3.28 (dd, J=13.4, 3.4 Hz, 1H), 2.90 (d, J=3.4 Hz, 1H), 2.81 (dd, J=13.4, 9.4 Hz, 1H), 1.75 (dp, J=8.5, 6.6 Hz, 1H), 1.27 (d, J=7.0 Hz, 3H), 1.06 (d, J=6.6 Hz, 3H), 0.93 (d, J=6.7 Hz, 3H) ppm. ESI-MS m/z calc. 305.1627, found 306.05 (M+1)$^+$.

Step 3

To a solution of (4R)-4-benzyl-3-[(2R,3S)-3-hydroxy-2,4-dimethyl-pentanoyl]oxazolidin-2-one (100 g, 301.27 mmol) in MeOH (750 mL) stirring at 0° C. was added sodium methoxide (19.609 g, 83 mL of 25% w/w in methanol, 90.74 mmol). The mixture was stirred for 30 mins at ambient temperature before being quenched with saturated aqueous NH$_4$Cl solution (300 mL) and the aqueous layer extrated with DCM (3×200 mL). The combined organic layers were dried (Na$_2$SO$_4$), filtered and concentrated in vacuo. Purification by flash column chromatography (SiO$_2$, 10 to 20% diethyl ether in hexane) gave methyl (2R,3S)-3-hydroxy-2,4-dimethyl-pentanoate (40.24 g, 73%) as a colorless liquid, containing 12% hexane by weight. $^1$H NMR (300 MHz, Chloroform-d) δ 3.73 (s, 3H), 3.59 (dt, J=7.9, 3.9 Hz, 1H), 2.70 (qd, J=7.2, 3.6 Hz, 1H), 2.45 (dd, J=4.1, 1.8 Hz, 1H), 1.69 (ddd, J=13.3, 8.0, 6.7 Hz, 1H), 1.21 (d, J=7.2 Hz, 3H), 1.03 (d, J=6.6 Hz, 3H), 0.90 (d, J=6.8 Hz, 3H) ppm.

Step 4

To a solution of diisopropylamine (67.146 g, 93 mL, 663.56 mmol) in THF (1 L) cooled to −65° C. was added n-BuLi (228 mL of 2.5 M in hexanes, 570 mmol). The mixture was stirred for 30 mins at −65° C. before a solution of tert-butyl acetate (66.143 g, 77 mL, 569.42 mmol) in THF (100 mL) was added dropwise followed by solution of methyl (2R,3S)-3-hydroxy-2,4-dimethyl-pentanoate (40 g, 189.75 mmol) in THF (100 mL). The mixture was stirred for 1 hour at −50° C. and then allowed to warm to ambient temperature overnight. The reaction was quenched by addition of ice-water (800 mL) and extracted with DCM (3×400 mL). The combined organic layers were washed with saturated NaHCO$_3$ (500 mL), water (2×500 mL), dried (Na$_2$SO$_4$), filtered and evaporated in vacuo. Purification by reverse phase flash chromatography (SiO$_2$ C18, acetonitrile/water 0 to 60%) gave tert-butyl (4R,5S)-5-hydroxy-4,6-dimethyl-3-oxo-heptanoate (7.95 g, 16%) as a yellow oil. $^1$H NMR (300 MHz, Chloroform-d) δ 3.62 (dt, J=8.7, 3.2 Hz, 1H), 3.54-3.39 (m, 2H), 2.88 (qd, J=7.2, 2.8 Hz, 1H), 2.57 (d, J=3.7 Hz, 1H), 1.71 (ddt, J=13.3, 8.6, 6.7 Hz, 1H), 1.49 (s, 9H), 1.17 (d, J=7.2 Hz, 3H), 1.05 (d, J=6.5 Hz, 3H), 0.89 (d, J=6.8 Hz, 3H) ppm.

Step 5

To a solution of N-(4-azidosulfonylphenyl)acetamide (10.33 g, 43.00 mmol) in acetonitrile (160 mL) was added tert-butyl (4R,5S)-5-hydroxy-4,6-dimethyl-3-oxo-heptanoate (7.9 g, 30.72 mmol). The mixture was cooled to 0° C. and triethylamine (9.29 g, 12.8 mL, 91.84 mmol) was added. The reaction mixture was warmed to ambient temperature and stirred overnight before being concentrated. Purification by flash chromatography gave tert-butyl (4R,5S)-2-diazo-5-hydroxy-4,6-dimethyl-3-oxo-heptanoate (7.58 g, 89%) as a yellow oil. $^1$H NMR (300 MHz, Chloroform-d) δ 3.78 (qd, J=7.1, 2.5 Hz, 1H), 3.54 (dt, J=8.6, 2.7 Hz, 1H), 3.10 (d, J=2.8 Hz, 1H), 1.81-1.66 (m, 1H), 1.55 (s, 9H), 1.16 (d, J=7.1 Hz, 3H), 1.05 (d, J=6.6 Hz, 3H), 0.92 (d, J=6.8 Hz, 3H) ppm. ESI-MS m/z calc. 270.158, found 271.1 (M+1)$^+$.

Step 6

To a suspension of rhodium (II) acetate (134 mg, 0.30 mmol) in toluene (25 mL) stirring at 60° C. was added a solution of tert-butyl (4R,5S)-2-diazo-5-hydroxy-4,6-dimethyl-3-oxo-heptanoate (8.63 g, 30.33 mmol) in toluene (78 mL). The mixture was stirred at 60° C. for 1 hour, then cooled to ambient temperature, filtered through filter paper and concentrated in vacuo to give tert-butyl (4R,5S)-5-isopropyl-4-methyl-3-oxo-tetrahydrofuran-2-carboxylate (7.34 g, 90%) as a light yellow oil.

Step 7

To a solution of tert-butyl (4R,5S)-5-isopropyl-4-methyl-3-oxo-tetrahydrofuran-2-carboxylate (500 mg, 2.06 mmol) in DCM (15 mL) stirring at a cooled −65° C. was added DIPEA (1.1 mL, 6.32 mmol) and trifluoromethylsulfonyl trifluoromethanesulfonate (0.45 mL, 2.67 mmol). The reaction mixture was stirred for 2 hours at −65° C. before further trifluoromethylsulfonyl trifluoromethanesulfonate (0.45 mL, 2.66 mmol) was added. The mixture was stirred at −60° C. for 1 hour and then further DIPEA (0.4 mL, 2.30 mmol) and trifluoromethylsulfonyl trifluoromethanesulfonate (0.45 mL, 2.66 mmol) were added and the mixture was stirred for 1 hour at −60° C. and 1 hour at −40° C. The mixture was quenched with saturated aqueous NaHCO$_3$ solution (15 mL) and the aqueous layer extracted with DCM (3×10 mL). The combined organic layers were dried (MgSO$_4$), filtered and evaporated in vacuo. The residue was dissolved in EtOAc (30 mL) and washed with 1M HCl (3×30 mL). The organic layer was dried (Na$_2$SO$_4$), filtered and concentrated in vacuo to give tert-butyl (2S,3R)-2-isopropyl-3-methyl-4-(trifluoromethylsulfonyloxy)-2,3-dihydrofuran-5-carboxylate (676 mg, 88%) as a brown oil, which was used without further purification.

Step 8

A mixture of crude tert-butyl (2S,3R)-2-isopropyl-3-methyl-4-(trifluoromethylsulfonyloxy)-2,3-dihydrofuran-5-carboxylate (676 mg, 1.81 mmol), 2-(3,4-difluoro-2-methoxy-phenyl)-4,4,5,5-tetramethyl-1,3,2-dioxaborolane (731 mg, 2.71 mmol) and sodium carbonate (478 mg, 4.51 mmol) in dioxane (13.5 mL) and water (3.5 mL) in a pressure glass reactor was degassed by bubbling argon through it for 15 mins. Next Pd(dppf)Cl$_2$.DCM (206 mg, 0.2523 mmol) was added and the reactor was sealed. The reaction mixture was stirred at 80° C. overnight before being cooled to ambient temperature, diluted with EtOAc (20 mL), filtered through celite and concentrated in vacuo. Purification by flash chromatography gave tert-butyl (2S,3S)-4-(3,4-difluoro-2-methoxy-phenyl)-2-isopropyl-3-methyl-2,3-dihydrofuran-5-carboxylate (107 mg, 14%) as a yellow oil. $^1$H NMR (300 MHz, Chloroform-d) δ 6.98-6.74 (m, 2H), 4.14 (dd, J=10.2, 8.0 Hz, 1H), 3.92 (d, J=1.8 Hz, 3H), 3.18-2.99 (m, 1H), 2.14 (dp, J=10.1, 6.4 Hz, 1H), 1.30 (s, 9H), 1.19 (d, J=6.5 Hz, 3H), 0.97 (dd, J=7.8, 6.8 Hz, 6H) ppm; $^{19}$F NMR (376 MHz, Chloroform-d) δ−136.92−−137.21 (m), −155.04−−155.40 (m) ppm.

Step 9

Ethanol (3.5 mL) was added to a mixture of tert-butyl (2S,3S)-4-(3,4-difluoro-2-methoxy-phenyl)-2-isopropyl-3-methyl-2,3-dihydrofuran-5-carboxylate (118 mg, 0.32 mmol) and Pd/C (Degussa, wet, 350 mg, 0.33 mmol). The mixture was degassed and stirred under a balloon of hydrogen for 4 days before being filtered through celite, washing with EtOAc. The filtrate was concentrated in vacuo to give tert-butyl (2S,3S,4S,5S)-3-(3,4-difluoro-2-methoxy-phenyl)-5-isopropyl-4-methyl-tetrahydrofuran-2-carboxylate (100 mg, 84%). $^1$H NMR (400 MHz, Chloroform-d) δ 7.11-7.03 (m, 1H), 6.83-6.75 (m, 1H), 4.45 (d, J=7.9 Hz, 1H), 4.23 (t, J=8.3 Hz, 1H), 3.93 (d, J=1.5 Hz, 3H), 3.49 (dd, J=9.9, 6.9 Hz, 1H), 2.76-2.63 (m, 1H), 1.97-1.83 (m, 1H), 1.15 (s, 9H), 1.13 (d, J=6.5 Hz, 3H), 0.90 (d, J=6.5 Hz, 3H), 0.70 (d, J=7.4 Hz, 3H) ppm.

Step 10

Tert-butyl (2S,3S,4S,5S)-3-(3,4-difluoro-2-methoxy-phenyl)-5-isopropyl-4-methyl-tetrahydrofuran-2-carboxylate (100 mg, 0.27 mmol) and potassium tert-butoxide (60 mg, 0.53 mmol) were mixed in tert-butanol (2.6 mL) and stirred at ambient temperature. After 1 hour the reaction was heated to 35° C. After 2 hours at this temperature the reaction was cooled to ambient temperature, LiOH (400 μL of 2 M, 0.80 mmol) was added and the reaction stirred at ambient temperature for 16 h. The reaction was diluted with EtOAc and quenched with 1 M aqueous HCl. The aqueous layer was separated and extracted with EtOAc. The combined organic layers were dried (MgSO$_4$), filtered and concentrated in vacuo to afford (2R,3S,4S,5S)-3-(3,4-difluoro-2-methoxy-phenyl)-5-isopropyl-4-methyl-tetrahydrofuran-2-carboxylic acid (100 mg) as a white solid, which was used without further purification.

Step 11

To a solution of (2R,3S,4S,5S)-3-(3,4-difluoro-2-methoxy-phenyl)-5-isopropyl-4-methyl-tetrahydrofuran-2-carboxylic acid (100 mg, 0.3181 mmol) in DCM (3 mL) stirring at 0° C. was added DMF (5 μL, 0.065 mmol) and oxalyl chloride (90 μL, 1.03 mmol). After 30 mins the reaction mixture was concentrated in vacuo. The residue was diluted in DCM (2 mL) and the solution added dropwise to a solution of methyl 4-aminopyridine-2-carboxylate (75 mg, 0.4929 mmol) and Et$_3$N (300 μL, 2.15 mmol) in DCM (1.5 mL) stirring at 0° C. DMAP (5 mg, 0.041 mmol) was added and the reaction stirred at this temperature for 10 mins before being warmed to ambient temperature and stirred for 16 h. The reaction mixture was diluted with DCM and washed with 1 M HC solution, the organic layer dried (MgSO$_4$), filtered and concentrated in vacuo directly onto silica. Purification by flash chromatography (24 g SiO$_2$, 0 to 100% EtOAc in petrol) gave methyl 4-[[(2R,3S,4S,5S)-3-(3,4-difluoro-2-methoxy-phenyl)-5-isopropyl-4-methyl-tetrahydrofuran-2-carbonyl]amino]pyridine-2-carboxylate (73 mg, 51%). ESI-MS m/z calc. 448.18097, found 449.2 (M+1)$^+$; 447.3 (M−1)$^−$.

Step 12

Methyl 4-[[(2R,3S,4S,5S)-3-(3,4-difluoro-2-methoxy-phenyl)-5-isopropyl-4-methyl-tetrahydrofuran-2-carbonyl]amino]pyridine-2-carboxylate (73 mg, 0.1628 mmol) was stirred in methanolic ammonia (5 mL of 7 M, 35.00 mmol) at ambient temperature overnight. The reaction mixture was concentrated in vacuo and purified by chiral SFC using a Chiralpak AS-H column (5 μm particle size, 25 cm×10 mm from Daicel) on a Minigram SFC instrument from Berger Instruments to remove a minor diastereomer to give 4-[[(2R,3S,4S,5S)-3-(3,4-difluoro-2-methoxy-phenyl)-5-isopropyl-4-methyl-tetrahydrofuran-2-carbonyl]amino]pyridine-2-carboxamide (113, 30.5 mg, 41%). $^1$H NMR (500 MHz, DMSO-d$_6$) δ 10.34 (s, 1H), 8.47 (d, 1H), 8.25 (d, J=2.2 Hz, 1H), 8.05 (d, J=2.8 Hz, 1H), 7.85 (dd, J=5.5, 2.2 Hz, 1H), 7.59 (d, J=2.8 Hz, 1H), 7.25-7.10 (m, 2H), 4.87 (d, J=10.1 Hz, 1H), 4.09 (dd, J=10.2, 5.8 Hz, 1H), 3.95-3.84 (m, 4H), 3.29 (s, 1H), 1.78-1.61 (m, 1H), 1.07 (d, J=6.4 Hz, 3H), 0.86 (d, J=6.6 Hz, 3H), 0.58 (d, J=7.0 Hz, 3H) ppm. ESI-MS m/z calc. 433.1813, found 434.2 (M+1)$^+$; 432.3 (M−1)$^−$.

Example 23

6-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide (114)

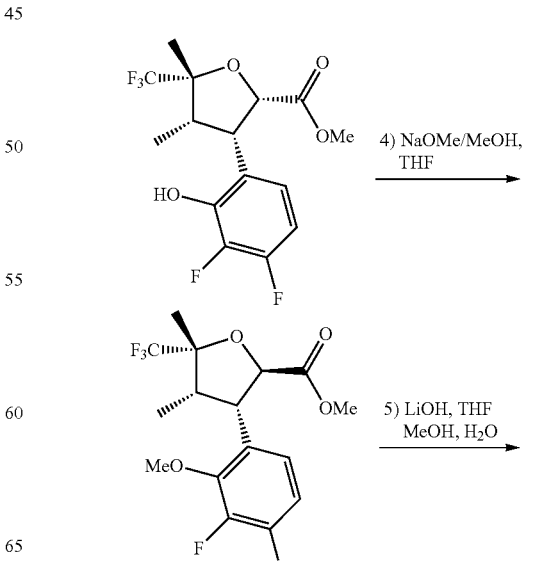

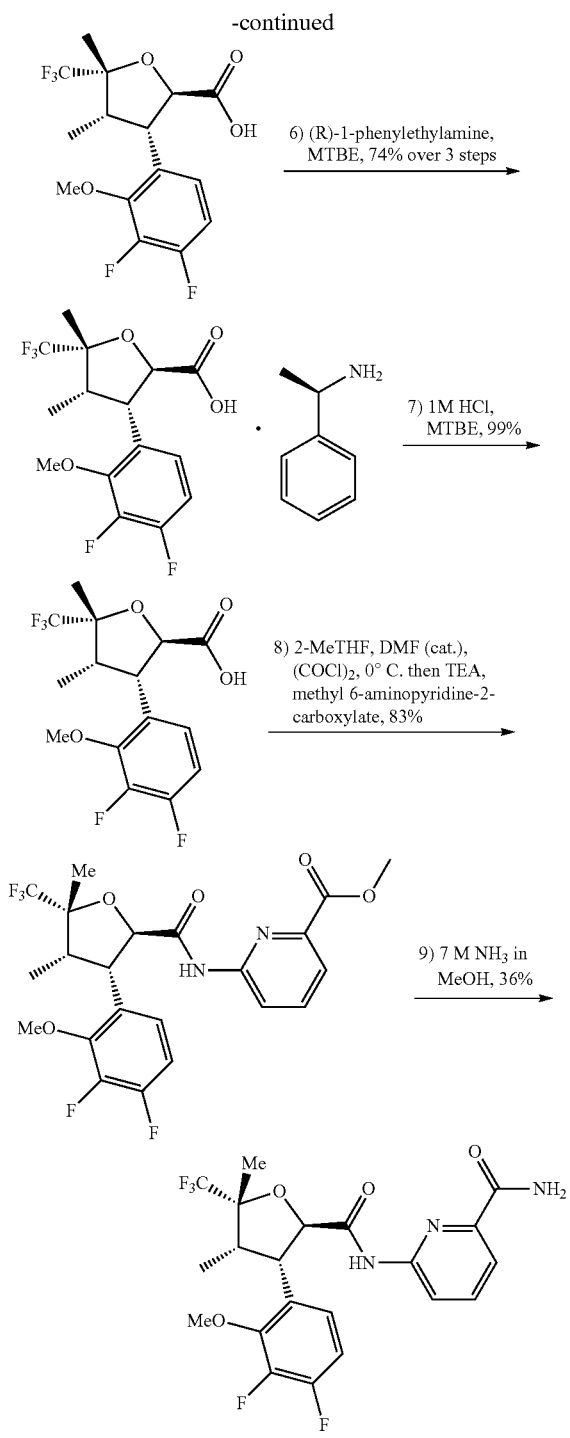

Step 1 rac-(1S,2R)-6,7-difluoro-1,2-dimethyl-2-(trifluoromethyl)-1,2-dihydro-4H-furo[2,3-c]chromen-4-one (1348 g, 4.366 mol) was separated by chiral SFC using a (R,R)-Whelk-O1 column, 5 μm particle size, 15 cm×3 cm from Regis Technologies on a MultiGram III SFC instrument from Berger Instruments to give:

First Eluting Isomer (rt=1.85 min): (R,2S)-6,7-difluoro-1,2-dimethyl-2-(trifluoromethyl)-1,2-dihydro-4H-furo[2,3-c]chromen-4-one (only an analytical sample was collected). $^1$H NMR (400 MHz, DMSO-d$_6$) δ 7.57 (ddd, J=9.0, 5.5, 2.0 Hz, 1H), 7.51 (ddd, J=10.3, 9.0, 7.0 Hz, 1H), 4.03 (q, J=7.2 Hz, 1H), 1.65 (s, 3H), 1.45 (dt, J=6.9, 2.2 Hz, 3H) ppm. ESI-MS m/z calc. 320.04718, found 321.3 (M+1)$^+$; 319.4 (M−1)$^−$.

Second Eluting Isomer (rt=2.38 min): (1S,2R)-6,7-Difluoro-1,2-dimethyl-2-(trifluoromethyl)-1,2-dihydro-4H-furo[2,3-c]chromen-4-one (366.99 g, 26%). $^1$H NMR (400 MHz, DMSO-d$_6$) δ 7.57 (ddd, J=9.0, 5.5, 2.0 Hz, 1H), 7.50 (ddd, J=10.3, 9.0, 7.0 Hz, 1H), 4.03 (q, J=7.2 Hz, 1H), 1.65 (s, 3H), 1.45 (dt, J=6.9, 2.2 Hz, 3H) ppm. ESI-MS m/z calc. 320.04518, found 321.4 (M+1)$^+$; 319.4 (M−1)$^−$.

Step 2

A solution of (1S,2R)-6,7-Difluoro-1,2-dimethyl-2-(trifluoromethyl)-1,2-dihydro-4H-furo[2,3-c]chromen-4-one (0.89 kg, 2.78 mol) and 20% palladium hydroxide on carbon (50% wet, 0.39 kg, 0.278 mol) in MeOH (12 L) was stirred under a 40 psi pressure of hydrogen overnight. An increase in the reaction temperature to 37° C. was observed after reacting overnight and the mixture was cooled to 24° C. and hydrogenation was continued for a total of 48 hours. The mixture was filtered through celite, washing with MeOH (20 L) and the filtrate was concentrated in vacuo. The residue was dissolved in toluene (4 L) and concentrated in vacuo, and this process repeated. The residue was dried under vacuum at 40° C. overnight to give methyl (2S,3S,4S,5R)-3-(3,4-difluoro-2-hydroxyphenyl)-4,5-dimethyl-5-(trifluoromethyl)tetrahydrofuran-2-carboxylate (1.0 kg at 91% purity, 100%) as a beige solid. $^1$H NMR (400 MHz, DMSO-d$_6$) 10.20 (br s, 1H), 6.94 (br t, J=7.4 Hz, 1H), 6.79-6.69 (m, 1H), 5.10 (d, J=6.0 Hz, 1H), 4.20 (dd, J=6.1, 8.2 Hz, 1H), 3.43 (s, 3H), 2.94 (quin, J=7.7 Hz, 1H), 1.46 (s, 3H), 0.77 (br d, J=6.8 Hz, 3H) ppm.

Step 3

Potassium carbonate (2.0 kg, 14.4 mol) and iodomethane (800 mL, 12.8 mol) were sequentially added to a solution of methyl (2S,3S,4S,5R)-3-(3,4-difluoro-2-hydroxyphenyl)-4,5-dimethyl-5-(trifluoromethyl)tetrahydrofuran-2-carboxylate (1.0 kg, 2.82 mol) in acetonitrile (10 L) under nitrogen stirring at ambient temperature. After stirring overnight, additional iodomethane (120 mL, 2 mmol) was added. After stirring overnight, additional iodomethane (60 mL, 0.85 mmol) was added and the mixture was stirred for 3 days. The reaction mixture was diluted with MTBE (30 L), treated with celite (1 kg) and filtered through a bed of celite (1 kg) washing with MTBE (10 L). The filtrate was filtered a second time through celite (1 kg) washing with MTBE (4 L) and the filtrate concentrated in vacuo. The residue was dissolved in toluene (4 L) and concentrated in vacuo, and this process repeated. The residue was dried under vacuum at 40° C. overnight to give methyl (2S,3S,4S,5R)-3-(3,4-difluoro-2-methoxyphenyl)-4,5-dimethyl-5-(trifluoromethyl)tetrahydrofuran-2-carboxylate (0.99 kg at 90% purity, 95%) as a brown solid. $^1$H NMR (400 MHz, DMSO-d$_6$) 7.14-7.00 (m, 2H), 5.14 (d, J=6.0 Hz, 1H), 4.15 (dd, J=6.2, 8.4 Hz, 1H), 3.88 (d, J=1.7 Hz, 3H), 2.97 (quin, J=7.8 Hz, 1H), 1.48 (s, 3H), 0.72 (br d, J=6.6 Hz, 3H) ppm.

Step 4 and 5

Sodium methoxide (25% in methanol, 65 mL, 0.28 mol) was added to a solution of methyl (2S,3S,4S,5R)-3-(3,4- difluoro-2-methoxyphenyl)-4,5-dimethyl-5-(trifluoromethyl) tetrahydrofuran-2-carboxylate (0.98 kg, 2.66 mol) in THF (10 L) stirring at ambient temperature under nitrogen. After 5 hours, MeOH (1 L), water (1 L) and lithium hydroxide monohydrate (0.168 kg, 4.0 mol) were sequentially added and the mixture was stirred overnight. The reaction mixture was poured into 1M HCl (4.4 L, 4.4 mol) then extracted with MTBE (20 L). The aqueous layer was further extracted with MTBE (2×5 L) and the combined organic layers washed with brine (2 L), dried ($Na_2SO_4$) then treated with activated carbon (50 g, 5% w/w) with stirring for 1 h. The mixture was filtered through celite, washing with MTBE (2×4 L) and the filtrate concentrated in vacuo. The residue was dissolved in toluene (4 L) and concentrated in vacuo, then dissolved in MTBE (4 L) and concentrated in vacuo again to give (2R,3S,4S,5R)-3-(3,4-difluoro-2-methoxyphenyl)-4,5-dimethyl-5-(trifluoromethyl)tetrahydrofuran-2-carboxylic acid (1.06 kg at 77.7% purity) as an amber oil, which was used without further purification.

Step 6

Crude (2R,3S,4S,5R)-3-(3,4-difluoro-2-methoxyphenyl)-4,5-dimethyl-5-(trifluoromethyl)tetrahydrofuran-2-carboxylic acid (2.09 kg at 77% purity, 4.54 mol) was dissolved in MTBE (25 L) in a 100 L Chemglass reactor then stirred at 84 rpm at ambient temperature. A mixture of (R)-1-phenylethylamine (0.704 kg, 5.81 mol) and MTBE (2 L) was added to the reactor, followed by additional MTBE to give a total volume of 30 L in the reactor. After 2 hours additional MTBE (2 L) was added to the reaction and after a total of 3.5 hours the mixture was filtered, washing with MTBE (2 L). The reactor was rinsed with MTBE (4 L), which was used to rinse the solids, which were then compressed and dried on the Buchner funnel for 2 hours. The solid product cake was loosened then dried under a stream of nitrogen and under vacuum overnight on the Buchner funnel. The isolated solids were dried in a convection oven at 40° C. for 24 hours to give (2R,3S,4S,5R)-3-(3,4-Difluoro-2-methoxyphenyl)-4,5-dimethyl-5-(trifluoromethyl)tetrahydrofuran-2-carboxylic acid (R)-1-phenylethan-1-amine salt (1.86 kg at 95.7% purity, 74% over 3 steps) as an off-white solid. $^1$H NMR, 400 MHz, DMSO-$d_6$) 8.34 (br s, 2H), 7.46-7.41 (m, 2H), 7.36-7.27 (m, 3H), 7.16-7.11 (m, 1H), 7.10-7.03 (m, 1H), 4.58 (d, J=9.9 Hz, 1H), 4.23 (q, J=6.7 Hz, 1H), 3.99 (dd, J=7.8, 9.8 Hz, 1H), 3.90 (d, J=2.0 Hz, 3H), 2.60 (quin, J=7.5 Hz, 1H), 1.50 (s, 3H), 1.40 (d, J=6.7 Hz, 3H), 0.71-0.59 (m, 3H) ppm.

Step 7

To a suspension of (2R,3S,4S,5R)-3-(3,4-difluoro-2-methoxy-phenyl)-4,5-dimethyl-5-(trifluoromethyl)tetrahydrofuran-2-carboxylic acid (1R)-1-phenylethanamine salt (10.6 g, 22.29 mmol) in MTBE (250 mL) was added HCl (200 mL of 2 M, 400.0 mmol). The layers were separated and the organic layer was washed with water (200 mL), dried ($MgSO_4$), filtered and concentrated in vacuo to give (2R,3S,4S,5R)-3-(3,4-difluoro-2-methoxy-phenyl)-4,5-dimethyl-5-(trifluoromethyl)tetrahydrofuran-2-carboxylic acid (8.4 g, 99%) as an oil. $^1$H NMR (400 MHz, Chloroform-d) δ 6.96 (ddd, J=7.9, 5.6, 2.0 Hz, 1H), 6.88 (td, J=9.2, 7.3 Hz, 1H), 4.96 (d, J=10.5 Hz, 1H), 4.15 (dd, J=10.5, 8.0 Hz, 1H), 4.02 (d, J=2.8 Hz, 3H), 2.74 (p, J=7.6 Hz, 1H), 1.64 (t, J=1.2 Hz, 3H), 0.79 (dq, J=7.4, 2.3 Hz, 3H) ppm.

Step 8

To an ice cooled solution of (2R,3S,4S,5R)-3-(3,4-difluoro-2-methoxy-phenyl)-4,5-dimethyl-5-(trifluoromethyl) tetrahydrofuran-2-carboxylic acid (63 mg, 0.1672 mmol) in 2-methyltetrahydrofuran (0.6 mL) was added DMF (1.8880 mg, 2 µL, 0.0258 mmol) followed by carefully addition of oxalyl chloride (37.830 mg, 26 µL, 0.2980 mmol). The reaction mixture was warmed up to room temperature and stirred for 1 hr. The reaction mixture was concentrated in vacuo and the residue dissolved in 2-methyltetrahydrofuran (0.6 mL). To this was added methyl 6-aminopyridine-2-carboxylate (25 mg, 0.1643 mmol) and triethylamine (34.122 mg, 47 L, 0.3372 mmol). The resulting mixture was stirred at room temperature for 1 hour. The reaction mixture was quenched with water (5 mL) and partitioned with ethyl acetate (10 mL). The layers were separated and the organic phase was washed with brine (5 mL), dried (sodium sulfate), filtered and concentrated under reduced pressure. Purification by flash chromatography (Biotage Isolera, 12 g SiliaSep 25 µm Silicycle flash cartridge, 0 to 100% ethyl acetate in heptane) gave methyl 6-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxylate (72 mg, 83%) as a pale yellow glassy oil. $^1$H NMR (400 MHz, Chloroform-d) δ 9.04 (s, 1H), 8.37 (dd, J=8.2, 1.1 Hz, 1H), 7.87 (dd, J=7.6, 0.9 Hz, 1H), 7.84-7.75 (m, 1H), 7.09-7.04 (m, 1H), 6.88 (td, J=9.2, 7.5 Hz, 1H), 5.00 (d, J=11.0 Hz, 1H), 4.12-4.06 (m, 1H), 3.99 (d, J=3.4 Hz, 3H), 3.97 (d, J=3.0 Hz, 3H), 2.76-2.68 (m, 1H), 1.69 (s, 3H), 0.82-0.69 (m, 3H) ppm. ESI-MS m/z calc. 488.1371, found 489.14 $(M+1)^+$.

Step 9

A solution of methyl 6-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxylate (72 mg, 0.1388 mmol) in ammonia (7 M in methanol) (1 mL of 7 M, 7.0000 mmol) was stirred at room temperature overnight and then concentrated in vacuo to give a colourless oil. Purification by flash chromatography (Biotage Isolera, 12 g SiliaSepC18 Monomeric 25 µm Silicycle flash cartridge, 30 to 90% acetonitrile containing 0.1% ammonium hydroxide in water containing 0.1% ammonium hydroxide). Fractions containing product were freeze dried to give 6-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide (114, 24.5 mg, 36%) as a white solid. $^1$H NMR (400 MHz, Chloroform-d) δ 8.85 (s, 1H), 8.31 (dd, J=8.2, 0.7 Hz, 1H), 7.97 (dd, J=7.6, 0.7 Hz, 1H), 7.84 (t, J=7.9 Hz, 1H), 7.59 (s, 1H), 7.12-7.08 (m, 1H), 6.90 (td, J=9.2, 7.5 Hz, 1H), 5.62 (s, 1H), 5.03 (d, J=11.0 Hz, 1H), 4.11 (dd, J=10.9, 8.1 Hz, 1H), 3.99 (d, J=2.7 Hz, 3H), 2.79-2.70 (m, 1H), 1.71 (s, 3H), 0.81-0.78 (m, 3H) ppm. ESI-MS m/z calc. 473.1374, found 474.15 $(M+1)^+$.

The following compounds were made using the method described in Example 23, except that different coupling partners were used in the amide coupling step 8:

| Cmpd No. | Compound Name | LC/MS | NMR (shifts in ppm) |
|---|---|---|---|
| 117 | 6-[[(2R,3S,4S,5R)-3-(3,4-difluoro-2-methoxy-phenyl)- | ESI-MS m/z calc. 474.1326, found 475.48 | $^1$H NMR (400 MHz, Chloroform-d) δ 9.64 (s, |

| Cmpd No. | Compound Name | LC/MS | NMR (shifts in ppm) |
| --- | --- | --- | --- |
| | 4,5-dimethyl-5-(trifluoromethyl)tetrahydrofuran-2-carbonyl]amino]pyrazine-2-carboxamide | (M + 1)⁺; Retention time: 2.4 minutes | 1H), 9.17 (d, J = 0.5 Hz, 1H), 8.85 (s, 1H), 7.39 (s, 1H), 7.10-7.04 (m, 1H), 6.92 (td, J = 9.2, 7.4 Hz, 1H), 5.70 (s, 1H), 5.07 (d, J = 11.0 Hz, 1H), 4.13 (dd, J = 11.0, 8.2 Hz, 1H), 4.01 (d, J = 3.0 Hz, 3H), 2.81-2.73 (m, 1H), 1.71 (s, 3H), 0.81-0.78 (m, 3H) ppm. |
| 118 | 5-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-3-carboxamide | ESI-MS m/z calc. 473.1374, found 474.46 (M + 1)⁺; Retention time: 2.24 minutes | ¹H NMR (400 MHz, Chloroform-d) δ 8.88 (d, J = 2.3 Hz, 1H), 8.80 (d, J = 1.8 Hz, 1H), 8.60 (s, 1H), 8.49 (t, J = 2.2 Hz, 1H), 7.10-7.06 (m, 1H), 6.90 (td, J = 9.2, 7.5 Hz, 1H), 6.32 (br. s, 1H), 5.88 (br. s, 1H), 5.04 (d, J = 11.0 Hz, 1H), 4.11 (dd, J = 11.1, 8.1 Hz, 1H), 4.01 (d, J = 3.0 Hz, 3H), 2.80-2.70 (m, 1H), 1.69 (s, 3H), 0.80-0.74 (m, 3H) ppm. |
| 119 | 4-[[(2R,3S,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide | ESI-MS m/z calc. 487.153, found 488.13 (M + 1)⁺; Retention time: 2.54 minutes | ¹H NMR (400 MHz, Chloroform-d) δ 8.89 (s, 1H), 8.58 (s, 1H), 8.32 (s, 1H), 7.71 (s, 1H), 7.12-7.08 (m, 1H), 6.90 (td, J = 9.2, 7.5 Hz, 1H), 5.54 (s, 1H), 5.05 (d, J = 11.0 Hz, 1H), 4.08 (dd, J = 11.0, 7.8 Hz, 1H), 4.00 (d, J = 3.0 Hz, 3H), 2.80-2.72 (m, 1H), 2.32 (s, 3H), 1.68 (d, J = 0.7 Hz, 3H), 0.78 (td, J = 4.9, 2.4 Hz, 3H) ppm. |
| 120 | 2-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-4-carboxamide | ESI-MS m/z calc. 473.1374, found 474.1 (M + 1)⁺; Retention time: 2.37 minutes | 1H NMR (400 MHz, Chloroform-d) δ 9.05 (s, 1H), 8.45 (d, J = 5.0 Hz, 1H), 8.42 (s, 1H), 7.55 (dd, J = 5.0, 1.6 Hz, 1H), 7.12-7.08 (m, 1H), 6.94-6.87 (m, 1H), 6.24 (s, 1H), 5.68 (s, 1H), 5.03 (d, J = 11.2 Hz, 1H), 4.10 (dd, J = 11.0, 8.2 Hz, 1H), 3.99 (d, J = 3.0 Hz, 3H), 2.78-2.70 (m, 1H), 1.69 (s, 3H), 0.80-0.77 (m, 3H) ppm. |
| 121 | 6-[[(2R,3S,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide | ESI-MS m/z calc. 474.1326, found 475.17 (M + 1)⁺; Retention time: 2.3 minutes | ¹HNMR (400 MHz, Chloroform-d) δ 9.22 (br s, 1H), 8.67 (d, J = 5.5 Hz, 1H), 8.27 (d, J = 5.5 Hz, 1H), 7.81 (br s, 1H), 7.07-7.03 (m, 1H), 6.90 (dd, J = 16.9, 8.7 Hz, 1H), 5.85 (br s, 1H), 5.02 (d, J = 11.0 Hz, 1H), 4.07 (dd, J = 11.0, 8.7 Hz, 1H), 3.99 (d, J = 1.8 Hz, 3H), 2.77-2.69 (m, 1H), 1.69 (s, 3H), 0.78 (d, J = 6.4 Hz, 3H) ppm. |

The following compound was made using a method similar to that described in Example 23, except that ethyl 4-amino-5-fluoropyridine-2 carboxylate was used as coupling partner in the amide formation step 8 in place of methyl 6-aminopyridine-2-carboxylate and in step 9, the product was further purified by MDAP (XBridge C18, 19×150 mm, 5 μm) using acetonitrile and water containing 0.1% ammonium hydroxide (30-80% over 10 minutes) before freeze drying:

| Cmpd No. | Compound Name | LC/MS | NMR (shifts in ppm) |
|---|---|---|---|
| 122 | 4-[[(2R,3S,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide | ESI-MS m/z calc. 491.128, found 492.1 (M + 1)+; Retention time: 2.57 minutes | $^1$H NMR (400 MHz, Chloroform-d) δ 9.10 (d, J = 6.4 Hz, 1H), 8.85 (s, 1H), 8.37 (d, J = 1.8 Hz, 1H), 7.61 (s, 1H), 7.10-7.06 (m, 1H), 6.94-6.87 (m, 1H), 5.48 (s, 1H), 5.05 (d, J = 11.0 Hz, 1H), 4.08 (dd, J = 10.8, 8.0 Hz, 1H), 4.00 (d, J = 3.0 Hz, 3H), 2.76 (t, J = 7.8 Hz, 1H), 1.68 (s, 3H), 0.80-0.77 (m, 3H) ppm. |

The following compound was made using a method similar to that described in Example 23, except step 9 was omitted and 5-amino-2-fluorobenzamide was used as a coupling partner in step 8:

| Cmpd No. | Compound Name | LC/MS | NMR (shifts in ppm) |
|---|---|---|---|
| 123 | (2R,3S,4S,5R)-N-(3-carbamoyl-4-fluoro-phenyl)-3-(3,4-difluoro-2-methoxy-phenyl)-4,5-dimethyl-5-(trifluoromethyl)tetrahydrofuran-2-carboxamide | ESI-MS m/z calc. 490.1327, found 491.43 (M + 1)+; Retention time: 2.5 minutes | $^1$H NMR (400 MHz, Chloroform-d) δ 8.55 (s, 1H), 8.16 (qd, J = 4.5, 3.0 Hz, 1H), 7.89 (q, J = 3.2 Hz, 1H), 7.12-7.04 (m, 2H), 6.88 (td, J = 9.2, 7.6 Hz, 1H), 6.77-6.69 (m, 1H), 5.92 (s, 1H), 5.00 (d, J = 11.0 Hz, 1H), 4.07 (dd, J = 10.9, 8.1 Hz, 1H), 3.99 (d, J = 2.7 Hz, 3H), 2.77-2.70 (m, 1H), 1.68 (s, 3H), 0.79-0.76 (m, 3H) ppm. |

The following compound was made using a method similar to that described in Example 23, except that methyl 5-deuterio-4-aminopyridine-2-carboxylate was used in place of methyl 6-aminopyridine-2-carboxylate in Step 8. Purification was performed by normal phase chromatography (Biotage Isolera, 12 g, SiliaSep 25 μm Silicycle flash cartridge) using heptane-ethyl acetate (0 to 100%).

| Cmpd No. | Compound Name | LC/MS | NMR (shifts in ppm) |
|---|---|---|---|
| 124 | 5-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 474.1437, found 475.15 (M + 1)+; Retention time: 2.51 minutes | $^1$H NMR (400 MHz, Chloroform-d) δ 8.73 (br s, 1H), 8.45 (s, 1H), 7.95 (s, 1H), 7.88 (br s, 1H), 7.10-7.06 (m, 1H), 6.93-6.87 (m, 1H), 5.63 (br s, 1H), 5.02 (d, J = 11.0 Hz, 1H), 4.08 (dd, J = 11.0, 8.2 Hz, 1H), 3.99 (d, J = 2.7 Hz, 3H), 2.79-2.71 (m, 1H), 1.68 (s, 3H), 0.80-0.77 (m, 3H) ppm. |

Example 24

4-[[(2R,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide (126)

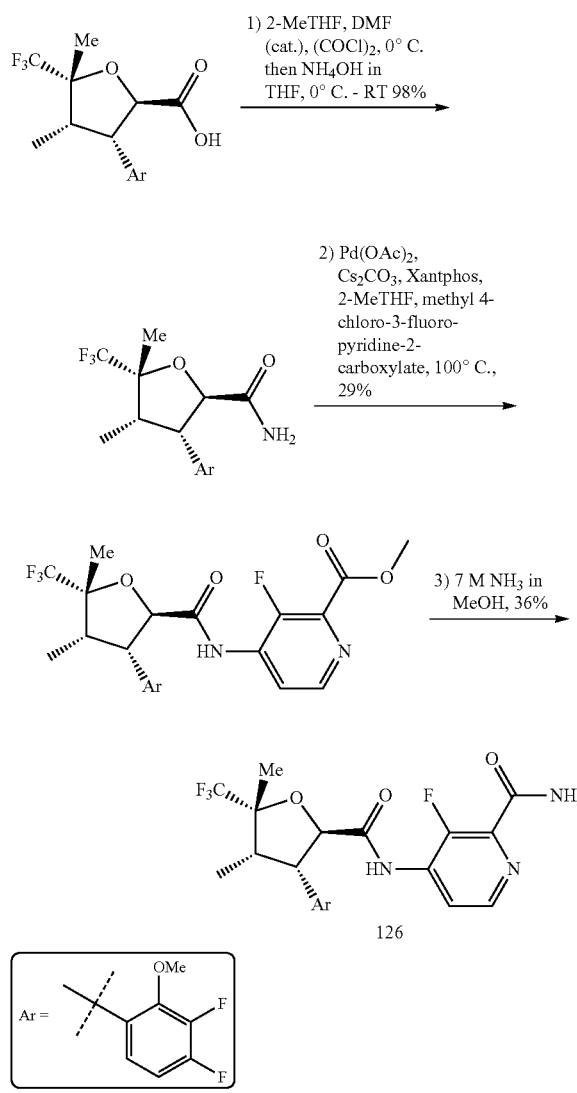

Step 1

To an ice cooled solution of (2R,3S,4S,5R)-3-(3,4-difluoro-2-methoxy-phenyl)-4,5-dimethyl-5-(trifluoromethyl)tetrahydrofuran-2-carboxylic acid (99 mg, 0.2571 mmol) (see Example 23, step 7) in 2-methyltetrahydrofuran (1 mL) was added DMF (1.8880 mg, 2 µL, 0.0258 mmol) followed by careful addition of oxalyl chloride (58.200 mg, 40 µL, 0.4585 mmol). The reaction mixture warmed to room temperature and stirred for 1 hr. The reaction mixture was concentrated in vacuo and the residue dissolved in 2-methyltetrahydrofuran (0.4 mL). To this, was added ammonium hydroxide (28% w/w) (360.00 mg, 0.4 mL of 28% w/v, 10.272 mmol). The resulting mixture was stirred at room temperature for 1.5 hr. The reaction mixture was quenched with water (10 mL) and partitioned with ethyl acetate (15 mL). The layers were separated and the organic phase was washed with brine (10 mL), dried (sodium sulfate), filtered and concentrated under reduced pressure to give (2R,3S,4S,5R)-3-(3,4-difluoro-2-methoxy-phenyl)-4,5-dimethyl-5-(trifluoromethyl)tetrahydrofuran-2-carboxamide (105 mg, 98%) as a pale yellow oil. $^1$H NMR (400 MHz, DMSO-$d_6$) δ 7.51 (s, 1H), 7.35-7.31 (m, 1H), 7.16-7.12 (m, 2H), 4.82 (d, J=10.8 Hz, 1H), 4.06-4.00 (m, 1H), 3.93 (d, J=2.3 Hz, 3H), 2.69-2.62 (m, 1H), 1.55 (s, 3H), 0.67 (dd, J=7.3, 2.1 Hz, 3H) ppm.

Step 2

(2R,3S,4S,5R)-3-(3,4-difluoro-2-methoxy-phenyl)-4,5-dimethyl-5-(trifluoromethyl)tetrahydrofuran-2-carboxamide (100 mg, 0.2354 mmol), methyl 4-chloro-3-fluoro-pyridine-2-carboxylate (144 mg, 0.2583 mmol), Pd(OAc)$_2$ (11 mg, 0.0490 mmol), cesium carbonate (153 mg, 0.4696 mmol) and Xantphos (55 mg, 0.0951 mmol) were suspended in 2-MeTHF (2 mL) and heated to 100° C. for 16 hrs. The reaction was diluted with ethyl acetate (5 mL) and washed with water (5 mL), followed by brine (5 mL). The organic layer was dried (sodium sulfate), filtered and concentrated in vacuo. Purification by flash chromatography (Biotage Isolera, 12 g SiliaSep 25 µm Silicycle flash cartridge, loaded from DCM, 0 to 100% ethyl acetate in heptane) to give methyl 4-[[(2R,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxylate (42 mg, 29%) as a pale yellow oil. ESI-MS m/z calc. 506.1276, found 507.5 (M+1)$^+$.

Step 3

A mixture of methyl 4-[[(2R,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxylate (37 mg, 0.0599 mmol) and ammonia (7 M in methanol) (1 mL of 7 M, 7.0000 mmol) in methanol (0.5 mL) was stirred for 1 h and then concentrated in vacuo. Purification by MDAP (XBridge C18, 19×150 mm, 5 µm) using acetonitrile and water containing 0.1% ammonium hydroxide (30-80% over 10 minutes) to give 4-[[(2R,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide (126, 5.9 mg, 20%) as a white solid. $^1$H NMR (400 MHz, Chloroform-d) δ 9.09 (br s, 1H), 8.46 (t, J=5.3 Hz, 1H), 8.26 (d, J=5.5 Hz, 1H), 7.69 (br s, 1H), 7.11-7.07 (m, 1H), 6.94-6.87 (m, 1H), 5.53 (br s, 1H), 5.04 (d, J=11.0 Hz, 1H), 4.06 (dd, J=11.3, 7.7 Hz, 1H), 4.00 (d, J=2.7 Hz, 3H), 2.79-2.71 (m, 1H), 1.68 (s, 3H), 0.80-0.78 (m, 3H) ppm. ESI-MS m/z calc. 491.128, found 492.13 (M+1)$^+$.

The following compounds were made using a method similar to that described in Example 24, except that different coupling partners were used in the amide coupling step 2 and, for compounds 128 and 127, the purification in step 3 was conducted by reverse phase chromatography (Biotage Isolera, 12 g, SiliaSepC18 Monomeric 25 µm Silicycle flash cartridge) using a gradient of acetonitrile containing 0.1% ammonium hydroxide and water containing 0.1% ammonium hydroxide before freeze drying:

| Cmpd No. | Compound Name | LC/MS | NMR (shifts in ppm) |
| --- | --- | --- | --- |
| 128 | 4-[[(2R,3S,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide | ESI-MS m/z calc. 487.153, found 488.12 (M + 1)$^+$; Retention time: 2.58 minutes | $^1$H NMR (400 MHz, Chloroform-d) δ 8.75 (s, 1H), 8.08 (d, J = 2.1 Hz, 1H), 7.90 (d, J = 2.7 Hz, 1H), 7.78 (d, J = 1.8 Hz, 1H), 7.11-7.07 (m, 1H), 6.90 (td, J = 9.2, 7.5 Hz, 1H), 5.68 (d, J = 3.9 Hz, 1H), 5.02 (d, J = 11.0 Hz, 1H), 4.08 (dd, J = 11.2, 8.0 Hz, 1H), 4.00 (d, J = 2.7 Hz, 3H), 2.79-2.71 (m, 1H), 2.50 (d, J = 4.4 Hz, 3H), 1.69 (s, 3H), 0.80-0.78 (m, 3H) ppm. |
| 127 | 4-[[(2R,3S,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide | ESI-MS m/z calc. 491.128, found 492.41 (M + 1)$^+$; Retention time: 2.66 minutes | $^1$H NMR (400 MHz, Chloroform-d) δ 8.77 (br s, 1H), 7.91 (d, J = 1.8 Hz, 1H), 7.76 (s, 1H), 7.51 (br s, 1H), 7.08-7.04 (m, 1H), 6.94-6.87 (m, 1H), 5.56 (br s, 1H), 5.02 (d, J = 11.0 Hz, 1H), 4.06 (dd, J = 11.2, 8.0 Hz, 1H), 4.00 (d, J = 2.7 Hz, 3H), 2.79-2.71 (m, 1H), 1.68 (s, 3H), 0.80-0.77 (m, 3H) ppm. |
| 128 | 4-[[(2R,3S,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide | ESI-MS m/z calc. 487.153, found 488.17 (M + 1)$^+$; Retention time: 2.42 minutes | $^1$H NMR (400 MHz, Chloroform-d) δ 8.88 (br s, 1H), 8.37 (d, J = 5.5 Hz, 1H), 8.32 (d, J = 5.5 Hz, 1H), 7.93 (br s, 1H), 7.12-7.08 (m, 1H), 6.91 (dd, J = 16.7, 8.9 Hz, 1H), 5.54 (br s, 1H), 5.06 (d, J = 11.0 Hz, 1H), 4.08 (dd, J = 11.0, 7.8 Hz, 1H), 4.00 (d, J = 2.7 Hz, 3H), 2.80-2.75 (m, 1H), 2.71 (s, 3H), 1.69 (s, 3H), 0.80 (dd, J = 7.3, 1.8 Hz, 3H) ppm. |
| 129 | 3-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 474.1437, found 475.21 (M + 1)$^+$; Retention time: 2.48 minutes | $^1$H NMR (400 MHz, Chloroform-d) δ 8.77 (s, 1H), 8.44 (dd, J = 10.8, 4.8 Hz, 1H), 8.18-8.12 (m, 1H), 7.86 (s, 1H), 7.10-7.06 (m, 1H), 6.90 (td, J = 9.2, 7.3 Hz, 1H), 5.66 (s, 1H), 5.02 (d, J = 11.0 Hz, 1H), 4.08 (dd, J = 11.0, 8.2 Hz, 1H), 3.99 (d, J = 2.7 Hz, 3H), 2.79-2.70 (m, 1H), 1.68 (s, 3H), 0.80-0.77 (m, 3H) ppm. |
| 130 | 6-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide | ESI-MS m/z calc. 474.1437, found 475.19 (M + 1)$^+$; Retention time: 2.5 minutes | $^1$H NMR (400 MHz, Chloroform-d) δ 8.67 (br s, 1H), 8.15 (d, J = 2.3 Hz, 1H), 7.93 (d, J = 2.3 Hz, 1H), 7.84 (br s, 1H), 7.10-7.06 (m, 1H), 6.90 (td, J = 9.2, 7.3 Hz, 1H), 5.59 (br s, 1H), 5.01 (d, J = 11.0 Hz, 1H), 4.07 (dd, J = 11.2, 8.0 Hz, 1H), 3.99 (d, J = 2.7 Hz, 3H), 2.78-2.71 (m, 1H), 1.68 (s, 3H), 0.80-0.77 (m, 3H) ppm. |

Example 25 rel-(2S,3R,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide (131), rel-(2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide (132), rel-(2R,3S,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide (133) and rel-(2S,3R,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide (134)

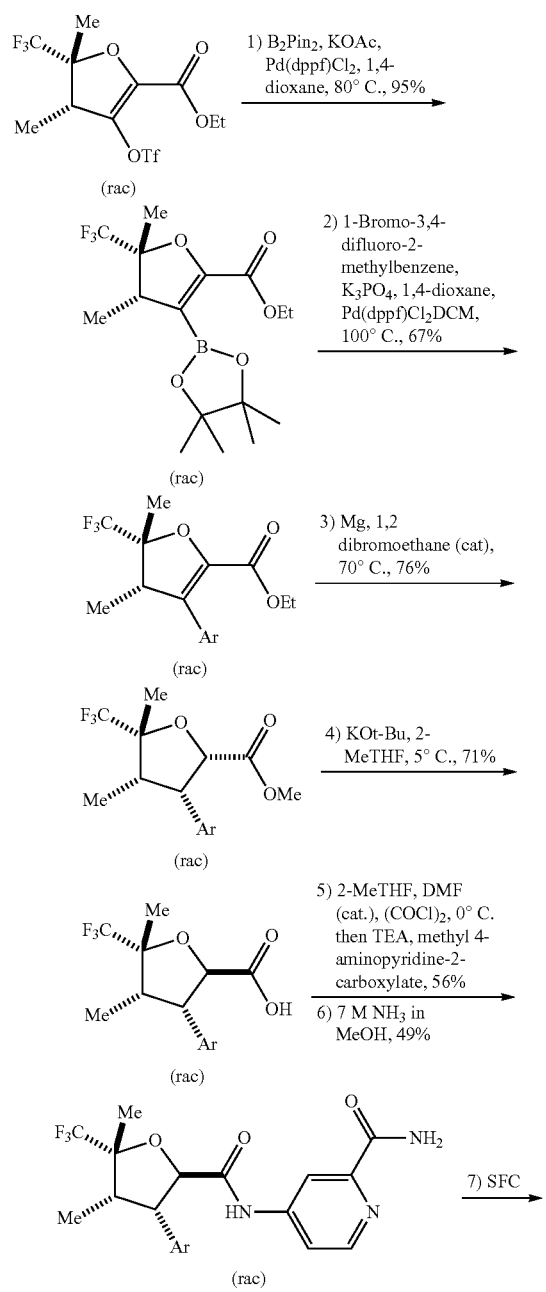

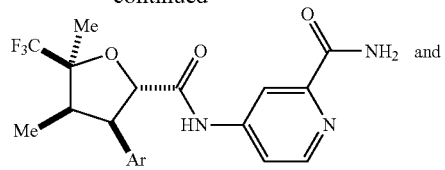

131, first eluting isomer

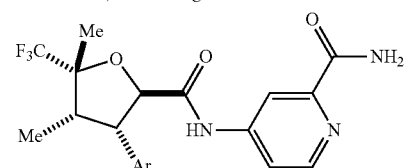

132, second eluting isomer

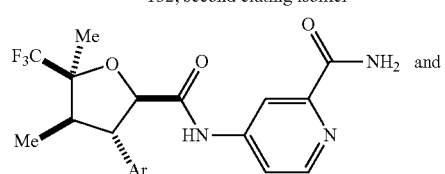

133, third eluting isomer

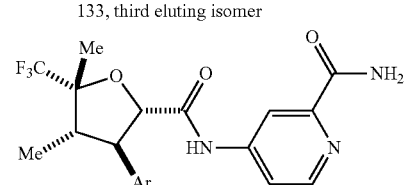

134, fourth eluting isomer

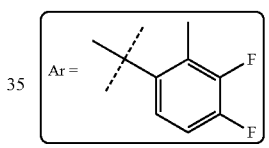

Step 1

To a 3 neck 1 litre flask hooked up with a thermometer and air condenser is added ethyl rac-(4R,5R)-4,5-dimethyl-5-(trifluoromethyl)-3-(((trifluoromethyl)sulfonyl)oxy)-4,5-dihydrofuran-2-carboxylate (42 g, 108.7 mmol) and 1,4-dioxane (500 mL). The mixture was stirred and degassed and flushed with nitrogen. KOAc (32 g, 326.1 mmol) was added followed by bis(pinacolato)diboron (32 g, 126.0 mmol). The reaction mixture was evacuated and back filled with nitrogen (×3). Pd(dppf)Cl$_2$ (4 g, 5.467 mmol) was added to this reaction mixture which was heated to 60° C. first then when stable, the temperature was increased to 80° C. (to avoid exotherm). The reaction was allowed to proceed with stirring at 80° C. under nitrogen for 20 hours. The reaction mixture was then cooled to ambient temperature and diluted with ethyl acetate (300 mL) and water (100 mL). The mixture was filtered through a pad of celite, washing several times with ethyl acetate until no more product came off (5×100 ml). The filtrate is then separated, and the aqueous layer was extracted with ethyl acetate twice (100 mL). The combined organic layers were dried and filtered using Whatman 1PS hydrophobic phase separator filter paper. The filtrates were concentrated in vacuo to give 47 g of a brown oil. The crude product (47 g) was absorbed onto diatomaceous earth (Telos nm) and passed through a Florisil (magnesium silicate) pad, washing with 100% heptane until no more product came off (4 fractions in total). The filtrates were combined and concentrated in vacuo to give ethyl rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (47 g, 95%) as a thick viscous yellow oil. $^1$H NMR (500 MHz, Chloroform-d) δ 4.33-4.23 (m, 2H), 3.27-3.18 (m, 1H), 1.55 (d, J=1.1 Hz, 3H), 1.32 (s, 12H), 1.28 (d, J=2.3 Hz, 2H), 1.24 (s, 3H) ppm. ESI-MS m/z calc. 364.1669, found 365.3 (M+1)$^+$.

Step 2

To a solution of rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (3 g, 7.414 mmol), 1-bromo-3,4-difluoro-2-methyl-benzene (1.4 g, 6.763 mmol) and Pd(dppf)Cl$_2$.CH$_2$Cl$_2$ (350 mg, 0.4286 mmol) in 1,4-dioxane (60 mL), was added an aqueous solution of K$_3$PO$_4$ (8 mL of 2 M, 16.00 mmol). The mixture was degassed and placed under a nitrogen atmosphere. The reaction was stirred at 100° C. for 2 hours. The mixture was partitioned between water and ethyl acetate. The aqueous layer was extracted 3 times with ethyl acetate. The organics were combined, dried and filtered using Whatman 1PS hydrophobic phase separator filter paper. The filtrates were concentrated in vacuo to give a brown oil. Purification by flash chromatography (RF combiflash companion, 24 g pre-packed gold silica column, 0 to 100% EtOAc in heptane gave ethyl rac-(4S,5R)-3-(3,4-difluoro-2-methylphenyl)-4,5-dimethyl-5-(trifluoromethyl)-4,5-dihydrofuran-2-carboxylate (2.21 g, 67%) as a pale yellow oil. $^1$H NMR (500 MHz, Methanol-d$_4$) δ 7.10 (dt, J=10.3, 8.4 Hz, 1H), 6.90 (s, 1H), 4.14-4.00 (m, 2H), 3.54 (d, J=8.2 Hz, 1H), 2.19 (d, J=2.7 Hz, 3H), 1.70 (d, J=1.2 Hz, 3H), 1.09 (dq, J=7.5, 2.4 Hz, 3H), 1.05 (t, J=7.1 Hz, 3H) ppm. ESI-MS m/z calc. 364.10977, found 365.2 (M+1)$^+$.

Step 3

A pressure tube was loaded with magnesium powder (200 mg, 8.229 mmol) and purged with nitrogen. To the reaction vessel was added a solution of ethyl rac-(4S,5R)-3-(3,4-difluoro-2-methylphenyl)-4,5-dimethyl-5-(trifluoromethyl)-4,5-dihydrofuran-2-carboxylate (2.02 g, 5.545 mmol) in MeOH (30 mL). The mixture was degassed and placed under a nitrogen atmosphere. A few drops of 1,2-dibromoethane (5 μL, 0.05802 mmol) were added. The reaction mixture was stirred vigorously and heated at 70° C. for 6 hrs.
A further 3 consecutive portions of magnesium powder (200 mg, 8.229 mmol) were added followed by a drop of 1,2-dibromoethane (5 μL, 0.05802 mmol). The mixture was stirred overnight at 70° C. for 88 hours. The reaction mixture was cooled to 0° C. prior to opening the pressure vessel. The cooled mixture is added dropwise to a cooled beaker containing 1 M HCl. The reaction was stirred at 0° C. for 30 minutes until all Mg solids dissolved. The mixture was concentrated in vacuo to remove the MeOH. The remaining aqueous solution was extracted with ethyl acetate (×3). The combined organic extracts were dried and filtered using a Whatman 1PS hydrophobic phase separator filter paper. The filtrates were concentrated in vacuo to give methyl rac-(2S,3S,4S,5R)-3-(3,4-difluoro-2-methylphenyl)-4,5-dimethyl-5-(trifluoromethyl)tetrahydrofuran-2-carboxylate (1.487 g, 76%) as the major diastereomer as a colourless oil. ESI-MS m/z calc. 352.10977, found 353.0 (M+1)$^+$.

Step 4

To a cooled solution of methyl rac-(2S,3S,4S,5R)-3-(3,4-difluoro-2-methylphenyl)-4,5-dimethyl-5-(trifluoromethyl) tetrahydrofuran-2-carboxylate (1.487 g, 4.221 mmol) in 2-Me-THF (20 mL) was added potassium tert-butoxide (1.4 g, 12.48 mmol) (internal temperature increased to −5° C.) and the reaction was stirred for 1 hour at ambient temperature. The reaction mixture colour turned yellow on addition of potassium t-butoxide. The reaction was diluted with ethyl acetate and 1 N NaOH. The aqueous layer was separated. The organics were washed further with 1M NaOH (×2). The combined organic layers were dried and filtered using a Whatman 1PS hydrophobic phase separator filter paper. The filtrates were concentrated in vacuo to give rac-(2R,3S,4S,5R)-3-(3,4-difluoro-2-methylphenyl)-4,5-dimethyl-5-(trifluoromethyl)tetrahydrofuran-2-carboxylic acid (1.01 g, 71%) as the major diastereomer as a colourless oil. ESI-MS m/z calc. 338.09415, found 337.0 (M−1)$^-$.

Step 5

To a solution of rac-(2R,3S,4S,5R)-3-(3,4-difluoro-2-methylphenyl)-4,5-dimethyl-5-(trifluoromethyl)tetrahydrofuran-2-carboxylic acid (200 mg, 0.591 mmol) and DMF (2 μL, 0.026 mmol) in 2-methyl-tetrahydrofuran (4.8 mL) stirring at 0° C. under nitrogen was added oxalyl chloride (154.2 mg, 106.0 μL, 1.215 mmol). The mixture was warmed up to room temperature over 30 minutes. The reaction mixture was concentrated in vacuo and the residue dissolved in 2-methyl-tetrahydrofuran (4.8 mL). This solution was added to an ice cooled solution of methyl 4-aminopyridine-2-carboxylate (110.7 mg, 0.728 mmol) and TEA (278.6 mg, 383.7 μL, 2.753 mmol) in 2-methyl-tetrahydrofuran (4.8 mL). The resulting mixture was stirred and warmed to ambient temperature over 18 hrs. The reaction mixture was quenched with water (5 mL) and the layers separated. The aqueous layer was extracted with EtOAc (2×10 mL). The combined organics extracts were dried and filtered using a Whatman 1PS hydrophobic phase separator filter paper. The filtrates were concentrated in vacuo to give an oil. Purification by flash chromatography (RF combiflash companion, 4 g pre-packed silica column, 0-50% EtOAc:EtOH (3:1) containing 2% NH$_4$OH in heptane) gave methyl rac-(2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxylate (235 mg, 59%) as the major diastereomer. ESI-MS m/z calc. 472.14215, found 473.3 (M+1)$^+$; 471.3 (M−1)$^-$.

Step 6

Methyl rac-(2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxylate (235 mg, 0.4975 mmol) was taken up in a solution of ammonia (1 mL of 7 M, 7.000 mmol) in methanol (10 mL) and stirred at room temperature for 2 hours. The reaction mixture was concentrated in vacuo to give rac-(2R,3S,4S,5R)-4-[[3-(3,4-difluoro-2-methyl-phenyl)-4,5-dimethyl-5-(trifluoromethyl) tetrahydrofuran-2-carbonyl]amino]pyridine-2-carboxamide (221.4 mg, 49%) as the major diastereomer as a yellow oil. ESI-MS m/z calc. 457.1425, found 458.4 (M+1)$^+$; 456.4 (M−1)$^-$.

Step 7 rac-(2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide (221.4 mg, 49%) was purified by chiral SFC using a Chiralpak IG column, 5 um particle size, 25 cm×10 mm from Daicel on a Minigram SFC instrument from Berger Instruments followed by reversed phase HPLC-MS using a X-bridge C18 OBD column (150× 19 mm, 5 mm particle size) from Waters (using gradient elution over 16.0 minutes; mobile phase A=H$_2$O (0.1% ammonium hydroxide), mobile phase B=CH$_3$CN. Flow rate=19 mL/min; injection volume=<2000 μL, column temperature=25° C.) to give:

First Eluting Isomer (rt=3.93 min): rel-(2S,3R,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide (131, 4.1 mg, 14%). $^1$H NMR (500 MHz, DMSO-d$_6$) δ 10.71 (s, 1H), 8.47 (d, J=5.5 Hz, 1H), 8.26 (s, 1H), 8.04 (s, 1H), 7.81 (d, J=5.5 Hz, 1H), 7.59 (s, 1H), 7.26 (q, J=9.0 Hz, 1H), 7.18 (dd, J=9.0, 4.3 Hz, 1H), 5.16 (d, J=10.4 Hz, 1H), 4.19 (dd, J=10.5, 7.5 Hz, 1H), 2.85 (p, J=7.5 Hz, 1H), 2.28 (d, J=2.1 Hz, 3H), 1.64 (s, 3H), 0.71-0.66 (m, 3H) ppm. ESI-MS m/z calc. 457.1425, found 458.2 (M+1)$^+$; 456.2 (M−1)$^-$.

Second Eluting Isomer (rt=4.33 min): rel-(2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide (132, 3.6 mg, 13%). $^1$H NMR (500 MHz, DMSO-d$_6$) δ 10.69 (s, 1H), 8.48 (d, J=5.5 Hz, 1H), 8.27 (d, J=2.2 Hz, 1H), 8.04 (s, 1H), 7.82 (dd, J=5.5, 2.2 Hz, 1H), 7.59 (s, 1H), 7.26 (q, J=9.0 Hz, 1H), 7.17 (dd, J=8.9, 4.3 Hz, 1H), 5.16 (d, J=10.5 Hz, 1H), 4.19 (dd, J=10.4, 7.6 Hz, 1H), 2.85 (p, J=7.5 Hz, 1H), 2.27 (d, J=2.2 Hz, 3H), 1.63 (s, 3H), 0.73-0.62 (m, 3H) ppm. ESI-MS m/z calc. 457.1425, found 458.2 (M+1)$^+$; 456.2 (M−1)$^-$.

Third Eluting Isomer (rt=5.05 min): rel-(2R,3S,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide (133, 2.4 mg, 8%). ESI-MS m/z calc. 457.1425, found 458.2 (M+1)$^+$; 456.2 (M−1)$^-$.

Fourth Eluting Isomer (rt=6.87 min): rel-(2S,3R,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide (134, 2.2 mg, 8%). ESI-MS m/z calc. 457.1425, found 458.2 (M+1)$^+$; 456.2 (M−1)$^-$.

The following compounds were made using the method described in Example 25, except that the conditions used for the Suzuki coupling step 2 were similar to the ones used in Example 11 step 3 starting with 1-bromo-4-(difluoromethyl)-3-fluoro-2-methoxy-benzene. The reduction step 3 was conducted with Pd(OH)$_2$ using an atmospheric pressure of hydrogen in conditions similar to those described in Example 11 step 4. In step 7, purification was performed by chiral SFC using a Chiralart Amylose-SA column, 5 μm particle size, 25 cm×20 mm from YMC Co., Ltd on a Minigram SFC instrument from Berger Instruments:

| Cmpd No. | Compound Name | LC/MS | NMR (shifts in ppm) |
|---|---|---|---|
| 135 | rel-(2S,3R,4R,5S)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide (first eluting isomer by SFC on Chiralart Amylose-SA column, rt = 3.36 min) | ESI-MS m/z calc. 505.14362. found 506.3 (M + 1)$^+$; 504.3 (M − 1)$^-$; Retention time: 3.28 minutes | |
| 136 | rel-(2R,3S,4S,5R)-4-[[3-[4-(difluoromethyl)-3-fluoro-2-methoxy-phenyl]-4,5-dimethyl-5-(trifluoromethyl)tetrahydrofuran-2-carbonyl]amino]pyridine-2-carboxamide (second eluting isomer by SFC on Chiralart Amylose-SA column, rt = 4.40 min) | ESI-MS m/z calc. 505.14362, found 506.3 (M + 1)$^+$; 504.3 (M − 1)$^-$; Retention time: 3.28 minutes | |

Example 26 rel-(2S,3R,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide (137) and rel-(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide (138)

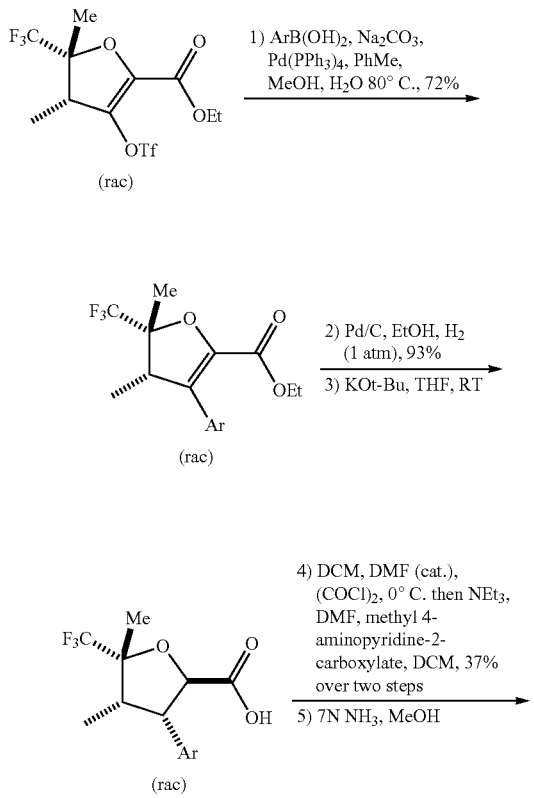

-continued

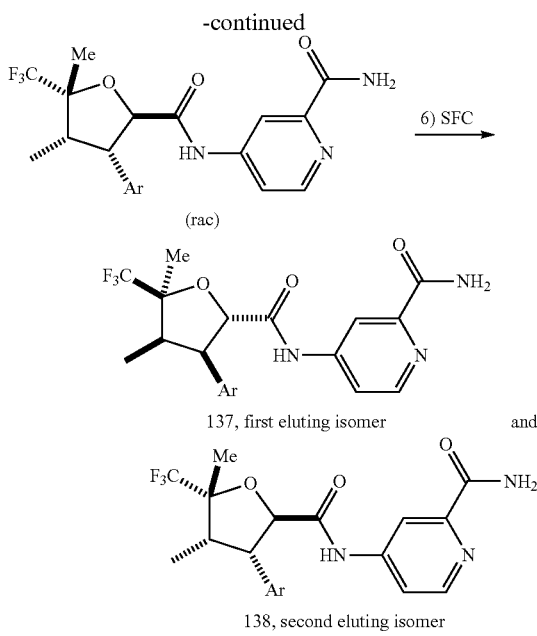

(rac)

137, first eluting isomer and 138, second eluting isomer

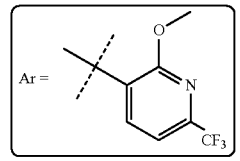

Step 1

A mixture of ethyl rac-(4R,5R)-4,5-dimethyl-5-(trifluoromethyl)-3-(((trifluoromethyl)sulfonyl)oxy)-4,5-dihydrofuran-2-carboxylate (3.48 g, 9.00 mmol), [2-methoxy-6-(trifluoromethyl)-3-pyridyl]boronic acid (1.977 g, 8.95 mmol), Na$_2$CO$_3$ (1.9 g, 17.93 mmol) and Pd(PPh$_3$)$_4$ (520 mg, 0.45 mmol) in PhMe (50 mL), MeOH (5 mL) and water (5 mL) was degassed before being heated at 80° C. for 16 hours. The mixture was cooled to ambient temperature and diluted with EtOAc. The organic layer was washed with brine, dried (MgSO$_4$), filtered and concentrated in vacuo. Purification by flash chromatography (40 g SiO$_2$, 0 to 30% EtOAc in petrol) gave ethyl rac-(4S,5R)-3-(2-methoxy-6-(trifluoromethyl)pyridin-3-yl)-4,5-dimethyl-5-(trifluoromethyl)-4,5-dihydrofuran-2-carboxylate (2.67 g, 72%) as a colourless oil. ESI-MS m/z calc. 413.10617, found 414.6 (M+1)$^+$.

Step 2

EtOH (50 mL) was added to rac-(4S,5R)-3-(2-methoxy-6-(trifluoromethyl)pyridin-3-yl)-4,5-dimethyl-5-(trifluoromethyl)-4,5-dihydrofuran-2-carboxylate (2.16 g, 5.226 mmol) and Pd/C (wet, Degussa, 5.2 g, 4.89 mmol). The mixture was degassed and stirred under a balloon of hydrogen for 16 hours before being filtered through celite, washing with methanol. The filtrate was concentrated in vacuo. Pd/C (wet, Degussa, 5.2 g, 4.89 mmol) was added to the residue and the mixture resuspended in EtOH (50 mL). The mixture was degassed and stirred under a balloon of hydrogen for 16 hours before being filtered through celite, washing with methanol. The filtrate was concentrated in vacuo to give a mixture of diastereomers including ethyl rac-(2S,3S, 4S,5R)-3-(2-methoxy-6-(trifluoromethyl)pyridin-3-yl)-4,5-dimethyl-5-(trifluoromethyl)tetrahydrofuran-2-carboxylate (2.01 g, 93%) as an off-white solid. ESI-MS m/z calc. 415.12183, found 416.7 (M+1)$^+$.

Step 3

To a solution of ethyl rac-(2S,3S,4S,5R)-3-(2-methoxy-6-(trifluoromethyl)pyridin-3-yl)-4,5-dimethyl-5-(trifluoromethyl)tetrahydrofuran-2-carboxylate obtained from Step 2 (2.01 g, 4.84 mmol) in THF (32 mL) was added potassium tert-butoxide (1.63 g, 14.53 mmol). The reaction was stirred for 3 days, then diluted with EtOAc and quenched with 1 M HCl. The aqueous layer was extracted with EtOAc, and the combined organic layers dried (MgSO$_4$), filtered and concentrated in vacuo to give a mixture of diastereomers including rac-(2R,3S,4S,5R)-3-(2-methoxy-6-(trifluoromethyl)pyridin-3-yl)-4,5-dimethyl-5-(trifluoromethyl)tetrahydrofuran-2-carboxylic acid (2.09 g), which was used without further purification.

Step 4

To a solution of rac-(2R,3S,4S,5R)-3-(2-methoxy-6-(trifluoromethyl)pyridin-3-yl)-4,5-dimethyl-5-(trifluoromethyl)tetrahydrofuran-2-carboxylic acid obtained from Step 3 (500 mg, 1.29 mmol) in DCM (11 mL) stirring at 0° C. was added DMF (10 μL, 0.13 mmol) and oxalyl chloride (340 μL, 3.90 mmol). The reaction mixture was concentrated in vacuo and the residue dissolved in DCM (8 mL) and added dropwise to a solution of methyl 4-aminopyridine-2-carboxylate (300 mg, 1.97 mmol) and Et$_3$N (1000 μL, 7.18 mmol) in DCM (4 mL) stirring at 0° C. DMAP (15 mg, 0.1228 mmol) was added and the reaction stirred at this temperature for 10 mins before being warmed to ambient temperature. After stirring overnight the reaction mixture was diluted in DCM and washed with 1 M HCl solution. The organic layer was dried (MgSO$_4$), filtered and concentrated in vacuo, directly onto silica gel. Purification by flash chromatography (40 g SiO2, 0 to 100% EtOAc in petrol) gave a mixture of diastereomers including methyl rac-(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxylate (252 mg, 37%). ESI-MS m/z calc. 521.13855, found 522.6 (M+1)$^+$; 520.7 (M−1)$^−$.

Step 5

Methyl rac-(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxylate obtained from Step 4 (252 mg, 0.4833 mmol) was dissolved in methanolic ammonia (15 mL of 7 M, 105.0 mmol) and stirred for 16 hours. The reaction mixture was concentrated in vacuo to give a mixture of diastereomers including rac-(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide (250 mg).

Step 6 rac-(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide obtained from Step 5 (250 mg, 0.4937 mmol) was separated by chiral SFC using a (R,R)-Whelk-O1 column, 5 μm particle size, 25 cm×21.2 mm from Regis Technologies to give:

First Eluting Isomers (rt=1.04 min and 1.10 min): a mixture of two stereoisomers of 4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide, which were not purified further.

Second Eluting Isomers (rt=1.28 min and 1.34 min): a mixture of two stereoisomers of 4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide. Further separation steps are listed below.

Third Eluting Isomer (rt=1.52 min): a stereoisomer of 4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide, that was not characterized further.

Fourth Eluting Isomer (rt=1.93 min): re-(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide (138, 26.4 mg, 10%). $^1$H NMR (500 MHz, DMSO-$d_6$) δ 10.64 (s, 1H), 8.49 (d, J=5.5 Hz, 1H), 8.30 (dd, J=2.2, 0.6 Hz, 1H), 8.05 (d, J=2.8 Hz, 1H), 7.98 (d, J=7.7 Hz, 1H), 7.85 (dd, J=5.5, 2.2 Hz, 1H), 7.60 (d, J=2.9 Hz, 1H), 7.53 (d, J=7.6 Hz, 1H), 5.25 (d, J=9.5 Hz, 1H), 4.22 (t, 1H), 3.96 (s, 3H), 2.93 (p, J=7.5 Hz, 1H), 1.63 (s, 3H), 0.76-0.66 (m, 3H) ppm. ESI-MS m/z calc. 506.1389, found 507.6 (M+1)$^+$; 505.7 (M−1)$^-$.

The second eluting peak was further separated by chiral SFC using a Chiralpak AS-H column, 5 μm particle size, 25 cm×10 mm from Daicel on a Minigram SFC instrument from Berger Instruments to give:

First Eluting Isomer (rt=3.01 min): re-(2S,3R,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide (137, 18.4 mg, 7%). ESI-MS m/z calc. 506.1389, found 507.5 (M+1)$^+$; 505.5 (M−1)$^-$.

Second Eluting Isomer (rt=4.09 min): a stereoisomer of 4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide, that was not characterized further.

The following compound was made using the method described above, except that the conditions used for the Suzuki coupling step 1 were similar to the ones used in Example 13 step 4 starting with 4-methoxy-5-(4,4,5,5-tetramethyl-1,3,2-dioxaborolan-2-yl)-2-(trifluoromethyl)pyridine. The reduction step 2 was conducted using 5 atm of hydrogen. The chiral SFC separation step 6 was not carried out and the product was isolated as a pair of enantiomers:

Example 27 rel-(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide (140) and rel-(2S,3R,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide (141)

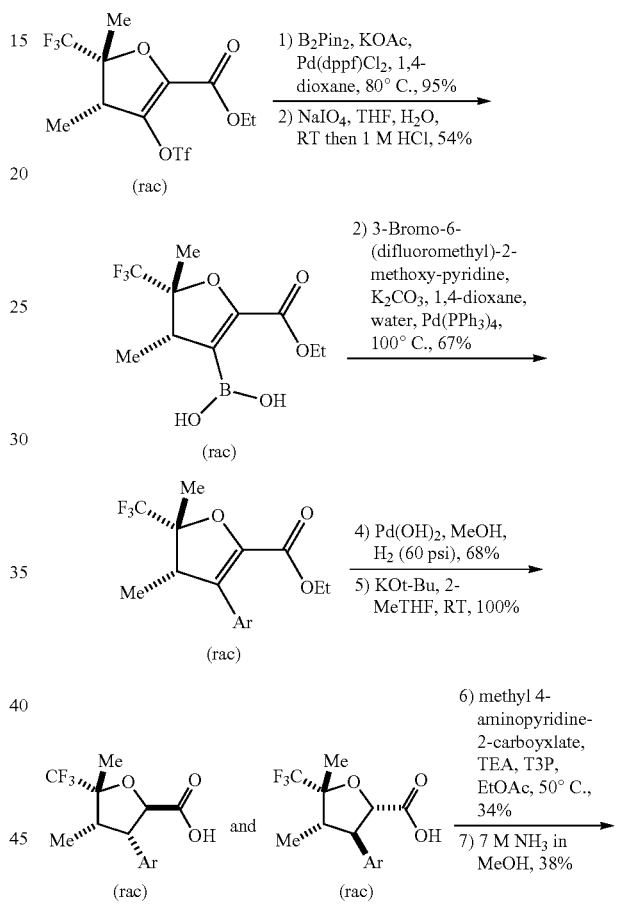

| Cmpd No. | Compound Name | LC/MS | NMR (shifts in ppm) |
|---|---|---|---|
| 139 | rac-(2R,3S,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide | ESI-MS m/z calc. 506.1389, found 507.1 (M + 1)$^+$; Retention time: 2.327 minutes | $^1$H NMR (301 MHz, Chloroform-d) δ 8.71 (s, 1H), 8.64 (s, 1H), 8.46 (d, J = 5.5 Hz, 1H), 8.16 (dd, J = 5.5. 2.1 Hz, 1H), 7.93 (d, J = 2.1 Hz, 1H), 7.84 (br s, 1H), 7.18 (s, 1H), 5.63 (br s, 1H), 5.24 (d, J = 10.7 Hz, 1H), 4.13 (dd, J = 10.8, 8.1 Hz, 1H), 3.97 (d, J = 5.2 Hz, 3H), 2.85 (t, J = 7.6 Hz, 1H), 1.70 (s, 3H), 0.80 (d, J = 5.5 Hz, 3H) ppm. |

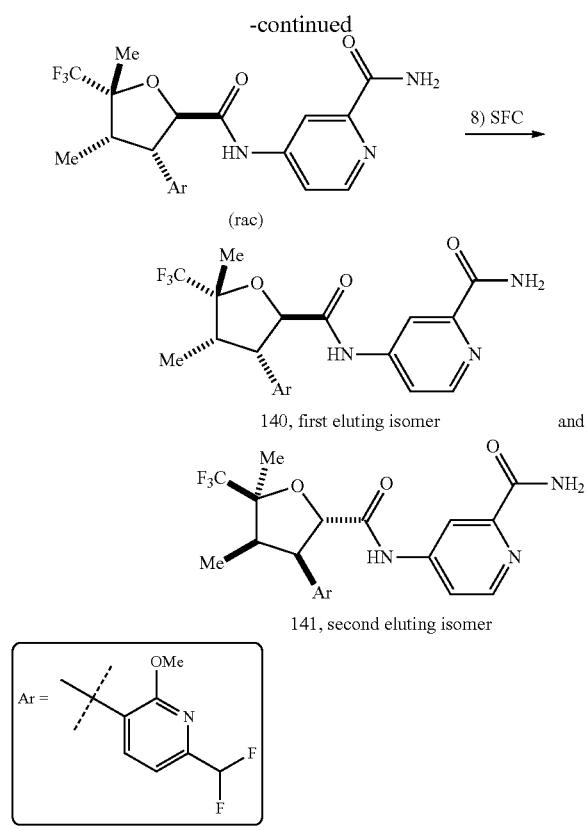

140, first eluting isomer and 141, second eluting isomer

Step 1: To a 3 neck 1 litre flask hooked up with a thermometer and air condenser is added ethyl rac-(4R,5R)-4,5-dimethyl-5-(trifluoromethyl)-3-(((trifluoromethyl)sulfonyl)oxy)-4,5-dihydrofuran-2-carboxylate (42 g, 108.7 mmol) and 1,4-dioxane (500 mL). The mixture was stirred and degassed and flushed with nitrogen. KOAc (32 g, 326.1 mmol) was added followed by bis(pinacolato)diboron (32 g, 126.0 mmol). The reaction mixture was evacuated and back filled with nitrogen (×3). Pd(dppf)Cl$_2$ (4 g, 5.467 mmol) was added to this reaction mixture which was heated to 60° C. first then when stable, the temperature was increased to 80° C. (to avoid exotherm). The reaction was allowed to proceed with stirring at 80° C. under nitrogen for 20 hours. The reaction mixture was then cooled to ambient temperature and diluted with ethyl acetate (300 mL) and water (100 mL). The mixture was filtered through a pad of celite, washing several times with ethyl acetate until no more product came off (5×100 ml). The filtrate is then separated, and the aqueous layer was extracted with ethyl acetate twice (100 mL). The combined organic layers were dried and filtered using Whatman 1PS hydrophobic phase separator filter paper. The filtrates were concentrated in vacuo to give 47 g of a brown oil. The crude product (47 g) was absorbed onto diatomaceous earth (Telos nm) and passed through a Florisil (magnesium silicate) pad, washing with 100% heptane until no more product came off (4 fractions in total). The filtrates were combined and concentrated in vacuo to give ethyl rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (47 g, 95%) as a thick viscous yellow oil. $^1$H NMR (500 MHz, Chloroform-d) δ 4.33-4.23 (m, 2H), 3.27-3.18 (m, 1H), 1.55 (d, J=1.1 Hz, 3H), 1.32 (s, 12H), 1.28 (d, J=2.3 Hz, 2H), 1.24 (s, 3H) ppm. ESI-MS m/z calc. 364.1669, found 365.3 (M+1)$^+$.

Step 2 ethyl rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (47 g) was dissolved in a 1:2 mixture of water (50 mL) and THF (100 mL). Sodium periodate (50 g, 233.8 mmol) was added and the reaction was stirred for 1 hour at ambient temperature. The reaction mixture was cooled with an ice bath. 1M HCl (60 mL) was added and reaction mixture was stirred for 60 mins (a white solid precipitates). The mixture was diluted with water (50 mL) and ethyl acetate (100 mL). A white solid was filtered and washed with ethyl acetate. The filtrate was washed with sodium thiosulphate (shaken vigorously at every wash to remove traces of iodine) (3×50 ml) followed by a brine solution. The combined organic layers were dried over anhydrous sodium sulfate, filtered and concentrated under vacuum (keeping water bath at room temp). A cream solid (23 g) was obtained and triturated with cold heptane to afford rac-((4S,5R)-2-(ethoxycarbonyl)-4,5-dimethyl-5-(trifluoromethyl)-4,5-dihydrofuran-3-yl)boronic acid (16.66 g, 54%) as a white solid. $^1$H NMR (500 MHz, Chloroform-d) δ 6.84 (s, 2H), 4.38 (q, J=7.1 Hz, 2H), 3.18 (q, J=7.3 Hz, 1H), 1.51 (d, J 1.2 Hz, 3H), 1.39 (t, J 7.1 Hz, 3H), 1.32 (dq, J 7.2, 2.4 Hz, 3H) ppm. ESI-MS m/z calc. 282.08865, found 281.2 (M−1)$^−$.

Step 3

To a solution of rac-((4S,5R)-2-(ethoxycarbonyl)-4,5-dimethyl-5-(trifluoromethyl)-4,5-dihydrofuran-3-yl)boronic acid (902 mg, 3.79 mmol) and Pd(PPh$_3$)$_4$ (82 mg, 0.071 mmol) in dioxane (20 mL) was added an aqueous solution of K$_2$CO$_3$ (3.5 mL of 2 M, 7.000 mmol). The reaction was initially stirred at 100° C. for 2 hours, then at 115° C. for 3 hours. A further 30 mg of Pd(PPh$_3$)$_4$ was added and the mixture was stirred for a further 30 mins at reflux. The mixture was partitioned between water and ethyl acetate. The aqueous layer was washed twice more with ethyl acetate. The combined organic phases were washed with brine, dried (MgSO$_4$) and concentrated in vacuo. Purification by flash chromatography (SiO$_2$, 0 to 25% EtOAc in heptane) gave ethyl rac-(4S,5R)-3-(6-(difluoromethyl)-2-methoxypyridin-3-yl)-4,5-dimethyl-5-(trifluoromethyl)-4,5-dihydrofuran-2-carboxylate (1.05 g, 75%) as a colourless oil. $^1$H NMR (500 MHz, Chloroform-d) δ 7.61 (d, J=7.5 Hz, 1H), 7.22 (d, J=7.4 Hz, 1H), 6.52 (t, J=55.6 Hz, 1H), 4.23-4.07 (m, 2H), 3.96 (s, 3H), 3.63 (q, J=7.4 Hz, 1H), 1.70 (d, J=1.1 Hz, 3H), 1.13 (t, J=7.1 Hz, 3H), 1.06 (dq, J=7.3, 2.2 Hz, 3H) ppm. ESI-MS m/z calc. 395.1156, found 396.3 (M+1)$^+$.

Step 4

A solution of ethyl rac-(4S,5R)-3-(6-(difluoromethyl)-2-methoxypyridin-3-yl)-4,5-dimethyl-5-(trifluoromethyl)-4,5-dihydrofuran-2-carboxylate (250 mg, 0.632 mmol) in MeOH (50 mL) was added to Pd(OH)$_2$ (475 mg of 20% w/w, 0.67 mmol) under nitrogen in a Parr flask. The flask was connected to the Parr shaker and put under an atmosphere of hydrogen (60 psi, 4 bar). The reaction was shaken at ambient temperature overnight. The reaction mixture was carefully filtered through a pad of celite. The collected filtrates were concentrated in vacuo to give a 1:1 mixture of diastereomers of ethyl rac-(4S,5R)-3-[6-(difluoromethyl)-2-methoxy-3- pyridyl]-4,5-dimethyl-5-(trifluoromethyl)tetrahydrofuran-2-carboxylate (170 mg, 68%). ESI-MS m/z calc. 397.13126, found 398.2 (M+1)+.

Step 5

To a solution of ethyl rac-(4S,5R)-3-[6-(difluoromethyl)-2-methoxy-3-pyridyl]-4,5-dimethyl-5-(trifluoromethyl)tetrahydrofuran-2-carboxylate (160 mg, 0.4027 mmol) in 2-MeTHF (6 mL) was added KOt-Bu (95 mg, 0.8466 mmol) and the reaction was stirred at ambient temperature for 30 minutes. The reaction was quenched by addition of a 2M HCl solution. Ethyl acetate was added. The separated organic layer was washed with brine, dried (MgSO$_4$), filtered and concentrated in vacuo to give rac-(4S,5R)-3-[6-(difluoromethyl)-2-methoxy-3-pyridyl]-4,5-dimethyl-5-(trifluoromethyl)tetrahydrofuran-2-carboxylic acid (150 mg, 100%) as a colourless oil, one of the diastereoisomers being the major component. ESI-MS m/z calc. 369.09995, found 368.1 (M−1)−.

Step 6

To a solution of rac-(4S,5R)-3-[6-(difluoromethyl)-2-methoxy-3-pyridyl]-4,5-dimethyl-5-(trifluoromethyl)tetrahydrofuran-2-carboxylic acid (150 mg, 0.4062 mmol) and methyl 4-aminopyridine-2-carboxylate (79 mg, 0.5192 mmol) in ethyl acetate (3 mL) was added TEA (170 µL, 1.220 mmol) and T3P (325 µL of 50% w/w, 0.5460 mmol). The reaction was stirred at 50° C. for 3 hours. The reaction mixture was diluted with water and ethyl acetate. The aqueous layer was further extracted with ethyl acetate. The combined organics were washed with brine, dried (MgSO$_4$), filtered and concentrated in vacuo. Purification by flash chromatography (SiO$_2$, 75% EtOAc in heptane) gave the main diastereoisomer methyl rac-(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxylate (70 mg, 34%) as a colourless oil. $^1$H NMR (500 MHz, Chloroform-d) δ 8.63 (d, J=5.5 Hz, 1H), 8.58 (d, J=10.2 Hz, 1H), 8.08 (d, J=2.1 Hz, 1H), 7.91 (dd, J=5.5, 2.2 Hz, 1H), 7.83 (d, J=7.6 Hz, 1H), 6.52 (t, J=55.6 Hz, 1H), 5.10 (d, J=11.1 Hz, 1H), 4.05 (dd, J=11.1, 7.8 Hz, 1H), 4.00 (s, 3H), 3.98 (s, 3H), 2.92 (q, J=7.6 Hz, 1H), 1.72 (d, J=2.9 Hz, 3H), 0.77 (dt, J=7.5, 2.3 Hz, 3H) ppm. ESI-MS m/z calc. 503.14795, found 504.4 (M+1)+; 502.3 (M−1)−.

Step 7 rac-(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxylate (70 mg, 0.1390 mmol) was dissolved in methanolic ammonia (3 mL of 7 M, 21.00 mmol) and stirred at ambient temperature overnight. The reaction mixture was concentrated in vacuo to give rac-(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide (26 mg, 38%). ESI-MS m/z calc. 488.1483, found 489.3 (M+1)+; 487.3 (M−1)−.

Step 8 rac-(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide (26 mg, 0.053 mmol) was separated by chiral SFC using a Lux i-Cellulose-5 column, 5 µm particle size, 25 cm×10 mm from Phenomenex, Inc. on a Minigram SFC instrument from Berger Instruments to give:

First Eluting Isomer (rt=4.12 min): rel-(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide (140, 8.2 mg). $^1$H NMR (500 MHz, Methanol-d$_4$) δ 8.48 (d, J=5.6 Hz, 1H), 8.27 (d, J=2.2 Hz, 1H), 7.91 (dd, J=5.5, 2.2 Hz, 1H), 7.85 (d, J=7.6 Hz, 1H), 7.25 (d, J=7.6 Hz, 1H), 6.59 (t, J=55.5 Hz, 1H), 5.19 (d, J=10.1 Hz, 1H), 4.26 (t, J=9.0 Hz, 1H), 4.00 (s, 3H), 2.95 (p, J=7.6 Hz, 1H), 1.67 (s, 3H), 0.79 (dd, J=7.7, 2.6 Hz, 3H) ppm; amide NH and NH$_2$ protons not observed. ESI-MS m/z calc. 488.1483, found 489.4 (M+1)+; 487.3 (M−1)−.

Second Eluting Isomer (rt=4.71 min): rel-(2S,3R,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide (141, 10.1 mg). $^1$H NMR (500 MHz, Methanol-d$_4$) δ 8.52 (d, J=5.7 Hz, 1H), 8.38 (d, J=2.1 Hz, 1H), 7.99 (dd, J=5.8, 2.2 Hz, 1H), 7.86 (d, J=7.6 Hz, 1H), 7.25 (d, J=7.6 Hz, 1H), 6.59 (t, J=55.5 Hz, 1H), 5.22 (d, J=10.1 Hz, 1H), 4.33-4.23 (m, 1H), 4.00 (s, 3H), 2.96 (p, J=7.6 Hz, 1H), 1.68 (d, J=1.4 Hz, 3H), 0.80 (dq, J=7.4, 2.3 Hz, 3H) ppm; amide NH and NH$_2$ protons not observed. ESI-MS m/z calc. 488.1483, found 489.3 (M+1)+; 487.3 (M−1)−.

The following compounds were made using a similar method to that described in Example 27, except that 2-bromo-3-methoxypyridine was used in place of 3-bromo-6-(difluoromethyl)-2-methoxy-pyridine in step 3 and the conditions used for the reduction step 4 were similar to the ones used in Example 1 step 2. In step 8, purification was performed by chiral SFC using a Chiralpak IC column for 142 and 143 and using a Chiralcel OD-H column for 144 and 145, 5 µm particle size, 25 cm×20 mm from Daicel on a Minigram SFC instrument from Berger Instruments:

| Cmpd No. | Compound Name | LC/MS | NMR (shifts in ppm) |
|---|---|---|---|
| 142 | rel-(2N,3R,4R,5S)-4-[[3-(3-methoxy-2-pyridyl)-4,5-dimethyl-5-(trifluoromethyl)tetrahydrofuran-2-carbonyl]amino]pyridine-2-carboxamide (first eluting peak by SFC on Chiralpak IC column, rt = 1.84 min) | ESI-MS m/z calc. 438.1515, found 440.3 (M + 1)+; 437.2 (M − 1)−; Retention time: 2.84 minutes | $^1$H NMR (500 MHz, Methanol-d4) δ 8.46 (d, J = 5.5 Hz, 1H), 8.22 (d, J = 2.1 Hz, 1H), 8.13 (dd, J = 4.8, 1.3 Hz, 1H), 7.88 (dd, J = 5.5, 2.2 Hz, 1H), 7.38 (dd, J = 8.3, 1.4 Hz, 1H), 7.28 (dd, J = 8.3, 4.8 Hz, 1H), 5.61 (d, J = 10.4 Hz, 1H), 4.39 (dd, J = 10.4, 7.6 Hz, 1H), 3.91 (s, 3H), 3.01 (p, J = 7.5 Hz, 1H), 1.62 (d, J = 1.4 Hz, |

-continued

| Cmpd No. | Compound Name | LC/MS | NMR (shifts in ppm) |
|---|---|---|---|
| 143 | rel-(2R,3S,4S,5R)-4-[[3-(3-methoxy-2-pyridyl)-4,5-dimethyl-5-(trifluoromethyl)tetrahydrofuran-2-carbonyl]amino]pyridine-2-carboxamide (second eluting peak by SFC on Chiralpak IC column, rt = 2.20 min) | ESI-MS m/z calc. 438.1515, found 440.1 (M + 1)+; 437.2 (M − 1)−; Retention time: 2.84 minutes | $^1$H NMR (500 MHz, Methanol-d4) δ 8.46 (d, J = 5.5 Hz, 1H), 8.22 (d, J = 2.2 Hz, 1H), 8.13 (dd, J = 4.8, 1.3 Hz, 1H), 7.88 (dd, J = 5.5, 2.2 Hz, 1H), 7.38 (dd, J = 8.4, 1.4 Hz, 1H), 7.28 (dd, J = 8.3, 4.8 Hz, 1H), 5.61 (d, J = 10.4 Hz, 1H), 4.39 (dd, J = 10.4, 7.5 Hz, 1H), 3.91 (s, 3H), 3.01 (p, J = 7.5 Hz, 1H), 1.62 (d, J = 1.5 Hz, 3H), 0.73 (dq, J = 7.5, 2.3 Hz, 3H) ppm. |
| 144 | rel-(2S,3R,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide (first eluting peak by SFC on Chiralcel OD-H column, rt = 4.26 min) | ESI-MS m/z calc. 452.16714, found 453.2 (M + 1)+; 451.3 (M − 1)−; Retention time: 2.64 minutes | $^1$H NMR (500 MHz, Chloroform-d) δ 8.68 (s, 1H), 8.50 (d, J = 5.5 Hz, 1H), 8.36 (d, J = 5.3 Hz, 1H), 8.21-8.12 (m, 1H), 7.98 (t, J = 1.6 Hz, 1H), 7.86 (s, 1H), 7.32 (s, 1H), 5.60 (s, 1H), 5.07 (d, J = 10.5 Hz, 1H), 4.22 (t, J = 9.5 Hz, 1H), 3.83 (d, J = 1.9 Hz, 3H), 2.86 (p, J = 7.9 Hz, 1H), 2.68 (s, 3H), 1.72 (s, 3H), 0.94-0.74 (m, 3H) ppm. |
| 145 | rel-(2R,3S,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide (second eluting peak by SFC on Chiralcel OD-H column, rt = 5.04 min) | ESI-MS m/z calc. 452.16714, found 453.3 (M + 1)+; 451.3 (M − 1)−; Retention time: 2.64 minutes | $^1$H NMR (500 MHz, Chloroform-d) δ 8.62 (s, 1H), 8.41 (d, J = 5.5 Hz, 1H), 8.29 (d, J = 5.4 Hz, 1H), 8.04 (dd, J = 5.6, 2.2 Hz, 1H), 7.90 (d, J = 2.2 Hz, 1H), 7.76 (s, 1H), 7.31 (s, 1H), 5.52 (d, J = 4.4 Hz, 1H), 4.99 (d, J = 10.4 Hz, 1H), 4.14 (t, J = 9.5 Hz, 1H), 3.76 (s, 3H), 2.79 (p, J = 7.9 Hz, 1H), 2.64 (s, 3H), 1.63 (s, 3H), 0.75 (dt, J = 7.3, 2.4 Hz, 3H) ppm. |

Example 28

4-[[(2R,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide (146)

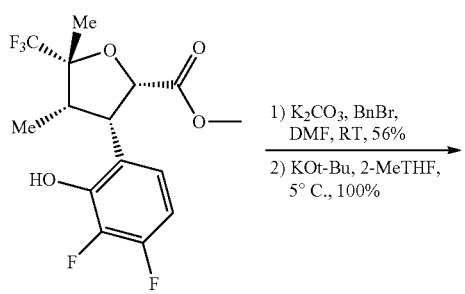

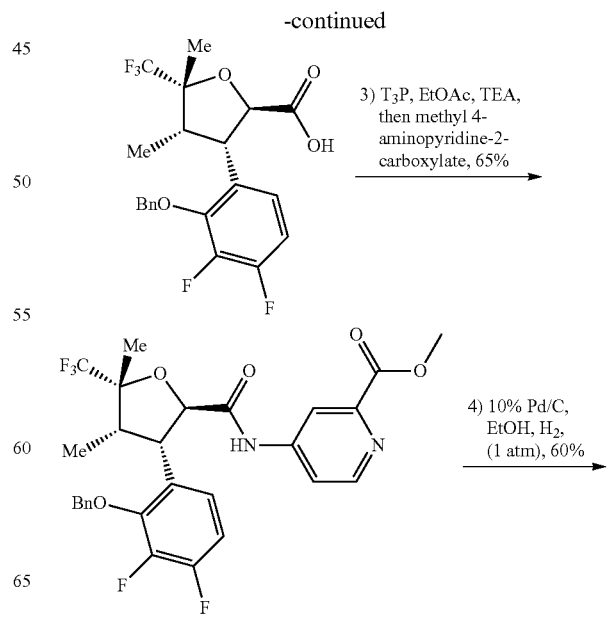

-continued

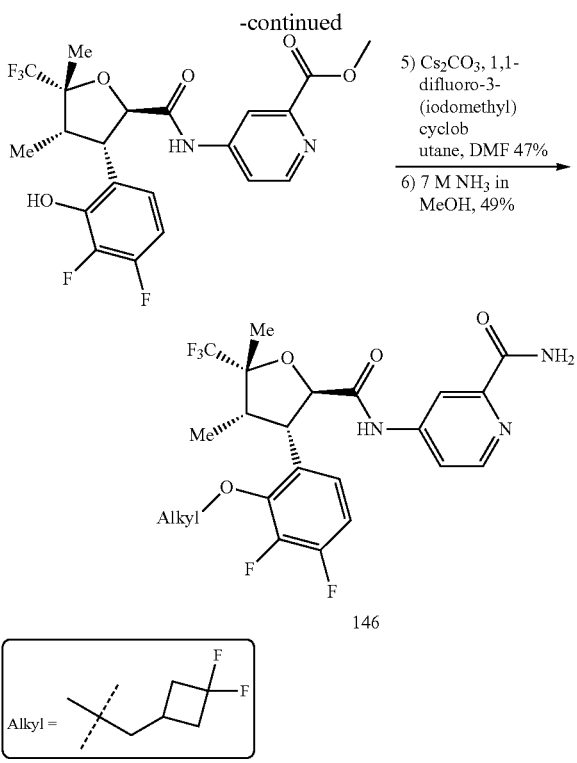

146

Step 1

To a stirred mixture of methyl (2S,3S,4S,5R)-3-(3,4-difluoro-2-hydroxy-phenyl)-4,5-dimethyl-5-(trifluoromethyl)tetrahydrofuran-2-carboxylate (13.5 g, 38.107 mmol) and potassium carbonate (6.85 g, 49.564 mmol) in N,N-dimethylformamide (50 mL) at room temperature, was added benzyl bromide (9.7784 g, 6.8 mL, 57.172 mmol). The reaction mixture was stirred overnight at room temperature. A further portion of benzyl bromide (3.3074 g, 2.3 mL, 19.338 mmol) was added and the stirring was continued for 6 hrs. A further portion of potassium carbonate (2.6 g, 18.812 mmol) and benzyl bromide (3.3074 g, 2.3 mL, 19.338 mmol) were added and reaction mixture was stirred overnight. The reaction mixture was diluted with water (100 mL) and extracted with diethyl ether (3×100 mL). The combined organic extracts were washed with brine (50 mL), dried ($Na_2SO_4$), filtered and concentrated in vacuo. Purification by flash chromatography ($SiO_2$, 0 to 50% EtOAc in heptane) gave a 2:3 mixture of methyl and benzyl (2S,3S,4S,5R)-3-(2-benzyloxy-3,4-difluoro-phenyl)-4,5-dimethyl-5-(trifluoromethyl)tetrahydrofuran-2-carboxylate (12.2 g) as a yellow oil, which was used without further purification in the next step.

Step 2

To a stirred mixture of 2:3 methyl and benzyl (2S,3S,4S,5R)-3-(2-benzyloxy-3,4-difluoro-phenyl)-4,5-dimethyl-5-(trifluoromethyl)tetrahydrofuran-2-carboxylate (1.5 g, 1.3007 mmol) in 2-methyl tetrahydrofuran (5 mL), was added potassium tert-butoxide (438 mg, 3.9033 mmol) at 0° C. under argon. The reaction mixture was stirred at 0° C. for 15 min then room temperature for 30 min. The reaction mixture was diluted with diethyl ether (20 mL) and acidified with aqueous hydrochloric acid (2 M solution). The aqueous phase was extracted with diethyl ether (20 mL) and the combined organic extracts were washed with brine (20 mL), dried ($Na_2SO_4$), filtered and concentrated in vacuo. Purification by reverse phase chromatography (Biotage Isolera, 120 g, SiliaSep C18 Monomeric 25 μm Silicycle flash cartridge) using acetonitrile containing 0.1% ammonium hydroxide and water containing 0.1% ammonium hydroxide (0:100 to 100:0) gave (2R,3S,4S,5R)-3-(2-benzyloxy-3,4-difluoro-phenyl)-4,5-dimethyl-5-(trifluoromethyl)tetrahydrofuran-2-carboxylic acid (760 mg) as a white solid. $^1$H NMR (400 MHz, chloroform-d) δ 7.37-7.33 (m, 5H), 6.99-6.87 (m, 2H), 5.23 (d, J=11.0 Hz, 1H), 5.07 (d, J=11.0 Hz, 1H), 4.83 (d, J=11.0 Hz, 1H), 3.91 (dd, J=11.0, 7.8 Hz, 1H), 2.44 (dd, J=15.3, 7.6 Hz, 1H), 1.37 (s, 3H), 0.66 (dd, J=7.3, 2.3 Hz, 3H) ppm; alcohol OH not observed. ESI-MS m/z calc. 430.1204, found 429.04 (M−1)⁻.

Step 3

To a solution of (2R,3S,4S,5R)-3-(2-benzyloxy-3,4-difluoro-phenyl)-4,5-dimethyl-5-(trifluoromethyl)tetrahydrofuran-2-carboxylic acid (3.3 g, 5.378 mmol) in ethyl acetate (20 mL) was added methyl 4-aminopyridine-2-carboxylate (1.22 g, 8.018 mmol), TEA (2.24 mL, 16.07 mmol) and T3P (6.4 mL, 21.52 mmol). The mixture was stirred at ambient temperature for 4 hours. The reaction mixture was partitioned between ethyl acetate (30 ml) and water (60 ml). The organic layer was separated and washed with water (1×50 ml) and brine (1×20 mL), dried ($MgSO_4$), filtered and concentrated in vacuo. Purification by flash chromatography (24 g pre-packed $SiO_2$, with 0-100% EtOAc/petroleum ether) gave the product methyl 4-[[(2R,3S,4S,5R)-3-(2-benzyloxy-3,4-difluoro-phenyl)-4,5-dimethyl-5-(trifluoromethyl)tetrahydrofuran-2-carbonyl]amino]pyridine-2-carboxylate (2.3 g, 65%) as an oil. ESI-MS m/z calc. 564.16833, found 565.1 (M+1)⁺.

Step 4

A mixture of methyl 4-[[(2R,3S,4S,5R)-3-(2-benzyloxy-3,4-difluoro-phenyl)-4,5-dimethyl-5-(trifluoromethyl)tetrahydrofuran-2-carbonyl]amino]pyridine-2-carboxylate (1.5 g, 2.438 mmol) and palladium on carbon 10% (75 mg, 0.705 mmol) in ethanol (20 mL) was stirred under an atmosphere of hydrogen gas (1 atm, balloon) for 3.5 hrs. The reaction mixture was filtered through celite and concentrated in vacuo to give a solid which was triturated with heptane, filtered and dried in vacuo. The solid was dissolved in dichloromethane/methanol (9:1, 50 mL) and a saturated aqueous solution of sodium hydrogencarbonate (50 mL). The aqueous phase was extracted with dichloromethane/methanol (9:1, 2×50 mL). The combined organic extracts were washed with water (50 mL), dried ($Na_2SO_4$), filtered and concentrated in vacuo. The solid was triturated with heptane to give methyl 4-[[(2R,3S,4S,5R)-3-(3,4-difluoro-2-hydroxy-phenyl)-4,5-dimethyl-5-(trifluoromethyl)tetrahydrofuran-2-carbonyl]amino]pyridine-2-carboxylate (1.07 g, 60%) as a beige solid. $^1$H NMR (400 MHz, DMSO-$d_6$) δ 11.23 (br s, 1H), 10.82 (br s, 1H), 8.52 (d, J=5.3 Hz, 1H), 8.29 (d, J=1.5 Hz, 1H), 7.78 (q, J=2.5 Hz, 1H), 6.91 (s, 1H), 6.65 (s, 1H), 5.17 (d, J=9.9 Hz, 1H), 4.14 (t, J=8.8 Hz, 1H), 3.83 (s, 3H), 2.81-2.72 (m, 1H), 1.55 (s, 3H), 0.67 (d, J=6.9 Hz, 3H) ppm. ESI-MS m/z calc. 474.1214, found 475.15 (M+1)⁺.

Step 5

To a solution of methyl 4-[[(2R,3S,4S,5R)-3-(3,4-difluoro-2-hydroxy-phenyl)-4,5-dimethyl-5-(trifluoromethyl)

tetrahydrofuran-2-carbonyl]amino]pyridine-2-carboxylate (100 mg, 0.2108 mmol) in DMF (2 mL) was added 1,1-difluoro-3-(iodomethyl)cyclobutane (244 mg, 1.052 mmol) and cesium carbonate (103 mg, 0.3161 mmol). The mixture was stirred at ambient temperature for 48 hrs. The reaction mixture was partitioned between TBME (10 ml) and water (10 ml). The aqueous layer was further extracted with TBME (10 mL). The combined organic fractions were washed with brine (1×10 mL), dried (MgSO$_4$), filtered and concentrated in vacuo to yield the crude product methyl 4-[[(2R,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxylate (80 mg, 47%). ESI-MS m/z calc. 578.16516, found 579.2 (M+1)$^+$.

Step 6

To a solution of methyl 4-[[(2R,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxylate (80 mg, 0.1383 mmol) in methanol (1 mL) was added methanolic ammonia (500 μL of 7 M, 3.500 mmol) and the mixture stirred at ambient temperature overnight. The mixture was concentrated in vacuo and the product was purified by reverse phase preparative (basic eluent) to give 4-[[(2R,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide (146, 39 mg, 49%). $^1$H NMR (500 MHz, DMSO-d$_6$) δ 10.73 (s, 1H), 8.50 (d, J=5.5 Hz, 1H), 8.28 (d, J=2.1 Hz, 1H), 8.06 (d, J=2.7 Hz, 1H), 7.83 (dd, J=5.5, 2.2 Hz, 1H), 7.61 (d, J=2.9 Hz, 1H), 7.23-7.16 (m, 2H), 5.12 (d, J=10.3 Hz, 1H), 4.26 (dt, J=10.4, 6.5 Hz, 2H), 4.14 (dd, J=9.8, 6.5 Hz, 1H), 2.79-2.66 (m, 3H), 2.65-2.45 (m, 3H), 1.61 (s, 3H), 0.76-0.64 (m, 3H) ppm. ESI-MS m/z calc. 563.1655, found 564.2 (M+1)$^+$.

Example 29

4-[[(2R,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide (147)

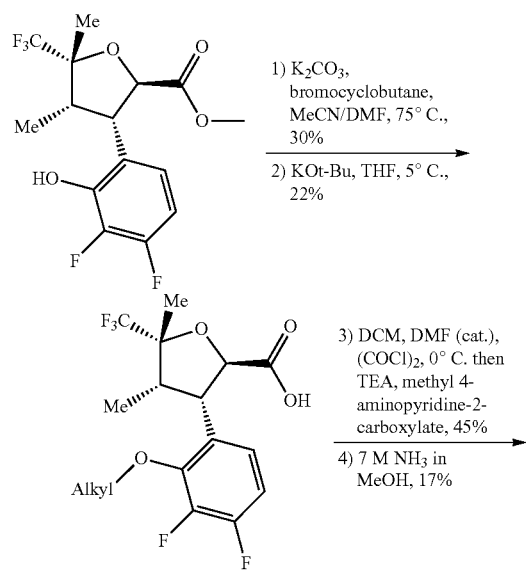

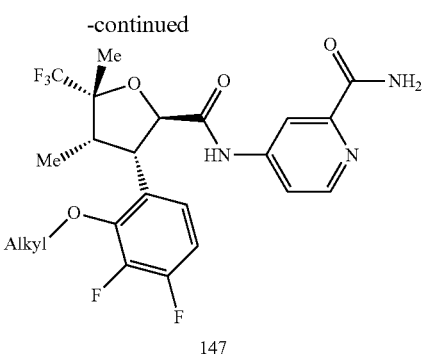

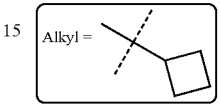

Step 1 and 2

To a solution of methyl (2R,3S,4S,5R)-3-(3,4-difluoro-2-hydroxy-phenyl)-4,5-dimethyl-5-(trifluoromethyl)tetrahydrofuran-2-carboxylate (200 mg, 0.5645 mmol) in a mixture of MeCN (2 mL) and DMF (1 mL) was added K$_2$CO$_3$ (250 mg, 1.809 mmol) and bromocyclobutane (200 mg, 1.481 mmol). The mixture was heated to 75° C. in a sealed vial for 90 min. Upon completion the mixture was diluted with DCM and partitioned with water. The organic phase was dried (MgSO$_4$), filtered and concentrated in vacuo. Purification by flash chromatography gave methyl (2R,3S,4S,5R)-3-[2-(cyclobutoxy)-3,4-difluoro-phenyl]-4,5-dimethyl-5-(trifluoromethyl)tetrahydrofuran-2-carboxylate (70 mg, 30%). This was immediately taken in THF (1 mL) and potassium tert-butoxide (60 mg, 0.5347 mmol) was added at ambient temperature. The mixture is diluted with DCM (10 mL) and partitioned with a saturated solution of ammonium chloride (10 mL). The organics were separated, dried (MgSO$_4$), filtered and concentrated in vacuo to give (2R,3S,4S,5R)-3-[2-(cyclobutoxy)-3,4-difluoro-phenyl]-4,5-dimethyl-5-(trifluoromethyl)tetrahydrofuran-2-carboxylic acid (50 mg, 22%), which was used without further purification. ESI-MS m/z calc. 394.12036, found 393.5 (M−1)$^-$.

Step 3 and 4

Oxalyl chloride (30 μL, 0.3439 mmol) was added dropwise to a stirred solution of (2R,3S,4S,5R)-3-[2-(cyclobutoxy)-3,4-difluoro-phenyl]-4,5-dimethyl-5-(trifluoromethyl)tetrahydrofuran-2-carboxylic acid (50 mg, 0.1268 mmol) and DMF (2 μL, 0.02583 mmol) in DCM (500 μL) at ambient temperature. The mixture was stirred for 30 min. Upon complete acid chloride formation, the solution was concentrated in vacuo and the residue dissolved in DCM (300 μL). The obtained solution was added to a stirred solution of methyl 4-aminopyridine-2-carboxylate (25 mg, 0.1643 mmol) and TEA (30 μL, 0.2152 mmol) in DCM (300 μL) at ambient temperature and allowed to stir for 2 hrs. The mixture was quenched with 100 μL of methanol and purified by flash chromatography to afford methyl 4-[[(2R,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxylate (30 mg, 45%). ESI-MS m/z calc. 528.16833, found 527.6 (M+1)$^+$.

The residue was taken up in methanolic ammomia (4 mL of 7 M, 28.00 mmol) and stirred at ambient temperature until complete conversion. Purification by flash chromatography gave 4-[[(2R,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide (147, 13 mg, 17%). $^1$H NMR (500 MHz, DMSO-$d_6$) δ 10.73 (s, 1H), 8.49 (d, J=5.5 Hz, 1H), 8.27 (d, J=2.3 Hz, 1H), 8.05 (d, J=2.6 Hz, 1H), 7.82 (dd, J=5.5, 2.2 Hz, 1H), 7.63-7.55 (m, 1H), 7.15 (t, J=6.4 Hz, 2H), 5.09 (d, J=10.4 Hz, 1H), 4.65 (p, J=7.3 Hz, 1H), 4.28 (dd, J=10.5, 7.5 Hz, 1H), 2.77 (h, J=7.8 Hz, 1H), 2.36-2.22 (m, 2H), 2.14 (ddt, J=35.2, 19.5, 10.2 Hz, 2H), 1.70 (dd, J=11.7, 9.0 Hz, 1H), 1.62 (s, 3H), 1.48 (dtd, J=18.2, 10.3, 7.8 Hz, 1H), 0.72 (d, J=7.1 Hz, 3H) ppm. ESI-MS m/z calc. 513.1687, found 514.6 (M+1) and 512.5 (M−1)$^-$.

Example 30

4-[[(2R,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide (148)

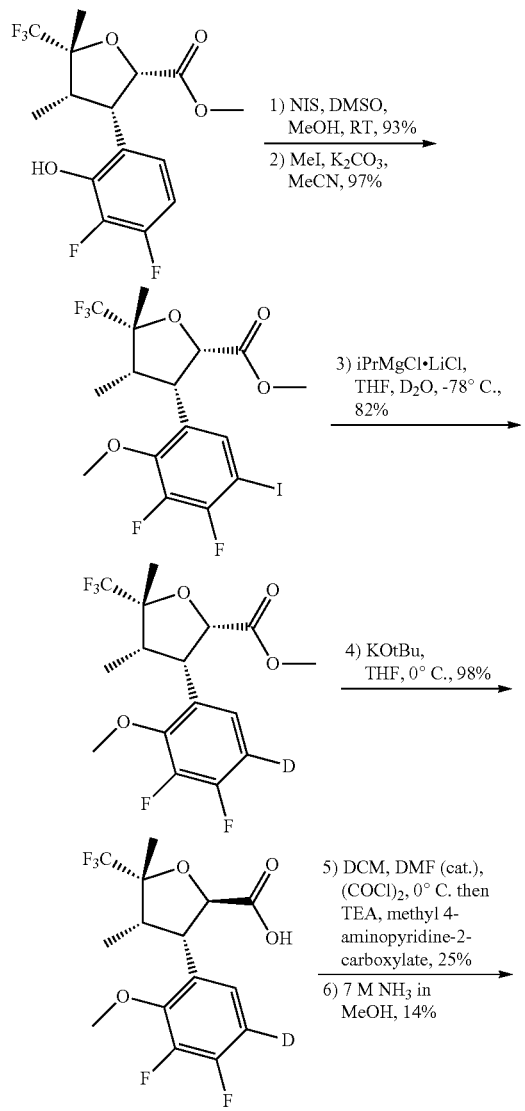

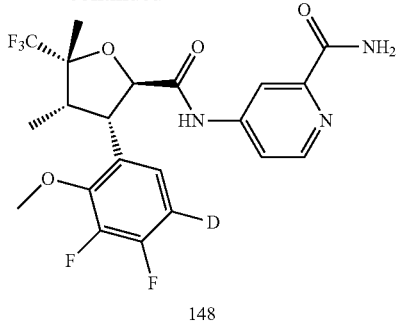

148

Step 1

DMSO (80 μL, 1.127 mmol) and NIS (1.7 g, 7.556 mmol) were added to a stirred solution of methyl (2S,3S,4S,5R)-3-(3,4-difluoro-2-hydroxy-phenyl)-4,5-dimethyl-5-(trifluoromethyl)tetrahydrofuran-2-carboxylate (2.2 g, 6.210 mmol) in MeOH (20 mL) at ambient temperature. The mixture was stirred at ambient temperature under air for 30 min. Upon completion, the mixture was concentrated in vacuo. Purification by flash chromatography gave methyl (2S,3S,4S,5R)-3-(3,4-difluoro-2-hydroxy-5-iodo-phenyl)-4,5-dimethyl-5-(trifluoromethyl)tetrahydrofuran-2-carboxylate (2.78 g, 93%). $^1$H NMR (500 MHz, Chloroform-d) δ 7.49 (dt, J=6.4, 2.1 Hz, 1H), 5.56 (d, J=4.9 Hz, 1H), 4.81 (d, J=5.9 Hz, 1H), 4.16 (dd, J=8.3, 5.9 Hz, 1H), 3.60 (s, 3H), 2.75 (p, J=7.7 Hz, 1H), 1.45 (d, J=1.2 Hz, 3H), 0.90-0.85 (m, 3H) ppm. ESI-MS m/z calc. 479.9857, found 481.1 (M+1)$^+$ and 479.1 (M−1)$^-$.

Step 2

$K_2CO_3$ (2.5 g, 18.09 mmol) and MeI (1 mL, 16.06 mmol) were added to a solution of methyl (2S,3S,4S,5R)-3-(3,4-difluoro-2-hydroxy-5-iodo-phenyl)-4,5-dimethyl-5-(trifluoromethyl)tetrahydrofuran-2-carboxylate (2.8 g, 5.831 mmol) in MeCN (25 mL). The mixture was heated to 75° C. in a sealed vial for 90 min. The mixture was diluted in DCM and partitioned with an aqueous saturated solution of NaCl. The organic extracts were dried (MgSO$_4$), filtered and concentrated in vacuo to afford methyl (2S,3S,4S,5R)-3-(3,4-difluoro-5-iodo-2-methoxy-phenyl)-4,5-dimethyl-5-(trifluoromethyl)tetrahydrofuran-2-carboxylate (2.8 g, 97%). $^1$H NMR (500 MHz, Chloroform-d) δ 7.53 (dq, J=6.5, 1.5 Hz, 1H), 4.80 (d, J=6.1 Hz, 1H), 4.11 (dd, J=8.5, 5.8 Hz, 1H), 3.88 (d, J=2.4 Hz, 3H), 3.56 (s, 3H), 2.73 (p, J=8.4, 7.8 Hz, 1H), 1.45 (d, J=1.1 Hz, 3H), 0.80 (dd, J=7.4, 1.9 Hz, 3H) ppm. ESI-MS m/z calc. 494.00134, found 495.2 (M+1)$^+$.

Step 3 iPrMgCl.LiCl (100 μL of 1.3 M, 0.1300 mmol) was added dropwise to a stirred solution of methyl (2S,3S,4S,5R)-3-(3,4-difluoro-5-iodo-2-methoxy-phenyl)-4,5-dimethyl-5-(trifluoromethyl)tetrahydrofuran-2-carboxylate (70 mg, 0.1416 mmol) in THF (1.5 mL) at −78° C. The resulting mixture was stirred at −78° C. for 10 min. The resulting mixture was quenched at −78° C. with a solution of D$_2$O (0.1 mL, 5.542 mmol) in THF (1.5 mL). The reaction mixture was allowed to warm up to ambient temperature, diluted with DCM and partitioned with brine. The organic layer was separated, dried (MgSO$_4$), filtered and concentrated in vacuo to afford methyl (2S,3S,4S,5R)-3-(5-deuterio-3,4-difluoro-2-methoxy-phenyl)-4,5-dimethyl-5-(trifluoromethyl)tetrahydrofuran-2-carboxylate (43 mg, 82%). $^1$H NMR (500 MHz, Chloroform-d) δ 7.16 (d, J=5.8 Hz, 1H), 4.87 (d, J=6.1 Hz, 1H), 4.23 (dd, J=8.6, 6.1 Hz, 1H), 3.94 (d, J=2.0 Hz, 3H), 3.54 (s, 3H), 2.82 (p, J=7.8 Hz, 1H), 1.53 (s, 3H), 0.86 (dt, J=7.6, 1.9 Hz, 3H) ppm.

Step 4

Potassium tert-butoxide (120 mg, 1.069 mmol) was added to a stirred solution of methyl (2S,3S,4S,5R)-3-(5-deuterio-3,4-difluoro-2-methoxy-phenyl)-4,5-dimethyl-5-(trifluoromethyl)tetrahydrofuran-2-carboxylate (100 mg, 0.2708 mmol) in THF (1.5 mL) at room temperature. After 5 minutes, the mixture was quenched by the addition of a saturated solution of ammonium chloride (3 mL) and diluted with DCM (3 mL). The aqueous phase was washed with DCM (5 mL), acidified with 1 N HCl to pH 0 and extracted with DCM (2×10 mL). The combined organic extracts were dried (MgSO$_4$), filtered and concentrated in vacuo to afford (2R,3S,4S,5R)-3-(5-deuterio-3,4-difluoro-2-methoxy-phenyl)-4,5-dimethyl-5-(trifluoromethyl)tetrahydrofuran-2-carboxylic acid (95 mg, 99%), which was used in the next step without further purification. ESI-MS m/z calc. 355.09534, found 354.2 (M−1)$^-$.

Step 5 and 6

Oxalyl chloride (70 μL, 0.8024 mmol) was added dropwise to a stirred solution of (2R,3S,4S,5R)-3-(5-deuterio-3,4-difluoro-2-methoxy-phenyl)-4,5-dimethyl-5-(trifluoromethyl)tetrahydrofuran-2-carboxylic acid (90 mg, 0.2533 mmol) and DMF (3 μL, 0.03874 mmol) in DCM (1000 μL) at ambient temperature. The mixture was stirred at room temperature for 30 min. Upon activation completion, the mixture was concentrated in vacuo and re-dissolved in DCM (500 μL). This obtained solution was added to a stirring solution of methyl 4-aminopyridine-2-carboxylate (50 mg, 0.3286 mmol) and triethylamine (50 μL, 0.3587 mmol) in DCM (500 μL) at ambient temperature. Upon complete conversion, the mixture was quenched with 0.1 mL of MeOH. Purification by flash chromatography gave methyl 4-[[(2R,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxylate (31 mg, 25%), which was used as is in the next step. ESI-MS m/z calc. 489.14334, found 490.4 (M+1)$^+$; 488.4 (M−1)$^-$.

Methyl 4-[[(2R,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxylate (31 mg) was taken in a methanolic solution of ammonia (8.5 mL of 7 M, 59.50 mmol) and stirred at ambient temperature until complete conversion to the corresponding amide. The final compound was lyophilized from MeCN:Water 3:1 to provide 4-[[(2R,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide (148, 17.4 mg, 14%, 93% isotopic purity for D). $^1$H NMR (500 MHz, DMSO-d$_6$) δ 10.70 (s, 1H), 8.49 (d, J 5.5 Hz, 1H), 8.28 (d, J 2.2 Hz, 1H), 8.05 (s, 1H), 7.83 (dd, J 5.6, 2.2 Hz, 1H), 7.60 (s, 1H), 7.17-7.12 (m, 1H), 5.10 (d, J 10.2 Hz, 1H), 4.26 (dd, J 10.2, 7.7 Hz, 1H), 3.95 (d, J 2.0 Hz, 3H), 2.77 (p, J 7.5 Hz, 1H), 1.61 (s, 3H), 0.73 (d, J 7.4 Hz, 3H) ppm. ESI-MS m/z calc. 474.14368, found 475.4 (M+1)$^+$; 473.4 (M−1)$^-$.

Example 31

4-[[(2R,3S,4S,5R)-3-(3,4-difluoro-2-vinyl-phenyl)-4,5-dimethyl-5-(trifluoromethyl)tetrahydrofuran-2-carbonyl]amino]pyridine-2-carboxamide (149)

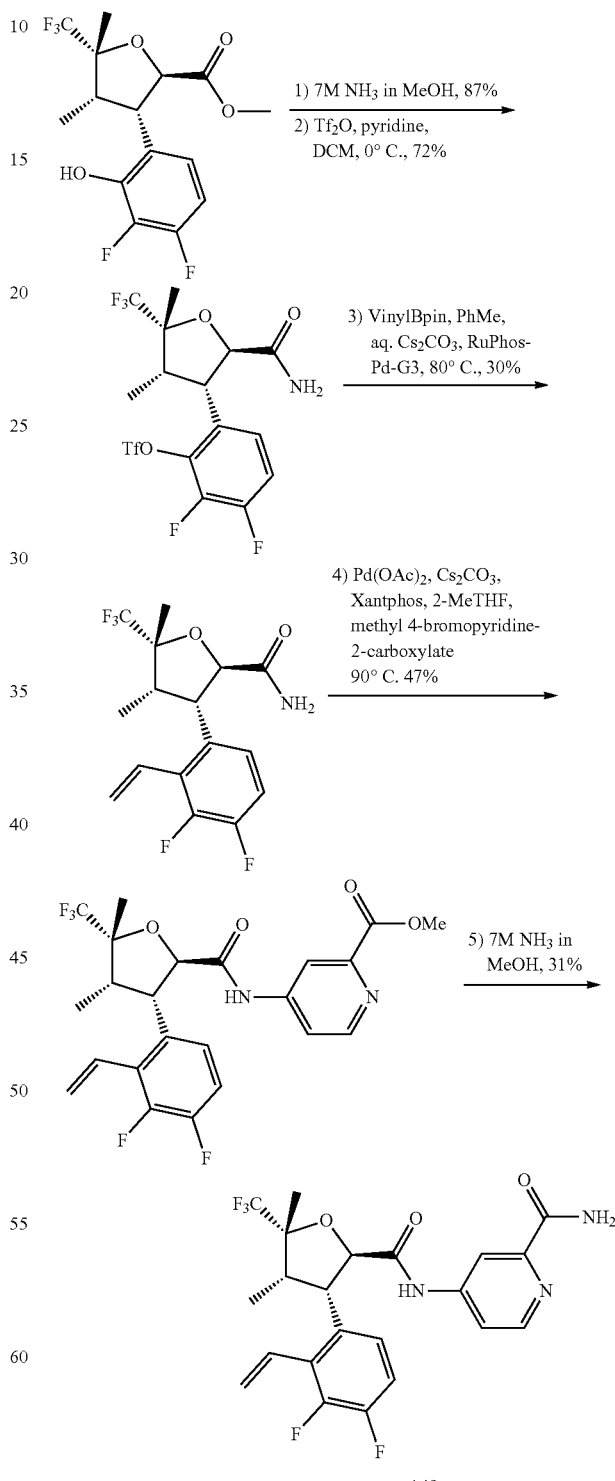

149

Step 1

To a solution of methyl (2R,3S,4S,5R)-3-(3,4-difluoro-2-hydroxy-phenyl)-4,5-dimethyl-5-(trifluoromethyl)tetrahydrofuran-2-carboxylate (1.3 g, 3.670 mmol) in methanol (5 mL) was added methanolic ammonia (10 mL of 7 M, 70.00 mmol) and the mixture was stirred at ambient temperature for 14 hours. The mixture was concentrated in vacuo to give (2R,3S,4S,5R)-3-(3,4-difluoro-2-hydroxy-phenyl)-4,5-dimethyl-5-(trifluoromethyl)tetrahydrofuran-2-carboxamide (1.2 g, 87%) as a white solid. ESI-MS m/z calc. 339.0894, found 340.2 (M+1)$^+$.

Step 2

To a solution of (2R,3S,4S,5R)-3-(3,4-difluoro-2-hydroxy-phenyl)-4,5-dimethyl-5-(trifluoromethyl)tetrahydrofuran-2-carboxamide (1.2 g, 3.537 mmol) in DCM (10 mL) cooled with an ice-bath was added pyridine (572 μL, 7.072 mmol) followed by trifluoromethylsulfonyl trifluoromethanesulfonate (4.59 mL of 1 M, 4.590 mmol) in portions over 5 mins. The reaction mixture was allowed to warm up to ambient temperature and was partitioned between DCM (20 ml) and water (20 ml). The organic phase was washed with brine (1×10 mL), dried (MgSO$_4$), filtered and concentrated in vacuo. Purification by flash chromatography (12 g SiO$_2$, 0 to 100% EtOAc in heptane) gave [6-[(2R,3S,4S,5R)-2-carbamoyl-4,5-dimethyl-5-(trifluoromethyl)tetrahydrofuran-3-yl]-2,3-difluoro-phenyl]trifluoromethanesulfonate (1.2 g, 72%) as a white solid. ESI-MS m/z calc. 471.03867, found 472.2 (M+1)$^+$.

Step 3

A mixture of [6-[(2R,3S,4S,5R)-2-carbamoyl-4,5-dimethyl-5-(trifluoromethyl)tetrahydrofuran-3-yl]-2,3-difluoro-phenyl]trifluoromethanesulfonate (200 mg, 0.4243 mmol), 4,4,5,5-tetramethyl-2-vinyl-1,3,2-dioxaborolane (130 mg, 0.8441 mmol), cesium carbonate (276 mg, 0.8471 mmol) and RuPhos-Pd-G3 (35 mg, 0.04185 mmol) was suspended in toluene (2 mL) and water (0.2 mL). The suspension was degassed (N$_2$/vac 3 cycles) and heated to 80° C. for 5 hours. The reaction mixture was cooled down to ambient temperature and partitioned between TBME (20 ml) and water (20 ml). The aqueous layer was further extracted with TBME (10 mL). The combined organic extracts were washed with brine (1×10 mL), dried (MgSO$_4$), filtered and concentrated in vacuo. Purification by flash chromatography (12 g SiO$_2$, 0 to 100% EtOAc in heptane) gave (2R,3S,4S,5R)-3-(3,4-difluoro-2-vinyl-phenyl)-4,5-dimethyl-5-(trifluoromethyl)tetrahydrofuran-2-carboxamide (50 mg, 30%) as a white solid. $^1$H NMR (500 MHz, Chloroform-d) δ 7.13 (ddd, J=17.3, 8.3, 3.3 Hz, 2H), 6.63-6.51 (m, 2H), 5.75-5.63 (m, 3H), 4.94 (d, J=10.6 Hz, 1H), 3.99 (dd, J=10.7, 8.1 Hz, 1H), 2.62 (p, J=7.7 Hz, 1H), 1.61 (s, 3H), 0.76 (d, J=7.6 Hz, 3H) ppm. ESI-MS m/z calc. 349.1101, found 350.2 (M+1)$^+$.

Step 4

Methyl 4-bromopyridine-2-carboxylate (35 mg, 0.1620 mmol), Xantphos (20 mg, 0.03457 mmol), cesium carbonate (85 mg, 0.2609 mmol), Pd(OAc)$_2$ (4 mg, 0.01782 mmol) and (2R,3S,4S,5R)-3-(3,4-difluoro-2-vinyl-phenyl)-4,5-dimethyl-5-(trifluoromethyl)tetrahydrofuran-2-carboxamide (30 mg, 0.08589 mmol) were combined in dioxane (3 mL). The suspension was degassed (N$_2$/vac 3 cycles) and heated at 90° C. under nitrogen for 4 hours. The reaction mixture was cooled down to ambient temperature and partitioned between TBME (10 ml) and water (10 ml). The aqeuous layer was further extracted with TBME (10 mL). The combined organic layers were washed with brine (1×10 mL), dried (MgSO$_4$), filtered and concentrated in vacuo. Purification by column chromatography (12 g SiO$_2$, 0 to 100% EtOAc in heptane gave methyl 4-[[(2R,3S,4S,5R)-3-(3,4-difluoro-2-vinyl-phenyl)-4,5-dimethyl-5-(trifluoromethyl)tetrahydrofuran-2-carbonyl]amino]pyridine-2-carboxylate (20 mg, 47%) as a white solid. ESI-MS m/z calc. 484.14215, found 485.4 (M+1)$^+$.

Step 5

To a solution of methyl 4-[[(2R,3S,4S,5R)-3-(3,4-difluoro-2-vinyl-phenyl)-4,5-dimethyl-5-(trifluoromethyl)tetrahydrofuran-2-carbonyl]amino]pyridine-2-carboxylate (8 mg, 0.01651 mmol) in methanol (1 mL) was added methanolic ammonia (235 μL of 7 M, 1.645 mmol) and the mixture was stirred at ambient temperature for 14 hours. The mixture was concentrated in vacuo. Purification by reverse phase preparative HPLC (Waters Sunfire C18, 10 M, 100 Å column, gradient 0%-100% B (solvent A: 0.1% NH$_3$ in water; solvent B: MeCN) over 14 minutes at 25 mL/min) gave 4-[[(2R,3S,4S,5R)-3-(3,4-difluoro-2-vinyl-phenyl)-4,5-dimethyl-5-(trifluoromethyl)tetrahydrofuran-2-carbonyl]amino]pyridine-2-carboxamide 149 (2.5 mg, 31%). $^1$H NMR (500 MHz, Methanol-d$_4$) δ 8.50 (dd, J=5.5, 0.6 Hz, 1H), 8.26 (dd, J=2.2, 0.6 Hz, 1H), 7.91 (dd, J=5.5, 2.2 Hz, 1H), 7.24-7.13 (m, 2H), 6.76 (dd, J=17.8, 11.6 Hz, 1H), 5.81-5.64 (m, 2H), 5.14 (d, J=10.4 Hz, 1H), 4.33 (dd, J=10.4, 8.0 Hz, 1H), 2.77 (p, J=7.7 Hz, 1H), 1.66 (d, J=1.2 Hz, 3H), 0.82 (dq, J=7.4, 2.3 Hz, 3H) ppm. ESI-MS m/z calc. 469.1425, found 470.4 (M+1)$^+$.

4-[[(2R,3S,4S,5R)-3-(2-ethyl-3,4-difluoro-phenyl)-4,5-dimethyl-5-(trifluoromethyl)tetrahydrofuran-2-carbonyl]amino]pyridine-2-carboxamide can be obtained by hydrogenation of compound 149 (e.g., Pd/C, H$_2$)

Example 32 rel-(2R,3S,4S,5R)-4-[[3-[2-(difluoromethoxy)-3,4-difluoro-phenyl]-4,5-dimethyl-5-(trifluoromethyl) tetrahydrofuran-2-carbonyl]amino]-5-methyl-pyridine-2-carboxamide (150) and rel-(2S,3R,4R,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide (151)

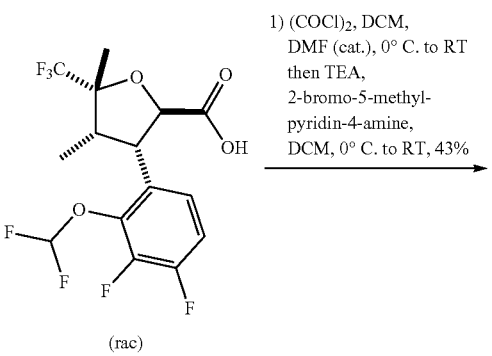

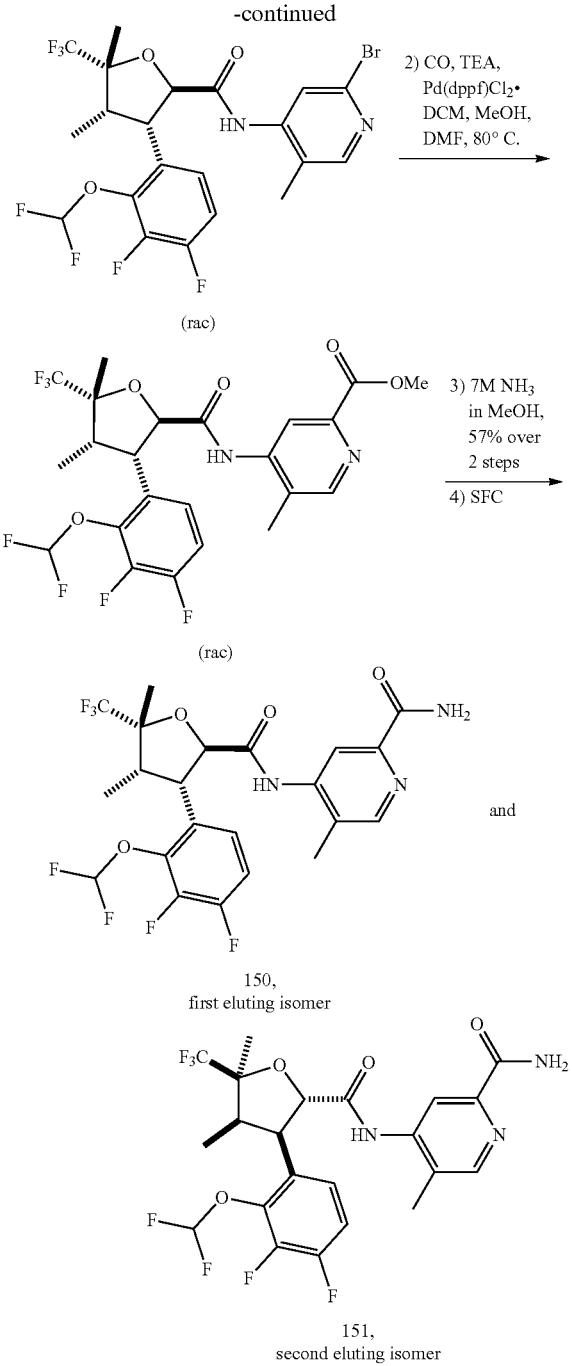

and TEA (40 µL, 0.2870 mmol) in DCM (750 µL). The resulting mixture was stirred and warmed to ambient temperature over 2 hours. The reaction mixture was quenched with 1 drop of water and MeOH (2 mL) and concentrated in vacuo. Purification by flash chromatography (4 g SiO$_2$, 0 to 100% EtOAc in hexanes) gave rac-(2R,3S,4S,5R)—N-(2-bromo-5-methyl-4-pyridyl)-3-[2-(difluoromethoxy)-3,4-difluoro-phenyl]-4,5-dimethyl-5-(trifluoromethyl)tetrahydrofuran-2-carboxamide (55 mg, 43%). ESI-MS m/z calc. 558.0389, found 561.4 (M+1)$^+$; 559.5 (M−1)$^-$.

Step 2 and 3

A suspension of rac-(2R,3S,4S,5R)—N-(2-bromo-5-methyl-4-pyridyl)-3-[2-(difluoromethoxy)-3,4-difluoro-phenyl]-4,5-dimethyl-5-(trifluoromethyl)tetrahydrofuran-2-carboxamide (50 mg, 0.08940 mmol), Pd(dppf)Cl$_2$DCM (7 mg, 0.008572 mmol) and TEA (30 µL, 0.2152 mmol) in DMF (700 µL) and MeOH (300 µL). CO was bubbled through the reaction mixture, the vessel sealed and heated to 80° C. for 20 hours. The reaction mixture was concentrated in vacuo to give methyl rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxylate, which was used as is in the next step. ESI-MS m/z calc. 538.13385, found 539.6 (M+1)$^+$; 537.7 (M−1)$^-$.

Methyl rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxylate (40 mg, 0.07429 mmol) was taken in a methanolic solution of ammonia (2.4 mL of 7 M, 16.80 mmol) in MeOH (2.4 mL). The mixture was stirred at ambient temperature. Upon completion, the mixture was concentrated in vacuo. Purification by flash chromatography gave rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide (22 mg, 57% over 2 steps). ESI-MS m/z calc. 523.1342, found 524.5 (M+1)$^+$; 522.6 (M−1)$^-$.

Step 4 rac-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide (20 mg, 0.038 mmol) was separated by chiral SFC using a Chiralpak AS-H column, 5 µm particle size, 25 cm×10 mm from Daicel on a Minigram SFC instrument from Berger Instruments to give:

First Eluting Isomer (rt=2.12 min): rel-(2R,3S,4S,5R)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide (150, 9 mg, 44%). $^1$H NMR (400 MHz, Methanol-d$_4$) δ 8.51-8.42 (m, 2H), 7.46-7.36 (m, 1H), 7.29 (td, J=9.4, 7.6 Hz, 1H), 6.95 (td, J=73.1, 1.2 Hz, 1H), 5.23 (d, J=10.8 Hz, 1H), 4.35 (dd, J=10.8, 7.9 Hz, 1H), 2.86 (p, J=7.6 Hz, 1H), 2.31 (s, 3H), 1.72 (d, J=1.1 Hz, 3H), 0.89 (dq, J=7.5, 2.4 Hz, 3H) ppm. ESI-MS m/z calc. 523.1342, found 524.4 (M+1)$^+$; 522.4 (M−1)$^-$.

Second Eluting Isomer (rt=3.44 min): rel-(2S,3R,4R,5S)-4-[[3-[2-(difluoromethoxy)-3,4-difluoro-phenyl]-4,5-dimethyl-5-(trifluoromethyl)tetrahydrofuran-2-carbonyl]amino]-5-methyl-pyridine-2-carboxamide (151, 7 mg, 35%). $^1$H NMR (400 MHz, Methanol-d$_4$) δ 8.54-8.42 (m, 2H), 7.41 (ddd, J=9.0, 5.4, 2.3 Hz, 1H), 7.29 (td, J=9.4, 7.6

Hz, 1H), 6.95 (td, J=73.0, 1.1 Hz, 1H), 5.23 (d, J=10.8 Hz, 1H), 4.35 (dd, J=10.8, 7.9 Hz, 1H), 2.86 (p, J=7.6 Hz, 1H), 2.31 (s, 3H), 1.72 (d, J=1.1 Hz, 3H), 0.89 (dq, J=7.5, 2.4 Hz, 3H) ppm. ESI-MS m/z calc. 523.1342, found 524.4 (M+1)⁺; 522.4 (M−1)⁻.

Example 33

4-[[(2R,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide (152)

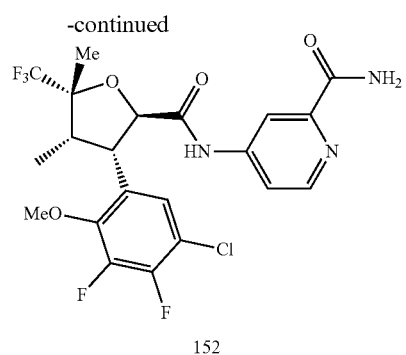

152

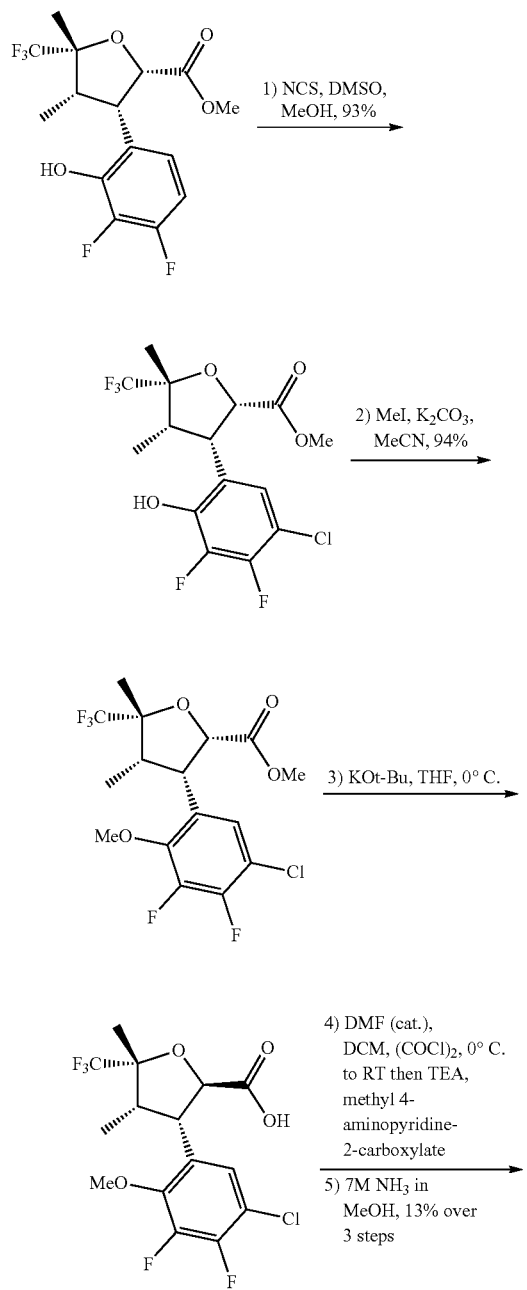

Step 1

NCS (1 g, 7.489 mmol) and DMSO (80 μL, 1.127 mmol) were added to a solution of methyl (2S,3S,4S,5R)-3-(3,4-difluoro-2-hydroxy-phenyl)-4,5-dimethyl-5-(trifluoromethyl)tetrahydrofuran-2-carboxylate (2 g, 5.645 mmol) in MeOH (18 mL) at room temperature and under air. The mixture was stirred until complete conversion. The reaction mixture was concentrated in vacuo. Purification by flash chromatography gave methyl (2S,3S,4S,5R)-3-(5-chloro-3,4-difluoro-2-hydroxy-phenyl)-4,5-dimethyl-5-(trifluoromethyl)tetrahydrofuran-2-carboxylate (2.05 g, 93%). ¹H NMR (500 MHz, Chloroform-d) δ 7.23-7.19 (m, 1H), 5.44 (d, J=4.8 Hz, 1H), 4.81 (d, J=5.9 Hz, 1H), 4.19 (dd, J=8.4, 5.8 Hz, 1H), 3.57 (s, 3H), 2.81-2.71 (m, 1H), 1.46 (d, J=1.3 Hz, 3H), 0.90-0.85 (m, 3H) ppm. ESI-MS m/z calc. 388.05008, found 386.9 (M−1)⁻.

Step 2

Potassium carbonate (2 g, 14.47 mmol) and iodomethane (650 μL, 10.44 mmol) were added to a mixture of methyl (2S,3S,4S,5R)-3-(5-chloro-3,4-difluoro-2-hydroxy-phenyl)-4,5-dimethyl-5-(trifluoromethyl)tetrahydrofuran-2-carboxylate (1.9 g, 4.888 mmol) in MeCN (20 mL) in a sealed tube. The mixture was heated to 75° C. for 2 h. The mixture was diluted with water/brine 1:1 (20 mL) and extracted with DCM. The organic extracts were dried (MgSO₄), filtered and concentrated in vacuo. Purification by flash chromatography gave methyl (2S,3S,4S,5R)-3-(5-chloro-3,4-difluoro-2-methoxy-phenyl)-4,5-dimethyl-5-(trifluoromethyl)tetrahydrofuran-2-carboxylate (1.85 g, 94%) as a yellow crystalline solid. ¹H NMR (500 MHz, Chloroform-d) δ 7.30 (ddq, J=7.6, 3.0, 1.6 Hz, 1H), 4.87 (d, J=5.9 Hz, 1H), 4.21 (dd, J=8.6, 6.0 Hz, 1H), 3.94 (d, J=2.1 Hz, 3H), 3.61 (s, 3H), 2.82 (p, J=7.8 Hz, 1H), 1.52 (d, J=1.3 Hz, 3H), 0.87 (dq, J=7.7, 2.0 Hz, 3H) ppm.

Step 3

Potassium tert-butoxide (450 mg, 4.010 mmol) was added to a stirred solution of methyl (2S,3S,4S,5R)-3-(5-chloro-3,4-difluoro-2-methoxy-phenyl)-4,5-dimethyl-5-(trifluoromethyl)tetrahydrofuran-2-carboxylate (800 mg, 1.986 mmol) in THF (40 mL) at 0° C. The mixture was stirred until complete conversion. The reaction mixture was quenched by addition of a saturated solution of ammonium chloride (3 mL) and partitioned with DCM (3 mL). The aqueous phase extracted with DCM (5 mL), and the pH was adjusted to 0 by addition of a 1 N solution of HCl. The aqueous phase was extracted twice with DCM (2×10 mL). The combined organic extracts were dried (MgSO$_4$), filtered and concentrated in vacuo to give (2R,3S,4S,5R)-3-(5-chloro-3,4-difluoro-2-methoxy-phenyl)-4,5-dimethyl-5-(trifluoromethyl)tetrahydrofuran-2-carboxylic acid, which was used in the next step without further purification. ESI-MS m/z calc. 388.05008, found 386.9 (M−1)$^-$.

Step 4 and 5

Oxalyl chloride (130 µL, 1.490 mmol) was added dropwise to a stirred solution of (2R,3S,4S,5R)-3-(5-chloro-3,4-difluoro-2-methoxy-phenyl)-4,5-dimethyl-5-(trifluoromethyl)tetrahydrofuran-2-carboxylic acid (250 mg, 0.643 mmol) and DMF (7 µL, 0.090 mmol) in DCM (2.5 mL). The reaction mixture was stirred at ambient temperature for 30 min. The solution was concentrated in vacuo. The residue was dissolved in DCM (1.5 mL) and added to a solution of methyl 4-aminopyridine-2-carboxylate (130 mg, 0.8544 mmol) and TEA (130 µL, 0.9327 mmol) in DCM (1.5 mL) at ambient temperature. The reaction mixture was stirred for 2 h. The mixture was quenched by addition of methanol (100 µL). Purification by flash chromatography gave methyl 4-[[(2R,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxylate which was used in the next step without further purification. ESI-MS m/z calc. 522.0981, found 523.0 (M+1)$^+$; 521.0 (M−1)$^-$.

Methyl 4-[[(2R,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxylate was taken in a methanolic solution of ammonia (20 mL of 7 M, 140.0 mmol) and stirred at ambient temperature. Upon completion, the mixture was concentrated in vacuo and freeze-dried (MeCN:water, 3:1) to give 4-[[(2R,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide 152 (45 mg, 13%). $^1$H NMR (500 MHz, DMSO-d$_6$) δ 10.62 (s, 1H), 8.50 (d, J=5.5 Hz, 1H), 8.33 (d, J=2.2 Hz, 1H), 8.06 (d, J=3.0 Hz, 1H), 7.86 (dd, J=5.6, 2.3 Hz, 1H), 7.62 (d, J=3.0 Hz, 1H), 7.42 (dd, J=7.7, 2.4 Hz, 1H), 5.18 (d, J=9.9 Hz, 1H), 4.24 (dd, J=10.1, 7.6 Hz, 1H), 3.97 (d, J=2.4 Hz, 3H), 2.78 (p, J=7.4 Hz, 1H), 1.62 (s, 3H), 0.76 (dd, J=7.6, 2.2 Hz, 3H) ppm. ESI-MS m/z calc. 507.09842, found 508.0 (M+1)$^+$; 506.1 (M−1)$^-$.

Intermediate A 3,3-Difluorobutan-2-one

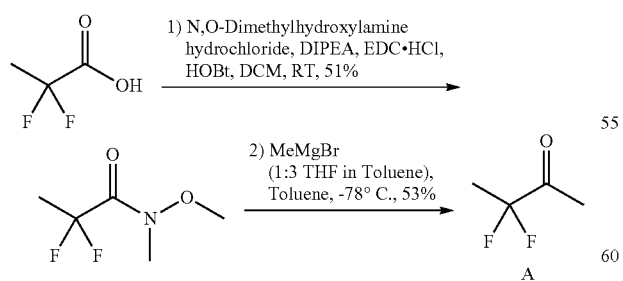

Step 1

To a stirred solution of 2,2-difluoropropanoic acid (100 g, 908.60 mmol) in DCM (1000 mL) was added DIPEA (348.74 g, 470 mL, 2.6983 mol) at 25° C. The reaction mixture was stirred for 15 minutes. EDC.HCl (209 g, 1.0902 mol) and HOBt (147 g, 1.0879 mol) were added and the reaction mixture was stirred for 15 minutes at 25° C. N,O-Dimethylhydroxylamine hydrochloride (133 g, 1.3635 mol) was added to the reaction which was stirred for 16 hrs. Water was added and the mixture was extracted with DCM (2×200 ml). The combined organic layers were washed with water (2×200 ml) and brine (200 ml). Purification by distillation under vacuo (192-196° C.) gave 2,2-difluoro-N-methoxy-N-methyl-propanamide (70.5 g, 51%) as a colourless oil. $^1$H NMR (400 MHz, Chloroform-d) δ 3.72 (s, 3H), 3.24 (s, 3H), 1.81 (t, J=19.20 Hz, 3H) ppm.

Step 2

MeMgBr (1:3 THF in toluene) (489 mL of 1.4 M, 684.60 mmol) was slowly added dropwise to a stirred solution of 2,2-difluoro-N-methoxy-N-methyl-propanamide (70 g, 457.14 mmol) in toluene (350 mL) at −78° C. The reaction mixture was stirred for 2 hours at −78° C. The mixture was quenched by addition of HCl (685 mL of 2 M, 1.3700 mol) at 0° C. Cold water was added. The organic layer was washed with water. Purification by distillation (100° C.) gave 3,3-difluorobutan-2-one (26.3 g, 53%). $^1$H NMR (400 MHz, Chloroform-d) δ 2.33 (s, 3H), 1.69 (t, J=19.12 Hz, 3H) ppm.

Intermediate B

2-[2-(Difluoromethoxy)-4-fluoro-phenyl]-4,4,5,5-tetramethyl-1,3,2-dioxaborolane

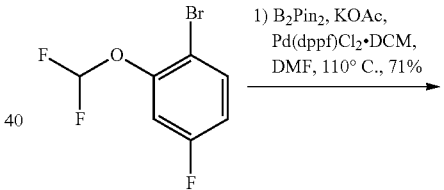

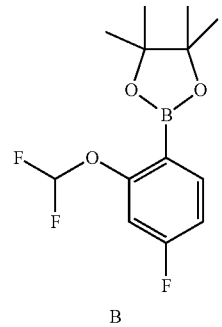

Step 1

1-Bromo-2-(difluoromethoxy)-4-fluoro-benzene (10 g, 41.49 mmol), bis(pinacol)diboron (11.00 g, 43.32 mmol) and Potassium acetate (12.00 g, 122.3 mmol) were mixed in dry DMF (100 mL). The mixture was degassed (Vac/N$_2$ 3 cycles). Pd(dppf)Cl$_2$DCM (3.4 g, 4.163 mmol) was added, and the reaction mixture was degassed (Vac/$N_2$ 3 cycles). The reaction mixture was heated to 110° C. for 18 hours. The reaction mixture was diluted with water (300 mL) and EtOAc (150 mL), stirred for 30 min, filtered through a pad of celite, washing with EtOAc. The organic phase was separated and washed with water (2×150 ml) and brine (2×150 ml), dried ($MgSO_4$), filtered and concentrated in vacuo. Purification on a pad of florisil (200 g, 0 to 10% DCM in hexanes) gave 2-[2-(difluoromethoxy)-4-fluoro-phenyl]-4,4,5,5-tetramethyl-1,3,2-dioxaborolane (8.43 g, 71%) as a yellow oil. $^1$H NMR (500 MHz, DMSO-$d_6$) δ 7.71 (dd, J=8.4, 7.3 Hz, 1H), 7.28-7.96 (m, 3H), 1.28 (s, 12H); $^{19}$F NMR (471 MHz, DMSO-$d_6$) δ −82.70 (d, J=74.5 Hz), −106.63 (s) ppm.

The following intermediates were made using a method similar to that described in Intermediate B except that 1,4-dioxane was used as the solvent in place of DMF:

4,4,5,5-tetramethyl-1,3,2-dioxaborolane (1.6 mL, 11.03 mmol) and TEA (2.5 mL, 17.94 mmol). The mixture was degassed by bubbling nitrogen through for 5 minutes. The reaction was heated at 100° C. in a sealed vial for 3 hours. The reaction was concentrated in vacuo and loaded onto solid support. Purification by flash chromatography (0 to 25% EtOAc in heptane) gave 2-[3-(difluoromethyl)-4-fluoro-2-methoxy-phenyl]-4,4,5,5-tetramethyl-1,3,2-dioxaborolane (1.15 g, 53%) as a white solid. $^1$H NMR (400 MHz, Chloroform-d) δ 7.84 (ddt, J=8.2, 6.9, 1.2 Hz, 1H), 6.99 (td, J=53.9, 1.1 Hz, 1H), 6.91 (dd, J=9.7, 8.5 Hz, 1H), 3.90 (s, 3H), 1.36 (s, 12H). ESI-MS m/z calc. 302.1301, Retention time: 1.03 minutes.

| Cmpd No. | Compound Name | LC/MS | NMR (shifts in ppm) |
| --- | --- | --- | --- |
| M | 2-[2-(difluoromethoxy)-4-fluoro-3-methyl-phenyl]-4,4,5,5-tetramethyl-1,3,2-dioxaborolane | | $^1$H NMR (400 MHz, DMSO-$d_6$) δ 7.57 (t, J = 7.76 Hz, 1H), 7.17 (t, J = 8.72 Hz, 1H), 6.95 (t, J = 75.08 Hz, 1H) 2.16 (s, 3H) 1.32 (s, 12H) ppm. |
| N | 4-methoxy-5-(4,4,5,5-tetramethyl-1,3,2-dioxaborolan-2-yl)-2-(trifluoromethyl)pyridine | | |

Intermediate C 2-(3-(Difluoromethyl)-4-fluoro-2-methoxyphenyl)-4,4,5,5-tetramethyl-1,3,2-dioxaborolane Intermediate D 2-(3-Chloro-4-fluoro-2-methoxyphenyl)-4,4,5,5-tetramethyl-1,3,2-dioxaborolane

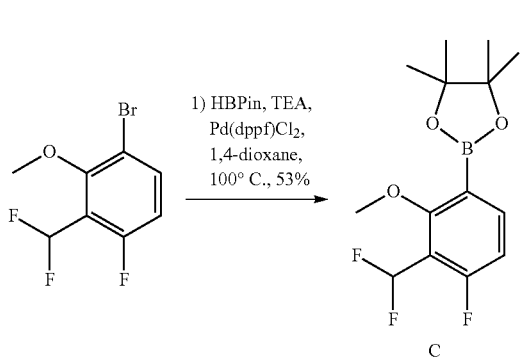

C

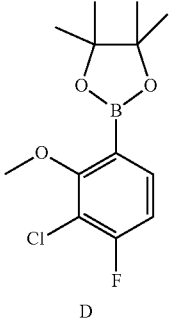

D

Step 1

To a solution of 1-bromo-3-(difluoromethyl)-4-fluoro-2-methoxy-benzene (1.60 g, 6.274 mmol) and Pd(PPh$_3$)$_2$Cl$_2$ (200 mg, 0.2849 mmol) in 1,4-dioxane (25 mL) was added Step 1

An oven dried 500 ml three necked flask was flanked with a condenser and a thermometer. Magnesium (321 mg, 13.21 mmol) turnings were added. The flask was evacuated three times with vac/$N_2$ and then left under vacuum for thirty minutes while the flask was heated to 65° C. Using a nitrogen flushed needle, THF (12.5 mL) was added to the flask and the mixture was flushed once again with nitrogen.

Iodine (3 mg, 0.01182 mmol) was added to the reaction. The mixture was stirred at 65° C. until the reaction turned into a clear pale yellow colour (1 hour). The mixture was taken off the heat. Pinacolborane (1.74 g, 13.60 mmol) was added dropwise. Gas evolution was observed. A solution of 1-bromo-3-chloro-4-fluoro-2-methoxy-benzene (2500 mg, 10.44 mmol) in THF (12.5 mL) was added dropwise. The reaction mixture was left to cool to ambient temperature over 30 minutes and stirred for 1.5 h at ambient temperature. The reaction mixture was added carefully dropwise to a stirred solution of 1 M HCl (50 ml) (vigorous effervescence observed) and left to stand for 10 minutes until all the Mg solids had dissolved. The mixture was diluted with TBME. The aqueous layer was separated and extracted with TBME (×2), passed through a phase separator cartridge and concentrated in vacuo to give 2-(3-chloro-4-fluoro-2-methoxy-phenyl)-4,4,5,5-tetramethyl-1,3,2-dioxaborolane (2.8152 g, 94%). $^1$H NMR (500 MHz, DMSO-d$_6$) δ 7.57 (dd, J=8.4, 7.0 Hz, 1H), 7.24-7.15 (m, 1H), 3.81 (s, 3H), 1.30 (s, 12H). ESI-MS m/z calc. 286.09433, found 287.0 (M+1)$^+$; Retention time: 1.06 minutes.

The following intermediate was made using a method similar to that described in Intermediate D using 1-bromo-4-fluoro-2-methoxy-3-methyl-benzene as starting material:

| Cmpd No. | Compound Name | LC/MS | NMR (shifts in ppm) |
|---|---|---|---|
| O | 2-(4-fluoro-2-methoxy-3-methyl-phenyl)-4,4,5,5-tetramethyl-1,3,2-dioxaborolane | | $^1$H NMR (400 MHz, DMSO-d$_6$) δ 7.44 (t, J = 7.9 Hz, 1H), 6.93 (t, J = 8.7 Hz, 1H), 3.72 (s, 3H), 2.11 (d, J = 2.1 Hz, 3H), 1.29 (s, 12H) ppm. $^{19}$F NMR (376 MHz, DMSO-d$_6$) δ −110.32 (ddt, J = 9.5, 7.3, 2.2 Hz) ppm. |

Intermediate E (4-Fluoro-2-methoxy-3-methylphenyl)boronic acid

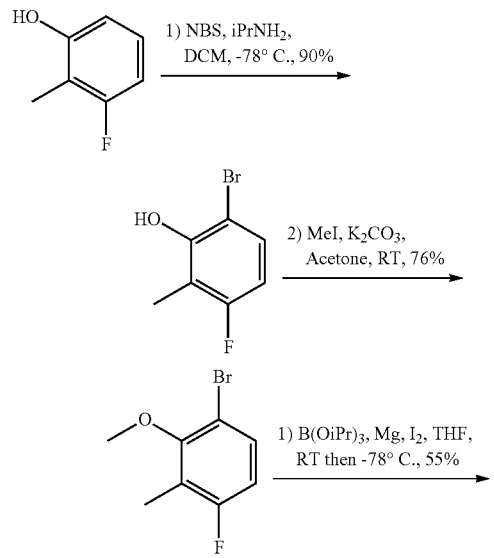

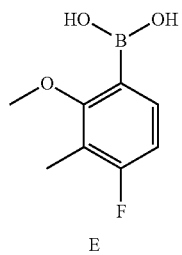

Step 1

Isopropylamine (23.460 g, 34.5 mL, 396.89 mmol) was slowly added to a stirred solution of 3-fluoro-2-methyl-phenol (50 g, 396.42 mmol) in DCM (2.5 L). The reaction mixture was cooled to −78° C. N-bromosuccinimide (NBS) (70 g, 393.29 mmol) was added portion wise over 2 hrs 10 min and the mixture was stirred for a further 30 min. The mixture was warmed up to 25° C. 2N HCl (500 ml) was added and the mixture was stirred for 15 min. The organic layer was separated and concentrated in vacuo, keeping the water bath at 15° C. Hexane (500 ml) was added to the residue and the mixture was stirred for 10 min. The mixture was filtered and the liquors were concentrated in vacuo, keeping the water bath at 15° C. to give 6-bromo-3-fluoro-2-methyl-phenol (73 g, 90%) as a light brown oil. $^1$H NMR (400 MHz, Chloroform-d) δ 7.24-7.21 (m, 1H), 6.55 (t, J=8.8 Hz, 1H), 5.61 (s, 1H), 2.20 (s, 3H) ppm.

Step 2

To a stirred solution of 6-bromo-3-fluoro-2-methyl-phenol (40 g, 195.10 mmol) in acetone (400 mL) at ambient temperature was added potassium carbonate (135 g, 976.80 mmol). The reaction mixture was stirred for 10 min at 25° C. Methyl iodide (39 g, 17.105 mL, 274.77 mmol) was added dropwise over 10 min and the mixture was stirred for 16 hrs at 25° C. The reaction mixture was filtered and the solid residues washed with acetone (50 ml). The mother liquors were concentrated at 15° C. under reduced pressure. Hexane (200 ml) was added and the mixture was stirred for 15 minutes. The solid was collected and washed with hexane (8 ml). The mother liquors were concentrated under reduced pressure at 15° C. Purification by distillation (520 mm Hg, 192-196° C.) gave 1-bromo-4-fluoro-2-methoxy-3-methyl-benzene (32.4 g, 76%). $^1$H NMR (400 MHz, Chloroform-d) δ 7.33-7.30 (m, 1H), 6.72 (t, J=8.7 Hz, 1H), 3.80 (s, 3H), 2.23 (s, 3H) ppm.

Step 3

Iodine (50 mg, 0.1970 mmol) was added at 25° C. to a stirred mixture of Mg turnings (5 g, 205.72 mmol) in THF (50 ml). The mixture was stirred until the reaction turned into a clear pale yellow colour. 1-bromo-4-fluoro-2-methoxy-3-methyl-benzene (2.5 g, 11.4 mmol) was added dropwise at ambient temperature. When reaction initiation was observed, the remaining solution of 1-bromo-4-fluoro-2-methoxy-3-methyl-benzene (22.5 g, 102.71 mmol) in THF (200 ml) was added dropwise. The mixture was stirred for 40 minutes. Reaction was cooled down to −78° C. and triisopropylborate (64.385 g, 79 mL, 342.34 mmol) was added dropwise. The mixture was warmed up to ambient temperature and stirred for 16 hrs. The reaction was quenched by addition of a 2N aqueous solution of HCl (25 ml) and stirred for 15 minutes. The mixture was diluted with water (125 ml) and extracted with ethyl acetate (2×250 ml). The organic layer was separated, washed with water (250 ml), dried ($Na_2SO_4$) and concentrated in vacuo. Hexane (2 5 ml) was added to the residue at 0° C. and the mixture was stirred for 5 minutes. The resulting solid was filtered, washed with 10 ml of chilled hexane and dried to give (4-fluoro-2-methoxy-3-methyl-phenyl)boronic acid (11.5 g, 55%). $^1$H NMR (400 MHz, DMSO-$d_6$) δ 7.96 (br s, 2H), 7.32 (t, J=8.0 Hz, 1H), 6.88 (t, J=8.7 Hz, 1H), 3.75 (s, 3H), 2.11 (s, 3H) ppm.

Intermediate F

1-Bromo-3-ethyl-4-fluoro-2-methoxy-benzene

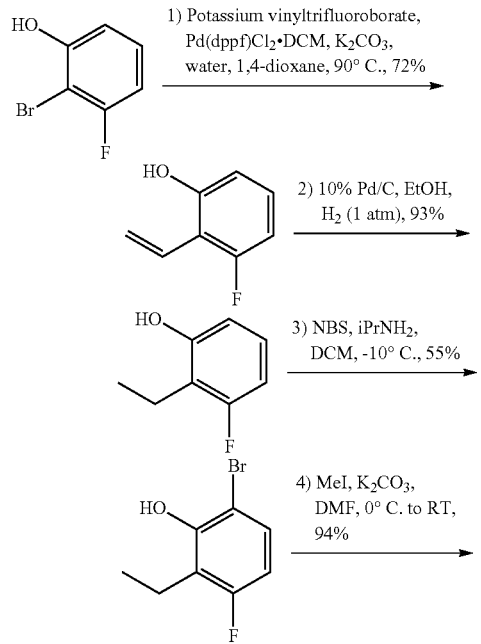

Step 1

Pd(dppf)$Cl_2$.DCM (7.5 g, 9.1840 mmol) was added to a stirred mixture of 2-bromo-3-fluoro-phenol (25 g, 130.89 mmol), potassium vinyltrifluoroborate (52 g, 388.20 mmol) and $K_2CO_3$ (55 g, 397.96 mmol) in a mixture of 1,4-dioxane (250 mL) and water (25 mL). The mixture was degassed by bubbling through nitrogen gas for 15 minutes. The mixture was heated to 90° C. for 16 h. The reaction mixture was filtered through a pad of celite. The collected mother liquors were diluted with water (300 mL). The aqueous phase was extracted with EtOAc (2×50 mL). The combined organic extracts were dried (MgSO$_4$), filtered and concentrated in vacuo. Purification by flash chromatography (SiO$_2$, 0-1% EtOAc in hexanes) gave 3-fluoro-2-vinyl-phenol (14.5 g, 72%) as a colourless oil. $^1$H NMR (400 MHz, Chloroform-d) δ 7.06 (q, J=8.16 Hz, 1H), 6.80-6.73 (m, 1H), 6.66-6.61 (m, 2H), 5.88 (d, J=18.04, 1H), 5.60 (d, J=11.7, 1H), 5.48 (s, 1H) ppm.

Step 2

Palladium on carbon (2.9 g, 10% w/w, 2.3877 mmol) was added to a stirred solution of 3-fluoro-2-vinyl-phenol (14.5 g, 94.470 mmol) in ethanol (145 mL). The mixture was degassed by bubbling through nitrogen gas for 10 minutes. The reaction mixture was stirred under a balloon pressure of hydrogen for 6 h. The mixture was filtered through celite, washing with ethanol, and the filtrate concentrated in vacuo. Purification by flash chromatography (SiO$_2$, 0-1% EtOAc in hexanes) gave 2-ethyl-3-fluoro-phenol (13 g, 93%) as a colourless oil. $^1$H NMR (400 MHz, Chloroform-d) δ 7.0 (q, J=7.96 Hz, 1H), 6.62 (t, J=8.7 Hz, 1H), 6.54 (d, J=8.08 Hz, 1H), 4.90 (br s, 1H), 2.66 (q, J=7.24 Hz, 2H), 1.17 (t, J=7.52 Hz, 3H) ppm.

Step 3

NBS (14 g, 78.659 mmol) was added portion wise to a stirred solution of 2-ethyl-3-fluoro-phenol (13 g, 88.117 mmol) and isopropylamine (4.6920 g, 6.9 mL, 79.377 mmol) in DCM (274 mL) at −10° C. The reaction mixture was stirred for 15 minutes. The reaction was quenched by addition of a 2N aqueous solution of HCl. The mixture was extracted with DCM (2×500 mL). The combined organic layers were dried (Na$_2$SO$_4$) and concentrated in vacuo. Purification by flash chromatography (SiO$_2$, 0-1% EtOAc in hexanes) gave 6-bromo-2-ethyl-3-fluoro-phenol (11 g, 55%) as a colourless oil. $^1$H NMR (400 MHz, Chloroform-d) δ 7.23 (dd, J=4.76 Hz, J=5.8 Hz, 1H), 6.55 (t, J=8.72 Hz, 1H), 5.6 (d, J=1.64 Hz, 1H), 2.74 (q, J=7.08 Hz, 2H), 1.16 (t, J=7.4 Hz, 3H) ppm.

Step 4

Methyl iodide (13.680 g, 6 mL, 96.379 mmol) was added dropwise at 0° C. to a stirred solution of 6-bromo-2-ethyl-3-fluoro-phenol (11 g, 48.208 mmol) and K$_2$CO$_3$ (16.5 g, 119.39 mmol) in DMF (110 mL). The reaction mixture was stirred for 12 h at ambient temperature. The mixture was diluted with ice water (250 mL). The aqueous phase was extracted with hexane (3×500 mL). The organic layer was separated, dried (MgSO$_4$), filtered and concentrated in vacuo. Purification by flash chromatography (SiO$_2$, 0-1% EtOAc in hexanes) gave 1-bromo-3-ethyl-4-fluoro-2-methoxy-benzene (11 g, 94%) as a colourless oil. $^1$H NMR (400 MHz, Chloroform-d) δ 7.32 (dd, J=6.08 Hz, J=6.04 Hz 1H), 6.72 (t, J=8.84 Hz, 1H), 3.84 (s, 3H), 2.70 (q, 2H), 1.18 (t, J=7.52 Hz, 3H) ppm.

Intermediate G

3-Bromo-6-(difluoromethyl)-2-methoxypyridine

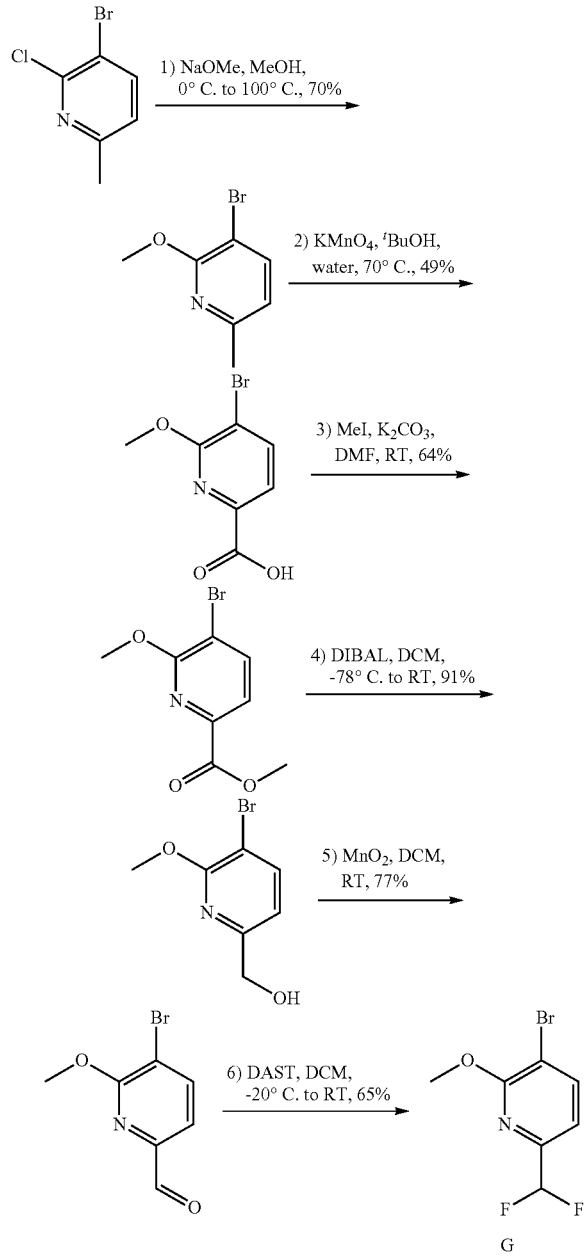

Step 1

Sodium methoxide (20 mL of 25% w/v solution in MeOH, 92.552 mmol) was added at 0° C. to a stirred solution of 3-bromo-2-chloro-6-methyl-pyridine (8 g, 38.747 mmol) in MeOH (50 mL) in a sealed tube. The reaction mixture was heated at 100° C. for 16 h. The reaction mixture was concentrated in vacuo. The residue was diluted with water (100 mL) and extracted with EtOAc (3×100 mL). The combined organic layers were dried ($Na_2SO_4$), filtered and concentrated in vacuo to give 3-bromo-2-methoxy-6-methyl-pyridine (5.5 g, 70%) as a colourless oil. $^1$H NMR (400 MHz, DMSO-$d_6$) δ 7.82 (d, J=7.7 Hz, 1H), 6.76 (d, J=7.7 Hz, 1H), 3.88 (s, 3H), 2.35 (s, 3H) ppm. ESI-MS m/z calc. 200.9789, found 202.01 (M+1)$^+$; Retention time: 1.69 minutes.

Step 2

$KMnO_4$ (13 g, 82.261 mmol) was added at ambient temperature to a stirred solution of 3-bromo-2-methoxy-6-methyl-pyridine (5.5 g, 27.221 mmol) in tert-butanol (150 mL) and water (300 mL). The reaction mixture was heated at 70° C. for 16 h. The reaction mixture was quenched by addition of a 1M aqueous solution of HCl (80 mL). The resulting mixture was stirred for 30 min, filtered and washed with EtOAc (2×100 mL). The mother liquors were extracted with EtOAc (2×50 mL). The combined organic layers were washed with a 0.5 N aqueous solution of NaOH (2×100 mL). The aqueous layer was collected, acidified by addition of a 12N aqueous solution of HCl and extracted with DCM (2×100 mL). The combined organic extracts were washed with brine, dried ($Na_2SO_4$), filtered and concentrated in vacuo to give 5-bromo-6-methoxy-pyridine-2-carboxylic acid (3.1 g, 49%) as white solid. $^1$H NMR (400 MHz, DMSO-$d_6$) δ 13.27 (br s, 1H), 8.19 (d, J=7.9 Hz, 1H), 7.57 (d, J=7.9 Hz, 1H), 3.98 (s, 3H) ppm. ESI-MS m/z calc. 230.9531, found 232.0 (M+1)$^+$; Retention time: 1.34 minutes.

Step 3

Sodium carbonate (1.5 g, 14.153 mmol) was added to a stirred solution of 5-bromo-6-methoxy-pyridine-2-carboxylic acid (3 g, 12.929 mmol) in DMF (40 mL). Methyl iodide (3.8760 g, 1.7 mL, 27.308 mmol) was then added and the mixture was stirred at ambient temperature for 16 h. The reaction mixture was quenched by addition of ice cold water (50 mL). The aqueous phase was extracted with ethyl acetate (3×50 mL). The combined organic layers were washed with water (2×100 mL), brine (50 mL), dried ($Na_2SO_4$), filtered and concentrated in vacuo to give methyl 5-bromo-6-methoxy-pyridine-2-carboxylate (2.02 g, 63%) as an off-white solid. $^1$H NMR (400 MHz, DMSO-$d_6$) δ 8.22 (d, J=7.8 Hz, 1H), 7.59 (d, J=7.8 Hz, 1H), 3.98 (s, 3H), 3.87 (s, 3H) ppm. ESI-MS m/z calc. 244.9688, found 246.1 (M+1)$^+$; Retention time: 3.21 minutes.

Step 4

Diisobutylaluminum hydride (14 mL of 25% w/v solution in toluene, 24.610 mmol) was added at −78° C. to a stirred solution of methyl 5-bromo-6-methoxy-pyridine-2-carboxylate (2 g, 8.128 mmol) in DCM (80 mL). The reaction mixture was stirred at ambient temperature for 1 h. The reaction mixture was quenched by addition of a saturated aqueous solution of sodium tartrate (50 mL). The mixture was stirred for 30 min then extracted with DCM (3×100 mL). The combined organic layers were dried ($Na_2SO_4$), filtered and concentrated in vacuo to give (5-bromo-6-methoxy-2-pyridyl)methanol (1.62 g, 91%) as a white solid. $^1$H NMR (400 MHz, DMSO-$d_6$) δ 7.99 (d, J=7.8 Hz, 1H), 7.00 (d, J=7.6 Hz, 1H), 5.45 (t, J=11.8 Hz, 1H), 4.45 (d, J=5.9 Hz, 2H), 3.89 (s, 3H) ppm. ESI-MS m/z calc. 216.9738, found 218.0 (M+1)$^+$; Retention time: 2.93 minutes.

Step 5

$MnO_2$ (8 g, 92.021 mmol) was added to a stirred solution of (5-bromo-6-methoxy-2-pyridyl)methanol (1.6 g, 7.3378 mmol) in DCM (80 mL). The reaction mixture was stirred at ambient temperature for 16 h. The reaction mixture was filtered and concentrated in vacuo to give 5-bromo-6-methoxy-pyridine-2-carbaldehyde (1.22 g, 77%) as off-white solid. $^1$H NMR (400 MHz, DMSO-d$_6$) δ 9.88 (s, 1H), 8.29 (d, J=7.7 Hz, 1H), 7.49 (d, J=7.7 Hz, 1H), 4.03 (s, 3H) ppm.

Step 6

DAST (1.9740 g, 1.5 mL, 12.246 mmol) was slowly added at −20° C. to a stirred solution of 5-bromo-6-methoxy-pyridine-2-carbaldehyde (1.2 g, 5.5547 mmol) in DCM (30.000 mL). The reaction mixture was stirred at ambient temperature for 16 h. The reaction mixture was quenched by addition of ice-water. The pH of the solution was adjusted to 8-10 by addition of solid sodium hydrogen carbonate. The organic phase was collected, washed with water and brine, dried (Na$_2$SO$_4$), filtered and concentrated in vacuo. Purification by flash chromatography (SiO$_2$, 100% hexanes) gave 3-bromo-6-(difluoromethyl)-2-methoxy-pyridine (900 mg, 65%) as pale yellow oil. $^1$H NMR (400 MHz, DMSO-d$_6$) δ 8.22 (d, J=7.8 Hz, 1H), 7.23 (d, J=7.7 Hz, 1H), 7.03-6.75 (m, 1H), 3.96 (s, 3H) ppm.

Intermediate H

Ethyl 4-amino-5-fluoropicolinate

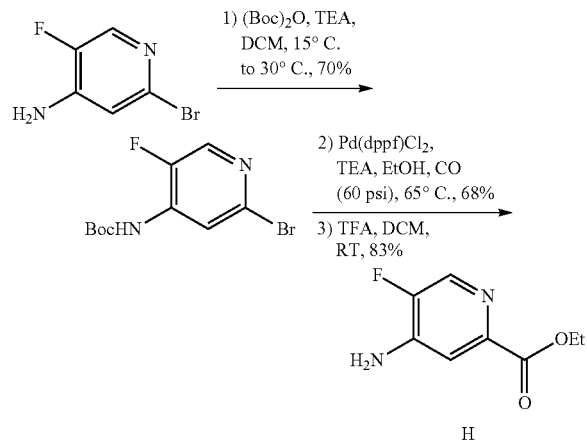

Step 1

TEA (66.17 g) was added to a mixture of 2-bromo-5-fluoropyridin-4-amine (25 g, 0.131 mol) in DCM (250 mL) at 25-30° C. under a nitrogen atmosphere. The reaction mixture was cooled down to 15-20° C. Boc anhydride (57.13 g, 0.262 mol) was slowly added over 15 to 30 min. A 3 to 5° exotherm was observed. The temperature was raised to 25-30° C. and maintained for 24-36 h. Further TEA (13.23 g, 0.131 mol) and Boc anhydride (14.27 g, 0.065 mol) were added and the mixture was stirred for a further 12-18 h at 25-30° C. The reaction mixture was quenched by slow addition of water (250 mL) at 10-20° C. over 1-2 h. The aqueous layer was separated and extracted with DCM (125 mL×2). The combined organic extracts were washed with a 10% aqueous solution of NaCl (250 mL), dried (Na$_2$SO$_4$), filtered and concentrated in vacuo. EtOAc (25 ml) was added to the brown colour solid and the mixture was stirred for 10-15 min at 25-30° C. Hexane (50.0 mL) was slowly added at 25-30° C., which caused a solid to precipitate. The mixture was stirred for 30 to 45 min at 25-30° C. The solid was filtered, washed with hexane (12.5 mL) and dried under vacuum for 2-3 h at 40-45° C. to give tert-butyl (2-bromo-5-fluoropyridin-4-yl)carbamate (26.68 g, 70% yield). $^1$H NMR (400 MHz, Chloroform-d) δ 8.33 (d, J=6.0 Hz, 1H), 8.11 (d, J=2.4 Hz, 1H), 6.91 (br s, 1H), 1.56 (s, 9H) ppm.

Step 2

Pd(dppf)Cl$_2$ (7.54 g, 10.3 mmol) and TEA (15.64 g, 154.5 mmol) were added to a mixture of tert-butyl (2-bromo-5-fluoropyridin-4-yl)carbamate (15 g, 51.25 mmol) in ethanol (300 mL) at 25-30° C. under nitrogen atmosphere in a Parr bottle. The resulting mixture was shaken in the Parr hydrogenator under a carbon monoxide pressure of 60 psi at 75-80° C. for 16-20 h. The reaction mixture was cooled down to 25-30° C. The mixture was filtered through a pad of celite and washed with ethanol (150 mL). The filtrates were concentrated concentrated in vacuo at 40-45° C. Purification by flash chromatography (SiO$_2$, 0 to 10% EtOAc in hexanes) gave ethyl 4-((tert-butoxycarbonyl)amino)-5-fluoropicolinate (10 g, 68%). $^1$H NMR (400 MHz, Chloroform-d) δ 8.92 (d, J=6.4 Hz, 1H), 8.46 (d, J=2.0 Hz, 1H), 6.95 (br s, 1H), 4.46 (q, J=7.2 Hz, 2H), 1.56 (s, 9H), 1.43 (t, J=7.2 Hz, 3H) ppm.

Step 3

Ethyl 4-((tert-butoxycarbonyl)amino)-5-fluoropicolinate (14 g, 49.25 mmol) was stirred at ambient temperature in a mixture of TFA (56 mL) and DCM (140 mL). Upon reaction completion, the mixture was concentrated in vacuo and the pH of the solution was adjusted to 8-9 by addition of a saturated solution of sodium bicarbonate. The aqueous phase was extracted with ethyl acetate. The organic extracts were concentrated in vacuo to give ethyl 4-amino-5-fluoropicolinate (7.53 g, 83%). $^1$H NMR (400 MHz, DMSO-d$_6$) δ 8.17 (d, J=3.2 Hz, 1H), 7.45 (d, J=7.2 Hz, 1H), 6.50 (br s, 1H), 4.26 (q, J=6.8 Hz, 2H), 1.29 (t, J=7.2 Hz, 3H) ppm. ESI-MS m/z calc. 184.0648, found 184.84 (M+1)$^+$.

Intermediate I

Methyl 4-chloro-6-fluoropicolinate

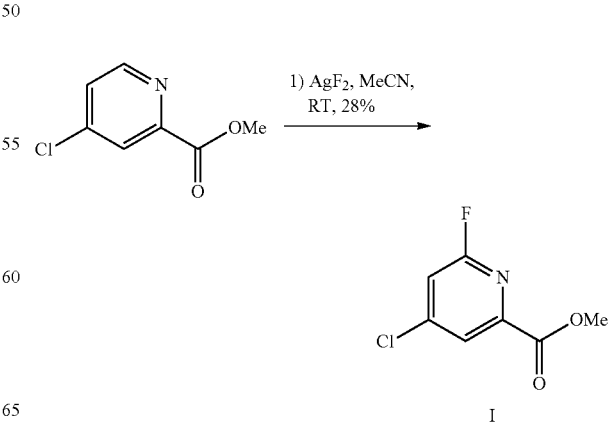

Step 1

To a stirred mixture of methyl 4-chloropyridine-2-carboxylate (625 mg, 3.643 mmol) in acetonitrile (15 mL) was added silver fluoride (1.7 g, 11.655 mmol) in one portion at room temperature. The reaction mixture was stirred at room temperature for 18 h. Additional silver fluoride (530 mg, 3.634 mmol) was added and the stirring was continued for an additional 24 h. The reaction mixture was poured into a saturated aqueous solution of sodium bicarbonate (50 mL) and ethyl acetate (50 mL) and filtered through a pad of Celite. The organic extracts were washed with brine (20 mL), dried ($Na_2SO_4$) and concentrated in vacuo. Purification by flash chromatography (25 g $SiO_2$, 0 to 100% EtOAc in heptane) gave methyl 4-chloro-6-fluoropicolinate (200 mg, 28%) as a white solid. H NMR (400 MHz, Chloroform-d) δ 8.03 (dd, J=1.4, 0.9 Hz, 1H), 7.18 (dd, J=2.7, 1.8 Hz, 1H), 4.00 (s, 3H) ppm.

Intermediate J

Methyl 4-aminopicolinate-5-d

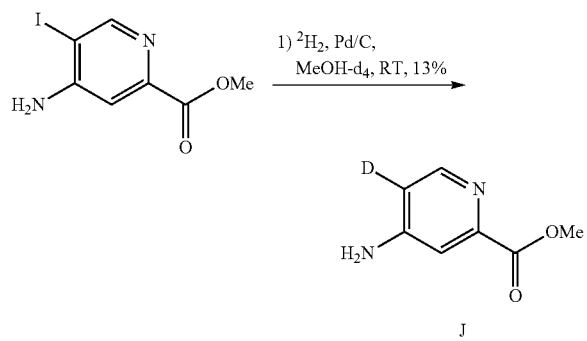

Step 1

A mixture of methyl 4-amino-5-iodo-pyridine-2-carboxylate (1 g, 3.5965 mmol), $K_2CO_3$ (0.5 g, 3.6178 mmol) and palladium on carbon (200 mg, 5% w/w, 0.0940 mmol) in methanol-d4 (8 mL) was stirred at room temperature under an atmosphere of deuterium gas (balloon) for 20 h. The mixture was filtered through Celite, washing with methanol and concentrated in vacuo to give a white solid. Purification by reverse phase chromatography (Biotage Isolera, 30 g, SiliaSep C18 Monomeric 25 μm Silicycle flash cartridge, 0 to 100% acetonitrile containing 0.1% ammonium hydroxide in water containing 0.1% ammonium hydroxide) to give methyl 4-amino-5-deuterio-pyridine-2-carboxylate (77 mg, 13%) as a white solid. $^1$H NMR (400 MHz, DMSO-$d_6$) δ 8.03 (s, 1H), 7.18 (s, 1H), 6.29 (br s, 2H), 3.77 (s, 3H) ppm. ESI-MS m/z calc. 153.0649, found 154.08 (M+1)$^+$.

Intermediate K

Methyl 4-chloropicolinate-3-d

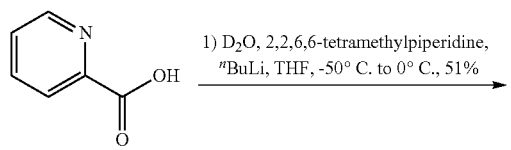

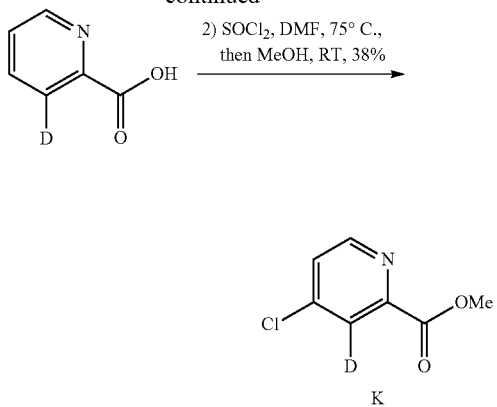

Step 1

A solution of 2,2,6,6-tetramethylpiperidine (3.442 g, 4.147 mL, 24.369 mmol) in THF (40 mL) was cooled to −50° C. $^n$BuLi (1.6M in hexanes) (20.307 mL of 1.6 M, 32.492 mmol) was added dropwise over 10 min. The reaction mixture was stirred for 5 min, then pyridine-2-carboxylic acid (1 g, 8.1229 mmol) was added. After stirring for 10 min, the reaction mixture was allowed to warm to 0° C. and deuterium oxide (813.40 mg, 0.813 mL, 40.614 mmol) was added. The reaction mixture was stirred for 30 min. The mixture was concentrated in vacuo to give a pale brown solid which was stirred in a 9:1 mixture of DCM and MeOH (20 mL) for 30 min. The solid was filtered and the filtrates concentrated in vacuo to give a first crop of 3-deuteriopyridine-2-carboxylic acid (353 mg, 32%). The solid was subjected a second time to the same treatment to give a second crop of 3-deuteriopyridine-2-carboxylic acid (214 mg, 19%). $^1$H NMR (400 MHz, Methanol-d4) δ 8.53 (q, J=2.1 Hz, 1H), 7.87 (dd, J=7.3, 1.4 Hz, 1H), 7.43 (dd, J=7.6, 4.8 Hz, 1H) ppm. 93% deuterium incorporation observed by NMR.

Step 2

DMF (47.200 mg, 0.05 mL, 0.6457 mmol) was added at 45° C. to a solution of thionyl chloride (1.957 g, 1.2 mL, 16.451 mmol). 3-deuteriopyridine-2-carboxylic acid (400 mg, 3.0617 mmol) was added and the reaction mixture was heated at 75° C. for 16 h. The reaction mixture was cooled to room temperature and toluene was added (1 mL). The mixture was concentrated in vacuo and the same process was repeated. Methanol was added and the mixture was stirred at room temperature for 30 minutes then concentrated in vacuo. The residue was partitioned between a saturated aqueous solution of sodium hydrogen carbonate (3 mL) and ethyl acetate. The aqueous phase was extracted with ethyl acetate and the combined organic extracts were dried (MgSO4), filtered and concentrated in vacuo. Purification by flash chromatography (Biotage Isolera, 25 g, SiliaSep 25 μm Silicycle flash cartridge, 30% to 100% ethyl acetate in heptane) gave methyl 4-chloro-3-deuterio-pyridine-2-carboxylate (210 mg, 38%) as a pale brown solid. $^1$H NMR (400 MHz, Chloroform-d) δ 8.64 (d, J=5.0 Hz, 1H), 7.49 (d, J=5.0 Hz, 1H), 4.02 (s, 3H) ppm.

Intermediate L

Methyl 4-chloropicolinate-6-d

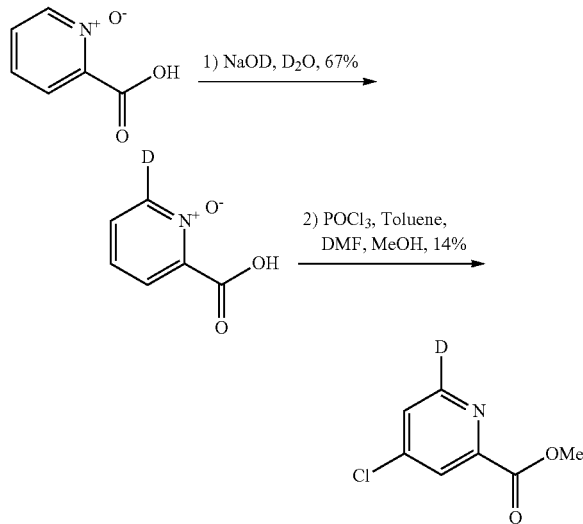

Step 1

A mixture of 2-carboxypyridine 1-oxide (2.94 g, 21.135 mmol) and sodium deuteroxide (5 mL of 40% w/v solution in water, 46.493 mmol) in deuterated water (5 mL) was stirred at 80° C. for 4 h. The reaction mixture was cooled to ambient temperature. The mixture was poured into concentrated hydrochloric acid (6 mL) at 0° C. and the solid collected by filtration. The filtrate was acidified to pH 1 with concentrated hydrochloric acid and additional solid collected by filtration. The solids were combined to give 2-carboxypyridine 1-oxide-6-d (2.08 g, 67%) as a white solid. $^1$H NMR (400 MHz, DMSO-$d_6$) δ 18.67 (s, 1H), 8.28 (dd, J=7.6, 2.3 Hz, 1H), 7.91-7.85 (m, 2H) ppm. 95% deuterium incorporation observed by NMR.

Step 2

$POCl_3$ (822.50 mg, 0.5 mL, 5.3642 mmol) was added to a stirred mixture of toluene (2.5 mL) and DMF (5 mL) at room temperature. The mixture was cooled to 0° C. and 2-carboxypyridine 1-oxide-6-d (150 mg, 1.0170 mmol) was added. The reaction mixture was stirred for 5 min at 0° C. then, for a further 18 h at ambient temperature. The mixture was concentrated in vacuo to approximately 50% of its volume. Methanol (5 mL) was added, and the mixture was again concentrated in vacuo to approximately 50% of its volume. The obtained solution was added to an aqueous saturated solution of $NaHCO_3$ (20 mL) and extracted with ethyl acetate (3×10 mL). The organic extracts were washed with brine (10 mL), dried ($Na_2SO_4$), filtered and concentrated in vacuo. The crude material was combined with another batch of the same scale. Purification by flash chromatography (Biotage Isolera, 12 g, SiliaSep 25 μm Silicycle flash cartridge, 0 to 50% ethyl acetate in heptane) gave methyl 4-chloropicolinate-6-d (29 mg, 14%) as a colourless oil. $^1$H NMR (400 MHz, Chloroform-d) δ 8.14 (d, J=1.5 Hz, 1H), 7.49 (s, 1H), 4.01 (s, 3H) ppm. ESI-MS m/z calc. 172.015, found 173.01 (M+1)$^+$; Retention time: 1.15 minutes.

Example 34

E-VIPR Assay Detecting and Measuring $Na_V$ Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential*, 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human $Na_V1.8$ with full channel activity were seeded into microtiter 384-well plates, pre-coated with matrigel, at a density of 25,000 cells per well. 2.5-5% KIR2.1 Bacmam virus was added to the final cell suspension before seeding into cell plates. HEK cells were grown in Dulbecco's Modified Eagle's Medium (DMEM) supplemented with 10% FBS (Fetal Bovine Serum, qualified; Sigma #F4135), 1% NEAA (Non-Essential Amino Acids, Gibco #11140), 1% HEPES (Gibco #15630), 1% Pen-Strep (Penicillin-Streptomycin; Gibco #15140) and 5 μg/ml Blasticidin (Gibco #R210-01). Cells were expanded in vented cap cell culture flasks, with 90-95% humidity and 5% $CO_2$.

Reagents and Stock Solutions:

100 mg/mL Pluronic F-127 (Sigma #P2443), in dry DMSO

Compound Plates: Corning 384-well Polypropylene Round Bottom #3656

Cell Plates: 384-well tissue culture treated plates (Greiner #781091-1B)

2.5-5% KIR 2.1 Bacmam virus (produced in-house), prepared as described in Section 3.3 of J. A. Fornwald et al., *Gene Expression in Mammalian Cells Using BacMam, a Modified Baculovirus System*, 1350 Methods in Molecular Biology 95-116 (2016), the entire contents of which are incorporated by reference. The concentration used can be dependent on viral titer of each batch.

5 mM $DiSBAC_6(3)$, a voltage sensitive oxonol acceptor (CAS number 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione), in dry DMSO. The preparation of $DiSBAC_6(3)$ is analogous to that of $DiSBAC_4(3)$ as described in *Voltage Sensing by Fluorescence Resonance Energy Transfer in Single Cells*, Gonzalez, J. E. and Tsien, R. Y. (1995) *Biophys. J* 69, 1272-1280.

5 mM CC2-DMPE, a commercially available membrane-bound coumarin phospholipid FRET donor (ThermoFisher Scientific catalog number K1017, CAS number 393782-57-

5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl]ester) was prepared in dry DMSO. See also, *Improved indicators of cell membrane potential that use fluorescence resonance energy transfer*, Gonzalez, J. E. and Tsien, R. Y. (1997) *Chem. Biol.* 4, 269-277.

Voltage Assay Background Suppression Compound (VABSC-1) is prepared in $H_2O$ (89-363 mM, range used to maintain solubility)

Human Serum (HS, Millipore #S1P1-01KL, or Sigma SLBR5469V and SLBR5470V as a 50%/50% mixture, for 25% assay final concentration)

Bath 1 Buffer:
Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath 1 Buffer:
Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2× Concentration):
Bath 1 Buffer containing 0.5% 3-cyclodextrin (made fresh prior to each use, Sigma #C4767), 8 µM CC2-DMPE and 2 M $DiSBAC_6(3)$. The solution was made by adding 10% Pluronic F127 stock equal to combined volumes of CC2-DMPE and $DiSBAC_6(3)$. The order of preparation was first mix Pluronic and CC2-DMPE, then add $DiSBAC_6(3)$, then while vortexing add Bath 1/β-Cyclodextrin.

Compound Loading Buffer (2× concentration): Na/TMA Cl Bath 1 Buffer containing HS (omitted in experiments run in the absence of human serum (HS)) 50%, VABSC-1 1 mM, BSA 0.2 mg/ml (in Bath-1), KCl 9 mM, DMSO 0.75%.

Assay Protocol (7 Key Steps):

1) To reach the final concentration in each well, 400 nL of each compound was pre-spotted (in neat DMSO) into polypropylene compound plates at 250× desired final concentration from an intermediate stock concentration of 0.075 mM, in an 11 point dose response, 3-fold dilution, resulting in a top dose of 300 nM final concentration in the cell plate. Vehicle control (neat DMSO), and positive control (an established $Na_V1.8$ inhibitor, 25 µM final in assay in DMSO) were added manually to the outermost columns of each plate respectively. The compound plate was backfilled with 45 µL per well of Compound Loading Buffer resulting in a 250 fold dilution of compound following a 1:1 transfer of compound into the cell plate (see Step 6). Final DMSO concentration for all wells in the assay was 0.625% (0.75% DMSO was supplemented to the Compound Loading Buffer for a final DMSO concentration of 0.625%). This assay dilution protocol was adjusted to enable a higher dose range to be tested in the presence of HS or if the final assay volume was altered.

2) Hexyl Dye Solution was prepared.

3) Cell plates were prepared. On the day of the assay, the media was aspirated, and the cells were washed three times with 80 µL of Bath-1 buffer, maintaining 25 µL residual volume in each well.

4) 25 µL per well of Hexyl Dye Solution was dispensed into the cell plates. The cells were incubated for 20 minutes at room temperature or ambient conditions in darkness.

5) 45 µL per well of Compound Loading Buffer was dispensed into compound plates.

6) The cell plates were washed three times with 80 µL per well of Bath-1 Buffer, leaving 25 L of residual volume. Then 25 µL per well from compound plate was transferred to each cell plate. The mixture was incubated for 30 minutes at room temperature/ambient conditions.

7) The cell plate containing compound was read on E-VIPR using the current-controlled amplifier to deliver stimulation wave pulses using a symmetrical biphasic waveform. The user-programmed electrical stimulus protocols were 1.25-4 Amps and 4-6 millisecond pulse width (dependent on electrode composition) were delivered at 10 Hz for 10 seconds. A pre-stimulus recording was performed for each well for 0.5 seconds to obtain the un-stimulated intensities baseline. The stimulatory waveform was followed by 0.5 seconds of post-stimulation recording to examine the relaxation to the resting state. All E-VIPR responses were measured at 200 Hz acquisition rate.

Data Analysis:

Data were analyzed and reported as normalized ratios of emission intensities measured in the 460 nm and 580 nm channels. The response as a function of time was reported as the ratios obtained using the following formula:

$$R(t) = \frac{(\text{intensity}_{460\,nm})}{(\text{intensity}_{580\,nm})}$$

The data were further reduced by calculating the initial $(R_i)$ and final $(R_f)$ ratios. These were the average ratio values during part or all of the pre-stimulation period and during sample points during the stimulation period. The fluorescence ratio $(R_f/R_i)$ was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound. Using this analysis protocol, dose response curves were plotted and $IC_{50}$ values were generated for various compounds of the present invention as reported below in Tables 1 and 2.

TABLE 1

$IC_{50}$ Values of Compounds of the Invention Generated in the Presence of Human Serum in the E-VIPR Assay (A = $IC_{50}$ < 0.01 µM; B = 0.1 µM > $IC_{50}$ ≥ 0.01 µM; C = 1 µM > $IC_{50}$ ≥ 0.1 µM; D = $IC_{50}$ ≥ 1 µM)

| Cmpd # | $IC_{50}$ (µM) |
|---|---|
| 1 | B |
| 2 | C |
| 3a | D |
| 3b | A |
| 4 | D |
| 5 | B |
| 6 | D |
| 7 | A |

TABLE 1-continued

IC$_{50}$ Values of Compounds of the Invention Generated in the Presence of Human Serum in the E-VIPR Assay (A = IC$_{50}$ < 0.01 µM; B = 0.1 µM > IC$_{50}$ ≥ 0.01 µM; C = 1 µM > IC$_{50}$ ≥ 0.1 µM; D = IC$_{50}$ ≥ 1 µM)

| Cmpd # | IC$_{50}$ (µM) |
|---|---|
| 8 | D |
| 9 | A |
| 10 | D |
| 11 | A |
| 12 | D |
| 13 | B |
| 14 | D |
| 15 | A |
| 16 | D |
| 17 | A |
| 18 | A |
| 19 | A |
| 20 | D |
| 21 | D |
| 22 | B |
| 23 | B |
| 24 | D |
| 25 | A |
| 26 | A |
| 27 | B |
| 28 | B |
| 29 | D |
| 30 | C |
| 31 | D |
| 32 | A |
| 33 | C |
| 34 | D |
| 35 | C |
| 36 | D |
| 37 | C |
| 38 | D |
| 39 | C |
| 40 | D |
| 41 | B |
| 44 | A |
| 45 | B |
| 46 | D |
| 47 | B |
| 51 | D |
| 52 | A |
| 53 | A |
| 54 | C |
| 55 | A |
| 56 | A |
| 57 | D |
| 58 | D |
| 59 | D |
| 60 | B |
| 61 | C |
| 63 | D |
| 64 | B |
| 65 | D |
| 66 | C |
| 67 | D |
| 68 | B |
| 69 | D |
| 70 | D |
| 71 | D |
| 72 | B |
| 73 | D |
| 74 | B |
| 75 | D |
| 76 | C |
| 77 | D |
| 78 | B |
| 79 | D |
| 80 | D |
| 81 | C |
| 82 | D |
| 83 | C |
| 84 | D |
| 85 | D |
| 86 | D |
| 87 | C |
| 88 | D |
| 89 | A |
| 90 | D |
| 91 | C |
| 92 | D |
| 93 | A |
| 94 | A |
| 95 | D |
| 96 | D |
| 97 | D |
| 98 | D |
| 99 | D |
| 100 | D |
| 101 | D |
| 102 | D |
| 103 | D |
| 104 | D |
| 105 | B |
| 106 | D |
| 107 | D |
| 108 | C |
| 109 | D |
| 110 | C |
| 111 | D |
| 112 | C |
| 113 | B |
| 115 | A |
| 116 | A |
| 137 | D |
| 138 | B |
| 146 | B |
| 150 | D |
| 151 | B |

TABLE 2

IC$_{50}$ Values of Compounds of the Invention Generated in the Absence of Human Serum in the E-VIPR Assay (A = IC$_{50}$ < 0.01 µM; B = 0.1 µM > IC$_{50}$ ≥ 0.01 µM; C = 1 µM > IC$_{50}$ ≥ 0.1 µM; D = IC$_{50}$ ≥ 1 µM)

| Cmpd # | IC$_{50}$ (µM) |
|---|---|
| 42 | A |
| 43 | C |
| 50 | B |
| 114 | B |
| 117 | B |
| 118 | A |
| 119 | A |
| 120 | B |
| 121 | A |
| 122 | A |
| 123 | A |
| 124 | A |
| 126 | A |
| 127 | A |
| 128 | A |
| 128 | B |
| 129 | A |
| 131 | D |
| 132 | A |
| 133 | B |
| 134 | C |
| 135 | D |
| 136 | A |
| 139 | D |
| 140 | B |
| 141 | D |

TABLE 2-continued

IC$_{50}$ Values of Compounds of the Invention Generated in the Absence of Human Serum in the E-VIPR Assay (A = IC$_{50}$ < 0.01 µM; B = 0.1 µM > IC$_{50}$ ≥ 0.01 µM; C = 1 µM > IC$_{50}$ ≥ 0.1 µM; D = IC$_{50}$ ≥ 1 µM)

| Cmpd # | IC$_{50}$ (µM) |
| --- | --- |
| 147 | A |
| 148 | A |
| 149 | A |
| 152 | A |

Many modifications and variations of the embodiments described herein may be made without departing from the scope, as is apparent to those skilled in the art. The specific embodiments described herein are offered by way of example only.

What is claimed is:

1. A compound of formula (I)

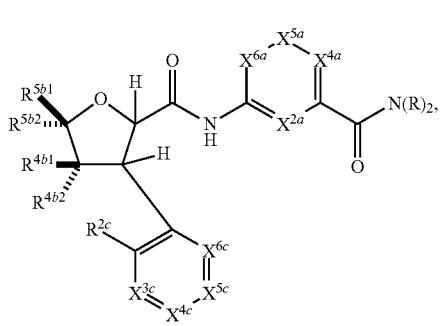

or a pharmaceutically acceptable salt thereof, wherein:
$X^{2a}$ is N, N$^+$—O$^-$, or C—R$^{2a}$;
$X^{4a}$ is N or N$^+$—O$^-$;
$X^{5a}$ is N, N$^+$—O$^-$, or C—R$^{5a}$;
$X^{6a}$ is N, N$^+$—O$^-$, or C—R$^{6a}$;
each R is independently H or C$_1$-C$_6$ alkyl;
$R^{2a}$, $R^{4a}$, $R^{5a}$, and $R^{6a}$ are each independently H, halo, C$_1$-C$_6$ alkyl, or C$_1$-C$_6$ haloalkyl;
$R^{4b1}$ and $R^{4b2}$ are each independently H, C$_1$-C$_6$ alkyl, C$_3$-C$_6$ cycloalkyl, or C$_1$-C$_6$ haloalkyl;
$R^{5b1}$ and $R^{5b2}$ are each independently H, C$_1$-C$_6$ alkyl, C$_3$-C$_6$ cycloalkyl, or C$_1$-C$_6$ haloalkyl;
$X^{3c}$ is N or C—R$^{3c}$;
$X^{4c}$ is N or C—R$^{4c}$;
$X^{5c}$ is N or C—R$^{5c}$;
$X^{6c}$ is N or C—R$^{6c}$;
$R^{2c}$ is H, OH, halo, C$_1$-C$_6$ alkyl, C$_2$-C$_6$ alkenyl, C$_1$-C$_6$ haloalkyl, C$_1$-C$_6$ alkoxy, C$_1$-C$_6$ haloalkoxy, or -L$^1$-L$^2$-(C$_3$-C$_6$ cycloalkyl), wherein said cycloalkyl of R$^{2c}$ is optionally substituted with 1-2 halo;
L$^1$ is a bond or O;
L$^2$ is a bond or C$_1$-C$_6$ alkylene;
$R^{3c}$ is H, halo, C$_1$-C$_6$ alkyl, or C$_1$-C$_6$ haloalkyl;
$R^{4c}$ is H, halo, C$_1$-C$_6$ alkyl, or C$_1$-C$_6$ haloalkyl;
$R^{5c}$ is H, halo, C$_1$-C$_6$ alkyl, or C$_1$-C$_6$ haloalkyl; and
$R^{6c}$ is H, halo, C$_1$-C$_6$ alkyl, or C$_1$-C$_6$ haloalkyl;
provided that no more than two of $X^{2a}$, $X^{4a}$, $X^{5a}$, and $X^{6a}$ are N or N$^+$—O$^-$; and
provided that no more than one of $X^{3c}$, $X^{4c}$, $X^{5c}$, and $X^{6c}$ are N.

2. The compound of claim 1, or a pharmaceutically acceptable salt thereof, wherein:
$X^{2a}$ is C—R$^{2a}$;
$X^{5a}$ is C—R$^{5a}$;
$X^{6a}$ is C—R$^{6a}$;
$R^{4b1}$ and $R^{4b2}$ are each independently H, C$_1$-C$_6$ alkyl, or C$_1$-C$_6$ haloalkyl;
$R^{5b1}$ and $R^{5b2}$ are each independently H, C$_1$-C$_6$ alkyl, or C$_1$-C$_6$ haloalkyl;
$X^{3c}$ is C—R$^{3c}$;
$X^{4c}$ is C—R$^{4c}$;
$X^{5c}$ is C—R$^{5c}$;
$X^{6c}$ is C—R$^{6c}$; and
$R^{2c}$ is H, OH, halo, C$_1$-C$_6$ alkyl, C$_1$-C$_6$ haloalkyl, C$_1$-C$_6$ alkoxy, or C$_1$-C$_6$ haloalkoxy.

3. The compound of claim 1, wherein the compound has formula (I-A)

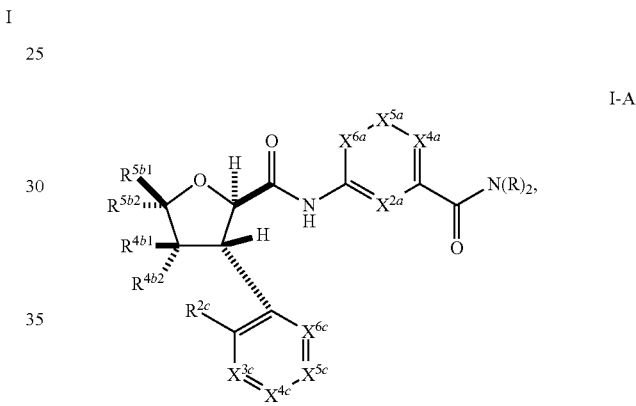

or a pharmaceutically acceptable salt thereof.

4. The compound of claim 1, wherein the compound has formula (I-B)

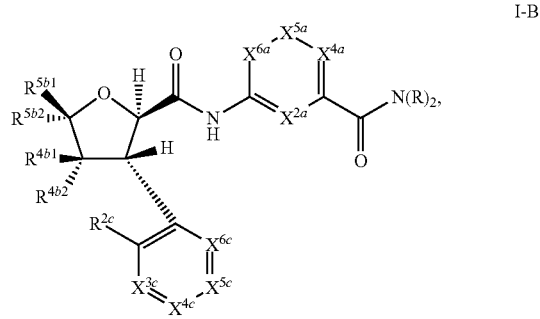

or a pharmaceutically acceptable salt thereof.

5. The compound of claim 1, or a pharmaceutically acceptable salt therof, wherein the compound is selected from

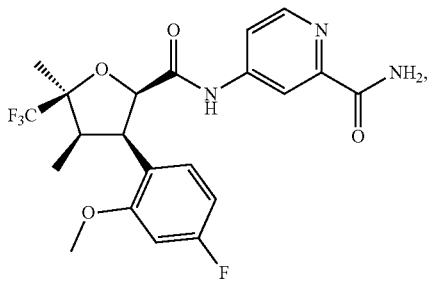

4-((2R,3R,4R,5S)-3-(4-fluoro-2-methoxyphenyl)-4,5-dimethyl-5-(trifluoromethyl)tetrahydrofuran-2-carboxamido)picolinamide

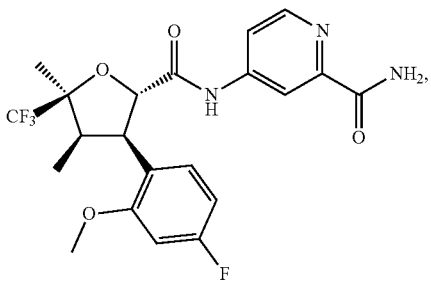

4-((2S,3R,4R,5S)-3-(4-fluoro-2-methoxyphenyl)-4,5-dimethyl-5-(trifluoromethyl)tetrahydrofuran-2-carboxamido)picolinamide

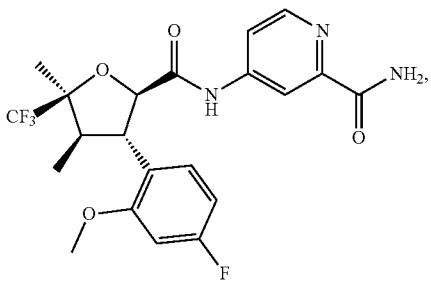

4-((2R,3S,4R,5S)-3-(4-fluoro-2-methoxyphenyl)-4,5-dimethyl-5-(trifluoromethyl)tetrahydrofuran-2-carboxamido)picolinamide

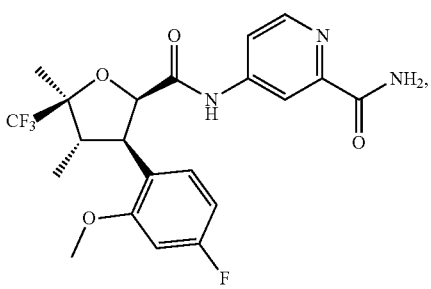

4-((2R,3R,4S,5S)-3-(4-fluoro-2-methoxyphenyl)-4,5-dimethyl-5-(trifluoromethyl)tetrahydrofuran-2-carboxamido)picolinamide -continued

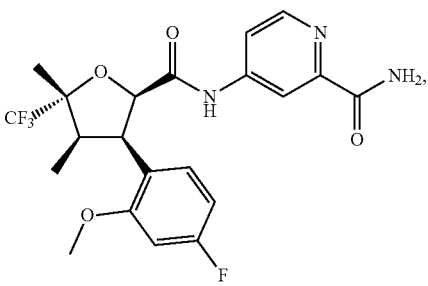

4-((2R,3R,4R,5R)-3-(4-fluoro-2-methoxyphenyl)-4,5-dimethyl-5-(trifluoromethyl)tetrahydrofuran-2-carboxamido)picolinamide

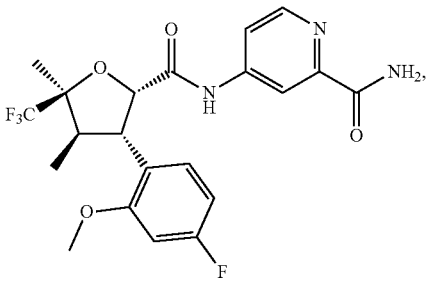

4-((2S,3S,4R,5S)-3-(4-fluoro-2-methoxyphenyl)-4,5-dimethyl-5-(trifluoromethyl)tetrahydrofuran-2-carboxamido)picolinamide

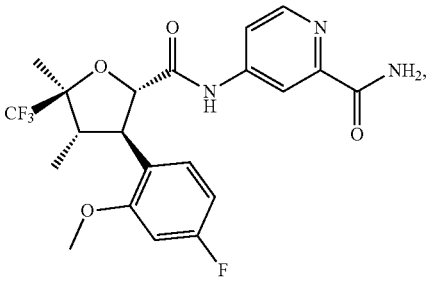

4-((2S,3R,4S,5S)-3-(4-fluoro-2-methoxyphenyl)-4,5-dimethyl-5-(trifluoromethyl)tetrahydrofuran-2-carboxamido)picolinamide

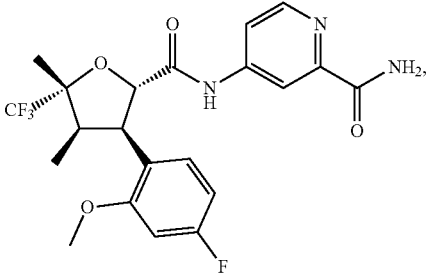

4-((2S,3R,4R,5R)-3-(4-fluoro-2-methoxyphenyl)-4,5-dimethyl-5-(trifluoromethyl)tetrahydrofuran-2-carboxamido)picolinamide -continued

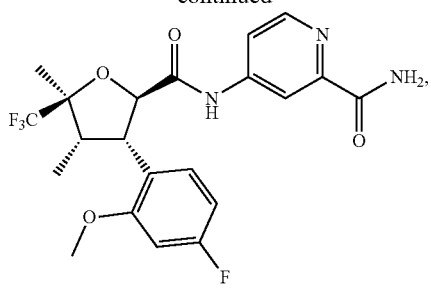

4-((2R,3S,4S,5S)-3-(4-fluoro-2-
methoxyphenyl)-4,5-dimethyl-5-
(trifluoromethyl)tetrahydrofuran-
2-carboxamido)picolinamide

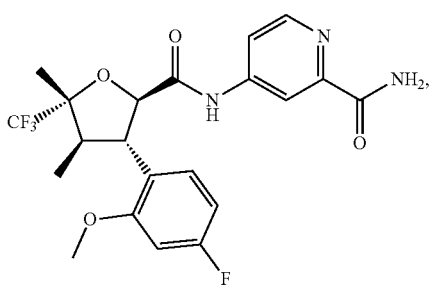

4-((2R,3S,4R,5R)-3-(4-fluoro-2-
methoxyphenyl)-4,5-dimethyl-5-
(trifluoromethyl)tetrahydrofuran-
2-carboxamido)picolinamide

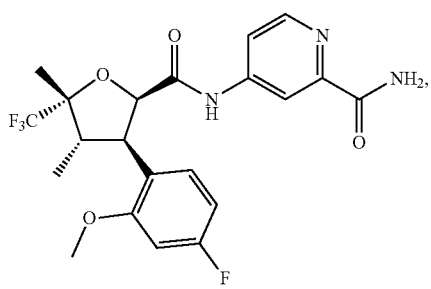

4-((2R,3R,4S,5R)-3-(4-fluoro-2-
methoxyphenyl)-4,5-dimethyl-5-
(trifluoromethyl)tetrahydrofuran-
2-carboxamido)picolinamide

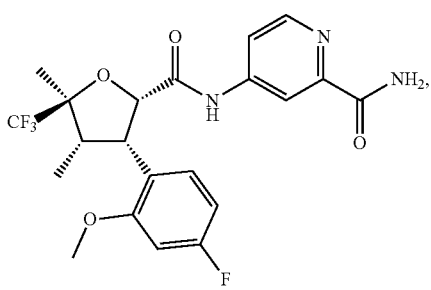

4-((2S,3S,4S,5R)-3-(4-fluoro-2-
methoxyphenyl)-4,5-dimethyl-5-
(trifluoromethyl)tetrahydrofuran-
2-carboxamido)picolinamide -continued

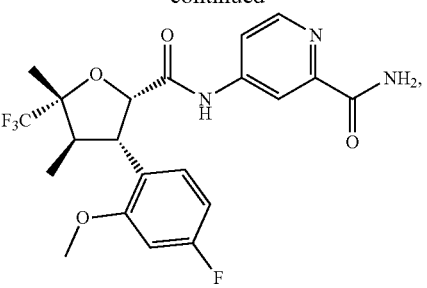

4-((2S,3S,4R,5R)-3-(4-fluoro-2-
methoxyphenyl)-4,5-dimethyl-5-
(trifluoromethyl)tetrahydrofuran-
2-carboxamido)picolinamide

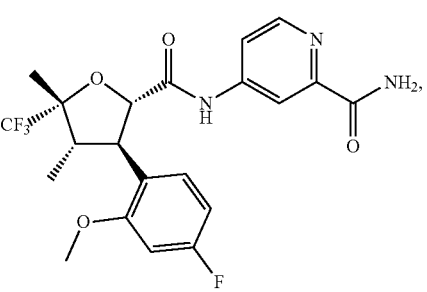

4-((2S,3R,4S,5R)-3-(4-fluoro-2-
methoxyphenyl)-4,5-dimethyl-5-
(trifluoromethyl)tetrahydrofuran-
2-carboxamido)picolinamide

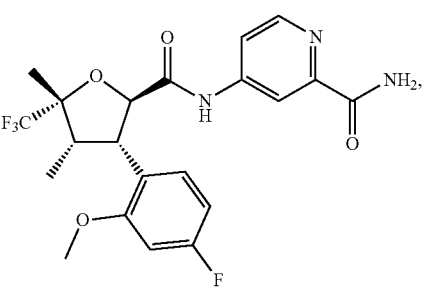

4-((2R,3S,4S,5R)-3-(4-fluoro-2-
methoxyphenyl)-4,5-dimethyl-5-
(trifluoromethyl)tetrahydrofuran-
2-carboxamido)picolinamide

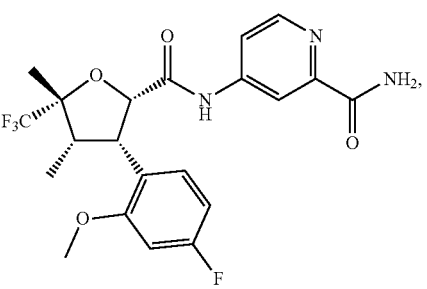

4-((2S,3S,4S,5R)-3-(4-fluoro-2-
methoxyphenyl)-4,5-dimethyl-5-
(trifluoromethyl)tetrahydrofuran-
2-carboxamido)picolinamide

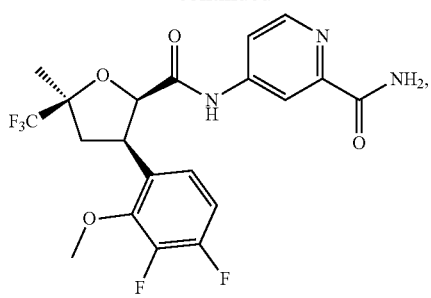

4-((2R,3R,5S)-3-(3,4-difluoro-2-methoxyphenyl)-5-
methyl-5-(trifluoromethyl)tetrahydrofuran-2-
carboxamido)picolinamide

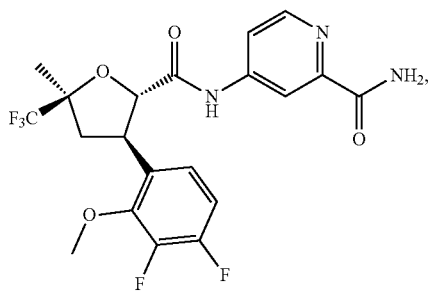

4-((2S,3R,5S)-3-(3,4-difluoro-2-methoxyphenyl)-5-
methyl-5-(trifluoromethyl)tetrahydrofuran-2-
carboxamido)picolinamide

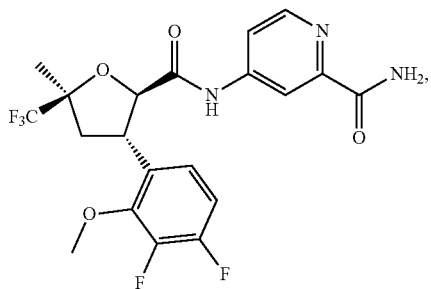

4-((2R,3S,5S)-3-(3,4-difluoro-2-methoxyphenyl)-5-
methyl-5-(trifluoromethyl)tetrahydrofuran-2-
carboxamido)picolinamide

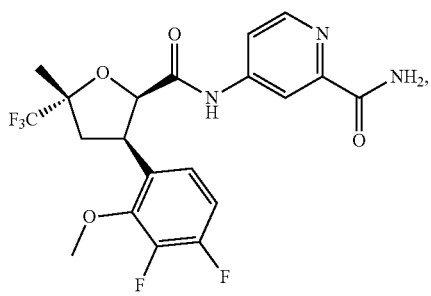

4-((2R,3R,5R)-3-(3,4-difluoro-2-methoxyphenyl)-5-
methyl-5-(trifluoromethyl)tetrahydrofuran-2-
carboxamido)picolinamide

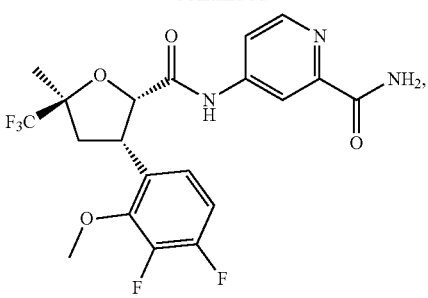

4-((2S,3S,5S)-3-(3,4-difluoro-2-methoxyphenyl)-5-
methyl-5-(trifluoromethyl)tetrahydrofuran-2-
carboxamido)picolinamide

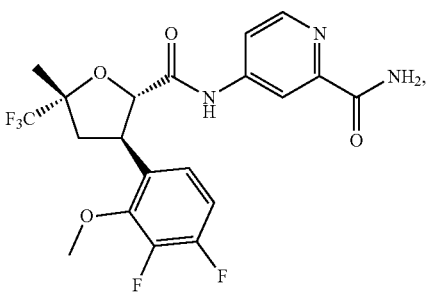

4-((2S,3R,5R)-3-(3,4-difluoro-2-methoxyphenyl)-5-
methyl-5-(trifluoromethyl)tetrahydrofuran-2-
carboxamido)picolinamide

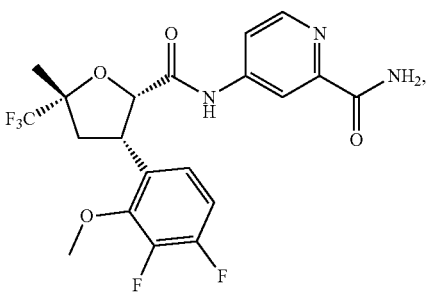

4-((2S,3S,5R)-3-(3,4-difluoro-2-methoxyphenyl)-5-
methyl-5-(trifluoromethyl)tetrahydrofuran-2-
carboxamido)picolinamide -continued

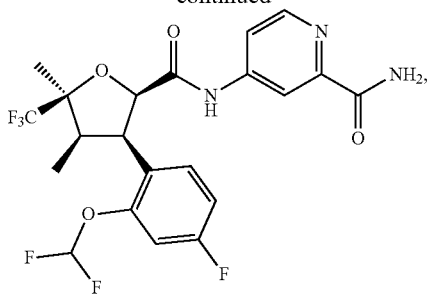

4-((2R,3R,4R,5S)-3-(2-(difluoromethoxy)-4-
fluorophenyl)-4,5-dimethyl-5-
(trifluoromethyl)tetrahydrofuran-2-
carboxamido)picolinamide

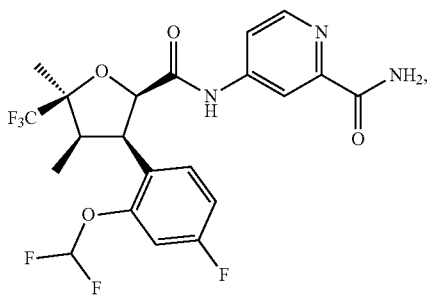

4-((2R,3R,4R,5S)-3-(2-(difluoromethoxy)-4-
fluorophenyl)-4,5-dimethyl-5-
(trifluoromethyl)tetrahydrofuran-2-
carboxamido)picolinamide

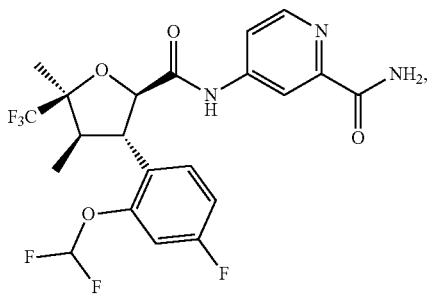

4-((2R,3S,4R,5S)-3-(2-(difluoromethoxy)-4-
fluorophenyl)-4,5-dimethyl-5-
(trifluoromethyl)tetrahydrofuran-2-
carboxamido)picolinamide

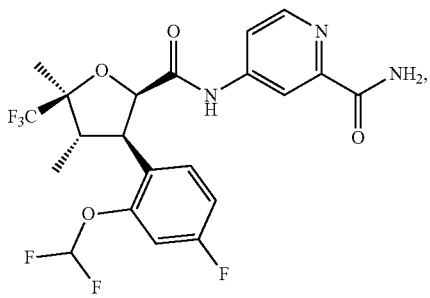

4-((2R,3R,4S,5S)-3-(2-(difluoromethoxy)-4-
fluorophenyl)-4,5-dimethyl-5-
(trifluoromethyl)tetrahydrofuran-2-
carboxamido)picolinamide -continued

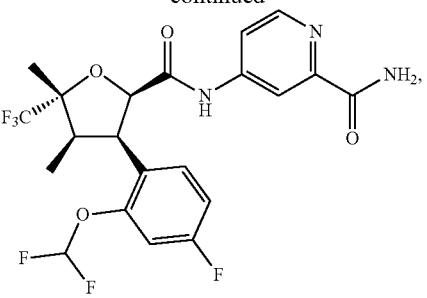

4-((2R,3R,4R,5R)-3-(2-(difluoromethoxy)-4-
fluorophenyl)-4,5-dimethyl-5-
(trifluoromethyl)tetrahydrofuran-2-
carboxamido)picolinamide

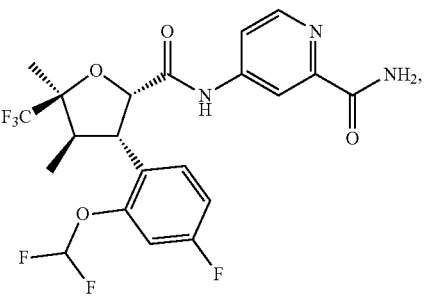

4-((2S,3S,4R,5S)-3-(2-(difluoromethoxy)-4-
fluorophenyl)-4,5-dimethyl-5-
(trifluoromethyl)tetrahydrofuran-2-
carboxamido)picolinamide

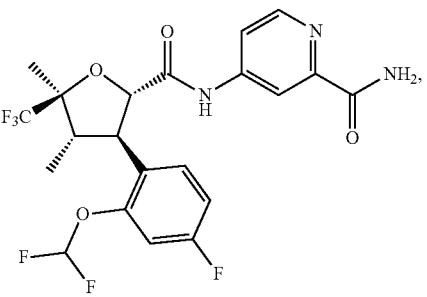

4-((2S,3R,4S,5S)-3-(2-(difluoromethoxy)-4-
fluorophenyl)-4,5-dimethyl-5-
(trifluoromethyl)tetrahydrofuran-2-
carboxamido)picolinamide

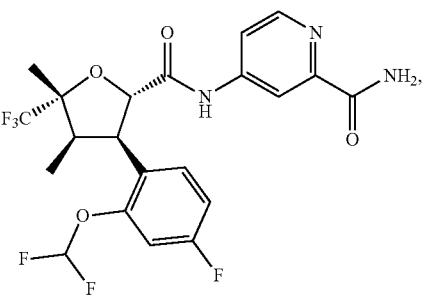

4-((2S,3R,4R,5R)-3-(2-(difluoromethoxy)-4-
fluorophenyl)-4,5-dimethyl-5-
(trifluoromethyl)tetrahydrofuran-2-
carboxamido)picolinamide -continued

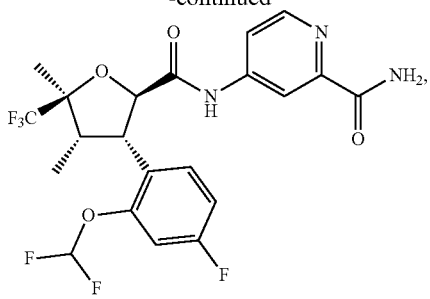

4-((2R,3S,4S,5S)-3-(2-(difluoromethoxy)-4-fluorophenyl)-4,5-dimethyl-5-(trifluoromethyl)tetrahydrofuran-2-carboxamido)picolinamide

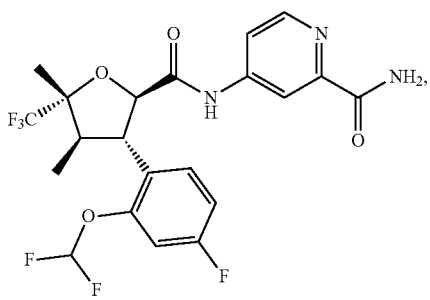

4-((2R,3S,4R,5R)-3-(2-(difluoromethoxy)-4-fluorophenyl)-4,5-dimethyl-5-(trifluoromethyl)tetrahydrofuran-2-carboxamido)picolinamide

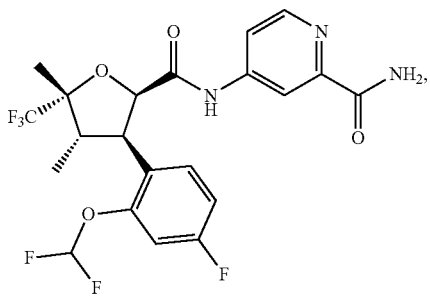

4-((2R,3R,4S,5R)-3-(2-(difluoromethoxy)-4-fluorophenyl)-4,5-dimethyl-5-(trifluoromethyl)tetrahydrofuran-2-carboxamido)picolinamide

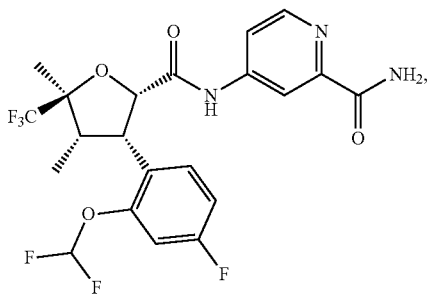

4-((2S,3S,4S,5S)-3-(2-(difluoromethoxy)-4-fluorophenyl)-4,5-dimethyl-5-(trifluoromethyl)tetrahydrofuran-2-carboxamido)picolinamide

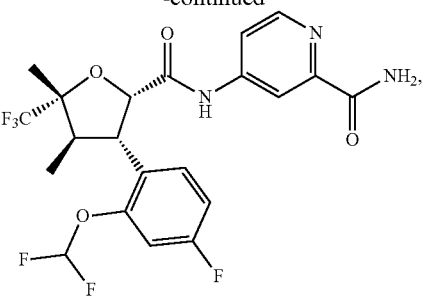

4-((2S,3S,4R,5R)-3-(2-(difluoromethoxy)-4-fluorophenyl)-4,5-dimethyl-5-(trifluoromethyl)tetrahydrofuran-2-carboxamido)picolinamide

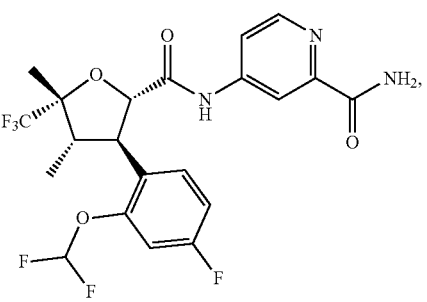

4-((2S,3R,4S,5R)-3-(2-(difluoromethoxy)-4-fluorophenyl)-4,5-dimethyl-5-(trifluoromethyl)tetrahydrofuran-2-carboxamido)picolinamide

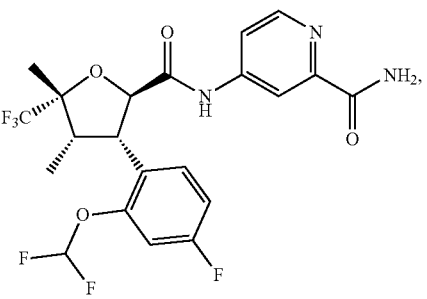

4-((2R,3S,4S,5R)-3-(2-(difluoromethoxy)-4-fluorophenyl)-4,5-dimethyl-5-(trifluoromethyl)tetrahydrofuran-2-carboxamido)picolinamide

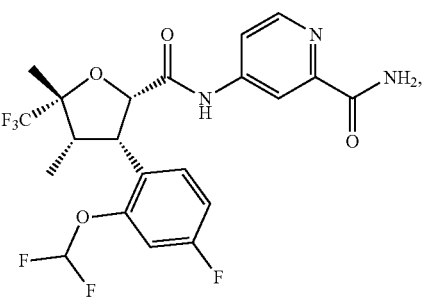

4-((2S,3S,4S,5R)-3-(2-(difluoromethoxy)-4-fluorophenyl)-4,5-dimethyl-5-(trifluoromethyl)tetrahydrofuran-2-carboxamido)picolinamide -continued

| 425 | 426 |
|---|---|

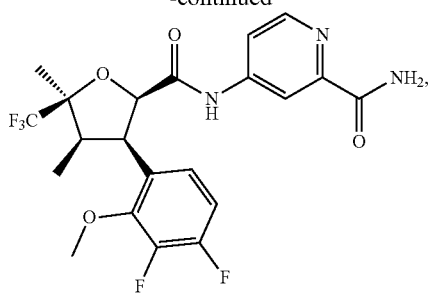

4-((2R,3R,4R,5S)-3-(3,4-difluoro-2-methoxyphenyl)-4,5-dimethyl-5-(trifluoromethyl)tetrahydrofuran-2-carboxamido)picolinamide

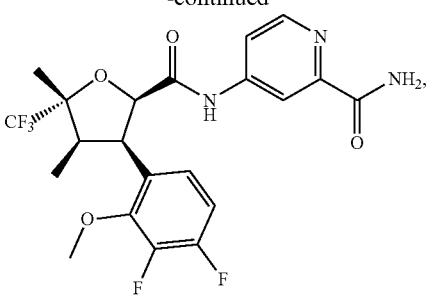

4-((2R,3R,4R,5R)-3-(3,4-difluoro-2-methoxyphenyl)-4,5-dimethyl-5-(trifluoromethyl)tetrahydrofuran-2-carboxamido)picolinamide

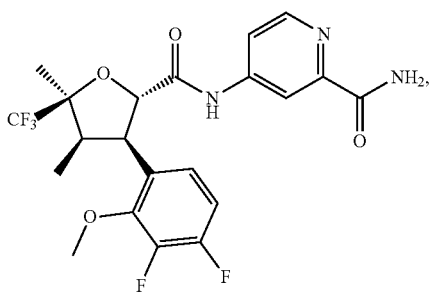

4-((2S,3R,4R,5S)-3-(3,4-difluoro-2-methoxyphenyl)-4,5-dimethyl-5-(trifluoromethyl)tetrahydrofuran-2-carboxamido)picolinamide

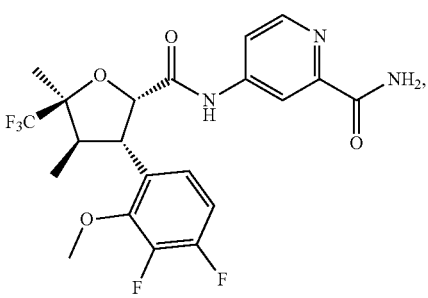

4-((2S,3S,4R,5S)-3-(3,4-difluoro-2-methoxyphenyl)-4,5-dimethyl-5-(trifluoromethyl)tetrahydrofuran-2-carboxamido)picolinamide

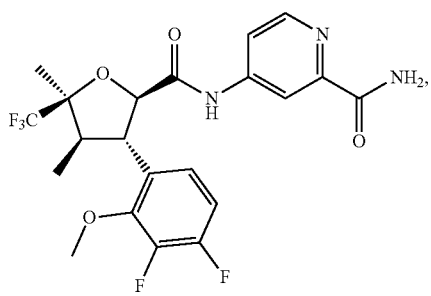

4-((2R,3S,4R,5S)-3-(3,4-difluoro-2-methoxyphenyl)-4,5-dimethyl-5-(trifluoromethyl)tetrahydrofuran-2-carboxamido)picolinamide

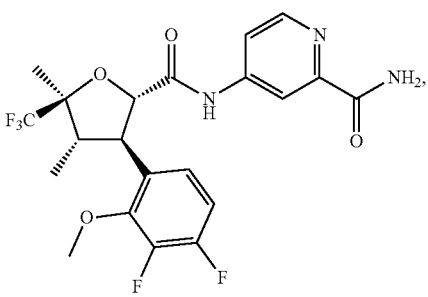

4-((2S,3R,4S,5S)-3-(3,4-difluoro-2-methoxyphenyl)-4,5-dimethyl-5-(trifluoromethyl)tetrahydrofuran-2-carboxamido)picolinamide

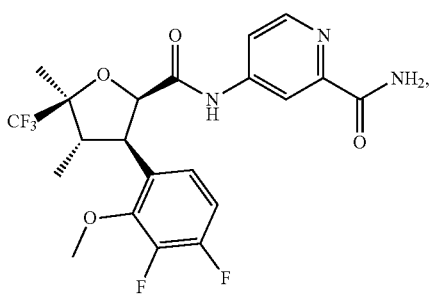

4-((2R,3R,4S,5S)-3-(3,4-difluoro-2-methoxyphenyl)-4,5-dimethyl-5-(trifluoromethyl)tetrahydrofuran-2-carboxamido)picolinamide

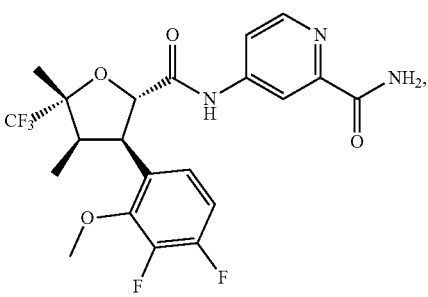

4-((2S,3R,4R,5R)-3-(3,4-difluoro-2-methoxyphenyl)-4,5-dimethyl-5-(trifluoromethyl)tetrahydrofuran-2-carboxamido)picolinamide -continued

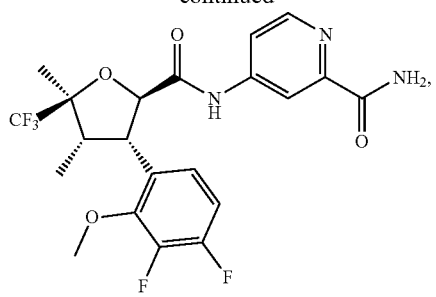

4-((2R,3S,4S,5S)-3-(3,4-difluoro-2-methoxyphenyl)-4,5-dimethyl-5-(trifluoromethyl)tetrahydrofuran-2-carboxamido)picolinamide

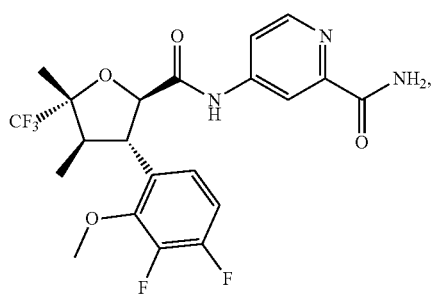

4-((2R,3S,4R,5R)-3-(3,4-difluoro-2-methoxyphenyl)-4,5-dimethyl-5-(trifluoromethyl)tetrahydrofuran-2-carboxamido)picolinamide

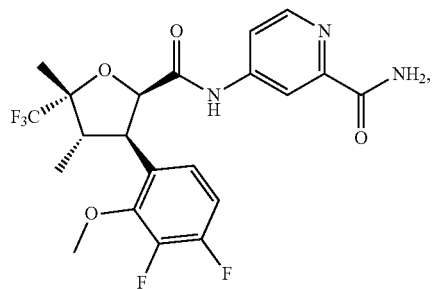

4-((2R,3R,4S,5R)-3-(3,4-difluoro-2-methoxyphenyl)-4,5-dimethyl-5-(trifluoromethyl)tetrahydrofuran-2-carboxamido)picolinamide

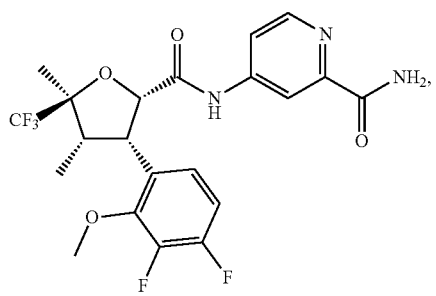

4-((2S,3S,4S,5S)-3-(3,4-difluoro-2-methoxyphenyl)-4,5-dimethyl-5-(trifluoromethyl)tetrahydrofuran-2-carboxamido)picolinamide -continued

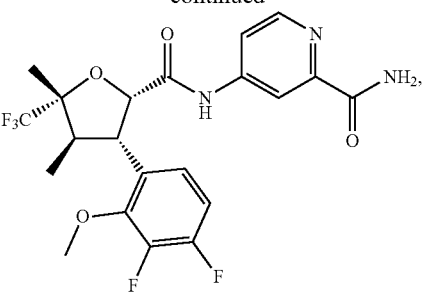

4-((2S,3S,4R,5R)-3-(3,4-difluoro-2-methoxyphenyl)-4,5-dimethyl-5-(trifluoromethyl)tetrahydrofuran-2-carboxamido)picolinamide

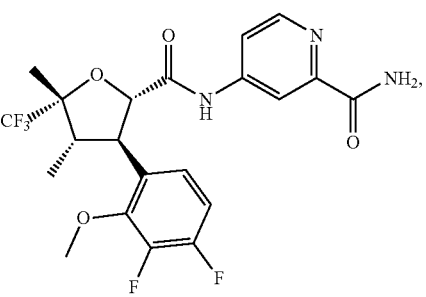

4-((2S,3R,4S,5R)-3-(3,4-difluoro-2-methoxyphenyl)-4,5-dimethyl-5-(trifluoromethyl)tetrahydrofuran-2-carboxamido)picolinamide

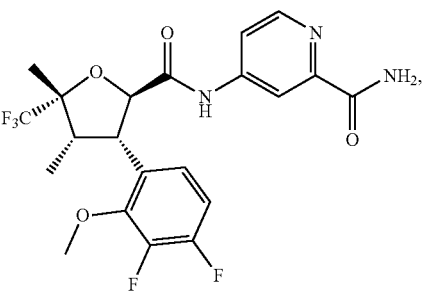

4-((2R,3S,4S,5R)-3-(3,4-difluoro-2-methoxyphenyl)-4,5-dimethyl-5-(trifluoromethyl)tetrahydrofuran-2-carboxamido)picolinamide

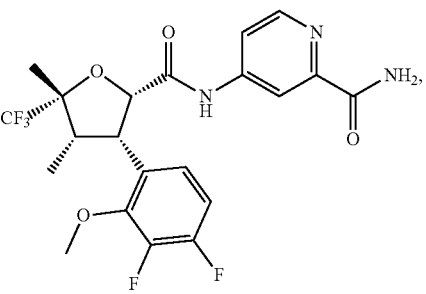

4-((2S,3S,4S,5R)-3-(3,4-difluoro-2-methoxyphenyl)-4,5-dimethyl-5-(trifluoromethyl)tetrahydrofuran-2-carboxamido)picolinamide

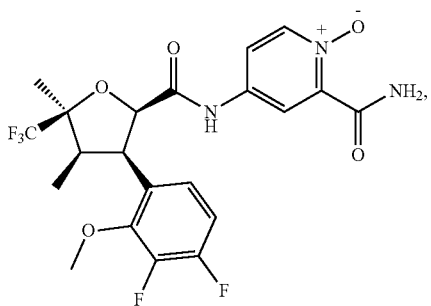

2-carbamoyl-4-((2R,3R,4R,5S)-3-(3,4-difluoro-2-methoxyphenyl)-4,5-dimethyl-5-(trifluoromethyl)tetrahydrofuran-2-carboxamido)pyridine 1-oxide

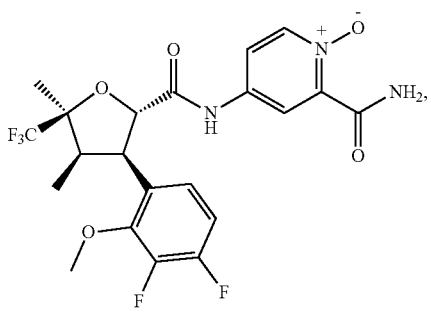

2-carbamoyl-4-((2S,3R,4R,5S)-3-(3,4-difluoro-2-methoxyphenyl)-4,5-dimethyl-5-(trifluoromethyl)tetrahydrofuran-2-carboxamido)pyridine 1-oxide

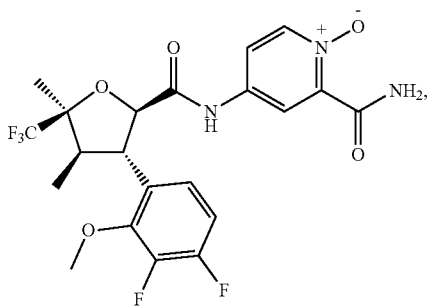

2-carbamoyl-4-((2R,3S,4R,5S)-3-(3,4-difluoro-2-methoxyphenyl)-4,5-dimethyl-5-(trifluoromethyl)tetrahydrofuran-2-carboxamido)pyridine 1-oxide

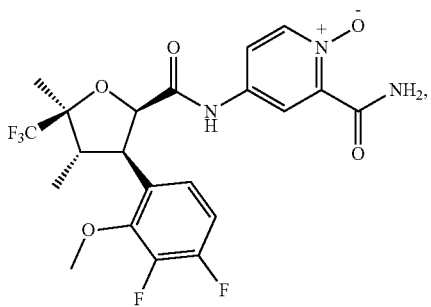

2-carbamoyl-4-((2R,3R,4S,5S)-3-(3,4-difluoro-2-methoxyphenyl)-4,5-dimethyl-5-(trifluoromethyl)tetrahydrofuran-2-carboxamido)pyridine 1-oxide

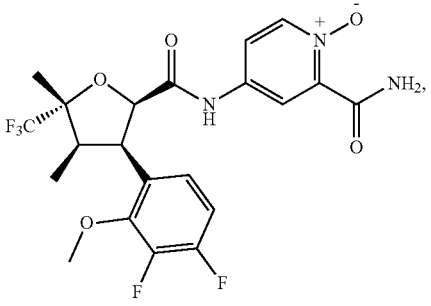

2-carbamoyl-4-((2R,3R,4R,5R)-3-(3,4-difluoro-2-methoxyphenyl)-4,5-dimethyl-5-(trifluoromethyl)tetrahydrofuran-2-carboxamido)pyridine 1-oxide

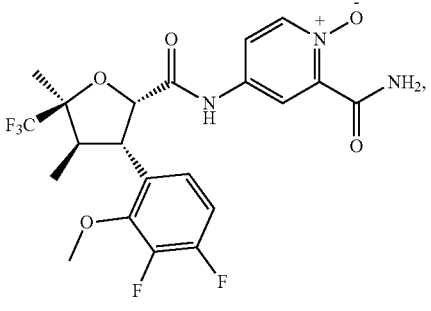

2-carbamoyl-4-((2S,3S,4R,5S)-3-(3,4-difluoro-2-methoxyphenyl)-4,5-dimethyl-5-(trifluoromethyl)tetrahydrofuran-2-carboxamido)pyridine 1-oxide

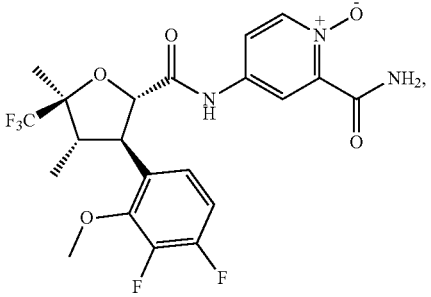

2-carbamoyl-4-((2S,3R,4S,5S)-3-(3,4-difluoro-2-methoxyphenyl)-4,5-dimethyl-5-(trifluoromethyl)tetrahydrofuran-2-carboxamido)pyridine 1-oxide

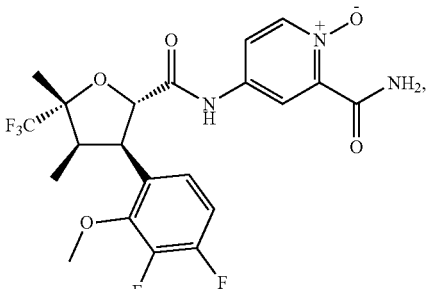

2-carbamoyl-4-((2S,3R,4R,5R)-3-(3,4-difluoro-2-methoxyphenyl)-4,5-dimethyl-5-(trifluoromethyl)tetrahydrofuran-2-carboxamido)pyridine 1-oxide

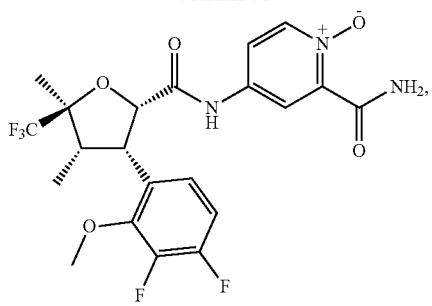

2-carbamoyl-4-((2R,3S,4S,5S)-3-(3,4-difluoro-2-
methoxyphenyl)-4,5-dimethyl-5-
(trifluoromethyl)tetrahydrofuran-2-
carboxamido)pyridine 1-oxide

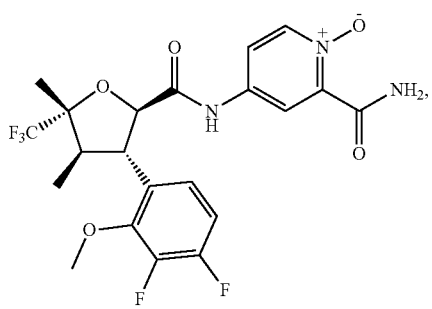

2-carbamoyl-4-((2R,3S,4R,5R)-3-(3,4-difluoro-2-
methoxyphenyl)-4,5-dimethyl-5-
(trifluoromethyl)tetrahydrofuran-2-
carboxamido)pyridine 1-oxide

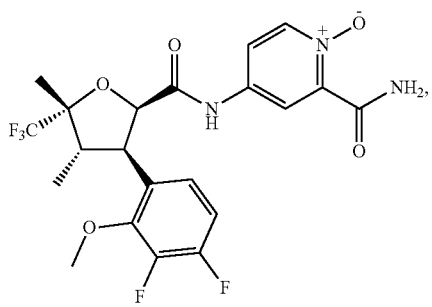

2-carbamoyl-4-((2R,3R,4S,5R)-3-(3,4-difluoro-2-
methoxyphenyl)-4,5-dimethyl-5-
(trifluoromethyl)tetrahydrofuran-2-
carboxamido)pyridine 1-oxide

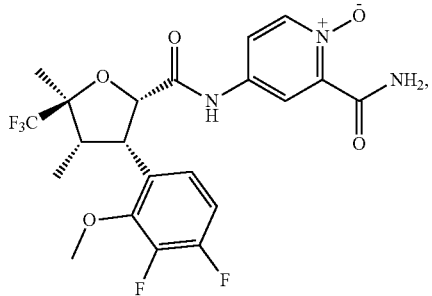

2-carbamoyl-4-((2S,3S,4S,5S)-3-(3,4-difluoro-2-
methoxyphenyl)-4,5-dimethyl-5-
(trifluoromethyl)tetrahydrofuran-2-
carboxamido)pyridine 1-oxide

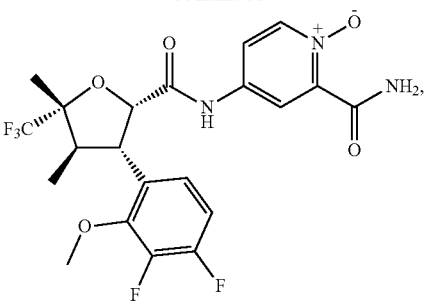

2-carbamoyl-4-((2S,3S,4R,5R)-3-(3,4-difluoro-2-
methoxyphenyl)-4,5-dimethyl-5-
(trifluoromethyl)tetrahydrofuran-2-
carboxamido)pyridine 1-oxide

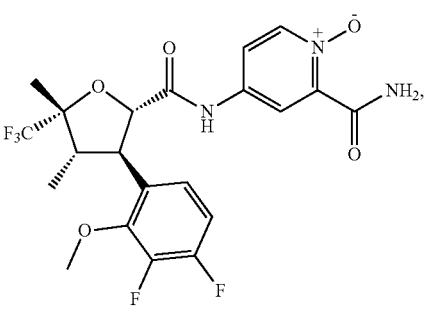

2-carbamoyl-4-((2S,3R,4S,5R)-3-(3,4-difluoro-2-
methoxyphenyl)-4,5-dimethyl-5-
(trifluoromethyl)tetrahydrofuran-2-
carboxamido)pyridine 1-oxide

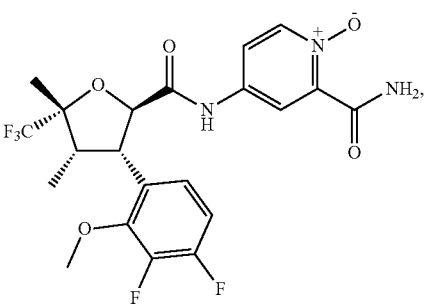

2-carbamoyl-4-((2R,3S,4S,5R)-3-(3,4-difluoro-2-
methoxyphenyl)-4,5-dimethyl-5-
(trifluoromethyl)tetrahydrofuran-2-
carboxamido)pyridine 1-oxide

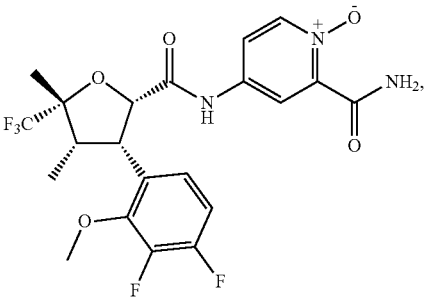

2-carbamoyl-4-((2S,3S,4S,5R)-3-(3,4-difluoro-2-
methoxyphenyl)-4,5-dimethyl-5-
(trifluoromethyl)tetrahydrofuran-2-
carboxamido)pyridine 1-oxide

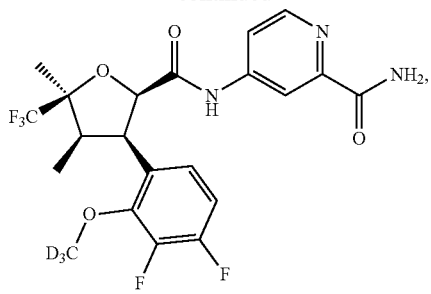

4-((2R,3R,4R,5S)-3-(3,4-difluoro-2-(methoxy-d₃)phenyl)-4,5-dimethyl-5-(trifluoromethyl)tetrahydrofuran-2-carboxamido)picolinamide

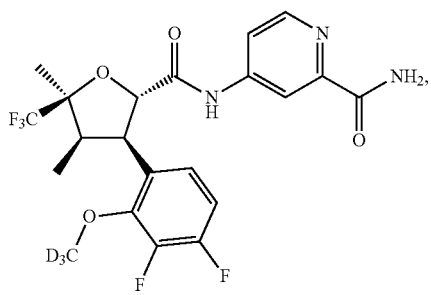

4-((2S,3R,4R,5S)-3-(3,4-difluoro-2-(methoxy-d₃)phenyl)-4,5-dimethyl-5-(trifluoromethyl)tetrahydrofuran-2-carboxamido)picolinamide

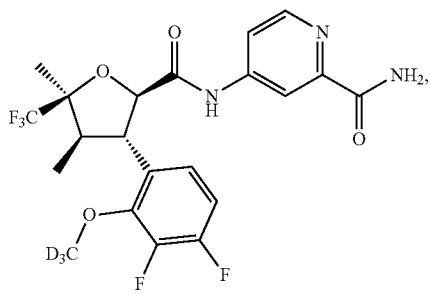

4-((2R,3S,4R,5S)-3-(3,4-difluoro-2-(methoxy-d₃)phenyl)-4,5-dimethyl-5-(trifluoromethyl)tetrahydrofuran-2-carboxamido)picolinamide

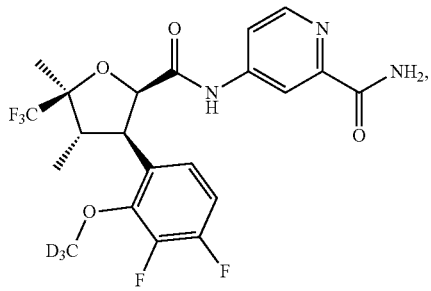

4-((2R,3R,4S,5S)-3-(3,4-difluoro-2-(methoxy-d₃)phenyl)-4,5-dimethyl-5-(trifluoromethyl)tetrahydrofuran-2-carboxamido)picolinamide

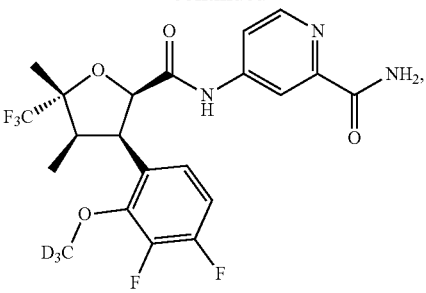

4-((2R,3R,4R,5R)-3-(3,4-difluoro-2-(methoxy-d₃)phenyl)-4,5-dimethyl-5-(trifluoromethyl)tetrahydrofuran-2-carboxamido)picolinamide

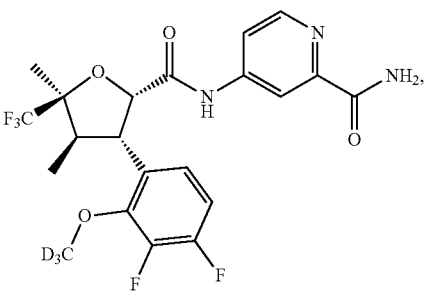

4-((2S,3S,4R,5S)-3-(3,4-difluoro-2-(methoxy-d₃)phenyl)-4,5-dimethyl-5-(trifluoromethyl)tetrahydrofuran-2-carboxamido)picolinamide

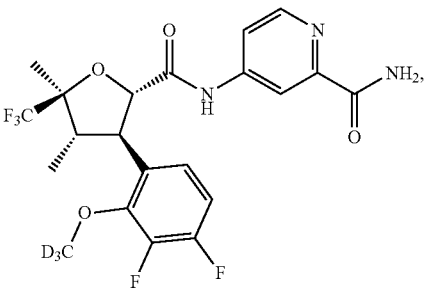

4-((2S,3R,4S,5S)-3-(3,4-difluoro-2-(methoxy-d₃)phenyl)-4,5-dimethyl-5-(trifluoromethyl)tetrahydrofuran-2-carboxamido)picolinamide

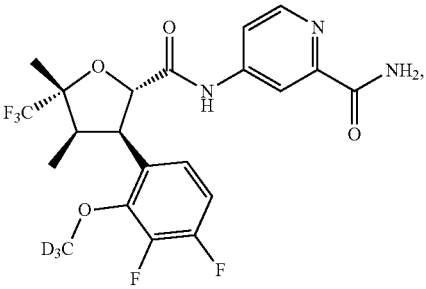

4-((2S,3R,4R,5R)-3-(3,4-difluoro-2-(methoxy-d₃)phenyl)-4,5-dimethyl-5-(trifluoromethyl)tetrahydrofuran-2-carboxamido)picolinamide

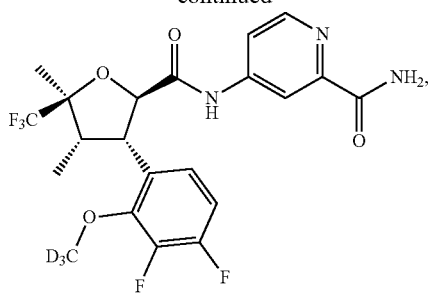

4-((2R,3S,4S,5S)-3-(3,4-difluoro-2-(methoxy-d₃)phenyl)-4,5-dimethyl-5-(trifluoromethyl)tetrahydrofuran-2-carboxamido)picolinamide

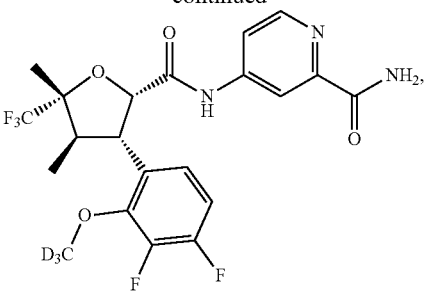

4-((2S,3S,4R,5R)-3-(3,4-difluoro-2-(methoxy-d₃)phenyl)-4,5-dimethyl-5-(trifluoromethyl)tetrahydrofuran-2-carboxamido)picolinamide

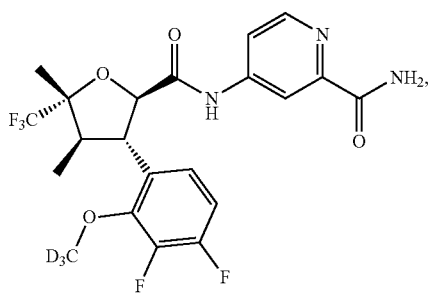

4-((2R,3S,4R,5R)-3-(3,4-difluoro-2-(methoxy-d₃)phenyl)-4,5-dimethyl-5-(trifluoromethyl)tetrahydrofuran-2-carboxamido)picolinamide

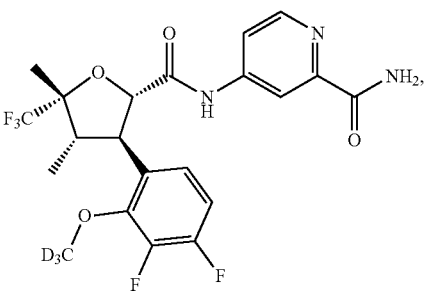

4-((2S,3R,4S,5R)-3-(3,4-difluoro-2-(methoxy-d₃)phenyl)-4,5-dimethyl-5-(trifluoromethyl)tetrahydrofuran-2-carboxamido)picolinamide

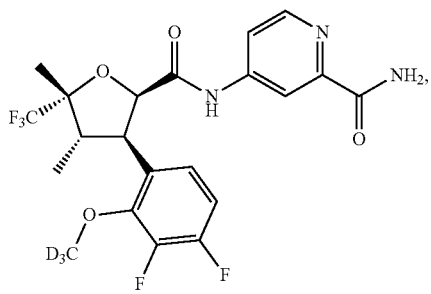

4-((2R,3R,4S,5R)-3-(3,4-difluoro-2-(methoxy-d₃)phenyl)-4,5-dimethyl-5-(trifluoromethyl)tetrahydrofuran-2-carboxamido)picolinamide

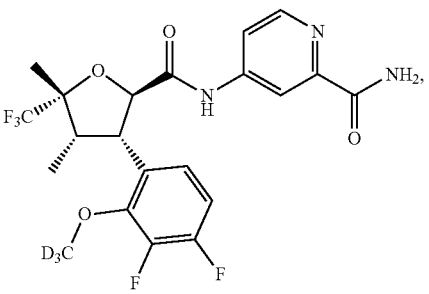

4-((2R,3S,4S,5R)-3-(3,4-difluoro-2-(methoxy-d₃)phenyl)-4,5-dimethyl-5-(trifluoromethyl)tetrahydrofuran-2-carboxamido)picolinamide

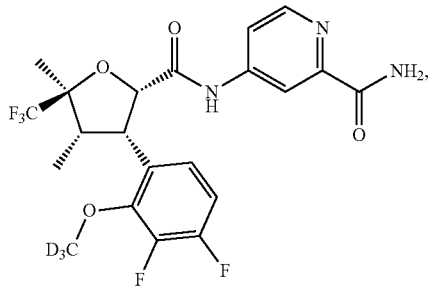

4-((2S,3S,4S,5S)-3-(3,4-difluoro-2-(methoxy-d₃)phenyl)-4,5-dimethyl-5-(trifluoromethyl)tetrahydrofuran-2-carboxamido)picolinamide

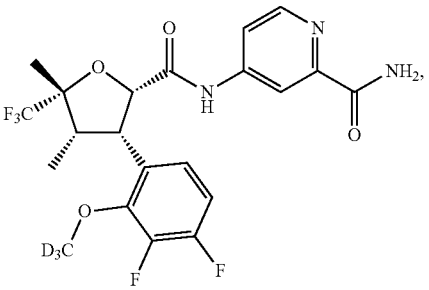

4-((2S,3S,4S,5R)-3-(3,4-difluoro-2-(methoxy-d₃)phenyl)-4,5-dimethyl-5-(trifluoromethyl)tetrahydrofuran-2-carboxamido)picolinamide -continued

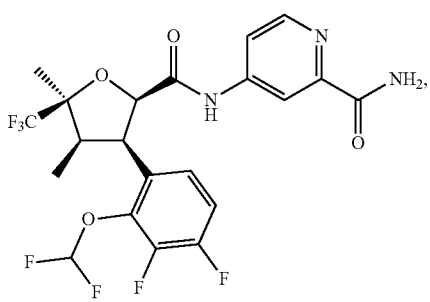

4-((2R,3R,4R,5S)-3-(2-(difluoromethoxy)-3,4-difluorophenyl)-4,5-dimethyl-5-(trifluoromethyl)tetrahydrofuran-2-carboxamido)picolinamide

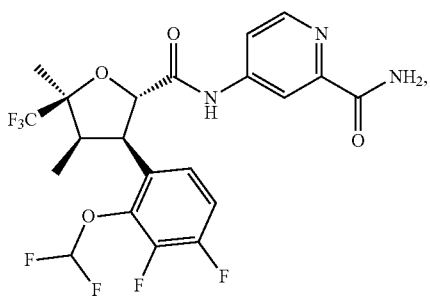

4-((2S,3R,4R,5S)-3-(2-(difluoromethoxy)-3,4-difluorophenyl)-4,5-dimethyl-5-(trifluoromethyl)tetrahydrofuran-2-carboxamido)picolinamide

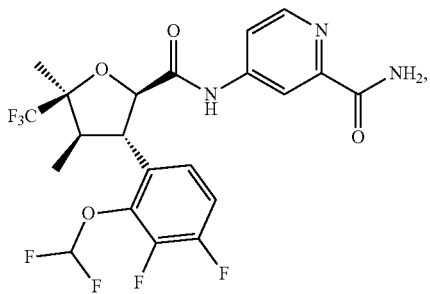

4-((2R,3S,4R,5S)-3-(2-(difluoromethoxy)-3,4-difluorophenyl)-4,5-dimethyl-5-(trifluoromethyl)tetrahydrofuran-2-carboxamido)picolinamide

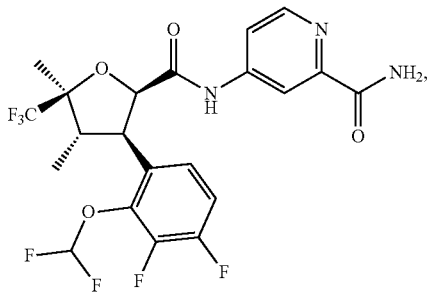

4-((2R,3R,4S,5S)-3-(2-(difluoromethoxy)-3,4-difluorophenyl)-4,5-dimethyl-5-(trifluoromethyl)tetrahydrofuran-2-carboxamido)picolinamide

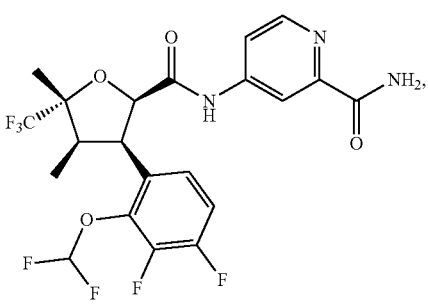

4-((2R,3R,4R,5R)-3-(2-(difluoromethoxy)-3,4-difluorophenyl)-4,5-dimethyl-5-(trifluoromethyl)tetrahydrofuran-2-carboxamido)picolinamide

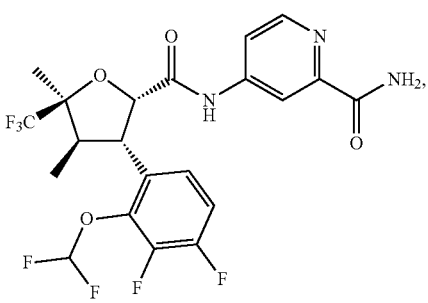

4-((2S,3R,4R,5R)-3-(2-(difluoromethoxy)-3,4-difluorophenyl)-4,5-dimethyl-5-(trifluoromethyl)tetrahydrofuran-2-carboxamido)picolinamide

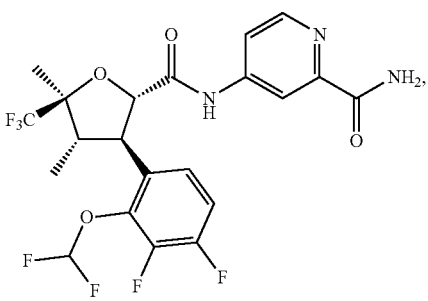

4-((2S,3R,4S,5S)-3-(2-(difluoromethoxy)-3,4-difluorophenyl)-4,5-dimethyl-5-(trifluoromethyl)tetrahydrofuran-2-carboxamido)picolinamide

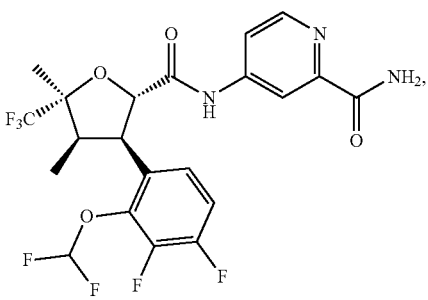

4-((2S,3R,4R,5R)-3-(2-(difluoromethoxy)-3,4-difluorophenyl)-4,5-dimethyl-5-(trifluoromethyl)tetrahydrofuran-2-carboxamido)picolinamide -continued

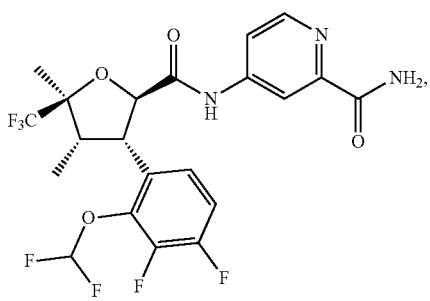

4-((2R,3S,4S,5S)-3-(2-(difluoromethoxy)-3,4-difluorophenyl)-4,5-dimethyl-5-(trifluoromethyl)tetrahydrofuran-2-carboxamido)picolinamide

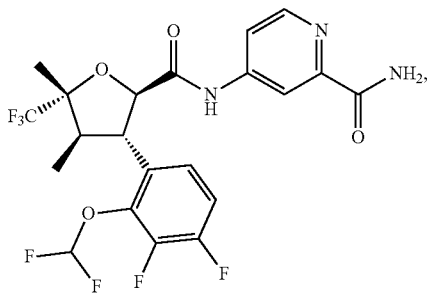

4-((2R,3S,4R,5R)-3-(2-(difluoromethoxy)-3,4-difluorophenyl)-4,5-dimethyl-5-(trifluoromethyl)tetrahydrofuran-2-carboxamido)picolinamide

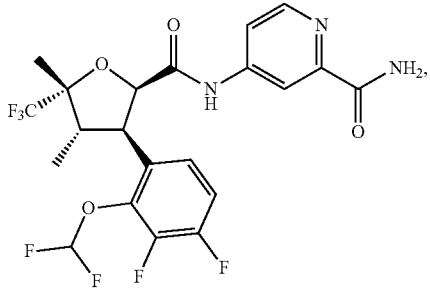

4-((2R,3R,4S,5R)-3-(2-(difluoromethoxy)-3,4-difluorophenyl)-4,5-dimethyl-5-(trifluoromethyl)tetrahydrofuran-2-carboxamido)picolinamide

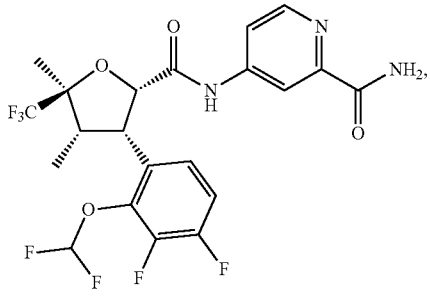

4-((2S,3S,4S,5S)-3-(2-(difluoromethoxy)-3,4-difluorophenyl)-4,5-dimethyl-5-(trifluoromethyl)tetrahydrofuran-2-carboxamido)picolinamide -continued

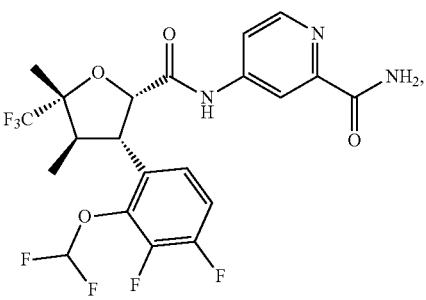

4-((2S,3S,4R,5R)-3-(2-(difluoromethoxy)-3,4-difluorophenyl)-4,5-dimethyl-5-(trifluoromethyl)tetrahydrofuran-2-carboxamido)picolinamide

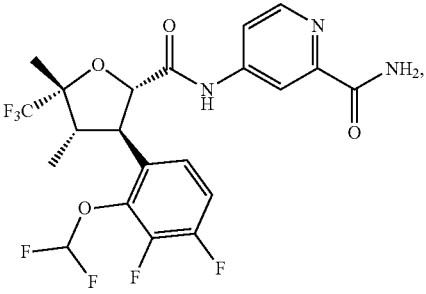

4-((2S,3R,4S,5R)-3-(2-(difluoromethoxy)-3,4-difluorophenyl)-4,5-dimethyl-5-(trifluoromethyl)tetrahydrofuran-2-carboxamido)picolinamide

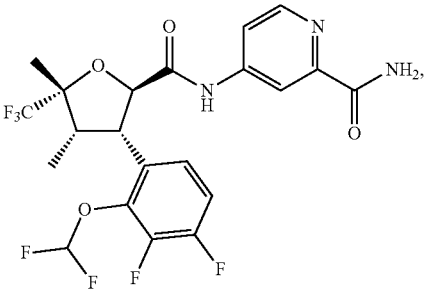

4-((2R,3S,4S,5R)-3-(2-(difluoromethoxy)-3,4-difluorophenyl)-4,5-dimethyl-5-(trifluoromethyl)tetrahydrofuran-2-carboxamido)picolinamide

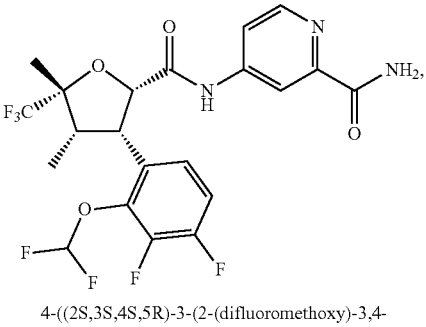

4-((2S,3S,4S,5R)-3-(2-(difluoromethoxy)-3,4-difluorophenyl)-4,5-dimethyl-5-(trifluoromethyl)tetrahydrofuran-2-carboxamido)picolinamide -continued

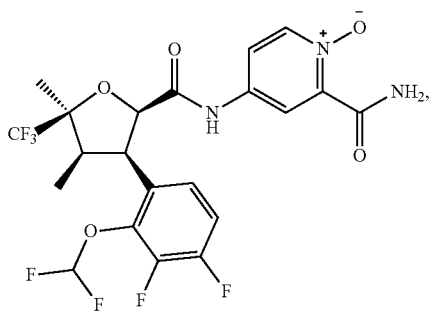

2-carbamoyl-4-((2R,3R,4R,5S)-3-(2-(difluoromethoxy)-3,4-difluorophenyl)-4,5-dimethyl-5-(trifluoromethyl)tetrahydrofuran-2-carboxamido)pyridine 1-oxide

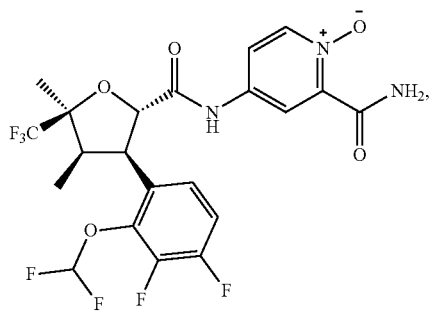

2-carbamoyl-4-((2S,3R,4R,5S)-3-(2-(difluoromethoxy)-3,4-difluorophenyl)-4,5-dimethyl-5-(trifluoromethyl)tetrahydrofuran-2-carboxamido)pyridine 1-oxide

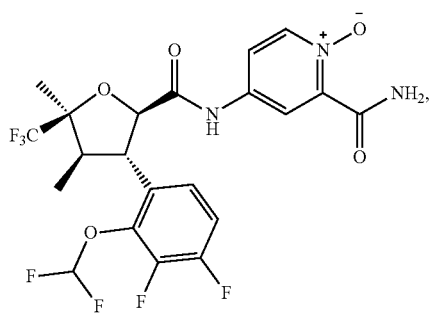

2-carbamoyl-4-((2R,3S,4R,5S)-3-(2-(difluoromethoxy)-3,4-difluorophenyl)-4,5-dimethyl-5-(trifluoromethyl)tetrahydrofuran-2-carboxamido)pyridine 1-oxide

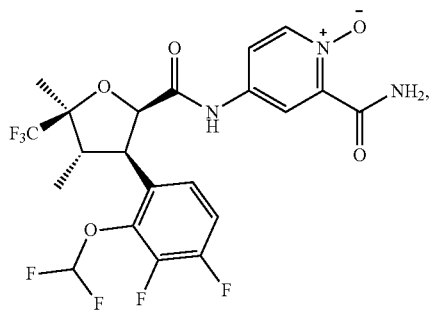

2-carbamoyl-4-((2R,3R,4S,5S)-3-(2-(difluoromethoxy)-3,4-difluorophenyl)-4,5-dimethyl-5-(trifluoromethyl)tetrahydrofuran-2-carboxamido)pyridine 1-oxide -continued

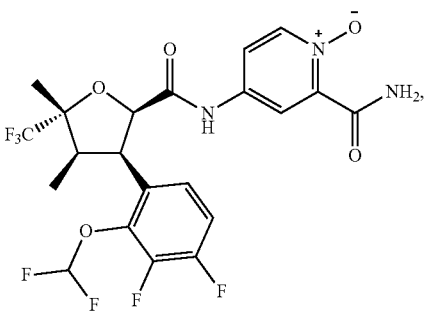

2-carbamoyl-4-((2R,3R,4R,5R)-3-(2-(difluoromethoxy)-3,4-difluorophenyl)-4,5-dimethyl-5-(trifluoromethyl)tetrahydrofuran-2-carboxamido)pyridine 1-oxide

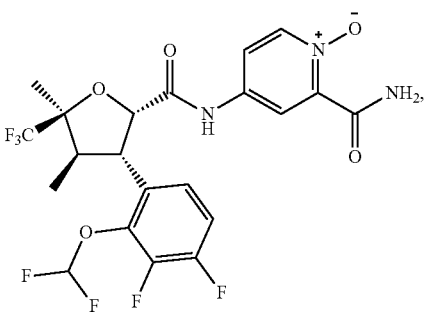

2-carbamoyl-4-((2S,3S,4R,5S)-3-(2-(difluoromethoxy)-3,4-difluorophenyl)-4,5-dimethyl-5-(trifluoromethyl)tetrahydrofuran-2-carboxamido)pyridine 1-oxide

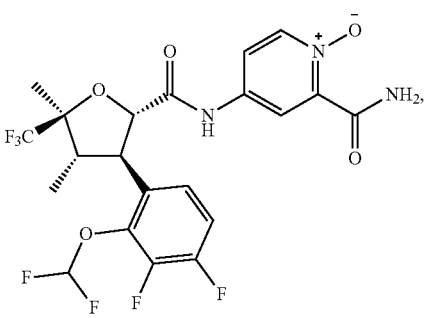

2-carbamoyl-4-((2S,3R,4S,5S)-3-(2-(difluoromethoxy)-3,4-difluorophenyl)-4,5-dimethyl-5-(trifluoromethyl)tetrahydrofuran-2-carboxamido)pyridine 1-oxide

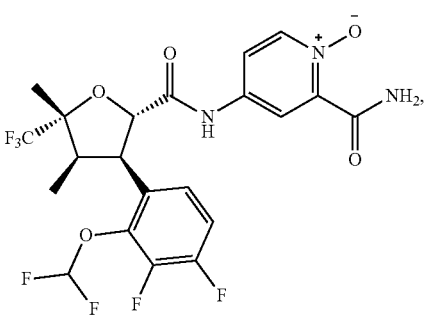

2-carbamoyl-4-((2S,3R,4R,5R)-3-(2-(difluoromethoxy)-3,4-difluorophenyl)-4,5-dimethyl-5-(trifluoromethyl)tetrahydrofuran-2-carboxamido)pyridine 1-oxide

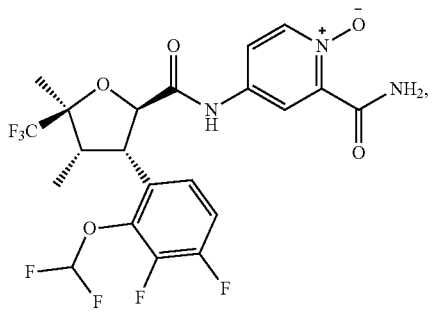

2-carbamoyl-4-((2R,3S,4S,5S)-3-(2-(difluoromethoxy)-3,4-difluorophenyl)-4,5-dimethyl-5-(trifluoromethyl)tetrahydrofuran-2-carboxamido)pyridine 1-oxide

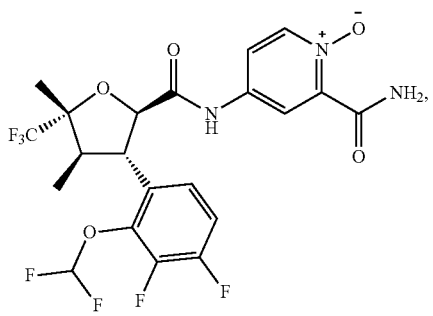

2-carbamoyl-4-((2R,3S,4R,5R)-3-(2-(difluoromethoxy)-3,4-difluorophenyl)-4,5-dimethyl-5-(trifluoromethyl)tetrahydrofuran-2-carboxamido)pyridine 1-oxide

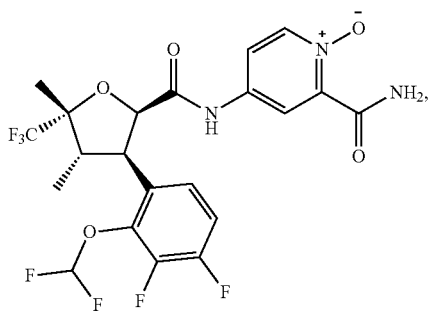

2-carbamoyl-4-((2R,3R,4S,5R)-3-(2-(difluoromethoxy)-3,4-difluorophenyl)-4,5-dimethyl-5-(trifluoromethyl)tetrahydrofuran-2-carboxamido)pyridine 1-oxide

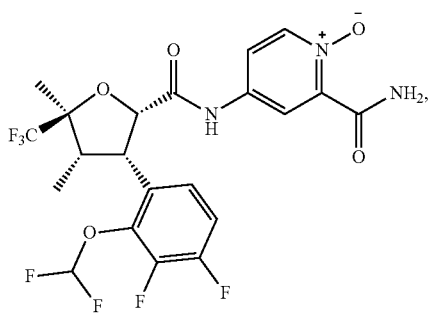

2-carbamoyl-4-((2S,3S,4S,5S)-3-(2-(difluoromethoxy)-3,4-difluorophenyl)-4,5-dimethyl-5-(trifluoromethyl)tetrahydrofuran-2-carboxamido)pyridine 1-oxide

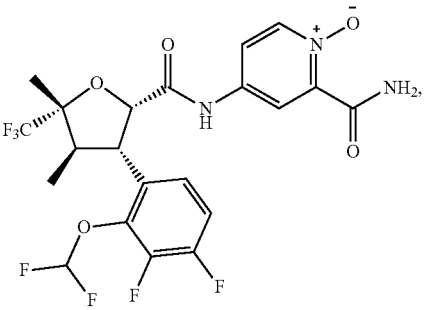

2-carbamoyl-4-((2S,3S,4R,5R)-3-(2-(difluoromethoxy)-3,4-difluorophenyl)-4,5-dimethyl-5-(trifluoromethyl)tetrahydrofuran-2-carboxamido)pyridine 1-oxide

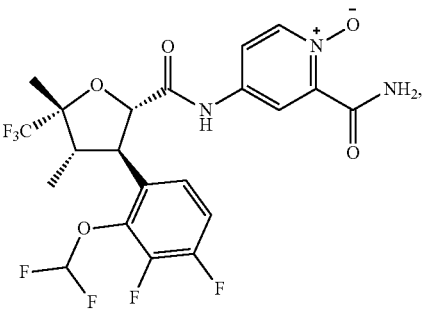

2-carbamoyl-4-((2S,3R,4S,5R)-3-(2-(difluoromethoxy)-3,4-difluorophenyl)-4,5-dimethyl-5-(trifluoromethyl)tetrahydrofuran-2-carboxamido)pyridine 1-oxide

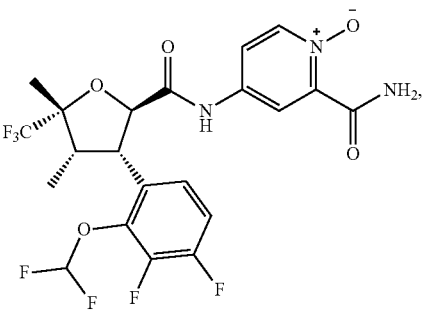

2-carbamoyl-4-((2R,3S,4S,5R)-3-(2-(difluoromethoxy)-3,4-difluorophenyl)-4,5-dimethyl-5-(trifluoromethyl)tetrahydrofuran-2-carboxamido)pyridine 1-oxide

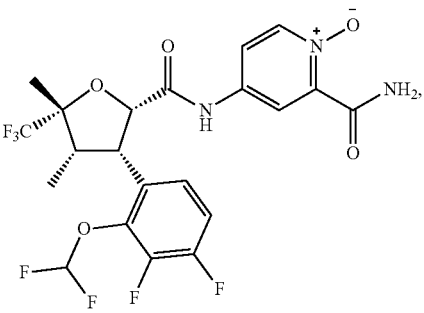

2-carbamoyl-4-((2S,3S,4S,5R)-3-(2-(difluoromethoxy)-3,4-difluorophenyl)-4,5-dimethyl-5-(trifluoromethyl)tetrahydrofuran-2-carboxamido)pyridine 1-oxide -continued

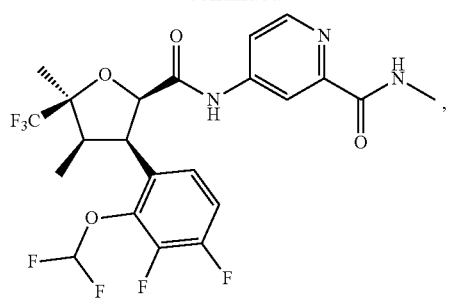

4-((2R,3R,4R,5S)-3-(2-(difluoromethoxy)-3,4-difluorophenyl)-4,5-dimethyl-5-(trifluoromethyl)tetrahydrofuran-2-carboxamido)-N-methylpicolinamide

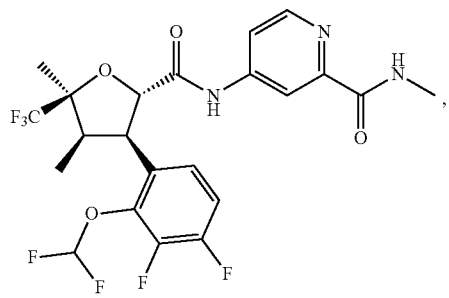

4-((2S,3R,4R,5S)-3-(2-(difluoromethoxy)-3,4-difluorophenyl)-4,5-dimethyl-5-(trifluoromethyl)tetrahydrofuran-2-carboxamido)-N-methylpicolinamide

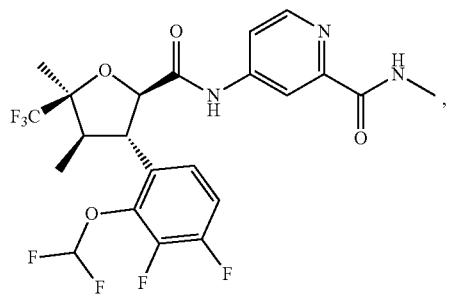

4-((2R,3S,4R,5S)-3-(2-(difluoromethoxy)-3,4-difluorophenyl)-4,5-dimethyl-5-(trifluoromethyl)tetrahydrofuran-2-carboxamido)-N-methylpicolinamide

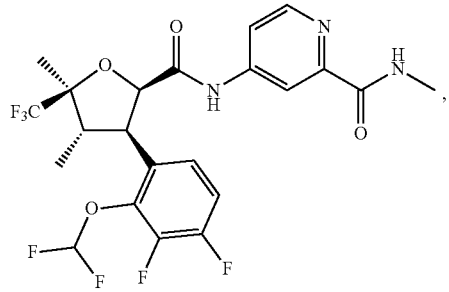

4-((2R,3R,4S,5S)-3-(2-(difluoromethoxy)-3,4-difluorophenyl)-4,5-dimethyl-5-(trifluoromethyl)tetrahydrofuran-2-carboxamido)-N-methylpicolinamide -continued

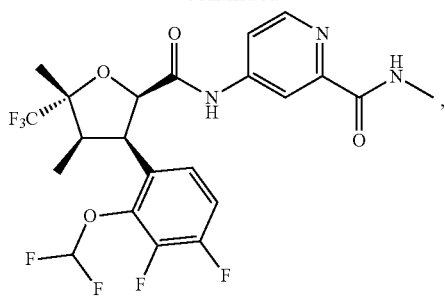

4-((2R,3R,4R,5R)-3-(2-(difluoromethoxy)-3,4-difluorophenyl)-4,5-dimethyl-5-(trifluoromethyl)tetrahydrofuran-2-carboxamido)-N-methylpicolinamide

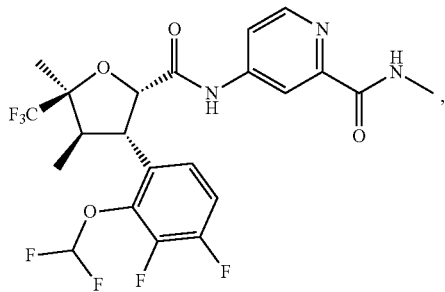

4-((2S,3S,4R,5S)-3-(2-(difluoromethoxy)-3,4-difluorophenyl)-4,5-dimethyl-5-(trifluoromethyl)tetrahydrofuran-2-carboxamido)-N-methylpicolinamide

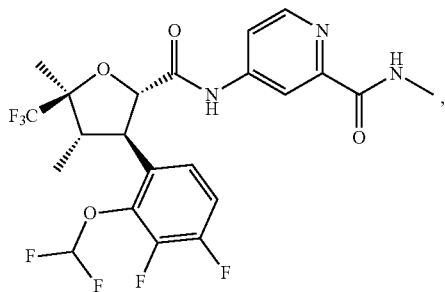

4-((2S,3R,4S,5S)-3-(2-(difluoromethoxy)-3,4-difluorophenyl)-4,5-dimethyl-5-(trifluoromethyl)tetrahydrofuran-2-carboxamido)-N-methylpicolinamide

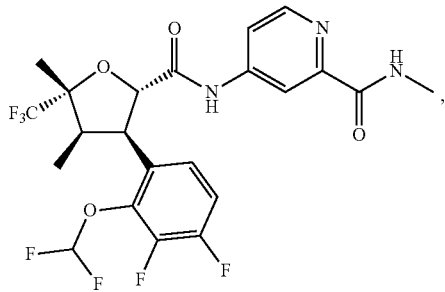

4-((2S,3R,4R,5R)-3-(2-(difluoromethoxy)-3,4-difluorophenyl)-4,5-dimethyl-5-(trifluoromethyl)tetrahydrofuran-2-carboxamido)-N-methylpicolinamide -continued

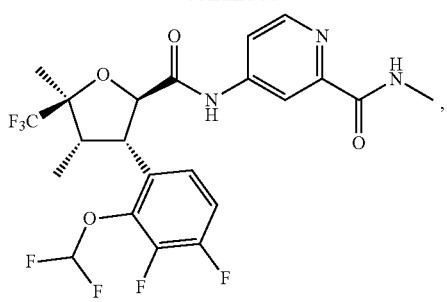

4-((2R,3S,4S,5S)-3-(2-(difluoromethoxy)-3,4-difluorophenyl)-4,5-dimethyl-5-(trifluoromethyl)tetrahydrofuran-2-carboxamido)-N-methylpicolinamide

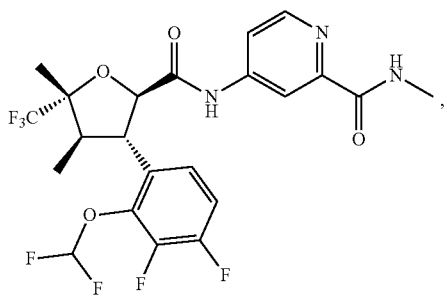

4-((2R,3S,4R,5R)-3-(2-(difluoromethoxy)-3,4-difluorophenyl)-4,5-dimethyl-5-(trifluoromethyl)tetrahydrofuran-2-carboxamido)-N-methylpicolinamide

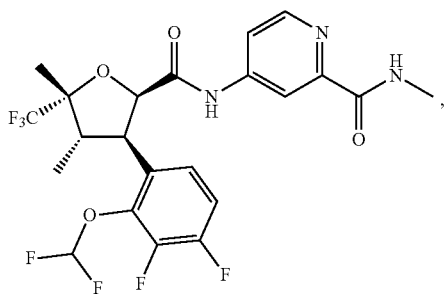

4-((2R,3R,4S,5R)-3-(2-(difluoromethoxy)-3,4-difluorophenyl)-4,5-dimethyl-5-(trifluoromethyl)tetrahydrofuran-2-carboxamido)-N-methylpicolinamide

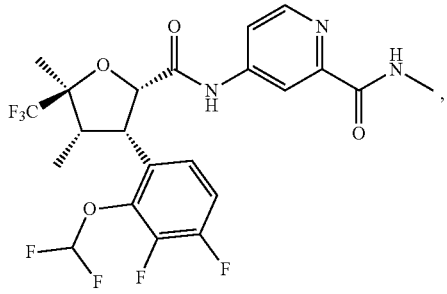

4-((2S,3S,4S,5S)-3-(2-(difluoromethoxy)-3,4-difluorophenyl)-4,5-dimethyl-5-(trifluoromethyl)tetrahydrofuran-2-carboxamido)-N-methylpicolinamide -continued

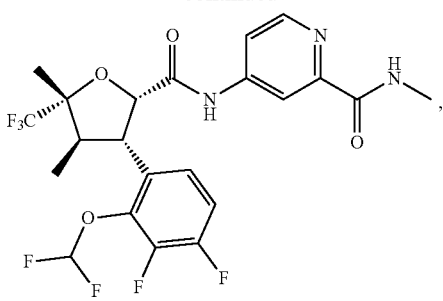

4-((2S,3S,4R,5R)-3-(2-(difluoromethoxy)-3,4-difluorophenyl)-4,5-dimethyl-5-(trifluoromethyl)tetrahydrofuran-2-carboxamido)-N-methylpicolinamide

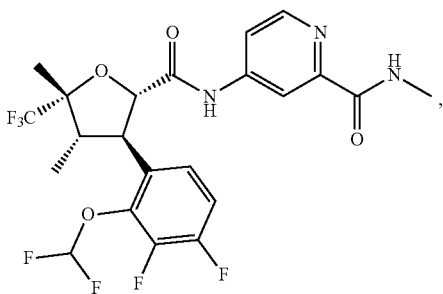

4-((2S,3R,4S,5R)-3-(2-(difluoromethoxy)-3,4-difluorophenyl)-4,5-dimethyl-5-(trifluoromethyl)tetrahydrofuran-2-carboxamido)-N-methylpicolinamide

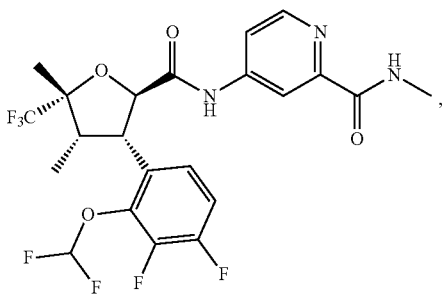

4-((2R,3S,4S,5R)-3-(2-(difluoromethoxy)-3,4-difluorophenyl)-4,5-dimethyl-5-(trifluoromethyl)tetrahydrofuran-2-carboxamido)-N-methylpicolinamide

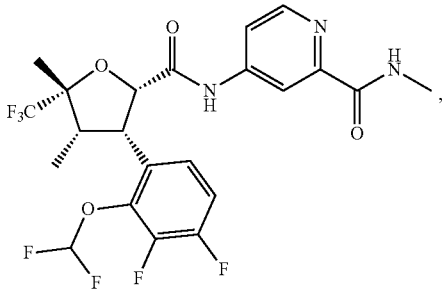

4-((2S,3S,4S,5R)-3-(2-(difluoromethoxy)-3,4-difluorophenyl)-4,5-dimethyl-5-(trifluoromethyl)tetrahydrofuran-2-carboxamido)-N-methylpicolinamide -continued

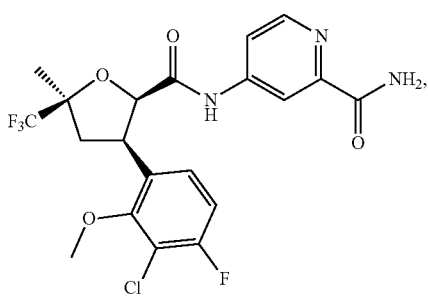

4-((2R,3R,5S)-3-(3-chloro-4-fluoro-2-
methoxyphenyl)-5-methyl-5-(trifluoromethyl)
tetrahydrofuran-2-
carboxamido)picolinamide

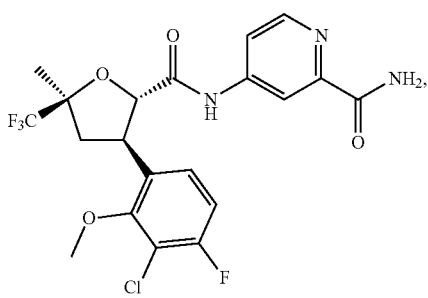

4-((2S,3R,5S)-3-(3-chloro-4-fluoro-2-
methoxyphenyl)-5-methyl-5-(trifluoromethyl)
tetrahydrofuran-2-
carboxamido)picolinamide

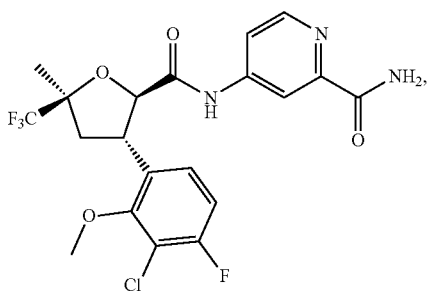

4-((2R,3S,5S)-3-(3-chloro-4-fluoro-2-
methoxyphenyl)-5-methyl-5-(trifluoromethyl)
tetrahydrofuran-2-
carboxamido)picolinamide

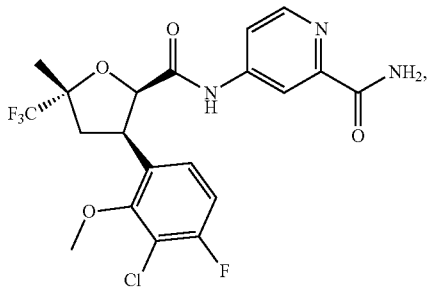

4-((2R,3R,5R)-3-(3-chloro-4-fluoro-2-
methoxyphenyl)-5-methyl-5-(trifluoromethyl)
tetrahydrofuran-2-
carboxamido)picolinamide -continued

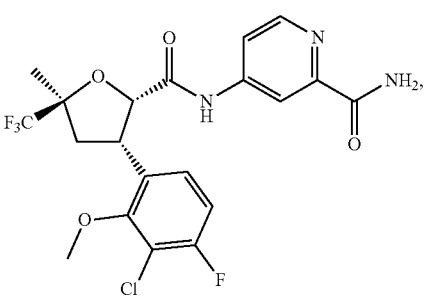

4-((2S,3S,5S)-3-(3-chloro-4-fluoro-2-
methoxyphenyl)-5-methyl-5-(trifluoromethyl)
tetrahydrofuran-2-
carboxamido)picolinamide

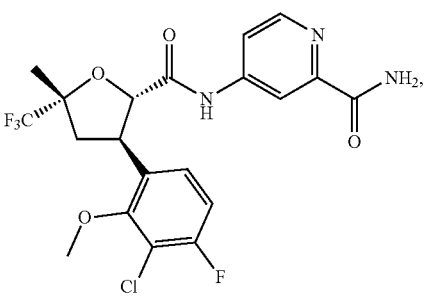

4-((2S,3R,5R)-3-(3-chloro-4-fluoro-2-
methoxyphenyl)-5-methyl-5-(trifluoromethyl)
tetrahydrofuran-2-
carboxamido)picolinamide

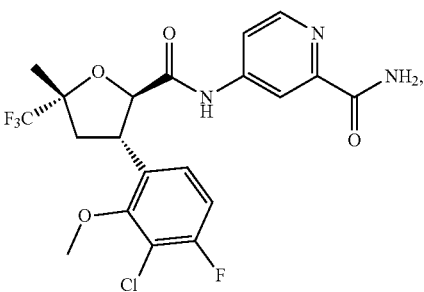

4-((2R,3S,5R)-3-(3-chloro-4-fluoro-2-
methoxyphenyl)-5-methyl-5-(trifluoromethyl)
tetrahydrofuran-2-
carboxamido)picolinamide

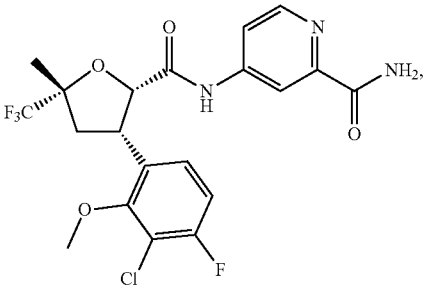

4-((2S,3S,5R)-3-(3-chloro-4-fluoro-2-
methoxyphenyl)-5-methyl-5-(trifluoromethyl)
tetrahydrofuran-2-
carboxamido)picolinamide

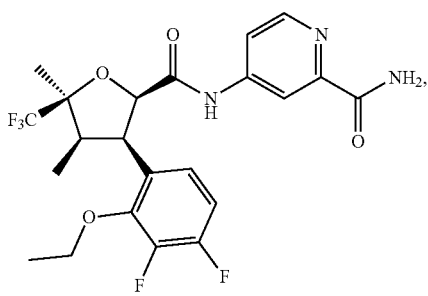

4-((2R,3R,4R,5S)-3-(2-ethoxy-3,4-difluorophenyl)-4,5-dimethyl-5-(trifluoromethyl)tetrahydrofuran-2-carboxamido)picolinamide

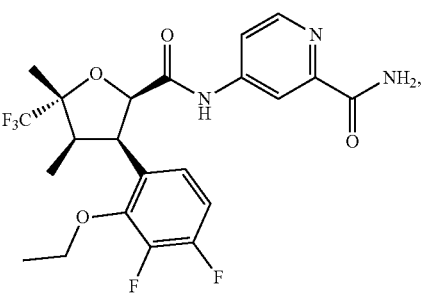

4-((2R,3R,4R,5R)-3-(2-ethoxy-3,4-difluorophenyl)-4,5-dimethyl-5-(trifluoromethyl)tetrahydrofuran-2-carboxamido)picolinamide

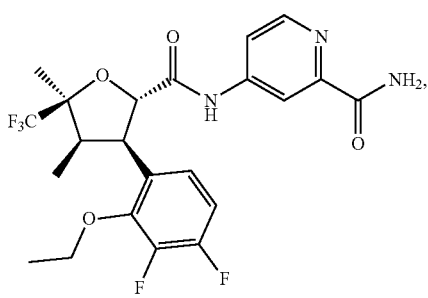

4-((2S,3R,4R,5S)-3-(2-ethoxy-3,4-difluorophenyl)-4,5-dimethyl-5-(trifluoromethyl)tetrahydrofuran-2-carboxamido)picolinamide

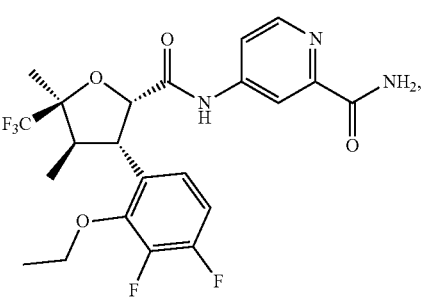

4-((2S,3S,4R,5S)-3-(2-ethoxy-3,4-difluorophenyl)-4,5-dimethyl-5-(trifluoromethyl)tetrahydrofuran-2-carboxamido)picolinamide

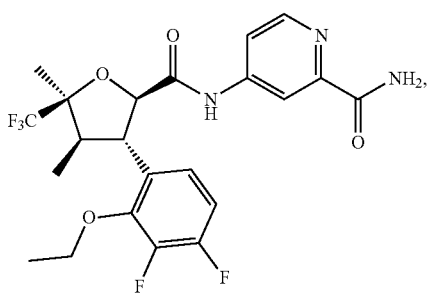

4-((2R,3S,4R,5S)-3-(2-ethoxy-3,4-difluorophenyl)-4,5-dimethyl-5-(trifluoromethyl)tetrahydrofuran-2-carboxamido)picolinamide

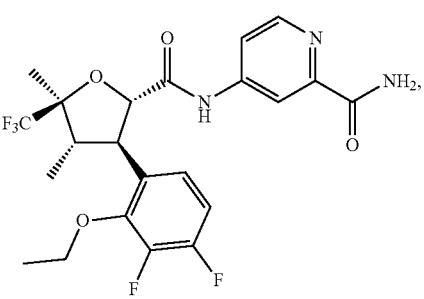

4-((2S,3R,4S,5S)-3-(2-ethoxy-3,4-difluorophenyl)-4,5-dimethyl-5-(trifluoromethyl)tetrahydrofuran-2-carboxamido)picolinamide

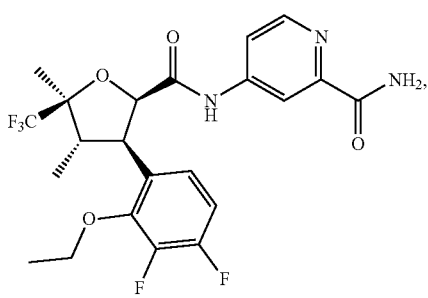

4-((2R,3R,4S,5S)-3-(2-ethoxy-3,4-difluorophenyl)-4,5-dimethyl-5-(trifluoromethyl)tetrahydrofuran-2-carboxamido)picolinamide

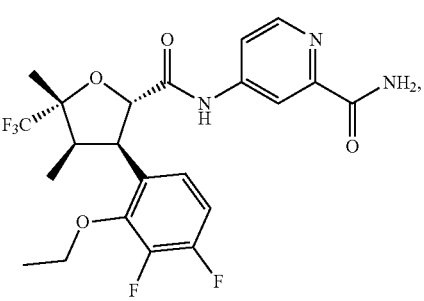

4-((2S,3R,4R,5R)-3-(2-ethoxy-3,4-difluorophenyl)-4,5-dimethyl-5-(trifluoromethyl)tetrahydrofuran-2-carboxamido)picolinamide -continued

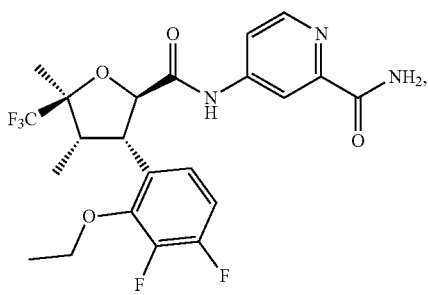

4-((2R,3S,4S,5S)-3-(2-ethoxy-3,4-
difluorophenyl)-4,5-dimethyl-5-(trifluoromethyl)
tetrahydrofuran-2-carboxamido)picolinamide

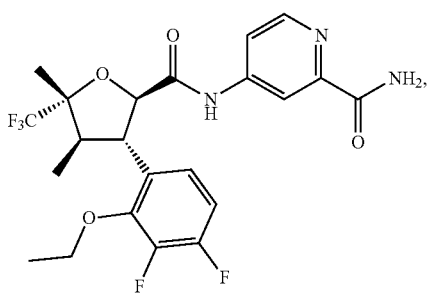

4-((2R,3S,4R,5R)-3-(2-ethoxy-3,4-
difluorophenyl)-4,5-dimethyl-5-(trifluoromethyl)
tetrahydrofuran-2-carboxamido)picolinamide

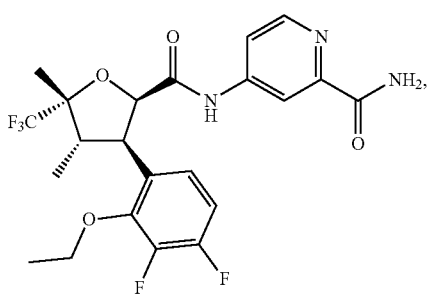

4-((2R,3R,4S,5R)-3-(2-ethoxy-3,4-
difluorophenyl)-4,5-dimethyl-5-(trifluoromethyl)
tetrahydrofuran-2-carboxamido)picolinamide

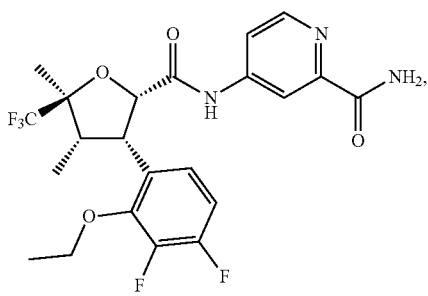

4-((2S,3S,4S,5S)-3-(2-ethoxy-3,4-
difluorophenyl)-4,5-dimethyl-5-(trifluoromethyl)
tetrahydrofuran-2-carboxamido)picolinamide -continued

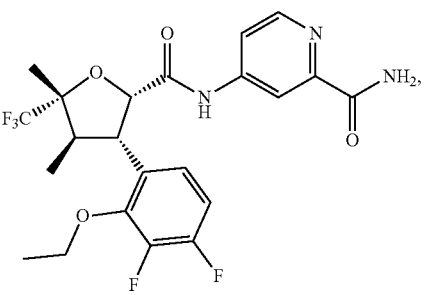

4-((2S,3S,4R,5R)-3-(2-ethoxy-3,4-
difluorophenyl)-4,5-dimethyl-5-(trifluoromethyl)
tetrahydrofuran-2-carboxamido)picolinamide

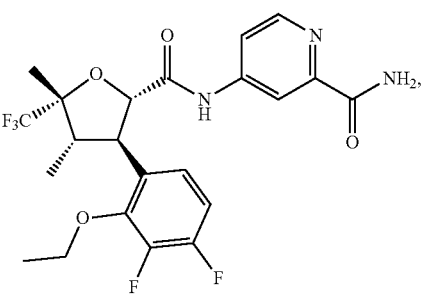

4-((2S,3R,4S,5R)-3-(2-ethoxy-3,4-
difluorophenyl)-4,5-dimethyl-5-(trifluoromethyl)
tetrahydrofuran-2-carboxamido)picolinamide

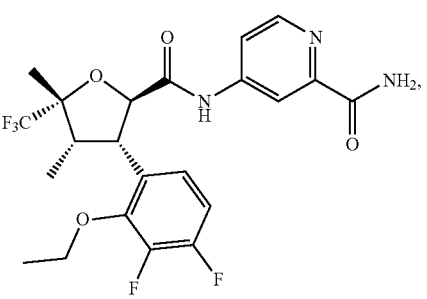

4-((2R,3S,4S,5R)-3-(2-ethoxy-3,4-
difluorophenyl)-4,5-dimethyl-5-(trifluoromethyl)
tetrahydrofuran-2-carboxamido)picolinamide

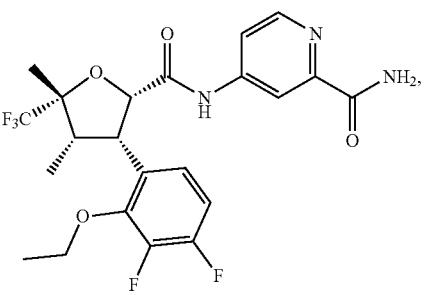

4-((2S,3S,4S,5R)-3-(2-ethoxy-3,4-
difluorophenyl)-4,5-dimethyl-5-(trifluoromethyl)
tetrahydrofuran-2-carboxamido)picolinamide

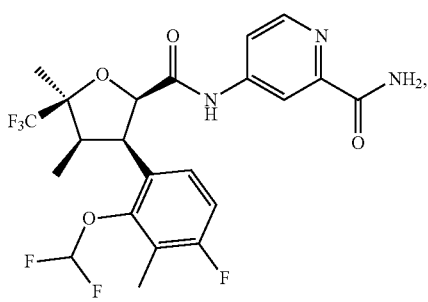

4-((2R,3R,4R,5S)-3-(2-(difluoromethoxy)-4-fluoro-3-methylphenyl)-4,5-dimethyl-5-(trifluoromethyl)tetrahydrofuran-2-carboxamido)picolinamide

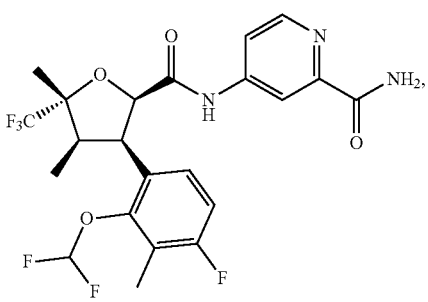

4-((2R,3R,4R,5R)-3-(2-(difluoromethoxy)-4-fluoro-3-methylphenyl)-4,5-dimethyl-5-(trifluoromethyl)tetrahydrofuran-2-carboxamido)picolinamide

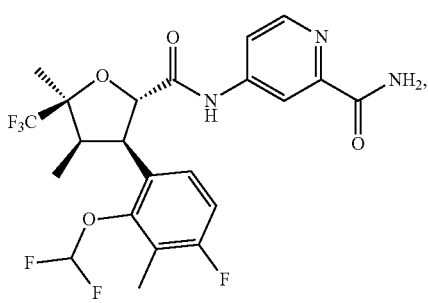

4-((2S,3R,4R,5S)-3-(2-(difluoromethoxy)-4-fluoro-3-methylphenyl)-4,5-dimethyl-5-(trifluoromethyl)tetrahydrofuran-2-carboxamido)picolinamide

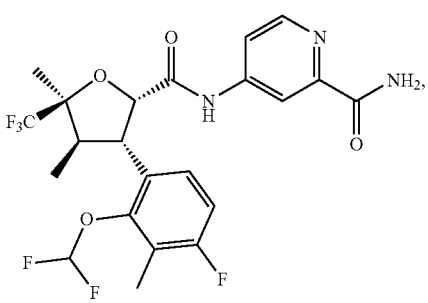

4-((2S,3S,4R,5S)-3-(2-(difluoromethoxy)-4-fluoro-3-methylphenyl)-4,5-dimethyl-5-(trifluoromethyl)tetrahydrofuran-2-carboxamido)picolinamide

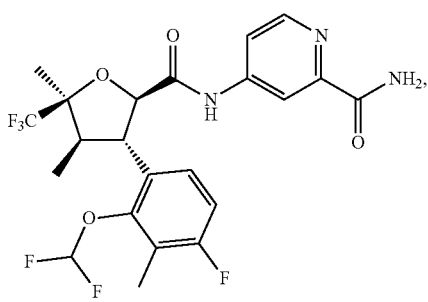

4-((2R,3S,4R,5S)-3-(2-(difluoromethoxy)-4-fluoro-3-methylphenyl)-4,5-dimethyl-5-(trifluoromethyl)tetrahydrofuran-2-carboxamido)picolinamide

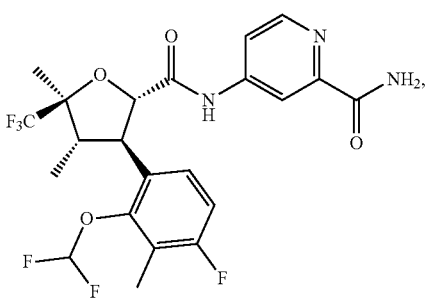

4-((2S,3R,4S,5S)-3-(2-(difluoromethoxy)-4-fluoro-3-methylphenyl)-4,5-dimethyl-5-(trifluoromethyl)tetrahydrofuran-2-carboxamido)picolinamide

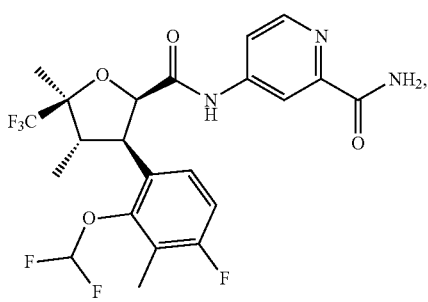

4-((2R,3R,4S,5S)-3-(2-(difluoromethoxy)-4-fluoro-3-methylphenyl)-4,5-dimethyl-5-(trifluoromethyl)tetrahydrofuran-2-carboxamido)picolinamide

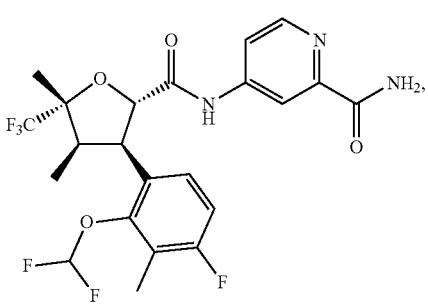

4-((2S,3R,4R,5R)-3-(2-(difluoromethoxy)-4-fluoro-3-methylphenyl)-4,5-dimethyl-5-(trifluoromethyl)tetrahydrofuran-2-carboxamido)picolinamide -continued

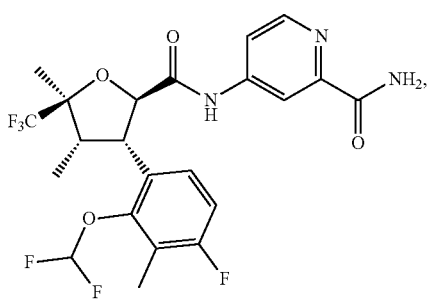

4-((2R,3S,4S,5S)-3-(2-(difluoromethoxy)-4-fluoro-3-methylphenyl)-4,5-dimethyl-5-(trifluoromethyl)tetrahydrofuran-2-carboxamido)picolinamide

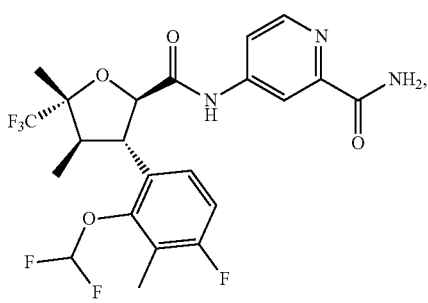

4-((2R,3S,4R,5R)-3-(2-(difluoromethoxy)-4-fluoro-3-methylphenyl)-4,5-dimethyl-5-(trifluoromethyl)tetrahydrofuran-2-carboxamido)picolinamide

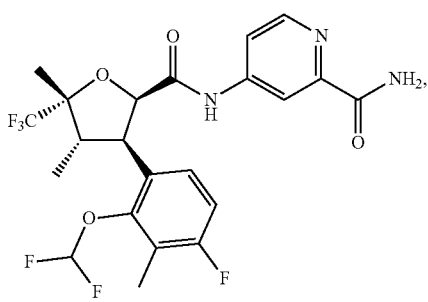

4-((2R,3R,4S,5R)-3-(2-(difluoromethoxy)-4-fluoro-3-methylphenyl)-4,5-dimethyl-5-(trifluoromethyl)tetrahydrofuran-2-carboxamido)picolinamide

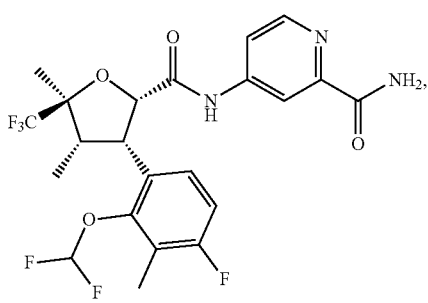

4-((2S,3S,4S,5S)-3-(2-(difluoromethoxy)-4-fluoro-3-methylphenyl)-4,5-dimethyl-5-(trifluoromethyl)tetrahydrofuran-2-carboxamido)picolinamide -continued

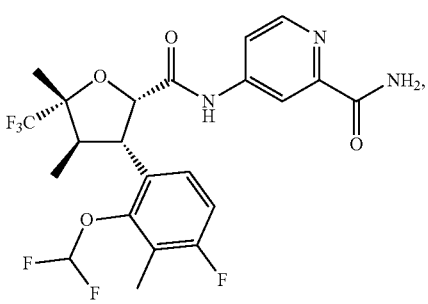

4-((2S,3S,4R,5R)-3-(2-(difluoromethoxy)-4-fluoro-3-methylphenyl)-4,5-dimethyl-5-(trifluoromethyl)tetrahydrofuran-2-carboxamido)picolinamide

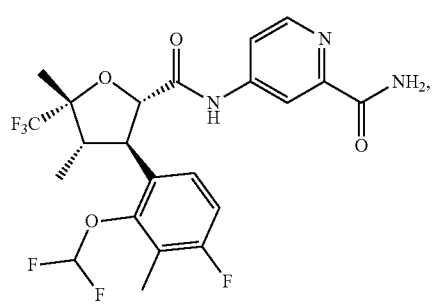

4-((2S,3R,4S,5R)-3-(2-(difluoromethoxy)-4-fluoro-3-methylphenyl)-4,5-dimethyl-5-(trifluoromethyl)tetrahydrofuran-2-carboxamido)picolinamide

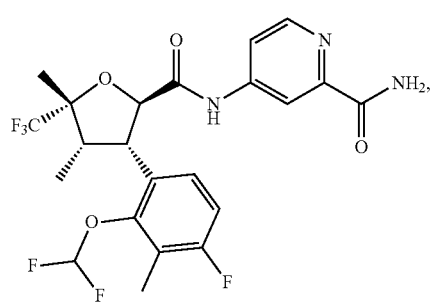

4-((2R,3S,4S,5R)-3-(2-(difluoromethoxy)-4-fluoro-3-methylphenyl)-4,5-dimethyl-5-(trifluoromethyl)tetrahydrofuran-2-carboxamido)picolinamide

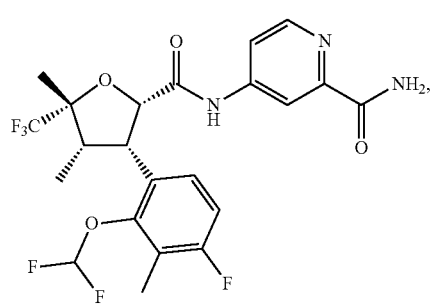

4-((2S,3S,4S,5R)-3-(2-(difluoromethoxy)-4-fluoro-3-methylphenyl)-4,5-dimethyl-5-(trifluoromethyl)tetrahydrofuran-2-carboxamido)picolinamide -continued

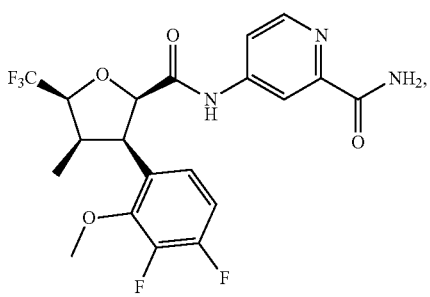

4-((2R,3R,4R,5S)-3-(3,4-difluoro-2-methoxyphenyl)-4-methyl-5-(trifluoromethyl)tetrahydrofuran-2-carboxamido)picolinamide

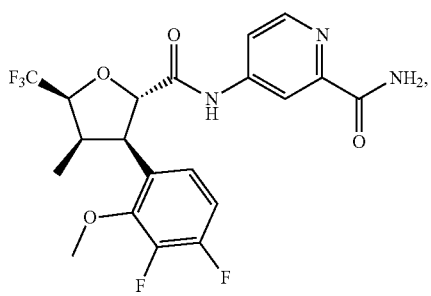

4-((2S,3R,4R,5S)-3-(3,4-difluoro-2-methoxyphenyl)-4-methyl-5-(trifluoromethyl)tetrahydrofuran-2-carboxamido)picolinamide

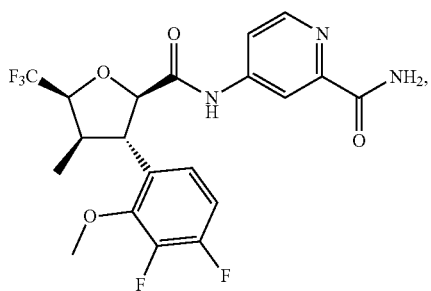

4-((2R,3S,4R,5S)-3-(3,4-difluoro-2-methoxyphenyl)-4-methyl-5-(trifluoromethyl)tetrahydrofuran-2-carboxamido)picolinamide

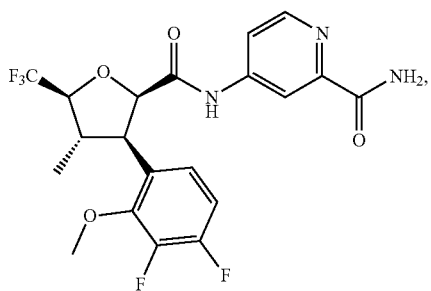

4-((2R,3R,4S,5S)-3-(3,4-difluoro-2-methoxyphenyl)-4-methyl-5-(trifluoromethyl)tetrahydrofuran-2-carboxamido)picolinamide -continued

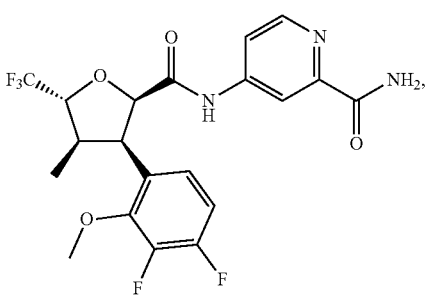

4-((2R,3R,4R,5R)-3-(3,4-difluoro-2-methoxyphenyl)-4-methyl-5-(trifluoromethyl)tetrahydrofuran-2-carboxamido)picolinamide

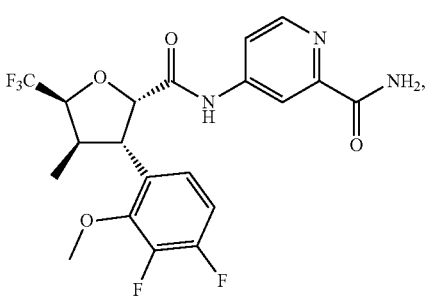

4-((2S,3S,4R,5S)-3-(3,4-difluoro-2-methoxyphenyl)-4-methyl-5-(trifluoromethyl)tetrahydrofuran-2-carboxamido)picolinamide

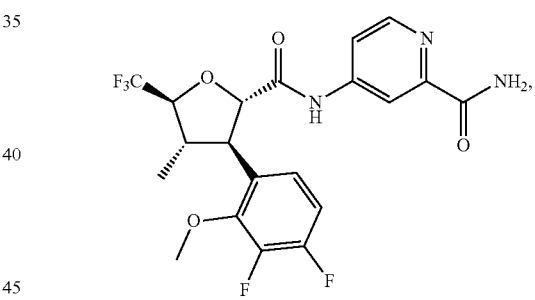

4-((2S,3R,4S,5S)-3-(3,4-difluoro-2-methoxyphenyl)-4-methyl-5-(trifluoromethyl)tetrahydrofuran-2-carboxamido)picolinamide

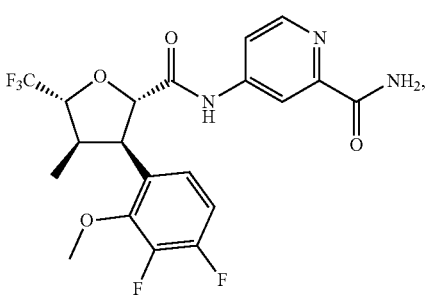

4-((2S,3R,4R,5R)-3-(3,4-difluoro-2-methoxyphenyl)-4-methyl-5-(trifluoromethyl)tetrahydrofuran-2-carboxamido)picolinamide -continued

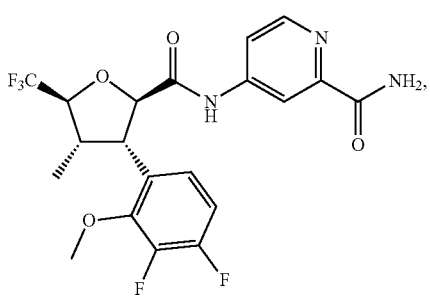

4-((2R,3S,4S,5S)-3-(3,4-difluoro-2-methoxyphenyl)-4-methyl-5-(trifluoromethyl)tetrahydrofuran-2-carboxamido)picolinamide

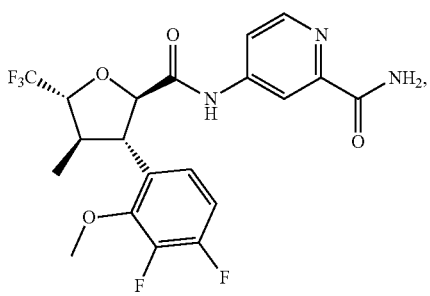

4-((2R,3S,4R,5R)-3-(3,4-difluoro-2-methoxyphenyl)-4-methyl-5-(trifluoromethyl)tetrahydrofuran-2-carboxamido)picolinamide

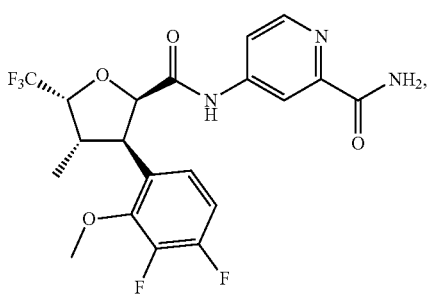

4-((2R,3R,4S,5R)-3-(3,4-difluoro-2-methoxyphenyl)-4-methyl-5-(trifluoromethyl)tetrahydrofuran-2-carboxamido)picolinamide

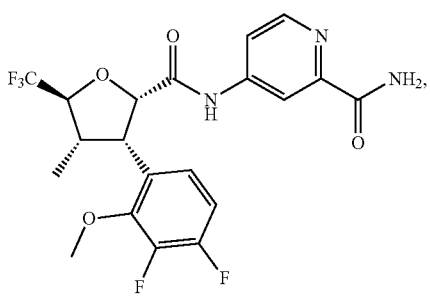

4-((2S,3S,4S,5S)-3-(3,4-difluoro-2-methoxyphenyl)-4-methyl-5-(trifluoromethyl)tetrahydrofuran-2-carboxamido)picolinamide -continued

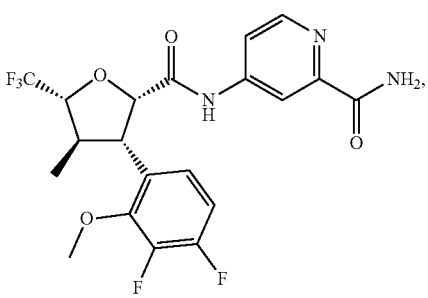

4-((2S,3S,4R,5R)-3-(3,4-difluoro-2-methoxyphenyl)-4-methyl-5-(trifluoromethyl)tetrahydrofuran-2-carboxamido)picolinamide

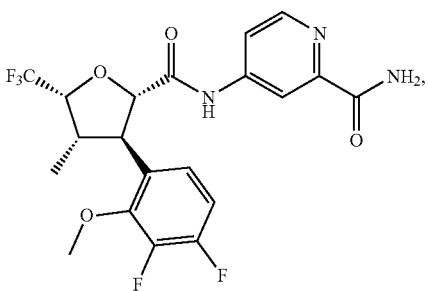

4-((2S,3R,4S,5R)-3-(3,4-difluoro-2-methoxyphenyl)-4-methyl-5-(trifluoromethyl)tetrahydrofuran-2-carboxamido)picolinamide

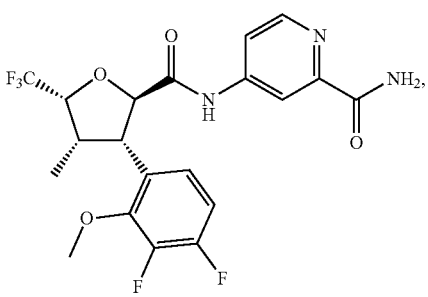

4-((2R,3S,4S,5R)-3-(3,4-difluoro-2-methoxyphenyl)-4-methyl-5-(trifluoromethyl)tetrahydrofuran-2-carboxamido)picolinamide

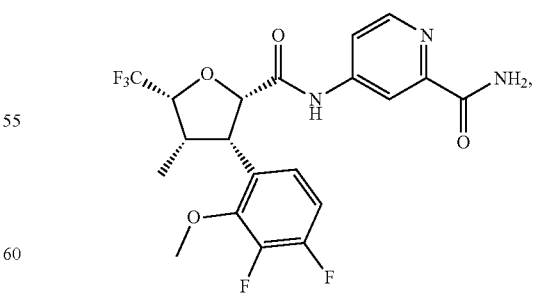

4-((2S,3S,4S,5R)-3-(3,4-difluoro-2-methoxyphenyl)-4-methyl-5-(trifluoromethyl)tetrahydrofuran-2-carboxamido)picolinamide -continued

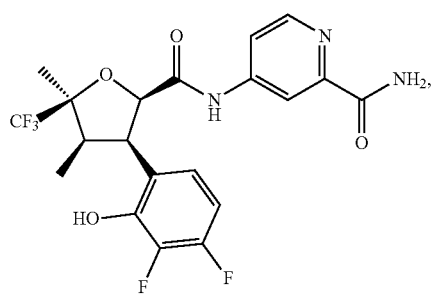

4-((2R,3R,4R,5S)-3-(3,4-difluoro-2-methoxyphenyl)-4-methyl-5-(trifluoromethyl)tetrahydrofuran-2-carboxamido)picolinamide

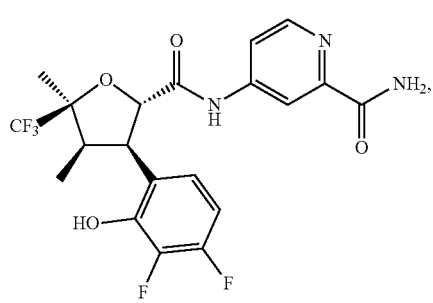

4-((2S,3R,4R,5S)-3-(3,4-difluoro-2-methoxyphenyl)-4-methyl-5-(trifluoromethyl)tetrahydrofuran-2-carboxamido)picolinamide

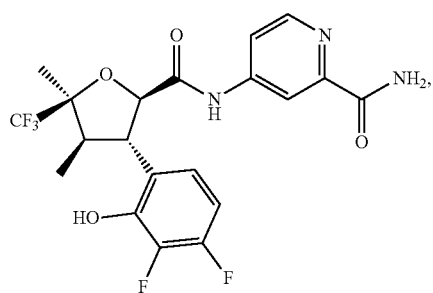

4-((2R,3S,4R,5S)-3-(3,4-difluoro-2-methoxyphenyl)-4-methyl-5-(trifluoromethyl)tetrahydrofuran-2-carboxamido)picolinamide

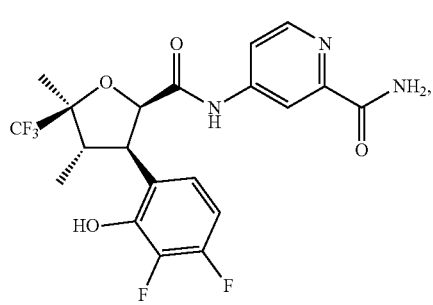

4-((2R,3R,4S,5S)-3-(3,4-difluoro-2-methoxyphenyl)-4-methyl-5-(trifluoromethyl)tetrahydrofuran-2-carboxamido)picolinamide -continued

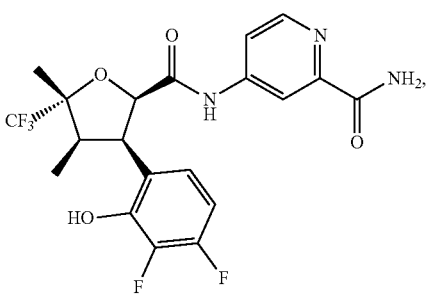

4-((2R,3R,4R,5R)-3-(3,4-difluoro-2-methoxyphenyl)-4-methyl-5-(trifluoromethyl)tetrahydrofuran-2-carboxamido)picolinamide

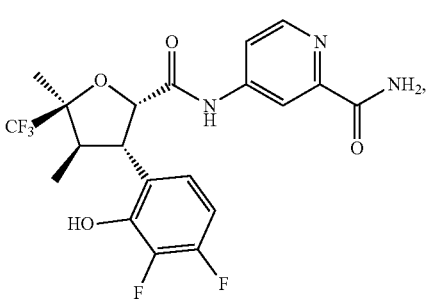

4-((2S,3S,4R,5S)-3-(3,4-difluoro-2-methoxyphenyl)-4-methyl-5-(trifluoromethyl)tetrahydrofuran-2-carboxamido)picolinamide

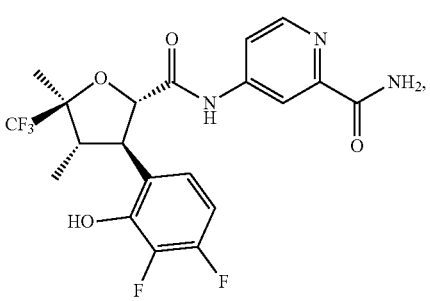

4-((2S,3R,4S,5S)-3-(3,4-difluoro-2-methoxyphenyl)-4-methyl-5-(trifluoromethyl)tetrahydrofuran-2-carboxamido)picolinamide

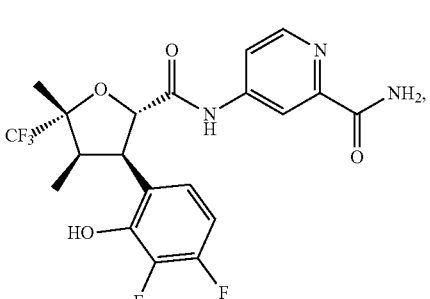

4-((2S,3R,4R,5R)-3-(3,4-difluoro-2-methoxyphenyl)-4-methyl-5-(trifluoromethyl)tetrahydrofuran-2-carboxamido)picolinamide -continued

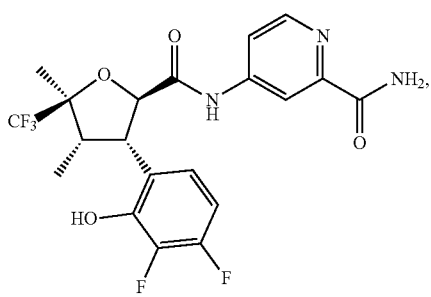

4-((2R,3S,4S,5S)-3-(3,4-difluoro-2-methoxyphenyl)-4-methyl-5-(trifluoromethyl)tetrahydrofuran-2-carboxamido)picolinamide

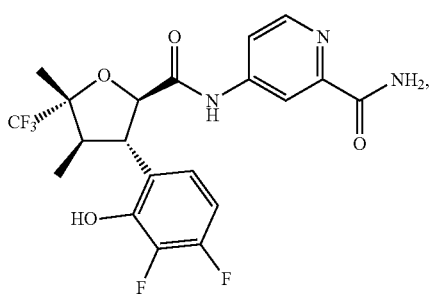

4-((2R,3S,4R,5R)-3-(3,4-difluoro-2-methoxyphenyl)-4-methyl-5-(trifluoromethyl)tetrahydrofuran-2-carboxamido)picolinamide

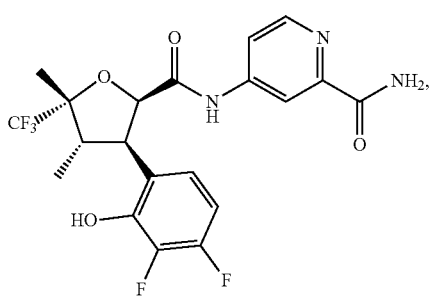

4-((2R,3R,4S,5R)-3-(3,4-difluoro-2-methoxyphenyl)-4-methyl-5-(trifluoromethyl)tetrahydrofuran-2-carboxamido)picolinamide

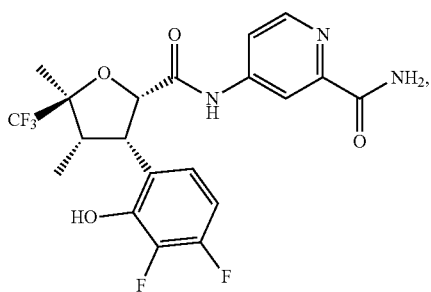

4-((2S,3S,4S,5S)-3-(3,4-difluoro-2-methoxyphenyl)-4-methyl-5-(trifluoromethyl)tetrahydrofuran-2-carboxamido)picolinamide -continued

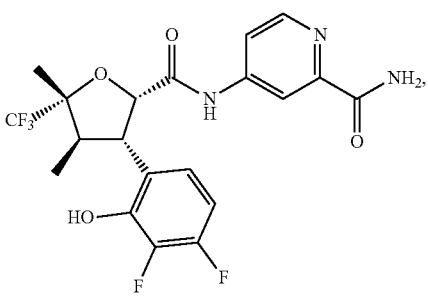

4-((2S,3S,4R,5R)-3-(3,4-difluoro-2-methoxyphenyl)-4-methyl-5-(trifluoromethyl)tetrahydrofuran-2-carboxamido)picolinamide

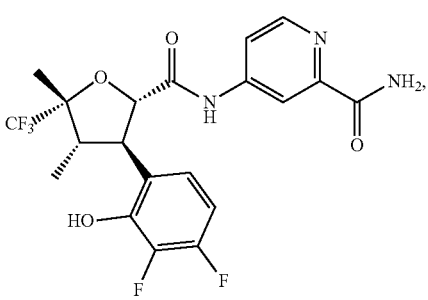

4-((2S,3R,4S,5R)-3-(3,4-difluoro-2-methoxyphenyl)-4-methyl-5-(trifluoromethyl)tetrahydrofuran-2-carboxamido)picolinamide

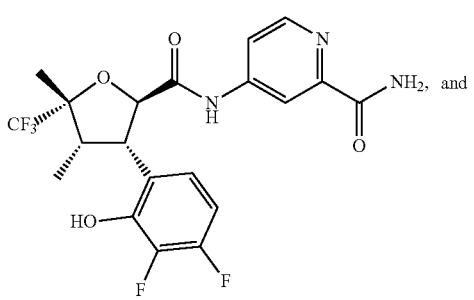

4-((2R,3S,4S,5R)-3-(3,4-difluoro-2-methoxyphenyl)-4-methyl-5-(trifluoromethyl)tetrahydrofuran-2-carboxamido)picolinamide

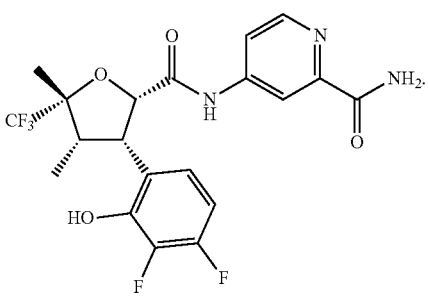

4-((2S,3S,4S,5R)-3-(3,4-difluoro-2-methoxyphenyl)-4-methyl-5-(trifluoromethyl)tetrahydrofuran-2-carboxamido)picolinamide.

6. The compound of claim 1, or a pharmaceutically acceptable salt thereof, wherein the compound is selected from

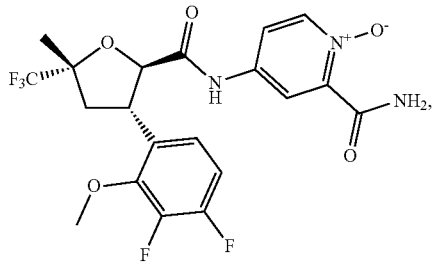

2-carbamoyl-4-((2R,3S,5R)-3-(3,4-difluoro-2-methoxyphenyl)-5-methyl-5-(trifluoromethyl)tetrahydrofuran-2-carboxamido)pyridine 1-oxide

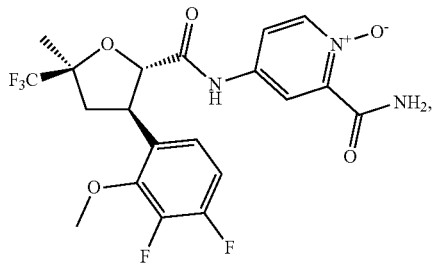

2-carbamoyl-4-((2S,3R,5S)-3-(3,4-difluoro-2-methoxyphenyl)-5-methyl-5-(trifluoromethyl)tetrahydrofuran-2-carboxamido)pyridine 1-oxide

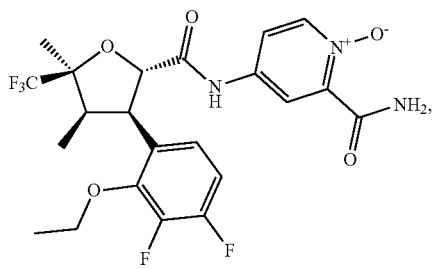

2-carbamoyl-4-((2S,3R,4R,5S)-3-(2-ethoxy-3,4-difluorophenyl)-4,5-dimethyl-5-(trifluoromethyl)tetrahydrofuran-2-carboxamido)pyridine 1-oxide

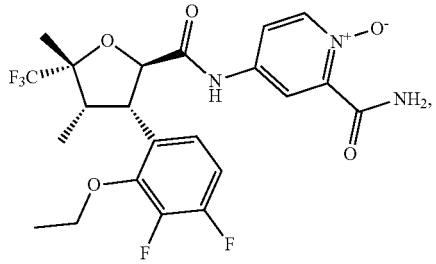

2-carbamoyl-4-((2R,3S,4S,5R)-3-(2-ethoxy-3,4-difluorophenyl)-4,5-dimethyl-5-(trifluoromethyl)tetrahydrofuran-2-carboxamido)pyridine 1-oxide

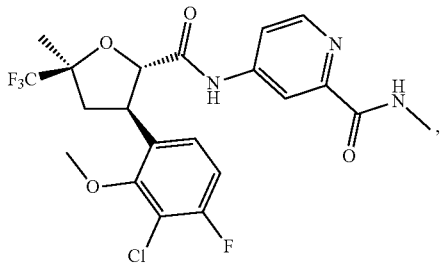

4-((2S,3R,5S)-3-(3-chloro-4-fluoro-2-methoxyphenyl)-5-methyl-5-(trifluoromethyl)tetrahydrofuran-2-carboxamide)-N-methylpicolinamide

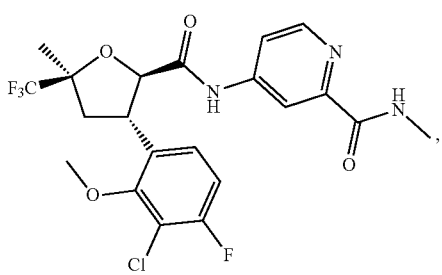

4-((2R,3S,5S)-3-(3-chloro-4-fluoro-2-methoxyphenyl)-5-methyl-5-(trifluoromethyl)tetrahydrofuran-2-carboxamido)-N-methylpicolinamide

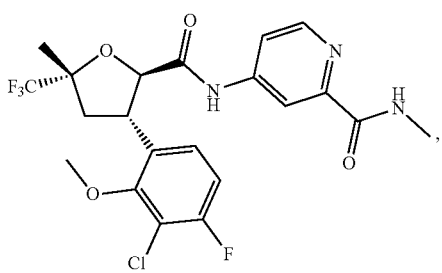

4-((2R,3S,5R)-3-(3-chloro-4-fluoro-2-methoxyphenyl)-5-methyl-5-(trifluoromethyl)tetrahydrofuran-2-carboxamido)-N-methylpicolinamide

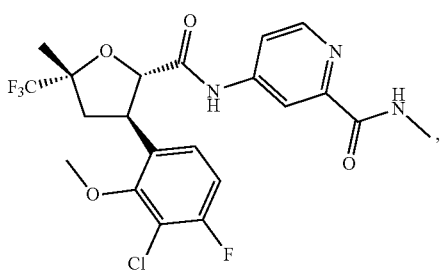

4-((2S,3R,5R)-3-(3-chloro-4-fluoro-2-methoxyphenyl)-5-methyl-5-(trifluoromethyl)tetrahydrofuran-2-carboxamido)-N-methylpicolinamide

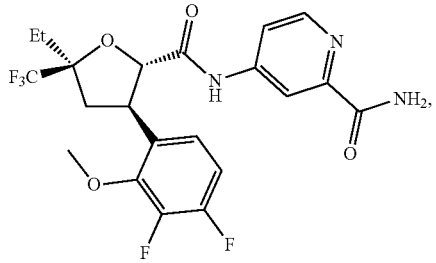

4-((2S,3R,5S)-3-(3,4-difluoro-2-methoxyphenyl)-5-ethyl-5-(trifluoromethyl)tetrahydrofuran-2-carboxamido)picolinamide

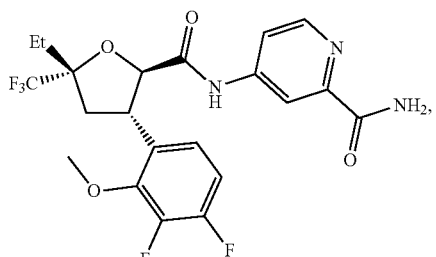

4-((2R,3S,5R)-3-(3,4-difluoro-2-methoxyphenyl)-5-ethyl-5-(trifluoromethyl)tetrahydrofuran-2-carboxamido)picolinamide

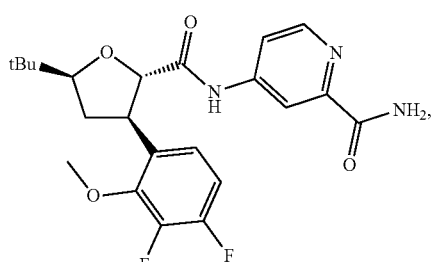

4-((2S,3R,5S)-5-(tert-butyl)-3-(3,4-difluoro-2-methoxyphenyl)tetrahydrofuran-2-carboxamido)picolinamide

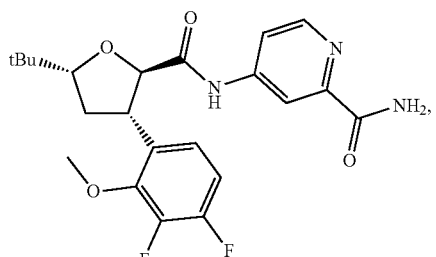

4-((2R,3S,5R)-5-(tert-butyl)-3-(3,4-difluoro-2-methoxyphenyl)tetrahydrofuran-2-carboxamido)picolinamide

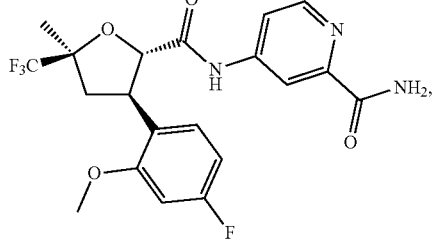

4-((2R,3R,5S)-3-(4-fluoro-2-methoxyphenyl)-5-methyl-5-(trifluoromethyl)tetrahydrofuran-2-carboxamido)picolinamide

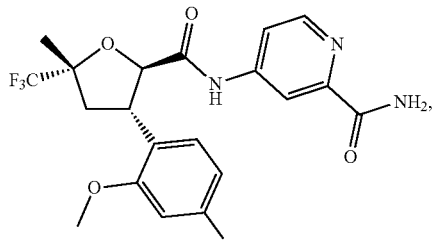

4-((2R,3S,5R)-3-(4-fluoro-2-methoxyphenyl)-5-methyl-5-(trifluoromethyl)tetrahydofuran-2-carboxamido)picolinamide

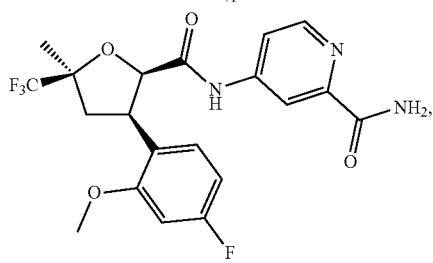

4-((2R,3R,5S)-3-(4-fluoro-2-methoxyphenyl)-5-methyl-5-(trifluoromethyl)tetrahydrofuran-2-carboxamido)picolinamide

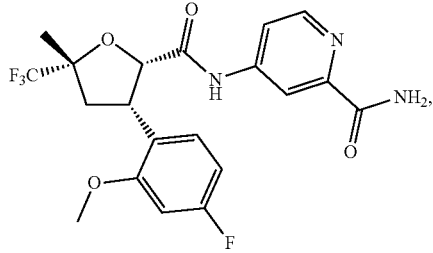

4-((2S,3S,5R)-3-(4-fluoro-2-methoxyphenyl)-5-methyl-5-(trifluoromethyl)tetrahyrdofuran-2-carboxamido)picolinamide

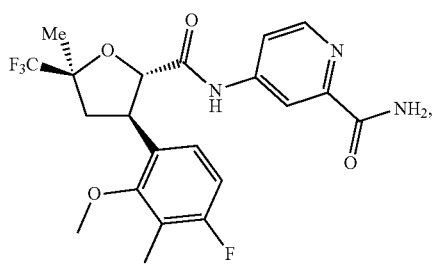

4-((2S,3R,5S)-3-(4-fluoro-2-methoxy-3-methylphenyl)-5-methyl-5-(trifluoromethyl)tetrahydrofuran-2-carboxamido)picolinamide -continued

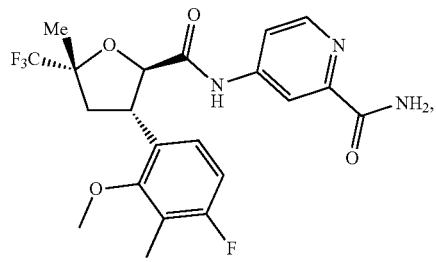

4-((2R,3S,5R)-3-(4-fluoro-2-methoxy-3-
methylphenyl)-5-methyl-5-
(trifluoromethyl)tetrahydrofuran-2-
carboxamido)picolinamide

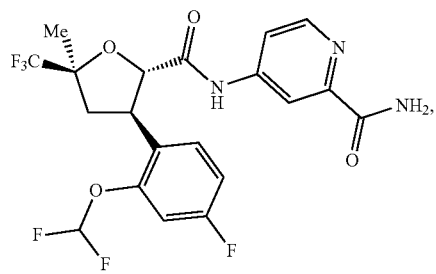

4-((2S,3R,5S)-3-(2-(difluoromethoxy)-4-
fluorophenyl)-5-methyl-5-
(trifluoromethyl)tetrahydrofuran-2-
carboxamido)picolinamide

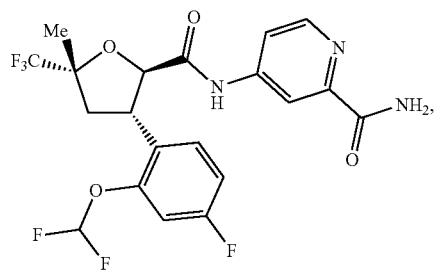

4-((2R,3S,5R)-3-(2-(difluoromethoxy)-4-
fluorophenyl)-5-methyl-5-
(trifluoromethyl)tetrahydrofuran-2-
carboxamido)picolinamide

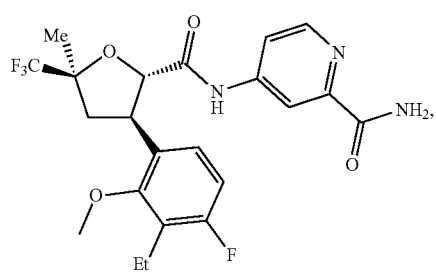

4-((2S,3R,5S)-3-(3-ethyl-4-fluoro-2-
methoxyphenyl)-5-methyl-5-
(trifluoromethyl)tetrahydrofuran-2-
carboxamido(picolinamide)

-continued

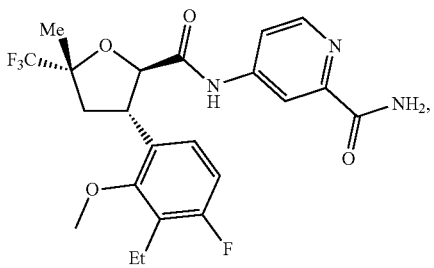

4-((2R,3S,5R)-3-(3-ethyl-4-fluoro-2-
methoxyphenyl)-5-methyl-5-
(trifluoromethyl)tetrahydrofuran-2-
carboxamido)picolinamide

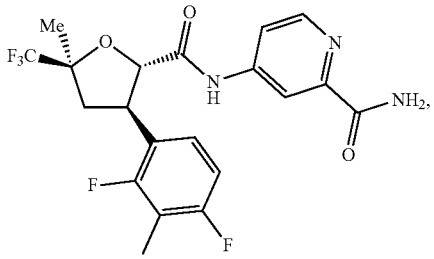

4-((2S,3R,5S)-3-(2,4-difluoro-3-
methylphenyl)-5-methyl-5-
(trifluoromethyl)tetrahydrofuran-2-
carboxamido)picolinamide

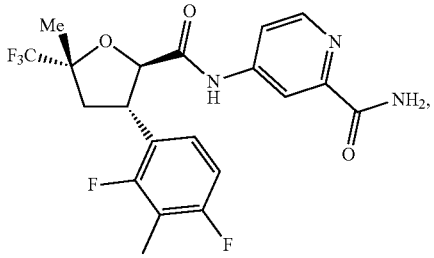

4-((2R,3S,5R)-3-(2,4-difluoro-3-
methylphenyl)-5-methyl-5-
(trifluoromethyl)tetrahydrofuran-2-
carboxamido)picolinamide

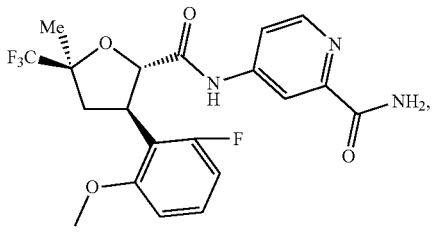

4-((2S,3R,5S)-3-(2-fluoro-6-
methoxyphenyl)-5-methyl-5-
(trifluoromethyl)tetrahydrofuran-2-
carboxamido)picolinamide

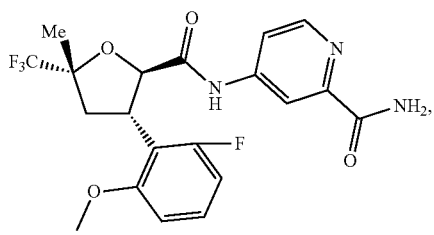

4-((2R,3S,5R)-3-(2-fluoro-6-methoxyphenyl)-5-methyl-5-(trifluoromethyl)tetrahydrofuran-2-carboxamido)picolinamide

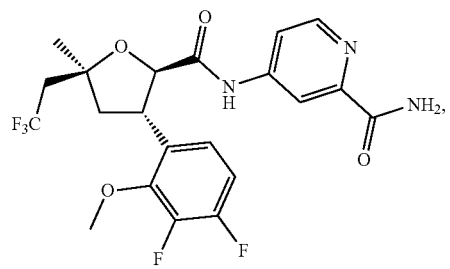

4-((2R,3S,5S)-3-(3,4-difluoro-2-methoxyphenyl)-5-methyl-5-(2,2,2-trifluoroethyl)tetrahydrofuran-2-carboxamido)picolinamide

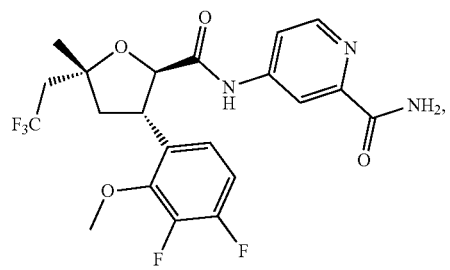

4-((2R,3S,5R)-3-(3,4-difluoro-2-methoxyphenyl)-5-methyl-5-(2,2,2-trifluoroethyl)tetrahydrofuran-2-carboxamido)picolinamide

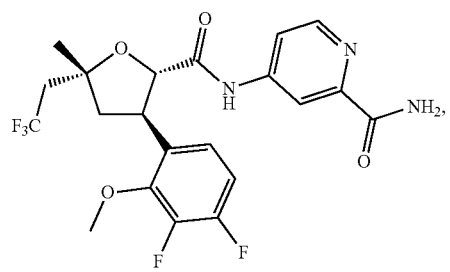

4-((2S,3R,5R)-3-(3,4-difluoro-2-methoxyphenyl)-5-methyl-5-(2,2,2-trifluoroethyl)tetrahydrofuran-2-carboxamido)picolinamide

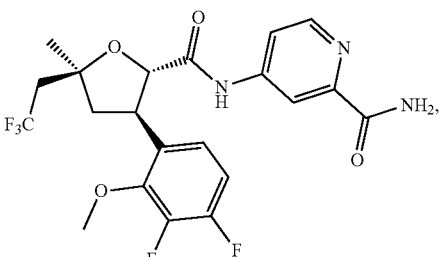

4-((2S,3R,5S)-3-(3,4-difluoro-2-methoxyphenyl)-5-methyl-5-(2,2,2-trifluoroethyl)tetrahydrofuran-2-carboxamido)picolinamide

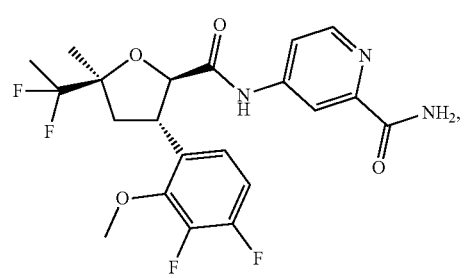

4-((2R,3S,5S)-3-(3,4-difluoro-2-methoxyphenyl)-5-(1,1-difluoroethyl)-5-methyltetrahydrofuran-2-carboxamido)picolinamide

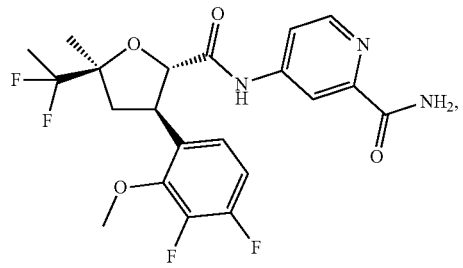

4-((2S,3R,5S)-3-(3,4-difluoro-2-methoxyphenyl)-5-(1,1-difluoroethyl)-5-methyltetrahydrofuran-2-carboxamido)picolinamide

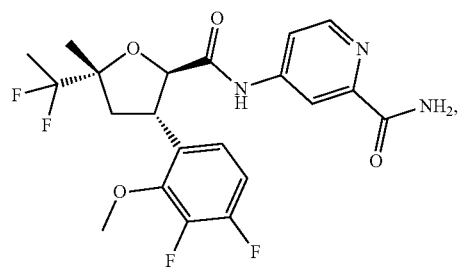

4-((2R,3S,5R)-3-(3,4-difluoro-2-methoxyphenyl)-5-(1,1-difluoroethyl)-5-methyltetrahydrofuran-2-carboxamido)picolinamide

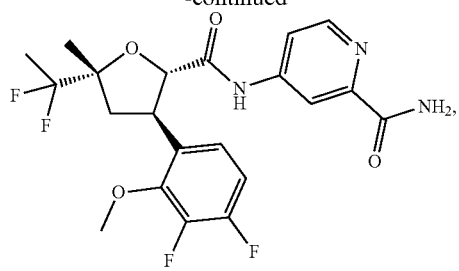

4-((2S,3R,5R)-3-(3,4-difluoro-2-methoxyphenyl)-
5-(1,1-difluoroethyl)-5-methyltetrahydrofuran-2-
carboxamido)picolinamide

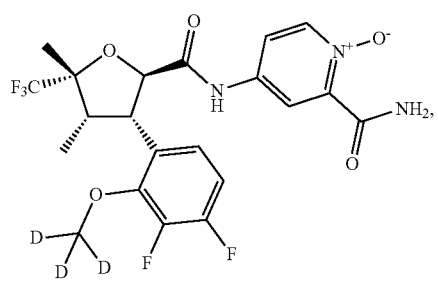

2-carbamoyl-4-((2R,3S,4S,5R)-3-(3,4-difluoro-2-
(methoxy-d₃)phenyl-4,5-dimethyl-5-
(trifluoromethyl)tetrahydrofuran-2-
carboxamido)pyridine 1-oxide

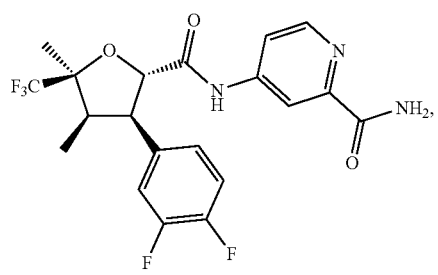

4-((2S,3R,4R,5S)-3-(3,4-difluorophenyl)-
4,5-dimethyl-5-
(trifluoromethyl)tetrahydrofuran-2-
carboxamido)picolinamide

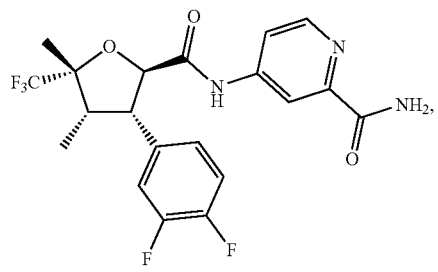

4-((2R,3S,4S,5R)-3-(3,4-difluorophenyl)-
4,5-dimethyl-5-
(trifluoromethyl)tetrahydrofuran-2-
carboxamido)picolinamide

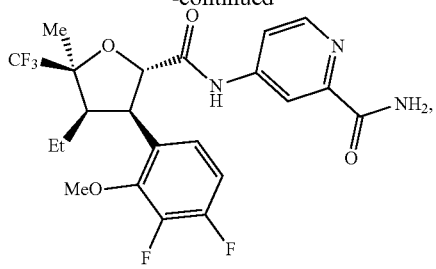

4-((2S,3R,4R,5S)-3-(3,4-difluoro-2-
methoxyphenyl)-4-ethyl-5-methyl-5-
(trifluoromethyl)tetrahydrofuran-2-
carboxamido)picolinamide

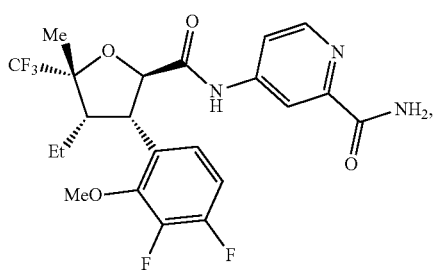

4-((2R,3S,4S,5R)-3-(3,4-difluoro-2-
methoxyphenyl)-4-ethyl-5-methyl-5-
(trifluoromethyl)tetrahydrofuran-2-
carboxamido)picolinamide

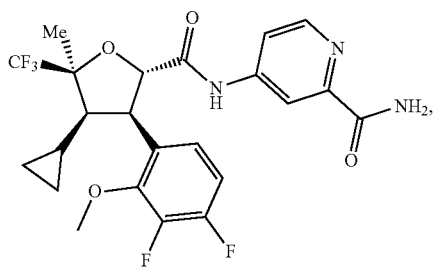

4-((2S,3R,4R,5S)-4-cyclopropyl-3-(3,4-
difluoro-2-methoxyphenyl)-5-methyl-5-
(trifluoromethyl)tetrahydrofuran-2-
carboxamido)picolinamide

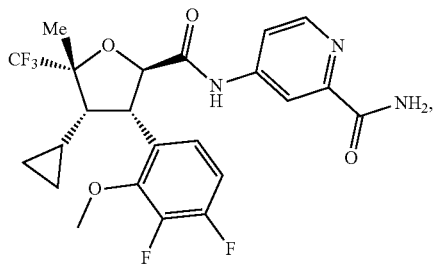

4-((2R,3S,4S,5R)-4-cyclopropyl-3-(3,4-
difluoro-2-methoxyphenyl)-5-methyl-5-
(trifluoromethyl)tetrahydrofuran-2-
carboxamido)picolinamide

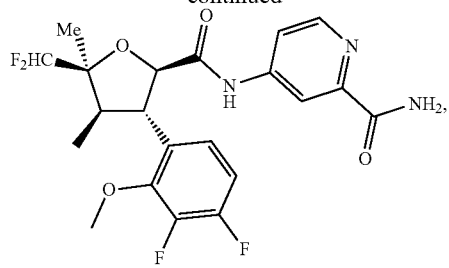

4-((2R,3S,4R,5S)-3-(3,4-difluoro-2-methoxyphenyl)-5-(difluoromethyl)-4,5-dimethyltetrahydrofuran-2-carboxamido)picolinamide

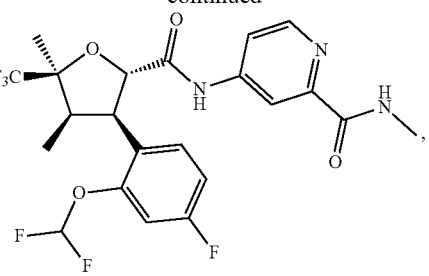

4-((2S,3R,4R,5S)-3-(2-(difluoromethoxy)-4-fluorophenyl)-4,5-dimethyl-5-(trifluoromethyl)tetrahydrofuran-2-carboxamido)-N-methylpicolinamide

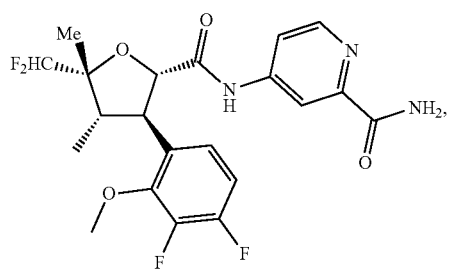

4-((2S,3R,4S,5R)-3-(3,4-difluoro-2-methoxyphenyl)-5-(difluoromethyl)-4,5-dimethyltetrahydrofuran-2-carboxamido)picolinamide

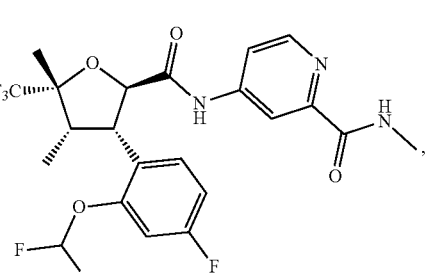

4-((2R,3S,4S,5R)-3-(2-(difluoromethoxy)-4-fluorophenyl)-4,5-dimethyl-5-(trifluoromethyl)tetrahydrofuran-2-carboxamido)-N-methylpicolinamide

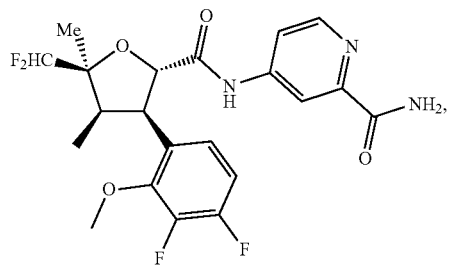

4-((2S,3R,4R,5S)-3-(3,4-difluoro-2-methoxyphenyl)-5-(difluoromethyl)-4,5-dimethyltetrahydrofuran-2-carboxamido)picolinamide

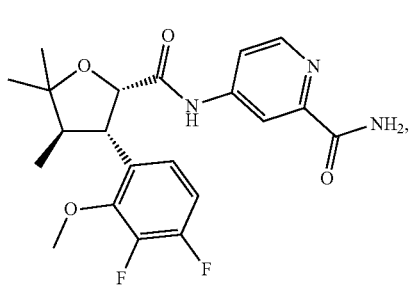

4-((2S,3S,4R)-3-(3,4-difluro-2-methoxyphenyl)-4,5,5-trimethyltetrahydrofuran-2-carboxamido)picolinamide

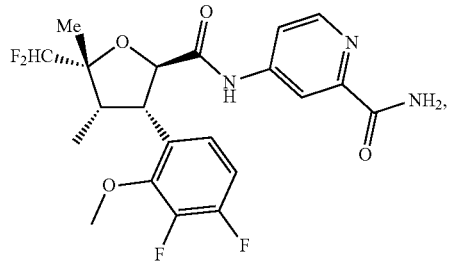

4-((2R,3S,4S,5R)-3-(3,4-difluoro-2-methoxyphenyl)-5-(difluoromethyl)-4,5-dimethyltetrahydrofuran-2-carboxamido)picolinamide

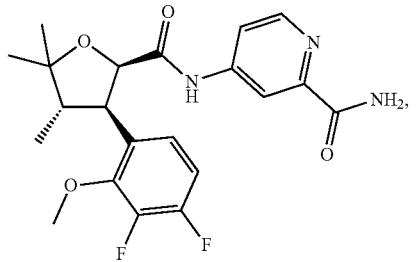

4-((2R,3R,4S)-3-(3,4-difluoro-2-methoxyphenyl)-4,5,5-trimethyltetrahydrofuran-2-carboxmido)picolinamide -continued

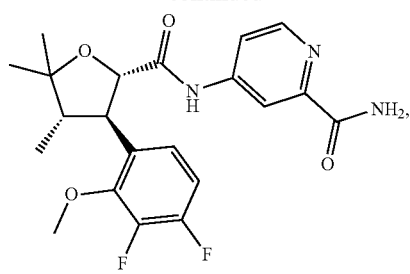

4-((2S,3R,4S)-3-(3,4-difluoro-2-methoxyphenyl)-
4,5,5-trimethyltetrahydrofuran-2-
carboxamido)picolinamide

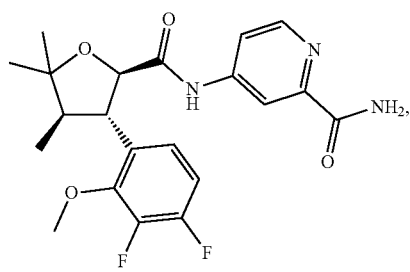

4-((2R,3S,4R)-3-(3,4-difluoro-2-
methoxyphenyl)-4,5,5-trimethyltetrahydrofuran-
2-carboxamido)picolinamide

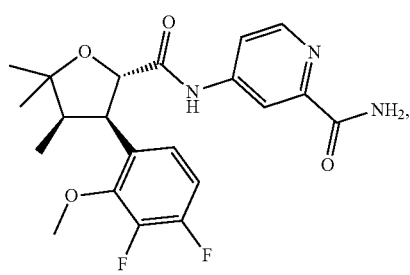

4-((2S,3R,4R)-3-(3,4-difluoro-2-
methoxyphenyl)-4,5,5-
trimethyltetrahydrofuran-2-
carboxamido)picolinamide

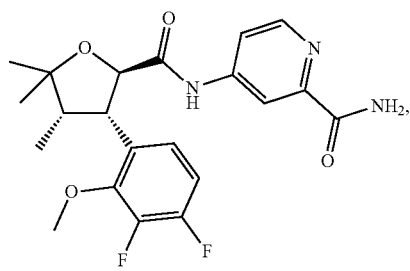

4-((2R,3S,4S)-3-(3,4-difluoro-2-
methoxyphenyl)-4,5,5-
trimethyltetrahydrofuran-2-
carboxamido)picolinamide -continued

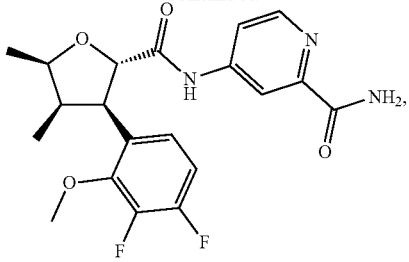

4-((2S,3R,4R,5R)-3-(3,4-difluoro-2-
methoxyphenyl)-4,5-
dimethyltetrahydrofuran-2-
carboxamido)picolinamide

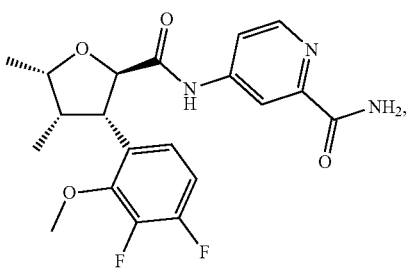

4-((2R,3S,4S,5S)-3-(3,4-difluoro-2-
methoxyphenyl)-4,5-
dimethyltetrahydrofuran-2-
carboxamido)picolinamide

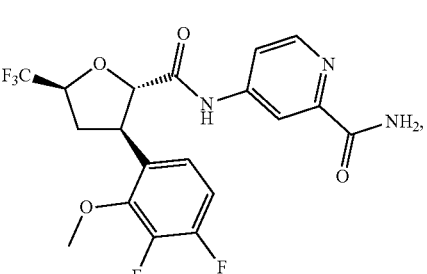

4-((2S,3R,5S)-3-(3,4-difluoro-2-
methoxyphenyl)-5-
(trifluoromethyl)tetrahydrofuran-2-
carboxamido)picolinamide

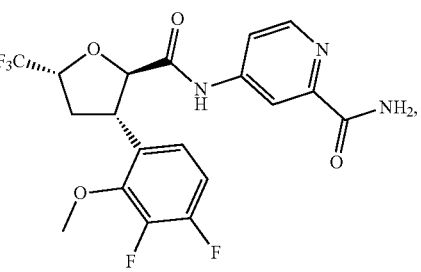

4-((2R,3S,5R)-3-(3,4-difluoro-2-
methoxyphenyl)-5-
(trifluoromethyl)tetrahydrofuran-2-
carboxamido)picolinamide -continued

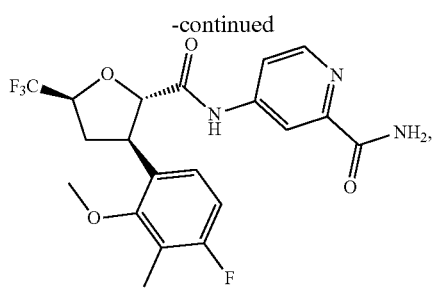

4-((2S,3R,5S)-3-(4-fluoro-2-
methoxy-3-methylphenyl)-5-
(trifluoromethyl)tetrahydrofuran-2-
carboxamido)picolinamide

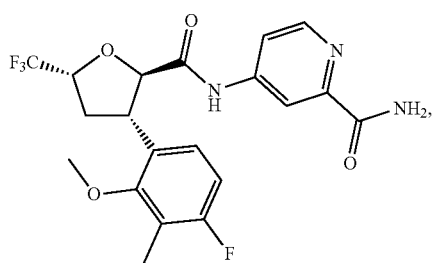

4-((2R,3S,5R)-3-(4-fluoro-2-methoxy-
3-methylphenyl)-5-
(trifluoromethyl)tetrahydrofuran-2-
carboxamido)picolinamide

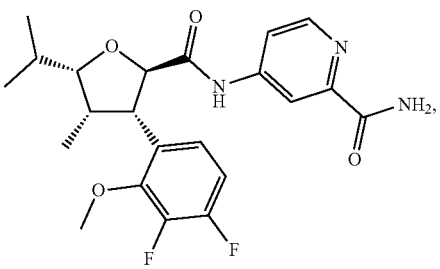

4-((2R,3S,4S,5S)-3-(3,4-difluoro-2-
methoxyphenyl)-5-isopropyl-4-
methyltetrahydrofuran-2-
carboxamido)picolinamide

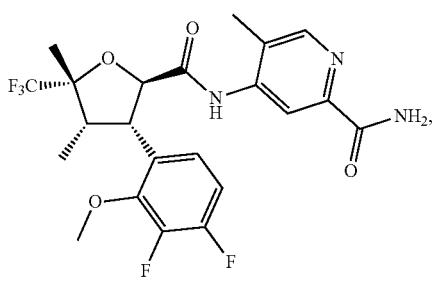

4-((2R,3S,4S,5R)-3-(3,-4-difluoro-2-
methoxyphenyl)-4,5-dimethyl-5-
(trifluoromethyl)tetrahydrofuran-2-
carboxamido)-5-methylpicolinamide -continued

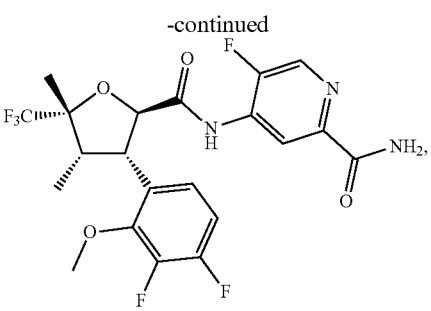

4-((2R,3S,4S,5R)-3-(3,4-difluoro-2-
methoxyphenyl)-4,5-dimethyl-5-
(trifluoromethyl)tetrahydrofuran-2-
carboxamido)-5-fluoropicolinamide

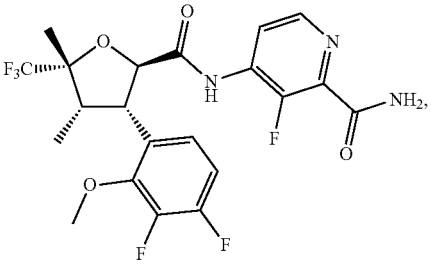

4-((2R,3S,4S,5R)-3-(3,4-difluoro-2-
methoxyphenyl)-4,5-dimethyl-5-
(trifluoromethyl)tetrahydrofuran-2-
carboxamido)-3-fluoropicolinamide

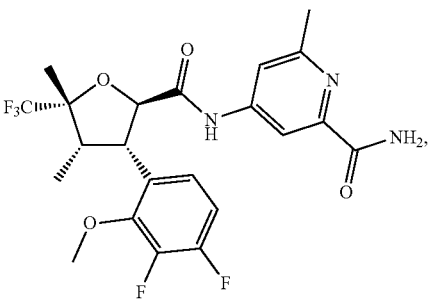

4-((2R,3S,4S,5R)-3-(3,4-difluoro-2-
methoxyphenyl)-4,5-dimethyl-5-
(trifluoromethyl)tetrahydrofuran-2-
carboxamido)-6-methylpicolinamide

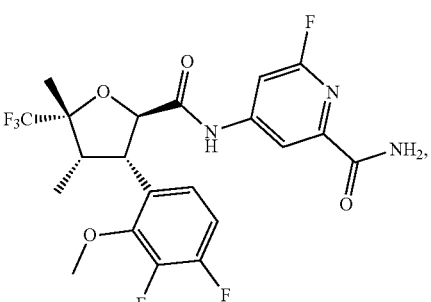

4-((2R,3S,4S,5R)-3-(3,4-difluoro-2-
methoxyphenyl)-4,5-dimethyl-5-
(trifluoromethyl)tetrahydrofuran-2-
carboxamido)-6-fluoropicolinamide -continued

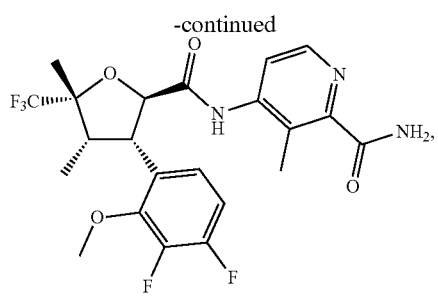

4-((2R,3S,4S,5R)-3-(3,4-difluoro-2-methoxyphenyl)-4,5-dimethyl-5-(trifluoromethyl)tetrahydrofuran-2-carboxamido)-3-methylpicolinamide

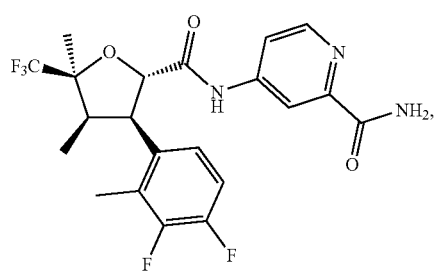

4-((2S,3R,4R,5S)-3-(3,4-difluoro-2-methylphenyl)-4,5-dimethyl-5-(trifluoromethyl)tetrahydrofuran-2-carboxamido)picolinamide

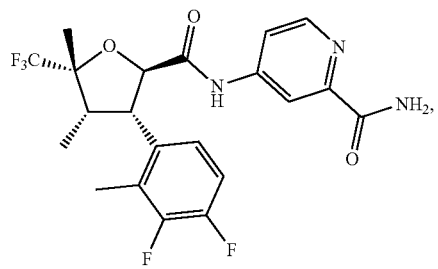

4-((2R,3S,4S,5R)-3-(3,4-difluoro-2-methylphenyl)-4,5-dimethyl-5-(trifluoromethyl)tetrahydrofuran-2-carboxamido)picolinamide

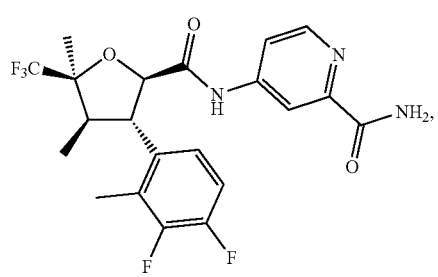

4-((2R,3S,4R,5S)-3-(3,4-difluoro-2-methylphenyl)-4,5-dimethyl-5-(trifluoromethyl)tetrahydrofuran-2-carboxamido)picolinamide

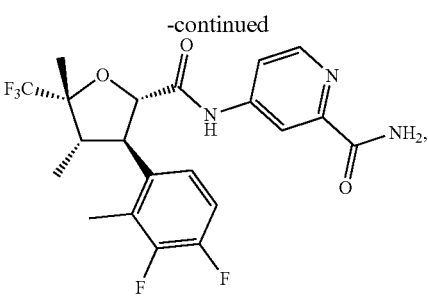

4-((2S,3R,4S,5R)-3-(3,4-difluoro-2-methylphenyl)-4,5-dimethyl-5-(trifluoromethyl)tetrahydrofuran-2-carboxamido)picolinamide

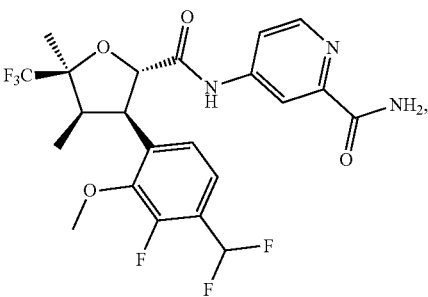

4-((2S,3R,4R,5S)-3-(4-(difluoromethyl)-3-fluoro-2-methoxyphenyl)-4,5-dimethyl-5-(trifluoromethyl)tetrahydrofuran-2-carboxamido)picolinamide

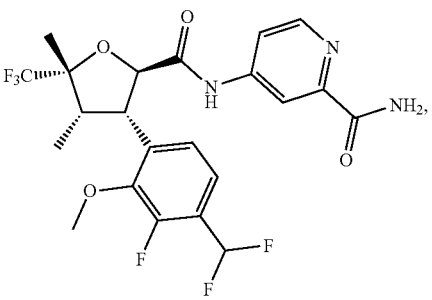

4-((2R,3S,4S,5R)-3-(4-difluoromethyl)-3-fluoro-2-methoxyphenyl)-4,5-dimethyl-5-(trifluoromethyl)tetrahydrofuran-2-carboxamido)picolinamide

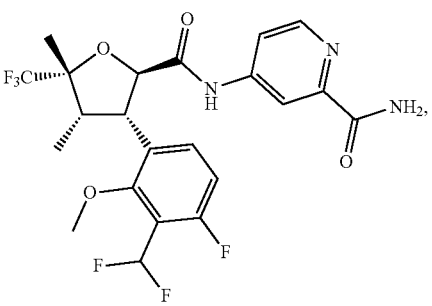

4-((2R,3S,4S,5R)-3-(3-(difluoromethyl)-4-fluoro-2-methoxyphenyl)-4,5-dimethyl-5-(trifluoromethyl)tetrahydrofuran-2-carboxamido)picolinamide

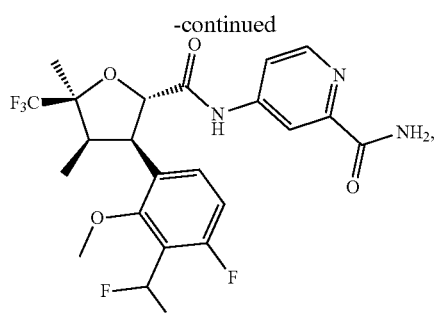

4-((2S,3R,4R,5S)-3-(3-(difluoromethyl)-4-
fluoro-2-methoxyphenyl)-4,5-dimethyl-5-
(trifluoromethyl)tetrahydrofuran-2-
carboxamido)picolinamide

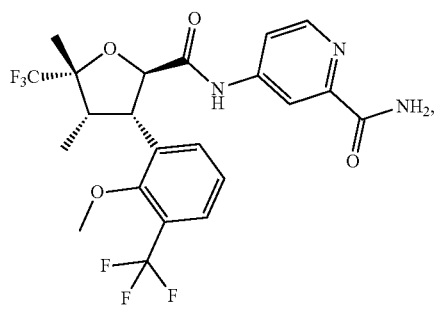

4-((2R,3S,4S,5R)-3-(2-methoxy-3-
(trifluoromethyl)phenyl)-4,5-dimethyl-5-
(trifluoromethyl)tetrahdyrofuran-2-
carboxamido)picolinamide

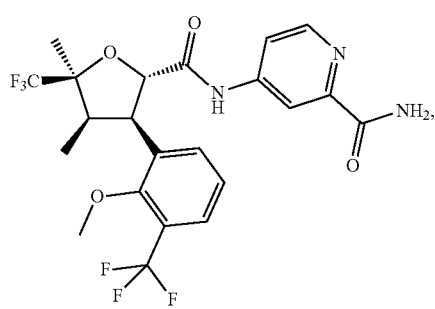

4-((2S,3R,4R,5S)-3-(2-methoxy-3-
(trifluoromethyl)phenyl)-4,5-dimethyl-5-
(trifluoromethyl)tetrahydrofuran-2-
carboxamido)picolinamide

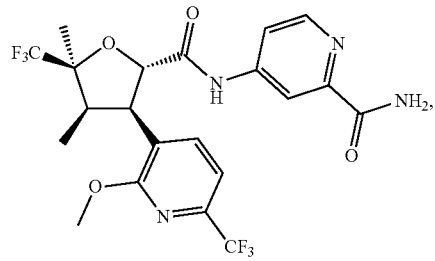

4-((2S,3R,4R,5S)-3-(2-methoxy-6-
(trifluoromethyl)pyridin-3-yl)-4,5-dimethyl-5-
(trifluoromethyl)tetrahydrofuran-2-
carboxamido)picolinamide

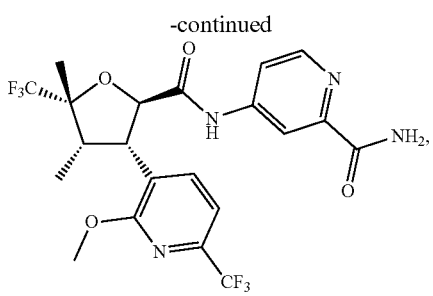

4-((2R,3S,4S,5R)-3-(2-methoxy-6-
(trifluoromethyl)pyridin-3-yl)-4,5-dimethyl-5-
(trifluoromethyl)tetrahydrofuran-2-
carboxamido)picolinamide

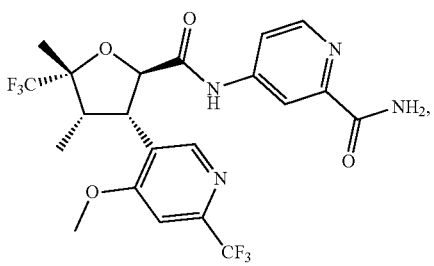

4-((2R,3S,4S,5R)-3-(4-methoxy-6-
(trifluoromethyl)pyridin-3-yl)-4,5-dimethyl-5-
(trifluoromethyl)tetrahydrofuran-2-
carboxamido)picolinamide

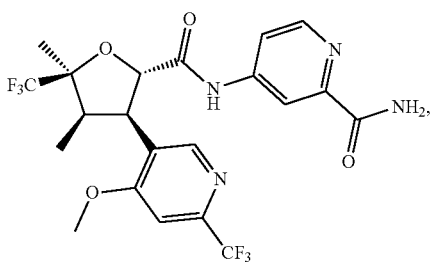

4-((2S,3R,4R,5S)-3-(4-methoxy-6-
(trifluoromethyl)pyridin-3-yl)-4,5-dimethyl-5-
(trifluoromethyl)tetrahydrofuran-2-
carboxamido)picolinamide

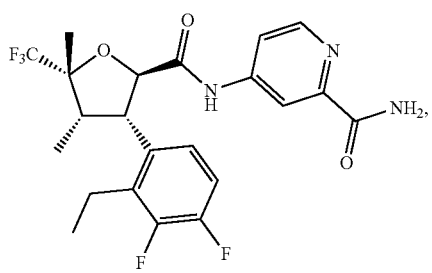

4-((2R,3S,4S,5R)-3-(2-ethyl-3,4-
difluorophenyl)-4,5-dimethyl-5-
(trifluoromethyl)tetrahydrofuran-2-
carboxamido)picolinamide

487

-continued

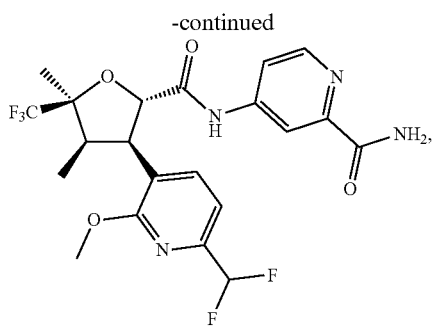

4-((2S,3R,4R,5S)-3-(6-(difluoromethyl)-2-
methoxypyridin-3-yl)-4,5-dimethyl-5-
(trifluoromethyl)tetrahydrofuran-2-
carboxamido)picolinamide

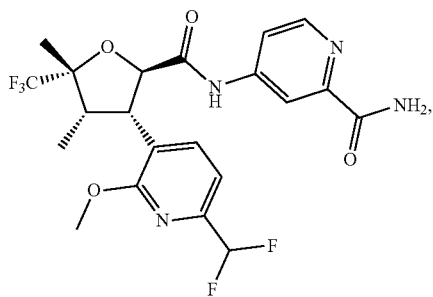

4-((2R,3S,4S,5R)-3-(6-(difluoromethyl)-2-
methoxypyridin-3-yl)-4,5-dimethyl-5-
(trifluoromethyl)tetrahydrofuran-2-
carboxamido)picolinamide

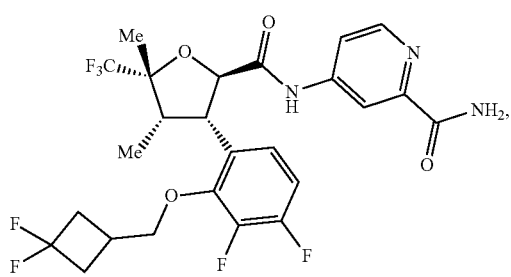

4-((2R,3S,4S,5R)-3-(2-((3,3-
difluorocyclobutyl)methoxy)-3,4-difluorophenyl)-4,5-
dimethyl-5-(trifluoromethyl)tetrahydrofuran-2-
carboxamido)picolinamide

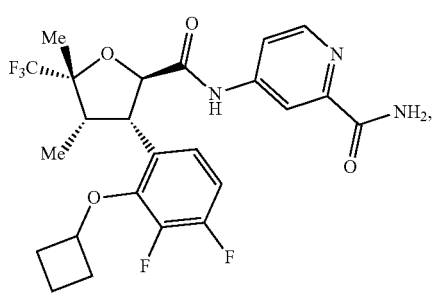

4-((2R,3S,4S,5R)-3-(2-cyclobutoxy-3,4-
difluorophenyl)-4,5-dimethyl-5-
(trifluoromethyl)tetrahydrofuran-2-
carboxamido)picolinamide

488

-continued

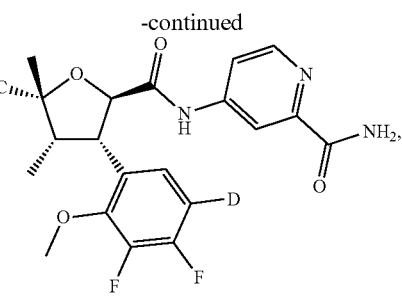

4-((2R,3S,4S,5R)-3-(3,4-difluoro-2-
methoxyphenyl-5-d)-4,5-dimethyl-5-
(trifluoromethyl)tetrahydrofuran-2-
carboxamido)picolinamide

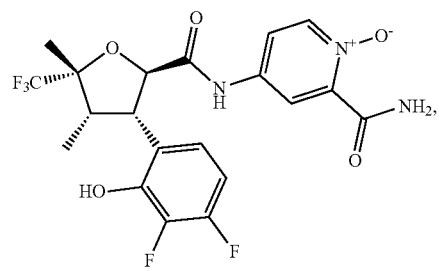

2-carbamoyl-4-((2R,3S,4S,5R)-3-(3,4-
difluoro-2-hydroxyphenyl)-4,5-dimethyl-5-
(trifluoromethyl)tetrahydrofuran-2-
carboxamido)pyridine 1-oxide

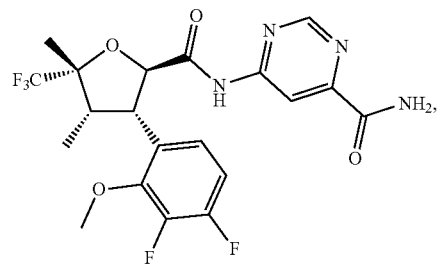

6-((2R,3S,4S,5R)-3-(3,4-difluoro-2-
methoxyphenyl)-4,5-dimethyl-5-
(trifluoromethyl)tetrahydrofuran-2-
carboxamido)pyrimidine-4-carboxamide

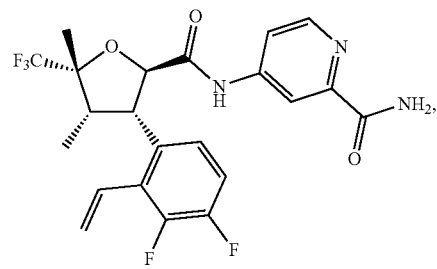

4-((2R,3S,4S,5R)-3-(3,4-difluoro-2-
vinylphenyl)-4,5-dimethyl-5-
(trifluoromethyl)tetrahydrofuran-2-
carboxamido)picolinamide

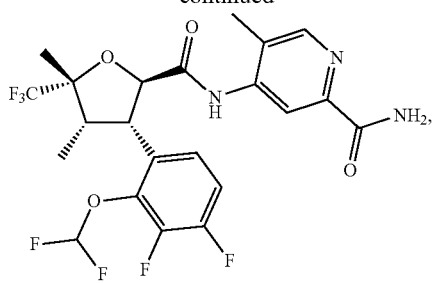

4-((2R,3S,4S,5R)-3-(2-(difluoromethoxy)-3,4-difluorophenyl)-4,5-dimethyl-5-(trifluoromethyl)tetrahydrofuran-2-carboxamido)-5-methylpicolinamide

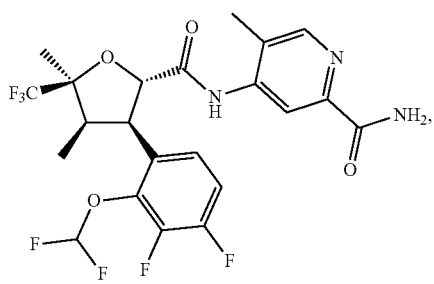

4-((2S,3R,4R,5S)-3-(2-(difluoromethoxy)-3,4-difluorophenyl)-4,5-dimethyl-5-(trifluoromethyl)tetrahydrofuran-2-carboxamido)-5-methylpicolinamide

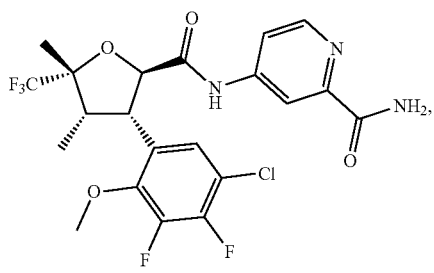

4-((2R,3S,4S,5R)-3-(5-chloro-3,4-difluoro-2-methoxyphenyl)-4,5-dimethyl-5-(trifluoromethyl)tetrahydrofuran-2-carboxamido)picolinamide

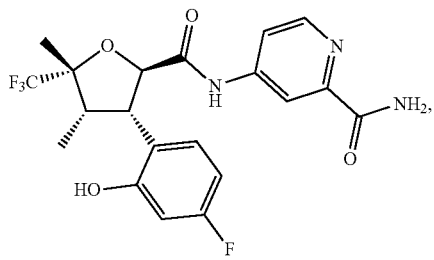

4-((2R,3S,4S,5R)-3-(4-fluoro-2-hydrophenyl)-4,5-dimethyl-5-(trifluoromethyl)tetrahydrofuran-2-carboxamido)picolinamide

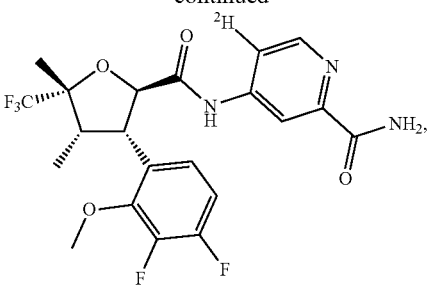

4-((2R,3S,4S,5R)-3-(3,4-difluoro-2-methoxyphenyl)-4,5-dimethyl-5-(trifluoromethyl)tetrahydrofuran-2-carboxamido)picolinamide-5-d

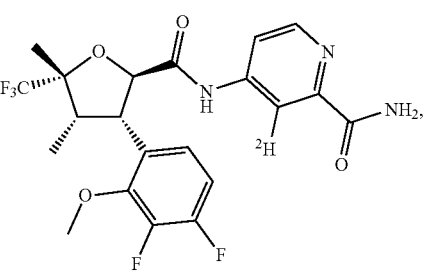

4-((2R,3S,4S,5R)-3-(3,4-difluoro-2-methoxyphenyl)-4,5-dimethyl-5-(trifluoromethyl)tetrahydrofuran-2-carboxamido)picolinamide-3-d

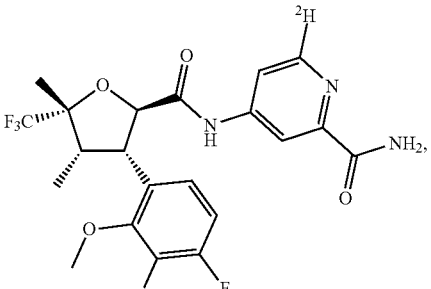

4-((2R,3S,4S,5R)-3-(3,4-difluoro-2-methoxyphenyl)-4,5-dimethyl-5-(trifluoromethyl)tetrahydrofuran-2-carboxamido)picolinamide-6-d

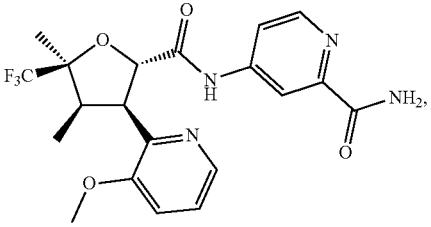

4-((2S,3R,4R,5S)-3-(3-methoxypyridin-2-yl)-4,5-dimethyl-5-(trifluoromethyl)tetrahydrofuran-2-carboxamido)picolinamide -continued

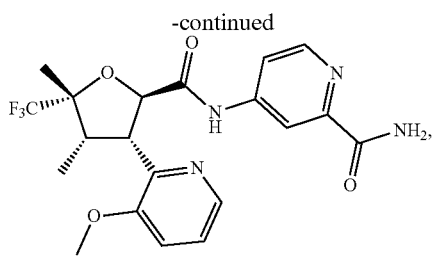

4-((2R,3S,4S,5R)-3-(3-methoxypyridin-2-yl)-4,5-dimethyl-5-(trifluoromethyl)tetrahydrofuran-2-carboxamido)picolinamide

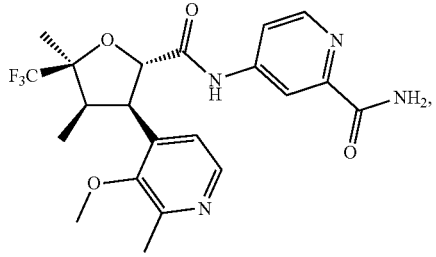

4-((2S,3R,4R,5S)-3-(3-methoxy-2-methylpyridin-4-yl)-4,5-dimethyl-5-(trifluoromethyl)tetrahydrofuran-2-carboxamido)picolinamide

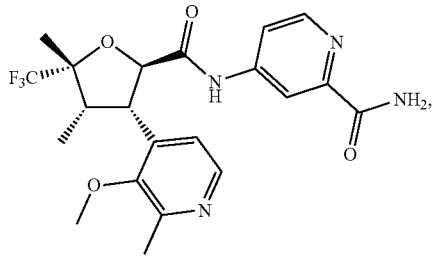

4-((2R,3S,4S,5R)-3-(3-methoxy-2-methylpyridin-4-yl)-4,5-dimethyl-5-(trifluoromethyl)tetrahydrofuran-2-carboxamido)picolinamide (2R,3R,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3R,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3R,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3S,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3R,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3R,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3S,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3R,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3S,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3R,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3S,4R,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3S,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3R,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3S,4R,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3S,4S,5R)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2S,3S,4S,5S)-4-[[3-[2-(difluoromethoxy)-4-fluoro-phenyl]-4,5-dimethyl-5-(trifluoromethyl)tetrahydrofuran-2-carbonyl]amino]-N-methyl-pyridine-2-carboxamide,
(2R,3R,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3R,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3R,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3S,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2S,3R,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3R,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3S,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2S,3R,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3S,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2S,3R,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2S,3S,4R,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2R,3S,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2S,3R,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide,
(2S,3S,4R,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide, (2S,3S,4S,5R)-4-[[3-[2-methoxy-3-(trifluoromethyl)phenyl]-4,5-dimethyl-5-(trifluoromethyl)tetrahydrofuran-2-carbonyl]amino]pyridine-2-carboxamide, (2S,3S,4S,5S)-4-[[3-[2-methoxy-3-(trifluoromethyl)phenyl]-4,5-dimethyl-5-(trifluoromethyl)tetrahydrofuran-2-carbonyl]amino]pyridine-2-carboxamide, (2R,3R,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3R,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3R,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3S,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3R,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3R,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3S,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3R,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3S,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3R,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3S,4R,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3S,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3R,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3S,4R,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3S,4S,5R)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2S,3S,4S,5S)-4-[[3-[3-(difluoromethyl)-4-fluoro-2-methoxy-phenyl]-4,5-dimethyl-5-(trifluoromethyl)tetrahydrofuran-2-carbonyl]amino]pyridine-2-carboxamide, (2R,3R,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2R,3R,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2R,3S,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2S,3R,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2R,3S,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2S,3R,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2S,3S,5R)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2S,3S,5S)-4-[[3-(3,4-difluoro-2-methoxy-phenyl)-5-methyl-5-(trifluoromethyl)tetrahydrofuran-2-carbonyl]amino]-1-oxido-pyridin-1-ium-2-carboxamide, (2R,3R,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3R,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3R,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3S,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2S,3R,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3R,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3S,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2S,3R,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3S,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2S,3R,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2S,3S,4R,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2R,3S,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2S,3R,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide, (2S,3S,4R,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide,
(2S,3S,4S,5R)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide,
(2S,3S,4S,5S)-4-[[3-(2-ethoxy-3,4-difluoro-phenyl)-4,5-dimethyl-5-(trifluoromethyl)tetrahydrofuran-2-carbonyl]amino]-1-oxido-pyridin-1-ium-2-carboxamide,
4-[[(2R,3R,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3R,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3R,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3S,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3R,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3R,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3S,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3R,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3S,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3R,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3S,4R,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3S,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3R,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3S,4R,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3S,4S,5R)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2S,3S,4S,5S)-3-[3,4-difluoro-2-(trideuteriomethoxy)phenyl]-4,5-dimethyl-5-(trifluoromethyl)tetrahydrofuran-2-carbonyl]amino]-1-oxido-pyridin-1-ium-2-carboxamide,
4-[[(2R,3R,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3R,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3R,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3S,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3R,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3R,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3S,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3R,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3S,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3R,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3S,4R,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2R,3S,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3R,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3S,4R,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3S,4S,5R)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
4-[[(2S,3S,4S,5S)-3-(3,4-difluoro-2-hydroxy-phenyl)-4,5-dimethyl-5-(trifluoromethyl)tetrahydrofuran-2-carbonyl]amino]-1-oxido-pyridin-1-ium-2-carboxamide,
(2R,3R,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3R,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3R,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide, (2R,3S,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3R,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3R,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3S,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3R,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3S,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3R,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3S,4R,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3S,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3R,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3S,4R,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3S,4S,5R)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2S,3S,4S,5S)-4-[[3-(3-chloro-4-fluoro-2-methoxy-phenyl)-5-methyl-5-(trifluoromethyl)tetrahydrofuran-2-carbonyl]amino]-N-methyl-pyridine-2-carboxamide,
(2R,3R,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3R,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3R,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3S,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3R,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3R,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3S,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3R,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3S,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3R,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3S,4R,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3S,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3R,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3S,4R,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3S,4S,5R)-4-[[3-(4-fluoro-2-hydroxy-phenyl)-4,5-dimethyl-5-(trifluoromethyl)tetrahydrofuran-2-carbonyl]amino]pyridine-2-carboxamide,
(2S,3S,4S,5S)-4-[[3-(4-fluoro-2-hydroxy-phenyl)-4,5-dimethyl-5-(trifluoromethyl)tetrahydrofuran-2-carbonyl]amino]pyridine-2-carboxamide,
(2R,3R,5R)-4-[[3-(3,4-difluoro-2-methoxy-phenyl)-5-ethyl-5-(trifluoromethyl)tetrahydrofuran-2-carbonyl]amino]pyridine-2-carboxamide,
(2R,3R,5S)-4-[[3-(3,4-difluoro-2-methoxy-phenyl)-5-ethyl-5-(trifluoromethyl)tetrahydrofuran-2-carbonyl]amino]pyridine-2-carboxamide,
(2R,3S,5R)-4-[[3-(3,4-difluoro-2-methoxy-phenyl)-5-ethyl-5-(trifluoromethyl)tetrahydrofuran-2-carbonyl]amino]pyridine-2-carboxamide,
(2S,3R,5R)-4-[[3-(3,4-difluoro-2-methoxy-phenyl)-5-ethyl-5-(trifluoromethyl)tetrahydrofuran-2-carbonyl]amino]pyridine-2-carboxamide,
(2R,3S,5S)-4-[[3-(3,4-difluoro-2-methoxy-phenyl)-5-ethyl-5-(trifluoromethyl)tetrahydrofuran-2-carbonyl]amino]pyridine-2-carboxamide,
(2S,3R,5S)-4-[[3-(3,4-difluoro-2-methoxy-phenyl)-5-ethyl-5-(trifluoromethyl)tetrahydrofuran-2-carbonyl]amino]pyridine-2-carboxamide,
(2S,3S,5R)-4-[[3-(3,4-difluoro-2-methoxy-phenyl)-5-ethyl-5-(trifluoromethyl)tetrahydrofuran-2-carbonyl]amino]pyridine-2-carboxamide,
(2S,3S,5S)-4-[[3-(3,4-difluoro-2-methoxy-phenyl)-5-ethyl-5-(trifluoromethyl)tetrahydrofuran-2-carbonyl]amino]pyridine-2-carboxamide,
(2R,3R,5R)-4-[[5-tert-butyl-3-(3,4-difluoro-2-methoxy-phenyl)tetrahydrofuran-2-carbonyl]amino]pyridine-2-carboxamide,
(2R,3R,5S)-4-[[5-tert-butyl-3-(3,4-difluoro-2-methoxy-phenyl)tetrahydrofuran-2-carbonyl]amino]pyridine-2-carboxamide,
(2R,3S,5R)-4-[[5-tert-butyl-3-(3,4-difluoro-2-methoxy-phenyl)tetrahydrofuran-2-carbonyl]amino]pyridine-2-carboxamide,
(2S,3R,5R)-4-[[5-tert-butyl-3-(3,4-difluoro-2-methoxy-phenyl)tetrahydrofuran-2-carbonyl]amino]pyridine-2-carboxamide,
(2R,3S,5S)-4-[[5-tert-butyl-3-(3,4-difluoro-2-methoxy-phenyl)tetrahydrofuran-2-carbonyl]amino]pyridine-2-carboxamide,
(2S,3R,5S)-4-[[5-tert-butyl-3-(3,4-difluoro-2-methoxy-phenyl)tetrahydrofuran-2-carbonyl]amino]pyridine-2-carboxamide,
(2S,3S,5R)-4-[[5-tert-butyl-3-(3,4-difluoro-2-methoxy-phenyl)tetrahydrofuran-2-carbonyl]amino]pyridine-2-carboxamide, (2S,3S,5S)-4-[[5-tert-butyl-3-(3,4-difluoro-2-methoxy-phenyl)tetrahydrofuran-2-carbonyl]amino]pyridine-2-carboxamide,
(2R,3R,5R)-4-[[3-(4-fluoro-2-methoxy-phenyl)-5-methyl-5-(trifluoromethyl)tetrahydrofuran-2-carbonyl]amino]pyridine-2-carboxamide,
(2R,3R,5S)-4-[[3-(4-fluoro-2-methoxy-phenyl)-5-methyl-5-(trifluoromethyl)tetrahydrofuran-2-carbonyl]amino]pyridine-2-carboxamide,
(2R,3S,5R)-4-[[3-(4-fluoro-2-methoxy-phenyl)-5-methyl-5-(trifluoromethyl)tetrahydrofuran-2-carbonyl]amino]pyridine-2-carboxamide,
(2S,3R,5R)-4-[[3-(4-fluoro-2-methoxy-phenyl)-5-methyl-5-(trifluoromethyl)tetrahydrofuran-2-carbonyl]amino]pyridine-2-carboxamide,
(2R,3S,5S)-4-[[3-(4-fluoro-2-methoxy-phenyl)-5-methyl-5-(trifluoromethyl)tetrahydrofuran-2-carbonyl]amino]pyridine-2-carboxamide,
(2S,3S,5S)-4-[[3-(4-fluoro-2-methoxy-phenyl)-5-methyl-5-(trifluoromethyl)tetrahydrofuran-2-carbonyl]amino]pyridine-2-carboxamide,
(2S,3S,5R)-4-[[3-(4-fluoro-2-methoxy-phenyl)-5-methyl-5-(trifluoromethyl)tetrahydrofuran-2-carbonyl]amino]pyridine-2-carboxamide,
(2S,3S,5S)-4-[[3-(4-fluoro-2-methoxy-phenyl)-5-methyl-5-(trifluoromethyl)tetrahydrofuran-2-carbonyl]amino]pyridine-2-carboxamide,
(2R,3R,5R)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2R,3R,5S)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2R,3S,5R)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2S,3R,5R)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2R,3S,5S)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2S,3R,5S)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2S,3S,5R)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2S,3S,5S)-4-[[3-(4-fluoro-2-methoxy-3-methyl-phenyl)-5-methyl-5-(trifluoromethyl)tetrahydrofuran-2-carbonyl]amino]pyridine-2-carboxamide,
(2R,3R,5R)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2R,3R,5S)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2R,3S,5R)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2S,3R,5R)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2R,3S,5S)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2S,3R,5S)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2S,3S,5R)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2S,3S,5S)-4-[[3-[2-(difluoromethoxy)-4-fluoro-phenyl]-5-methyl-5-(trifluoromethyl)tetrahydrofuran-2-carbonyl]amino]pyridine-2-carboxamide,
(2R,3R,5R)-4-[[3-(2,4-difluoro-3-methyl-phenyl)-5-methyl-5-(trifluoromethyl)tetrahydrofuran-2-carbonyl]amino]pyridine-2-carboxamide,
(2R,3R,5S)-4-[[3-(2,4-difluoro-3-methyl-phenyl)-5-methyl-5-(trifluoromethyl)tetrahydrofuran-2-carbonyl]amino]pyridine-2-carboxamide,
(2R,3S,5R)-4-[[3-(2,4-difluoro-3-methyl-phenyl)-5-methyl-5-(trifluoromethyl)tetrahydrofuran-2-carbonyl]amino]pyridine-2-carboxamide,
(2S,3R,5R)-4-[[3-(2,4-difluoro-3-methyl-phenyl)-5-methyl-5-(trifluoromethyl)tetrahydrofuran-2-carbonyl]amino]pyridine-2-carboxamide,
(2R,3S,5S)-4-[[3-(2,4-difluoro-3-methyl-phenyl)-5-methyl-5-(trifluoromethyl)tetrahydrofuran-2-carbonyl]amino]pyridine-2-carboxamide,
(2S,3R,5S)-4-[[3-(2,4-difluoro-3-methyl-phenyl)-5-methyl-5-(trifluoromethyl)tetrahydrofuran-2-carbonyl]amino]pyridine-2-carboxamide,
(2S,3S,5R)-4-[[3-(2,4-difluoro-3-methyl-phenyl)-5-methyl-5-(trifluoromethyl)tetrahydrofuran-2-carbonyl]amino]pyridine-2-carboxamide,
(2S,3S,5S)-4-[[3-(2,4-difluoro-3-methyl-phenyl)-5-methyl-5-(trifluoromethyl)tetrahydrofuran-2-carbonyl]amino]pyridine-2-carboxamide,
(2R,3R,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2R,3R,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2R,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2S,3R,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2R,3S,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2S,3R,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2S,3S,5R)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2S,3S,5S)-4-[[3-(3-ethyl-4-fluoro-2-methoxy-phenyl)-5-methyl-5-(trifluoromethyl)tetrahydrofuran-2-carbonyl]amino]pyridine-2-carboxamide,
(2R,3R,5R)-4-[[3-(2-fluoro-6-methoxy-phenyl)-5-methyl-5-(trifluoromethyl)tetrahydrofuran-2-carbonyl]amino]pyridine-2-carboxamide,
(2R,3R,5S)-4-[[3-(2-fluoro-6-methoxy-phenyl)-5-methyl-5-(trifluoromethyl)tetrahydrofuran-2-carbonyl]amino]pyridine-2-carboxamide,
(2R,3S,5R)-4-[[3-(2-fluoro-6-methoxy-phenyl)-5-methyl-5-(trifluoromethyl)tetrahydrofuran-2-carbonyl]amino]pyridine-2-carboxamide, (2S,3R,5R)-4-[[3-(2-fluoro-6-methoxy-phenyl)-5-methyl-5-(trifluoromethyl)tetrahydrofuran-2-carbonyl]amino]pyridine-2-carboxamide,
(2R,3S,5S)-4-[[3-(2-fluoro-6-methoxy-phenyl)-5-methyl-5-(trifluoromethyl)tetrahydrofuran-2-carbonyl]amino]pyridine-2-carboxamide,
(2S,3R,5S)-4-[[3-(2-fluoro-6-methoxy-phenyl)-5-methyl-5-(trifluoromethyl)tetrahydrofuran-2-carbonyl]amino]pyridine-2-carboxamide,
(2S,3S,5R)-4-[[3-(2-fluoro-6-methoxy-phenyl)-5-methyl-5-(trifluoromethyl)tetrahydrofuran-2-carbonyl]amino]pyridine-2-carboxamide,
(2S,3S,5S)-4-[[3-(2-fluoro-6-methoxy-phenyl)-5-methyl-5-(trifluoromethyl)tetrahydrofuran-2-carbonyl]amino]pyridine-2-carboxamide,
(2R,3R,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2R,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2R,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2S,3R,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2R,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2S,3R,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2S,3S,5R)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2S,3S,5S)-4-[[3-(3,4-difluoro-2-methoxy-phenyl)-5-methyl-5-(2,2,2-trifluoroethyl)tetrahydrofuran-2-carbonyl]amino]pyridine-2-carboxamide,
(2R,3R,5R)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2R,3R,5S)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2R,3S,5R)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2S,3R,5R)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2R,3S,5S)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2S,3R,5S)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2S,3S,5R)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2S,3S,5S)-4-[[5-(1,1-difluoroethyl)-3-(3,4-difluoro-2-methoxy-phenyl)-5-methyl-tetrahydrofuran-2-carbonyl]amino]pyridine-2-carboxamide,
(2R,3R,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3R,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3R,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3S,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3R,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3R,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3S,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3R,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3R,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3S,4R,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3S,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3R,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3S,4R,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3S,4S,5R)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2S,3S,4S,5S)-4-[[3-(3,4-difluoro-2-isopropoxy-phenyl)-4,5-dimethyl-5-(trifluoromethyl)tetrahydrofuran-2-carbonyl]amino]pyridine-2-carboxamide,
(2R,3R,4R,5R)-4-[[3-(3,4-difluorophenyl)-4,5-dimethyl-5-(trifluoromethyl)tetrahydrofuran-2-carbonyl]amino]pyridine-2-carboxamide,
(2R,3R,4R,5S)-4-[[3-(3,4-difluorophenyl)-4,5-dimethyl-5-(trifluoromethyl)tetrahydrofuran-2-carbonyl]amino]pyridine-2-carboxamide,
(2R,3R,4S,5R)-4-[[3-(3,4-difluorophenyl)-4,5-dimethyl-5-(trifluoromethyl)tetrahydrofuran-2-carbonyl]amino]pyridine-2-carboxamide,
(2R,3S,4R,5R)-4-[[3-(3,4-difluorophenyl)-4,5-dimethyl-5-(trifluoromethyl)tetrahydrofuran-2-carbonyl]amino]pyridine-2-carboxamide,
(2S,3R,4R,5R)-4-[[3-(3,4-difluorophenyl)-4,5-dimethyl-5-(trifluoromethyl)tetrahydrofuran-2-carbonyl]amino]pyridine-2-carboxamide,
(2R,3R,4S,5S)-4-[[3-(3,4-difluorophenyl)-4,5-dimethyl-5-(trifluoromethyl)tetrahydrofuran-2-carbonyl]amino]pyridine-2-carboxamide,
(2R,3S,4R,5S)-4-[[3-(3,4-difluorophenyl)-4,5-dimethyl-5-(trifluoromethyl)tetrahydrofuran-2-carbonyl]amino]pyridine-2-carboxamide, (2S,3R,4R,5S)-4-[[3-(3,4-difluorophenyl)-4,5-dimethyl-5-(trifluoromethyl)tetrahydrofuran-2-carbonyl]amino]pyridine-2-carboxamide,
(2R,3S,4S,5R)-4-[[3-(3,4-difluorophenyl)-4,5-dimethyl-5-(trifluoromethyl)tetrahydrofuran-2-carbonyl]amino]pyridine-2-carboxamide,
(2S,3R,4S,5R)-4-[[3-(3,4-difluorophenyl)-4,5-dimethyl-5-(trifluoromethyl)tetrahydrofuran-2-carbonyl]amino]pyridine-2-carboxamide,
(2S,3S,4R,5R)-4-[[3-(3,4-difluorophenyl)-4,5-dimethyl-5-(trifluoromethyl)tetrahydrofuran-2-carbonyl]amino]pyridine-2-carboxamide,
(2R,3S,4S,5S)-4-[[3-(3,4-difluorophenyl)-4,5-dimethyl-5-(trifluoromethyl)tetrahydrofuran-2-carbonyl]amino]pyridine-2-carboxamide,
(2S,3R,4S,5S)-4-[[3-(3,4-difluorophenyl)-4,5-dimethyl-5-(trifluoromethyl)tetrahydrofuran-2-carbonyl]amino]pyridine-2-carboxamide,
(2S,3S,4R,5S)-4-[[3-(3,4-difluorophenyl)-4,5-dimethyl-5-(trifluoromethyl)tetrahydrofuran-2-carbonyl]amino]pyridine-2-carboxamide,
(2S,3S,4S,5R)-4-[[3-(3,4-difluorophenyl)-4,5-dimethyl-5-(trifluoromethyl)tetrahydrofuran-2-carbonyl]amino]pyridine-2-carboxamide,
(2S,3S,4S,5S)-4-[[3-(3,4-difluorophenyl)-4,5-dimethyl-5-(trifluoromethyl)tetrahydrofuran-2-carbonyl]amino]pyridine-2-carboxamide,
(2R,3R,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3R,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3R,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3S,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3R,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3R,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3S,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3R,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3R,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3S,4R,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3S,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3R,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3S,4R,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3S,4S,5R)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2S,3S,4S,5S)-4-[[3-(3,4-difluoro-2-methoxy-phenyl)-4-ethyl-5-methyl-5-(trifluoromethyl)tetrahydrofuran-2-carbonyl]amino]pyridine-2-carboxamide,
(2R,3R,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3R,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3R,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3S,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3R,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3R,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3S,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3R,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3S,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3R,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3S,4R,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3S,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3R,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3S,4R,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3S,4S,5R)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2S,3S,4S,5S)-4-[[4-cyclopropyl-3-(3,4-difluoro-2-methoxy-phenyl)-5-methyl-5-(trifluoromethyl)tetrahydrofuran-2-carbonyl]amino]pyridine-2-carboxamide,
(2R,3R,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3R,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3R,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide, (2R,3S,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3R,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3R,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3S,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3R,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3S,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3R,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3S,4R,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3S,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3R,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3S,4R,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3S,4S,5R)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2S,3S,4S,5S)-4-[[3-(3,4-difluoro-2-methoxy-phenyl)-5-(difluoromethyl)-4,5-dimethyl-tetrahydrofuran-2-carbonyl]amino]pyridine-2-carboxamide,
(2R,3R,5R)-4-[[3-(3,4-difluoro-2-methoxy-phenyl)-4,5,5-trimethyl-tetrahydrofuran-2-carbonyl]amino]pyridine-2-carboxamide,
(2R,3R,5S)-4-[[3-(3,4-difluoro-2-methoxy-phenyl)-4,5,5-trimethyl-tetrahydrofuran-2-carbonyl]amino]pyridine-2-carboxamide,
(2R,3S,5R)-4-[[3-(3,4-difluoro-2-methoxy-phenyl)-4,5,5-trimethyl-tetrahydrofuran-2-carbonyl]amino]pyridine-2-carboxamide,
(2S,3R,5R)-4-[[3-(3,4-difluoro-2-methoxy-phenyl)-4,5,5-trimethyl-tetrahydrofuran-2-carbonyl]amino]pyridine-2-carboxamide,
(2R,3S,5S)-4-[[3-(3,4-difluoro-2-methoxy-phenyl)-4,5,5-trimethyl-tetrahydrofuran-2-carbonyl]amino]pyridine-2-carboxamide,
(2S,3R,5S)-4-[[3-(3,4-difluoro-2-methoxy-phenyl)-4,5,5-trimethyl-tetrahydrofuran-2-carbonyl]amino]pyridine-2-carboxamide,
(2S,3S,5R)-4-[[3-(3,4-difluoro-2-methoxy-phenyl)-4,5,5-trimethyl-tetrahydrofuran-2-carbonyl]amino]pyridine-2-carboxamide,
(2S,3S,5S)-4-[[3-(3,4-difluoro-2-methoxy-phenyl)-4,5,5-trimethyl-tetrahydrofuran-2-carbonyl]amino]pyridine-2-carboxamide,
(2R,3R,4R,5R)-4-[[3-(3,4-difluoro-2-methoxy-phenyl)-4,5-dimethyl-tetrahydrofuran-2-carbonyl]amino]pyridine-2-carboxamide,
(2R,3R,4R,5S)-4-[[3-(3,4-difluoro-2-methoxy-phenyl)-4,5-dimethyl-tetrahydrofuran-2-carbonyl]amino]pyridine-2-carboxamide,
(2R,3R,4S,5R)-4-[[3-(3,4-difluoro-2-methoxy-phenyl)-4,5-dimethyl-tetrahydrofuran-2-carbonyl]amino]pyridine-2-carboxamide,
(2R,3S,4R,5R)-4-[[3-(3,4-difluoro-2-methoxy-phenyl)-4,5-dimethyl-tetrahydrofuran-2-carbonyl]amino]pyridine-2-carboxamide,
(2S,3R,4R,5R)-4-[[3-(3,4-difluoro-2-methoxy-phenyl)-4,5-dimethyl-tetrahydrofuran-2-carbonyl]amino]pyridine-2-carboxamide,
(2R,3R,4S,5S)-4-[[3-(3,4-difluoro-2-methoxy-phenyl)-4,5-dimethyl-tetrahydrofuran-2-carbonyl]amino]pyridine-2-carboxamide,
(2R,3S,4R,5S)-4-[[3-(3,4-difluoro-2-methoxy-phenyl)-4,5-dimethyl-tetrahydrofuran-2-carbonyl]amino]pyridine-2-carboxamide,
(2R,3S,4S,5R)-4-[[3-(3,4-difluoro-2-methoxy-phenyl)-4,5-dimethyl-tetrahydrofuran-2-carbonyl]amino]pyridine-2-carboxamide,
(2S,3R,4S,5R)-4-[[3-(3,4-difluoro-2-methoxy-phenyl)-4,5-dimethyl-tetrahydrofuran-2-carbonyl]amino]pyridine-2-carboxamide,
(2S,3S,4R,5R)-4-[[3-(3,4-difluoro-2-methoxy-phenyl)-4,5-dimethyl-tetrahydrofuran-2-carbonyl]amino]pyridine-2-carboxamide,
(2R,3S,4S,5S)-4-[[3-(3,4-difluoro-2-methoxy-phenyl)-4,5-dimethyl-tetrahydrofuran-2-carbonyl]amino]pyridine-2-carboxamide,
(2S,3R,4S,5S)-4-[[3-(3,4-difluoro-2-methoxy-phenyl)-4,5-dimethyl-tetrahydrofuran-2-carbonyl]amino]pyridine-2-carboxamide,
(2S,3S,4R,5S)-4-[[3-(3,4-difluoro-2-methoxy-phenyl)-4,5-dimethyl-tetrahydrofuran-2-carbonyl]amino]pyridine-2-carboxamide,
(2S,3S,4S,5R)-4-[[3-(3,4-difluoro-2-methoxy-phenyl)-4,5-dimethyl-tetrahydrofuran-2-carbonyl]amino]pyridine-2-carboxamide,
(2S,3S,4S,5S)-4-[[3-(3,4-difluoro-2-methoxy-phenyl)-4,5-dimethyl-tetrahydrofuran-2-carbonyl]amino]pyridine-2-carboxamide,
(2R,3R,5R)-4-[[3-(3,4-difluoro-2-methoxy-phenyl)-5-(trifluoromethyl)tetrahydrofuran-2-carbonyl]amino]pyridine-2-carboxamide,
(2R,3R,5S)-4-[[3-(3,4-difluoro-2-methoxy-phenyl)-5-(trifluoromethyl)tetrahydrofuran-2-carbonyl]amino]pyridine-2-carboxamide,
(2R,3S,5R)-4-[[3-(3,4-difluoro-2-methoxy-phenyl)-5-(trifluoromethyl)tetrahydrofuran-2-carbonyl]amino]pyridine-2-carboxamide,
(2S,3R,5R)-4-[[3-(3,4-difluoro-2-methoxy-phenyl)-5-(trifluoromethyl)tetrahydrofuran-2-carbonyl]amino]pyridine-2-carboxamide,
(2R,3S,5S)-4-[[3-(3,4-difluoro-2-methoxy-phenyl)-5-(trifluoromethyl)tetrahydrofuran-2-carbonyl]amino]pyridine-2-carboxamide,
(2S,3R,5S)-4-[[3-(3,4-difluoro-2-methoxy-phenyl)-5-(trifluoromethyl)tetrahydrofuran-2-carbonyl]amino]pyridine-2-carboxamide,
(2S,3S,5R)-4-[[3-(3,4-difluoro-2-methoxy-phenyl)-5-(trifluoromethyl)tetrahydrofuran-2-carbonyl]amino]pyridine-2-carboxamide, (2S,3S,5S)-4-[[3-(3,4-difluoro-2-methoxy-phenyl)-5-(trifluoromethyl)tetrahydrofuran-2-carbonyl]amino]pyridine-2-carboxamide,
(2R,3R,5R)-4-[[3-(4-fluoro-2-methoxy-3-methyl-phenyl)-5-(trifluoromethyl)tetrahydrofuran-2-carbonyl]amino]pyridine-2-carboxamide,
(2R,3R,5S)-4-[[3-(4-fluoro-2-methoxy-3-methyl-phenyl)-5-(trifluoromethyl)tetrahydrofuran-2-carbonyl]amino]pyridine-2-carboxamide,
(2R,3S,5R)-4-[[3-(4-fluoro-2-methoxy-3-methyl-phenyl)-5-(trifluoromethyl)tetrahydrofuran-2-carbonyl]amino]pyridine-2-carboxamide,
(2S,3R,5R)-4-[[3-(4-fluoro-2-methoxy-3-methyl-phenyl)-5-(trifluoromethyl)tetrahydrofuran-2-carbonyl]amino]pyridine-2-carboxamide,
(2R,3S,5S)-4-[[3-(4-fluoro-2-methoxy-3-methyl-phenyl)-5-(trifluoromethyl)tetrahydrofuran-2-carbonyl]amino]pyridine-2-carboxamide,
(2S,3R,5S)-4-[[3-(4-fluoro-2-methoxy-3-methyl-phenyl)-5-(trifluoromethyl)tetrahydrofuran-2-carbonyl]amino]pyridine-2-carboxamide,
(2S,3S,5R)-4-[[3-(4-fluoro-2-methoxy-3-methyl-phenyl)-5-(trifluoromethyl)tetrahydrofuran-2-carbonyl]amino]pyridine-2-carboxamide,
(2S,3S,5S)-4-[[3-(4-fluoro-2-methoxy-3-methyl-phenyl)-5-(trifluoromethyl)tetrahydrofuran-2-carbonyl]amino]pyridine-2-carboxamide,
4-[[(2R,3R,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3R,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3R,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3S,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3R,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3R,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3S,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3R,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3S,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3R,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3S,4R,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3S,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3R,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3S,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3S,4S,5R)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2R,3R,4R,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
4-[[(2S,3S,4S,5S)-3-(3,4-difluoro-2-methoxy-phenyl)-4,5-dimethyl-5-(trifluoromethyl)tetrahydrofuran-2-carbonyl]amino]-5-methyl-pyridine-2-carboxamide,
6-[[(2R,3R,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3R,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3R,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3S,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3R,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3R,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3S,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3R,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3S,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3R,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3S,4R,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2R,3S,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3R,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3S,4R,5S)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3S,4S,5R)-3-(3,4-difluoro-2-methoxy-phenyl)-4,5-dimethyl-5-(trifluoromethyl)tetrahydrofuran-2-carbonyl]amino]pyrimidine-4-carboxamide,
6-[[(2S,3S,4S,5S)-3-(3,4-difluoro-2-methoxy-phenyl)-4,5-dimethyl-5-(trifluoromethyl)tetrahydrofuran-2-carbonyl]amino]pyrimidine-4-carboxamide,
4-[[(2R,3R,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2R,3R,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2R,3R,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide, 4-[[(2R,3S,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3R,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2R,3R,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2R,3S,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3R,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2R,3S,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3R,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3S,4R,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2R,3S,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3R,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3S,4R,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3S,4S,5R)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
4-[[(2S,3S,4S,5S)-3-(3,4-difluoro-2-methoxy-phenyl)-4,5-dimethyl-5-(trifluoromethyl)tetrahydrofuran-2-carbonyl]amino]-5-fluoro-pyridine-2-carboxamide,
5-deuterio-4-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide,
5-deuterio-4-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide,
4-[[(2R,3R,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3R,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3R,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3S,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2S,3R,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3R,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3S,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2S,3R,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2S,3R,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2S,3S,4R,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2R,3S,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide,
4-[[(2S,3R,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide, 4-[[(2S,3R,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide, 4-[[(2S,3S,4R,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide, 4-[[(2S,3S,4S,5R)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide, 4-[[(2S,3S,4S,5S)-3-(3,4-difluoro-2-methoxy-phenyl)-4,5-dimethyl-5-(trifluoromethyl)tetrahydrofuran-2-carbonyl]amino]-3-fluoro-pyridine-2-carboxamide, 4-[[(2R,3R,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3R,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3R,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3S,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3R,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3R,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3S,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3R,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3S,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3R,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3S,3S,4R,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3S,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3R,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3S,4R,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3S,4S,5R)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2S,3S,4S,5S)-3-(3,4-difluoro-2-methoxy-phenyl)-4,5-dimethyl-5-(trifluoromethyl)tetrahydrofuran-2-carbonyl]amino]-6-fluoro-pyridine-2-carboxamide, 4-[[(2R,3R,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3R,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3R,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3S,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3R,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3R,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3S,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3R,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3S,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3R,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3S,4R,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3S,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3R,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3S,4R,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3S,4S,5R)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2S,3S,4S,5S)-3-(3,4-difluoro-2-methoxy-phenyl)-4,5-dimethyl-5-(trifluoromethyl)tetrahydrofuran-2-carbonyl]amino]-6-methyl-pyridine-2-carboxamide, 4-[[(2R,3R,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3R,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3R,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3S,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3R,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3R,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3S,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3R,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3S,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3R,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3S,4R,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2R,3S,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3R,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3S,4R,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3S,4S,5R)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 4-[[(2S,3S,4S,5S)-3-(3,4-difluoro-2-methoxy-phenyl)-4,5-dimethyl-5-(trifluoromethyl)tetrahydrofuran-2-carbonyl]amino]-3-methyl-pyridine-2-carboxamide, 3-deuterio-4-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 3-deuterio-4-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3R,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3R,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3R,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3S,4R,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2R,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3R,4S,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3S,4R,5S)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3S,4S,5R)-3-(3,4-difluoro-2-methoxy-phenyl)-4,5-dimethyl-5-(trifluoromethyl)tetrahydrofuran-2-carbonyl]amino]pyridine-2-carboxamide, 6-deuterio-4-[[(2S,3S,4S,5S)-3-(3,4-difluoro-2-methoxy-phenyl)-4,5-dimethyl-5-(trifluoromethyl)tetrahydrofuran-2-carbonyl]amino]pyridine-2-carboxamide, (2R,3R,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3R,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3R,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3S,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3R,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3R,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3S,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3R,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3R,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3S,4R,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3S,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3R,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3S,4R,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3S,4S,5R)-4-[[3-(3,4-difluoro-2-methyl-phenyl)-4,5-dimethyl-5-(trifluoromethyl)tetrahydrofuran-2-carbonyl]amino]pyridine-2-carboxamide, (2S,3S,4S,5S)-4-[[3-(3,4-difluoro-2-methyl-phenyl)-4,5-dimethyl-5-(trifluoromethyl)tetrahydrofuran-2-carbonyl]amino]pyridine-2-carboxamide, (2R,3R,4R,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3R,4R,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3R,4S,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3S,4R,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3R,4R,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3R,4S,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3S,4R,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3R,4R,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3S,4S,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3R,4S,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3S,4R,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3S,4S,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3R,4S,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3S,4R,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3S,4S,5R)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2S,3S,4S,5S)-4-[[3-[4-(difluoromethyl)-3-fluoro-2-methoxy-phenyl]-4,5-dimethyl-5-(trifluoromethyl) tetrahydrofuran-2-carbonyl]amino]pyridine-2-carboxamide, (2R,3R,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide, (2R,3R,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide, (2R,3R,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3R,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4R,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4R,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4S,5R)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4S,5S)-4-[[3-[2-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3R,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3R,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3R,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3R,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4R,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3S,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3R,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4R,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4S,5R)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2S,3S,4S,5S)-4-[[3-[4-methoxy-6-(trifluoromethyl)-3-pyridyl]-4,5-dimethyl-5-(trifluoromethyl)tetrahydrofuran-2-carbonyl]amino]pyridine-2-carboxamide,
(2R,3R,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3R,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3R,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3S,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2S,3R,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3R,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3S,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2S,3R,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2S,3R,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2S,3S,4R,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2R,3S,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2S,3R,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide,
(2S,3S,4R,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide, (2S,3S,4S,5R)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide, (2S,3S,4S,5S)-4-[[3-[6-(difluoromethyl)-2-methoxy-3-pyridyl]-4,5-dimethyl-5-(trifluoromethyl)tetrahydrofuran-2-carbonyl]amino]pyridine-2-carboxamide, (2R,3R,4R,5R)-4-[[3-(3-methoxy-2-pyridyl)-4,5-dimethyl-5-(trifluoromethyl)tetrahydrofuran-2-carbonyl]amino]pyridine-2-carboxamide, (2R,3R,4R,5S)-4-[[3-(3-methoxy-2-pyridyl)-4,5-dimethyl-5-(trifluoromethyl)tetrahydrofuran-2-carbonyl]amino]pyridine-2-carboxamide, (2R,3R,4S,5R)-4-[[3-(3-methoxy-2-pyridyl)-4,5-dimethyl-5-(trifluoromethyl)tetrahydrofuran-2-carbonyl]amino]pyridine-2-carboxamide, (2R,3S,4R,5R)-4-[[3-(3-methoxy-2-pyridyl)-4,5-dimethyl-5-(trifluoromethyl)tetrahydrofuran-2-carbonyl]amino]pyridine-2-carboxamide, (2S,3R,4R,5R)-4-[[3-(3-methoxy-2-pyridyl)-4,5-dimethyl-5-(trifluoromethyl)tetrahydrofuran-2-carbonyl]amino]pyridine-2-carboxamide, (2R,3R,4S,5S)-4-[[3-(3-methoxy-2-pyridyl)-4,5-dimethyl-5-(trifluoromethyl)tetrahydrofuran-2-carbonyl]amino]pyridine-2-carboxamide, (2R,3S,4R,5S)-4-[[3-(3-methoxy-2-pyridyl)-4,5-dimethyl-5-(trifluoromethyl)tetrahydrofuran-2-carbonyl]amino]pyridine-2-carboxamide, (2S,3R,4R,5S)-4-[[3-(3-methoxy-2-pyridyl)-4,5-dimethyl-5-(trifluoromethyl)tetrahydrofuran-2-carbonyl]amino]pyridine-2-carboxamide, (2R,3S,4S,5R)-4-[[3-(3-methoxy-2-pyridyl)-4,5-dimethyl-5-(trifluoro,omethyl)tetrahydrofuran-2-carbonyl]amino]pyridine-2-carboxamide, (2S,3R,4S,5R)-4-[[3-(3-methoxy-2-pyridyl)-4,5-dimethyl-5-(trifluoromethyl)tetrahydrofuran-2-carbonyl]amino]pyridine-2-carboxamide, (2S,3S,4R,5R)-4-[[3-(3-methoxy-2-pyridyl)-4,5-dimethyl-5-(trifluoromethyl)tetrahydrofuran-2-carbonyl]amino]pyridine-2-carboxamide, (2R,3S,4S,5S)-4-[[3-(3-methoxy-2-pyridyl)-4,5-dimethyl-5-(trifluoromethyl)tetrahydrofuran-2-carbonyl]amino]pyridine-2-carboxamide, (2S,3R,4S,5S)-4-[[3-(3-methoxy-2-pyridyl)-4,5-dimethyl-5-(trifluoromethyl)tetrahydrofuran-2-carbonyl]amino]pyridine-2-carboxamide, (2S,3S,4R,5S)-4-[[3-(3-methoxy-2-pyridyl)-4,5-dimethyl-5-(trifluoromethyl)tetrahydrofuran-2-carbonyl]amino]pyridine-2-carboxamide, (2S,3S,4S,5R)-4-[[3-(3-methoxy-2-pyridyl)-4,5-dimethyl-5-(trifluoromethyl)tetrahydrofuran-2-carbonyl]amino]pyridine-2-carboxamide, (2S,3S,4S,5S)-4-[[3-(3-methoxy-2-pyridyl)-4,5-dimethyl-5-(trifluoromethyl)tetrahydrofuran-2-carbonyl]amino]pyridine-2-carboxamide, (2R,3R,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3R,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3R,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3S,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3R,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3R,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3S,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3R,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3S,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3R,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3S,4R,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2R,3S,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3R,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3S,4R,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3S,4S,5R)-4-[[3-(3-methoxy-2-methyl-4-pyridyl)-4,5-dimethyl-5-(trifluoromethyl)tetrahydrofuran-2-carbonyl]amino]pyridine-2-carboxamide, (2S,3S,4S,5S)-4-[[3-(3-methoxy-2-methyl-4-pyridyl)-4,5-dimethyl-5-(trifluoromethyl)tetrahydrofuran-2-carbonyl]amino]pyridine-2-carboxamide, 4-[[(2R,3R,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3R,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3R,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3S,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3R,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3R,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3S,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3R,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3R,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3S,4R,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3S,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3R,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3S,4R,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3S,4S,5R)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2S,3S,4S,5S)-3-[2-[(3,3-difluorocyclobutyl)methoxy]-3,4-difluoro-phenyl]-4,5-dimethyl-5-(trifluoromethyl)tetrahydrofuran-2-carbonyl]amino]pyridine-2-carboxamide, 4-[[(2R,3R,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3R,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3R,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3S,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3R,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3R,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3S,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3R,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3R,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3S,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3S,4R,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3S,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3R,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3S,4R,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3S,4S,5R)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2S,3S,4S,5S)-3-[2-(cyclobutoxy)-3,4-difluoro-phenyl]-4,5-dimethyl-5-(trifluoromethyl)tetrahydrofuran-2-carbonyl]amino]pyridine-2-carboxamide, 4-[[(2R,3R,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3R,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3R,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3S,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3R,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3R,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3S,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3R,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3S,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3R,4S,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3S,4R,5R)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3S,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3R,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3S,4R,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2R,3S,4S,5S)-3-(5-deuterio-3,4-difluoro-2-methoxy-phenyl)-4,5-dimethyl-5-(trifluoromethyl)tetrahydrofuran-2-carbonyl]amino]pyridine-2-carboxamide, 4-[[(2S,3R,4S,5S)-3-(5-deuterio-3,4-difluoro-2-methoxyphenyl)-4,5-dimethyl-5-(trifluoromethyl)tetrahydrofuran-2-carbonyl]amino]pyridine-2-carboxamide,
4-[[(2S,3S,4R,5S)-3-(5-deuterio-3,4-difluoro-2-methoxyphenyl)-4,5-dimethyl-5-(trifluoromethyl)tetrahydrofuran-2-carbonyl]amino]pyridine-2-carboxamide,
4-[[(2S,3S,4S,5R)-3-(5-deuterio-3,4-difluoro-2-methoxyphenyl)-4,5-dimethyl-5-(trifluoromethyl)tetrahydrofuran-2-carbonyl]amino]pyridine-2-carboxamide,
4-[[(2S,3S,4S,5S)-3-(5-deuterio-3,4-difluoro-2-methoxyphenyl)-4,5-dimethyl-5-(trifluoromethyl)tetrahydrofuran-2-carbonyl]amino]pyridine-2-carboxamide,
4-[[(2R,3R,4R,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3R,4R,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3R,4S,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3S,4R,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3R,4R,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3R,4S,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3S,4R,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3R,4R,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3S,4S,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3R,4S,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3S,4R,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2R,3S,4S,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3R,4S,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3S,4R,5S)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3S,4S,5R)-3-(3,4-difluoro-2-vinyl-phenyl)-4,5-dimethyl-5-(trifluoromethyl)tetrahydrofuran-2-carbonyl]amino]pyridine-2-carboxamide,
4-[[(2S,3S,4S,5S)-3-(3,4-difluoro-2-vinyl-phenyl)-4,5-dimethyl-5-(trifluoromethyl)tetrahydrofuran-2-carbonyl]amino]pyridine-2-carboxamide,
(2R,3R,4R,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3R,4R,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3R,4S,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3S,4R,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3R,4R,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3R,4S,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3S,4R,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3R,4R,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3S,4S,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3R,4S,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3S,4R,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2R,3S,4S,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3R,4S,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3S,4R,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3S,4S,5R)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
(2S,3S,4S,5S)-4-[[3-[2-(difluoromethoxy)-3,4-difluorophenyl]-4,5-dimethyl-5-(trifluoromethyl)tetrahydrofuran-2-carbonyl]amino]-5-methyl-pyridine-2-carboxamide,
4-[[(2R,3R,4R,5R)-3-(5-chloro-3,4-difluoro-2-methoxyphenyl)-4,5-dimethyl-5-(trifluoromethyl)tetrahydrofuran-2-carbonyl]amino]pyridine-2-carboxamide,
4-[[(2R,3R,4R,5S)-3-(5-chloro-3,4-difluoro-2-methoxyphenyl)-4,5-dimethyl-5-(trifluoromethyl)tetrahydrofuran-2-carbonyl]amino]pyridine-2-carboxamide, 4-[[(2R,3R,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2R,3S,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3R,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2R,3R,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2R,3S,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3R,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2R,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3R,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3S,4R,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2R,3S,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3R,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3S,4R,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3S,4S,5R)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2S,3S,4S,5S)-3-(5-chloro-3,4-difluoro-2-methoxy-phenyl)-4,5-dimethyl-5-(trifluoromethyl)tetrahydrofuran-2-carbonyl]amino]pyridine-2-carboxamide,
4-[[(2R,3R,4R,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3R,4R,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3R,4S,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3S,4R,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3R,4R,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3R,4S,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3S,4R,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3R,4R,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3S,4S,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3R,4S,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3S,4R,5R)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2R,3S,4S,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3R,4S,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3S,4R,5S)-3-(2-ethyl-3,4-difluoro-phenyl)-4,5-dimethyl-5-(trifluoromethyl)tetrahydrofuran-2-carbonyl]amino]pyridine-2-carboxamide,
4-[[(2S,3S,4S,5R)-3-(2-ethyl-3,4-difluoro-phenyl)-4,5-dimethyl-5-(trifluoromethyl)tetrahydrofuran-2-carbonyl]amino]pyridine-2-carboxamide, and
4-[[(2S,3S,4S,5S)-3-(2-ethyl-3,4-difluoro-phenyl)-4,5-dimethyl-5-(trifluoromethyl)tetrahydrofuran-2-carbonyl]amino]pyridine-2-carboxamide.

7. The compound of claim 1.

8. The compound of claim 7, wherein the compound has formula

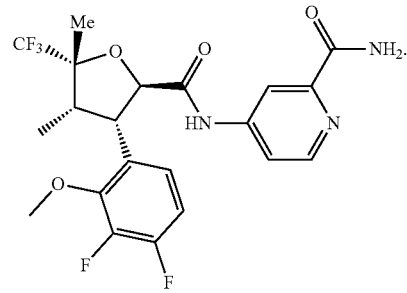 [SMILES: COc1c([C@H]2[C@H](C(=O)Nc3ccnc(C(N)=O)c3)O[C@@](C)(C(F)(F)F)[C@H]2C)ccc(F)c1F]

9. The compound of claim 8, wherein the compound is in crystalline solid form.

10. The compound of claim 9, wherein the crystalline solid form is Form A,
wherein:
Form A is characterized by an XRPD pattern having diffractions at angles degrees 2 theta ±0.2 of 9.9, 13.9, 15.7, and 19.0; and/or
Form A is characterized by a DSC thermogram having a melting onset of 186° C. with a peak at 187° C.

11. The compound of claim 9, wherein the crystalline solid form is Form B,
wherein Form B is characterized by one or more of:
(a) an XRPD pattern having diffractions at angles degrees 2 theta ±0.2 of 12.8, 14.1, 15.2, 18.5, and 20.3; and/or
(b) a solid state $^{13}$C NMR spectrum having peaks at chemical shifts of 172.5, 172.1, 168.5, 168.3, 168.0, 151.5, 148.3, 147.8, 127.7, 122.7, 116.6, 115.1, 110.6, 86.5, 80.2, 63.2, 44.3, 23.0, and 13.1 ppm or a solid state $^{19}$F NMR spectrum having peaks at chemical shifts of −137.1 and −152.8 ppm; and/or
(c) a DSC thermogram having a melting onset of 182° C. with a peak at 183° C.; and/or (d) an IR spectrum having peaks at 3501, 3356, 1684, 1565, 1505, and 1122 cm$^{-1}$; and/or
(e) an orthorhombic crystal system, as determined by single-crystal X-ray analysis; and/or
(f) a unit cell, as determined by single-crystal X-ray analysis, of the following dimensions: a=7.3929(2) Å; b=14.5827(4) Å; c=18.9312(6) Å; α=90°; β=90°; and γ=90°; and/or
(g) being obtainable by dissolving the compound in ethyl acetate and then crystallizing the compound by adding n-heptane as an antisolvent.

12. The compound of claim 7, wherein the compound has formula

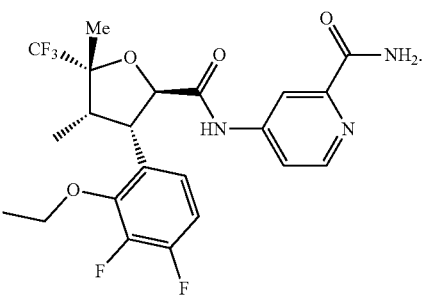 [SMILES: CCOc1c([C@H]2[C@H](C(=O)Nc3ccnc(C(N)=O)c3)O[C@@](C)(C(F)(F)F)[C@H]2C)ccc(F)c1F]

13. The compound of claim 12, wherein the compound is in crystalline solid form.
14. The compound of claim 13, wherein the crystalline solid form is Form A,
wherein Form A is characterized by one or more of:
(a) an orthorhombic crystal system, as determined by single-crystal X-ray analysis; and/or
(b) an 1222 space group, as determined by single-crystal X-ray analysis; and/or
(c) a unit cell, as determined by single-crystal X-ray analysis, of the following dimensions: a=12.0172(5) Å; b=15.6682(6) Å; c=24.1406(11) Å; α=90°; β=90°; and γ=90°.

15. The compound of claim 7, wherein the compound has formula

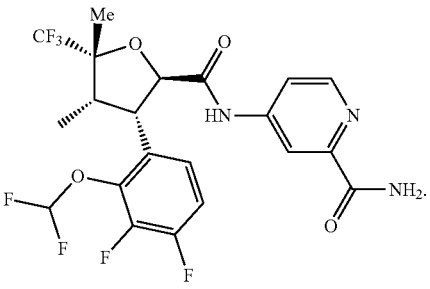 [SMILES: C[C@H]1[C@@H](c2ccc(F)c(F)c2OC(F)F)[C@H](C(=O)Nc2ccnc(C(N)=O)c2)O[C@@]1(C)C(F)(F)F]

16. The compound of claim 15, wherein the compound is in crystalline solid form.
17. The compound of claim 16, wherein the crystalline solid form is Form A,
wherein Form A is characterized by one or more of:
(a) an XRPD pattern having diffractions at angles (degrees 2 theta ±0.2) of 10.1, 13.7, 14.1, 16.3, and 20.0; and/or
(b) a monoclinic crystal system, as determined by single-crystal X-ray analysis; and/or (c) a P2$_1$ space group, as determined by single-crystal X-ray analysis; and/or
(d) a unit cell, as determined by single-crystal X-ray analysis, of the following dimensions: a=12.0863(2) Å; b=7.48310(10) Å; c=23.9904(4) Å; α=90°; β=90.0130(10)°; and γ=90°.

18. The compound of claim 16, wherein the crystalline solid form is Form B,
wherein Form B is characterized by an XRPD pattern having diffractions at angles (degrees 2 theta ±0.2) of 6.8, 13.2, 16.1, 20.6 and 21.3.

19. The compound of claim 7, wherein the compound has formula

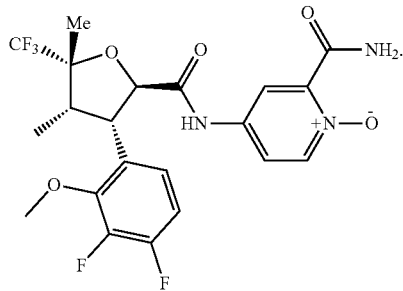

20. The compound of claim 19, wherein the compound is in crystalline solid form.
21. The compound of claim 20, wherein the crystalline solid form is Form A,
wherein Form A is characterized by one or more of:
(a) an XRPD pattern having diffractions at angles (degrees 2 theta ±0.2) of 13.7, 15.2, and 18.2; and/or
(b) a solid state $^{13}$C NMR spectrum having peaks at chemical shifts of 171.4, 141.6, 118.0, 112.2, 23.0, and 11.6 ppm or a solid state $^{19}$F NMR spectrum having peaks at chemical shifts of −74.6, −141.5, and −154.6 ppm; and/or
(c) a monoclinic crystal system, as determined by single-crystal X-ray analysis; and/or
(d) a P2$_1$ space group, as determined by single-crystal X-ray analysis; and/or
(e) a unit cell, as determined by single-crystal X-ray analysis, of the following dimensions: a=11.2266(3) Å; b=7.3948(2) Å; c=13.1432(4) Å; α=90°; β=100.3980(1°); and γ=90°.

22. The compound of claim 7, wherein the compound has formula

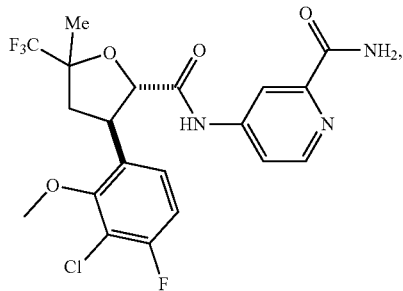 [SMILES: COc1c([C@H]2CC(C)(C(F)(F)F)O[C@@H]2C(=O)Nc2ccnc(C(N)=O)c2)ccc(F)c1Cl]

wherein the compound has the absolute stereochemistry of the third eluting isomer when a mixture of racemic diastereomers (epimeric at the 5-position) is separated by chiral SFC using a 25 cm×21.2 mm (R,R)-WHELK-O®1 (1-(3,5-dinitrobenzamido)-1,2,3,4-tetrahydrophenanthrene modified 5 μm silica) column.

23. The compound of claim 22, wherein the compound is in crystalline solid form.

24. The compound of claim 23, wherein the crystalline solid form is Form A,
wherein Form A is characterized by an XRPD pattern having diffractions at angles (degrees 2 theta ±0.2) of 9.2, 10.4, and 15.7; and/or
wherein Form A is characterized by a solid state $^{13}$C NMR spectrum having peaks at chemical shifts of 167.7, 126.0, 115.9, 43.5, and 20.3 ppm or a solid state $^{19}$F NMR spectrum having peaks at chemical shifts of −82.2, −83.1, −111.7, and −114.4 ppm.

25. The compound of claim 7, wherein the compound has formula

26. The compound of claim 25, wherein the compound is in crystalline solid form.

27. The compound of claim 26, wherein the crystalline solid form is Form A,
wherein Form A is characterized by one or more of:
(a) an XRPD pattern having diffractions at angles (degrees 2 theta ±0.2) of 17.2, 19.3, and 22.3; and/or
(b) a solid state $^{13}$C NMR spectrum having peaks at chemical shifts of 171.1, 149.3, 123.3, 41.6, and 20.0 ppm or a solid state $^{19}$F NMR spectrum having peaks at chemical shifts of −78.2, −113.5, and −115.1 ppm; and/or
(c) a monoclinic crystal system, as determined by single-crystal X-ray analysis; and/or
(d) a P2$_1$ space group, as determined by single-crystal X-ray analysis; and/or
(e) a unit cell, as determined by single-crystal X-ray analysis, of the following dimensions: a=7.8661(3) Å; b=7.9167(3) Å; c=16.8777(7) Å; α=90°; β=98.487(2)°; and γ=90°.

28. The compound of claim 7, wherein the compound has formula wherein the compound has the absolute stereochemistry of the second eluting isomer when a racemic mixture of enantiomers is separated by chiral SFC as described in Example 7, Step 11 using a 25 cm×10 mm CHIRALPAK® AS-H (amylose tris-[(S)-α-methylbenzylcarbamate] coated on 5 μm silica) column.

29. The compound of claim 28, wherein the compound is in crystalline solid form.

30. The compound of claim 29, wherein the crystalline solid form is Form A,
wherein Form A is characterized by an XRPD pattern having diffractions at angles (degrees 2 theta ±0.2) of 6.8, 7.9, and 13.8.

31. A pharmaceutical composition comprising the compound of claim 1, or a pharmaceutically acceptable salt thereof, and one or more pharmaceutically acceptable carriers or vehicles.

32. A method of inhibiting a voltage-gated sodium channel in a subject comprising administering to the subject the compound of claim 1, or a pharmaceutically acceptable salt thereof.

33. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 1, or a pharmaceutically acceptable salt thereof.

34. A method of treating or lessening the severity in a subject of pain comprising administering to the subject an effective amount of the compound of claim 1, or a pharmaceutically acceptable salt thereof.

35. A pharmaceutical composition comprising the compound of claim 8, and one or more pharmaceutically acceptable carriers or vehicles.

36. A method of inhibiting a voltage-gated sodium channel in a subject comprising administering to the subject the compound of claim 8.

37. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 8.

38. A method of treating or lessening the severity in a subject of pain comprising administering to the subject an effective amount of the compound of claim 8.

39. A pharmaceutical composition comprising the compound of claim 12, and one or more pharmaceutically acceptable carriers or vehicles.

40. A method of inhibiting a voltage-gated sodium channel in a subject comprising administering to the subject the compound of claim 12.

41. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 12.

42. A method of treating or lessening the severity in a subject of pain comprising administering to the subject an effective amount of the compound of claim 12.

43. A pharmaceutical composition comprising the compound of claim 15, and one or more pharmaceutically acceptable carriers or vehicles.

44. A method of inhibiting a voltage-gated sodium channel in a subject comprising administering to the subject the compound of claim 15.

45. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 15.

46. A method of treating or lessening the severity in a subject of pain comprising administering to the subject an effective amount of the compound of claim 15.

47. A pharmaceutical composition comprising the compound of claim 19, and one or more pharmaceutically acceptable carriers or vehicles.

48. A method of inhibiting a voltage-gated sodium channel in a subject comprising administering to the subject the compound of claim 19.

49. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 19.

50. A method of treating or lessening the severity in a subject of pain comprising administering to the subject an effective amount of the compound of claim 19.

51. A pharmaceutical composition comprising the compound of claim 22, and one or more pharmaceutically acceptable carriers or vehicles.

52. A method of inhibiting a voltage-gated sodium channel in a subject comprising administering to the subject the compound of claim 22.

53. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 22.

54. A method of treating or lessening the severity in a subject of pain comprising administering to the subject an effective amount of the compound of claim 22.

55. A pharmaceutical composition comprising the compound of claim 25, and one or more pharmaceutically acceptable carriers or vehicles.

56. A method of inhibiting a voltage-gated sodium channel in a subject comprising administering to the subject the compound of claim 25.

57. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 25.

58. A method of treating or lessening the severity in a subject of pain comprising administering to the subject an effective amount of the compound of claim 25.

59. A pharmaceutical composition comprising the compound of claim 28, and one or more pharmaceutically acceptable carriers or vehicles.

60. A method of inhibiting a voltage-gated sodium channel in a subject comprising administering to the subject the compound of claim 28.

61. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 28.

62. A method of treating or lessening the severity in a subject of pain comprising administering to the subject an effective amount of the compound of claim 28.

* * * * *